(12) United States Patent
Hewitt et al.

(10) Patent No.: US 11,053,213 B2
(45) Date of Patent: Jul. 6, 2021

(54) PHARMACEUTICAL COMPOUNDS

(71) Applicant: ALMAC DISCOVERY LIMITED, Craigavon (GB)

(72) Inventors: Peter Hewitt, Craigavon (GB); Mary Melissa McFarland, Craigavon (GB); James Samuel Shane Rountree, Craigavon (GB); Frank Burkamp, Craigavon (GB); Christina Bell, Craigavon (GB); Lauren Proctor, Craigavon (GB); Matthew Duncan Helm, Craigavon (GB); Colin O'Dowd, Craigavon (GB); Timothy Harrison, Craigavon (GB)

(73) Assignee: ALMAC DISCOVERY LIMITED, Craigavon (GB)

( * ) Notice: Subject to any disclaimer, the term of this patent is extended or adjusted under 35 U.S.C. 154(b) by 0 days.

(21) Appl. No.: 16/319,961

(22) PCT Filed: Jul. 26, 2017

(86) PCT No.: PCT/GB2017/052178
§ 371 (c)(1),
(2) Date: Jan. 23, 2019

(87) PCT Pub. No.: WO2018/020242
PCT Pub. Date: Feb. 1, 2018

(65) Prior Publication Data
US 2019/0233394 A1 Aug. 1, 2019

(30) Foreign Application Priority Data
Jul. 26, 2016 (GB) .................................... 1612938

(51) Int. Cl.
| C07D 401/06 | (2006.01) |
| C07D 401/14 | (2006.01) |
| C07D 405/14 | (2006.01) |
| C07D 409/14 | (2006.01) |
| C07D 413/14 | (2006.01) |
| C07D 417/14 | (2006.01) |
| A61P 35/00 | (2006.01) |
| A61P 21/00 | (2006.01) |
| A61P 25/16 | (2006.01) |
| C07D 491/10 | (2006.01) |
| C07D 401/04 | (2006.01) |

(52) U.S. Cl.
CPC ............ C07D 401/06 (2013.01); A61P 21/00 (2018.01); A61P 25/16 (2018.01); A61P 35/00 (2018.01); C07D 401/04 (2013.01); C07D 401/14 (2013.01); C07D 405/14 (2013.01); C07D 409/14 (2013.01); C07D 413/14 (2013.01); C07D 417/14 (2013.01); C07D 491/10 (2013.01)

(58) Field of Classification Search
CPC .......... A61P 21/00; A61P 25/16; A61P 35/00; C07D 401/04; C07D 401/06; C07D 401/14; C07D 405/14; C07D 409/14; C07D 413/14; C07D 417/14; C07D 491/10
USPC ......................................................... 514/318
See application file for complete search history.

(56) References Cited

U.S. PATENT DOCUMENTS 7,358,239 B2 * 4/2008 De Bruyn ............ C07D 405/12
514/211.08

FOREIGN PATENT DOCUMENTS

| EP | 3085700 A1 | 10/2016 |
| WO | 2013/027001 A1 * | 2/2013 |
| WO | 2015/090224 A1 | 6/2015 |

* cited by examiner

Primary Examiner — Tracy Vivlemore
Assistant Examiner — Ebenezer O Sackey
(74) Attorney, Agent, or Firm — Brian C. Trinque; Lathrop GPM LLP

(57) ABSTRACT

The present invention relates to compounds of Formula (I) that are useful as inhibitors of the activity of the ubiquitin specific protease USP19. The present invention also relates to pharmaceutical compositions comprising these compounds and to methods of using these compounds in therapy.

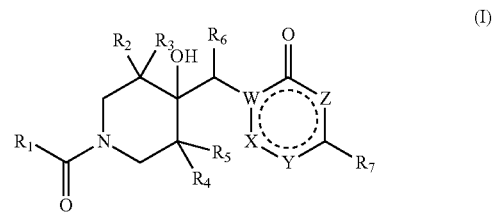

21 Claims, 1 Drawing Sheet

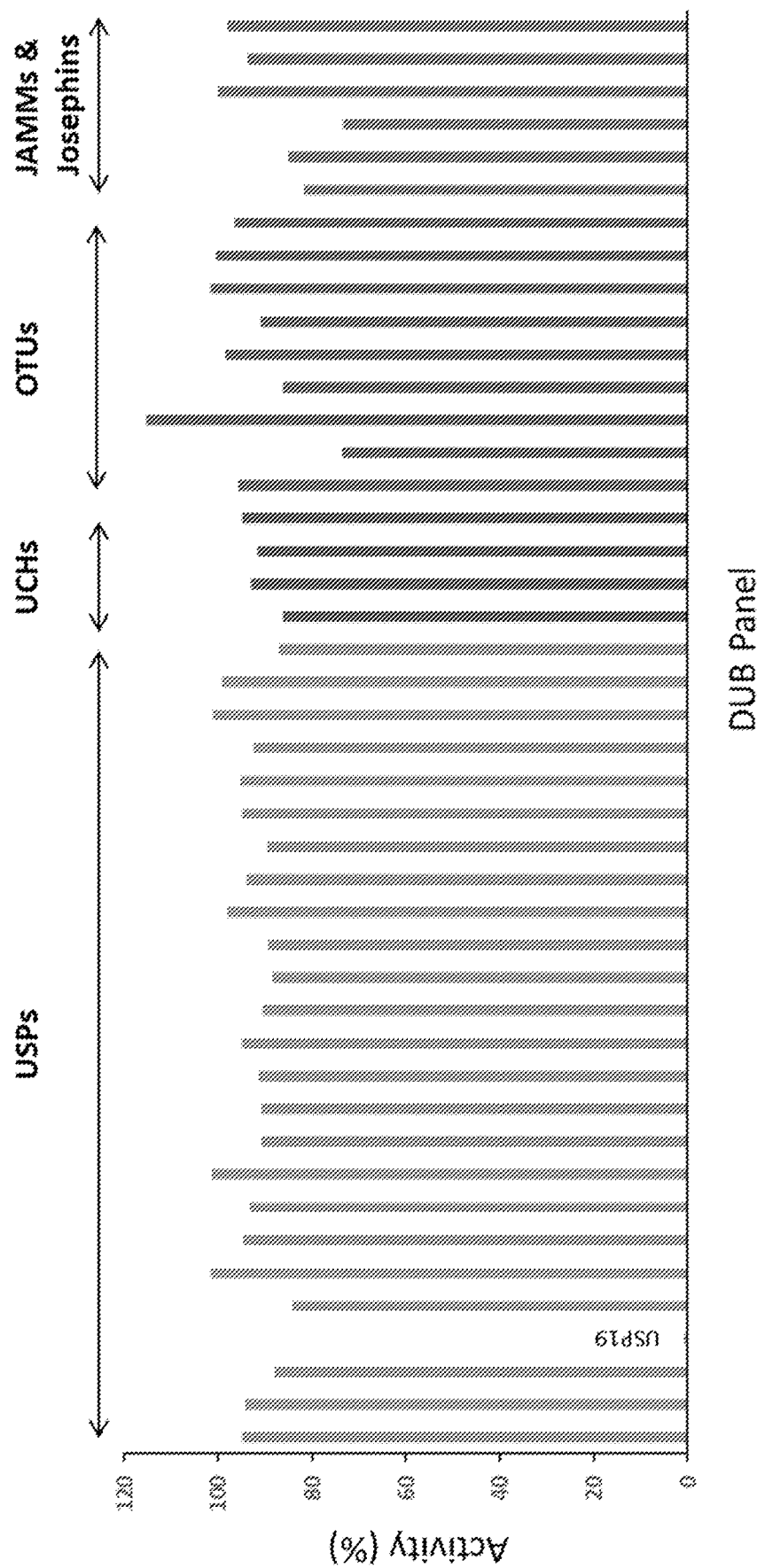

PHARMACEUTICAL COMPOUNDS

RELATED APPLICATIONS

This application is a 35 U.S.C. § 371 filing of International Application No. PCT/GB2017/052178, filed Jul. 26, 2017, which claims the benefit of Great Britain Patent Application No. 1612938.9, filed Jul. 26, 2016. The entire contents of these applications are incorporated herein by reference in their entireties.

FIELD OF INVENTION

The present invention concerns inhibitors of ubiquitin specific protease 19 (USP19) and methods of use thereof.

BACKGROUND

Over the past decade, protein ubiquitination has emerged as an important post-translational modification with roles in a plethora of cellular processes including amongst others proteolysis, gene expression, DNA repair, immune response, metabolism or cell cycle regulation. Dysregulation of the Ubiquitin Proteasome System (UPS) has also been implicated in the pathogenesis of multiple human diseases including but not limited to cancer (Hoeller D. et al., *Nat. Rev. Cancer* (2006), 6, 776-788), viral infection (Gao et al., *J. Physiol., Pharmacol.* (2006), 84, 5-14), metabolic or neurodegenerative disorders (Loosdregt J. et al., *Immunity* (2013), 39, 259-271; Rubinsztein D., et al., *Nature* (2006), 443, 780-786) as well as immune and inflammatory-related medical conditions (Wang J. et al., *J. Cell Immunol.* (2006), 3, 255-261; Corn J. et al., *Nat. Struct. & Mol. Biol.* (2014), 21, 297-300; Nicholson B. et al., *Cell Biochem. Biophys.* (2013), 60, 61-68).

The approval and clinical success of the proteasome inhibitors Velcade® (bortezomib) or Kyprolis® (carfilzomib) for the treatment of mantel cell lymphoma (AML) and multiple myeloma (MM) have validated the UPS as a cancer target amenable for pharmacological intervention. Although effective, their clinical utility has however been severely limited due to poor selectivity and acute toxicity issues. By inhibiting the 26S proteasome, the current proteasome inhibitors indiscriminately impair proteolysis in both cancer and normal cells and are characterised by a low therapeutic index. To circumvent this issue, a promising alternative approach may be to target the UPS upstream of the proteasome. Interfering with the ubiquitin (Ub) conjugation/deconjugation machinery, for instance at the level of the Ubiquitin Specific Proteases (USPs), would allow for the development of improved therapeutics with enhanced specificity and reduced toxicity profiles.

USPs are the largest subfamily of the deubiquitinating enzymes (DUBs) family with over 60 family members reported to date (Komander D. et al., *Nat. Rev. Mol.* (2009), 10, 550-563; Claque M. et al., *Physiol. Rev.* (2013), 93, 1289-1315). USPs are typically cysteine proteases that catalyse the removal of Ub from specific target substrates thus preventing their induced degradation by the proteasome, or regulating their activation and/or subcellular localization (Colland F. et al., *Biochimie* (2008), 90, 270-283; Nicholson B. et al., *Cell Biochem. Biophys.* (2013), 60, 61-68). It is now well established that USPs regulate the stability and activation of numerous proteins involved in the pathogenesis of human diseases including both oncogenes and tumor suppressors. As such, USPs represent an emerging and attractive target class for pharmacological intervention.

Amongst all USPs, USP19 is an important member due to its implications in pathological conditions including but not restricted to cancer, muscle atrophy disorders, neurodegeneration and degenerative diseases as well as antiviral immune response. USP19 expresses as multiple isoforms varying in length from 71.09 kDa (isoform 2) to 156.03 kDa (isoform 5) with the canonical sequence (isoform 1) of 145.65 kDa in size (uniprot.org). The cellular localisation of USP19 may be both cytosolic or bound to the endoplasmic reticulum (Lee J. et al., *J. Biol. Chem.* (2014), 289, 3510-3507; Lee J. et al., *Nat. Cell Biol.* (2016), 18, 765-776). Localised to the endoplasmic reticulum, USP19 is a key component of the endoplasmic reticulum-associated degradation (ERAD) pathway (Hassink B. et al., *EMBO J.* (2009), 10, 755-761; Lee J. et al., *J. Biol. Chem.* (2014), 289, 3510-3507; Lee J. et al., *Nat. Cell Biol.* (2016), 18, 765-776). In particular, USP19 is involved in the latter steps of the protein quality-control machinery rescuing ERAD substrates that have been retro-translocated to the cytosol. USP19 has also been demonstrated to regulate the stability of the E3 ligases MARCH6 and HRD1 (Nakamura N. et al., *Exp. Cell Res.* (2014), 328, 207-216; Harada K. et al., *Int. J. Mol. Sci.* (2016), 17, E1829). In addition, USP19 has recently been implicated in the stabilisation of multiple and potentially important protein substrates. For instance, USP19 interacts with SIAH proteins to rescue HIF1α from degradation under hypoxic conditions (Altun M. et al., *J. Biol. Chem.* (2012), 287, 1962-1969; Velasco K. et al., *Biochem. Biophys. Res. Commun.* (2013), 433, 390-395). USP19 also stabilises the KPC1 ubiquitin ligase which is involved in the regulation of the $p27^{Kip1}$ cyclin-dependent kinase inhibitor (Lu Y. et al., *Mol. Cell Biol.* (2009), 29, 547-558). Knock-out of USP19 by RNAi leads to $p27^{Kip1}$ accumulation and inhibition of cell proliferation (Lu L. et al., *PLoS ONE* (2011), 6, e15936). USP19 was also found to interact with the inhibitors of apoptosis (IAPs) including c-IAP1 and c-IAP2 Wei Y. et al., *J. Biol. Chem.* (2011), 286, 35380-35387). Knockdown of USP18 decreases the total levels of these c-IAPs whilst overexpression increases the levels of both BIRC2/cIAP1 and BIRC3/cIAP2. Knockdown of USP19 also enhances TNFα-induced caspase activation and apoptosis in a BIRC2/c-IAP1 and BIRC3/c-IAP2 dependent manner. In addition to some direct involvement in regulating hypoxia response and ER stress, USP19 has also been implicated recently as a positive regulator of autophagy and negative regulator of type I interferon signalling (IFN, antiviral immune response) by deubiquitinating Beclin-1. USP19 was found to stabilise Beclin-1 at the post-translational level by removing the KI 1-linked ubiquitin chains of Beclin-1 at Lysine 437 (Jin S. et al., *EMBO J.* (2016), 35, 866-880). USP19 negatively regulates type I IFN signalling pathway, by blocking RIG-I-MAVS interaction in a Beclin-1 dependent manner. Depletion of either USP19 or Beclin-1 inhibits autophagic flux and promotes type I IFN signalling as well as cellular antiviral immunity (Jin S. et al., *EMBO J.* (2016), 35, 866-880; Cui J. et al., *Autophagy* (2016), 12, 1210-1211). Recent findings also indicate USP19 may negatively affect the cellular antiviral type I IFN signalling by regulating the TRAF3 substrate (Gu Z. et al., *Future Microbiol.* (2017), 12, 767-779) USP19 has also been recently implicated in the Wnt signalling pathway by stabilising the coreceptor LRP6 (Perrody E. et al., *eLife* (2016), 5, e19083) and in the DNA repair processes, most particularly chromosomal stability and integrity, by regulating the HDAC1 and HDAC2 proteins (Wu M. et al., *Oncotarget* (2017), 8, 2197-2208).

In addition to cancer and associated conditions, USP19 has been increasingly implicated in muscle-wasting syndromes and other skeletal muscle atrophy disorders (Wing S., *Int. J. Biochem. Cell Biol.* (2013), 45, 2130-2135; Wing S. et al., *Int. J. Biochem. Cell Biol.* (2016), 79, 426-468; Wiles B. et al., *Mol. Biol. Cell* (2015), 26, 913-923; Combaret L. et al., *Am. J. Physiol. Endocrinol. Metab.* (2005), 288, E693-700). This was supported for instance by studies which demonstrated that USP19-silencing induced the expression of myofibrillar proteins and promoted myogenesis (Sundaram P. et al., *Am. J. Physiol. Endocrinol. Metab.* (2009), 297, E1283-90; Ogawa M. et al., *J. Biol. Chem.* (2011), 286, 41455-41465; Ogawa M. et al., *J. Endocrinol.* (2015), 225, 135-145). More recently, in vivo studies further demonstrated that mice lacking the USP19 gene (USP19 KO mice) were resistant to muscle wasting in response to both glucocorticoids, a common systemic cause of muscle atrophy, as well as in response to denervation, a model of disuse atrophy (Bedard N. et al., *FASEB J.* (2015), 29, 3889-3898). USP19 KO mice typically retained more strength and had less myofiber atrophy with both type I and type IIb fibers being protected. The rates of muscle protein synthesis were similar in both the wild-type and KO mice, suggesting that the sparing of atrophy was attributed to suppressed protein degradation. Consistent with this, expression of the ubiquitin ligases MuRF1 and MAFbx/atrogin-1 as well as several autophagy genes was decreased in the muscles of catabolic KO mice (Bedard N. et al., *FASEB J.* (2015), 29, 3889-3898). Inhibition of USP19 may therefore be a useful approach to the treatment of many muscle-wasting conditions including but not limited to cachexia and sarcopenia. It is well known for instance that cachexia impairs quality of life and response to therapy, which increase morbidity and mortality of cancer patients. The above findings however have potentially much broader clinical implications beyond cancer as muscle wasting is also associated with other serious illnesses such as HIV/AIDS, heart failure, rheumatoid arthritis and chronic obstructive pulmonary disease (Wiles B. et al., *Mol. Biol. Cell* (2015), 26, 913-923). Muscle wasting is also a prominent feature of aging. Beyond the above pathological conditions, USP19 may also have implications in the pathogenesis of degenerative diseases including but not restricted to Parkinson's disease and other prion-like transmission disorders by regulating important substrates such as α-synuclein or polyglutamine-containing proteins, Ataxin3, Huntington (He W. et al., *PLoS ONE* (2016), 11, e0147515; Bieri G. et al., *Neurobiol Dis.* (2017), doi: 10.1016/j.nbd.2017.03.007). The regulation of coronin 2A (CORO2A) through the activity of USP19 has been shown to affect the transcriptional repression activity of the retinoic acid receptor (RAR), suggesting that USP19 may also be involved in the regulation of RAR-mediated adipogenesis (Lim K. et al., *Oncotarget* (2016), 7, 34759-34772).

The established and ever growing connections between USP19 and numerous proteins involved in human pathologies indicate that small molecule inhibitors of USP19 may have broad therapeutic applications beneficial to human health. Insofar as is known however, no inhibitors targeting USP19 have been reported and the identification of such inhibitors with drug-like potential therefore remains of prime importance and high priority.

SUMMARY OF INVENTION

In a first aspect the invention provides a compound of formula (I)

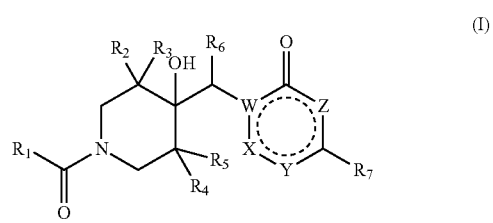

including a pharmaceutically acceptable salt, tautomer, stereoisomer or N-oxide derivative thereof, wherein:

$R_1$ is an optionally substituted alkyl, alkenyl, alkynyl, ether, cycloalkyl, alkylcycloalkyl, heterocycloalkyl, alkylheterocycloalkyl, aryl, arylalkyl, heteroaryl, or heteroarylalkyl group;

$R_2$ is H or an optionally substituted alkyl group, $R_3$ is H or an optionally substituted alkyl group, $R_4$ is H or an optionally substituted alkyl group, $R_5$ is H or an optionally substituted alkyl group, $R_2$ and $R_4$ may be joined to one another to form an optionally substituted cycloalkyl or heterocycloalkyl ring that includes the carbons to which they are attached, $R_4$ and $R_5$ may be joined to one another to form an optionally substituted cycloalkyl or heterocycloalkyl ring that includes the carbon to which they are attached;

$R_6$ is H or an optionally substituted alkyl group;

W is C or N;

X is N or $CR_8$, wherein $R_8$ is H or optionally substituted C1-C6 alkyl,

Y is N or $CR_9$

Z is CH, or NH, wherein $R_9$ is H or optionally substituted alkyl, amido, amino, aryl, heteroaryl, cycloalkyl, cycloheteroalkyl, halo, carbonyl, ester, aminoalkyl, or cyano;

$R_7$ is hydrogen, halo, or an optionally substituted alkyl, alkenyl, alkynyl, amino, aryl, cycloalkyl, cycloalkenyl, alkoxy, aryloxy, heteroaryl or heterocycloalkyl group;

or the compound

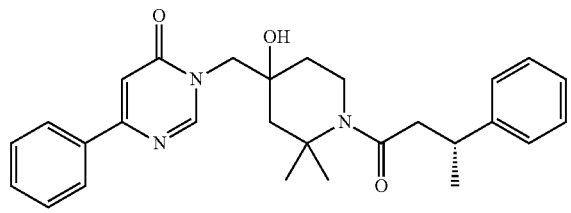 [SMILES: C[C@H](CC(=O)N1CCC(O)(Cn2cnc(-c3ccccc3)cc2=O)CC1(C)C)c1ccccc1]

or a pharmaceutically acceptable salt, tautomer, stereoisomer or N-oxide derivative thereof.

In a second aspect, the invention provides a pharmaceutical composition comprising a compound according to the first aspect and a pharmaceutically acceptable carrier or diluent.

USP19 has been associated with a number of diseases and conditions including (but not limited to) cancer and neoplastic conditions, as well as muscle atrophy including (but not limited to) cachexia and sarcopenia.

The compounds described herein are able to selectively inhibit USP19 activity. The compounds provided herein may therefore be suitable for the treatment and prevention of cancer and neoplastic conditions, immunological and inflammatory conditions for example by promoting antiviral immune response, as well as for treatment and prevention of muscular atrophy, for example cachexia and sarcopenia, neurodegenerative diseases including Parkinson's disease and other prion-based disorders. The compounds may be used as monotherapy or as combination therapy with radiation and/or additional therapeutic agents.

Therefore, in a further aspect, the invention provides a compound according to the first aspect or a pharmaceutical composition according to the second aspect for use in therapy. In a further aspect, the invention provides a compound according to the first aspect or a pharmaceutical composition according to the second aspect for use in a method of treating or preventing cancer. In a further aspect, the invention provides a compound according to the first aspect or a pharmaceutical composition according to the second aspect for use in a method of treating or preventing muscular atrophy, optionally cachexia or sarcopenia. In a further aspect, the invention provides a compound according to the first aspect or a pharmaceutical composition according to the second aspect for use in a method of treating or preventing Parkinson's Disease.

In a further aspect, the invention provides a method of treating cancer or muscular atrophy comprising administering to a subject an effective amount of a compound according to the first aspect or a pharmaceutical composition according to the second aspect.

In a further aspect, the invention provides a method of treating Parkinson's Disease comprising administering to a subject an effective amount of a compound according to the first aspect or a pharmaceutical composition according to the second aspect.

Other preferred embodiments of the compounds according to the invention appear throughout the specification and in particular in the examples. Particularly preferred are those named compounds having greater activity as tested. Compounds having higher activity are more preferred over those having lower activity.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

FIGURES

FIG. 1 Overall selectivity profile of Example 124 against a panel of DUBs. Included in this screen were 24 USPs and 19 other DUBs (as indicated). Example 124 was screened at a fixed concentration of 100 µM using the Ub-Rh110 substrate (Ubiquigent). Residual activity is shown on the y-axis normalised to the no compound (DMSO) control.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedence over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbon substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbon substituent containing one or more double bonds and typically 2 to 15 carbon atoms; such as 2 to 10, 2 to 8, 2 to 6 or 2 to 4 carbon atoms. Examples of such substituents include ethenyl (vinyl), 1-propenyl, 3-propenyl, 1,4-pentadienyl, 1,4-butadienyl, 1-butenyl, 2-butenyl, 3-butenyl, pentenyl and hexenyl.

The term "alkynyl group" (alone or in combination with another term(s)) means a straight- or branched-chain hydrocarbon substituent containing one or more triple bonds and typically 2 to 15 carbon atoms; such as 2 to 10, 2 to 8, 2 to 6 or 2 to 4 carbon atoms. Examples of such substituents include ethynyl, 1-propynyl, 3-propynyl, 1-butynyl, 3-butynyl and 4-butynyl.

The term "heteroalkyl group" (alone or in combination with another term(s)) means a straight- or branched-chain saturated hydrocarbyl substituent typically containing 1 to 15 atoms, such as 1 to 10, 1 to 8, 1 to 6, or 1 to 4 atoms, wherein at least one of the atoms is a heteroatom (i.e. oxygen, nitrogen, or sulfur), with the remaining atoms being carbon atoms. A "$C_n$ heteroalkyl" group refers to an aliphatic group containing n carbon atoms and one or more heteroatoms, for example one heteroatom. For example, a $C_1$-$C_{10}$ heteroalkyl group contains 1, 2, 3, 4, 5, 6, 7, 8, 9 or 10 carbon atoms in addition to one or more heteroatoms, for example one heteroatom. Attachment to the heteroalkyl group occurs through a carbon atom or through a heteroatom.

The term "heteroalkenyl group" (alone or in combination with another term(s)) means a straight- or branched-chain hydrocarbon substituent containing one or more carbon-carbon double bonds and typically 2 to 15 atoms; such as 2 to 10, 2 to 8, 2 to 6 or 2 to 4 atoms, wherein at least one of the atoms is a heteroatom (i.e. oxygen, nitrogen, or sulfur), with the remaining atoms being carbon atoms. A "$C_n$ heteroalkenyl" group refers to an aliphatic group containing n carbon atoms and one or more heteroatoms, for example one heteroatom. For example, a $C_2$-$C_{10}$ heteroalkenyl group contains 2, 3, 4, 5, 6, 7, 8, 9 or 10 carbon atoms in addition to one or more heteroatoms, for example one heteroatom. Attachment to the heteroalkenyl group occurs through a carbon atom or through a heteroatom.

The term "heteroalkynyl group" (alone or in combination with another term(s)) means a straight- or branched-chain hydrocarbon substituent containing one or more carbon-carbon triple bonds and typically 2 to 15 carbon atoms; such as 2 to 10, 2 to 8, 2 to 6 or 2 to 4 carbon atoms, wherein at least one of the atoms is a heteroatom (i.e. oxygen, nitrogen, or sulfur), with the remaining atoms being carbon atoms. A "$C_n$ heteroalkynyl" group refers to an aliphatic group containing n carbon atoms and one or more heteroatoms, for example one heteroatom. For example, a $C_2$-$C_{10}$ heteroalkynyl group contains 1, 2, 3, 4, 5, 6, 7, 8, 9 or 10 carbon atoms in addition to one or more heteroatoms, for example one heteroatom. Attachment to the heteroalkynyl group occurs through a carbon atom or through a heteroatom.

The term "carbocyclyl group" (alone or in combination with another term(s)) means a saturated cyclic (i.e. "cycloalkyl"), partially saturated cyclic (i.e. "cycloalkenyl"), or completely unsaturated (i.e. "aryl") hydrocarbon substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains 3 to 8 ring atoms, more typically 3 to 7 ring atoms, and more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e. may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl group" (alone or in combination with another term(s)) means a saturated cyclic hydrocarbon substituent containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Polycyclic cycloalkyls include bridged, fused, and spirocyclic cycloalkyls.

The term "alkylcycloalkyl" refers to a cycloalkyl substituent attached via an alkyl chain. Examples of an alkylcycloalkyl substitent include cyclohexylethane, where the cyclohexane is attached via an ethane linker. Other examples include cyclopropylethane, cyclobutylethane, cyclopentylethane, cycloheptylethane, cyclohexylmethane. In a "$C_n$" alkylcycloalkyl, $C_n$ includes the carbon atoms in the alkyl chain and in the cycloalkyl ring. For example, cyclohexylethane is a C8 alkylcycloalkyl.

The term "aryl group" (alone or in combination with another term(s)) means an aromatic carbocyclyl containing from 5 to 14 carbon ring atoms, optionally 5 to 8, 5 to 7, optionally 5 to 6 carbon ring atoms. A "$C_n$ aryl" group refers to an aromatic group containing n carbon atoms. For example, a $C_6$-$C_{10}$ aryl group contains 6, 7, 8, 9 or 10 carbon atoms. Attachment to the aryl group occurs through a carbon atom. An aryl group may be monocyclic or polycyclic (i.e. may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, acridinyl, indenyl, indanyl, and tetrahydronapthyl.

The term "arylalkyl" refers to an aryl substituent attached via an alkyl chain. Examples of an arylalkyl substitent include phenylethane/ethylbenzene, where the ethane chain links to a phenyl group to the point of attachment. In a "$C_n$," arylalkyl, $C_n$ includes the carbon atoms in the alkyl chain and in the aryl group. For example, ethylbenzene is a C8 arylalkyl.

The term "heterocyclyl group" (alone or in combination with another term(s)) means a saturated (i.e. "heterocycloalkyl"), partially saturated (i.e. "heterocycloalkenyl"), or completely unsaturated (i.e. "heteroaryl") ring structure containing a total of 3 to 14 ring atoms, wherein at least one of the ring atoms is a heteroatom (i.e. oxygen, nitrogen, or sulfur), with the remaining ring atoms being carbon atoms. A heterocyclyl group may, for example, contain one, two, three, four or five heteroatoms. Attachment to the heterocyclyl group may occur through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl) or 1,3,4-oxadiazolyl), oxatriazolyl, dioxazolyl oxathiolyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl) or pyrazinyl (1,4-diazinyl)), piperazinyl, triazinyl (including 1,3,5-triazinyl, 1,2,4-triazinyl and 1,2,3-triazinyl)), oxazinyl (including 1,2-oxazinyl, 1,3-oxazinyl or 1,4-oxazinyl)), oxadiazinyl (including 1,2,3-oxadiazinyl, 1,2,4-oxadiazinyl, 1,4,2-oxadiazinyl or 1,3,5-oxadiazinyl)), morpholinyl, azepinyl, oxepinyl, thiepinyl, and diazepinyl.

A heterocyclyl group may alternatively be polycyclic (i.e. may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common non-adjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), and benzisoxazinyl (including 1,2-benzisoxazinyl or 1,4-benzisoxazinyl).

The term "heterocycloalkyl group" (alone or in combination with another term(s)) means a saturated heterocyclyl. A "$C_n$ heterocycloalkyl" group refers to a cyclic aliphatic group containing n carbon atoms in addition to at least one heteroatom, for example nitrogen. For example, a $C_1$-$C_{10}$ heterocycloalkyl group contains 1, 2, 3, 4, 5, 6, 7, 8, 9 or 10 carbon ring atoms in addition to the at least one heteroatom. Attachment to the heterocycloalkyl group occurs through a carbon atom or one of the at least one heteroatoms.

The term "alkylheterocycloalkyl" refers to a heterocycloalkyl substituent attached via an alkyl chain. In a "$C_n$" alkylheterocycloalkyl, $C_n$ includes the carbon atoms in the alkyl chain and in the heterocycloalkyl ring. For example, ethylpiperidine is a C7 alkylheterocycloalkyl.

The term "heteroaryl group" (alone or in combination with another term(s)) means an aromatic heterocyclyl containing from 5 to 14 ring atoms. A "$C_n$ heteroaryl" group refers to an aromatic group containing n carbon atoms and at least one heteroatom. For example, a $C_2$-$C_{10}$ aryl group contains 2, 3, 4, 5, 6, 7, 8, 9 or 10 carbon atoms in addition to at least one heteroatom. Attachment to the heteroaryl group occurs through a carbon atom or through a heteroatom. A heteroaryl group may be monocyclic or polycyclic. A heteroaryl may be a single ring or 2 or 3 fused rings. Examples of monocyclic heteroaryl groups include 6-membered rings such as pyridyl, pyrazinyl, pyrimidinyl, pyridazinyl, and 1,3,5-, 1,2,4- or 1,2,3-triazinyl; 5-membered rings such as imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. Polycyclic heteroaryl groups may be 2 or 3 fused rings. Examples of polycyclic heteroaryl groups include 6/5-membered fused ring groups such as benzothiofuranyl, benzisoxazolyl, benzoxazolyl, and purinyl; and 6/6-membered fused ring groups such as benzopyranyl, quinolinyl, isoquinolinyl, cinnolinyl, quinazolinyl, and benzoxazinyl. In the case of polycyclic heteroaryl groups, only one ring in the polycyclic system is required to be unsaturated while the remaining ring(s) may be saturated, partially saturated or unsaturated.

A nitrogen-containing heteroaryl group is a heteroaryl group in which at least one of the one or more heteroatoms in the ring is nitrogen.

The term "heteroarylalkyl" refers to a heteroaryl substituent attached via an alkyl chain. Examples of a heteroarylalkyl substitent include ethylpyridine, where the ethane chain links a pyridine group to the point of attachment.

The term "amino group" refers to the —NR'R" group. The amino group can be optionally substituted. In an unsubstituted amino group, R' and R" are hydrogen. In a substituted amino group R' and R" each independently may be, but are not limited to, hydrogen, an alkyl, heteroalkyl, cycloalkyl, heterocycloalkyl, alkylcycloalkyl, alkylheterocycloalkyl, alkoxy, sulfonyl, alkenyl, alkanoyl, aryl, arylalkyl, or a heteroaryl group, provided R' and R" are not both hydrogen. In a substituted amino group R' and R" may cyclise to form a cyclic amino group, e.g. a pyrrolidine group or a piperidine group. Such a cyclic amino group may incorporate other heteroatoms, for example to form a piperazine or morpholine group. Such a cyclic amino group may be optionally substituted, e.g. with an amino group, a hydroxyl group or an oxo group.

The term "aminoalkyl" group refers to the —$R^a$NR'R" group, wherein $R^a$ is an alkyl chain as defined above and NR'R" is an optionally substituted amino group as defined above. "$C_n$ aminoalkyl" group refers to a group containing n carbon atoms. For example, a $C_1$-$C_{10}$ aminoalkyl group contains 1, 2, 3, 4, 5, 6, 7, 8, 9 or 10 carbon atoms. When the amino group of the aminoalkyl group is a substituted amino group, the number of carbon atoms includes any carbon atoms in the substituent groups. Attachment to the aminoalkyl group occurs through a carbon atom of the $R^a$ alkyl group. Examples of aminoalkyl substituents include methylamine, ethylamine, methylaminomethyl, dimethylaminomethyl, methylaminoethyl, dimethylaminoethyl, methylpyrrolidine, and ethylpyrrolidine The term "amido group" refers to the C(=O)—NR— group. Attachment may be through the carbon and/or nitrogen atom. For example, the amido group may be attached as a substituent via the carbon atom only, in which case the nitrogen atom has two R groups attached (—C(=O)—NR$_2$). The amido group may be attached by the nitrogen atom only, in which case the carbon atom has an R group attached (—NR—C(=O)R).

The term "ether" refers to an —O-alkyl group or an alkyl-O-alkyl group, for example a methoxy group, a methoxymethyl group or an ethoxyethyl group. The alkyl chain(s) of an ether can be linear, branched or cyclic chains. The ether group can be optionally substituted (a "substituted ether") with one or more substituents. A $C_n$ ether refers to an ether group having n carbons in all alkyl chains of the ether group. For example, a CH(CH3)-O—C6H11 ether is a $C_8$ ether group.

The term "alkoxy group" refers to an —O-alkyl group. The alkoxy group can refer to linear, branched, or cyclic, saturated or unsaturated oxy-hydrocarbon chains, including, for example, methoxyl, ethoxyl, propoxyl, isopropoxyl, butoxyl, t-butoxyl and pentoxyl. The alkoxy group can be optionally substituted (a "substituted alkoxy") with one or more alkoxy group substituents.

The term "aryloxy group" refers to an —O-aryl group, for example a phenoxy group. An aryloxy substituent may itself be optionally substituted, for example with a halogen.

The term "alkylester" refers to a —C(O)OR group, where R is an alkyl group as defined herein. An example of an alkylester is ethyl methanoate i.e. R is an ethyl group.

The term "hydroxyl" refers to an OH group.

The term "oxo group" refers to the (=O) group, i.e. a substituent oxygen atom connected to another atom by a double bond. For example, a carbonyl group (—C(=O)—) is a carbon atom connected by a double bond to an oxygen atom, i.e. an oxo group attached to a carbon atom. Examples of carbonyl substituents include aldehydes (—C(=O)H), acetyl (—C(=O)CH3) and carboxyl/carboxylic acid groups (—C(=O)OH).

The term "halo group" refers to a group selected from chlorine, fluorine, bromine and iodine. Preferably, the halo group is selected from chlorine and fluorine.

An alkyl, alkenyl, alkynyl, carbocyclyl (including cycloalkyl, cycloalkenyl and aryl), heterocyclyl (including heterocycloalkyl, heterocyloalkenyl, heteroaryl, nitrogen-containing heterocyclyl), amino, amido, ester, ether, alkoxy, or sulfonamide group can be optionally substituted with one or more substituents, which can be the same or different. A substituent can be attached through a carbon atom and/or a heteroatom in the alkyl, alkenyl, alkynyl, carbocyclyl (including cycloalkyl, cycloalkenyl and aryl), heterocyclyl (including heterocycloalkyl, heterocyloalkenyl, heteroaryl, nitrogen-containing heterocyclyl, nitrogen-containing heteroaryl), amino, amido, ester, ether, alkoxy, or sulfonamide group. The term "substituent" (or "radical") includes but is not limited to alkyl, substituted alkyl, heteroalkyl, substituted heteroalkyl, aralkyl, substituted aralkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl, arylsulfonyl and sulfoximinyl.

In certain aspects, the substituent is alkyl, substituted alkyl, heteroalkyl, substituted heteroalkyl, alkenyl, substituted alkenyl, alkynyl, substituted alkynyl, halo, hydroxyl, cyano, amino, amido, alkylamino, arylamino, carbocyclyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, nitro, thio, alkanoyl, hydroxyl, aryloxyl, alkoxyl, alkylthio, arylthio, aralkyloxyl, aralkylthio, carboxyl, alkoxycarbonyl, oxo, alkylsulfonyl and arylsulfonyl.

If a group, for example an alkyl group, is "optionally substituted", it is understood that the group has one or more substituents attached (substituted) or does not have any substituents attached (unsubstituted).

If a group is substituted with a further optionally substituted group, it is understood that the first substituent may itself be either unsubstituted or substituted.

For completeness, it is also noted that certain chemical formulae used herein define delocalized systems. This definition is known in the art as a definition of aromaticity and may indicate the presence of, for example, a planar mono-, di- or tri-cyclic system that contains (4n+2) electrons where n is an integer. In other words, these systems may display Nikkei aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures, unless otherwise specified. Stereoisomers are known in the art to be molecules that have the same molecular formula and sequence of bonded atoms, but which differ in their spatial orientations of their atoms and/or groups.

In addition, the compounds of the present invention may exhibit tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein.

In addition, it will be understood that the elements described herein may be the common isotope or an isotope other than the common isotope. For example, a hydrogen atom may be $^1H$, $^2H$ (deuterium) or $^3H$ (tritium).

In addition, the compounds of the present invention may be provided in the form of their pharmaceutically acceptable salts or as co-crystals.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the handbook of pharmaceutical salts published by IUPAC.

In addition, the compounds of the present invention may sometimes exist as zwitterions, which are considered as part of the invention.

Accordingly, in a first aspect the present invention provides a compound according to formula (I):

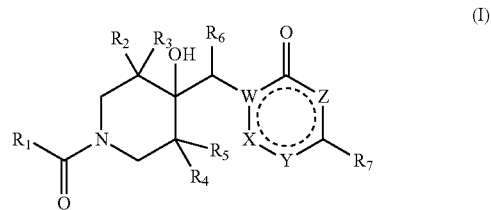

including a pharmaceutically acceptable salt, tautomer, stereoisomer or N-oxide derivative thereof, wherein:

$R_1$ is an optionally substituted alkyl, alkenyl, alkynyl, ether, cycloalkyl, alkylcycloalkyl, heterocycloalkyl, alkylheterocycloalkyl, aryl, arylalkyl, heteroaryl, or heteroarylalkyl group;

$R_2$ is H or an optionally substituted alkyl group, $R_3$ is H or an optionally substituted alkyl group, $R_4$ is H or an optionally substituted alkyl group, $R_5$ is H or an optionally substituted alkyl group, $R_2$ and $R_4$ may be joined to one another to form an optionally substituted cycloalkyl or heterocycloalkyl that includes the carbons to which they are attached, $R_4$ and $R_5$ may be joined to one another to form an optionally substituted cycloalkyl or heterocycloalkyl that includes the carbon to which they are attached;

$R_6$ is H or an optionally substituted alkyl group;

W is C or N;

X is N or $CR_8$, wherein $R_8$ is H or optionally substituted C1-C6 alkyl,

Y is N or $CR_9$

Z is CH, or NH, wherein $R_9$ is H or optionally substituted alkyl, amido, amino, aryl, heteroaryl, cycloalkyl, cycloheteroalkyl, halo, carbonyl, ester, aminoalkyl, or cyano;

$R_7$ is hydrogen, halo, or an optionally substituted alkyl, alkenyl, alkynyl, amino, aryl, cycloalkyl, cycloalkenyl, alkoxy, aryloxy, heteroaryl or heterocycloalkyl group;

or the compound

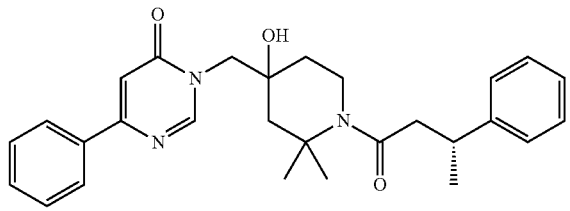 [SMILES: C[C@H](CC(=O)N1CCC(O)(Cn2cnc(-c3ccccc3)cc2=O)CC1(C)C)c1ccccc1]

or a pharmaceutically acceptable salt, tautomer, stereoisomer or N-oxide derivative thereof.

In certain embodiments, $R_1$ is optionally substituted C1-C6 alkyl, optionally substituted C4-C10 alkylcycloalkyl, optionally substituted C7-C10 arylalkyl, optionally substituted C3-C6 cycloalkyl, or optionally substituted C3-C6 heteroaryl, wherein the optional substituent is selected from C1-C6 alkyl, C2-C6 alkenyl, methoxymethyl, benzyloxymethyl, phenyl, C3-C6 cycloalkyl, $CF_3$, $CHF_2$, OH, or halo. In certain such embodiments, $R_1$ is optionally substituted cyclohexylalkane, preferably optionally substituted cyclohexylethane; optionally substituted alkylbenzene, preferably ethylbenzene; or optionally substituted 3,3,3-trifluoropropane and the optional substituent is selected from C1-C6 alkyl, C2-C6 alkenyl, hydroxymethyl, methoxymethyl, OH, or halo. In certain embodiments, $R_1$ is substituted and the substituent is C1-C6 alkyl, optionally methyl.

In certain embodiments, $R_7$ is optionally substituted C6-C10 aryl, C1-C12 heteroaryl, C1-C10 alkyl, C2-C10 alkenyl, C3-C10 cycloalkyl, amino, C1-C3 alkoxy, or halo, and the optional substituent is selected from C1-C6 alkyl, hydroxysubstituted C1-C6 alkyl, C3-C6 cycloalkyl or C1-C6 heterocycloalkyl, C1-C6 alkoxy, halo-substituted C1-C6 alkoxy, amido, cyano or halo. In certain embodiments, $R_7$ is optionally substituted phenyl, naphthalenyl, indazole, pyrimidine, thiophene, or pyrazole, wherein the optional substituent is selected from C1-C6 alkyl, hydroxy-substituted C1-C6 alkyl, C3-C6 cycloalkyl or C1-C6 heterocycloalkyl, C1-C6 alkoxy, halo-substituted C1-C6 alkoxy, C1-C6 alkylamine, amido, cyano or halo.

In certain embodiments, $R_2$, $R_3$, $R_4$, $R_5$ and $R_6$ are independently selected from H and C1-C6 alkyl.

In certain such embodiments, $R_2$, $R_3$ and $R_6$ are H, and $R_4$ and $R_5$ are methyl. That is, the compound includes the core structure:

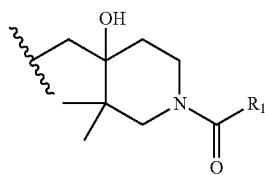

In certain alternative embodiments, $R_4$ and $R_5$ are joined to one another to form an optionally substituted C3-C6 cycloalkyl or C3-C6 heterocycloalkyl that includes the carbon to which they are attached and $R_2$, $R_3$ and $R_6$ are independently selected from H and C1-C6 alkyl. In certain such embodiments, $R_2$, $R_3$ and $R_6$ are H and $R_4$ and $R_5$ are joined to one another to form a C3-C6 cycloalkyl that includes the carbon to which they are attached, optionally a C4 or C5 cycloalkyl that includes the carbon to which they are attached. That is, the compound includes the core structure:

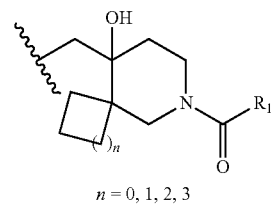

$n = 0, 1, 2, 3$

These core structures are particularly advantageous as they possess unanticipated high potency for inhibiting USP19. In certain embodiments, compounds having one of these core structures have increased potency compared to equivalent unsubstituted compounds (i.e. where $R_2$, $R_3$, $R_4$, $R_5$ and $R_6$ are H).

When $R_2$ and/or $R_3$ are not hydrogen and $R_4$ and $R_5$ are hydrogen (or in the opposite case in which, $R_2$ and $R_3$ are hydrogen and $R_4$ and/or $R_5$ are not hydrogen), the tertiary alcohol of the piperidinol is chiral. Embodiments relating to compounds with this arrangement encompass all stereoisomers, unless indicated otherwise. That is, embodiments relating to chiral compounds encompass both the R and S stereoisomers, unless the R or S stereoisomer is explicitly specified. In certain preferred embodiments of such chiral compounds, the stereoisomer is the S isomer.

In certain embodiments, $R_2$ and $R_4$ are joined to one another to form a C5 cycloalkyl that includes the carbons to which they are attached, and wherein $R_3$, $R_5$ and $R_6$ are independently H or C1-C6 alkyl.

In certain embodiments, W is N and X is $CR_8$, wherein $R_8$ is H or methyl.

In certain embodiments, Y is N or $CR_9$, wherein $R_9$ is H, C1-C6 alkyl, NR'R", C(O)NR'R", cyano, carboxyl, halo, C1-C6 alkylamine, C3-C6 alkylester, optionally substituted C6-C10 aryl or optionally substituted C2-C6 heteroaryl, wherein the one or more heteroatoms are selected from N and O, and the one or more optional substituents of the aryl or heteroaryl are selected from C1-C6 alkyl, C1-C6 alkylamine, amido, and cyano, and wherein R' and R" are independently selected from H, C1-C6 alkyl optionally substituted with OH, C3-C7 cycloalkyl, C3-C7 heterocycloalkyl, C4-C7 alkylcycloalkyl, C3-C7 alkylheterocycloalkyl, benzyl, phenyl, and methoxy. Alternatively, R' and R" may be joined to one another to form a C2-C7 heterocycle that includes the N to which they are attached, wherein the heterocycle is optionally hydroxyl-substituted, oxo-substituted, methyl-substituted, CH2OH-substituted or acetyl-substituted.

In certain embodiments, $R_9$ is selected from: phenyl optionally substituted with amido, cyano or methyl amine; pyridine; oxazole, pyrazole; carboxyl; C(O)NR'R"; or NR'R"; wherein R' and R" are independently selected from H, C1-C6 alkyl, C3-C7 cycloalkyl, C3-C7 heterocycloalkyl wherein the heteroatom is N or O, or alternatively R' and R" may be joined to one another to form a C2-C7 heterocycloalkyl that includes the N to which they are attached, wherein the heterocycloalkyl is optionally hydroxyl-substituted, oxo-substituted, methyl-substituted, CH2OH-substituted or acetyl-substituted.

In certain embodiments the heterocycloalkyl formed by R' and R" incorporates one or more heteroatoms selected from N, O or S in addition to the N to which they are attached. For example, in certain embodiments the heterocycloalkyl formed by R' and R" is a pyrrolidine, piperidine, piperazine or morpholine group, wherein the heterocycloalkyl is optionally hydroxyl-substituted, oxo-substituted, methyl-substituted, CH2OH-substituted or acetyl-substituted.

In certain embodiments:
$R_1$ is selected from optionally substituted ethylcyclohexane, optionally substituted ethylbenzene, and optionally substituted 3,3,3-trifluoropropane, wherein the optional substituent is one or more of methyl, ethyl, propyl, propenyl, hydroxymethyl, and methoxymethyl,
$R_2$ and $R_3$, are independently selected from H, methyl,
$R_4$ and $R_5$ are independently selected from H, methyl, or are joined to one another to form a C3-C6 cycloalkyl or heterocycloalkyl that includes the carbon to which they are attached, optionally a C4 or C5 cycloalkyl that includes the carbon to which they are attached
$R_6$ is H or methyl,
$R_7$ is selected from optionally substituted phenyl, indazole, thiophene, or pyrazole, wherein the optional substituent is selected from C1-C6 alkyl, hydroxysubstituted C1-C6 alkyl, C3-C6 cycloalkyl, C1-C6 heterocycloalkyl, C1-C6 alkoxy, halo-substituted C1-C6 alkoxy, C1-C6 alkylamine, amido, cyano or halo,
W is N or C
X is CH or N
Z is C or NH
Y is N or $CR_9$, wherein $R_9$ is phenyl optionally substituted with amido, cyano or methyl amine; pyridine; oxazole; pyrazole; C(O)NR'R"; or NR'R";
wherein R' and R" are independently selected from H, C1-C6 alkyl, C3-C7 cycloalkyl, C3-C7 heterocycloalkyl wherein the heteroatom is N or O, or wherein R' and R" are joined to one another to form a C2-C7 heterocycloalkyl that includes the N to which they are attached, wherein the heterocycloalkyl is optionally hydroxyl-substituted, oxo-substituted, methyl-substituted, CH2OH-substituted or acetyl-substituted. In certain embodiments, Y is $CR_9$, wherein $R_9$ is C(O)NR'R" and wherein R' and R" are joined to one another to form an optionally substituted pyrrolidine, piperidine, piperazine or morpholine that includes the N to which they are attached, wherein the pyrrollidine, piperidine, piperazine or morpholine is optionally hydroxyl-substituted, oxo-substituted, methyl-substituted, CH2OH-substituted, or acetyl-substituted.

In certain embodiments, the compound of formula (I) is selected from:
(R)-5-Bromo-1-((4-hydroxy-1-(3-phenylbutanoyl)piperidin-4-yl)methyl)-4-phenylpyridin-2(1H)-one
6-(2-Fluorophenyl)-3-((4-hydroxy-1-(3-phenylpropanoyl)piperidin-4-yl)methyl)pyrimidin-4(3H)-one
3-((1-(3-Cyclobutylpropanoyl)-4-hydroxypiperidin-4-yl)methyl)-6-(2-fluorophenyl)pyrimidin-4(3H)-one
3-((1-(3-Cyclopentylpropanoyl)-4-hydroxypiperidin-4-yl)methyl)-6-(2-fluorophenyl)pyrimidin-4(3H)-one
(R,S)-6-(2-Fluorophenyl)-3-((4-hydroxy-1-(2-methyl-3-phenylpropanoyl)piperidin-4-yl)methyl)pyrimidin-4(3H)-one
(R)—N-(3-(1-((4-Hydroxy-1-(3-phenylbutanoyl)piperidin-4-yl)methyl)-6-oxo-4-phenyl-1,6-dihydropyridin-3-yl)phenyl)acetamide
(R)-3-(1-((4-Hydroxy-1-(3-phenylbutanoyl)piperidin-4-yl)methyl)6-oxo-4-phenyl-1,6-dihydropyridin-3-yl)benzamide
(R)-5-(Furan-2-yl)-1-((4-hydroxy-1-(3-phenylbutanoyl)piperidin-4-yl)methyl)-4-phenylpyridin-2(1H)-one
(R)-1-((4-Hydroxy-1-(3-phenylbutanoyl)piperidin-4-yl)methyl)-5-(1-methyl-1H-pyrazol-5-yl)-4-phenylpyridin-2(1H)-one
(R)-4-Chloro-1-((4-hydroxy-1 (3-phenylbutanoyl)piperidin-4-yl)methyl)-5-phenylpyridin-2(1H)-one
(R)-4-(Dimethylamino)-1-((4-hydroxy-1-(3-phenylbutanoyl)piperidin-4-yl)methyl)-5-phenylpyridin-2(1H)-one
(R)-1-((4-Hydroxy-1-(3-phenylbutanoyl)piperidin-4-yl)methyl)-5-phenyl-4-(prop-1-en-2-yl)pyridine-2(1H)-one
(R)-Ethyl 1-((4-hydroxy-1-(3-phenylbutanoyl)piperidin-4-yl)methyl)-6-oxo-4-phenyl-1,6-dihydropyridine-3-carboxylate
(R,S)-4-(2-Fluorophenyl)-1-((4-hydroxy-1-(2-methyl-1,2,3,4-tetrahydronaphthalene-2-carbonyl)piperidin-4-yl)methyl)-N-isopropyl-N-methyl-6-oxo-1,6-dihydropyridine-3-carboxamide
(R,S)-1-((1-(3-Cyclobutyl-2-methylpropanoyl)-4-hydroxypiperidin-4-yl)methyl)-4-phenyl-5-(piperidine-1-carbonyl)pyridin-2(1H)-one
(R)-3-((4-Hydroxy-1-(3-phenylbutanoyl)piperidin-4-yl)methyl)-6-(1-methyl-1H-indazol-7-yl)pyrimidin-4(3H)-one
(R)-3-((4-Hydroxy-1-(3-phenylbutanoyl)piperidin-4-yl)methyl)-6-(2-methoxyphenyl)pyrimidin-4(3H)-one
(R)-3-((4-Hydroxy-1-(3-phenylbutanoyl)piperidin-4-yl)methyl)-2-methyl-6-phenylpyrimidin-4(3H)-one
(R)-2-((4-Hydroxy-1-(3-phenylbutanoyl)piperidin-4-yl)methyl)-5,6-diphenylpyridazin-3(2H)-one
(R)-3-((4-Hydroxy-1-(3-phenylbutanoyl)piperidin-4-yl)methyl)-6-(naphthalen-1-yl)pyrimidin-4(3H)-one
(R)-6-(3-(1,3-Dioxolan-2-yl)phenyl)-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-(thiophen-3-yl)pyrimidin-4(3H)-one
4-(2-Fluorophenyl)-1-((4-hydroxy-1-(1-methylcyclopentane-1-carbonyl)piperidin-4-yl)methyl)-N-isopropyl-N-methyl-6-oxo-1,6-dihydropyridine-3-carboxamide
3-((1-(1-Ethylcyclohexane-1-carbonyl)-4-hydroxypiperidin-4-yl)methyl)-6-(2-fluorophenyl)pyrimidin-4(3H)-one
3-((1-(2-Cyclohexylmethyl)-3-methylbutanoyl)-4-hydroxy-3,3-dimethylpiperidin-4-yl)methyl)-6-(2-fluorophenyl)pyrimidin-4(3H)-one
(R)-6-(Furan-2-yl)-3-((4-hydroxy-1-(3-phenylbutanoyl)piperidin-4-yl)methyl)pyrimidin-4(3H)-one
(R)-1-((4-Hydroxy-1-(3-phenylbutanoyl)piperidin-4-yl)methyl)-4-phenylpyridin-2(1H)-one
(R)-6-(Cyclohex-1-en-1-yl)-3-((4-hydroxy-1-(3-phenylbutanoyl)piperidin-4-yl)methyl)pyrimidin-4(3H)-one
(R)-3-((4-Hydroxy-1-(3-phenylbutanoyl)piperidin-4-yl)methyl)-6-(prop-1-en-2-yl)pyrimidin-4(3H)-one
(R)-3-((4-Hydroxy-1-(3-phenylbutanoyl)piperidin-4-yl)methyl)-6-(2-(trifluoromethoxy)phenyl)pyrimidin-4(3H)-one
3-(((1R,5S)-3-((R)-3-Cyclohexyl-2-methylpropanoyl)-8-hydroxy-3-azabicyclo[3.2.1]octan-8-yl)methyl)-6-(2-fluorophenyl)pyrimidin-4(3H)-one
(R)-6-(2-Fluorophenyl)-3-((4-hydroxy-1-(3-phenylbutanoyl)piperidin-4-yl)methyl)pyrimidin-4(3H)-one
(R)-5-((4-Hydroxy-1-(3-phenylbutanoyl)piperidin-4-yl)methyl)-2-phenylpyrimidin-4(3H)-one
3-((4-Hydroxy-1-(3-phenylpropanoyl)piperidin-4-yl)methyl)-6-phenylpyrimidin-4(3H)-one
(R)-3-((4-Hydroxy-1-(3-phenylbutanoyl)piperidin-4-yl)methyl)-6-(isobutylamino)pyrimidin-4(3H)-one (R)-1-((1-(3-Cyclohexyl-2-methylpropanoyl)-4-hydroxypiperidin-4-yl)methyl)-4-phenyl-5-(piperidine-1-carbonyl)pyridin-2(1H)-one
(R)-2-((4-Hydroxy-1-(3-phenylbutanoyl)piperidin-4-yl)methyl)-5-phenylpyridazin-3(2H)-one
(R)-4-(2-Cyanophenyl)-1-((4-hydroxy-1-(3-phenylbutanoyl)piperidin-4-yl)methyl)-N-isopropyl-N-methyl-6-oxo-1,6-dihydropyridine-3-carboxamide
(R)-3-((1-(3-Cyclohexyl-2-methylpropanoyl)-4-hydroxypiperidin-4-yl)methyl)-6-(2-fluorophenyl)pyrimidin-4(3H)-one
3-((1-(2-(Cyclohexylmethyl)butanoyl)-4-hydroxypiperidin-4-yl)methyl)-6-(2-fluorophenyl)pyrimidin-4(3H)-one
rac-6-(2-Fluorophenyl)-3-((4-hydroxy-1-(cis-2-phenylcyclopropanecarbonyl)piperidin-4-yl)methyl)pyrimidin-4(3H)-one
6-(2-Fluorophenyl)-3-((4-hydroxy-1-(1-methylcyclohexanecarbonyl)piperidin-4-yl)methyl)pyrimidin-4(3H)-one
3-((S)-1-(1-((R)-3-Cyclohexyl-2-methylpropanoyl)-4-hydroxypiperidin-4-yl)propyl)-6-phenylpyrimidin-4(3H)-one
3-((R)-1-(1-((R)-3-cyclohexyl-2-methylpropanoyl)-4-hydroxypiperidin-4-yl)propyl)-6-phenylpyrimidin-4(3H)-one
(R,S)-3-((1-(3-Cyclohexyl-2-hydroxypropanoyl)-4-hydroxypiperidin-4-yl)methyl)-6-(2-fluorophenyl)pyrimidin-4(3H)-one
(R)-1-((4-Hydroxy-1-(3-phenylbutanoyl)piperidin-4-yl)methyl)-6-oxo-4-phenyl-1,6-dihydropyridine-3-carbaldehyde
(R)-5-((Dimethylamino)methyl)-1-((4-hydroxy-1-(3-phenylbutanoyl)piperidin-4-yl)methyl)-4-phenylpyridin-2(1H)-one
3-((R)-1-(4-Hydroxy-1-((R)-3-phenylbutanoyl)piperidin-4-yl)ethyl)-6-phenylpyrimidin-4(3H)-one
3-((S)-1-(4-Hydroxy-1-((R)-3-phenylbutanoyl)piperidin-4-yl)ethyl)-6-phenylpyrimidin-4(3H)-one
(R)-6-(2-Fluorophenyl)-3-((4-hydroxy-1-(4,4,4-trifluoro-3-phenylbutanoyl)piperidin-4-yl)methyl)pyrimidin-4(3H)-one
(R,S)-3-((1-(3-Cyclohexyl-2-fluoropropanoyl)-4-hydroxypiperidin-4-yl)methyl)-6-(2-fluorophenyl)pyrimidin-4(3H)-one
3-(((R)-1-((R)-3-Cyclohexyl-2-methylpropanoyl)-4-hydroxy-3,3-dimethylpiperidin-4-yl)methyl)-6-phenylpyrimidin-4(3H)-one
3-(((S)-1-((R)-3-Cyclohexyl-2-methylpropanoyl)-4-hydroxy-3,3-dimethylpiperidin-4-yl)methyl)-6-phenylpyrimidin-4(3H)-one
3-(((R)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one
3-(((S)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one
(R)-5-(3-(Aminomethyl)phenyl)-1-((1-(3-cyclohexyl-2-methylpropanoyl)-4-hydroxypiperidin-4-yl)methyl)-4-(2-fluorophenyl)pyridin-2(1H)-one
3-(((S)-4-Hydroxy-3,3-dimethyl-1-((R)-3-phenylbutanoyl)piperidin-4-yl)methyl)-6-phenylpyrimidin-4(3H)-one
3-(((R)-4-Hydroxy-3,3-dimethyl-1-((R)-3-phenylbutanoyl)piperidin-4-yl)methyl)-6-phenylpyrimidin-4(3H)-one
(R)-6-(4-Fluorophenoxy)-3-((4-hydroxy-1-(3-phenylbutanoyl)piperidin-4-yl)methyl)pyrimidin-4(3H)-one
(R)-1-((4-Hydroxy-1-(3-phenylbutanoyl)piperidin-4-yl)methyl)-5-(2-oxopyrrolidin-1-yl)-4-phenylpyridin-2(1H)-one
6-(2-Fluorophenyl)-3-((4-hydroxy-1-(1-methyl-4-methylenecyclohexanecarbonyl)piperidin-4-yl)methyl)pyrimidin-4(3H)-one
(R,S)-3-((1-(3-Cyclobutyl-2-methylpropanoyl)-4-hydroxypiperidin-4-yl)methyl)-6-(2-fluorophenyl)pyrimidin-4(3H)-one
(R,S)-3-((1-(3-Cycloheptyl-2-methylpropanoyl)-4-hydroxypiperidin-4-yl)methyl)-6-(2-fluorophenyl)pyrimidin-4(3H)-one
3-((1-(3-Cyclobutyl-2,2-dimethylpropanoyl)-4-hydroxypiperidin-4-yl)methyl)-6-(2-fluorophenyl)pyrimidin-4(3H)-one
6-(2-Fluorophenyl)-3-(((1R,5S)-8-hydroxy-3-((R)-3-phenylbutanoyl)-3-azabicyclo[3.2.1]octan-8-yl)methyl)pyrimidin-4(3H)-one
3-(((R)-4-Hydroxy-2,2-dimethyl-1-((R)-3-phenylbutanoyl)piperidin-4-yl)methyl)-6-phenylpyrimidin-4(3H)-one
3-(((S)-4-Hydroxy-2,2-dimethyl-1-((R)-3-phenylbutanoyl)piperidin-4-yl)methyl)-6-phenylpyrimidin-4(3H)-one
(R)-1-((4-Hydroxy-1-(3-phenylbutanoyl)piperidin-4-yl)methyl)-5-(4-hydroxypiperidine-1-carbonyl)-4-phenylpyridin-2(1H)-one
(R)-1-((4-Hydroxy-1-(3-phenylbutanoyl)piperidin-4-yl)methyl)-4-phenyl-5-(pyrrolidine-1-carbonyl)pyridin-2(1H)-one
(R)-1-((4-Hydroxy-1-(3-phenylbutanoyl)piperidin-4-yl)methyl)-4-phenyl-5-(1,4-dioxa-8-azaspiro[4.5]decane-8-carbonyl)pyridin-2(1H)-one
(R)—N-Cyclohexyl-1-((4-hydroxy-1-(3-phenylbutanoyl)piperidin-4-yl)methyl)-6-oxo-4-phenyl-1,6-dihydropyridine-3-carboxamide
6-(2-Fluorophenyl)-3-((4-hydroxy-3,3-dimethyl-1-(cis-2-phenylcyclopropane-1-carbonyl)piperidin-4-yl)methyl)pyrimidin-4(3H)-one
(R,S)-3-((1-(3-Cyclohexyl-1H-pyrazole-4-carbonyl)-4-hydroxy-3,3-dimethylpiperidin-4-yl)methyl)-6-(2-fluorophenyl)pyrimidin-4(3H)-one
(R,S)-6-(2-Fluorophenyl)-3-((4-hydroxy-3,3-dimethyl-1-(3-phenylpropanoyl)piperidin-4-yl)methyl)pyrimidin-4(3H)-one
(R,S)-6-(2-Fluorophenyl)-3-((4-hydroxy-1-(1-isobutylcyclopropane-1-carbonyl)-3,3-dimethylpiperidin-4-yl)methyl)pyrimidin-4(3H)-one
(R,S)-6-(2-Fluorophenyl)-3-((4-hydroxy-3,3-dimethyl-1-(3-methyl-3-phenylbutanoyl)piperidin-4-yl)methyl)pyrimidin-4(3H)-one
(S)-1-((1-(4,4-Difluoro-3-phenylbutanoyl)-4-hydroxypiperidin-4-yl)methyl)-N-isopropyl-N-methyl-6-oxo-4-phenyl-1,6-dihydropyridine-3-carboxamide
1-((4-Hydroxy-1-(1-(thiophen-2-yl)cyclopropane-1-carbonyl)piperidin-4-yl)methyl)-N-isopropyl-N-methyl-6-oxo-4-phenyl-1,6-dihydropyridine-3-carboxamide
1-(((R)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide
1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide
(R)-3-((4-Hydroxy-1-(3-phenylbutanoyl)piperidin-4-yl)methyl)-6-(2-(hydroxymethyl)phenyl)pyrimidin-4(3H)-one
(R)—N,N-Diethyl-1-((4-hydroxy-1-(3-phenylbutanoyl)piperidin-4-yl)methyl)-6-oxo-4-phenyl-1,6-dihydropyridine-3-carboxamide 3-((1-(3-Cyclohexylbutanoyl)-4-hydroxy-3,3-dimethylpiperidin-4-yl)methyl)-6-(2-fluorophenyl)pyrimidin-4(3H)-one
(R)-1-((4-Hydroxy-1-(3-phenylbutanoyl)piperidin-4-yl)methyl)-5-(morpholine-4-carbonyl)-4-phenylpyridin-2(1H)-one
(R,S)-3-((1-(3-Cyclohexylpropanoyl)-4-hydroxy-3,3-dimethylpiperidin-4-yl)methyl)-6-(2-fluorophenyl)pyrimidin-4(3H)-one
(R,S)-1-((1-(3-Cyclobutylpropanoyl)-4-hydroxy-3,3-dimethylpiperidin-4-yl)methyl)-N-isopropyl-N-methyl-6-oxo-4-phenyl-1,6-dihydropyridine-3-carboxamide
(R,S)-1-((1-(2-Ethyl hexanoyl)-4-hydroxypiperidin-4-yl)methyl)-N-isopropyl-N-methyl-6-oxo-4-phenyl-1,6-dihydropyridine-3-carboxamide
(R,S)-6-(2-Fluorophenyl)-3-((4-hydroxy-3,3-dimethyl-1-(1-methylcyclohexane-1-carbonyl)piperidin-4-yl)methyl)pyrimidin-4(3H)-one
6-(2-Fluorophenyl)-3-((1-(3-(4-fluorophenyl)propanoyl)-4-hydroxypiperidin-4-yl)methyl)pyrimidin-4(3H)-one
(R,S)-3-((1-(3-Cyclopropylpropanoyl)-4-hydroxy-3,3-dimethylpiperidin-4-yl)methyl)-6-(2-fluorophenyl)pyrimidin-4(3H)-one
1-((1-(2,2-Dimethylbutanoyl)-4-hydroxypiperidin-4-yl)methyl)-N-isopropyl-N-methyl-6-oxo-4-phenyl-1,6-dihydropyridine-3-carboxamide
(R)—N-(2-(1-((4-Hydroxy-1-(3-phenylbutanoyl)piperidin-4-yl)methyl)-6-oxo-1,6-dihydropyrimidin-4-yl)phenyl)acetamide
(R)-5-(4-(Aminomethyl)phenyl)-1-((4-hydroxy-1-(3-phenylbutanoyl)piperidin-4-yl)methyl)-4-phenylpyridin-2(1H)-one
(R)-1-((1-(3-Cyclohexyl-2-methylpropanoyl)-4-hydroxypiperidin-4-yl)methyl)-N-isopropyl-N-methyl-6-oxo-4-phenyl-1,6-dihydropyridine-3-carboxamide
(R)-1-((4-Hydroxy-1-(3-phenylbutanoyl)piperidin-4-yl)methyl)-4-phenyl-5-(piperidine-1-carbonyl)pyridin-2(1H)-one
(R)-1-((4-Hydroxy-1-(3-phenylbutanoyl)piperidin-4-yl)methyl)-N-isopropyl-4-(2-methoxyphenyl)-N-methyl-6-oxo-1,6-dihydropyridine-3-carboxamide
(R)-4-(2-Fluorophenyl)-1-((4-hydroxy-1-(3-phenylbutanoyl)piperidin-4-yl)methyl)-N-isopropyl-N-methyl-6-oxo-1,6-dihydropyridine-3-carboxamide
(R)-1'-((4-Hydroxy-1-(3-phenylbutanoyl)piperidin-4-yl)methyl)-4'-phenyl-[2,3'-bipyridin]-6'(1'H)-one
1-((1-(3-Cyclohexylpropanoyl)-4-hydroxypiperidin-4-yl)methyl)-N-isopropyl-N-methyl-6-oxo-4-phenyl-1,6-dihydropyridine-3-carboxamide
(R)-tert-Butyl 4-(1-((4-hydroxy-1-(3-phenylbutanoyl)piperidin-4-yl)methyl)-6-oxo-4-phenyl-1,6-dihydropyridine-3-carbonyl)piperazine-1-carboxylate
(R)-1-((4-Hydroxy-1-(3-phenylbutanoyl)piperidin-4-yl)methyl)-4-phenyl-5-(piperazine-1-carbonyl)pyridin-2(1H)-one
(R)-1-((4-Hydroxy-1-(3-phenylbutanoyl)piperidin-4-yl)methyl)-N,N-dimethyl-6-oxo-4-phenyl-1,6-dihydropyridine-3-carboxamide
(R)-1-((4-Hydroxy-1-(3-phenylbutanoyl)piperidin-4-yl)methyl)-N-isopropyl-N-methyl-6-oxo-4-(p-tolyl)-1,6-dihydropyridine-3-carboxamide
(R)-1-((4-Hydroxy-1-(3-phenylbutanoyl)piperidin-4-yl)methyl)-N-methoxy-N-methyl-6-oxo-4-phenyl-1,6-dihydropyridine-3-carboxamide
(R)-1-((4-Hydroxy-1-(3-phenylbutanoyl)piperidin-4-yl)methyl)-4,5-diphenylpyridin-2(1H)-one
(R)-1-((4-Hydroxy-1-(3-phenylbutanoyl)piperidin-4-yl)methyl)-4-phenyl-[3,3'-bipyridin]-6(1H)-one
(R)-5-(3-(Aminomethyl)phenyl)-1-((4-hydroxy-1-(3-phenylbutanoyl)piperidin-4-yl)methyl)-4-phenylpyridin-2(1H)-one
(R)-1-((4-Hydroxy-1-(3-phenylbutanoyl)piperidin-4-yl)methyl)-N-isopropyl-N-methyl-6-oxo-4-phenyl-1,6-dihydropyridine-3-carboxamide
(R)-1-((4-Hydroxy-1-(3-phenylbutanoyl)piperidin-4-yl)methyl)-N-isopropyl-N-methyl-6-oxo-4-(m-tolyl)-1,6-dihydropyridine-3-carboxamide
(R)-1-((4-Hydroxy-1-(3-phenylbutanoyl)piperidin-4-yl)methyl)-4-phenyl-5-(pyrimidin-5-yl)pyridin-2(1H)-one
(R)—N-(Cyclopropylmethyl)-1-((4-hydroxy-1-(3-phenylbutanoyl)piperidin-4-yl)methyl)-6-oxo-4-phenyl-1,6-dihydropyridine-3-carboxamide
(R)—N-Benzyl-1-((4-hydroxy-1-(3-phenylbutanoyl)piperidin-4-yl)methyl)-N-methyl-6-oxo-4-phenyl-1,6-dihydropyridine-3-carboxamide
(R)-2-(1-((4-Hydroxy-1-(3-phenylbutanoyl)piperidin-4-yl)methyl)-6-oxo-4-phenyl-1,6-dihydropyridin-3-yl)benzonitrile
(R)-1-((4-Hydroxy-1-(3-phenylbutanoyl)piperidin-4-yl)methyl)-N-methyl-6-oxo-N,4-diphenyl-1,6-dihydropyridine-3-carboxamide
3-(1-(1-((R)-3-Cyclohexyl-2-methylpropanoyl)-4-hydroxypiperidin-4-yl)ethyl)-6-phenylpyrimidin-4(3H)-one
(R)-1-((4-Hydroxy-1-(3-phenylbutanoyl)piperidin-4-yl)methyl)-5-(1-methyl-1H-pyrazol-4-yl)-4-phenylpyridin-2(1H)-one
(R)-3-((1-(2-(Cyclohexylmethyl)pent-4-enoyl)-4-hydroxypiperidin-4-yl)methyl)-6-(2-fluorophenyl)pyrimidin-4(3H)-one
(R)-1-((4-Hydroxy-1-(3-phenylbutanoyl)piperidin-4-yl)methyl)-5-methyl-4-phenylpyridin-2(1H)-one
(R)-6-(1,5-Dimethyl-1H-pyrazol-4-yl)-3-((4-hydroxy-1-(3-phenylbutanoyl)piperidin-4-yl)methyl)pyrimidin-4(3H)-one
3-(((1R,5S)-3-(3-Cyclohexylpropanoyl)-8-hydroxy-3-azabicyclo[3.2.1]octan-8-yl)methyl)-6-(2-fluorophenyl)pyrimidin-4(3-)-one
(R)-1-((4-Hydroxy-1-(3-phenylbutanoyl)piperidin-4-yl)methyl)-6-oxo-4-phenyl-1,6-dihydropyridine-3-carbonitrile
(R)-1-((4-Hydroxy-1-(3-phenylbutanoyl)piperidin-4-yl)methyl)-N-(2-hydroxyethyl)-6-oxo-4-phenyl-1,6-dihydropyridine-3-carboxamide
1-((4-Hydroxy-1-((R)-3-phenylbutanoyl)piperidin-4-yl)methyl)-5-((S)-2-methylpyrrolidine-1-carbonyl)-4-phenylpyridin-2(1H)-one
(R)-1-((4-Hydroxy-1-(3-phenylbutanoyl)piperidin-4-yl)methyl)-5-(4-(hydroxymethyl)piperidine-1-carbonyl)-4-phenylpyridin-2(1H)-one
3-((1-(2-(Cyclohexylmethyl)butanoyl)-4-hydroxy-3,3-dimethylpiperidin-4-yl)methyl)-6-(2-fluorophenyl)pyrimidin-4(3H)-one
3-((7-((R)-3-Cyclohexyl-2-methylpropanoyl)-1-hydroxy-7-azaspiro[4.5]decan-1-yl)methyl)-6-(2-fluorophenyl)pyrimidin-4(3H)-one
1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide
1-(((S)-1-((R)-3-Cyclohexyl-2-methylpropanoyl)-4-hydroxy-3,3-dimethylpiperidin-4-yl)methyl)-N,N-dimethyl-6-oxo-4-phenyl-1,6-dihydropyridine-3-carboxamide 1-(((R)-1-((R)-3-Cyclohexyl-2-methylpropanoyl)-4-hydroxy-3,3-dimethylpiperidin-4-yl)methyl)-N,N-dimethyl-6-oxo-4-phenyl-1,6-dihydropyridine-3-carboxamide 1-(((S)-1-((R)-3-Cyclohexyl-2-methylpropanoyl)-4-hydroxy-3,3-dimethylpiperidin-4-yl)methyl)-4-phenyl-5-(pyrrolidine-1-carbonyl)pyridin-2(1H)-one 1-(((S)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one 1-(((R)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one 3-((1-(2-(Cyclohexyloxy)propanoyl)-4-hydroxy-3,3-dimethylpiperidin-4-yl)methyl)-6-(2-fluorophenyl)pyrimidin-4(3H)-one 1-((7-((R)-3-Cyclohexyl-2-methylpropanoyl)-10-hydroxy-7-azaspiro[4.5]decan-10-yl)methyl)-N,N-dimethyl-6-oxo-1,6-dihydropyridine-3-carboxamide 1-((1-((R)-3-Cyclobutyl-2-methylpropanoyl)-4-hydroxy-3,3-dimethylpiperidin-4-yl)methyl)-N,N-dimethyl-6-oxo-4-phenyl-1,6-dihydropyridine-3-carboxamide 1-((1-((R)-3-Cyclopropyl-2-methylpropanoyl)-4-hydroxy-3,3-dimethylpiperidin-4-yl)methyl)-N,N-dimethyl-6-oxo-4-phenyl-1,6-dihydropyridine-3-carboxamide 1-((1-((R)-3-Cyclohexyl-2-methylpropanoyl)-4-hydroxy-3,3-dimethylpiperidin-4-yl)methyl)-[4,5'-bipyrimidin]-6(1H)-one 3-((1-((R)-3-Cyclohexyl-2-methylpropanoyl)-4-hydroxy-3,3-dimethylpiperidin-4-yl)methyl)-6-(1-methyl-1H-pyrazol-5-yl)pyrimidin-4(3H)-one 3-((1-((R)-3-Cyclohexyl-2-methylpropanoyl)-4-hydroxy-3,3-dimethylpiperidin-4-yl)methyl)-6-(1H-pyrazol-4-yl)pyrimidin-4(3H)-one 3-((1-((R)-3-Cyclohexyl-2-methylpropanoyl)-4-hydroxy-3,3-dimethylpiperidin-4-yl)methyl)-6-(1H-pyrazol-5-yl)pyrimidin-4(3H)-one 3-((7-((R)-3-Cyclohexyl-2-methylpropanoyl)-1-hydroxy-7-azaspiro[4.5]decan-10-yl)methyl)pyrimidin-4(3H)-one 3-((1-((R)-3-Cyclohexyl-2-methylpropanoyl)-4-hydroxy-3,3-dimethylpiperidin-4-yl)methyl)-6-(thiophen-3-yl)pyrimidin-4(3H)-one 1-((1-((R)-3-Cyclohexyl-2-methylpropanoyl)-4-hydroxy-3,3-dimethylpiperidin-4-yl)methyl)-5-(oxazol-2-yl)-4-phenylpyridin-2(1H)-one 3-((1-((R)-3-Cyclohexyl-2-methylpropanoyl)-4-hydroxy-3,3-dimethylpiperidin-4-yl)methyl)-6-(2-(hydroxymethyl)phenyl)pyrimidin-4(3H)-one 3-((1-((R)-3-Cyclohexyl-2-methylpropanoyl)-4-hydroxy-3,3-dimethylpiperidin-4-yl)methyl)-6-(3-(hydroxymethyl)phenyl)pyrimidin-4(3H)-one 3-((1-((R)-3-Cyclohexyl-2-methylpropanoyl)-4-hydroxy-3,3-dimethylpiperidin-4-yl)methyl)-6-(4-(hydroxymethyl)phenyl)pyrimidin-4(3H)-one 6-(4-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one 6-(2-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one 6-(2-Fluorophenyl)-3-((4-hydroxy-3,3-dimethyl-1-(2,4,4-trimethylpentanoyl)piperidin-4-yl)methyl)pyrimidin-4(3H)-one 6-(2-Fluorophenyl)-3-((4-hydroxy-3,3-dimethyl-1-(4,4,4-trifluoro-2-methylbutanoyl)piperidin-4-yl)methyl)pyrimidin-4(3H)-one 4-Chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide 1-((7-((R)-3-Cyclohexyl-2-methylpropanoyl)-10-hydroxy-7-azaspiro[4.5]decan-10-yl)methyl)-4-(dimethylamino)-N,N-dimethyl-6-oxo-1,6-dihydropyridine-3-carboxamide 1-((1-((S)-3-(Benzyloxy)-2-(cyclohexylmethyl) propanoyl)-4-hydroxy-3,3-dimethylpiperidin-4-yl)methyl)-N,N-dimethyl-6-oxo-4-phenyl-1,6-dihydropyridine-3-carboxamide 1-((10-Hydroxy-7-iso butyryl-7-azaspiro[4.5]decan-10-yl)methyl)-N,N-dimethyl-6-oxo-4-phenyl-1,6-dihydropyridine-3-carboxamide 1-((10-Hydroxy-7-((R)-2-methylbutanoyl)-7-azaspiro[4.5]decan-10-yl)methyl)-N,N-dimethyl-6-oxo-4-phenyl-1,6-dihydropyridine-3-carboxamide 1-((7-((R)-3-Cyclopropyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide 6-(2-Fluorophenyl)-3-((4-hydroxy-3,3-dimethyl-1-(2-methyl-3-(1H-pyrazol-1-yl)propanoyl)piperidin-4-yl)methyl)pyrimidin-4(3H)-one 1-((7-((R)-3-Cyclohexyl-2-methylpropanoyl)-10-hydroxy-7-azaspiro[4.5]decan-10-yl)methyl)-4-(2-(hydroxymethyl)phenyl)-N,N-dimethyl-6-oxo-1,6-dihydropyridine-3-carboxamide 1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide 1'-((1-((R)-3-Cyclohexyl-2-methylpropanoyl)-4-hydroxy-3,3-dimethylpiperidin-4-yl)methyl)-4'-(2-fluorophenyl)-[2,3'-bipyridin]-6'(1'H)-one 1-((7-((R)-3-Cyclohexyl-2-methylpropanoyl)-10-hydroxy-7-azaspiro[4.5]decan-10-yl)methyl)-N,N-dimethyl-6-oxo-4-(thiophen-3-yl)-1,6-dihydropyridine-3-carboxamide 1-((7-((R)-3-Cyclohexyl-2-methylpropanoyl)-10-hydroxy-7-azaspiro[4.5]decan-10-yl)methyl)-4-(3-(hydroxymethyl)phenyl)-N,N-dimethyl-6-oxo-1,6-dihydropyridine-3-carboxamide 1-((7-(3-Cyclohexyl-2-hydroxypropanoyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(2-methyl-3-(piperidin-1-yl)propanoyl)-7-azaspiro[4.5]decan-10-yl)methyl)-N,N-dimethyl-6-oxo-4-phenyl-1,6-dihydropyridine-3-carboxamide 6-(3-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one 1-(((S)-1-((S)-3-Cyclohexyl-2-(methoxymethyl)propanoyl)-4-hydroxy-3,3-dimethylpiperidin-4-yl)methyl)-N,N-dimethyl-6-oxo-4-phenyl-1,6-dihydropyridine-3-carboxamide 4-(2-(Aminomethyl)phenyl)-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide 1-((7-((R)-3-Cyclohexyl-2-methylpropanoyl)-10-hydroxy-7-azaspiro[4.5]decan-10-yl)methyl)-4-(4-(hydroxymethyl)phenyl)-N,N-dimethyl-6-oxo-1,6-dihydropyridine-3-carboxamide 1-((10-Hydroxy-7-(2-methyl-3-morpholinopropanoyl)-7-azaspiro[4.5]decan-10-yl)methyl)-N,N-dimethyl-6-oxo-4-phenyl-1,6-dihydropyridine-3-carboxamide 1-(((S)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide 1-(((R)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide 1-(((S)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide 1-(((R)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide 1-((1-((R)-3-Cyclohexyl-2-methylpropanoyl)-4-hydroxy-3,3-dimethylpiperidin-4-yl)methyl)-5-(morpholine-4-carbonyl)-4-phenylpyridin-2(1H)-one 5-(4-Acetylpiperazine-1-carbonyl)-1-((1-((R)-3-cyclohexyl-2-methylpropanoyl)-4-hydroxy-3,3-dimethylpiperidin-4-yl)methyl)-4-phenylpyridin-2(1H)-one 1-((1-((R)-3-Cyclohexyl-2-methylpropanoyl)-4-hydroxy-3,3-dimethylpiperidin-4-yl)methyl)-5-(4-methylpiperazine-1-carbonyl)-4-phenylpyridin-2(1H)-one 1-((10-Hydroxy-7-(4,4,4-trifluoro-3-methylbutanoyl)-7-azaspiro[4.5]decan-10-yl)methyl)-N,N-dimethyl-6-oxo-4-phenyl-1,6-dihydropyridine-3-carboxamide 1-((10-Hydroxy-7-(4,4,4-trifluorobutanoyl)-7-azaspiro[4.5]decan-10-yl)methyl)-N,N-dimethyl-6-oxo-4-phenyl-1,6-dihydropyridine-3-carboxamide 1-((10-Hydroxy-7-(3-(tetrahydrofuran-3-yl)propanoyl)-7-azaspiro[4.5]decan-10-yl)methyl)-N,N-dimethyl-6-oxo-4-phenyl-1,6-dihydropyridine-3-carboxamide 1-((10-Hydroxy-7-((1R,2S)-2-phenylcyclopropane-1-carbonyl)-7-azaspiro[4.5]decan-10-yl)methyl)-N,N-dimethyl-6-oxo-4-phenyl-1,6-dihydropyridine-3-carboxamide 1-((7-(Cyclopropanecarbonyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(1-methylcyclohexane-1-carbonyl)-7-azaspiro[4.5]decan-10-yl)methyl)-N,N-dimethyl-6-oxo-4-phenyl-1,6-dihydropyridine-3-carboxamide 1-((7-(3-Fluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide 1-((7-(1-(2,2-Difluoroethyl)cyclopropane-1-carbonyl)-10-hydroxy-7-azaspiro[4.5]decan-10-yl)methyl)-N,N-dimethyl-6-oxo-4-phenyl-1,6-dihydropyridine-3-carboxamide 1-((7-(Bicyclo[2.2.1]heptane-1-carbonyl)-10-hydroxy-7-azaspiro[4.5]decan-10-yl)methyl)-N,N-dimethyl-6-oxo-4-phenyl-1,6-dihydropyridine-3-carboxamide 1-((7-((S)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide 1-((7-((R)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide 1-((7-(3-Ethoxypropanoyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-((S)-3-phenylbutanoyl)-7-azaspiro[4.5]decan-10-yl)methyl)-N,N-dimethyl-6-oxo-4-phenyl-1,6-dihydropyridine-3-carboxamide 1-((7-(3-(4-Fluorophenyl)propanoyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-((R)-3-phenylbutanoyl)-7-azaspiro[4.5]decan-10-yl)methyl)-N,N-dimethyl-6-oxo-4-phenyl-1,6-dihydropyridine-3-carboxamide 1-((10-Hydroxy-7-(1-methylcyclopentane-1-carbonyl)-7-azaspiro[4.5]decan-10-yl)methyl)-N,N-dimethyl-6-oxo-4-phenyl-1,6-dihydropyridine-3-carboxamide 1-((10-Hydroxy-7-(1H-pyrazole-3-carbonyl)-7-azaspiro[4.5]decan-10-yl)methyl)-N,N-dimethyl-6-oxo-4-phenyl-1,6-dihydropyridine-3-carboxamide 1-((10-Hydroxy-7-(1H-indazole-3-carbonyl)-7-azaspiro[4.5]decan-10-yl)methyl)-N,N-dimethyl-6-oxo-4-phenyl-1,6-dihydropyridine-3-carboxamide 1-((7-(3-Cyclohexyl-1H-pyrazole-4-carbonyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(1H-indole-3-carbonyl)-7-azaspiro[4.5]decan-10-yl)methyl)-N,N-dimethyl-6-oxo-4-phenyl-1,6-dihydropyridine-3-carboxamide 1-((7-(Bicyclo[1.1.1]pentane-1-carbonyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(5-phenyloxazole-4-carbonyl)-7-azaspiro[4.5]decan-10-yl)methyl)-N,N-dimethyl-6-oxo-4-phenyl-1,6-dihydropyridine-3-carboxamide 1-((7-(5-Cyclopropyloxazole-4-carbonyl)-10-hydroxy-7-azaspiro[4.5]decan-10-yl)methyl)-N,N-dimethyl-6-oxo-4-phenyl-1,6-dihydropyridine-3-carboxamide 1-((7-(2-(Cyclohexyloxy)acetyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(spiro[2.2]pentane-1-carbonyl)-7-azaspiro[4.5]decan-10-yl)methyl)-N,N-dimethyl-6-oxo-4-phenyl-1,6-dihydropyridine-3-carboxamide 1-((10-Hydroxy-7-(3-(trifluoromethyl)cyclopentane-1-carbonyl)-7-azaspiro[4.5]decan-10-yl)methyl)-N,N-dimethyl-6-oxo-4-phenyl-1,6-dihydropyridine-3-carboxamide 1-((7-(2,4-Dimethylpentanoyl)-10-hydroxy-7-azaspiro[4.5]decan-10-yl)methyl)-N,N-dimethyl-6-oxo-4-phenyl-1,6-dihydropyridine-3-carboxamide 1-((7-(1-Benzyl-1H-pyrrole-2-carbonyl)-10-hydroxy-7-azaspiro[4.5]decan-10-yl)methyl)-N,N-dimethyl-6-oxo-4-phenyl-1,6-dihydropyridine-3-carboxamide 1-((7-(2-(Cyclohexyloxy)propanoyl)-10-hydroxy-7-azaspiro[4.5]decan-10-yl)methyl)-N,N-dimethyl-6-oxo-4-phenyl-1,6-dihydropyridine-3-carboxamide 3-((1-((S)-3-Cyclobutyl-2-(hydroxymethyl)propanoyl)-4-hydroxy-3,3-dimethylpiperidin-4-yl)methyl)-6-(2-fluorophenyl)pyrimidin-4(3H)-one 1-((7-(2-Cyclobutoxyacetyl)-10-hydroxy-7-azaspiro[4.5]decan-10-yl)methyl)-N,N-dimethyl-6-oxo-4-phenyl-1,6-dihydropyridine-3-carboxamide 1-((7-(3,3-Difluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(2-hydroxy-3-phenylpropanoyl)-7-azaspiro[4.5]decan-10-yl)methyl)-N,N-dimethyl-6-oxo-4-phenyl-1,6-dihydropyridine-3-carboxamide 1-(((S)-4-Hydroxy-3,3-dimethyl-1-((R)-4,4,4-trifluoro-2-methylbutanoyl)piperidin-4-yl)methyl)-N,N-dimethyl-6-oxo-4-phenyl-1,6-dihydropyridine-3-carboxamide 1-(((S)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide 1-(((S)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one (S)-1-((4-Hydroxy-3,3-dimethyl-1-(4,4,4-trifluoro-2-(2,2,2-trifluoroethyl)butanoyl)piperidin-4-yl)methyl)-N,N-dimethyl-6-oxo-4-phenyl-1,6-dihydropyridine-3-carboxamide 1-(((S)-1-((R)-3-Cyclohexyl-2-methylpropanoyl)-4-hydroxy-3,3-dimethylpiperidin-4-yl)methyl)-5-((S)-2-(hydroxymethyl)piperazine-1-carbonyl)-4-phenylpyridin-2(1H)-one 1-(((R)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide 1-(((R)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one 1-(((S)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide 1-(((S)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one 1-(((S)-1-((R)-3-Cyclohexyl-2-methylpropanoyl)-4-hydroxy-3,3-dimethylpiperidin-4-yl)methyl)-5-((R)-3-methylpiperazine-1-carbonyl)-4-phenylpyridin-2(1H)-one 1-(((S)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide 1-(((S)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one 1-(((S)-10-Hydroxy-7-((R)-4,4,4-trifluoro-2-methylbutanoyl)-7-azaspiro[4.5]decan-10-yl)methyl)-N,N-dimethyl-6-oxo-4-phenyl-1,6-dihydropyridine-3-carboxamide 1-(((S)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one (S)-1-((10-Hydroxy-7-(4,4,4-trifluoro-2-(2,2,2-trifluoroethyl)butanoyl)-7-azaspiro[4.5]decan-10- yl)methyl)-N,N-dimethyl-6-oxo-4-phenyl-1,6-dihydropyridine-3-carboxamide (S)-1-((10-Hydroxy-7-(4,4,4-trifluoro-2-(2,2,2-trifluoroethyl)butanoyl)-7-azaspiro[4.5]decan-10-yl)methyl)-4-phenyl-5-(piperazine-1-carbonyl)pyridin-2(1H)-one 1-(((S)-1-((R)-3-Cyclohexyl-2-methylpropanoyl)-4-hydroxy-3,3-dimethylpiperidin-4-yl)methyl)-4-cyclopropyl-N,N-dimethyl-6-oxo-1,6-dihydropyridine-3-carboxamide 1-(((S)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one 1-(((S)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide 4-(2-Fluorophenyl)-1-(((S)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide 1-(((S)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one 4-(2-Fluorophenyl)-1-(((S)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one 1-(((S)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide 1-(((S)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one 1-(((S)-1-((R)-3-Cyclohexyl-2-methylpropanoyl)-4-hydroxy-3,3-dimethylpiperidin-4-yl)methyl)-5-(4-hydroxypiperidine-1-carbonyl)-4-phenylpyridin-2(1H)-one 1-((10-Hydroxy-7-(3-(trifluoromethyl)cyclobutane-1-carbonyl)-7-azaspiro[4.5]decan-10-yl)methyl)-N,N-dimethyl-6-oxo-4-phenyl-1,6-dihydropyridine-3-carboxamide 1-(((S)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide 1-(((S)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one 1-(((S)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide 1-(((S)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one 1-((2-((R)-3-Cyclohexyl-2-methylpropanoyl)-5-hydroxy-9-oxa-2-azaspiro[5.5]undecan-5-yl)methyl)-N,N-dimethyl-6-oxo-4-phenyl-1,6-dihydropyridine-3-carboxamide 1-(((S)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide 1-(((S)-1-((R)-3-Cyclobutyl-2-methylpropanoyl)-4-hydroxy-3,3-dimethylpiperidin-4-yl)methyl)-4-(2-fluorophenyl)-5-(piperazine-1-carbonyl)pyridin-2(1H)-one 1-((2-((R)-3-Cyclohexyl-2-methylpropanoyl)-5-hydroxy-2-azaspiro[5.5]undecan-5-yl)methyl)-N,N-dimethyl-6-oxo-4-phenyl-1,6-dihydropyridine-3-carboxamide 1-((2-((R)-3-Cyclohexyl-2-methylpropanoyl)-5-hydroxy-2-azaspiro[5.5]undecan-5-yl)methyl)-4-phenyl-5-(piperazine-1-carbonyl)pyridin-2(1H)-one 1-(((S)-7-((R)-3-Cyclohexyl-2-methylpropanoyl)-10-hydroxy-7-azaspiro[4.5]decan-10-yl)methyl)-5-(morpholine-4-carbonyl)-4-phenylpyridin-2(1H)-one 1-(((S)-7-((R)-3-Cyclohexyl-2-methylpropanoyl)-10-hydroxy-7-azaspiro[4.5]decan-10-yl)methyl)-5-(4-methylpiperazine-1-carbonyl)-4-phenylpyridin-2(1H)-one 1-((1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid 1-((7-((R)-3-Cyclohexyl-2-methylpropanoyl)-10-hydroxy-7-azaspiro[4.5]decan-10-yl)methyl)-4-methoxy-N,N-dimethyl-6-oxo-1,6-dihydropyridine-3-carboxamide 1-((7-(4,4-Difluoro-2-methylbutanoyl)-10-hydroxy-7-azaspiro[4.5]decan-10-yl)methyl)-N,N-dimethyl-6-oxo-4-phenyl-1,6-dihydropyridine-3-carboxamide 1-((7-(4,4-Difluoro-2,2-dimethylbutanoyl)-10-hydroxy-7-azaspiro[4.5]decan-10-yl)methyl)-N,N-dimethyl-6-oxo-4-phenyl-1,6-dihydropyridine-3-carboxamide 1-((10-Hydroxy-7-(4-(trifluoromethyl)thiazole-2-carbonyl)-7-azaspiro[4.5]decan-10-yl)methyl)-N,N-dimethyl-6-oxo-4-phenyl-1,6-dihydropyridine-3-carboxamide 1-((10-Hydroxy-7-(2-(trifluoromethyl)thiazole-4-carbonyl)-7-azaspiro[4.5]decan-10-yl)methyl)-N,N-dimethyl-6-oxo-4-phenyl-1,6-dihydropyridine-3-carboxamide 1-(((S)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide 1-(((S)-10-Hydroxy-7-((S)-4,4,4-trifluoro-2-(hydroxymethyl)butanoyl)-7-azaspiro[4.5]decan-10-yl)methyl)-5-(morpholine-4-carbonyl)-4-phenylpyridin-2(1H)-one 1-(((S)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one 1-(((S)-10-Hydroxy-7-((R)-4,4,4-trifluoro-2-methylbutanoyl)-7-azaspiro[4.5]decan-10-yl)methyl)-5-(morpholine-4-carbonyl)-4-phenylpyridin-2(1H)-one 1-(((S)-10-Hydroxy-7-((R)-4,4,4-trifluoro-2-methylbutanoyl)-7-azaspiro[4.5]decan-10-yl)methyl)-5-(4-methylpiperazine-1-carbonyl)-4-phenylpyridin-2(1H)-one Ethyl 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate 1-(((S)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid 1-(((R)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide 1-(((R)-1-((R)-3-Cyclohexyl-2-methylpropanoyl)-4-hydroxy-3,3-dimethylpiperidin-4-yl)methyl)-4-phenyl-5-(pyrrolidine-1-carbonyl)pyridin-2(1H)-one 1-(((R)-1-((S)-3-Cyclohexyl-2-(methoxymethyl)propanoyl)-4-hydroxy-3,3-dimethylpiperidin-4-yl)methyl)-N,N-dimethyl-6-oxo-4-phenyl-1,6-dihydropyridine-3-carboxamide 1-(((R)-4-Hydroxy-3,3-dimethyl-1-((R)-4,4,4-trifluoro-2-methylbutanoyl)piperidin-4-yl)methyl)-N,N-dimethyl-6-oxo-4-phenyl-1,6-dihydropyridine-3-carboxamide 1-(((R)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide 1-(((R)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one (R)-1-((4-Hydroxy-3,3-dimethyl-1-(4,4,4-trifluoro-2-(2,2,2-trifluoroethyl)butanoyl)piperidin-4-yl)methyl)-N,N-dimethyl-6-oxo-4-phenyl-1,6-dihydropyridine-3-carboxamide 1-(((R)-1-((R)-3-Cyclohexyl-2-methylpropanoyl)-4-hydroxy-3,3-dimethylpiperidin-4-yl)methyl)-5-((S)-2-(hydroxymethyl)piperazine-1-carbonyl)-4-phenylpyridin-2(1H)-one 1-(((R)-1-((R)-3-Cyclohexyl-2-methylpropanoyl)-4-hydroxy-3,3-dimethylpiperidin-4-yl)methyl)-5-((R)-3-methylpiperazine-1-carbonyl)-4-phenylpyridin-2(1H)-one 1-(((R)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide 1-(((R)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one 1-(((R)-10-Hydroxy-7-((R)-4,4,4-trifluoro-2-methylbutanoyl)-7-azaspiro[4.5]decan-10-yl)methyl)-N,N-dimethyl-6-oxo-4-phenyl-1,6-dihydropyridine-3-carboxamide 1-(((R)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one (R)-1-((10-Hydroxy-7-(4,4,4-trifluoro-2-(2,2,2-trifluoroethyl)butanoyl)-7-azaspiro[4.5]decan-10-yl)methyl)-N,N-dimethyl-6-oxo-4-phenyl-1,6-dihydropyridine-3-carboxamide (R)-1-((10-Hydroxy-7-(4,4,4-trifluoro-2-(2,2,2-trifluoroethyl)butanoyl)-7-azaspiro[4.5]decan-10-yl)methyl)-4-phenyl-5-(piperazine-1-carbonyl)pyridin-2(1H)-one 1-(((R)-1-((R)-3-Cyclohexyl-2-methylpropanoyl)-4-hydroxy-3,3-dimethylpiperidin-4-yl)methyl)-4-cyclopropyl-N,N-dimethyl-6-oxo-1,6-dihydropyridine-3-carboxamide 1-(((R)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one 1-(((R)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide 4-(2-Fluorophenyl)-1-(((R)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide 1-(((R)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one 4-(2-Fluorophenyl)-1-(((R)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one 1-(((R)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide 1-(((R)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one 1-(((R)-1-((R)-3-Cyclohexyl-2-methylpropanoyl)-4-hydroxy-3,3-dimethylpiperidin-4-yl)methyl)-5-(4-hydroxypiperidine-1-carbonyl)-4-phenylpyridin-2(1H)-one 1-(((R)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide 1-(((R)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one 1-(((R)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide 1-(((R)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one 1-(((R)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide 1-(((R)-1-((R)-3-Cyclobutyl-2-methylpropanoyl)-4-hydroxy-3,3-dimethylpiperidin-4-yl)methyl)-4-(2-fluorophenyl)-5-(piperazine-1-carbonyl)pyridin-2(1H)-one 1-(((R)-7-((R)-3-Cyclohexyl-2-methylpropanoyl)-10-hydroxy-7-azaspiro[4.5]decan-10-yl)methyl)-5-(morpholine-4-carbonyl)-4-phenylpyridin-2(1H)-one 1-(((R)-7-((R)-3-Cyclohexyl-2-methylpropanoyl)-10-hydroxy-7-azaspiro[4.5]decan-10-yl)methyl)-5-(4-methylpiperazine-1-carbonyl)-4-phenylpyridin-2(1H)-one 1-(((R)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide 1-(((R)-10-Hydroxy-7-((S)-4,4,4-trifluoro-2-(hydroxymethyl)butanoyl)-7-azaspiro[4.5]decan-10-yl)methyl)-5-(morpholine-4-carbonyl)-4-phenylpyridin-2(1H)-one 1-(((R)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one 1-(((R)-10-Hydroxy-7-((R)-4,4,4-trifluoro-2-methylbutanoyl)-7-azaspiro[4.5]decan-10-yl)methyl)-5-(morpholine-4-carbonyl)-4-phenylpyridin-2(1H)-one 1-(((R)-10-Hydroxy-7-((R)-4,4,4-trifluoro-2-methylbutanoyl)-7-azaspiro[4.5]decan-10-yl)methyl)-5-(4-methylpiperazine-1-carbonyl)-4-phenylpyridin-2(1H)-one Ethyl 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate 1-(((R)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid, or a pharmaceutically acceptable salt, tautomer, stereoisomer or N-oxide derivative thereof.

In a second aspect the present invention provides a pharmaceutical composition comprising a compound according to any embodiment of the first aspect and at least one pharmaceutically acceptable excipient.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

Suitable pharmaceutically acceptable excipients would be known by the person skilled in the art, for example: fats, water, physiological saline, alcohol (e.g. ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar-coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The anti-cancer agent may also be administered in the form of a suppository or pessary, or may be applied topically in the form of a lotion, solution, cream, ointment or dusting powder.

In a third aspect the invention provides a compound or composition according to any embodiment of the first aspect or second aspect for use in therapy. In certain embodiments the invention provides a compound or composition according to any embodiment of the first aspect or second aspect for use in the treatment and/or prevention of cancer. Cancers or neoplastic conditions suitable to be treated with the compounds or compositions according to the invention include, for example: prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

In certain embodiments the invention provides a compound or composition according to any embodiment of the first aspect or second aspect for use in the treatment and/or prevention of muscle atrophy. In certain embodiments, the invention provides a compound or composition according to any embodiment of the first aspect or second aspect for use in the treatment and/or prevention of cachexia or sarcopenia. Muscle atrophy, cachexia or sarcopenia may be asscoaited with or induced by HIV infection/AIDS, heart failure, rheumatoid arthritis, chronic obstructive pulmonary disease (COPD), cystic fibrosis, multiple sclerosis, motor neuron disease (MND), Parkinson's disease, dementia, or cancer.

The compound or composition of the invention may be used in monotherapy and/or a combination modality. Suitable agents to be used in such combination modalities with compounds or compositions according to the invention include one or more of anti-cancer agents, anti-inflammatory agents, immuno-modulatory agents, for example immuno-suppressive agents, neurological agents, anti-diabetic agents, anti-viral agents, anti-bacterial agents and/or radiation therapy.

Agents used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including *vinca* alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

In a fourth aspect the invention provides a method of treating or preventing cancer comprising administering to a subject a compound according to any embodiment of the first aspect of the invention or a composition according to any embodiment of the second aspect of the invention. Cancers or neoplastic conditions suitable to be treated or prevented according to these methods include, for example, prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

As part of a method according to the fourth aspect, the compound or composition may be used in monotherapy and/or a combination modality. Suitable agents to be used in such combination modalities with compounds or compositions according to the invention include one or more of anti-cancer agents, anti-inflammatory agents, immuno-modulatory agents, immuno-suppressive agents, neurological agents, anti-diabetic agents, anti-viral agents, anti-bacterial agents and/or radiation therapy.

Agents used in combination with the compounds of the present invention may target the same or a similar biological pathway to that targeted by the compounds of the present invention or may act on a different or unrelated pathway.

In a fifth aspect the invention provides a use of a compound according to any embodiment of the first aspect in the manufacture of a medicament for treating or preventing cancer. Cancers or neoplastic conditions suitable to be treated or prevented by such a medicament include, for example, prostate cancer, colon cancer, breast cancer, lung cancer, kidney cancer, CNS cancers (e.g. neuroblastomas, glioblastomas), osteosarcoma, haematological malignancies (e.g. leukemia, multiple myeloma and mantle cell lymphoma). In certain preferred embodiments the cancer is associated with p53 dysregulation. In certain preferred embodiments, the cancer is selected from a haematological malignancy (e.g. mantle cell lymphoma, multiple myeloma), prostate cancer, a neuroblastoma, or a glioblastoma.

In a sixth aspect the invention provides a method of treating or preventing muscle atrophy, optionally cachexia or sarcpenia, comprising administering to a subject a compound according to any embodiment of the first aspect of the invention or a composition according to any embodiment of the second aspect of the invention. Muscle atrophy, cachexia or sarcopenia may be associated with or induced by HIV infection/AIDS, heart failure, rheumatoid arthritis, chronic obstructive pulmonary disease (COPD), cystic fibrosis, multiple sclerosis, motor neuron disease (MND), Parkinson's disease, dementia, or cancer.

In a seventh aspect, the invention provides a use of a compound according to any embodiment of the first aspect in the manufacture of a medicament for treating or preventing muscle atrophy, optionally cachexia or sarcpenia. Muscle atrophy, cachexia or sarcopenia may be asscoaited with or induced by HIV infection/AIDS, heart failure, rheumatoid arthritis, chronic obstructive pulmonary disease (COPD), cystic fibrosis, multiple sclerosis, motor neuron disease (MND), Parkinson's disease, dementia, or cancer.

In a further aspect, the invention provides a compound or composition according to any embodiment of the first aspect or second aspect for use in the treatment and/or prevention of Parkinson's Disease. In a further aspect, the invention provides a method of treating or preventing Parkinson's Disease comprising administering an effective amount of a compound or pharmaceutical composition according to the invention to a subject. In a further aspect, the invention provides the use of a compound according to the invention in the manufacture of a medicament for the treatment of Parkinson's Disease.

In regard to aspects of the invention relating to therapeutic use of compounds according to the invention, the compounds may be administered with a combination partner. Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including *vinca* alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

In regard to aspects of the invention relating to therapeutic use of compounds according to the invention, the compounds may be administered to the subject in need of treatment in an "effective amount". The term "effective amount" refers to the amount or dose of a compound which, upon single or multiple dose administration to a subject, provides therapeutic efficacy in the treatment of disease. Therapeutically effective amounts of a compound according to the invention can comprise an amount in the range of from about 0.1 mg/kg to about 20 mg/kg per single dose. A therapeutic effective amount for any individual patient can be determined by the healthcare professional by methods understood by the skilled person. The amount of compound administered at any given time point may be varied so that optimal amounts of the compound, whether employed alone or in combination with any other therapeutic agent, are administered during the course of treatment. It is also contemplated to administer compounds according to the invention, or pharmaceutical compositions comprising such compounds, in combination with any other cancer treatment, as a combination therapy.

In regard to aspects of the invention relating to therapeutic use of compounds according to the invention, in preferred embodiments the subject to be treated is human.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The present invention will now be described in relation to several examples.

The examples indicated below were synthesised according to the methods described subsequently. $IC_{50}$ values were determined as described below and are represented in the following table.

TABLE 1

USP19 inhibition by exemplified compounds

| Example Number | USP19 $IC_{50}$ activity |
|---|---|
| 1 | * |
| 2 | * |
| 3 | * |
| 4 | * |
| 5 | ** |
| 6 | ** |
| 7 | *** |
| 8 | ** |
| 9 | ** |
| 10 | * |
| 11 | * |
| 12 | ** |
| 13 | * |
| 14 | *** |
| 15 | ** |
| 16 | ** |
| 17 | ** |
| 18 | ** |
| 19 | ** |
| 20 | ** |
| 21 | ** |
| 22 | ** |
| 23 | ** |
| 24 | ** |
| 25 | *** |
| 26 | * |
| 27 | * |
| 28 | * |
| 29 | * |
| 30 | * |
| 31 | *** |
| 32 | ** |
| 33 | ** |
| 34 | * |
| 35 | * |
| 36 | *** |
| 37 | * |
| 38 | * |
| 39 | ** |
| 40 | ** |
| 41 | ** |
| 42 | ** |
| 43 | ** |
| 44 | ** |
| 45 | * |
| 46 | * |
| 47 | * |
| 48 | * |
| 49 | * |
| 50 | **** |
| 51 | *** |
| 52 | *** |
| 53 | *** |
| 54 | * |
| 55 | ** |
| 56 | ** |
| 57 | ** |
| 58 | ** |
| 59 | ** |
| 60 | ** |
| 61 | * |
| 62 | *** |
| 63 | *** |
| 64 | ** |
| 65 | ** |
| 66 | N.D. |
| 67 | ** |
| 68 | ** |
| 69 | ** |
| 70 | ** |
| 71 | ** |
| 72 | * |
| 73 | **** |
| 74 | * |
| 75 | *** |
| 76 | *** |

TABLE 1-continued

USP19 inhibition by exemplified compounds

| | |
|---|---|
| 77 | *** |
| 78 | *** |
| 79 | *** |
| 80 | ** |
| 81 | * |
| 82 | * |
| 83 | * |
| 84 | * |
| 85 | * |
| 86 | ** |
| 87 | *** |
| 88 | *** |
| 89 | *** |
| 90 | *** |
| 91 | *** |
| 92 | *** |
| 93 | ** |
| 94 | *** |
| 95 | ** |
| 96 | ** |
| 97 | ** |
| 98 | ** |
| 99 | ** |
| 100 | ** |
| 101 | ** |
| 102 | *** |
| 103 | ** |
| 104 | ** |
| 105 | ** |
| 106 | ** |
| 107 | ** |
| 108 | *** |
| 109 | * |
| 110 | *** |
| 111 | * |
| 112 | * |
| 113 | * |
| 114 | ** |
| 115 | ** |
| 116 | *** |
| 117 | *** |
| 118 | *** |
| 119 | **** |
| 120 | **** |
| 121 | **** |
| 122 | * |
| 123 | **** |
| 124 | **** |
| 125 | ** |
| 126 | * |
| 127 | *** |
| 128 | *** |
| 129 | ** |
| 130 | *** |
| 131 | *** |
| 132 | ** |
| 133 | *** |
| 134 | ** |
| 135 | **** |
| 136 | *** |
| 137 | *** |
| 138 | **** |
| 139 | **** |
| 140 | *** |
| 141 | **** |
| 142 | * |
| 143 | ** |
| 144 | **** |
| 145 | **** |
| 146 | *** |
| 147 | * |
| 148 | ** |
| 149 | **** |
| 150 | * |
| 151 | ** |
| 152 | **** |
| 153 | ** |
| 154 | ** |
| 155 | **** |
| 156 | **** |
| 157 | **** |
| 158 | * |
| 159 | *** |
| 160 | **** |
| 161 | ** |
| 162 | **** |
| 163 | ** |
| 164 | **** |
| 165 | ** |
| 166 | **** |
| 167 | ** |
| 168 | **** |
| 169 | **** |
| 170 | **** |
| 171 | * |
| 172 | ** |
| 173 | * |
| 174 | **** |
| 175 | * |
| 176 | ** |
| 177 | * |
| 178 | * |
| 179 | * |
| 180 | ** |
| 181 | *** |
| 182 | ** |
| 183 | ** |
| 184 | *** |
| 185 | *** |
| 186 | * |
| 187 | * |
| 188 | * |
| 189 | *** |
| 190 | * |
| 191 | * |
| 192 | ** |
| 193 | ** |
| 194 | ** |
| 195 | ** |
| 196 | *** |
| 197 | **** |
| 198 | ** |
| 199 | ** |
| 200 | *** |
| 201 | ** |
| 202 | * |
| 203 | *** |
| 204 | *** |
| 205 | **** |
| 206 | **** |
| 207 | ** |
| 208 | **** |
| 209 | ** |
| 210 | ** |
| 211 | **** |
| 212 | **** |
| 213 | **** |
| 214 | **** |
| 215 | **** |
| 216 | **** |
| 217 | **** |
| 218 | *** |
| 219 | *** |
| 220 | *** |
| 221 | *** |
| 222 | **** |
| 223 | *** |
| 224 | **** |
| 225 | *** |
| 226 | **** |
| 227 | **** |
| 228 | **** |
| 229 | ** |
| 230 | *** |
| 231 | *** |
| 232 | **** |

TABLE 1-continued

USP19 inhibition by exemplified compounds

| | |
|---|---|
| 233 | **** |
| 234 | *** |
| 235 | *** |
| 236 | **** |
| 237 | **** |
| 238 | **** |
| 239 | **** |
| 240 | **** |
| 241 | *** |
| 242 | *** |
| 243 | ** |
| 244 | ** |
| 245 | ** |
| 246 | ** |
| 247 | **** |
| 248 | **** |
| 249 | **** |
| 250 | **** |
| 251 | **** |
| 252 | **** |
| 253 | **** |

For representative examples in Table 1, USP19 inhibitory activities are classified as the following:

| | **** | *** | ** | * | N.D. |
|---|---|---|---|---|---|
| USP19 $IC_{50}$ [μM] | $IC_{50} < 0.5$ | $0.5 \leq IC_{50} < 5$ | $5 \leq IC_{50} < 50$ | $50 \leq IC_{50} < 250$ | Not determined |

A representative overall selectivity profile of Example 124 is shown in FIG. 1, in which selectivity is demonstrated against a panel of 24 USPs and 19 other DUBs.

EXPERIMENTAL SECTION

Abbreviations and Acronyms aq: aqueous; dba: dibenzylideneacetone; Bn: benzyl; Boc: tert-butyloxycarbonyl; br: broad; DCM: dichloromethane; d: doublet (spectral); DIPEA: diisopropylethylamine; DME: dimethoxyethane; DMF: N,N-dimethylformamide; DMSO: dimethylsulfoxide; dppf: 1,1'-bis(diphenylphosphino)ferrocene; EDC: N-(3-dimethylaminopropyl)-N'-ethylcarbodiimide hydrochloride; equiv.: equivalents; EtOAc: ethyl acetate; PE: petroleum ether 40/60; ESI: electrospray ionisation; h: hour(s); HATU: N-[(dimethylamino)-1H-1,2,3-triazolo-[4,5-b]pyridin-1-ylmethylene]-N-methylmethanaminium hexafluorophosphate N-oxide; HBTU: N,N,N',N'-tetramethyl-O-(1H-benzotriazol-1-yl)uronium hexafluorophosphate; hept: heptet (spectral); HPLC: high pressure liquid chromatography; LC: liquid chromatography; LCMS: liquid chromatography mass spectrometry; M: molar; m/z: mass-to-charge ratio; m-CPBA: 3-chloroperbenzoic acid; MeCN: acetonitrile; MeOH: methanol; min: minute(s); MS: mass spectrometry; m: multiplet (spectral); NaHMDS: sodium bis(trimethylsilyl)amide; NMR: nuclear magnetic resonance; p: pentet (spectral); q: quartet (spectral); quint: quintet (spectral); $R_T$: retention time; RT: room temperature; s: singlet (spectral); SM: starting material; TBS: tert-butyldimethylsilyl; TFA: trifluoroacetic acid; THF: tetrahydrofuran; t: triplet (spectral); v/v: volume per unit volume; Xantphos: 4,5-bis(diphenylphosphino)-9,9-dimethylxanthene.

General Experimental Conditions

Solvents and Reagents

Common organic solvents that were used in reactions (e.g. THF, DMF, DCM, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Microwave experiments were carried out using a Biotage Initiator™ Eight system, unless otherwise stated for cases in which a CEM Discover™/Explorer24™ system controlled by Synergy 1.5 software was used. Both machines give good reproducibility and control at temperature ranges from 60-250° C. and pressures of up to a maximum of 20 bar.

Flash Chromatography Purification of compounds by flash chromatography was achieved using a Biotage Isolera Four system. Unless otherwise stated, Biotage KP-Sil SNAP cartridge columns (10-340 g) or Grace GraceResolv cartridge columns (Grace, 4-330 g) were used along with the stated solvent system and an appropriate solvent gradient depending on compound polarity. In the case of more polar and basic compounds, Biotage KP-NH SNAP cartridge columns (11 g) were used.

NMR Spectroscopy $^1$H NMR spectra were recorded at ambient temperature using a Bruker Avance (300 MHz), Bruker Avance III (400 MHz) or Bruker Ascend (500 MHz) spectrometer. All chemical shifts (δ) are expressed in ppm. Residual solvent signals were used as an internal standard and the characteristic solvent peaks were corrected to the reference data outlined in J. Org. Chem., 1997, 62, p 7512-7515; in other cases, NMR solvents contained tetramethylsilane, which was used as an internal standard.

Liquid Chromatography Mass Spectrometry (LCMS)

Liquid Chromatography Mass Spectrometry (LCMS) experiments to determine retention times ($R_T$) and associated mass ions were performed using the following methods:

Method A:

The system consisted of an Agilent Technologies 6130 quadrupole mass spectrometer linked to an Agilent Technologies 1290 Infinity LC system with UV diode array detector and autosampler. The spectrometer consisted of an electrospray ionization source operating in positive and negative ion mode. LCMS experiments were performed on each sample submitted using the following conditions: LC Column: Agilent Eclipse Plus C18 RRHD, 1.8 μm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 0.5 | 80 | 20 |
| 1.80 | 0.5 | 0 | 100 |
| 2.20 | 0.5 | 0 | 100 |
| 2.50 | 0.5 | 80 | 20 |
| 3.00 | 0.5 | 80 | 20 |

Method B:

The system consisted of an Agilent Technologies 6140 single quadrupole mass spectrometer linked to an Agilent Technologies 1290 Infinity LC system with UV diode array detector and autosampler. The spectrometer consisted of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD, 1.8 μm, 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Preparative High Pressure Liquid Chromatography

The system consisted of an Agilent Technologies 6120 single quadrupole mass spectrometer linked to an Agilent Technologies 1200 Preparative LC system with multiple wavelength detector and autosampler. The mass spectrometer used a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using the LCMS method. In cases where the basic conditions were unsuccessful, acidic conditions were employed.

Basic Conditions:

LC Column: Waters XBridge™ Prep C18 5 μm OBD™ 19×50 mm column at RT. Mobile phase: A) 0.1% (v/v) ammonium hydroxide in water; B) 0.1% (v/v) ammonium hydroxide in 95:5, acetonitrile/water. Total experiment time was ca. 10 min and a generic method is shown:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

Acidic Conditions:

LC Column: Waters XBridge™ Prep C18 5 μm OBD™ 19×50 mm column at RT. Mobile phase: A) Water 0.1% (v/v) formic acid in water; B) 0.1% (v/v) formic acid in 95:5, acetonitrile/water. Total experiment time was ca. 10 min and a generic method is shown:

| Gradient Time (min) | Flow (mL/min) | % A | % B |
|---|---|---|---|
| 0.00 | 20.0 | 95 | 5 |
| 7.00 | 20.0 | 0 | 100 |
| 9.00 | 20.0 | 0 | 100 |
| 9.20 | 20.0 | 95 | 5 |

The pure fractions were combined and concentrated using a Genevac EZ-2 Elite, unless stated otherwise.

Chiral Separation of Stereoimers by Supercritical Fluid Chromatography (SFC)

The separation of mixtures of stereoisomers was performed using the following general procedure. The mixture of stereoisomers was dissolved to 50 mg/mL in methanol and purified by SFC under the stated conditions. Combined fractions of each of stereoisomer were evaporated to near dryness using a rotary evaporator, transferred into final vessels using DCM, which was removed under a stream of compressed air at 40° C., before being stored in a vacuum oven at 40° C. and 5 mbar for 16 h.

Chiral Purity Analysis

After chiral separation of mixtures of stereoisomer was analysed to determine chiral purity using the following analytical SFC methods under the stated conditions.

Method A:

| | |
|---|---|
| Column Details | Lux A1 (4.6 mm × 250 mm, 5 μm) |
| Column Temperature | 40° C. |
| Flow Rate | 4 mL/min |
| BPR | 125 BarG |
| Detector Wavelength | 210-400 nm |
| Injection Volume | 1 μL |
| Isocratic Conditions | 20:80 IPA:$CO_2$ (0.1% v/v $NH_3$) |

Method B:

| | |
|---|---|
| Column Details | Lux C4 (4.6 mm × 250 mm, 5 μm) |
| Column Temperature | 40° C. |
| Flow Rate | 4 mL/min |
| BPR | 125 BarG |
| Detector Wavelength | 210-400 nm |
| Injection Volume | 1 μL |
| Isocratic Conditions | 35:65 MeOH:$CO_2$ |

Method C:

| | |
|---|---|
| Column Details | AMS (4.6 mm × 250 mm, 5 um) |
| Column Temperature | 40° C. |
| Flow Rate | 4 mL/min |
| Detector Wavelength | 210-400 nm |
| Injection Volume | 1.0 uL |
| BPR | 125 BarG |
| Isocratic Conditions | 25:75 MeOH:$CO_2$ (0.1% v/v $NH_3$) |

X-Ray Crystallography

A suitable crystal was selected and mounted on a MITIGEN holder silicon oil on a Rigaku AFC11 007-HF diffractometer. The crystal was kept at T=100(2) K during data collection. Using Olex2 (Dolomanov et al., *J. Appl. Cryst.,* 2009, 42, p 339-341), the structure was solved with the ShelXT (Sheldrick, *Acta Cryst.,* 2015, A71, p 3-8) structure solution program, using the Intrinsic Phasing solution method. The model was refined with version 2016/6 of ShelXL (Sheldrick, *Acta Cryst.,* 2015, C71, p 3-8) using Least Squares minimisation.

Nomenclature

Unless otherwise indicated, the nomenclature of structures was determined using the 'Convert Structure to Name' function of ChemBioDraw Ultra 12.0 or ChemDraw Professional 15.1 (CambridgeSoft/PerkinElmer). In the case of Amines 7 and 9, Acids 4 and 13, and Examples 120, 121, 122, 123, 204, 205, 206, 207, 208, 213, 220, 221, 228, 235 and 236, the configuration of the chiral tertiary alcohol has been assigned based on X-ray crystallography data of the enantiopure intermediate ethyl (S)-1-((1-(tert-butoxycarbonyl)-4-hydroxy-3,3-dimethylpiperidin-4-yl)methyl)-4- chloro-6-oxo-1,6-dihydropyridine-3-carboxylate (Amine 7, Step 2: $2^{nd}$ eluted compound from chiral supercritical fluid chromatography with 99.4% ee that when used to prepare target compounds was known to result in the more active stereoisomers). The absolute configuration of the molecule was determined by analysis of anomalous X-ray scattering by a single crystal that had been grown by ethyl acetate/cyclohexane diffusion. The differences in intensities of the anomalous scattering were compared with calculated scattering intensities for each enantiomer and the measured and calculated intensities were fitted to the Flack parameter (Chirality, 2008, 20, p 681-690; and references therein). The Flack parameter should be close to 0 if the configuration of the solved structure is correct or will be close to 1 if the inverse model is correct or close to 0.5 for a racemic mixture. The measured Flack parameter for ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate, shown in Table 2 along with other crystal data and data collection parameters, was refined to −0.005 with a standard uncertainty of 0.004.

TABLE 2

Crystal data and data collection parameters for ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate.

| Formula | $C_{21}H_{31}ClN_2O_6$ | Z | 2 |
|---|---|---|---|
| $D_{calc.}$/g cm$^{-3}$ | 1.335 | Z' | 1 |
| μ/mm$^{-1}$ | 1.873 | Wavelength/Å | 1.54184 |
| Formula Weight | 442.93 | Radiation type | CuK$_\alpha$ |
| Colour | clear colourless | $\Theta_{min}$/° | 4.458 |
| Shape | prism | $\Theta_{max}$/° | 70.578 |
| Size/mm$^3$ | 0.12 × 0.10 × 0.06 | Measured Refl. | 21281 |
| T/K | 100(2) | Independent Refl. | 4195 |
| Crystal System | monoclinic | Reflections Used | 4166 |
| Flack Parameter | −0.005(4) | $R_{int}$ | 0.0242 |
| Hooft Parameter | −0.010(3) | Parameters | 281 |
| Space Group | P2$_1$ | Restraints | 1 |
| a/Å | 10.22890(10) | Largest Peak | 0.268 |
| b/Å | 9.20890(10) | Deepest Hole | −0.211 |
| c/Å | 12.06510(10) | GooF | 1.048 |
| α/° | 90 | wR$_2$ (all data) | 0.0666 |
| β/° | 104.1540(10) | wR$_2$ | 0.0665 |
| γ/° | 90 | R$_1$ (all data) | 0.0254 |
| V/Å$^3$ | 1101.994(19) | R$_1$ | 0.0253 |

The measured Flack parameter of −0.005(4) is classified as strong/enantiopure-distinguishing and confirms S configuration to a high degree of certainty. Therefore, the absolute configuration of the model shown below is correct. The chiral center located at the tertiary alcohol has been confirmed to be of S configuration.

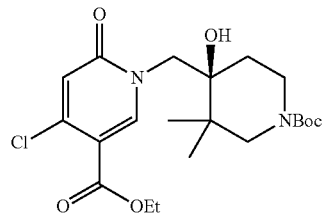 [SMILES: CCOC(=O)c1cn(C[C@]2(O)CCN(C(=O)OC(C)(C)C)CC2(C)C)c(=O)cc1Cl]

For Examples 124, 125, 152, 153, 160, 164, 165, 166 and 167, in which the compounds were not synthesised directly from this intermediate but did contain the same gem-dimethylpiperidinol, the configuration of the tertiary alcohol was inferred from the X-ray crystallography data for the intermediate. The most active diastereoisomers were assigned S configuration and less active diastereoisomers (typically 50-500 fold less potent) were assigned R configuration at the chiral tertiary alcohol. For Amines 10, 11 and 12, and Examples 209, 210, 211, 212, 214, 215, 216, 217, 218, 219, 222, 223, 224, 225, 226, 227, 230, 231, 232, 233, 239, 240, 247, 248, 249, 250, 251, 252, and 253, in which the compounds were not synthesised from this intermediate but contained a similar spirocyclopentyl piperidinol, the configuration of the tertiary alcohol was also inferred from the X-ray crystallography data for the gem-dimethylpiperidinol intermediate. The most active stereoisomers were assigned S configuration and less active stereoisomers (typically 5000-8000 fold less potent) were assigned R configuration at the chiral tertiary alcohol. However, it should be noted that for each of the Examples listed above, it may be the case that they have been assigned with the incorrect configuration at the tertiary alcohol position due to an unforeseen error in the determination of the X-ray crystallography data or the strategy of inferring the stereochemistry from other compounds may be incorrect for some or all Examples that were assigned in this way. Therefore, for each of these Examples, we also claim the compounds that have opposite configuration at this position.

General Procedures

General Procedure 1: Epoxide Opening with a Nucleophile

The appropriate nucleophile (1 equiv.), the epoxide (1-3 equiv.) and a base, either $Cs_2CO_3$ (1-3 equiv.) or DIPEA (1.5 equiv.), were suspended in DMF and the mixture was heated at 80° C. for 10-24 h or as indicated. The reaction was cooled to RT. Saturated aqueous ammonium chloride solution or water was added and the mixture was extracted with DCM or EtOAc (×3). The combined organic extracts were dried (Biotage phase separator or $MgSO_4$), concentrated and the residue was purified by flash chromatography (Biotage KP-Sil and/or KP-NH, 0-100% EtOAc in cyclohexane; then 0-30% MeOH in EtOAc) to give the product.

General Procedure 2: Acid Chloride Coupling

The appropriate amine (1 equiv.) was dissolved in DCM and DIPEA (2 equiv.) was added followed by the desired acid chloride (1.1 equiv.). The mixture was stirred for 30 min then quenched by the addition of water. The resulting mixture was extracted with DCM and the phases were separated using a Biotage phase separator. The organic layer was concentrated and the residue was purified by flash chromatography (GraceResolv, 0-90% EtOAc in cyclohexane) to give the product.

General Procedure 3: HATU Coupling

The appropriate amine (1 equiv.), carboxylic acid (1.5 equiv.) and HATU (1.5 equiv.) were dissolved in DCM or DMF and DIPEA (4 equiv.) was added. The reaction was stirred for 1-24 h then quenched by the addition of saturated aqueous sodium bicarbonate solution. The resulting mixture was extracted with DCM (×3) using a Biotage phase separator. The combined organic extracts were concentrated and the residue was purified by flash chromatography (GraceResolv, 0-100% EtOAc in cyclohexane; then 0-30% MeOH in EtOAc) to give the product.

General Procedure 4: Suzuki Coupling

A reaction vial was charged with a mixture of the appropriate halide (1 equiv.), the organoboron reagent (1-3 equiv.), a Pd catalyst (0.05-0.1 equiv.) and an inorganic base (2-5 equiv.) in a mixture of water and either 1,4-dioxane or DME. The mixture was de-gassed by evacuating and refilling with $N_2$ three times or by bubbling $N_2$ through for 5 min, then the reaction tube was sealed. The reaction was heated under the indicated conditions for the indicated time then cooled to RT. Water or saturated aqueous ammonium chloride solution was added and the mixture was extracted with DCM (×3). The combined organic extracts were dried (Biotage phase separator), concentrated and the residue was purified by flash chromatography (Biotage KP-Sil and/or KP-NH, 0-100% EtOAc in cyclohexne then 0-30% MeOH in EtOAc) to give the product.

General Procedure 5: HBTU Coupling

The amine intermediate (1 equiv.) was dissolved in DCM and the relevant carboxylic acid (1.1 equiv.) was added, followed by DIPEA (1-5 equiv.) at RT. HBTU (1.1 equiv.) was added, and in cases where poor solubility was observed DMF (0.2 mL) was added. The mixture was stirred at this temperature for 2-67 h until complete by LCMS. Water or 2 M aqueous sodium hydroxide (1-2.5 mL) was added and the resulting mixture was stirred at RT for 5-15 min. The biphasic mixture was then filtered through a Biotage phase separator and the organic layer was concentrated. The residue was purified by flash chromatography (Biotage KP-NH, 0-100% EtOAc in cyclohexane; then 0-30% MeOH in EtOAc, unless otherwise specified) to give the product.

General Procedure 6: Wittig Olefination

The appropriate triphenylphosphonium salt (1.4 equiv.) was dissolved in anhydrous THF (10 mL) and the solution was cooled to −78° C. n-Butyllithium (2.5 M in hexanes, 1.5 equiv.) was added dropwise. The resulting solution was stirred at this temperature for 5 min then warmed to RT and stirred for a further 20-30 min. The mixture was cooled to −78° C. and a solution of the ketone (1.0 equiv.) in THF (5 mL) was added over 10 min. The resulting suspension was allowed to warm to RT and stirred for 19-22 h. Water (5 mL) was added and the mixture was extracted with Et$_2$O (×3). The combined organic extracts were washed with saturated aqueous sodium bicarbonate solution, dried over anhydrous MgSO$_4$ and concentrated. The residue was purified by flash chromatography to give the product.

General Procedure 7: Boc Deprotection to Free Base

The appropriate Boc protected amine (1 equiv.) was dissolved in DCM (1-4 mL) and 2,2,2-trifluoroacetic acid (0.2-1.0 mL) was added. The mixture was stirred at RT for 1-3.5 h, then concentrated. The residue was dissolved in a mixture of MeOH and DCM and loaded onto an SCX-2 cartridge. The column was eluted with a mixture of DCM and MeOH, then with a 3:2 mixture of DCM: 2 M NH$_3$ in MeOH. The ammonical fractions were concentrated to give the desired product.

General Procedure 8: Epoxidation

A solution of m-CPBA (1.2 equiv.) in DCM (2.5-5 mL) was added to a solution of alkene (1 equiv.) in DCM (5-10 mL) at 0° C. dropwise. The reaction was allowed to warm to RT and stirred for 2-2.5 h. The reaction mixture was diluted with DCM (10 mL). The mixture was washed with aqueous sodium hydroxide (1 M), water and saturated aqueous sodium thiosulfate, then filtered through a Biotage phase separator and concentrated under reduced pressure to give the desired epoxide which was used without further purification.

General Procedure 9: Boc Deprotection to Hydrochloride Salt

The Boc-protected amine was dissolved in DCM (5 mL) and HCl (4 M in 1,4-dioxane, 1-15 equiv.) was added. The reaction mixture was stirred at RT for 1-24 h. The mixture was concentrated or the insoluble product was collected by filtration. In either case, the crude product was washed with excess Et$_2$O and dried in vacuo.

General Procedure 10: Heteroaryl Chloride Hydrolysis

The appropriate chlorinated heterocycle was suspended in water (1-3.5 mL) and acetic acid (4-10 mL) was added. The reaction was heated at reflux for 2-5 days. The mixture was concentrated and the residue was taken up in saturated aqueous sodium bicarbonate (10 mL). The mixture was extracted with DCM (3×10 mL) and the combined organic extracts were concentrated to give the product which was used without further purification.

General Procedure 11: Corey-Chaykovsky Epoxidation

Trimethylsulfonium iodide (2.5 equiv.) was suspended in DMSO (1-5 mL) under an atmosphere of N$_2$. Sodium hydride (60% dispersion in mineral oil, 2.5 equiv.) was added portionwise. The mixture was allowed to warm up to RT and stirred for 2 h then a solution of ketone (1 equiv.) in DMSO (0.5-2.5 mL) was added slowly. The mixture was heated to 50° C. and stirred for 16 h, then cooled to RT and the reaction was quenched by the addition of H$_2$O. The mixture was extracted with Et$_2$O. The organic layer was dried over MgSO$_4$ and concentrated to give the crude epoxide.

General Procedure 12: BioShake HATU Coupling

The appropriate carboxylic acid (1 equiv.) was dissolved in DMF (0.3 mL) and DIPEA (2 equiv.) and HATU (1-1.5 equiv.) were added as a solution in DMF (0.3 mL). The appropriate amine (1 equiv.) was added as a solution in DMF (0.3 mL) and the reaction mixture was agitated using a BioShake IQ at RT for 2 h. The crude reaction mixture was purified by preparative HPLC using the generic method.

General Procedure 13: EDC Amide Coupling Library

The relevant carboxylic acids (0.035 mmol, 1.2 equiv.) were added into 4 mL vials before a solution of EDC (11.23 mg, 0.059 mmol, 2 equiv.), DIPEA (0.01 mL, 0.059 mmol, 2 equiv.), DMAP (0.35 mg, 0.003 mmol) in DCM (0.5 mL) was added into each vial. The resulting suspensions were stirred for 10 min at RT (heater shaker). A solution of Amine 8 (12 mg, 0.029 mmol, 1 equiv.) in DCM (0.2 mL) was added to each vial and the resulting solutions were stirred at RT overnight. Parallel work-up was carried out using a 96 well phase separator in a 3 stage process: saturated sodium bicarbonate wash, 2 N HCl wash, followed by a second saturated sodium bicarbonate wash. The resulting DCM filtrates were diluted with DCM (0.5 mL), transferred into tared vials and concentrated. The residues were dissolved in methanol (1 mL), analysed by LCMS and concentrated in vacuo (Genevac).

Amine 1: 6-(2-Fluorophenyl)-3-((4-hydroxypiperidin-4-yl)methyl)pyrimidin-4(3H)-one hydrochloride

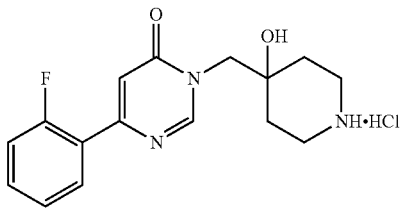

Step 1: tert-Butyl 4-((4-chloro-6-oxopyrimidin-1 (6H)-yl)methyl)-4-hydroxypiperidine-1-carboxylate Prepared according to General Procedure 1 using 6-chloropyrimidin-4(3H)-one (3.18 g, 24.4 mmol), tert-butyl 1-oxa-6-azaspiro[2.5]octane-6-carboxylate (5.2 g, 24.4 mmol) and N-ethyl-N-isopropylpropan-2-amine (6.39 mL, 36.6 mmol) in DMF (32 mL). The crude product was triturated with a mixture of cyclohexane and EtOAc to give the title compound (3.70 g, 44%). LCMS (Method B): $R_T$=1.01 min, m/z=244 [M+H-Boc]$^+$. $^1$H NMR (400 MHz CDCl$_3$): δ 8.08 (s, 1H), 6.57 (s, 1H), 4.0 (br d, 4H), 3.15 (br t, 2H), 2.78 (s, 1H), 1.69-1.59 (m, 1H), 1.54-1.49 (m, 1H), 1.46 (m, 11H).

Step 2: tert-Butyl 4-((4-(2-fluorophenyl)-6-oxopyrimidin-1 (6H)-yl)methyl)-4-hydroxypiperidine-1-carboxylate Prepared according to General Procedure 4 using tert-butyl 4-((4-chloro-6-oxopyrimidin-1(6H)-yl)methyl)-4-hydroxypiperidine-1-carboxylate (1 g, 2.91 mmol), (2-fluorophenyl)boronic acid (0.61 g, 4.36 mmol), sodium carbonate (0.617 g, 5.82 mmol), 1,4-dioxane (12 mL), water (4.8 mL) and Pd(Ph$_3$P)$_4$ (0.168 g, 0.145 mmol). The reaction was heated in a microwave at 150° C. for 15 min. The crude product was triturated with diethyl ether to give the title compound (1.71 g, 73%). LCMS (Method B): $R_T$=1.22 min, m/z=304 [M-Boc+H]$^+$. $^1$H NMR (400 MHz, CDCl$_3$): 8.19 (s, 1H), 8.05 (td, 1H), 7.44 (qd, 1H), 7.29 (d, 1H), 7.17 (dd, 1H), 7.11 (s, 1H), 4.0 (br d, 4H), 3.56 (s, 1H), 3.22-3.07 (m, 2H), 1.56-1.67 (m, 4H), 1.46 (s, 9H).

Step 3: 6-(2-Fluorophenyl)-3-((4-hydroxypiperidin-4-yl)methyl)pyrimidin-4(3H)-one hydrochloride Prepared according to General Procedure 9 using tert-butyl 4-((4-(2-fluorophenyl)-6-oxopyrimidin-1(6H)-yl)methyl)-4-hydroxypiperidine-1-carboxylate (3.37 g, 8.35 mmol) and hydrogen chloride (4 M in 1,4-dioxane, 30.6 mL, 122 mmol) in DCM (33.4 mL) to give the title compound (3.29 g, quantitative). LCMS (Method B): $R_T$=0.58 min, m/z=304 [M+H]$^+$. $^1$H NMR (400 MHz, methanol-d$_4$): δ 8.62 (s, 1H), 8.05 (td, 1H), 7.57 (br qd, 1H), 7.39 (d, 1H), 7.31 (dd, 1H), 7.00 (s, 1H), 4.19 (s, 2H), 3.34-3.27 (m, 4H), 2.03-1.90 (m, 2H), 1.80 (d, 2H).

Amine 2: (R,S)-3-(1-(4-Hydroxypiperidin-4-yl) ethyl)-6-phenylpyrimidin-4(3H)-one hydrochloride

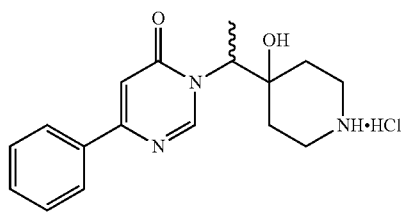

Step 1: tert-Butyl 4-ethylidenepiperidine-1-carboxylate

Prepared according to General Procedure 6 using ethyltriphenylphosphonium iodide (1.47 g, 3.51 mmol), n-butyllithium (2.5 M in hexanes, 1.51 mL, 3.76 mmol) and tert-butyl 4-oxopiperidine-1-carboxylate (0.5 g, 2.51 mmol) in anhydrous THF (15 mL) with a reaction time of 19 h. The crude product was purified by flash chromatography (GraceResolv 24 g, 100% cyclohexane; then isocratic 50% EtOAc in cyclohexane) to give the title compound (0.51 g, 83%). $^1$H NMR (400 MHz, CDCl$_3$): δ 5.28 (q, 1H), 3.38 (t, 4H), 2.20 (t, br, 2H), 2.12 (t, br, 2H), 1.60 (d, 3H), 1.47 (s, 9H).

Step 2: (R,S)-tert-Butyl 2-methyl-1-oxa-6-azaspiro [2.5]octane-6-carboxylate

Prepared according to General Procedure 8 using m-CPBA (0.56 g, 2.50 mmol), tert-butyl 4-ethylidenepiperidine-1-carboxylate (0.44 g, 2.09 mmol) in DCM (15 mL) and a reaction time of 2 h to give the title compound (0.46 g, 82%). $^1$H NMR (400 MHz, CDCl$_3$): δ 3.80-3.62 (br m, 2H), 3.45-3.33 (m, 2H), 2.93 (q, 1H), 1.82-1.70 (br m 2H), 1.56-1.36 (m, 11H), 1.31 (d. 3H).

Step 3: (R,S)-tert-Butyl 4-hydroxy-4-(1-(6-oxo-4-phenylpyrimidin-1(6H)-yl)ethyl)piperidine-1-carboxylate Prepared according to General Procedure 1 using tert-butyl 2-methyl-1-oxa-6-azaspiro[2.5]octane-6-carboxylate (0.39 g, 1.73 mmol), 6-phenylpyrimidin-4(3H)-one (0.248 g, 1.44 mmol) and cesium carbonate (1.41 g, 4.33 mmol) in DMF (20 mL) at 120° C. for 96 h and purified by flash chromatography (GraceResolv 24 g, 10-50% EtOAc in cyclohexane) to give the title compound (0.28 g, 49%). $^1$H NMR (400 MHz, DMSO-d$_6$): δ 8.50 (s, 1H), 8.12-8.05 (m, 2H), 7.54-7.47 (m, 3H), 6.98 (s, 1H), 5.16 (s, 1H), 4.99-4.86 (m, 1H), 3.85-3.7 (br m, 1H), 3.65 (br d, 1H), 3.17-2.81 (br m, 2H), 1.66 (d, 1H), 1.56-1.21 (m, 14H), 1.13-1.04 (m, br, 1H).

Step 4: (R,S)-3-(1-(4-Hydroxypiperidin-4-yl)ethyl)-6-phenylpyrimidin-4(3H)-one hydrochloride Prepared according to General Procedure 9 using tert-butyl 4-hydroxy-4-(1-(6-oxo-4-phenylpyrimidin-1(6H)-yl) ethyl)piperidine-1-carboxylate (250 mg, 0.63 mmol) in DCM (5 mL) and hydrogen chloride in 1,4-dioxane (4 M, 2.29 mL, 9.16 mmol) to give the title compound (0.20 g, 97%) that was used without further purification. LCMS (Method B): $R_T$=0.61 min, m/z=300 [M+H]$^+$. $^1$H NMR (400 MHz, methanol-d$_4$): δ 8.75 (br s, 1H), 8.04-7.98 (m, 2H), 7.59-7.52 (m, 3H), 6.99 (s, 1H), 5.18 (s, 1H), 3.44-3.13 (m, 4H), 2.08 (m, 1H), 2.00-1.88 (m, 1H), 1.87-1.76 (m, 1H), 1.58 (d, 3H), 1.55-1.47 (m, 1H).

Amine 3: (R,S)-1-((4-Hydroxy-3,3-dimethylpiperidin-4-yl)methyl)-N-isopropyl-N-methyl-6-oxo-4-phenyl-1,6-dihydropyridine-3-carboxamide

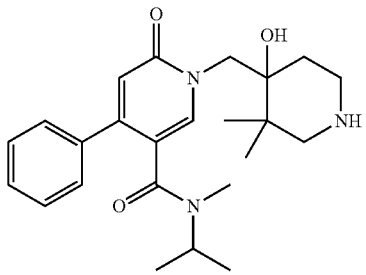 [SMILES: CC(C)N(C)C(=O)c1cn(CC2(O)CCNCC2(C)C)c(=O)cc1-c1ccccc1]

Step 1: (R,S)-tert-Butyl 4-((4-chloro-5-(isopropyl (methyl)carbamoyl)-2-oxopyridin-1(2H)-yl)methyl)-4-hydroxy-3,3-dimethylpiperidine-1-carboxylate Prepared according to General Procedure 1 using Epoxide 3 (197 mg, 0.818 mmol), 4-chloro-N-isopropyl-N-methyl-6-oxo-1,6-dihydropyridine-3-carboxamide (170 mg, 0.743 mmol), $Cs_2CO_3$ (363 mg, 1.12 mmol) and DMF (3 mL). The crude product was purified by flash chromatography (GraceResolv 24 g, 0-100% EtOAc in cyclohexane) to give the title compound (0.217 g, 62%). LCMS (Method B): $R_T$=1.25 min, m/z=414 [M+H-$^t$Bu]$^+$.

Step 2: (R,S)-tert-Butyl 4-hydroxy-4-((5-(isopropyl (methyl)carbamoyl)-2-oxo-4-phenylpyridin-1(2H)-yl)methyl)-3,3-dimethylpiperidine-1-carboxylate Prepared according to General Procedure 4 using tert-butyl 4-((4-chloro-5-(isopropyl(methyl)carbamoyl)-2-oxopyridin-1 (2H)-yl)methyl)-4-hydroxy-3,3-dimethylpiperidine-1-carboxylate (217 mg, 0.46 mmol), phenylboronic acid (84 mg, 0.693 mmol), sodium carbonate (122 mg, 1.15 mmol), Pd(dppf)$Cl_2$.$CH_2Cl_2$ (39.1 mg, 0.046 mmol), 1,4-dioxane (2 mL) and water (0.67 mL). The reaction was heated in a microwave at 150° C. for 15 min to give the title compound (205 mg, 87%). LCMS (Method B): $R_T$=1.37 min, m/z=456 [M+H-$^t$Bu]$^+$.

Step 3: (R,S)-1-((4-Hydroxy-3,3-dimethylpiperidin-4-yl)methyl)-N-isopropyl-N-methyl-6-oxo-4-phenyl-1,6-dihydropyridine-3-carboxamide Prepared according to General Procedure 7 using tert-butyl 4-hydroxy-4-((5-(isopropyl(methyl)carbamoyl)-2-oxo-4-phenylpyridin-1 (2H)-yl)methyl)-3,3-dimethylpiperidine-1-carboxylate (204 mg, 0.40 mmol), DCM (3 mL) and TFA (1 mL, 13.0 mmol) to give the title compound (151 mg, 92%). LCMS (Method B): $R_T$=0.76 min, m/z=412 [M+H]$^+$.

Amine 4: 4-(2-Fluorophenyl)-1-((4-hydroxypiperidin-4-yl)methyl)-N-isopropyl-N-methyl-6-oxo-1,6-dihydropyridine-3-carboxamide

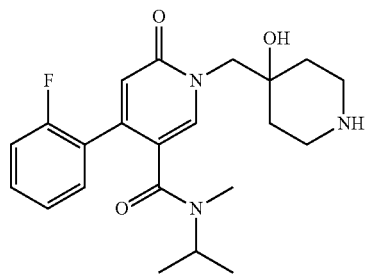 [SMILES: CC(C)N(C)C(=O)c1cn(CC2(O)CCNCC2)c(=O)cc1-c1ccccc1F]

Step 1: 4,6-Dichloro-N-isopropyl-N-methylnicotinamide

Prepared according to General Procedure 5 using 4,6-dichloronicotinic acid (5.04 g, 26.3 mmol), HBTU (11.0 g, 28.9 mmol), DCM (100 mL) and DIPEA (9.17 mL, 52.5 mmol). The crude product was purified by flash chromatography (GraceResolv 120 g, 10-33% EtOAc in cyclohexane) to give the title compound (5.77 g, 89%). LCMS (Method B): $R_T$=1.02 min, m/z=247, 249 [M+H]$^+$.

Step 2: 4-Chloro-N-isopropyl-N-methyl-6-oxo-1,6-dihydropyridine-3-carboxamide 4,6-Dichloro-N-isopropyl-N-methylnicotinamide (2.5 g, 10.1 mmol) and sodium acetate (4.15 g, 50.6 mmol) were dissolved in acetic acid (40 mL, 700 mmol) and the mixture was heated at reflux for 7 days. The mixture was concentrated and the residue was diluted with water and basified with solid potassium carbonate. The mixture was extracted with DCM. The organic layer was dried (phase separator), concentrated and the residue was purified by flash chromatography (GraceResolv, 50-100% EtOAc in cyclohexane) to give the title compound (600 mg, 26%). LCMS (Method B): $R_T$=0.64 min, m/z=229/231 [M+H]$^+$.

Step 3: tert-Butyl 4-((4-chloro-5-(isopropyl(methyl) carbamoyl)-2-oxopyridin-1(2H)-yl)methyl)-4-hydroxypiperidine-1-carboxylate Prepared according to General Procedure 1 using Epoxide 1 (233 mg, 1.09 mmol), 4-chloro-N-isopropyl-N-methyl-6-oxo-1,6-dihydropyridine-3-carboxamide (250 mg, 1.09 mmol), cesium carbonate (534 mg, 1.64 mmol) and DMF (5 mL). The mixture was heated at 90° C. for 16 h. The crude product was purified by flash chromatography (GraceResolv 12 g, 20-80% EtOAc in cyclohexane) to give the title compound (389 mg, 81%). LCMS (Method B): $R_T$=1.06 min, m/z=342 [M+H-Boc]$^+$.

Step 4: tert-Butyl 4-((4-(2-fluorophenyl)-5-(isopropyl(methyl)carbamoyl)-2-oxopyridin-1 (2H)-yl) methyl)-4-hydroxypiperidine-1-carboxylate Prepared according to General Procedure 4 using tert-butyl 4-((4-chloro-5-(isopropyl(methyl)carbamoyl)-2-oxopyridin-1 (2H)-yl)methyl)-4-hydroxypiperidine-1-carboxylate (100 mg, 0.23 mmol), 1,4-dioxane (1.5 mL), (2-fluorophenyl)boronic acid (47.5 mg, 0.34 mmol), sodium carbonate (2 M in water, 0.226 mL, 0.45 mmol), Pd(dppf) $Cl_2$.$CHCl_2$ (9.31 mg, 0.011 mmol) and water (0.3 mL). The mixture was heated in a microwave at 120° C. for 30 min. The crude product was chromatographed (GraceResolv, 0-100% EtOAc in cyclohexane; then 0-25% MeOH in EtOAc) to give the title compound (91 mg, 80%). LCMS (Method B): $R_T$=1.19 min, m/z=402 [M+H-Boc]$^+$.

Step 5: 4-(2-Fluorophenyl)-1-((4-hydroxypiperidin-4-yl)methyl)-N-isopropyl-N-methyl-6-oxo-1,6-dihydropyridine-3-carboxamide Prepared according to General Procedure 7 using tert-butyl 4-((4-(2-fluorophenyl)-5-(isopropyl(methyl)carbamoyl)-2-oxopyridin-1(2H)-yl)methyl)-4-hydroxypiperidine-1-carboxylate (190 mg, 0.379 mmol), TFA (2 mL) and DCM (2 mL) to give the title compound (152 mg, quantitative). LCMS (Method B): $R_T$=0.68 min, m/z=402 [M+H]$^+$.

Amine 5: (R,S)-6-(2-Fluorophenyl)-3-((4-hydroxy-3,3-dimethylpiperidin-4-yl)methyl)pyrimidin-4(3H)-one

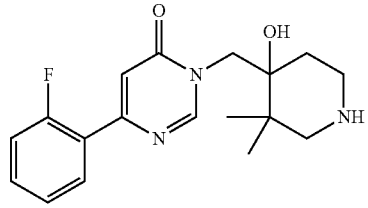 [SMILES: CC1(C)CNCCC1(O)Cn1cnc(-c2ccccc2F)cc1=O]

Step 1: (R,S)-tert-Butyl 4-((4-(2-fluorophenyl)-6-oxopyrimidin-1(6H)-yl)methyl)-4-hydroxy-3,3-dimethylpiperidine-1-carboxylate Prepared according to General Procedure 1 using 6-(2-fluorophenyl)pyrimidin-4(3H)-one (1.5 g, 7.89 mmol), Epoxide 3 (2.72 g, 7.89 mmol) and cesium carbonate (3.08 g, 9.47 mmol) in DMF (20 mL). The crude material was suspended in diethyl ether and the resulting solid collected by filtration to give the title compound (1.8 g, 53%). LCMS (Method B): $R_T$=1.39 min, m/z=432 [M+H]$^+$.

Step 2: (R,S)-6-(2-Fluorophenyl)-3-((4-hydroxy-3,3-dimethylpiperidin-4-yl)methyl)pyrimidin-4(3H)-one Prepared according to General Procedure 7 using tert-butyl 4-((4-(2-fluorophenyl)-6-oxopyrimidin-1 (6H)-yl)methyl)-4-hydroxy-3,3-dimethylpiperidine-1-carboxylate (1.4 g, 3.24 mmol), DCM (10 mL) and TFA (3 mL, 39 mmol) to give the title compound (920 mg, 86%). LCMS (Method B): $R_T$=0.65 min, m/z=332 [M+H]$^+$. $^1$H NMR (400 MHz, DMSO-d$_6$): δ (ppm) 8.44 (s, 1H), 8.07-8.00 (m, 1H), 7.58-7.52 (m, 1H), 7.40-7.34 (m, 2H), 6.80 (s, 1H), 4.64 (s, 1H), 4.45 (d, 1H), 3.67 (d, 1H), 2.76-2.63 (m, 3H), 2.26 (d, 1H), 1.61-1.50 (brm, 1H), 1.13-1.04 (m, 4H), 0.93 (s, 3H).

Amine 6: 1-((4-Hydroxy-3,3-dimethylpiperidin-4-yl)methyl)-N,N-dimethyl-6-oxo-4-phenyl-1,6-dihydropyridine-3-carboxamide hydrochloride

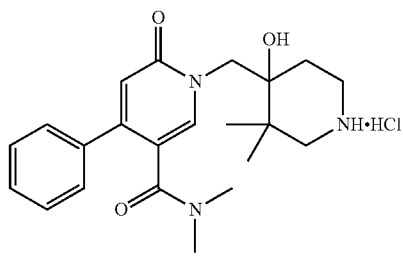

Step 1: Ethyl 1-((1-(tert-butoxycarbonyl)-4-hydroxy-3,3-dimethylpiperidin-4-yl)methyl)-6-oxo-4-phenyl-1,6-dihydropyridine-3-carboxylate Prepared according to General Procedure 1 using ethyl 6-oxo-4-phenyl-1,6-dihydropyridine-3-carboxylate (Intermediate 1, Step 2) (1.77 g, 7.28 mmol), Epoxide 3 (1.93 g, 8.00 mmol) and cesium carbonate (3.56 g, 10.9 mmol) in DMF (30 mL) heated to 80° C. for 24 h to give the title compound (2.15 g, 61%). LCMS (Method A): $R_T$=1.75 min, m/z=485 [M+H]$^+$.

Step 2: 1-((1-(tert-Butoxycarbonyl)-4-hydroxy-3,3-dimethylpiperidin-4-yl)methyl)-6-oxo-4-phenyl-1,6-dihydropyridine-3-carboxylic acid To a stirred solution of ethyl 1-((1-(tert-butoxycarbonyl)-4-hydroxy-3,3-dimethylpiperidin-4-yl)methyl)-6-oxo-4-phenyl-1,6-dihydropyridine-3-carboxylate (1.0 g, 2.06 mmol) in THF (10 mL) and water (2 mL) was added 4 M sodium hydroxide$_{(aq)}$ (2.58 mL, 10.3 mmol). The reaction mixture was heated to 60° C. and stirred overnight at this temperature. The solution was allowed to cool to RT and the solvent volume reduced in vacuo. The mixture was acidified with 2 M HCl$_{(aq)}$ and extracted with EtOAc (×3). The combined organic phases were washed with brine, dried over MgSO$_4$, filtered and concentrated in vacuo to afford the title compound (937 mg, 99%). LCMS (Method B): $R_T$=1.25 min, m/z=401 [M+H]$^+$.

Step 3: tert-Butyl 4-((5-(dimethylcarbamoyl)-2-oxo-4-phenylpyridin-1 (2H)-yl)methyl)-4-hydroxy-3,3-dimethylpiperidine-1-carboxylate Prepared according to General Procedure 5 using 1-((1-(tert-butoxycarbonyl)-4-hydroxy-3,3-dimethylpiperidin-4-yl)methyl)-6-oxo-4-phenyl-1,6-dihydropyridine-3-carboxylic acid (480 mg, 1.05 mmol), DIPEA (0.220 mL, 1.26 mmol), HBTU (439 mg, 1.16 mmol) and dimethylamine (2 M in THF, 0.790 mL, 1.58 mmol) in DCM (6 mL) at RT for 16 h to give the title compound (500 mg, 98%). LCMS (Method A): $R_T$=1.20 min, m/z=484 [M+H]$^+$.

Step 4: 1-((4-Hydroxy-3,3-dimethylpiperidin-4-yl)methyl)-N,N-dimethyl-6-oxo-4-phenyl-1,6-dihydropyridine-3-carboxamide hydrochloride Prepared according to General Procedure 9 using tert-butyl 4-((5-(dimethylcarbamoyl)-2-oxo-4-phenylpyridin-1 (2H)-yl)methyl)-4-hydroxy-3,3-dimethylpiperidine-1-carboxylate (500 mg, 1.03 mmol) and 4 M HCl in dioxane (3.1 mL, 12.4 mmol) in DCM (8 mL) to give the title compound (434 mg, quantitative). LCMS (Method A): $R_T$=0.60 min, m/z=384 [M+H]$^+$. $^1$H NMR (500 MHz, DMSO-d$_6$): δ 7.82 (s, 1H), 7.47-7.42 (m, 3H), 7.41-7.36 (m, 2H), 6.47 (s, 1H), 4.48 (d, 1H), 3.81 (d, 1H), 3.10 (br d, 1H), 3.00-2.88 (m, 2H), 2.83-2.72 (m, 4H), 2.63 (s, 3H), 1.96-1.83 (m, 1H), 1.43-1.34 (m, 1H), 1.33-1.23 (m, 1H), 1.19 (s, 3H), 1.03 (s, 3H).

Amine 7: (S)-1-((4-Hydroxy-3,3-dimethylpiperidin-4-yl)methyl)-N,N-dimethyl-6-oxo-4-phenyl-1,6-dihydropyridine-3-carboxamide

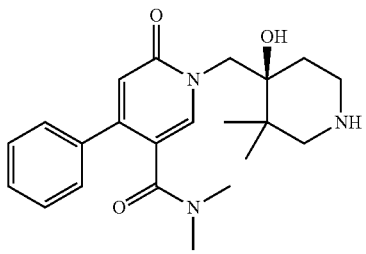 [SMILES: CN(C)C(=O)c1cn(C[C@]2(O)CCNCC2(C)C)c(=O)cc1-c1ccccc1]

Step 1: Ethyl 4-chloro-6-oxo-1,6-dihydropyridine-3-carboxylate

A mixture of ethyl 4,6-dichloronicotinate (25 g, 114 mmol) and sodium acetate (46.6 g, 568 mmol) in acetic acid (325 mL, 5.68 mol) was heated at reflux for 3 days. The reaction mixture was allowed to cool to RT, diluted with water (650 mL) and the resulting precipitate isolated by filtration. The precipitate was washed with water (6×100 mL) and dried in a vacuum oven at 50° C. to give the title compound (18.7 g, 81%) as a light beige solid. LCMS (Method A): $R_T$=0.73 min, m/z=202, 204 [M+H]$^+$. $^1$H NMR (500 MHz, DMSO-d$_6$): δ 12.40 (br. s, 1H), 8.11 (s, 1H), 6.55 (s, 1H), 4.22 (q, J=7.1 Hz, 2H), 1.27 (t, J=7.1 Hz, 3H).

Step 2: Ethyl 1-((1-(tert-butoxycarbonyl)-4-hydroxy-3,3-dimethylpiperidin-4-yl)methyl)-4-chloro-6-oxo-1,6-dihydropyridine-3-carboxylate A suspension of ethyl 4-chloro-6-oxo-1,6-dihydropyridine-3-carboxylate (4.00 g, 19.8 mmol), Epoxide 3 (6.22 g, 25.8 mmol) and cesium carbonate (8.40 g, 25.8 mmol) (dried at 120° C. under high vacuum for 5 h) in DMF (66 mL) were heated at 90° C. for 19 h. The reaction mixture was allowed to cool to RT, diluted with saturated NH$_4$Cl$_{(aq)}$ (200 mL) and the mixture extracted with EtOAc (3×100 mL). The combined organic phases were passed through a Biotage phase separator, concentrated in vacuo and the residue purified by flash chromatography (Biotage KP-Sil 100 g cartridge, 0-60% EtOAc in cyclohexane) to give the title compound (3.31 g, 37%) as a pale yellow foam. LCMS (Method A): $R_T$=1.54 min, m/z=443, 445 [M+H]$^+$. $^1$H NMR (500 MHz, DMSO-d$_6$): δ 8.44 (s, 1H), 6.64 (s, 1H), 4.84 (s, 1H), 4.49 (d, J=13.4 Hz, 1H), 4.27 (q, J=7.1 Hz, 2H), 3.74-3.60 (m, 2H), 3.30-2.85 (m, 3H), 1.62-1.48 (m, 1H), 1.38 (s, 9H), 1.29 (t, J=7.1 Hz, 3H), 1.08-0.99 (m, 1H), 0.97 (s, 3H), 0.92 (s, 3H). Ethyl 1-((1-(tert-butoxycarbonyl)-4-hydroxy-3,3-dimethylpiperidin-4-yl)methyl)-4-chloro-6-oxo-1,6-dihydropyridine-3-carboxylate (9.89 g) was resolved into the single stereoisomers by chiral supercritical fluid chromatography using an AmyC (20 mm×250 mm, 5 µm) column with isocratic solvent conditions: 20:80 IPA/CO$_2$ (0.1% v/v NH$_3$). The first eluted material afforded ethyl (R)-1-((1-(tert-butoxycarbonyl)-4-hydroxy-3,3-dimethylpiperidin-4-yl)methyl)-4-chloro-6-oxo-1,6-dihydropyridine-3-carboxylate (4.55 g, 46% recovery) as an orange solid. Chiral purity (Method A): $R_T$=1.85 min, 100% ee. The second eluted material afforded ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (4.36 g, 44% recovery) as an orange solid. Chiral purity (Method A): $R_T$=2.18 min, 99.4% ee.

Step 3: Ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate Prepared according to General Procedure 4 using ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (200 mg, 0.452 mmol), phenylboronic acid (82.5 mg, 0.677 mmol), Pd(dppf)Cl$_2$.DCM (19 mg, 22.6 µmol), sodium carbonate (96 mg, 0.903 mmol), 1,4-dioxane (1.5 mL) and water (0.5 mL). The reaction was heated under microwave irradiation at 120° C. for 30 min to give the title compound (220 mg, quantitative) as a pale yellow foam. LCMS (Method A): $R_T$=1.68 min, m/z=485 [M+H]$^+$.

Step 4: (S)-1-((1-(tert-Butoxycarbonyl)-4-hydroxy-3,3-dimethylpiperidin-4-yl)methyl)-6-oxo-4-phenyl-1,6-dihydropyridine-3-carboxylic acid A solution of ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate (220 mg, 0.454 mmol) in 1 M NaOH$_{(aq)}$ (0.910 mL, 0.910 mmol) and 1,4-dioxane (2.2 mL) was stirred at 50° C. for 5 h then allowed to cool to RT. The pH was adjusted to pH 3 by the addition of 1 M HCl$_{(aq)}$ and the mixture was extracted with DCM (3×20 mL) using a Biotage phase separator. The combined organic phases were concentrated in vacuo to give the title compound (193 mg, 93%) as a colourless foam. LCMS (Method A): $R_T$=1.31 min, m/z=457 [M+H]$^+$.

Step 5: tert-Butyl (S)-4-((5-(dimethylcarbamoyl)-2-oxo-4-phenylpyridin-1(2H)-yl)methyl)-4-hydroxy-3,3-dimethylpiperidine-1-carboxylate Prepared according to General Procedure 3 using (S)-1-((1-(tert-butoxycarbonyl)-4-hydroxy-3,3-dimethylpiperidin-4-yl)methyl)-6-oxo-4-phenyl-1,6-dihydropyridine-3-carboxylic acid (193 mg, 0.423 mmol), dimethylamine (2 M in THF, 0.254 mL, 0.507 mmol), DIPEA (0.295 mL, 1.69 mmol), HATU (193 mg, 0.507 mmol) and DCM (8.5 mL) to give the title compound (241 mg, >100%) as a pale yellow foam. This material was used without further purification. LCMS (Method A): $R_T$=1.29 min, m/z=484 [M+H]$^+$.

Step 6: (S)-1-((4-Hydroxy-3,3-dimethylpiperidin-4-yl)methyl)-N,N-dimethyl-6-oxo-4-phenyl-1,6-dihydropyridine-3-carboxamide Prepared according to General Procedure 7 using tert-butyl (S)-4-((5-(dimethylcarbamoyl)-2-oxo-4-phenylpyridin-1(2H)-yl)methyl)-4-hydroxy-3,3-dimethylpiperidine-1-carboxylate (204 mg, 0.422 mmol), TFA (1 mL) and DCM (2 mL) to give the title compound (157 mg, 97%) as a colourless solid. LCMS (Method A): $R_T$=0.46 min, m/z=384 [M+H]$^+$. $^1$H NMR (500 MHz, DMSO-d$_6$): δ 7.79 (s, 1H), 7.50-7.40 (m, 3H), 7.40-7.32 (m, 2H), 6.43 (s, 1H), 4.59 (s, 1H), 4.46 (d, J=13.3 Hz, 1H), 3.72 (d, J=13.3 Hz, 1H), 3.17 (s, 1H), 2.74 (s, 3H), 2.71-2.64 (m, 3H), 2.62 (s, 3H), 2.20 (d, J=12.5 Hz, 1H), 1.59-1.46 (m, 1H), 1.13-0.97 (m, 1H), 1.05 (s, 3H), 0.89 (s, 3H).

Amine 8: 1-((10-Hydroxy-7-azaspiro[4.5]decan-10-yl)methyl)-N,N-dimethyl-6-oxo-4-phenyl-1,6-dihydropyridine-3-carboxamide

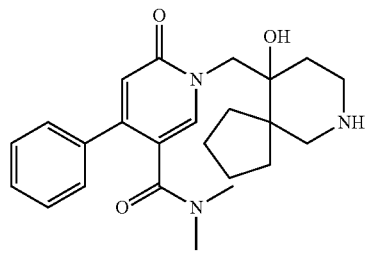 [SMILES: CN(C)C(=O)c1cn(CC2(O)CCNCC23CCCC3)c(=O)cc1-c1ccccc1]

Step 1: tert-Butyl 10-((4-chloro-5-(ethoxycarbonyl)-2-oxopyridin-(2H)-yl)methyl)-10-hydroxy-7-azaspiro[4.5]decane-7-carboxylate Prepared according to General Procedure 1 using ethyl 4-chloro-6-oxo-1,6-dihydropyridine-3-carboxylate (1.06 g, 5.24 mmol), Epoxide 6 (1.75 g, 5.24 mmol) and cesium carbonate (2.56 g, 7.85 mmol) in DMF (20 mL). The reaction was stirred at 80° C. for 16 h to give the title compound (1.02 g, 41%). LCMS (Method A): $R_T$=1.66 min, m/z=413, 415 [M-butene+H]$^+$.

Step 2: tert-Butyl 10-((5-(ethoxycarbonyl)-2-oxo-4-phenylpyridin-1 (2H)-yl)methyl)-10-hydroxy-7-azaspiro[4.5]decane-7-carboxylate Prepared according to General Procedure 4 using tert-butyl 10-((4-chloro-5-(ethoxycarbonyl)-2-oxopyridin-1 (2H)-yl)methyl)-10-hydroxy-7-azaspiro[4.5]decane-7-carboxylate (1.02 g, 2.18 mmol), phenylboronic acid (0.40 g, 3.26 mmol), Pd(dppf)Cl$_2$.DCM (186 mg, 0.218 mmol), sodium carbonate (0.58 g, 5.44 mmol), 1,4-dioxane (9 mL) and water (3 mL). The reaction was heated under microwave irradiation at 150° C. for 15 min to give the title compound (1.02 g, 91%). LCMS (Method A): $R_T$=1.77 min, m/z=511 [M+H]$^+$.

Step 3: 1-((7-(tert-Butoxycarbonyl)-10-hydroxy-7-azaspiro[4.5]decan-10-yl)methyl)-6-oxo-4-phenyl-1,6-dihydropyridine-3-carboxylic acid To a solution of tert-butyl 10-((5-(ethoxycarbonyl)-2-oxo-4-phenylpyridin-1 (2H)-yl)methyl)-10-hydroxy-7-azaspiro [4.5]decane-7-carboxylate (1.24 g, 2.43 mmol) in ethanol (9 mL) was added 2 M NaOH$_{(aq)}$ (9 mL). The resulting mixture was stirred at 55° C. for 3 h. The reaction was concentrated in vacuo and the residue taken up in water. The aqueous was washed with diethyl ether and 2 M HCl$_{(aq)}$ added to the aqueous phase until pH<4. The resulting precipitate was collected by filtration to give the title compound (900 mg, 76%). LCMS (Method A): $R_T$=1.42 min, m/z=483 [M+H]$^+$.

Step 4: tert-Butyl 10-((5-(dimethylcarbamoyl)-2-oxo-4-phenylpyridin-1 (2H)-yl)methyl)-10-hydroxy-7-azaspiro[4.5]decane-7-carboxylate Prepared according to General Procedure 3 using 1-((7-(tert-butoxycarbonyl)-10-hydroxy-7-azaspiro[4.5]decan-10-yl)methyl)-6-oxo-4-phenyl-1,6-dihydropyridine-3-carboxylic acid (1.00 g, 2.07 mmol), dimethylamine (2 M in THF, 1.55 mL, 3.11 mmol), HATU (0.87 g, 2.28 mmol) and DIPEA (1.09 mL, 6.22 mmol) in DCM (20 mL) to give the title compound (1.00 g, 94%). LCMS (Method A): $R_T$=1.39 min, m/z=510 [M+H]$^+$.

Step 5: 1-((10-Hydroxy-7-azaspiro[4.5]decan-10-yl)methyl)-N,N-dimethyl-6-oxo-4-phenyl-1,6-dihydropyridine-3-carboxamide Prepared according to General Procedure 7 using tert-butyl 10-((5-(dimethylcarbamoyl)-2-oxo-4-phenylpyridin-1 (2H)-yl)methyl)-10-hydroxy-7-azaspiro[4.5]decane-7-carboxylate (1.00 g, 1.95 mmol), DCM (20 mL) and TFA (10 mL) to give the title compound (0.56 g, 70%). LCMS (Method A): $R_T$=0.49 min, m/z=410 [M+H]$^+$.

Amine 9: Ethyl (S)-4-(2-fluorophenyl)-1-((4-hydroxy-3,3-dimethylpiperidin-4-yl)methyl)-6-oxo-1,6-dihydropyridine-3-carboxylate

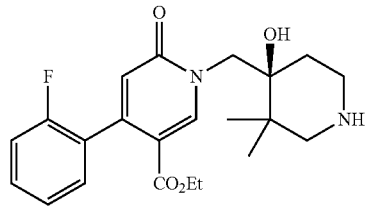 [SMILES: CCOC(=O)c1cn(C[C@]2(O)CCNCC2(C)C)c(=O)cc1-c1ccccc1F]

Step 1: Ethyl (S)-1-((1-(tert-butoxycarbonyl)-4-hydroxy-3,3-dimethylpiperidin-4-yl)methyl)-4-(2-fluorophenyl)-6-oxo-1,6-dihydropyridine-3-carboxylate Prepared according to General Procedure 4 using ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (Amine 7, Step 2) (100 mg, 0.226 mmol), (2-fluorophenyl)boronic acid (47 mg, 0.339 mmol), Pd(dppf)Cl$_2$.DCM (9.6 mg, 11.3 µmol), sodium carbonate (48 mg, 0.452 mmol), 1,4-dioxane (0.75 mL) and water (0.25 mL). The reaction was heated under microwave irradiation at 120° C. for 30 min to give the title compound (96 mg, 84%) as a glassy solid. LCMS (Method A): $R_T$=1.67 min, m/z=503 [M+H]$^+$.

Step 2: Ethyl (S)-4-(2-fluorophenyl)-1-((4-hydroxy-3,3-dimethylpiperidin-4-yl)methyl)-6-oxo-1,6-dihydropyridine-3-carboxylate Prepared according to General Procedure 7 using ethyl (S)-1-((1-(tert-butoxycarbonyl)-4-hydroxy-3,3-dimethylpiperidin-4-yl)methyl)-4-(2-fluorophenyl)-6-oxo-1,6-dihydropyridine-3-carboxylate (96 mg, 0.191 mmol), TFA (0.5 mL) and DCM (1 mL) to give the title compound (67 mg, 87%) as a colourless solid. LCMS (Method A): $R_T$=0.81 min, m/z=403 [M+H]$^+$.

Amine 10: Ethyl (S)-1-((10-hydroxy-7-azaspiro[4.5]decan-10-yl)methyl)-6-oxo-4-phenyl-1,6-dihydropyridine-3-carboxylate

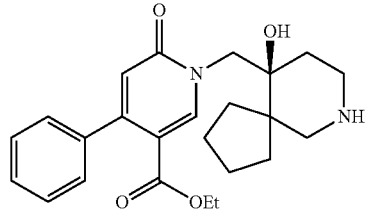 [SMILES: CCOC(=O)c1cn(C[C@]2(O)CCNCC23CCCC3)c(=O)cc1-c1ccccc1]

Step 1: tert-Butyl 10-((4-chloro-5-(ethoxycarbonyl)-2-oxopyridin-1(2H)-yl)methyl)-10-hydroxy-7-azaspiro[4.5]decane-7-carboxylate A solution of ethyl 4-chloro-6-oxo-1,6-dihydropyridine-3-carboxylate (377 mg, 1.87 mmol), Epoxide 6 (500 mg, 1.87 mmol) and DIPEA (1.63 mL, 9.35 mmol) in 1-methyl-2-pyrrolidinone (4 mL) was heated at 110° C. for 48 h. The reaction was allowed to cool to RT, diluted with saturated NaHCO$_{3(aq)}$ (30 mL) and the mixture was extracted with DCM (3×20 mL) using a Biotage phase separator. The combined organic phases were concentrated in vacuo and the residue purified by flash chromatography (GraceResolv silica 40 g cartridge, 0-50% EtOAc in cyclohexane) to give the title compound (338 mg, 38%) as a colourless foam. LCMS (Method A): R$_T$=1.67 min, m/z=469, 471 [M+H]$^+$. $^1$H NMR (500 MHz, DMSO-d$_6$): δ 8.48 (s, 1H), 6.64 (s, 1H), 4.86 (s, 1H), 4.64 (d, J=13.4 Hz, 1H), 4.27 (qd, J=7.1, 2.1 Hz, 2H), 3.61 (d, J=13.4 Hz, 1H), 3.57-3.47 (m, 1H), 3.27-3.11 (m, 3H), 1.93-1.83 (m, 1H), 1.68-1.49 (m, 5H), 1.68-1.49 (m, 1H), 1.38 (s, 9H), 1.32-1.23 (m, 4H), 1.13 (dq, J=12.6, 6.8, 6.4 Hz, 2H).

tert-Butyl 10-((4-Chloro-5-(ethoxycarbonyl)-2-oxopyridin-1 (2H)-yl)methyl)-10-hydroxy-7-azaspiro[4.5]decane-7-carboxylate (9.9 g) was resolved into the single stereoisomers by chiral supercritical fluid chromatography using a Lux C4 (21.2 mm×250 mm, 5 μm) column with isocratic solvent conditions: 35:65 MeOH/CO$_2$. The first eluted material afforded tert-butyl (S)-10-((4-chloro-5-(ethoxycarbonyl)-2-oxopyridin-1(2H)-yl)methyl)-10-hydroxy-7-azaspiro[4.5]decane-7-carboxylate (4.61 g, 46% recovery) as a white solid. Chiral purity (Method B): R$_T$=1.59 min, 100% ee. The second eluted material afforded tert-butyl (R)-10-((4-chloro-5-(ethoxycarbonyl)-2-oxopyridin-1(2H)-yl)methyl)-10-hydroxy-7-azaspiro[4.5]decane-7-carboxylate (4.65 g, 47% recovery) as a white solid. Chiral purity (Method B): R$_T$=2.29 min, 99.6% ee.

Step 2: tert-Butyl (S)-10-((5-(ethoxycarbonyl)-2-oxo-4-phenylpyridin-1 (2H)-yl)methyl)-10-hydroxy-7-azaspiro[4.5]decane-7-carboxylate Prepared according to General Procedure 4 using tert-butyl (S)-10-((4-chloro-5-(ethoxycarbonyl)-2-oxopyridin-1 (2H)-yl)methyl)-10-hydroxy-7-azaspiro[4.5]decane-7-carboxylate (250 mg, 0.533 mmol), phenylboronic acid (97.5 mg, 0.800 mmol), Pd(dppf)Cl$_2$.DCM (22.5 mg, 26.7 μmol), sodium carbonate (113 mg, 1.07 mmol), 1,4-dioxane (2 mL) and water (0.66 mL). The reaction was heated under microwave irradiation at 120° C. for 30 min to give the title compound (274 mg, quantitative) as a pale yellow foam. LCMS (Method A): R$_T$=1.79 min, m/z=511 [M+H]$^+$.

Step 3: Ethyl (S)-1-((10-hydroxy-7-azaspiro[4.5] decan-10-yl)methyl)-6-oxo-4-phenyl-1,6-dihydropyridine-3-carboxylate Prepared according to General Procedure 7 using tert-butyl (S)-10-((5-(ethoxycarbonyl)-2-oxo-4-phenylpyridin-1 (2H)-yl)methyl)-10-hydroxy-7-azaspiro[4.5]decane-7-carboxylate (272 mg, 0.533 mmol), TFA (1.5 mL) and DCM (3 mL) to give the title compound (206 mg, 94%) as a colourless solid. LCMS (Method B): R$_T$=0.82 min, m/z=411 [M+H]$^+$.

Amine 11: Ethyl (S)-4-(2-fluorophenyl)-1-((10-hydroxy-7-azaspiro[4.5]decan-10-yl)methyl)-6-oxo-1,6-dihydropyridine-3-carboxylate

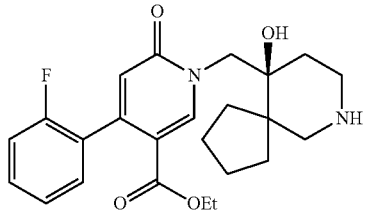 [SMILES: CCOC(=O)c1cn(C[C@]2(O)CCNCC23CCCC3)c(=O)cc1-c1ccccc1F]

Step 1: tert-Butyl (S)-10-((5-(ethoxycarbonyl)-4-(2-fluorophenyl)-2-oxopyridin-1 (2H)-yl)methyl)-10-hydroxy-7-azaspiro[4.5]decane-7-carboxylate Prepared according to General Procedure 4 using tert-butyl (S)-10-((4-chloro-5-(ethoxycarbonyl)-2-oxopyridin-1 (2H)-yl)methyl)-10-hydroxy-7-azaspiro[4.5]decane-7-carboxylate (Amine 10, Step 1) (250 mg, 0.533 mmol), (2-fluorophenyl)boronic acid (112 mg, 0.800 mmol), Pd(dppf)Cl$_2$.DCM (43.5 mg, 53.3 μmol), sodium carbonate (141 mg, 1.33 mmol), 1,4-dioxane (2.1 mL) and water (0.7 mL). The reaction was heated under microwave irradiation at 150° C. for 15 min to give the title compound (280 mg, quantitative) as a pale yellow foam. LCMS (Method A): R$_T$=1.78 min, m/z=529 [M+H]$^+$; 473 [M-butene+H]$^+$.

Step 2: Ethyl (S)-4-(2-fluorophenyl)-1-((10-hydroxy-7-azaspiro[4.5]decan-10-yl)methyl)-6-oxo-1,6-dihydropyridine-3-carboxylate Prepared according to General Procedure 7 using A solution of tert-butyl (S)-10-((5-(ethoxycarbonyl)-2-oxo-4-phenylpyridin-1 (2H)-yl)methyl)-10-hydroxy-7-azaspiro[4.5]decane-7-carboxylate (280 mg, 0.530 mmol), HCl (4 M in 1,4-dioxane, 5 mL) and DCM (5 mL) to give the title compound (200 mg, 88%) as a colourless solid. LCMS (Method A): R$_T$=0.85 min, m/z=429 [M+H]$^+$.

Amine 12: Ethyl (S)-4-cyclopropyl-1-((10-hydroxy-7-azaspiro[4.5]decan-10-yl)methyl)-6-oxo-1,6-dihydropyridine-3-carboxylate

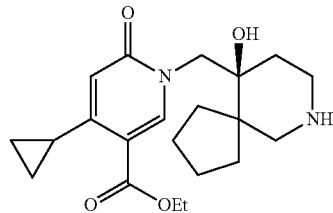 [SMILES: CCOC(=O)c1cn(C[C@]2(O)CCNCC23CCCC3)c(=O)cc1C1CC1]

Step 1: tert-Butyl (S)-10-((4-cyclopropyl-5-(ethoxycarbonyl)-2-oxopyridin-1 (2H)-yl)methyl)-10-hydroxy-7-azaspiro[4.5]decane-7-carboxylate Prepared according to General Procedure 4 using tert-butyl (S)-10-((4-chloro-5-(ethoxycarbonyl)-2-oxopyridin-1

(2H)-yl)methyl)-10-hydroxy-7-azaspiro[4.5]decane-7-carboxylate (250 mg, 0.533 mmol), cyclopropylboronic acid (183 mg, 2.13 mmol), Pd(dppf)Cl$_2$.DCM (21.8 mg, 26.7 μmol), sodium carbonate (339 mg, 3.20 mmol), 1,4-dioxane (1.5 mL) and water (0.5 mL). The reaction was heated under microwave irradiation at 120° C. for 1 h to give the title compound (182 mg, 71%) as a beige foam. LCMS (Method A): $R_T$=1.72 min, m/z=475 [M+H]$^+$.

Step 2: Ethyl (S)-4-cyclopropyl-1-((10-hydroxy-7-azaspiro[4.5]decan-10-yl)methyl)-6-oxo-1,6-dihydropyridine-3-carboxylate Prepared according to General Procedure 7 using a solution of tert-butyl (S)-10-((4-cyclopropyl-5-(ethoxycarbonyl)-2-oxopyridin-1(2H)-yl)methyl)-10-hydroxy-7-azaspiro[4.5]decane-7-carboxylate (180 mg, 0.379 mmol), TFA (2 mL) and DCM (5 mL) to give the title compound (140 mg, quantitative) as a beige foam. LCMS (Method A): $R_T$=0.78 min, m/z=375 [M+H]$^+$.

Intermediate 1: (R)-2,5-Dioxopyrrolidin-1-yl-1-((4-hydroxy-1-(3-phenylbutanoyl)piperidin-4-yl)methyl)-6-oxo-4-phenyl-1,6-dihydropyridine-3-carboxylate

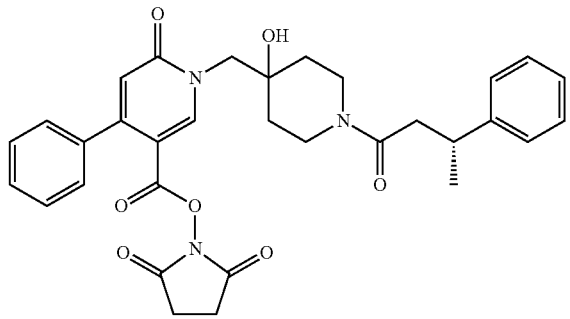 [SMILES: C[C@H](CC(=O)N1CCC(O)(Cn2cc(C(=O)ON3C(=O)CCC3=O)c(-c3ccccc3)cc2=O)CC1)c1ccccc1]

Step 1: Ethyl 6-chloro-4-phenylnicotinate

5-Bromo-2-chloro-4-phenylpyridine (0.5 g, 1.86 mmol) was dissolved in anhydrous THF (15 mL) and the mixture was cooled to −78° C. under N$_2$. n-Butyllithium (2.5 M in hexanes, 0.894 mL, 2.23 mmol) was added slowly and the mixture was stirred for 15 min. Ethyl chloroformate (0.197 mL, 2.05 mmol) was added and the mixture was stirred for 1 h at −60° C. then allowed to warm to RT. The reaction was quenched by the addition of water and extracted with EtOAc (×3). The combined organic extracts were washed with brine, dried (MgSO$_4$) and concentrated. The residue was purified by flash chromatography (GraceResolv, 0-5% EtOAc in cyclohexane) to give the title compound (279 mg, 57%). LCMS (Method B): $R_T$=1.44 min, m/z=262 [M+H]$^+$.

Step 2: Ethyl 6-oxo-4-phenyl-1,6-dihydropyridine-3-carboxylate

Prepared according to General Procedure 10 using ethyl 6-chloro-4-phenylnicotinate (100 mg, 0.382 mmol) in acetic acid (4 mL, 69.9 mmol) and water (1 mL) to give the title compound (90 mg, 97%). LCMS (Method B): $R_T$=0.91 min, m/z=244 [M+H]$^+$.

Step 3: (R)-Ethyl 1-((4-hydroxy-1-(3-phenylbutanoyl)piperidin-4-yl)methyl)-6-oxo-4-phenyl-1,6-dihydropyridine-3-carboxylate Ethyl 6-oxo-4-phenyl-1,6-dihydropyridine-3-carboxylate (1.45 g, 5.96 mmol) and Epoxide 2 (1.55 g, 5.96 mmol) were dissolved in DMF (30 mL) and pyridine (0.723 mL, 8.94 mmol) was added. The reaction was heated to 80° C. and stirred for 18 h. The solution was cooled to RT and diluted with water, then the mixture was extracted with EtOAc. The organic layer was washed with water (×3) then brine, dried over anhydrous sodium sulfate, filtered and concentrated. The residue was purified by flash chromatography (GraceResolv, 0-70% EtOAc in cyclohexane) to give the title compound (883 mg, 30%). LCMS (Method B): $R_T$=1.29 min, m/z=503 [M+H]$^+$.

Step 4: (R)-1-((4-Hydroxy-1-(3-phenylbutanoyl)piperidin-4-yl)methyl)-6-oxo-4-phenyl-1,6-dihydropyridine-3-carboxylic acid (R)-Ethyl 1-((4-hydroxy-1-(3-phenylbutanoyl)piperidin-4-yl)methyl)-6-oxo-4-phenyl-1,6-dihydropyridine-3-carboxylate (884 mg, 1.76 mmol) was dissolved in THF (2 mL) and sodium hydroxide (2 M in water, 4.4 mL, 8.8 mmol) was added. The reaction mixture was stirred for 18 h at RT. Further aqueous sodium hydroxide (2 mL) was added and the reaction mixture was stirred for 48 h at RT. The solution was concentrated to remove THF. The residue was diluted with water and extracted with diethyl ether (×3) and the organic layer was discarded. The aqueous layer was acidified to ~pH4 and extracted with EtOAc (×3). The combined organic extracts were dried (MgSO$_4$) and concentrated to give the title compound (738 mg, 88%). LCMS (Method B): $R_T$=1.04 min, m/z 475 [M+H]$^+$.

Step 5: (R)-2,5-Dioxopyrrolidin-1-yl 1-((4-hydroxy-1-(3-phenylbutanoyl)piperidin-4-yl)methyl)-6-oxo-4-phenyl-1,6-dihydropyridine-3-carboxylate (R)-1-((4-Hydroxy-1-(3-phenylbutanoyl)piperidin-4-yl)methyl)-6-oxo-4-phenyl-1,6-dihydropyridine-3-carboxylic acid (450 mg, 0.95 mmol) and 1-hydroxypyrrolidine-2,5-dione (142 mg, 1.23 mmol) were dissolved in DMF (6 mL) and EDC (273 mg, 1.42 mmol) was added. The reaction mixture was stirred for 19 h at RT. The solution was diluted with EtOAc and washed with water (×3). The organic layer was dried over anhydrous sodium sulfate, filtered and concentrated. The residue was purified by flash chromatography (GraceResolv, 0-100% EtOAc in cyclohexane) to give the title compound (532 mg, 98%). LCMS (Method B): $R_T$=1.19 min, m/z=572 [M+H]$^+$.

Intermediate 2: (R)-5-Bromo-4-chloro-1-((4-hydroxy-1-(3-phenylbutanoyl)piperidin-4-yl)methyl)pyridin-2(1H)-one

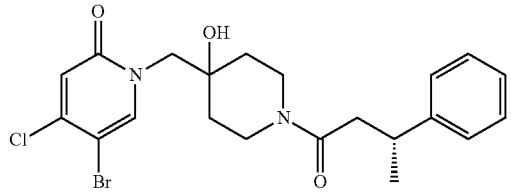 [SMILES: C[C@H](CC(=O)N1CCC(O)(Cn2cc(Br)c(Cl)cc2=O)CC1)c1ccccc1]

Step 1

5-Bromo-4-chloropyridin-2(1H)-one: A mixture of water (2.2 mL) and concentrated sulfuric acid (0.31 mL, 5.78 mmol) was cooled to 0° C. and 5-bromo-4-chloropyridin-2-amine (500 mg, 2.41 mmol) was added in one portion. A solution of sodium nitrite (183 mg, 2.65 mmol) in water (0.2 mL) was added dropwise so that the internal temperature did not rise above 5° C. The reaction was stirred at 0° C. for 3 h. The suspension was taken to pH 7 by addition of concentrated aqueous ammonia and the precipitate was collected by filtration to give the title compound (440 mg, 88%) as a pale yellow solid. LCMS (Method B): $R_T$=0.70 min, m/z=209 [M+H]$^+$. $^1$H NMR (400 MHz, DMSO-d$_6$): δ 7.94 (s, 1H), 6.75 (s, 1H).

Step 2: (R)-5-Bromo-4-chloro-1-((4-hydroxy-1-(3-phenylbutanoyl)piperidin-4-yl)methyl)pyridin-2(1H)-one A mixture of 5-bromo-4-chloropyridin-2(1H)-one (200 mg, 0.960 mmol), Epoxide 2 (299 mg, 1.15 mmol) and pyridine (0.2 mL, 2.88 mmol) in DMF (5 mL) was stirred at 80° C. for 16 h. The mixture was cooled and partitioned between EtOAc and 50% saturated brine. The organic layer was washed with 4×50% saturated brine and the aqueous layer was extracted with 3×EtOAc. The combined organic extracts were dried (MgSO$_4$) and concentrated. The residue was purified by flash chromatography (GraceResolv 12 g, 5-80% EtOAc in cyclohexane) to give the title compound (248 mg, 55%). LCMS (Method B): $R_T$=1.17 min, m/z=469 [M+H]$^+$. $^1$H NMR (400 MHz, methanol-d$_4$): δ 7.98-7.93 (m, 1H), 7.34-7.15 (m, 5H), 6.79 (s, 1H), 4.24-4.10 (m, 2H), 4.06-3.77 (m, 2H), 3.70-3.60 (m, 1H), 3.28-3.12 (m, 2H), 3.05-2.86 (m, 1H), 2.82-2.69 (m, 1H), 2.62-2.45 (m, 1H), 1.62-1.49 (m, 1H), 1.47-1.26 (m, 5H), 0.90-0.81 (m, 1H).

Intermediate 3: 6-Chloro-3-((1-((R)-3-cyclohexyl-2-methylpropanoyl)-4-hydroxy-3,3-dimethylpiperidin-4-yl)methyl)pyrimidin-4(3H)-one

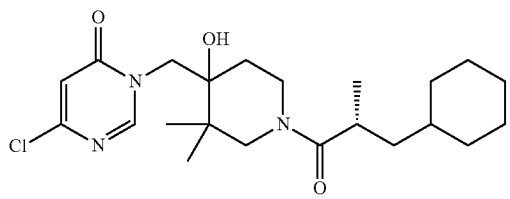 [SMILES: C[C@H](CC1CCCCC1)C(=O)N1CCC(O)(Cn2cnc(Cl)cc2=O)C(C)(C)C1]

Step 1: tert-Butyl 4-((4-chloro-6-oxopyrimidin-1(6H)-yl)methyl)-4-hydroxy-3,3-dimethylpiperidine-1-carboxylate Prepared according to General Procedure 1 using 6-chloropyrimidin-4(3H)-one (600 mg, 4.60 mmol), Epoxide 3 (1.22 g, 5.06 mmol) and potassium tert-butoxide (0.57 g, 5.06 mmol) in DMSO (6 mL), heated to 70° C. for 64 h to give the title compound (0.55 g, 32%). LCMS (Method A): $R_T$=1.36 min, m/z=316, 318 [M-butene+H]$^+$.

Step 2: 6-Chloro-3-((4-hydroxy-3,3-dimethylpiperidin-4-yl)methyl)pyrimidin-4(3H)-one hydrochloride Prepared according to General Procedure 9 using tert-butyl 4-((4-chloro-6-oxopyrimidin-1 (6H)-yl)methyl)-4-hydroxy-3,3-dimethylpiperidine-1-carboxylate (550 mg, 1.48 mmol) and HCl (4 M in 1,4-dioxane, 8 mL, 32.0 mmol), stirred at 45° C. for 1 h to give the title compound (0.42 g, 92%). LCMS (Method A): $R_T$=0.32 min, m/z=272 [M+H]$^+$.

Step 3: 6-Chloro-3-((1-((R)-3-cyclohexyl-2-methylpropanoyl)-4-hydroxy-3,3-dimethylpiperidin-4-yl)methyl)pyrimidin-4(3H)-one Prepared according to General Procedure 3 using 6-chloro-3-((4-hydroxy-3,3-dimethylpiperidin-4-yl)methyl)pyrimidin-4(3H)-one (420 mg, 1.36 mmol), (R)-3-cyclohexyl-2-methylpropanoic acid (Acid 1) (255 mg, 1.50 mmol), HATU (622 mg, 1.64 mmol) and DIPEA (0.952 mL, 5.45 mmol) in DCM (15 mL) to give the title compound (450 mg, 77%). LCMS (Method A): $R_T$=1.62 min, m/z=424 [M+H]$^+$.

Acid 1: (R)-3-Cyclohexyl-2-methylpropanoic acid

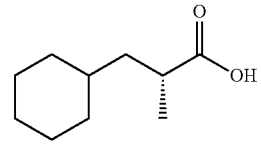

Step 1: 3-Cyclohexylpropanoyl Chloride

3-Cyclohexylpropanoic acid (2.19 mL, 12.8 mmol) was dissolved in anhydrous DCM (40 mL) and the mixture was cooled to 0° C. Thionyl chloride (1.88 mL, 25.6 mmol) was added. The colourless solution was heated to reflux for 1.75 h before the reaction was cooled to RT and stirred for a further 67.5 h. The mixture was concentrated and the yellow oil was dried by azeotropic distillation with toluene (2×10 mL) to give the crude title compound (2.3 g, quantitative) which was used without further purification. $^1$H NMR (400 MHz, CDCl$_3$): δ 2.90 (t, 2H), 1.76-1.47 (m, 7H), 1.33-1.07 (m, 4H), 0.96-0.84 (m, 2H).

Step 2: (R)-4-Benzyl-3-(3-cyclohexylpropanoyl)oxazolidin-2-one (R)-4-Benzyloxazolidin-2-one (2.33 g, 13.2 mmol) was dissolved in anhydrous THF (40 mL) and the mixture was cooled to −78° C. n-Butyllithium (2.5 M in hexanes, 5.27 mL, 13.2 mmol) was added dropwise to form a colourless solution which was stirred at −78° C. for 1.5 h. 3-Cyclohexylpropanoyl chloride (2.3 g, 13.2 mmol) was added dropwise as a solution in anhydrous THF (20 mL). The mixture was stirred at −78° C. for 1 h then allowed to warm to RT and stirred for a further 18 h. Saturated aqueous ammonium chloride (14 mL) was added and the mixture was concentrated. The residue was partitioned between EtOAc (20 mL) and water (20 mL). The aqueous layer was extracted with EtOAc (3×20 mL) and the combined organic extracts were washed with brine (1×20 mL), dried over anhydrous magnesium sulfate and concentrated. The crude product was washed with ice cold cyclohexane to give the title compound (3.84 g, 93%). $^1$H NMR (400 MHz, CDCl$_3$): δ 7.38-7.18 (m, 5H), 4.72-4.63 (m, 1H), 4.24-4.13 (m, 2H), 3.30 (dd, 1H), 3.04-2.87 (m, 2H), 2.77 (dd, 1H), 1.80-1.52 (m, 7H), 1.37-1.08 (m, 4H), 1.00-0.87 (m, 2H).

Step 3: (R)-4-Benzyl-3-((R)-3-cyclohexyl-2-methyl-propanoyl)oxazolidin-2-one (R)-4-Benzyl-3-(3-cyclohexylpropanoyl)oxazolidin-2-one (2.50 g, 7.93 mmol) was dissolved in anhydrous THF (40 mL) and cooled to −78° C. NaHMDS (1 M in THF, 8.72 mL, 8.72 mmol) was added dropwise and the yellow solution was stirred at −78° C. for 40 min. Methyl iodide (2.48 mL, 39.6 mmol) was added dropwise and the reaction mixture was left to stir for 21 h. Brine (10 mL) was added dropwise and the mixture was allowed to return to RT. The volatiles were removed then the residue was partitioned between DCM and water. The DCM was separated and the aqueous layer was extracted with DCM (×3). The combined organic extracts were washed with brine then filtered through a Biotage phase separator and concentrated. The residue was purified by flash chromatography (GraceResolv 40 g, 0 to 10% EtOAc in PE) to give the title compound (1.66 g, 64%). $^1$H NMR (400 MHz, CDCl$_3$): δ 7.39-7.17 (m, 5H), 4.71-4.64 (m, 1H), 4.24-4.14 (m, 2H), 3.84 (m, 1H), 3.27 (dd, 1H), 2.76 (dd, 1H), 1.78-1.58 (br m, 6H), 1.32-1.08 (br m, 8H), 0.96-0.82 (br m, 2H).

Step 4: (R)-3-Cyclohexyl-2-methylpropanoic acid

A solution of lithium hydroxide (0.143 g, 5.99 mmol) in water (3 mL) was added to hydrogen peroxide 30% w/w (3.06 mL, 29.9 mmol) at 0° C. and the solution was stirred for 10 min at this temperature. The resulting mixture was added dropwise to a solution of (R)-4-benzyl-3-((R)-3-cyclohexyl-2-methylpropanoyl)oxazolidin-2-one (0.99 g, 2.99 mmol) in a mixture of water (10 mL) and THF (40.0 mL) at 0° C. and the solution was allowed to warm to RT over 2 h before stirring at RT for 14 h. Saturated aqueous sodium thiosulfate solution (35 mL) was added dropwise at 0° C. and the reaction mixture was stirred for 30 min. The solution was partitioned between DCM (50 mL) and water (50 mL) and the layers were separated. The aqueous layer was extracted with DCM (3×20 mL) and the organic layers were discarded. The aqueous layer was acidified with HCl$_{(aq)}$ (2 M) until pH 2. The resulting solution was extracted with EtOAc (3×20 mL). The combined organic extracts were washed with water (3×20 mL), brine (2×20 mL), dried over anhydrous magnesium sulfate and concentrated to give the title compound (0.51 g, 95%) which was used without further purification. $^1$H NMR (400 MHz, DMSO-d$_6$): δ 11.99 (s, 1H), 2.44-2.35 (m, 1H), 1.75-1.55 (br m, 5H), 1.53-1.43 (m, 1H), 1.30-1.07 (m, 5H), 1.04 (d, 3H), 0.91-0.77 (m, 2H).

Acid 2: (R)-2-(Cyclohexylmethyl)pent-4-enoic acid

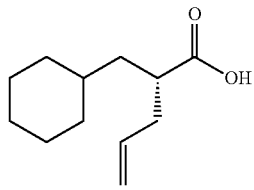

Prepared analogously to Acid 1, deviating as follows:

Step 3: (R)-4-Benzyl-3-((R)-2-(cyclohexylmethyl) pent-4-enoyl)oxazolidin-2-one Prepared using (R)-4-benzyl-3-(3-cyclohexylpropanoyl) oxazolidin-2-one (0.20 g, 0.63 mmol), NaHMDS (1 M in THF, 0.70 mL, 0.70 mmol) and 3-bromoprop-1-ene (0.27 mL, 3.17 mmol) in THF (3.5 mL), stirring for 1 h. The reaction mixture was then allowed to warm to RT over 21.5 h and the crude product was purified using flash chromatography (GraceResolv 12 g, 0-10% EtOAc in PE) to give the title compound (0.18 g, 80%). $^1$H NMR (400 MHz, CDCl$_3$): δ 7.36-7.20 (m, 5H), 5.89-5.77 (m, 1H), 5.13-5.01 (m, 2H), 4.69 (m, 1H), 4.21-4.09 (m, 2H), 4.08-4.00 (m, 1H), 3.31 (dd, 1H), 2.65 (dd, 1H), 2.47-2.27 (m, 2H), 1.75-1.78 (m, 6H), 1.38-1.29 (m, 1H), 1.28-1.05 (m, 4H), 0.97-0.79 (m, 2H).

Step 4: (R)-2-(Cyclohexylmethyl)pent-4-enoic acid

A mixture of (R)-4-benzyl-3-((R)-2-(cyclohexylmethyl) pent-4-enoyl)oxazolidin-2-one (173 mg, 0.487 mmol) and lithium hydroxide (23.3 mg, 0.973 mmol) was dissolved in water (0.5 mL). A solution of hydrogen peroxide 30% w/w (0.50 mL, 4.87 mmol) in a mixture of water (1 mL) and THF (4.00 mL) was added at 0° C. and the mixture was stirred at the same temperature for 1.5 h. The mixture was allowed to warm to RT and stirred for 20 h to give the title compound (79.8 mg, 84%) which was used without further purification. $^1$H NMR (400 MHz, DMSO-d$_6$): δ 12.08 (s, 1H), 5.77-5.65 (m, 1H), 5.06-4.94 (m, 2H), 2.43-2.33 (m, 1H), 2.25-2.06 (m, 2H), 1.73 (br d, 1H), 1.68-1.52 (br m, 4H), 1.48-1.36 (br m, 1H), 1.29-1.02 (br m, 5H), 0.91-0.73 (br m, 2H).

Acid 3: 1-((1-((R)-3-Cyclohexyl-2-methylpropanoyl)-4-hydroxy-3,3-dimethylpiperidin-4-yl) methyl)-6-oxo-4-phenyl-1,6-dihydropyridine-3-carboxylic acid

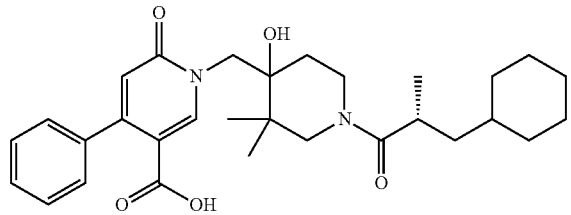 [SMILES: C[C@H](CC1CCCCC1)C(=O)N1CCC(O)(Cn2cc(C(=O)O)c(-c3ccccc3)cc2=O)C(C)(C)C1]

Step 1: 4-((5-(Ethoxycarbonyl)-2-oxo-4-phenylpyridin-1 (2H)-yl)methyl)-4-hydroxy-3,3-dimethylpiperidin-1-ium chloride Ethyl 1-((1-(tert-butoxycarbonyl)-4-hydroxy-3,3-dimethylpiperidin-4-yl)methyl)-6-oxo-4-phenyl-1,6-dihydropyridine-3-carboxylate (Amine 6, Step 1) (485 mg, 1.00 mmol) was added to 4 M HCl in 1,4-dioxane (5.0 mL) and the resulting mixture was stirred at RT. After 30 min, the solvents were removed in vacuo to give the crude title compound (535 mg, >100%) as an off-white solid that was carried through to the next step without purification. LCMS (Method A): R$_T$=0.86 min, m/z=385 [M-$^t$Bu+H]$^+$.

Step 2: Ethyl 1-((1-((R)-3-cyclohexyl-2-methylpropanoyl)-4-hydroxy-3,3-dimethylpiperidin-4-yl) methyl)-6-oxo-4-phenyl-1,6-dihydropyridine-3-carboxylate DIPEA (0.35 mL, 2.00 mmol) was added to a stirred solution of 4-((5-(ethoxycarbonyl)-2-oxo-4-phenylpyridin-1 (2H)-yl)methyl)-4-hydroxy-3,3-dimethylpiperidin-1-ium chloride (421 mg, 1.00 mmol), (R)-3-cyclohexyl-2-methylpropanoic acid (Acid 1) (170 mg, 1.00 mmol) and HATU (456 mg, 1.2 mmol) in DCM (10 mL) at RT. After 1 h, the reaction mixture was partitioned between DCM and saturated sodium bicarbonate (aq) solution. The resulting biphasic mixture was separated, dried (phase separator), the solvents were removed in vacuo, and the remaining residue was purified by flash chromatography (cyclohexane; then 0-10%, MeOH in EtOAc) to give the crude title compound (crude 841 mg, >100%) as a pale yellow oil that was carried through to the next step without further purification. LCMS (Method A): $R_T$=1.86 min, m/z=537 [M+H]$^+$.

Step 3: 1-((1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid 1 M NaOH (aq) solution (2.0 mL, 2.00 mmol) was added to a stirred solution of ethyl 1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylate (assumed 537 mg, 1.00 mmol) in 1,4-dioxane (2.0 mL) at RT. After 16 h, the temperature was increased to 50° C. After a further 2 h, the reaction mixture was cooled and the pH was adjusted to pH 2-3 by the addition of 2 M HCl (aq) solution, and was extracted using EtOAc (×3). The combined organic phase was washed using saturated sodium bicarbonate (aq) solution. After separation, due to incomplete extraction, pH of the basic aqueous phase was adjusted to ca. pH 6 and it was extracted using further EtOAc (×3). The combined organic phases that contained the product were concentrated in vacuo to give the crude title compound (539 mg, >100%) as a pale yellow solid that was carried through to subsequent steps without further purification. LCMS (Method A): $R_T$=1.52 min, m/z=509 [M+H]$^+$. $^1$H NMR (500 MHz, DMSO-d$_6$): δ 8.01 (s, 1H), 7.61-7.03 (m, 5H), 6.17-6.12 (m, 1H), 5.25 (brs, 1H), 4.46-4.28 (m, 1H), 4.13-3.58 (m, 3H), 3.29-2.78 (m, 3H, overlapping solvent peak), 1.85-1.37 (m, 7H), 1.33-0.62 (m, 18H).

Acid 4: 1-(((S)-1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid

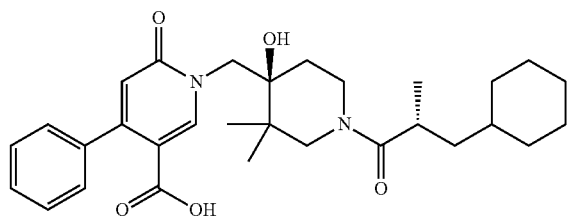 [SMILES: C[C@H](CC1CCCCC1)C(=O)N1CC[C@@](O)(Cn2cc(C(=O)O)c(-c3ccccc3)cc2=O)C(C)(C)C1]

Step 1: Ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate PdCl$_2$(dppf).DCM (18.4 mg, 0.0226 mmol) was added to a pre-degassed solution of ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (Amine 7, Step 2) (200 mg, 0.452 mmol), phenylboronic acid (82.6 mg, 0.677 mmol) and sodium carbonate (95.7 mg, 0.903 mmol) in 1,4-dioxane (0.75 mL)/water (0.25 mL) in a 10 mL vial. The vessel was sealed and heated under microwave irradiation (CEM) at 120° C. with stirring for 30 min. Due to incomplete reaction, the reaction was rerun under the same conditions. The reaction mixture was partitioned between EtOAc and brine, separated, extracted (EtOAc×2), the combined organic phase was dried (phase separator), the solvents were removed in vacuo, and the remaining residue was purified by flash chromatography (0-5%, MeOH in DCM) to give the title compound (227 mg, >100%) as a pale yellow oil. LCMS (Method A): $R_T$=1.67 min, m/z=485 [M+H]$^+$.

Step 2: (S)-4-((5-(Ethoxycarbonyl)-2-oxo-4-phenylpyridin-1 (2H)-yl)methyl)-4-hydroxy-3,3-dimethylpiperidin-1-ium chloride 4 M HCl in 1,4-dioxane (2.2 mL, 63.4 mmol) was added to ethyl (S)-1-((1-(tert-butoxycarbonyl)-4-hydroxy-3,3-dimethylpiperidin-4-yl)methyl)-6-oxo-4-phenyl-1,6-dihydropyridine-3-carboxylate and the resulting mixture was stirred at RT. After 1 h, the solvents were removed in vacuo to give the crude title compound (229 mg, >100%) as a pale yellow solid that was carried through to the next step without further purification. LCMS (Method A): $R_T$=0.82 min, m/z=419 [M−H]$^-$.

Step 3: Ethyl 1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylate DIPEA (0.24 mL, 1.35 mmol) was added to a stirred solution of (S)-4-((5-(ethoxycarbonyl)-2-oxo-4-phenylpyridin-1(2H)-yl)methyl)-4-hydroxy-3,3-dimethylpiperidin-1-ium chloride (190 mg, 0.452 mmol), (R)-3-cyclohexyl-2-methylpropanoic acid (Acid 1) (76.9 mg, 0.452 mmol) and HATU (206 mg, 0.542 mmol) in DCM (5.0 mL) at RT. After 2 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography (0-50%, EtOAc in cyclohexane) to give the title compound (153 mg, 63%) as a colourless gum.
LCMS (Method A): $R_T$=1.86 min, m/z=537 [M+H]$^+$.

Step 4: 1-(((S)-1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid 1 M Sodium hydroxide (aq) solution (0.57 mL, 0.571 mmol) was added to a stirred solution of ethyl 1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylate (153 mg, 0.285 mmol) in 1,4-dioxane (1.4 mL) at RT. The temperature was increased to 50° C. After 2 h, the reaction mixture was cooled and the pH was adjusted to pH 4-5 by the addition of 1 M HCl (aq) solution (ca. 0.75 mL) and extracted using EtOAc (×3). The combined organic phase was dried, the solvents were removed in vacuo and the remaining residue was purified by flash chromatography (0-100%, EtOAc in cyclohexane) to yield the title compound (101 mg, 70%) as a white solid. LCMS (Method A): $R_T$=1.53 min, m/z=509 [M+H]$^+$.

Acid 5: (R)-3-Cyclobutyl-2-methylpropanoic acid

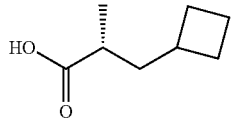

Step 1: (R)-4-Benzyl-3-(3-cyclobutylpropanoyl)oxazolidin-2-one

Pivaloyl chloride (1.2 mL, 9.75 mmol) and then triethylamine (1.41 mL, 10.1 mmol) were added to a suspension of 3-cyclobutylpropionic acid (500 mg, 3.90 mmol), (R)-4-benzyl-2-oxazolidinone (760 mg, 4.29 mmol) and lithium chloride (331 mg, 7.80 mmol) in THF (10 mL) at −20° C. After 30 min, the reaction was allowed to slowly warm to RT before being quenched by the addition of saturated $NaHCO_{3(aq)}$ (60 mL). The resulting mixture was extracted with DCM (3×30 mL) using a Biotage phase separator, the combined organic phases were concentrated in vacuo and the residue was purified by flash chromatography (GraceResolv silica 80 g cartridge, 0-30% EtOAc in cyclohexane) to give the title compound (966 mg, 86%) as a colourless viscous oil. $^1$H NMR (500 MHz, $CDCl_3$): δ 7.37-7.31 (m, 2H), 7.30-7.27 (m, 1H), 7.24-7.16 (m, 2H), 4.67 (ddt, J=10.5, 6.9, 3.2 Hz, 1H), 4.22-4.14 (m, 2H), 3.30 (dd, J=13.4, 3.4 Hz, 1H), 2.91-2.73 (m, 3H), 2.34 (hept, J=7.8 Hz, 1H), 2.12-2.03 (m, 2H), 1.92-1.72 (m, 4H), 1.69-1.60 (m, 2H).

Step 2: (R)-4-Benzyl-3-((R)-3-cyclobutyl-2-methylpropanoyl)oxazolidin-2-one NaHMDS (1 M in THF, 1.91 mL, 1.91 mmol) was dropwise added to a solution of (R)-4-benzyl-3-(3-cyclobutylpropanoyl)oxazolidin-2-one (500 mg, 1.74 mmol) in THF (8.7 mL) at −78° C. and after 90 min, iodomethane (0.542 mL, 8.70 mmol) was added dropwise. The reaction was allowed to stir at −78° C. overnight before being allowed to slowly warm to RT. The reaction was quenched by the addition of saturated $NH_4Cl_{(aq)}$ (60 mL) and the resulting mixture extracted with DCM (3×30 mL) using a Biotage phase separator. The combined organic phases were concentrated in vacuo and the residue purified by flash chromatography (GraceResolv silica 80 g cartridge, 0-30% EtOAc in cyclohexane) to give the title compound (360 mg, 68%) as a viscous colourless oil. LCMS (Method A): $R_T$=1.91 min, m/z=302 [M+H]$^+$. $^1$H NMR (500 MHz, $CDCl_3$): δ 7.36-7.24 (m, 3H), 7.23-7.17 (m, 2H), 4.65 (ddt, J=10.3, 7.0, 3.1 Hz, 1H), 4.23-4.13 (m, 2H), 3.69 (h, J=6.9 Hz, 1H), 3.27 (dd, J=13.4, 3.3 Hz, 1H), 2.76 (dd, J=13.4, 9.6 Hz, 1H), 2.33 (hept, J=7.9 Hz, 1H), 2.01 (dddt, J=19.0, 11.7, 7.7, 3.9 Hz, 2H), 1.89-1.73 (m, 3H), 1.63 (tt, J=18.3, 9.0 Hz, 2H), 1.56-1.49 (m, 1H), 1.19 (d, J=6.8 Hz, 3H).

Step 3: (R)-3-Cyclobutyl-2-methylpropanoic acid

A 30% aqueous hydrogen peroxide solution (0.453 mL, 4.43 mmol) was added to a solution of (R)-4-benzyl-3-((R)-3-cyclobutyl-2-methylpropanoyl)oxazolidin-2-one (334 mg, 1.11 mmol) in THF (5.5 mL) and water (5.5 mL) at 0° C. After 5 min, lithium hydroxide (53 mg, 2.22 mmol) was added and the mixture stirred for 2 h before the reaction was quenched by the addition of saturated sodium thiosulfate$_{(aq)}$ (2 mL). The reaction mixture was allowed to warm to RT, concentrated in vacuo to remove the THF and the resulting biphasic mixture extracted with DCM (3×10 mL). The pH of the aqueous phase was adjusted to pH 2 by the addition of 2 M HCl$_{(aq)}$ and the mixture extracted with Et$_2$O (3×10 mL). The combined ethereal extractions were passed through a Biotage phase separator, carefully concentrated at 45° C. (no vacuum) and the residue dried at 300 mbar (no heat) for 5 min to give the title compound (172 mg, 92%) as a very pale yellow oil containing 15% w/w Et$_2$O. $^1$H NMR (500 MHz, $CDCl_3$): δ 2.45-2.30 (m, 2H), 2.05 (dtt, J=19.1, 7.9, 3.9 Hz, 2H), 1.91-1.74 (m, 3H), 1.67-1.48 (m, 3H), 1.18-1.10 (m, 3H).

Acid 6: (R)-3-Cyclopropyl-2-methylpropanoic acid

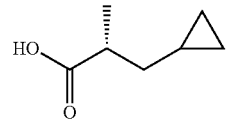

Step 1: (R)-4-Benzyl-3-(3-cyclopropylpropanoyl)oxazolidin-2-one

Pivaloyl chloride (1.36 mL, 11.0 mmol) and then triethylamine (1.60 mL, 11.5 mmol) were added to a suspension of 3-cyclopropylpropionic acid (504 mg, 4.42 mmol), (R)-4-benzyl-2-oxazolidinone (861 mg, 4.86 mmol) and lithium chloride (374 mg, 8.83 mmol) in THF (11 mL) at −20° C. After 30 min, the reaction was allowed to slowly warm to RT before being quenched by the addition of saturated $NaHCO_{3(aq)}$ (60 mL). The resulting mixture was extracted with DCM (3×30 mL) using a Biotage phase separator, the combined organic phases were concentrated in vacuo and the residue purified by flash chromatography (GraceResolv silica 80 g cartridge, 0-30% EtOAc in cyclohexane) to give the title compound (1.16 g, 96%) as a colourless viscous oil. LCMS (Method A): $R_T$=1.65 min, m/z=274 [M+H]$^+$. $^1$H NMR (500 MHz, $CDCl_3$): δ 7.38-7.30 (m, 2H), 7.30-7.26 (m, 1H), 7.24-7.17 (m, 2H), 4.68 (ddt, J=10.4, 6.9, 3.1 Hz, 1H), 4.23-4.14 (m, 2H), 3.31 (dd, J=13.4, 3.3 Hz, 1H), 3.05 (qt, J=16.8, 7.4 Hz, 2H), 2.77 (dd, J=13.4, 9.6 Hz, 1H), 1.60 (q, J=7.3 Hz, 2H), 0.79 (dtdd, J=15.0, 7.3, 6.2, 4.9, 2.4 Hz, 1H), 0.51-0.41 (m, 2H), 0.14-0.04 (m, 2H).

Step 2: (R)-4-Benzyl-3-((R)-3-cyclo-2-methypropanoyl)oxazolidin-2-one

NaHMDS (1 M in THF, 2.29 mL, 2.29 mmol) was added dropwise to a solution of (R)-4-benzyl-3-(3-cyclopropylpropanoyl)oxazolidin-2-one (500 mg, 1.83 mmol) in THF (9 mL) at −78° C. and after 90 min, iodomethane (0.569 mL, 9.15 mmol) was added dropwise. The reaction was allowed to stir at −78° C. for 18.5 h and quenched by the addition of saturated $NH_4Cl_{(aq)}$ (60 mL). After warming to RT, the mixture was extracted with DCM (3×30 mL) using a Biotage phase separator, the combined organic phases were concentrated in vacuo and the residue purified by flash chromatography (GraceResolv silica 80 g cartridge, 0-20% EtOAc in cyclohexane) to give the title compound (441 mg, 83%) as a viscous colourless oil. LCMS (Method A): $R_T$=1.78 min, m/z=288 [M+H]$^+$. $^1$H NMR (500 MHz, CDCl₃): δ 7.36-7.30 (m, 2H), 7.30-7.25 (m, 1H), 7.24-7.19 (m, 2H), 4.67 (ddt, J=10.1, 6.8, 3.3 Hz, 1H), 4.22-4.14 (m, 2H), 3.88 (h, J=6.9 Hz, 1H), 3.28 (dd, J=13.4, 3.3 Hz, 1H), 2.78 (dd, J=13.4, 9.6 Hz, 1H), 1.58 (dt, J=14.2, 7.2 Hz, 1H), 1.43 (dt, J=13.6, 6.7 Hz, 1H), 1.26 (d, J=6.9 Hz, 3H), 0.73 (ddt, J=10.2, 7.4, 3.7 Hz, 1H), 0.41 (dtt, J=21.1, 8.3, 4.2 Hz, 2H), 0.07 (ddt, J=14.8, 8.6, 4.2 Hz, 2H).

Step 4: (R)-3-Cyclopropyl-2-methylpropanoic acid

A 30% aqueous hydrogen peroxide solution (0.606 mL, 5.93 mmol) was added to a solution of (R)-4-benzyl-3-((R)-3-cyclopropyl-2-methylpropanoyl)oxazolidin-2-one (426 mg, 1.48 mmol) in THF (7.4 mL) and water (7.4 mL) at 0° C. After 5 min, lithium hydroxide (71 mg, 2.97 mmol) was added and the mixture stirred for 30 min before the reaction was quenched by the addition of saturated sodium thiosulfate$_{(aq)}$ (2 mL). The reaction mixture was allowed to warm to RT, concentrated in vacuo to remove the THF and the resulting biphasic mixture extracted with DCM (3×10 mL). The pH of the aqueous phase was adjusted to pH 2 by the addition of 2 M HCl$_{(aq)}$ and the mixture was extracted with Et₂O (3×10 mL). The combined ethereal extractions were passed through a Biotage phase separator, carefully concentrated at 45° C. (no vacuum) and the residue dried at 300 mbar (no heat) for 5 min to give the title compound (211 mg, 96%) as a very pale yellow oil containing 13% w/w Et₂O. ¹H NMR (500 MHz, CDCl₃): δ 2.60 (h, J=7.0 Hz, 1H), 1.59 (dt, J=14.1, 7.2 Hz, 1H), 1.39 (dt, J=13.8, 6.8 Hz, 1H), 1.23 (d, J=7.0 Hz, 3H), 0.74 (dqd, J=12.4, 7.5, 4.9 Hz, 1H), 0.54-0.37 (m, 2H), 0.14-0.00 (m, 2H).

Acid 7: (S)-3-(Benzyloxy)-2-(cyclohexylmethyl)propanoic acid

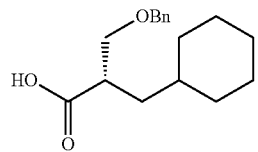 [SMILES: O=C(O)[C@H](COCc1ccccc1)CC1CCCCC1]

Step 1: (R)-4-Benzyl-3-((S)-3-(benzyloxy)-2-(cyclohexylmethyl)propanoyl)oxazolidin-2-one Under N₂, to a ice cooled solution of (R)-4-benzyl-3-(3-cyclohexylpropanoyl)oxazolidin-2-one (Acid 1, Step 2) (200 mg, 0.634 mmol) in DCM (4 mL) was added TiCl₄ (76 µL, 0.698 mmol). The mixture was stirred at 0° C. for 10 min before triethylamine (97 µL, 0.698 mmol) was added. The reaction was stirred at this temperature for 45 min before benzyl chloromethyl ether (0.106 mL, 0.761 mmol) was added. The reaction mixture was stirred at 0° C. for 2.5 h before being quenched with saturated NH₄Cl$_{(aq)}$ (50 mL). The mixture was extracted with DCM (3×50 mL) and the combined organic phases were washed with saturated NH₄Cl$_{(aq)}$ (50 mL). The organic phase was washed with brine (50 mL), passed through a Biotage phase separator, concentrated in vacuo and the residue purified by flash chromatography (GraceResolv silica 12 g cartridge, 0-50% EtOAc in cyclohexane) to give the title compound (223 mg, 80%) as a very pale yellow oil. LCMS (Method A): R$_T$=2.21 min, m/z=436 [M+H]⁺.

Step 2: (S)-3-(Benzyloxy)-2-(cyclohexylmethyl)propanoic acid

A 30% aqueous hydrogen peroxide solution (0.209 mL, 2.05 mmol) was added to a solution of (R)-4-benzyl-3-((S)-3-(benzyloxy)-2-(cyclohexylmethyl)propanoyl)oxazolidin-2-one (223 mg, 0.512 mmol) in THF (2.5 mL) and water (2.5 mL) at 0° C. and after 5 min lithium hydroxide (24.5 mg, 1.02 mmol) was added. After 2 h, the reaction was allowed to warm to RT and stirred for a further 16 h before the reaction was quenched by the addition of saturated sodium thiosulfate$_{(aq)}$ (2 mL). The reaction mixture was concentrated in vacuo without heating to remove the THF. The resulting biphasic mixture was diluted with water (2 mL) and extracted with DCM (3×5 mL). The aqueous phase was acidified to ~pH 2 by the addition of 2 M HCl$_{(aq)}$ and extracted with DCM (3×5 mL) using a Biotage phase separator. The DCM extractions under both basic and acidic conditions were combined, concentrated in vacuo and the residue purified by flash chromatography (GraceResolv silica 12 g cartridge, 0-60% EtOAc in cyclohexane) to give the title compound (73 mg, 51%) as a pale yellow gum. LCMS (Method A): R$_T$=1.71 min, m/z=275 [M−H]⁻. ¹H NMR (500 MHz, CDCl₃): δ 7.46-7.07 (m, 5H), 4.55 (s, 1H), 3.63 (t, J=8.7 Hz, 1H), 3.56 (dd, J=9.3, 4.9 Hz, 1H), 2.83 (tt, J=8.7, 5.3 Hz, 1H), 1.77 (d, J=12.8 Hz, 1H), 1.73-1.50 (m, 5H), 1.39-1.03 (m, 6H), 0.97-0.78 (m, 2H).

Acid 8: (S)-3-Cyclohexyl-2-(hydroxymethyl)propanoic acid

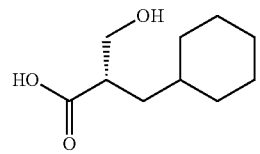 [SMILES: O=C(O)[C@H](CO)CC1CCCCC1]

Step 1: (R)-4-Benzyl-3-((S)-3-cyclohexyl-2-((2-(trimethylsilyl)ethoxy)methyl)propanoyl)oxazolidin-2-one DIPEA (0.210 mL, 1.20 mmol) was added to a solution of (R)-4-benzyl-3-(3-cyclohexylpropanoyl)oxazolidin-2-one (Acid 1, Step 2) (315 mg, 1.00 mmol) in DCM (5 mL) at 0° C. and after stirring for 5 min, titanium tetrachloride (0.121 mL, 1.10 mmol) was added dropwise and the resulting purple mixture was stirred at 0° C. for 1 h before 2-(chloromethoxyethyl)trimethylsilane (0.263 mL, 1.50 mmol) was added. After 70 min, the reaction was quenched by the addition of saturated NH₄Cl$_{(aq)}$ (20 mL) and water (20 mL). After warming to RT, the resulting mixture was extracted with DCM (3×30 mL) using a Biotage phase separator. The combined organic phases were concentrated in vacuo and the residue was purified by flash chromatography (GraceResolv silica 80 g cartridge, 0-15% EtOAc in cyclohexane; then GraceResolv silica 40 g cartridge, 0-15% EtOAc in cyclohexane) to give the title compound (184 mg, 41%) as colourless oil. ¹H NMR (500 MHz, CDCl₃): δ 7.40-7.16 (m, 5H), 4.72 (ddt, J=12.8, 6.9, 3.1 Hz, 1H), 4.32-4.24 (m, 1H), 4.22-4.12 (m, 2H), 3.65 (t, J=8.5 Hz, 1H), 3.60-3.46 (m, 3H), 3.28 (dd, J=13.5, 3.2 Hz, 1H), 2.75 (dd, J=13.4, 9.5 Hz, 1H), 1.78-1.58 (m, 6H), 1.35 (dt, J=13.5, 6.6 Hz, 1H), 1.29-1.07 (m, 4H), 0.97-0.82 (m, 4H), 0.00 (s, 9H). $^{13}$C NMR (126 MHz, CDCl$_3$): δ 175.80, 153.26, 135.66, 129.67, 129.05, 127.40, 71.93, 68.58, 65.94, 55.53, 41.12, 37.97, 36.79, 35.75, 33.68, 33.52, 26.62, 26.42, 26.37, 18.26, −1.21.

Step 2: (R)-4-Benzyl-3-((S)-3-cyclohexyl-2-(hydroxymethyl)propanoyl)oxazolidin-2-one was To a solution of (R)-4-benzyl-3-((S)-3-cyclohexyl-2-((2-(trimethylsilyl)ethoxy)methyl)propanoyl)oxazolidin-2-one (176 mg, 0.390 mmol) in DCM (4 mL) was added boron trifluoride diethyl etherate (0.150 mL, 1.18 mmol) and after 90 min the reaction was quenched by the addition of saturated NaHCO$_{3(aq)}$ (30 mL). The resulting mixture was extracted with DCM (3×15 mL), the combined organic phases were passed through a Biotage phase separator, concentrated in vacuo and the residue purified by flash chromatography (GraceResolv silica 12 g cartridge, 0-40% EtOAc in cyclohexane) to give the title compound (126 mg, 92%) as a colourless solid. $^1$H NMR (500 MHz, CDCl$_3$): δ 7.38-7.14 (m, 5H), 4.70 (ddt, J=10.0, 6.6, 3.1 Hz, 1H), 4.26-4.15 (m, 2H), 4.09 (qd, J=7.3, 4.2 Hz, 1H), 3.88 (dt, J=10.9, 4.3 Hz, 1H), 3.78 (dt, J=10.8, 8.1 Hz, 1H), 3.31 (dd, J=13.6, 3.4 Hz, 1H), 2.81 (dd, J=13.5, 9.4 Hz, 1H), 2.21 (dd, J=8.5, 4.4 Hz, 1H), 1.79-1.58 (m, 6H), 1.40 (dt, J=13.5, 6.7 Hz, 1H), 1.33-1.07 (m, 4H), 0.90 (pd, J=14.1, 13.4, 3.7 Hz, 2H).

Step 3: (S)-3-Cyclohexyl-2-(hydroxymethyl)propanoic acid

A 30% aqueous hydrogen peroxide solution (0.137 mL, 1.34 mmol) was added to a solution of (R)-4-benzyl-3-((S)-3-cyclohexyl-2-(hydroxymethyl)propanoyl)oxazolidin-2-one (116 mg, 0.340 mmol) in THF (1.5 mL) and water (1.5 mL) at 0° C. After 5 min, lithium hydroxide (16 mg, 0.670 mmol) was added and the mixture stirred for 45 min before the reaction was quenched by the addition of saturated sodium thiosulfate$_{(aq)}$ (0.5 mL). The reaction mixture was allowed to warm to RT before being concentrated in vacuo without heating to remove the THF. The resulting biphasic mixture was diluted with water (5 mL) and extracted with DCM (3×5 mL) to remove the oxazolidinone. The aqueous phase was acidified to ~pH 2 by the addition of 2 M HCl$_{(aq)}$ and extracted with DCM (3×5 mL). The combined organic layers form the acidic extractions were passed through a Biotage phase separator and concentrated in vacuo to give the title compound (81 mg, >100%) as colourless oil. This material was used without further purification.

Acid 9: (S)-4-((tert-Butyldimethylsilyl)oxy)-2-(cyclohexylmethyl)butanoic acid

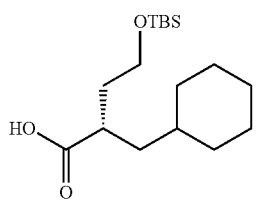 [SMILES: CC(C)(C)[Si](C)(C)OCC[C@H](CC1CCCCC1)C(=O)O]

Step 1: tert-Butyl (S)-4-((R)-4-benzyl-2-oxooxazolidin-3-yl)-3-(cyclohexylmethyl)-4-oxobutanoate NaHMDS (1 M in THF, 3.75 mL, 3.75 mmol) was slowly added to a solution of (R)-4-benzyl-3-(3-cyclohexylpropanoyl)oxazolidin-2-one (946 mg, 3.00 mmol) in THF (15 mL) at −78° C. After stirring at −78° C. for 90 min, tert-butyl bromoacetate (1.33 mL, 9.00 mmol) was added dropwise. The reaction was allowed to stir at −78° C. for 18 h before being quenched by the addition of saturated NH$_4$Cl$_{(aq)}$ (30 mL). The resulting mixture was allowed to warm to RT before being diluted with water (30 mL) and extracted with EtOAc (3×30 mL). The combined organic phases were passed through a Biotage phase separator, concentrated in vacuo and the residue was purified by flash chromatography (Biotage KP-Sil 100 g cartridge, 0-20% EtOAc in cyclohexane) to give the title compound (1.11 g, 86%) as colourless solid. LCMS (Method A): R$_T$=2.10 min, m/z=374 [M-butene+H]$^+$.

Step 2: (S)-4-((R)-4-Benzyl-2-oxooxazolidin-3-yl)-3-(cyclohexylmethyl)-4-oxobutanoic acid A solution of tert-butyl (S)-4-((R)-4-benzyl-2-oxooxazolidin-3-yl)-3-(cyclohexylmethyl)-4-oxobutanoate (1.10 g, 2.56 mmol) in TFA (3 mL) and DCM (12 mL) was stirred for 40 min before the reaction mixture concentrated in vacuo, the residue was azeotroped with toluene (2×5 mL) and dried in a vacuum oven at 50° C. to give the title compound (990 mg, >100%) as a colourless glassy solid. This material was used without further purification. LCMS (Method A): R$_T$=1.58 min, m/z=374 [M+H]$^+$.

Step 3: (R)-4-Benzyl-3-((S)-2-(cyclohexylmethyl)-4-hydroxybutanoyl)oxazolidin-2-one Borane dimethyl sulfide complex (2 M in THF, 1.70 mL, 17.9 mmol) was added dropwise to a solution of (S)-4-((R)-4-benzyl-2-oxooxazolidin-3-yl)-3-(cyclohexylmethyl)-4-oxobutanoic acid (956 mg, 2.56 mmol) in THF (6.4 mL) and after 90 min the reaction was cooled to 0° C. and MeOH (10 mL) was added slowly. The resulting solution was stirred at RT overnight, concentrated in vacuo and saturated NaHCO$_{3(aq)}$ (60 mL) added to the residue. The resulting mixture was extracted with DCM (3×30 mL) using a Biotage phase separator, the combined organic phases were concentrated in vacuo and the residue was purified by flash chromatography (GraceResolv silica 80 g cartridge, 0-30% EtOAc in cyclohexane) to give the title compound (331 mg, 36%) as a colourless oil. LCMS (Method A): R$_T$=1.65 min, m/z=360 [M+H]$^+$. $^1$H NMR (500 MHz, CDCl$_3$): δ 7.36-7.30 (m, 2H), 7.30-7.27 (m, 1H), 7.25-7.21 (m, 2H), 4.68 (ddt, J=9.8, 5.8, 3.8 Hz, 1H), 4.23-4.15 (m, 2H), 4.01 (tt, J=8.6, 5.3 Hz, 1H), 3.69 (t, J=5.9 Hz, 2H), 3.36 (dd, J=13.4, 3.3 Hz, 1H), 2.72 (dd, J=13.3, 10.1 Hz, 1H), 2.11 (t, J=5.5 Hz, 1H), 2.00-1.92 (m, 1H), 1.82 (ddt, J=14.1, 6.8, 5.2 Hz, 1H), 1.72 (ddt, J=23.5, 10.4, 4.7 Hz, 5H), 1.65-1.59 (m, 1H), 1.35 (ddd, J=13.5, 7.6, 5.7 Hz, 1H), 1.17 (dqd, J=24.8, 12.6, 11.8, 4.9 Hz, 4H), 0.90 (dtd, J=20.7, 11.7, 11.3, 5.6 Hz, 2H). $^{13}$C NMR (126 MHz, CDCl$_3$): δ 177.36, 153.86, 135.51, 129.56, 129.14, 127.52, 66.39, 60.80, 56.11, 40.27, 37.99, 37.44, 36.46, 35.87, 33.60, 33.44, 26.60, 26.43, 26.36.

Step 4: (R)-4-Benzyl-3-((S)-4-((tert-butyldimethylsilyl)oxy)-2-(cyclohexylmethyl)butanoyl)oxazolidin-2-one A solution of tert-butyldimethylsilyl chloride (195 mg, 1.29 mmol) in DCM (4.5 mL) was added dropwise to a suspension of (R)-4-benzyl-3-((S)-2-(cyclohexylmethyl)-4-hydroxybutanoyl)oxazolidin-2-one (310 mg, 0.860 mmol) and imidazole (117 mg, 1.72 mmol) in DCM (4.5 mL) at RT.

After 50 min, the resulting suspension was diluted with saturated NaHCO$_{3(aq)}$ (60 mL) and extracted with DCM (3×30 mL) using a Biotage phase separator. The combined organic phases were concentrated in vacuo and the residue was purified by flash chromatography (GraceResolv silica 40 g cartridge, 0-15% EtOAc in cyclohexane) to give the title compound (408 mg, 99%) as colourless oil. $^1$H NMR (500 MHz, CDCl$_3$): δ 7.37-7.30 (m, 2H), 7.30-7.26 (m, 1H), 7.25-7.20 (m, 2H), 4.70-4.63 (m, 1H), 4.20-4.10 (m, 2H), 4.02-3.94 (m, 1H), 3.73-3.61 (m, 2H), 3.35 (dd, J=13.3, 3.3 Hz, 1H), 2.68 (dd, J=13.3, 10.1 Hz, 1H), 1.96 (dtd, J=13.2, 7.5, 5.7 Hz, 1H), 1.78-1.58 (m, 7H), 1.36 (dt, J=13.5, 6.7 Hz, 1H), 1.30-1.07 (m, 4H), 1.03-0.75 (m, 2H), 0.90 (s, 9H), 0.05 (s, 3H), 0.05 (s, 3H). $^{13}$C NMR (126 MHz, CDCl$_3$): δ 177.03, 153.05, 135.65, 129.54, 129.11, 127.46, 66.06, 61.28, 55.77, 39.74, 38.23, 37.49, 35.70, 35.24, 33.73, 33.26, 26.65, 26.49, 26.38, 26.10, 18.47, −5.12, −5.16.

Step 5: (S)-4-((tert-Butyldimethylsilyl)oxy)-2-(cyclohexylmethyl)butanoic acid

A 30% aqueous hydrogen peroxide solution (0.345 mL, 3.38 mmol) was added to a solution of (R)-4-benzyl-3-((S)-4-((tert-butyldimethylsilyl)oxy)-2-(cyclohexylmethyl)butanoyl)oxazolidin-2-one (400 mg, 0.840 mmol) in THF (2 mL) and water (2 mL) at 0° C. After 5 min, lithium hydroxide (40 mg, 1.69 mmol) was added and the mixture stirred for 1 h 40 min before THF (2 mL) was added. The mixture was stirred for 4 h before being quenched by the addition of saturated sodium thiosulfate$_{(aq)}$ (2 mL). The resulting mixture was diluted with water (10 mL) and extracted with DCM (3×15 mL) using a Biotage phase separator. The combined organic phases were concentrated in vacuo and the residue was purified by flash chromatography (GraceResolv silica 24 g cartridge, 0-20% EtOAc in cyclohexane) to give the title compound (262 mg, 98%) as a colourless oil. $^1$H NMR (500 MHz, CDCl$_3$): δ 10.65 (br. s, 1H), 3.67 (t, J=6.2 Hz, 2H), 2.65 (tdd, J=8.8, 5.8, 4.4 Hz, 1H), 1.91-1.82 (m, 1H), 1.79 (d, J=13.2 Hz, 1H), 1.72-1.56 (m, 6H), 1.35-1.09 (m, 5H), 0.89 (s, 2H), 0.89 (s, 9H), 0.05 (s, 3H), 0.05 (s, 3H). $^{13}$C NMR (126 MHz, CDCl$_3$): δ 181.07, 61.29, 39.97, 39.52, 35.51, 35.11, 33.58, 33.17, 26.69, 26.35, 26.10, 26.04, 18.43, −5.29, −5.32.

Acid 10:
(S)-3-Cyclobutyl-2-(hydroxymethyl)propanoic acid

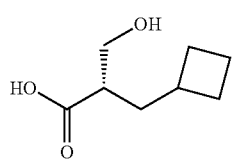 [SMILES: O=C(O)[C@H](CO)CC1CCC1]

Step 1: (R)-4-Benzyl-3-((S)-3-cyclobutyl-2-((2-(trimethylsilyl)ethoxy)methyl)propanoyl)oxazolidin-2-one DIPEA (0.328 mL, 1.88 mmol) was added to a stirred solution of (R)-4-benzyl-3-(3-cyclobutylpropanoyl)oxazolidin-2-one (Acid 5, Step 1) (449 mg, 1.56 mmol) in DCM (8 mL) at 0° C. After 15 min, titanium tetrachloride (0.189 mL, 1.72 mmol) was added dropwise and the resulting purple mixture was stirred at 0° C. for 1 h before 2-(chloromethoxyethyl)trimethylsilane (0.411 mL, 2.34 mmol) was added. After 1 h, the reaction was quenched by the addition of saturated NH$_4$Cl$_{(aq)}$ (20 mL) and water (20 mL). After warming to RT, the mixture was extracted with DCM (3×30 mL) using a Biotage phase separator. The combined organic phases were concentrated in vacuo and the residue was purified by flash chromatography (GraceResolv silica 40 g cartridge, 0-30% EtOAc in cyclohexane) to give the title compound (275 mg, 42%) as a colourless oil. $^1$H NMR (500 MHz, CDCl$_3$): δ 7.39-7.18 (m, 5H), 4.70 (ddt, J=9.3, 7.6, 3.2 Hz, 1H), 4.22-4.08 (m, 3H), 3.68 (t, J=8.7 Hz, 1H), 3.51 (tdd, J=9.9, 6.2, 2.2 Hz, 3H), 3.25 (dd, J=13.5, 3.3 Hz, 1H), 2.78 (dd, J=13.5, 9.3 Hz, 1H), 2.32 (hept, J=7.8 Hz, 1H), 2.02 (dqd, J=19.0, 7.9, 4.0 Hz, 2H), 1.88-1.72 (m, 3H), 1.62 (ddd, J=17.7, 13.4, 6.7 Hz, 3H), 0.97-0.85 (m, 2H), −0.01 (s, 9H). $^{13}$C NMR (126 MHz, CDCl$_3$): δ 175.55, 153.23, 135.59, 129.70, 129.04, 127.42, 71.48, 68.56, 65.88, 55.49, 42.17, 37.97, 36.48, 34.26, 29.03, 28.57, 18.52, 18.27, −1.21.

Step 2: (R)-4-Benzyl-3-((S)-3-cyclobutyl-2-(hydroxymethyl)propanoyl)oxazolidin-2-one Boron trifluoride diethyl etherate (0.250 mL, 1.98 mmol) was added to a solution of (R)-4-benzyl-3-((S)-3-cyclobutyl-2-((2-(trimethylsilyl)ethoxy)methyl)propanoyl)oxazolidin-2-one (275 mg, 0.660 mmol) in DCM (6.5 mL) and after 90 min the reaction was quenched by the addition of saturated NaHCO$_{3(aq)}$ (30 mL). The resulting mixture was extracted with DCM (3×15 mL), the combined organic phases were passed through a Biotage phase separator, concentrated in vacuo and the residue purified by flash chromatography (GraceResolv silica 12 g cartridge, 0-40% EtOAc in cyclohexane) to give the title compound (208 mg, 99%) as a colourless solid. LCMS (Method A): R$_T$=1.41 min, m/z=318 [M+H]$^+$. $^1$H NMR (500 MHz, CDCl$_3$): δ 7.36-7.30 (m, 2H), 7.30-7.26 (m, 1H), 7.25-7.20 (m, 2H), 4.68 (ddt, J=9.6, 7.2, 3.1 Hz, 1H), 4.24-4.15 (m, 2H), 3.93 (qd, J=7.1, 4.1 Hz, 1H), 3.88-3.75 (m, 2H), 3.29 (dd, J=13.5, 3.5 Hz, 1H), 2.81 (dd, J=13.5, 9.4 Hz, 1H), 2.34 (hept, J=7.9 Hz, 1H), 2.21 (br. s, 1H), 2.08-1.96 (m, 2H), 1.89-1.73 (m, 3H), 1.72-1.59 (m, 3H). $^{13}$C NMR (126 MHz, CDCl$_3$): δ 176.24, 153.61, 135.33, 129.62, 129.10, 127.52, 66.28, 63.96, 55.77, 44.13, 38.01, 35.72, 34.13, 28.97, 28.28, 18.49.

Step 3:
(S)-3-Cyclobutyl-2-(hydroxymethyl)propanoic acid

A 30% aqueous hydrogen peroxide solution (0.348 mL, 3.40 mmol) was added to a solution of (R)-4-benzyl-3-((S)-3-cyclobutyl-2-(hydroxymethyl)propanoyl)oxazolidin-2-one (270 mg, 0.850 mmol) in THF (2 mL) and water (2 mL) at 0° C. After 5 min, lithium hydroxide (41 mg, 1.70 mmol) was added and the mixture stirred for 50 min before the reaction was quenched by the addition of saturated sodium thiosulfate$_{(aq)}$ (0.5 mL). The reaction mixture was allowed to warm to RT before being concentrated in vacuo to remove the THF. The resulting biphasic mixture was diluted with water (2 mL) and extracted with DCM (3×2 mL) to remove the oxazolidinone. The aqueous phase was diluted with water (2×2 mL), acidified to ~pH 2 by the addition of 2 M HCl$_{(aq)}$ and extracted with DCM (3×5 mL) using a Biotage phase separator. The product was contained in the basic and acidic DCM extractions so these were combined, concentrated in vacuo and purified by flash chromatography (GraceResolv silica 12 g cartridge, 0-100% EtOAc in cyclohexane; the mixed fractions were re-purified GraceResolv silica 12 g cartridge, 0-100% EtOAc in cyclohexane) to give the title compound (121 mg, 89%) as a colourless oil. This material still contained the oxazolidinone and was used without further purification. $^1$H NMR (500 MHz, CDCl$_3$): δ 3.73 (d, J=6.0 Hz, 2H), 2.58-2.50 (m, 1H), 2.35 (dp, J=14.6, 7.5, 7.1 Hz, 1H), 2.12-2.00 (m, 2H), 1.91-1.71 (m, 3H), 1.67-1.51 (m, 3H). $^{13}$C NMR (126 MHz, CDCl$_3$): δ 180.46, 63.08, 45.95, 35.49, 34.03, 28.64, 28.45, 18.44.

Acid 11: (R)-4,4,4-Trifluoro-2-methylbutanoic acid

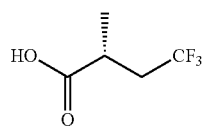

Step 1: (R)-4-Benzyl-3-(4,4,4-trifluorobutanoyl) oxazolidin-2-one

Pivaloyl chloride (6.50 mL, 52.8 mmol) and then triethylamine (7.65 mL, 54.9 mmol) were added to a suspension of 4,4,4-trifluorobutanoic acid (3.00 g, 21.1 mmol), (R)-4-benzyl-2-oxazolidinone (3.74 g, 21.1 mmol) and lithium chloride (1.79 g, 42.2 mmol) in THF (50 mL) at −20° C. After 30 min, the reaction was allowed to slowly warm to RT before being quenched by the addition of saturated NaHCO$_{3(aq)}$ (60 mL). The resulting mixture was extracted with DCM (3×30 mL) using a Biotage phase separator, the combined organic phases were concentrated in vacuo, the residue was dissolved in DCM (75 mL) and washed with ~15% NH$_{3(aq)}$. The organic phase was passed through a Biotage phase separator, concentrated in vacuo and the residue was purified by flash chromatography (Biotage KP-Sil 100 g cartridge, 0-15% EtOAc in cyclohexane) to give the title compound (2.04 g, 32%) as pale yellow viscous oil. $^1$H NMR (500 MHz, CDCl$_3$): δ 7.37-7.32 (m, 2H), 7.32-7.27 (m, 1H), 7.23-7.18 (m, 2H), 4.69 (ddt, J=9.5, 7.3, 3.2 Hz, 1H), 4.28-4.18 (m, 2H), 3.34-3.15 (m, 3H), 2.78 (dd, J=13.4, 9.6 Hz, 1H), 2.64-2.47 (m, 2H).

Step 2: (R)-4-Benzyl-3-((R)-4,4,4-trifluoro-2-methylbutanoyl)oxazolidin-2-one

NaHMDS (1 M in THF, 3.07 mL, 3.07 mmol) was added dropwise to a solution of (R)-4-benzyl-3-(4,4,4-trifluorobutanoyl)oxazolidin-2-one (0.740 g, 2.46 mmol) in THF (12 mL) at −78° C. and after 90 min iodomethane (0.765 mL, 12.3 mmol) was added dropwise. The reaction was allowed to slowly warm to −20° C. and stirred at −20° C. overnight. The reaction was quenched at −20° C. by the addition of saturated NH$_4$Cl$_{(aq)}$ (50 mL) and water (50 mL). After warming to RT, the mixture was extracted with DCM (3×50 mL), the combined organic phases were passed through a Biotage phase separator, concentrated in vacuo and the residue purified by flash chromatography (GraceResolv silica 80 g cartridge, 0-20% EtOAc in cyclohexane) to give the title compound (473 mg, 61%) as a pale yellow viscous oil. LCMS (Method A): R$_T$=1.59 min, m/z=316 [M+H]$^+$. $^1$H NMR (500 MHz, CDCl$_3$): δ 7.38-7.31 (m, 2H), 7.31-7.26 (m, 1H), 7.23-7.18 (m, 2H), 4.73-4.67 (m, 1H), 4.28-4.18 (m, 2H), 4.16-4.07 (m, 1H), 3.25 (dd, J=13.4, 3.4 Hz, 1H), 2.89-2.76 (m, 2H), 2.19 (dqd, J=15.5, 10.8, 4.8 Hz, 1H), 1.34 (d, J=7.0 Hz, 3H). $^{13}$C NMR (126 MHz, CDCl$_3$): δ 174.82, 152.97, 135.08, 129.57, 129.13, 127.62, 126.45 (q, J=276.9 Hz), 66.47, 55.44, 37.99, 36.62 (q, J=28.7 Hz), 32.52 (q, J=2.6 Hz), 18.56.

Step 3: (R)-4,4,4-Trifluoro-2-methylbutanoic acid

A 30% aqueous hydrogen peroxide solution (0.613 mL, 6.00 mmol) was added to a solution of (R)-4-benzyl-3-((R)-4,4,4-trifluoro-2-methylbutanoyl)oxazolidin-2-one (473 mg, 1.50 mmol) in THF (4 mL) and water (4 mL) at 0° C. After 5 min lithium hydroxide (72 mg, 3.00 mmol) was added and the mixture stirred for 70 min before the reaction was quenched by the addition of saturated sodium thiosulfate$_{(aq)}$ (2 mL). The reaction mixture was allowed to warm to RT, concentrated in vacuo to remove the THF and the resulting biphasic mixture extracted with DCM (3×10 mL). The pH of the aqueous phase was adjusted to pH 2 by the addition of 2 M HCl$_{(aq)}$ and the mixture was extracted with DCM (3×10 mL). The combined acidic DCM extractions were passed through a Biotage phase separator, carefully concentrated at 50° C. (no vacuum) and the residue dried at 50 mbar (no heat) for 5 min to give the title compound (250 mg, quantitative) as a very pale yellow oil containing 8% w/w DCM. $^1$H NMR (500 MHz, CDCl$_3$): δ 10.96 (s, 1H), 2.84 (h, J=7.0 Hz, 1H), 2.69 (dqd, J=15.1, 10.9, 7.0 Hz, 1H), 2.18 (dqd, J=15.1, 10.6, 6.3 Hz, 1H), 1.35 (d, J=7.2 Hz, 3H).

Acid 12: Lithium 4,4,4-trifluoro-2-(2,2,2-trifluoroethyl)butanoate

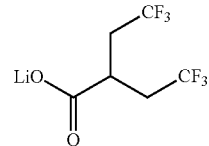

Step 1: Methyl 4,4,4-trifluoro-2-(triphenyl-λ$^5$-phosphaneylidene)butanoate

Lithium bis(trimethylsilyl)amide (1 M in THF, 167 mL, 167 mmol) was added dropwise to a suspension of triphenyl (3,3,3-trifluoropropyl)phosphonium iodide 40.7 g, 83.6 mmol) in THF (167 mL) at −5° C. over 1 h 40 min. The reaction was cooled to −78° C. and methyl chloroformate (13.0 mL, 167 mmol) was added dropwise over 15 min. The reaction was stirred for 1 h at −78° C. before being allowed to slowly warm to RT overnight, brine (300 mL) was added and after stirring for 30 min the layers were separated. The organic layer was washed with brine (40 mL) and the combined aqueous phases were extracted with DCM (2×40 mL). The combined organic phases were passed through a Biotage phase separator, concentrated in vacuo and purified by flash chromatography (Biotage KP-Sil 340 g cartridge, 50% EtOAc in cyclohexane). After concentration in vacuo, the resultant dark brown/orange material was slurried using Et$_2$O (50 mL). The precipitate collected by filtration, washed with Et$_2$O (50 mL) and dried under high vacuum to give the title compound (16.5 g, 47%) as a beige solid. LCMS (Method A): $R_T$=0.86 min, m/z=417 [M+H]$^+$. $^1$H NMR (500 MHz, CDCl$_3$): δ 7.68-7.43 (m, 15H), 3.60 (s, 1.3H (rotomer)), 3.11 (s, 1.7H (rotomer)), 2.83-2.63 (m, 2H).

Step 2: Methyl 4,4,4-trifluoro-2-(2,2,2-trifluoroethyl)but-2-enoate 2,2,2-Trifluoroethane-1,1-diol (2.00 mL, 25.7 mmol) was added to sodium bicarbonate (300 mg, 3.57 mmol) in a conical flask; some effervescence was observed. To this magnesium sulfate (1.2 g, 9.97 mmol) and tert-butyl methyl ether (6 mL) were added and the mixture was placed in a water bath at 10° C. After 10 min, the suspension was passed through a fluted filter paper into a reaction tube charged with methyl 4,4,4-trifluoro-2-(triphenyl-λ$^5$-phosphanylidene)butanoate (4.00 g, 9.61 mmol) and magnesium sulfate (1.2 g, 9.97 mmol), the solids in the filter paper were washed with tert-butyl methyl ether (2×5 mL). The reaction tube was sealed and heated at 70° C. for 19 h. The reaction was allowed to cool to RT, filtered through Celite® and the solids washed with Et$_2$O (2×10 mL). The filtrate was concentrated at 60° C. (no vacuum) and the residue was purified by Kugelrohr distillation (high vacuum, up 120° C.) to give the title compound (689 mg, 30%) as a colourless liquid. $^1$H NMR (500 MHz, CDCl$_3$): δ 6.96 (q, J=8.1 Hz, 1H), 3.88 (s, 3H), 3.50 (q, J=10.3, 9.8 Hz, 2H).

Step 3: Methyl 4,4,4-trifluoro-2-(2,2,2-trifluoroethyl)butanoate

A suspension of methyl 4,4,4-trifluoro-2-(2,2,2-trifluoroethyl)but-2-enoate (689 mg, 2.92 mmol), ammonium formate (1.84 g, 29.2 mmol) and 10% palladium on carbon (311 mg, 0.290 mmol) was heated at reflux for 70 min. The reaction mixture was allowed to cool to RT, diluted with DCM (5 mL) and the resulting suspension filtered through Celite®. The solids were washed with DCM (3×5 mL) and the filtrate concentrated at 50° C. (no vacuum, then 700 mbar) to give a colourless liquid. This material was diluted with water (70 mL) and the resulting mixture extracted with Et$_2$O (4×80 mL). The combined organic phases were washed with brine (30 mL), passed through Biotage phase separator and concentrated at 50° C. (no vacuum) to give the title compound (947 mg, 54%) as colourless liquid. This material was a 40% w/w solution in Et$_2$O. $^1$H NMR (500 MHz, CDCl$_3$): δ 3.77 (s, 3H), 3.03 (tt, J=8.2, 5.3 Hz, 1H), 2.65 (dqd, J=15.2, 10.4, 8.2 Hz, 2H), 2.38 (dqd, J=15.4, 10.3, 5.3 Hz, 2H).

Step 4: Lithium 4,4,4-trifluoro-2-(2,2,2-trifluoroethyl)butanoate

A solution of methyl 4,4,4-trifluoro-2-(2,2,2-trifluoroethyl)butanoate (40% w/w in Et$_2$O, 947 mg, 1.59 mmol) and lithium hydroxide (46 mg, 1.91 mmol) in THF (7.5 mL) and water (1.5 mL) was heated at 50° C. for 17 h. The reaction mixture was concentrated in vacuo and the residue dried in a vacuum oven at 50° C. to give the title compound (275 mg, 75%) as colourless solid. $^1$H NMR (500 MHz, DMSO-d$_6$): δ 2.77 (dqd, J=14.0, 11.8, 6.0 Hz, 2H), 2.38-2.20 (m, 3H).

Acid 13: 1-(((S)-1-((R)-3-Cyclohexyl-2-methylpropanoyl)-4-hydroxy-3,3-dimethylpiperidin-4-yl) methyl)-4-cyclopropyl-6-oxo-1,6-dihydropyridine-3-carboxylic acid

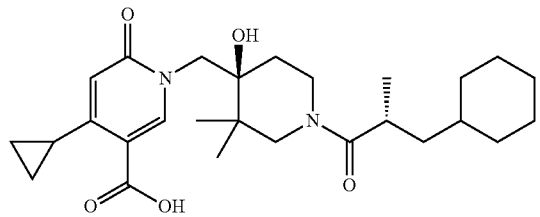 [SMILES: C[C@H](CC1CCCCC1)C(=O)N1CC[C@@](O)(Cn2cc(C(=O)O)c(C3CC3)cc2=O)C(C)(C)C1]

Step 1: Ethyl (S)-1-((1-(tert-butoxycarbonyl)-4-hydroxy-3,3-dimethylpiperidin-4-yl)methyl)-4-cyclopropyl-6-oxo-1,6-dihydropyridine-3-carboxylate PdCl$_2$(dppf).DCM (18.4 mg, 0.0226 mmol) was added to a pre-degassed solution of ethyl (S)-1-((1-(tert-butoxycarbonyl)-4-hydroxy-3,3-dimethylpiperidin-4-yl)methyl)-4-chloro-6-oxo-1,6-dihydropyridine-3-carboxylate (Amine 7, Step 2) (200 mg, 0.452 mmol), cyclopropylboronic acid (58.2 mg, 0.677 mmol) and sodium carbonate (95.7 mg, 0.903 mmol) in a 10 mL vial. The vessel was sealed and heated under microwave irradiation (CEM) at 120° C. with stirring for 30 min. Further cyclopropylboronic acid (58.2 mg, 0.677 mmol) and PdCl$_2$(dppf).DCM (18.4 mg, 0.0226 mmol) were added and reaction was rerun under the same conditions. Due to incomplete conversion, the reaction was rerun under the same conditions. Further cyclopropylboronic acid (77.6 mg, 0.903 mmol) and PdCl$_2$(dppf).DCM (18.4 mg, 0.0226 mmol) were added and the reaction was rerun at 120° C. for 1 h. The reaction mixture was partitioned between EtOAc and brine, separated, extracted (EtOAc×2), the combined organic phase was dried (phase separator), the solvents were removed in vacuo, and the remaining residue was purified by flash chromatography (0-40%, EtOAc in cyclohexane) to give the title compound (143 mg, 71%) as a pale yellow oil. LCMS (Method A): $R_T$=1.59 min, m/z=449 [M+H]$^+$.

Step 2: (S)-4-((4-Cyclopropyl-5-(ethoxycarbonyl)-2-oxopyridin-1 (2H)-yl)methyl)-4-hydroxy-3,3-dimethylpiperidin-1-ium chloride 4 M HCl in 1,4-dioxane (1.5 mL, 43.2 mmol) was added to ethyl (S)-1-((1-(tert-butoxycarbonyl)-4-hydroxy-3,3-dimethylpiperidin-4-yl)methyl)-4-cyclopropyl-6-oxo-1,6-dihydropyridine-3-carboxylate (143 mg, 0.320 mmol) and the resulting mixture was stirred at RT. After 30 min, the solvents were removed in vacuo to give the crude title compound (153 mg, >100%) as a pale yellow solid that was carried through to the next step without further purification. LCMS (Method A): $R_T$=0.71 min, m/z=385 [M+H]$^+$.

Step 3: Ethyl 1-(((S)-1-((R)-3-cyclohexyl-2-methylpropanoyl)-4-hydroxy-3,3-dimethylpiperidin-4-yl) methyl)-4-cyclopropyl-6-oxo-1,6-dihydropyridine-3-carboxylate DIPEA (0.17 mL, 0.959 mmol) was added to a stirred solution of (S)-4-((4-cyclopropyl-5-(ethoxycarbonyl)-2- oxopyridin-1(2H)-yl)methyl)-4-hydroxy-3,3-dimethylpiperidin-1-ium chloride (123 mg, 0.320 mmol), (R)-3-cyclohexyl-2-methylpropanoic acid (Acid 1) (54.4 mg, 0.320 mmol) and HATU (146 mg, 0.383 mmol) in DCM (5.0 mL) at RT. After 2 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography using a KP-NH column (0-100%, EtOAc in cyclohexane) to give the title compound (125 mg, 78%) as a pale yellow solid. LCMS (Method A): $R_T$=1.81 min, m/z=501 [M+H]$^+$.

Step 4: 1-(((S)-1-((R)-3-Cyclohexyl-2-methylpropanoyl)-4-hydroxy-3,3-dimethylpiperidin-4-yl)methyl)-4-cyclopropyl-6-oxo-1,6-dihydropyridine-3-carboxylic acid 1 M Sodium hydroxide(aq) solution (0.5 mL, 0.499 mmol) was added to a stirred solution of ethyl 1-(((S)-1-((R)-3-cyclohexyl-2-methylpropanoyl)-4-hydroxy-3,3-dimethylpiperidin-4-yl)methyl)-4-cyclopropyl-6-oxo-1,6-dihydropyridine-3-carboxylate (125 mg, 0.249 mmol) in 1,4-dioxane (1.5 mL) at RT. The temperature was increased to 50° C. After 2 h, the reaction mixture was cooled and the pH was adjusted to pH 4-5 by the addition of 1 M HCl (aq) solution and was extracted using EtOAc (×3). Due to product remaining in the aqueous phase, the pH was adjusted to ca. pH 2-3 using further 1 M HCl (aq) solution, followed by extraction using EtOAc (×3). The combined organic phases were dried (phase separator) and concentrated in vacuo. The remaining residue was purified by flash chromatography (0-5%, MeOH in DCM) to give the title compound (67.6 mg, 57%) as a white solid. LCMS (Method A): $R_T$=1.44 min, m/z=473 [M+H]$^+$.

Acid 14:
(S)-4,4,4-Trifluoro-2-(hydroxymethyl)butanoic acid

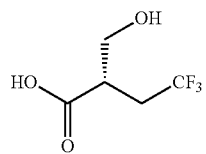 [SMILES: O=C(O)[C@H](CO)CC(F)(F)F]

Step 1: (R)-4-Benzyl-3-((S)-4,4,4-trifluoro-2-((2-(trimethylsilyl)ethoxy)methyl)butanoyl)oxazolidin-2-one DIPEA (0.696 mL, 3.98 mmol) was added dropwise to a solution of (R)-4-benzyl-3-(4,4,4-trifluorobutanoyl)oxazolidin-2-one (1 g, 3.32 mmol) and titanium tetrachloride (0.400 mL, 3.65 mmol) in DCM (16.5 mL) at 0° C. The resulting purple mixture was stirred at 0° C. for 1 h before 2-(chloromethoxyethyl)trimethylsilane (0.699 mL, 3.98 mmol) was added. After 1 h, the reaction was quenched by the addition of saturated NH$_4$Cl$_{(aq)}$ (20 mL) and water (20 mL). After warming to RT, the mixture was extracted with DCM (3×30 mL) using a Biotage phase separator. The combined organic phases were concentrated in vacuo and the residue purified by flash chromatography (GraceResolv silica 80 g cartridge, 0-60% EtOAc in cyclohexane; then GraceResolv silica 40 g cartridge, 0-40% EtOAc in cyclohexane) to give the title compound (373 mg, 26%) as a colourless oil. LCMS (Method A): $R_T$=2.04 min, m/z=404 [M−2Me+3H]$^+$. $^1$H NMR (500 MHz, CDCl$_3$): δ 7.37-7.30 (m, 2H), 7.30-7.26 (m, 1H), 7.25-7.18 (m, 2H), 4.73 (ddt, J=9.4, 7.9, 3.2 Hz, 1H), 4.44-4.36 (m, 1H), 4.24 (ddd, J=8.6, 7.9, 0.7 Hz, 1H), 4.19 (dd, J=9.1, 3.1 Hz, 1H), 3.72-3.61 (m, 2H), 3.61-3.49 (m, 2H), 3.25 (dd, J=13.5, 3.4 Hz, 1H), 2.90-2.73 (m, 2H), 2.44 (dqd, J=15.2, 11.1, 4.1 Hz, 1H), 0.96-0.88 (m, 2H), 0.01 (s, 9H).

Step 2: (R)-4-Benzyl-3-((S)-4,4,4-trifluoro-2-(hydroxymethyl)butanoyl)oxazolidin-2-one To a solution of (R)-4-benzyl-3-((S)-4,4,4-trifluoro-2-((2-(trimethylsilyl)ethoxy)methyl)butanoyl)oxazolidin-2-one (363 mg, 0.841 mmol) in DCM (8.4 mL) was added boron trifluoride diethyl etherate (0.320 mL, 2.52 mmol). After 2 h 15 min, the reaction was quenched by the addition of saturated NaHCO$_{3(aq)}$ (40 mL) and the mixture was extracted with DCM (3×20 mL). The combined organic phases were passed through a Biotage phase separator, concentrated in vacuo and the residue purified by flash chromatography (GraceResolv silica 12 g cartridge, 0-50% EtOAc in cyclohexane) to give the title compound (276 mg, 99%) as a colourless gum which solidified upon agitation. LCMS (Method A): $R_T$=1.30 min, m/z=332 [M+H]$^+$. $^1$H NMR (500 MHz, CDCl$_3$): δ 7.38-7.31 (m, 2H), 7.31-7.27 (m, 1H), 7.25-7.20 (m, 2H), 4.73 (dddd, J=9.3, 7.6, 3.6, 2.7 Hz, 1H), 4.37-4.31 (m, 1H), 4.30-4.25 (m, 1H), 4.22 (dd, J=9.1, 2.7 Hz, 1H), 3.93-3.83 (m, 2H), 3.28 (dd, J=13.6, 3.6 Hz, 1H), 2.88-2.75 (m, 2H), 2.38 (dqd, J=15.0, 10.9, 4.1 Hz, 1H), 2.04 (dd, J=7.5, 5.3 Hz, 1H).

Step 3:
(S)-4,4,4-Trifluoro-2-(hydroxymethyl)butanoic acid

A 30% aqueous hydrogen peroxide solution (91 µL, 0.894 mmol) was added to a solution of (R)-4-benzyl-3-((S)-4,4,4-trifluoro-2-(hydroxymethyl)butanoyl)oxazolidin-2-one (74 mg, 0.223 mmol) in THF (1.1 mL) and water (1.1 mL) at 0° C. After 5 min, the LiOH (10.7 mg, 0.447 mmol) was added and the reaction stirred for 2 h before being quenched by the addition of saturated sodium thiosulfate$_{(aq)}$ (0.5 mL). The reaction mixture was extracted with DCM (3×5 mL) and the pH of the aqueous phase adjusted to pH 2 by the addition of 1 M HCl$_{(aq)}$. The mixture was extracted with EtOAc (5×5 mL), the combined EtOAc extractions were passed through a Biotage phase separator and concentrated in vacuo to give the title compound (40 mg, quantitative) as a pale yellow oil. $^1$H NMR (500 MHz, CDCl$_3$): δ 3.98 (dd, J=11.1, 4.3 Hz, 1H), 3.88 (dd, J=11.1, 5.9 Hz, 1H), 2.94 (qd, J=6.3, 4.3 Hz, 1H), 2.70 (dqd, J=15.3, 11.0, 6.6 Hz, 1H), 2.48 (dqd, J=15.3, 10.7, 6.4 Hz, 1H).

Acid 15: (R)-4,4-Difluoro-3-phenylbutanoic acid

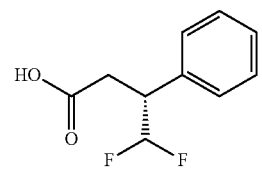 [SMILES: O=C(O)C[C@H](c1ccccc1)C(F)F]

Step 1: Ethyl 4,4-difluoro-3-phenylbut-2-enoate

A suspension of sodium hydride (60% dispersion in mineral oil, 1.54 g, 38.4 mmol) in anhydrous THF (100 mL) was cooled to 0° C. before triethyl phosphonoacetate (7.05 mL, 35.2 mmol) was added dropwise. After stirring at 0° C. for 30 min, 2,2-difluoro-1-phenylethanone (5.0 g, 32.0 mmol) was added dropwise and the mixture was stirred at 0° C. for a further 60 min. The reaction mixture was quenched by the addition of water (100 mL) and extracted into EtOAc (3×50 mL). The combined organic phases were washed with brine (50 mL), dried over $Na_2SO_4$, filtered, concentrated to dryness under reduced pressure and purified by flash chromatography (GraceResolv™ silica 120 g cartridge, cyclohexane:ethyl acetate, gradient elution from 95:5 to 60:40) to give the title compound (3.38 g, 47%) as a colourless oil.

Step 2: Ethyl 4,4-difluoro-3-phenylbutanoate

A solution of ethyl 4,4-difluoro-3-phenylbut-2-enoate (1.00 g, 4.42 mmol) in methanol (88 mL) was hydrogenated by H-Cube® (10% Pd/C cartridge, 60 bar $H_2$, 60° C., 1 mL/min). The reaction mixture was concentrated to dryness under reduced pressure and purified by flash chromatography (GraceResolv™ silica 80 g cartridge, cyclohexane:ethyl acetate, gradient elution from 100:0 to 80:20) to give the title compound (975 mg, 97%) as a colourless oil. LCMS (Method A): $R_T$=1.55 min, m/z=229 [M+H]$^+$. $^1$H NMR (300 MHz, CDCl$_3$): δ 7.23-7.39 (m, 5H), 5.94 (td, 1H), 3.98-4.15 (m, 2H), 3.51-3.74 (m, 1H), 2.96 (dd, 1H), 2.78 (dd, 1H), 1.15 (t, 3H).

Step 3: 4,4-Difluoro-3-phenylbutanoic acid

To a solution of ethyl 4,4-difluoro-3-phenylbutanoate (975 mg, 4.27 mmol) in 1,4-dioxane (8.5 mL) was added a 1 M sodium hydroxide solution (8.5 mL, 8.54 mmol) and the reaction was stirred at RT for 60 min. The reaction mixture was acidified to pH 4 by the addition of 2 M HCl$_{(aq)}$, followed by extraction into EtOAc (3×30 mL). The combined organic phases were washed with brine (30 mL), dried over Na$_2$SO$_4$, filtered, concentrated to dryness under reduced pressure and slurried in cyclohexane (20 mL) to give the title compound (682 mg, 80%) as a colourless solid. LCMS (Method A): $R_T$=1.10 min, m/z=199 [M−H]$^-$. $^1$H NMR (300 MHz, CDCl$_3$): 7.20-7.40 (m, 5H), 5.92 (td, 1H), 3.48-3.72 (m, 1H), 3.02 (dd, 1H), 2.83 (dd, 1H).

Step 4: (S)-4-Benzyl-3-((R)-4,4-difluoro-3-phenylbutanoyl)oxazolidin-2-one

A solution of 4,4-difluoro-3-phenylbutanoic acid (2.00 g, 10.0 mmol), (S)-4-benzyloxazolidin-2-one (1.95 g, 11.0 mmol) and lithium chloride (850 mg, 20.0 mmol) in anhydrous THF (25 mL) was cooled to −20° C. followed by the dropwise addition of pivaloyl chloride (3.07 mL, 25.0 mmol) then triethylamine (3.62 mL, 26.0 mmol). The resulting mixture was stirred at −20° C. for 30 min, then allowed to warm to RT, diluted with saturated ammonium chloride solution (30 mL) and extracted into EtOAc (3×20 mL). The combined organic phases were dried over Na$_2$SO$_4$, filtered, concentrated to dryness under reduced pressure and purified by flash chromatography (GraceResolv™ silica 330 g cartridge, cyclohexane:ethyl acetate, gradient elution from 95:5 to 60:40). The 2$^{nd}$ eluted diastereoisomer gave the title compound (1.42 g, 40%) as a colourless solid. LCMS (Method A): $R_T$=1.67 min, m/z=360 [M+H]$^+$. $^1$H NMR (300 MHz, CDCl$_3$): δ 7.19-7.43 (m, 8H), 6.96-7.06 (m, 2H), 5.99 (td, 1H), 4.59-4.69 (m, 1H), 4.20 (ddd, 1H), 4.14 (dd, 1H), 3.76-3.90 (m, 1H), 3.69 (dd, 1H), 3.44 (dd, 1H), 3.02 (dd, 1H), 2.62 (dd, 1H).

Step 5: (R)-4,4-Difluoro-3-phenylbutanoic acid

A solution of (S)-4-benzyl-3-((R)-4,4-difluoro-3-phenylbutanoyl)oxazolidin-2-one (1.42 g, 3.95 mmol) in a mixture of THF (28 mL) and water (5.6 mL) was cooled to 0° C. before a 30% aqueous hydrogen peroxide solution (1.01 mL, 9.88 mmol) and then a solution of lithium hydroxide (237 mg, 9.88 mmol) in water (5.6 mL) were added dropwise. The reaction mixture was stirred at 0° C. for 90 min then quenched by the addition of 2 M sodium thiosulfate$_{(aq)}$ (19.8 mL, 39.5 mmol), diluted with water (20 mL) and washed with EtOAc (3×20 mL). The organic phase was extracted into saturated sodium bicarbonate solution (3×20 mL) and the aqueous phases combined with that from above. The combined aqueous phases were adjusted to ~pH 4 by the addition of 2 M HCl solution, followed by extraction into EtOAc (3×20 mL). The combined organic phases were dried over Na$_2$SO$_4$, filtered, concentrated to dryness under reduced pressure and slurried in cyclohexane (15 mL) to give the title compound (683 mg, 86%) as a colourless solid. LCMS (Method A): $R_T$=1.11 min, m/z=199 [M−H]$^-$. $^1$H NMR (300 MHz, CDCl$_3$): δ 7.23-7.40 (m, 5H), 5.92 (td, 1H), 3.49-3.70 (m, 1H), 3.02 (dd, 1H), 2.82 (dd, 1H).

Acid 16: (R)-4,4,4-Trifluoro-3-phenylbutanoic acid

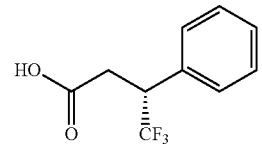

Step 1: (E)-4,4,4-Trifluoro-3-phenylbut-2-enoic acid

LiOH (132 mg, 5.5 mmol) was added to solution of (E)-ethyl 4,4,4-trifluoro-3-phenylbut-2-enoate (*J. Fluorine Chem.*, 2013, 152, p 56) (1.22 g, 5 mmol) in THF (10 mL) and water (5 mL) at RT. After 1 h, the pH of the reaction mixture was adjusted to pH 4 by the addition of 1 M HCl$_{(aq)}$ and the mixture was extracted with DCM (3×10 mL) using a Biotage phase separator. The combined organic phases were concentrated and the product dried in vacuo to give the title compound (1.06 g, 98%) as a colourless solid. LCMS (Method A): $R_T$=1.27 min, m/z=215 [M−H]$^-$. $^1$H NMR (300 MHz, DMSO-d$_6$): δ 13.22 (br s, 1H), 7.54-7.38 (m, 3H), 7.36-7.22 (m, 2H), 6.84 (s, 1H).

Step 2: (R)-4,4,4-Trifluoro-3-phenylbutanoic acid

A suspension of bis(norbornadiene)rhodium(I) tetrafluoroborate (3.46 mg, 9.25 μmol) and Walphos SL-W008-2 (8.7 mg, 9.25 μmol) in MeOH (6 mL) was degassed with N$_2$. After 30 min, a solution was obtained and (E)-4,4,4-trifluoro-3-phenylbut-2-enoic acid (200 mg, 0.925 mmol) was added. The reaction was then shaken in a Parr® Shaker apparatus at 3.5-4 bar H$_2$ for 22 h. Since there was no conversion, further bis(norbornadiene)rhodium(I) tetrafluoroborate (3.5 mg, 9.25 μmol) and Walphos SL-W008-2 (8.7 mg, 9.25 µmol) were added and the reaction was shaken in a Parr® Shaker apparatus at 5 bar H$_2$ for 24 h. The mixture was concentrated and the residue was purified by flash chromatography (10 g Biotage KP-Sil, 0-20% MeOH in DCM) to give the title compound (100 mg, 49%) as a colourless solid. LCMS (Method A): R$_T$=1.24 min, m/z=217 [M−H]$^-$. $^1$H NMR (300 MHz, CDCl$_3$): δ 10.67 (br s, 1H), 7.49-7.21 (m, 5H), 3.89 (m, 1H), 3.20-2.82 (m, 2H).

Epoxide 1: tert-Butyl 1-oxa-6-azaspiro[2.5]octane-6-carboxylate

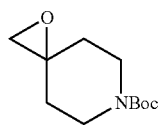

Prepared according to a variation of a literature procedure (*J. Med. Chem.*, 2008, 51, p 2170): Trimethylsulfoxonium iodide (22.5 g, 102 mmol) was suspended in DME (100 mL) under N$_2$ and potassium tert-butoxide (12.5 g, 111 mmol) was added. After 30 min, the mixture was cooled to 0° C. and a solution of tert-butyl 4-oxopiperidine-1-carboxylate (20 g, 100 mmol) in DME (20 mL) was added dropwise over 45 min. The reaction was allowed to warm to RT over 16 h then quenched by the addition of water (150 mL). The mixture was extracted with Et$_2$O (3×100 mL). The combined organic extracts were washed with brine (100 mL), dried over MgSO$_4$ and concentrated. The residue was dried by azeotropic distillation with toluene to give the title compound (16.5 g, 83%). $^1$H NMR (300 MHz, CDCl$_3$): δ 3.81-3.58 (m, 2H), 3.40 (ddd, 2H), 2.67 (s, 2H), 1.78 (ddd, 2H), 1.56-1.30 (m, 2H), 1.45 (s, 9H).

Epoxide 2: (R)-3-Phenyl-1-(1-oxa-6-azaspiro[2.5]octan-6-yl)butan-1-one

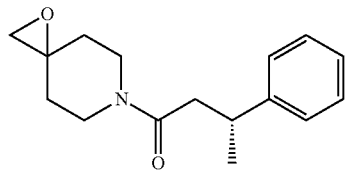 [SMILES: C[C@H](CC(=O)N1CCC2(CC1)CO2)c1ccccc1]

Step 1: (R)-1-(3-Phenylbutanoyl)piperidin-4-one

Piperidin-4-one hydrochloride (1.70 g, 12.6 mmol) was suspended in DCM (15 mL). EDC (2.89 g, 15.1 mmol) and DMAP (153 mg, 1.26 mmol) were added followed by DIPEA (11 mL, 62.7 mmol). The mixture was stirred for 10 min then a solution of (R)-3-phenylbutanoic acid (2.47 g, 15.1 mmol) in DCM (10 mL) was added. The mixture was stirred for 20 h then a further portion of EDC (2.89 g, 15.1 mmol) was added. The reaction was stirred for a further 4 h then quenched by the addition of saturated ammonium bicarbonate (150 mL). The mixture was extracted with EtOAc (3×50 mL). The combined organic extracts were washed with water (50 mL) and brine (50 mL), dried over MgSO$_4$ and concentrated. The residue was purified by flash chromatography (Biotage 50 g KP-Sil, 0-60% EtOAc in petroleum ether) to give the title compound (2.93 g, 95%). LCMS (Method B): R$_T$=1.07 min, m/z=246 [M+H]$^+$. $^1$H NMR (300 MHz, CDCl$_3$): δ 7.44-7.13 (m, 5H), 4.30-4.03 (m, 1H), 3.77-3.58 (m, 1H), 3.46 (tdd, 2H), 3.11-2.93 (m, 2H), 2.82-2.61 (m, 4H), 1.86 (m, 1H), 1.77-1.62 (m, 1H), 1.54-1.33 (m, 2H).

Step 2: (R)-3-Phenyl-1-(1-oxa-6-azaspiro[2.5]octan-6-yl)butan-1-one

Prepared according to General Procedure 11 using trimethylsulfonium iodide (6.09 g, 29.9 mmol), sodium hydride (60% dispersion in mineral oil, 1.19 g, 29.9 mmol), and (R)-1-(3-phenylbutanoyl)piperidin-4-one (2.93 g, 11.9 mmol) in DMSO (15 mL) to give the title compound (2.68 g, 87%). LCMS (Method B): R$_T$=1.02 min, m/z=260 [M+H]$^+$. $^1$H NMR (300 MHz, CDCl$_3$): δ 7.43-7.14 (m, 5H), 4.30-3.95 (m, 1H), 3.69-3.18 (m, 4H), 2.84-2.47 (m, 4H), 1.87-1.66 (m, 2H), 1.51-1.31 (m, 2H), 1.37 (d, 3H).

Epoxide 3: (R,S)-tert-Butyl 4,4-dimethyl-1-oxa-6-azaspiro[2.5]octane-6-carboxylate

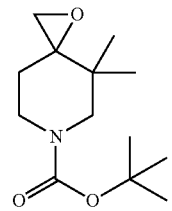 [SMILES: CC(C)(C)OC(=O)N1CCC2(CO2)C(C)(C)C1]

Prepared according to General Procedure 11 using trimethylsulfonium iodide (0.561 g, 2.75 mmol), sodium hydride (60% dispersion in mineral oil, 0.110 g, 2.75 mmol) and tert-butyl 3,3-dimethyl-4-oxopiperidine-1-carboxylate (0.25 g, 1.100 mmol) in DMSO (2.6 mL) to give the title compound (0.290 g, >100%) which was used without further purification. LCMS (Method B): R$_T$=1.47 min, m/z=142 [M+H-Boc]$^+$. $^1$H NMR (400 MHz, CDCl$_3$): δ 3.84-3.74 (m, 1H), 3.41-3.33 (m, 2H), 3.13 (d, 1H), 2.84 (d, 1H), 2.47 (d, 1H), 1.98-1.87 (m, 1H), 1.47 (s, 9H), 1.38 (d, 1H), 0.97 (s, 3H), 0.83 (s, 3H).

Epoxide 4: (R,S)-tert-Butyl 1-oxa-9-azadispiro[2.0.3$^4$.4$^3$]undecane-9-carboxylate

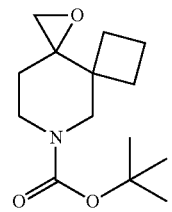 [SMILES: CC(C)(C)OC(=O)N1CCC2(CO2)C2(CCC2)C1]

Step 1: 6-Benzyl-6-azaspiro[3.5]nonan-9-one

1-Cyclobutylethanone (1.08 mL, 9.9 mmol) was dissolved in ethanol (5 mL) and concentrated aqueous HCl (0.81 mL, 9.8 mmol) was added. The mixture was heated to reflux. A mixture of benzylamine (1.02 mL, 9.33 mmol) and 37% aqueous formaldehyde (1.56 mL, 21 mmol) in ethanol (5 mL) was added and the mixture was heated at reflux for 16 h. Triethylamine (1.43 mL, 10.3 mmol) was added, followed by aqueous formaldehyde (0.21 mL, 2.80 mmol) and the reaction was heated at reflux for a further 24 h. The mixture was cooled to 5° C. and a solution of potassium hydroxide (0.55 g, 9.8 mmol) in water (1 mL) was added. The mixture was concentrated and the residue was taken up in water and extracted with $Et_2O$ (×2). The combined organic extracts were washed with brine, dried ($MgSO_4$) and concentrated. The residue was purified by flash chromatography (GraceResolv 40 g, 0-1% MeOH in DCM) to give the title compound (600 mg, 28%). $^1H$ NMR (400 MHz, $CDCl_3$): δ 7.27-7.40 (m, 5H), 3.60 (s, 2H), 2.67-2.71 (m, 4H), 2.44 (t, 2H), 2.32-2.40 (m, 2H), 1.75-1.89 (m, 4H).

Step 2: 6-Azaspiro[3.5]nonan-9-one Hydrochloride

6-Benzyl-6-azaspiro[3.5]nonane-9-one (150 mg, 0.65 mmol) was dissolved in DCM (2 mL) and cooled to 0° C. α-Chloroethyl chloroformate (0.071 mL, 0.65 mmol) was added and the reaction was stirred at 0° C. for 20 min. The mixture was concentrated and the residue was dissolved in MeOH. The resulting solution was heated at reflux for 40 min. The mixture was concentrated and the residue was taken up in chloroform. Diethyl ether was added and the precipitate was collected by filtration to give the title compound (70 mg, 61%). $^1H$ NMR (400 MHz, DMSO-$d_6$): δ 3.52-3.40 (m, 4H), 3.35 (m, 2H), 2.59 (t, 2H), 2.28 (m, 2H), 2.04-1.88 (m, 3H), 1.77-1.56 (m, 1H).

Step 3: tert-Butyl 9-oxo-6-azaspiro[3.5]nonane-6-carboxylate

6-Azaspiro[3.5]nonan-9-one hydrochloride (70 mg, 0.40 mmol) was suspended in a mixture of 1,4-dioxane (1 mL) and water (0.25 mL). DIPEA (0.17 mL, 1.00 mmol) was added, followed by di-tert-butyldicarbonate (0.14 mL, 0.60 mmol). The reaction was stirred at RT for 64 h. The mixture was concentrated and the residue was taken up in water and DCM. The organic layer was dried (Biotage phase separator) and concentrated to give the title compound (86 mg, 90%) $^1H$ NMR (400 MHz, $CDCl_3$): δ 3.61-3.76 (m, 4H), 2.41 (t, 2H), 2.30-2.41 (m, 2H), 1.92-2.08 (m, 1H), 1.75-1.92 (m, 3H), 1.50 (s, 9H).

Step 4: (R,S)-tert-Butyl 1-oxa-9-azadispiro[2.0.3$^4$.4$^3$]undecane-9-carboxylate Prepared according to General Procedure 11 using tert-butyl 9-oxo-6-azaspiro[3.5]nonane-6-carboxylate (0.30 g, 1.25 mmol), trimethylsulfonium iodide (0.640 g, 3.13 mmol) and sodium hydride (60% dispersion in mineral oil, 0.125 g, 3.13 mmol) in DMSO (6.3 mL). The crude product was purified by flash chromatography (GraceResolv 11 g, 0-40% EtOAc in cyclohexane) to give the title compound (200 mg, 63%). LCMS (Method B): $R_T$=1.48 min, m/z=154 [M+H-Boc]$^+$. $^1H$ NMR (400 MHz, $CDCl_3$): δ 4.02-3.72 (m, 2H), 3.23-3.06 (m, 2H), 2.74 (br dd, 1H), 2.60 (d, 1H), 1.98-1.68 (m, 6H), 1.49 (s, 9H), 1.45-1.35 (m, 2H).

Epoxide 5: tert-Butyl (1R,5S,8r)-3-azaspiro[bicyclo[3.2.1]octane-8,2'-oxirane]-3-carboxylate

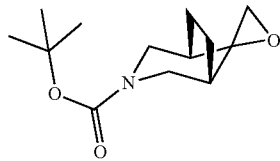 [SMILES: CC(C)(C)OC(=O)N1C[C@@H]2CC[C@@H](C1)C21CO1]

Prepared according to General Procedure 11 using (1R,5S)-tert-butyl 8-oxo-3-azabicyclo[3.2.1]octane-3-carboxylate (0.150 g, 0.67 mmol) in DMSO (2.2 mL), trimethylsulfonium iodide (0.34 g, 1.66 mmol) and (60% dispersion in mineral oil, 0.067 g, 1.67 mmol), giving the title compound (160 mg, quantitative) which was used without further purification. LCMS (Method B): $R_T$=1.26 min, m/z=140 [M+H-Boc]$^+$. $^1H$ NMR (400 MHz, $CDCl_3$): δ 4.00 (d, 1H), 3.84 (d, 1H), 3.30 (d, 1H), 3.20 (d, 1H), 2.86 (s, 2H), 1.90-1.80 (m, 2H), 1.75-1.55 (m, 4H), 1.47 (s, 9H).

Epoxide 6: tert-Butyl 1-oxa-10-azadispiro[2.0.4$^4$.4$^3$]dodecane-10-carboxylate

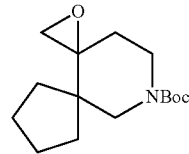 [SMILES: CC(C)(C)OC(=O)N1CCC2(CO2)C2(CCCC2)C1]

Step 1: tert-Butyl 10-oxo-7-azaspiro[4.5]decane-7-carboxylate

Potassium tert-butoxide (24.8 g, 221 mmol) was added portionwise to a solution of tert-butyl 4-oxopiperidine-1-carboxylate (20 g, 100 mmol) in toluene (200 mL) in a 3-necked 1 L RBF fitted with a reflux condenser under $N_2$ at RT. After 1 h, 1,4-dibromobutane (12.0 mL, 100 mmol) was added dropwise over 15 min and the reaction heated at reflux for 2 h. The reaction was allowed to cool to RT, diluted with 1:1 saturated $NH_4Cl_{(aq)}$/water (200 mL) and extracted with EtOAc (3×75 mL). The combined organic phases were washed with brine (100 mL), dried over $MgSO_4$ and concentrated in vacuo. The crude product was purified by flash chromatography (Biotage KP-Sil 340 g cartridge, 0-10% EtOAc in cyclohexane; mixed fractions were re-purified Biotage KP-Sil 100 g cartridge, 0-15% EtOAc in cyclohexane) to give the title compound (8.26 g, 32%) as a colurless solid. LCMS (Method A): $R_T$=1.52 min, m/z=198 [M-butene+H]$^+$. $^1H$ NMR (500 MHz, $CDCl_3$): δ 3.70 (t, J=6.6 Hz, 2H), 3.45 (s, 2H), 2.48 (t, J=6.4 Hz, 2H), 1.97-1.88 (m, 2H), 1.72-1.62 (m, 4H), 1.52-1.43 (m, 2H), 1.49 (s, 9H).

Step 2: tert-Butyl 1-oxa-10-azadispiro[2.0.4$^4$.4$^3$]dodecane-10-carboxylate

To a suspension of trimethylsulfonium iodide (18.8 g, 92.1 mmol) in DMF (200 mL) at 0° C. under $N_2$ was added sodium hydride (60% dispersion in mineral oil, 3.68 g, 92.1 mmol) portionwise over 15 min. After stirring for 30 min, the mixture was allowed to warm to RT and stirred for further 1 h before a solution of tert-butyl 10-oxo-7-azaspiro [4.5]decane-7-carboxylate (15.6 g, 61.4 mmol) in DMF (100 mL) was added dropwise over 30 min using a pressure-equalised dropping funnel. The reaction mixture was stirred at RT for 2 days and slowly quenched by the addition of water (20 mL). The resulting mixture was concentrated in vacuo, water (600 mL) was added and the mixture extracted with EtOAc (3×200 mL). The combined organic phases were dried over MgSO$_4$, filtered and concentrated in vacuo. The crude product was purified by flash chromatography (100 g Biotage KP-Sil, 0-20% EtOAc in cyclohexane) to give the title compound (14.0 g, 85%) as a colourless liquid. $^1$H NMR (500 MHz, DMSO-d$_6$): δ 3.57 (s, 2H), 3.35-3.16 (m, 2H), 2.75 (d, J=4.5 Hz, 1H), 2.53 (d, J=4.5 Hz, 1H), 1.47 (s, 9H), 1.78-1.21 (m, 10H (signal overlaps with HDO)).

Epoxide 7: tert-Butyl 1-oxa-11-azadispiro[2.0.5$^4$.4$^3$]tridecane-11-carboxylate

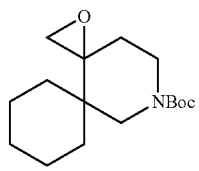 [SMILES: CC(C)(C)OC(=O)N1CCC2(CO2)C2(CCCCC2)C1]

Step 1: tert-Butyl 5-oxo-2-azaspiro[5.5]undecane-2-carboxylate

Potassium tert-butoxide (0.62 g, 5.52 mmol) was added portionwise to a solution of tert-butyl 4-oxopiperidine-1-carboxylate (0.5 g, 2.51 mmol) in toluene (5 mL) in a 3-necked 50 mL RBF fitted with a reflux condenser under N$_2$ at RT. After 1 h, 1,5-dibromopentane (0.342 mL, 2.51 mmol) was added dropwise over 10 min and the reaction heated at reflux for 3 h. The reaction was allowed to cool to RT, diluted with 1:1 saturated NH$_4$Cl$_{(aq)}$/water and extracted with EtOAc (×3). The combined organic phases were washed with brine, passed through a Biotage phase separator and concentrated in vacuo. The crude product was purified by flash chromatography (Biotage KP-Sil 50 g cartridge, 0-5% EtOAc in cyclohexane) to give the title compound (0.18 g, 26%). $^1$H NMR (500 MHz, CDCl$_3$): δ 3.77-3.61 (bs, 2H), 3.60-3.46 (bs, 2H), 2.48 (t, J=6.5 Hz, 2H), 1.77-1.29 (m, 10H (overlaps with HDO signal)), 1.50 (s, 9H).

Step 2: tert-Butyl 1-oxa-11-azadispiro[2.0.5$^4$.4$^3$]tridecane-11-carboxylate

To a suspension of trimethylsulfonium iodide (206 mg, 1.01 mmol) in DMF (2 mL) at 0° C. under N$_2$ was added sodium hydride (60% dispersion in mineral oil) (40.4 mg, 1.01 mmol) portionwise over 15 min. After stirring for 30 min, the mixture was allowed to warm to RT and stirred for further 30 min before a solution of tert-butyl 5-oxo-2-azaspiro[5.5]undecane-2-carboxylate (180 mg, 0.673 mmol) in DMF (1.5 mL) was added dropwise over 10 min. The reaction mixture was stirred at RT for 18 h and slowly quenched by the addition of water. The resulting mixture was concentrated in vacuo, water was added and the mixture extracted with EtOAc (×3). The combined organic phases were dried over MgSO$_4$, filtered and concentrated in vacuo. The crude product was purified by flash chromatography (50 g Biotage KP-Sil, 0-20% EtOAc in cyclohexane) to give the title compound (120 mg, 63%) as a colourless liquid. $^1$H NMR (500 MHz, CDCl$_3$): δ 3.73-3.51 (m, 2H), 3.51-3.29 (m, 2H), 2.92 (d, J=4.4 Hz, 1H), 2.42 (d, J=4.4 Hz, 1H), 1.48 (s, 9H), 1.72-1.33 (m, 9H (signal overlaps with HDO)), 1.23-1.02 (m, 3H).

Example 1: (R)-5-Bromo-1-((4-hydroxy-1-(3-phenylbutanoyl)piperidin-4-yl)methyl)-4-phenylpyridin-2(1H)-one

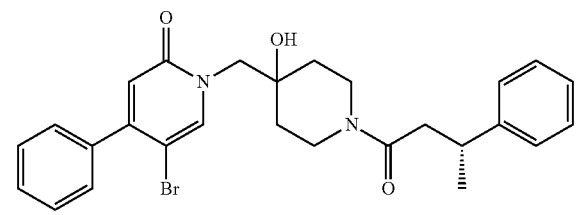 [SMILES: C[C@H](CC(=O)N1CCC(O)(Cn2cc(Br)c(-c3ccccc3)cc2=O)CC1)c1ccccc1]

Step 1: 5-Bromo-4-phenylpyridin-2(1H)-one

5-Bromo-2-chloro-4-phenylpyridine (1.13 g, 4.21 mmol) (prepared as described in Eur. J. Org. Chem., 2013, p 2316-2324) was dissolved in DMSO (14 mL) and a solution of sodium hydroxide (1.18 g, 29.5 mmol) in water (14.0 mL) was added. The mixture was heated in a microwave at 130° C. for 30 min. The mixture was acidified using 2 M HCl and extracted with EtOAc (×3). The combined organic extracts were washed with 1:1 water/brine, dried over MgSO$_4$, filtered and concentrated. The residue was taken up in a small volume of DCM and the solid precipitate was collected by filtration through a sintered funnel. The crude product was washed with diethyl ether and dried to give the title compound (0.60 g, 57%). LCMS (Method B): R$_T$=0.91 min, m/z=250, 252 [M+H]$^+$.

Step 2: (R)-5-Bromo-1-((4-hydroxy-1-(3-phenylbutanoyl)piperidin-4-yl)methyl)-4-phenylpyridin-2(1H)-one A mixture of 5-bromo-4-phenylpyridin-2(1H)-one (640 mg, 2.56 mmol), Epoxide 2 (796 mg, 3.07 mmol) and pyridine (0.62 mL, 7.68 mmol) in DMF (10 mL) was heated in a sealed tube at 80° C. for 64 h. The mixture was concentrated and the residue was purified by flash chromatography (Biotage KP-Sil, 0-100% EtOAc in cyclohexane then 0-10% MeOH in EtOAc) to give the title compound (368 mg, 28%). LCMS (Method B): R$_T$=1.27 min, m/z=509, 511 [M+H]$^+$. $^1$H NMR (400 MHz, methanol-d$_4$, this compound appears as two conformers): δ 7.96 (m, 1H), 7.48 (m, 5H), 7.30 (m, 5H), 6.55 (s, 1H), 4.26-3.87 (m, 3H), 3.70 (m, 1H), 3.22 (m, 2H), 3.01 (m, 1H), 2.77 (m, 1H), 2.54 (m, 1H), 1.61 (m, 1H), 1.51-1.29 (m, 6.4H), 0.93 (m, 0.6H, one conformer only).

Example 2: 6-(2-Fluorophenyl)-3-((4-hydroxy-1-(3-phenylpropanoyl)piperidin-4-yl)methyl)pyrimidin-4(3H)-one

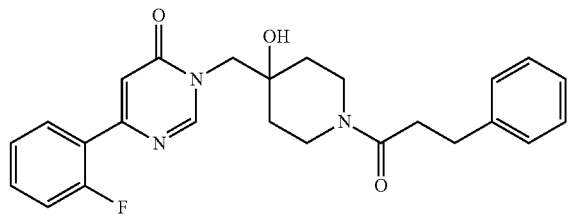

Prepared according to General Procedure 2 using Amine 1 (45 mg, 0.132 mmol), 3-phenylpropanoyl chloride (27.5 mg, 0.163 mmol), DIPEA (52 µL, 0.297 mmol) and DCM (3 mL) to give the title compound (48.4 mg, 84%). LCMS (Method B): $R_T$=1.10 min, m/z=436 [M+H]$^+$. $^1$H NMR (400 MHz, CDCl$_3$): δ 8.12 (s, 1H), 8.08-8.03 (m, 1H), 7.46-7.44 (m, 1H), 7.32-7.15 (m, 7H), 7.10 (s, 1H), 4.47-4.40 (m, 1H), 4.05-3.92 (m, 2H), 3.87 (s, 1H), 3.65-3.58 (m, 1H), 3.40-3.31 (m, 1H), 3.04-2.96 (m, 3H), 2.66-2.61 (m, 2H), 1.51-1.23 (m, 4H).

Example 3: 3-((1-(3-Cyclobutylpropanoyl)-4-hydroxypiperidin-4-yl)methyl)-6-(2-fluorophenyl)pyrimidin-4(3H)-one

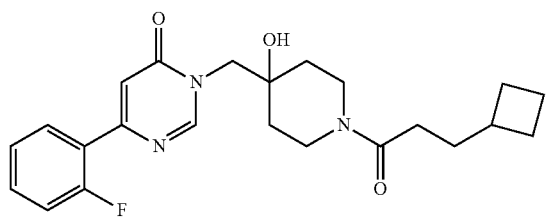 [SMILES: O=C(CCC1CCC1)N1CCC(O)(Cn2cnc(-c3ccccc3F)cc2=O)CC1]

Amine 1 (30 mg, 0.088 mmol), 3-cyclobutylpropanoic acid (12.7 mg, 0.099 mmol) and triethylamine (17 µL, 0.119 mmol) were dissolved in DMF and EDC (20.9 mg, 0.109 mmol) was added. The mixture was stirred overnight then partitioned between DCM and a mixture of brine and saturated aqueous sodium bicarbonate. The aqueous layer was extracted with DCM and the combined organic extracts were dried over MgSO$_4$ and concentrated. The residue was purified by flash chromatography (GraceResolv 4 g, 10-90% EtOAc in cyclohexane) to give the title compound (24.1 mg, 66%). LCMS (Method B): $R_T$=1.13 min, m/z=414 [M+H]$^+$. $^1$H NMR (400 MHz, CDCl$_3$): δ 8.17 (m, 1H), 8.08-8.03 (m, 1H), 7.48-7.42 (m, 1H), 7.30-7.24 (m, 1H), 7.20-7.14 (m, 1H), 7.12 (s, 1H), 4.45-4.38 (m, 1H), 4.18-4.12 (m, 1H), 3.99-3.93 (m, 1H), 3.81 (s, 1H), 3.73-3.65 (m, 1H), 3.48-3.39 (m, 1H), 3.10-3.01 (m, 1H), 2.31-2.19 (m, 3H), 2.09-2.00 (m, 2H), 1.90-1.76 (m, 2H), 1.74-1.60 (m, 6H), 1.58-1.53 (m, 2H).

Example 4: 3-((1-(3-Cyclopentylpropanoyl)-4-hydroxypiperidin-4-yl)methyl)-6-(2-fluorophenyl)pyrimidin-4(3H)-one

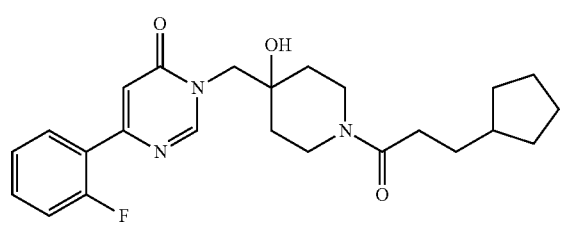 [SMILES: O=C(CCC1CCCC1)N1CCC(O)(Cn2cnc(-c3ccccc3F)cc2=O)CC1]

Prepared according to General Procedure 2 using Amine 1 (40 mg, 0.118 mmol), 3-cyclopentylpropanoyl chloride (23.3 mg, 0.145 mmol), DIPEA (46 µL, 0.264 mmol) and DCM (2 mL) to give the title compound (49.4 mg, 98%). LCMS (Method B): $R_T$=1.21 min, m/z=428 [M+H]$^+$. $^1$H NMR (400 MHz, CDCl$_3$): δ 8.17 (s, 1H), 8.08-8.04 (m, 1H), 7.48-7.43 (m, 1H), 7.30-7.25 (m, 1H), 7.20-7.15 (m, 1H), 7.12 (s, 1H), 4.47-4.38 (m, 1H), 4.19-3.92 (m, 2H), 3.81-3.78 (m, 1H), 3.75-3.67 (m, 1H), 3.49-3.40 (m, 1H), 3.11-3.01 (m, 1H), 2.38-2.30 (m, 2H), 1.83-1.72 (m, 3H), 1.69-1.45 (m, 10H), 1.16-1.05 (m, 2H).

Example 5: (R,S)-6-(2-Fluorophenyl)-3-((4-hydroxy-1-(2-methyl-3-phenylpropanoyl)piperidin-4-yl)methyl)pyrimidin-4(3H)-one

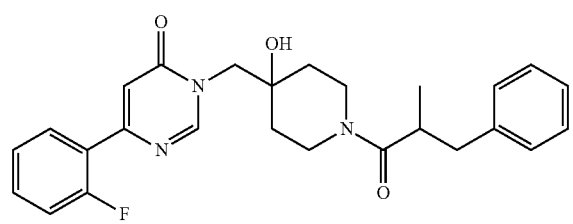 [SMILES: CC(Cc1ccccc1)C(=O)N1CCC(O)(Cn2cnc(-c3ccccc3F)cc2=O)CC1]

Prepared according to General Procedure 3 using Amine 1 (40 mg, 0.118 mmol), (R,S)-2-methyl-3-phenylpropanoic acid (21.7 mg, 0.132 mmol), DIPEA (46 µL, 0.264 mmol), HATU (105 mg, 0.277 mmol) and DMF (2 mL) to give the title compound (14.2 mg, 27%). LCMS (Method B): $R_T$=1.15 min, m/z=450 [M+H]$^+$. $^1$H NMR (400 MHz, methanol-d$_4$): δ 8.39-8.31 (m, 1H), 8.05-8.00 (m, 1H), 7.53-7.46 (m, 1H), 7.34-7.17 (m, 6H), 7.17-7.11 (m, 1H), 6.94-6.91 (m, 1H), 4.62-4.57 (s, 1H), 4.29-4.23 (m, 1H), 4.09-3.96 (m, 1H), 3.90-3.67 (m, 2H), 3.67-3.60 (m, 1H), 3.26-3.14 (m, 2H), 3.07-2.98 (m, 1H), 2.89-2.80 (m, 2H), 2.73-2.61 (m, 1H), 1.62-1.53 (m, 1H), 1.48-1.22 (m, 3H), 0.51-0.41 (m, 1H)

Example 6: (R)—N-(3-(1-((4-Hydroxy-1-(3-phenylbutanoyl)piperidin-4-yl)methyl)-6-oxo-4-phenyl-1,6-dihydropyridin-3-yl)phenyl)acetamide

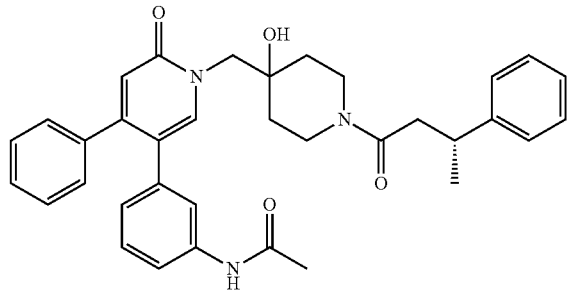 [SMILES: CC(=O)Nc1cccc(-c2cn(CC3(O)CCN(C(=O)C[C@@H](C)c4ccccc4)CC3)c(=O)cc2-c2ccccc2)c1]

Prepared according to General Procedure 4 using (R)-5-bromo-1-((4-hydroxy-1-(3-phenylbutanoyl)piperidin-4-yl)methyl)-4-phenylpyridin-2(1-H)-one (50 mg, 0.098 mmol), (3-acetamidophenyl)boronic acid (26.3 mg, 0.147 mmol), sodium carbonate (20.8 mg, 0.196 mmol), Pd(PPh$_3$)$_4$(5.7 mg, 0.005 mmol), 1,4-dioxane (1 mL) and water (0.4 mL). The mixture was heated in a microwave at 150° C. for 15 min to give the title compound (38 mg, 69%). LCMS (Method B): R$_T$=1.37 min, m/z=564 [M+H]$^+$. $^1$H NMR (400 MHz, methanol-d$_4$): δ 7.72-7.61 (m, 1H), 7.42-7.36 (m, 2H), 7.33-7.22 (m, 7H), 7.20-7.10 (m, 4H), 6.77-6.72 (m, 1H), 7.59 (s, 1H), 4.62 (s, 2H), 4.30-4.06 (m, 2.5H), 3.95-3.88 (m, 0.5H), 3.75-3.63 (m, 1H), 3.37-3.13 (m, 2H), 3.08-2.91 (m, 1H), 2.85-2.71 (m, 1H), 2.64-2.46 (m, 1H), 2.07 (s, 2H), 1.71-1.39 (m, 4H), 1.35-1.32 (m, 3H), 0.96-0.85 (m, 1H).

Example 7: (R)-3-(1-((4-Hydroxy-1-(3-phenylbutanoyl)piperidin-4-yl)methyl)6-oxo-4-phenyl-1,6-dihydropyridin-3-yl)benzamide

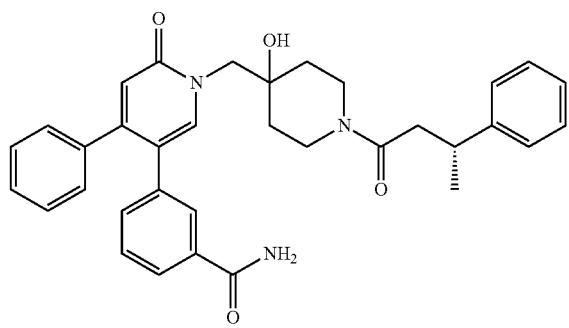 [SMILES: C[C@H](CC(=O)N1CCC(O)(Cn2cc(-c3cccc(C(N)=O)c3)c(-c3ccccc3)cc2=O)CC1)c1ccccc1]

Prepared according to General Procedure 4 using (R)-5-bromo-1-((4-hydroxy-1-(3-phenylbutanoyl)piperidin-4-yl)methyl)-4-phenylpyridin-2(1H)-one (50 mg, 0.098 mmol), (3-carbamoylphenyl)boronic acid (24.3 mg, 0.147 mmol), sodium carbonate (20.8 mg, 0.196 mmol), Pd(PPh$_3$)$_4$(5.7 mg, 0.005 mmol), 1,4-dioxane (1 mL) and water (0.4 mL). The mixture was heated in a microwave at 150° C. for 15 min to give the title compound (37.5 mg, 69%). LCMS (Method B): R$_T$=1.27 min, m/z=550 [M+H]$^+$. $^1$H NMR (400 MHz, methanol-d$_4$): δ 7.76-7.67 (m, 3H), 7.33-7.23 (m, 8H), 7.21-7.10 (m, 4H), 6.61 (s, 1H), 4.30-3.90 (m, 4H), 3.76-3.64 (m, 1H), 3.27-3.12 (m, 2H), 3.08-2.92 (m, 1H), 2.84-2.71 (m, 1H), 2.65-2.47 (m, 1H), 1.72-1.37 (m, 4H), 1.35-1.32 (m, 3H), 1.00-0.83 (m, 2H).

Example 8: (R)-5-(Furan-2-yl)-1-((4-hydroxy-1-(3-phenylbutanoyl)piperidin-4-yl)methyl)-4-phenylpyridin-2(1H)-one

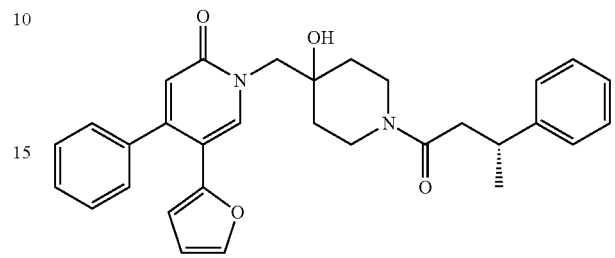

Prepared according to General Procedure 4 using (R)-5-bromo-1-((4-hydroxy-1-(3-phenylbutanoyl)piperidin-4-yl)methyl)-4-phenylpyridin-2(1H)-one (20 mg, 0.039 mmol), furan-2-ylboronic acid (4.4 mg, 0.039 mmol), sodium carbonate (8.3 mg, 0.079 mmol), Pd(PPh$_3$)$_4$(2.3 mg, 0.002 mmol), 1,4-dioxane (0.7 mL) and water (0.3 mL). The mixture was heated in a microwave at 150° C. for 15 min to give the title compound (4.9 mg, 25%). LCMS (Method B): R$_T$=1.33 min, m/z=497 [M+H]$^+$. $^1$H NMR (400 MHz, methanol-d$_4$): δ 8.00-7.93 (m, 1H), 7.45-7.15 (m, 11H), 6.49 (s, 1H), 6.30-6.27 (m, 1H), 5.66-5.64 (m, 1H), 4.61 (brs, 1H), 4.30-4.12 (m, 2H), 4.10-3.90 (m, 2H), 3.74-3.63 (m, 1H), 3.07-2.91 (m, 1H), 2.84-2.71 (m, 1H), 2.64-2.47 (m, 1H), 1.69-1.41 (m, 4H), 1.36-1.32 (m, 3H), 0.97-0.87 (m, 1H).

Example 9: (R)-1-((4-Hydroxy-1-(3-phenylbutanoyl)piperidin-4-yl)methyl)-5-(1-methyl-1H-pyrazol-5-yl)-4-phenylpyridin-2(1H)-one

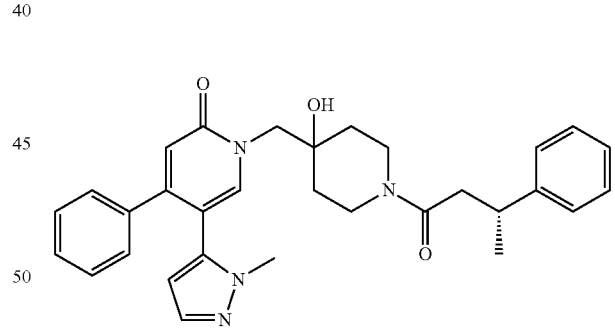

Prepared according to General Procedure 4 using (R)-5-bromo-1-((4-hydroxy-1-(3-phenylbutanoyl)piperidin-4-yl)methyl)-4-phenylpyridin-2(1H)-one (20 mg, 0.039 mmol), (1-methyl-1H-pyrazol-5-yl)boronic acid (4.9 mg, 0.039 mmol), sodium carbonate (8.3 mg, 0.079 mmol), Pd(PPh$_3$)$_4$(2.3 mg, 0.002 mmol), 1,4-dioxane (0.7 mL) and water (0.3 mL). The mixture was heated in a microwave at 150° C. for 15 min to give the title compound (3.7 mg, 18%). LCMS (Method B): R$_T$=1.13 min, m/z=511 [M+H]$^+$. $^1$H NMR (400 MHz, methanol-d$_4$): δ 7.77-7.69 (m, 1H), 7.40-7.16 (m, 11H), 6.66 (s, 1H), 6.30 (t, 1H), 4.51 (s, 1H), 4.19-3.77 (m, 3H), 3.66-3.50 (m, 1H), 3.27-3.06 (m, 5H), 3.01-2.81 (m, 1H), 2.77-2.59 (m, 1H), 2.56-2.36 (m, 1H), 1.63-0.97 (m, 6H), 0.89-0.71 (s, 1H).

Example 10: (R)-4-Chloro-1-((4-hydroxy-1-(3-phenylbutanoyl)piperidin-4-yl)methyl)-5-phenylpyridin-2(1H)-one

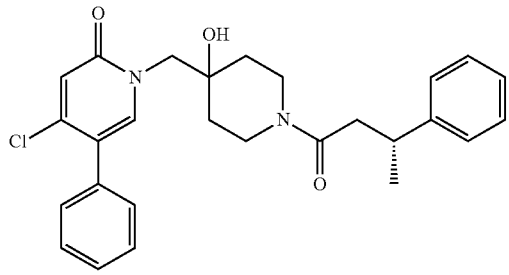 [SMILES: C[C@H](CC(=O)N1CCC(O)(Cn2cc(-c3ccccc3)c(Cl)cc2=O)CC1)c1ccccc1]

Prepared according to General Procedure 4 using Intermediate 2 (41 mg, 0.083 mmol), phenylboronic acid (9 mg, 0.075 mmol), sodium carbonate (11 mg, 0.183 mmol), Pd(PPh$_3$)$_4$ (1.1 mg, 0.004 mmol), 1,4-dioxane (0.7 mL) and water (0.3 mL). The mixture was heated in a microwave at 80° C. for 1 h. The crude product was purified by preparative HPLC to give the title compound (4.7 mg, 12%). LCMS (Method B): R$_T$=1.30 min, m/z=465 [M+H]$^+$. $^1$H NMR (300 MHz, methanol-d$_4$): δ 7.71-7.58 (m, 1H), 7.50-7.12 (m, 10H), 6.79-6.72 (s, 1H), 4.29-3.80 (m, 4H), 3.74-3.60 (m, 1H), 3.25-3.13 (m, 1H), 3.09-2.68 (m, 2H), 2.67-2.43 (m, 1H), 1.70-1.36 (m, 4H), 1.35-1.29 (m, 3H), 0.94-0.81 (m, 1H).

Example 11: (R)-4-(Dimethylamino)-1-((4-hydroxy-1-(3-phenylbutanoyl)piperidin-4-yl)methyl)-5-phenylpyridin-2(1H)-one

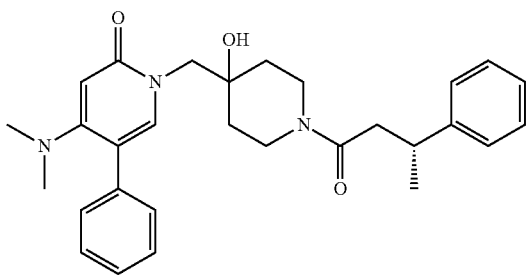 [SMILES: C[C@H](CC(=O)N1CCC(O)(Cn2cc(-c3ccccc3)c(N(C)C)cc2=O)CC1)c1ccccc1]

A mixture of Example 10 (46 mg, 0.10 mmol) and dimethylamine (2 M in THF, 1.1 mL, 2.2 mmol) in DMF (1.5 mL) was heated at reflux for 72 h. The mixture was cooled and partitioned between EtOAc and 50% saturated brine. The organics were washed with 50% saturated brine (×4) and the aqueous layer was extracted with EtOAc (×3). The combined organic extracts were dried (MgSO$_4$) and concentrated. The residue was purified by flash chromatography (GraceResolv, 5-100% EtOAc in cyclohexane; then 0-20% MeOH in EtOAc) to give the title compound (6.4 mg, 13%). LCMS (Method B): R$_T$=1.25 min, m/z=474 [M+H]$^+$. $^1$H NMR (400 MHz, methanol-d$_4$): 7.46-7.38 (m, 4H), 7.37-7.21 (m, 6H), 7.19-7.09 (m, 1H), 5.84 (s, 1H), 4.62 (br s, 1H), 4.28-4.11 (m, 2H), 3.98-3.71 (m, 2H), 3.69-3.61 (m, 1H), 3.05-2.89 (m, 1H), 2.83-2.69 (m, 1H), 2.66-2.62 (m, 6H), 2.62-2.46 (m, 1H), 1.63-1.36 (m, 4H), 1.34-1.30 (m, 3H), 0.92-0.79 (m, 1H).

Example 12: (R)-1-((4-Hydroxy-1-(3-phenylbutanoyl)piperidin-4-yl)methyl)-5-phenyl-4-(prop-1-en-2-yl)pyridine-2(1H)-one

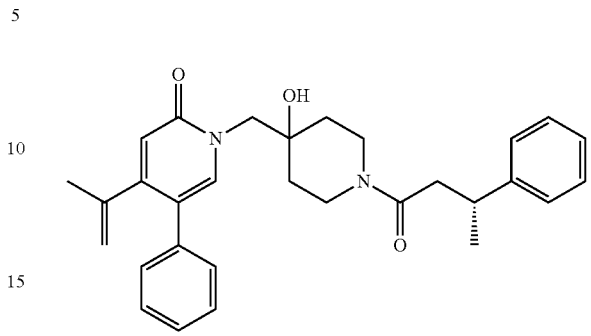

Prepared according to General Procedure 4 using Example 10 (46.5 mg, 0.100 mmol), prop-1-en-2-ylboronic acid (10.6 µL, 0.110 mmol), sodium carbonate (13.2 mg, 0.220 mmol), Pd(PPh$_3$)$_4$ (2.6 mg, 0.010 mmol), 1,4-dioxane (0.7 mL) and water (0.3 mL). The mixture was heated in a microwave at 150° C. for 15 min. The crude product was purified by preparative HPLC to give the title compound (14.7 mg, 31%). LCMS (Method B): R$_T$=1.36 min, m/z=471 [M+H]$^+$. $^1$H NMR (400 MHz, methanol-d$_4$): δ 7.57-7.47 (m, 1H), 7.44-7.22 (m, 9H), 7.19-7.13 (m, 1H), 6.47 (s, 1H), 5.17-5.14 (m, 1H), 5.12-5.10 (m, 1H), 4.28-4.13 (m, 2H), 4.06-3.85 (m, 2H), 3.74-3.62 (m, 1H), 3.28-3.21 (m, 1H), 3.06-2.89 (m, 1H), 2.89-2.70 (m, 1H), 2.63-2.46 (m, 1H), 1.68-1.55 (m, 4H), 1.53-1.27 (m, 6H), 0.94-0.85 (m, 1H).

Example 13: (R)-Ethyl 1-((4-hydroxy-1-(3-phenylbutanoyl)piperidin-4-yl)methyl)-6-oxo-4-phenyl-1,6-dihydropyridine-3-carboxylate

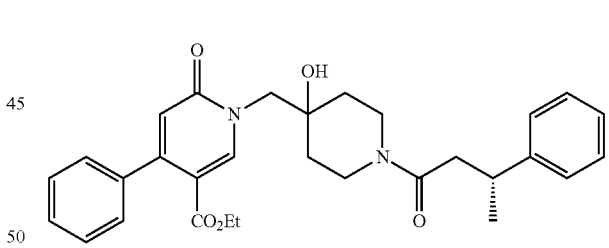

Prepared according to General Procedure 1 using Epoxide 2 (273 mg, 1.05 mmol), ethyl 6-oxo-4-phenyl-1,6-dihydropyridine-3-carboxylate (256 mg, 1.05 mmol) and DIPEA (0.28 mL, 1.58 mmol) in DMF (2 mL). The reaction was stirred at 80° C. for 64 h. The crude product was purified by flash chromatography (GraceResolv, 5-100% EtOAc in cyclohexane) to give the title compound (230 mg, 44%). LCMS (Method B): R$_T$=1.29 min, m/z=503 [M+H]$^+$. $^1$H NMR (400 MHz, methanol-d$_4$, this compound appears as two conformers A:B in a 2:3 ratio): δ 8.41 (s, 0.4H, conformer A), 8.36 (s, 0.6H, conformer B), 7.46-7.16 (m, 10H), 6.42 (s, 1H), 4.30-3.89 (m, 5H), 3.76-3.62 (m, 1H), 3.30-3.17 (m, 2H), 3.10-2.46 (m, 3H), 1.71-1.28 (m, 6H), 1.03 (t, 3H), 0.97-0.83 (m, 1H).

Example 14: (R,S)-4-(2-Fluorophenyl)-1-((4-hydroxy-1-(2-methyl-1,2,3,4-tetrahydronaphthalene-2-carbonyl)piperidin-4-yl)methyl)-N-isopropyl-N-methyl-6-oxo-1,6-dihydropyridine-3-carboxamide

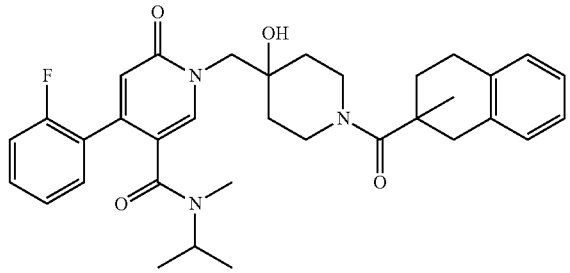

Prepared according to General Procedure 3 using 4-(2-fluorophenyl)-1-((4-hydroxypiperidin-4-yl)methyl)-N-isopropyl-N-methyl-6-oxo-1,6-dihydropyridine-3-carboxamide (20 mg, 0.05 mmol), DCM (2 mL), DIPEA (0.026 mL, 0.149 mmol), (R,S)-2-methyl-1,2,3,4-tetrahydronaphthalene-2-carboxylic acid (11.4 mg, 0.060 mmol) and HATU (24.6 mg, 0.065 mmol). The crude product was chromatographed (GraceResolv 4 g, 10-100% EtOAc in cyclohexane; then 0-10% MeOH in EtOAc) to give the title compound (27 mg, 94%). LCMS (Method B): $R_T$=1.30 min, m/z=574 [M+H]$^+$. $^1$H NMR (400 MHz, DMSO-d$_6$): δ 7.77 (s, 1H), 7.46 (m, 1H), 7.35 (m, 1H), 7.28 (m, 2H), 7.05 (m, 4H), 6.45 (s, 1H), 5.00 (s, 1H), 4.43 (br s, 1H), 4.01 (m, 4H), 3.20 (m, 3H), 2.75 (m, 1H), 2.67 (m, 3H), 2.58 (m, 1H), 2.11 (m, 1H), 1.82 (m, 1H), 1.49 (m, 4H), 1.26 (m, 4H), 0.94 (br s, 6H).

Example 15: (R,S)-1-((1-(3-Cyclobutyl-2-methylpropanoyl)-4-hydroxypiperidin-4-yl)methyl)-4-phenyl-5-(piperidine-1-carbonyl)pyridin-2(1H)-one

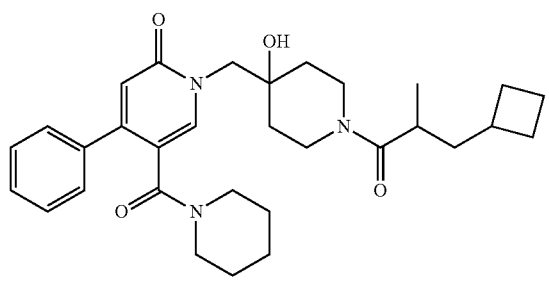 [SMILES: CC(CC1CCC1)C(=O)N1CCC(O)(Cn2cc(C(=O)N3CCCCC3)c(-c3ccccc3)cc2=O)CC1]

Step 1: Ethyl 1-((1-(tert-butoxycarbonyl)-4-hydroxypiperidin-4-yl)methyl)-6-oxo-4-phenyl-1,6-dihydropyridine-3-carboxylate Prepared according to General Procedure 1 using ethyl 6-oxo-4-phenyl-1,6-dihydropyridine-3-carboxylate (1 g, 4.11 mmol), Epoxide 1 (1.05 g, 4.93 mmol), DMF (20 mL) and pyridine (0.83 mL, 10.3 mmol). The mixture was stirred at 90° C. for 16 h. The crude product was purified by flash chromatography (GraceResolv 40 g, 10-100% EtOAc in cyclohexane) to give the title compound (640 mg, 34%). LCMS (Method B): $R_T$=1.38 min, m/z=357 [M+H-Boc]$^+$.

Step 2: 1-((1-(tert-Butoxycarbonyl)-4-hydroxypiperidin-4-yl)methyl)-6-oxo-4-phenyl-1,6-dihydropyridine-3-carboxylic acid Ethyl 1-((1-(tert-butoxycarbonyl)-4-hydroxypiperidin-4-yl)methyl)-6-oxo-4-phenyl-1,6-dihydropyridine-3-carboxylate (120 mg, 0.26 mmol) was dissolved in ethanol (1 mL) and sodium hydroxide solution (2 M in water, 1 mL, 2.00 mmol) was added. The mixture was stirred at 50° C. for 16 h. The solution was concentrated and 2 M aqueous HCl was added until pH was approximately 4. The mixture was extracted with EtOAc (×3). The combined organic extracts were washed with brine then dried over MgSO$_4$ and concentrated to give the title compound (91 mg, 81%) which was used without further purification. LCMS (Method B): $R_T$=1.12 min, m/z=329 [M+H-Boc]$^+$.

Steps 3 & 4: 1-((4-Hydroxypiperidin-4-yl)methyl)-4-phenyl-5-(piperidine-1-carbonyl)pyridine-2(1H)-one Prepared according to General Procedure 3 using 1-((1-(tert-butoxycarbonyl)-4-hydroxypiperidin-4-yl)methyl)-6-oxo-4-phenyl-1,6-dihydropyridine-3-carboxylic acid (70 mg, 0.16 mmol), piperidine (0.021 mL, 0.21 mmol), DIPEA (0.086 mL, 0.49 mmol), HATU (68 mg, 0.18 mmol) and DMF (1.5 mL) to give tert-butyl 4-hydroxy-4-((2-oxo-4-phenyl-5-(piperidine-1-carbonyl)pyridin-1(2H)-yl)methyl)piperidine-1-carboxylate. The crude product was dissolved in DCM (1 mL) and TFA (1 mL) and stirred at RT for 1 h. The solution was concentrated and the residue was dissolved in MeOH and added to a 2 g SCX-2 cartridge. The column was washed with MeOH then eluted with 2 M NH$_3$ in MeOH and the ammoniacal fractions were concentrated to give the title compound (61 mg, 94%). LCMS (Method B): $R_T$=0.74 min, m/z=396 [M+H]$^+$.

Step 5: (R,S)-1-((1-(3-Cyclobutyl-2-methylpropanoyl)-4-hydroxypiperidin-4-yl)methyl)-4-phenyl-5-(piperidine-1-carbonyl)pyridin-2(1H)-one Prepared according to General Procedure 3 using 1-((4-hydroxypiperidin-4-yl)methyl)-4-phenyl-5-(piperidine-1-carbonyl)pyridin-2(1H)-one (17 mg, 0.043 mmol), DCM (0.5 mL), DIPEA (0.019 mL, 0.107 mmol), (R,S)-3-cyclobutyl-2-methylpropanoic acid (commercially available) (7.3 mg, 0.052 mmol) and HATU (21.2 mg, 0.056 mmol). The crude product was purified by flash chromatography (GraceResolv 4 g, 10-100% EtOAc in cyclohexane; then 0-10% MeOH in EtOAc) to give the title compound (9 mg, 40%). LCMS (Method B): $R_T$=1.32 min, m/z=520 [M+H]$^+$. $^1$H NMR (400 MHz, DMSO-d$_6$): δ 7.73 (m, 1H), 7.40 (m, 5H), 6.45 (s, 1H), 4.99 (s, 1H), 4.02 (m, 3H), 3.71 (m, 1H), 3.45 (m, 1H), 3.28 (m, 1H), 3.10 (m, 1H), 2.96 (m, 2H), 2.70

(m, 1H), 2.46 (m, 1H), 2.18 (m, 1H), 1.95 (m, 2H), 1.76 (m, 3H), 1.24-1.64 (m, 12H), 0.94 (m, 3H), 0.63 (m, 1H).

Example 16: (R)-3-((4-Hydroxy-1-(3-phenylbutanoyl)piperidin-4-yl)methyl)-6-(1-methyl-1H-indazol-7-yl)pyrimidin-4(3H)-one

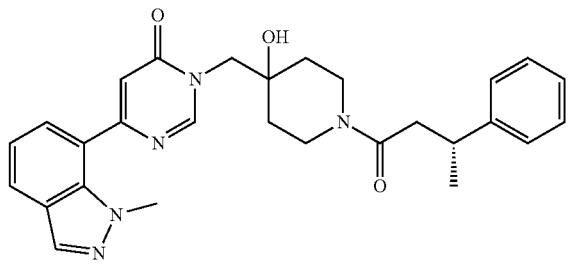 [SMILES: C[C@H](CC(=O)N1CCC(O)(Cn2cnc(-c3cccc4cnn(C)c34)cc2=O)CC1)c1ccccc1]

Step 1: (R)-6-Chloro-3-((4-hydroxy-1-(3-phenylbutanoyl)piperidin-4-yl)methy)pyrimidin-4(3H)-one Prepared according to General Procedure 1 using 6-chloropyrimidin-4(3H)-one (0.34 g, 2.60 mmol), Epoxide 2 (0.676 g, 2.60 mmol), DMF (7 mL) and DIPEA (0.682 mL, 3.91 mmol). The reaction was heated at 80° C. for 21 h. The crude product was purified by flash chromatography (GraceResolv, 0-100% EtOAc in cyclohexane) to give the title compound (0.372 g, 37%). LCMS (Method B): $R_T$=0.99 min, m/z=390 [M+H]$^+$.

Step 2: (R)-3-((4-Hydroxy-1-(3-phenylbutanoyl)piperidin-4-yl)methy)-6-(1-methy-1H-indazol-7-yl)pyrimidin-4(3H)-one Prepared according to General Procedure 4 using (R)-6-chloro-3-((4-hydroxy-1-(3-phenylbutanoyl)piperidin-4-yl)methyl)pyrimidin-4(3H)-one (40 mg, 0.10 mmol), (1-methyl-1H-indazol-7-yl)boronic acid (18 mg, 0.10 mmol), 1,4-dioxane (1.5 mL), water (0.3 mL), sodium carbonate (21.8 mg, 0.21 mmol) and Pd(dppf)Cl$_2$.CH$_2$Cl$_2$ (8.4 mg, 10.3 µmol). The mixture was heated in a microwave at 140° C. for 15 min. The crude product was purified by flash chromatography (Biotage 11 g KP-NH, 10-100% EtOAc in cyclohexane; then 0-15% MeOH in EtOAc) to give the title compound (21 mg, 42%). LCMS (Method B): $R_T$ 1.05 min, m/z=486 [M+H]$^+$. $^1$H NMR (400 MHz, DMSO-d$_6$): δ 8.43 (d, 1H), 8.17 (s, 1H), 7.88 (d, 1H), 7.43 (d, 1H), 7.22 (m, 6H), 6.70 (m, 1H), 5.04 (m, 1H), 4.00 (m, 2H), 3.90 (m, 4H), 3.69 (m, 1H), 3.19 (m, 2H), 2.90 (m, 1H), 2.60 (m, 2H), 1.40 (m, 3H), 1.21 (m, 4H).

Example 17: (R)-3-((4-Hydroxy-1-(3-phenylbutanoyl)piperidin-4-yl)methyl)-6-(2-methoxyphenyl)pyrimidin-4(3H)-one

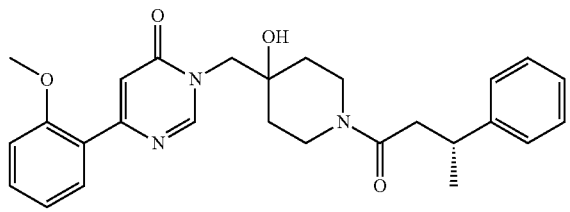 [SMILES: COc1ccccc1-c1cc(=O)n(CC2(O)CCN(C(=O)C[C@@H](C)c3ccccc3)CC2)cn1]

Prepared according to General Procedure 4 using (R)-6-chloro-3-((4-hydroxy-1-(3-phenylbutanoyl)piperidin-4-yl)methyl)pyrimidin-4(3H)-one (50 mg, 0.13 mmol), (2-methoxyphenyl)boronic acid (29 mg, 0.19 mmol), 1,4-dioxane (1.5 mL), water (0.5 mL), sodium carbonate (27 mg, 0.26 mmol) and Pd(PPh$_3$)$_4$(7.4 mg, 6.4 µmol). The mixture was heated in a microwave at 140° C. for 15 min. The crude product was purified by flash chromatography (Biotage KP-NH, 0-100% EtOAc in cyclohexane; then 0-15% MeOH in EtOAc) to give the title compound (14 mg, 0.030 mmol). LCMS (Method B): $R_T$=1.15 min, m/z=462 [M+H]$^+$. $^1$H NMR (300 MHz, DMSO-d$_6$): δ 8.35 (d, 1H), 7.96 (d, 1H), 7.45 (t, 1H), 7.25 (m, 4H), 7.17 (d, 2H), 7.06 (t, 1H), 7.01 (s, 1H), 4.99 (m, 1H), 3.80-4.05 (m, 6H), 3.72 (m, 1H), 3.23 (m, 2H), 2.92 (m, 1H), 2.59 (m, 2H), 1.25-1.55 (m, 4H), 1.20 (d, 3H).

Example 18: (R)-3-((4-Hydroxy-1-(3-phenylbutanoyl)piperidin-4-yl)methyl)-2-methyl-6-phenylpyrimidin-4(3H)-one

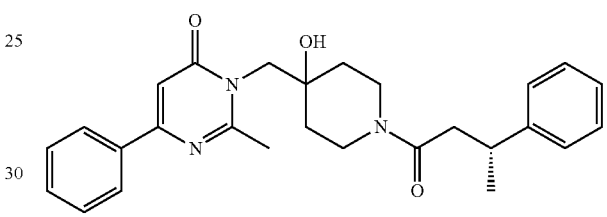

Prepared according to General Procedure 1 using Epoxide 2 (75 mg, 0.29 mmol), DMF (2 mL), cesium carbonate (188 mg, 0.58 mmol) and 2-methyl-6-phenylpyrimidin-4(3H)-one (53.9 mg, 0.29 mmol). The mixture was heated at 80° C. for 16 h to give the title compound (65 mg, 50%). LCMS (Method B): $R_T$=1.41, m/z=446 [M+H]$^+$. $^1$H NMR (300 MHz, DMSO-d$_6$): δ 8.08 (m, 2H), 7.49 (m, 3H), 7.25 (m, 4H), 7.14 (m, 1H), 6.85 (m, 1H), 5.05 (m, 1H), 4.05 (m, 3H), 3.66 (m, 1H), 3.17 (m, 2H), 2.82 (m, 1H), 2.73 (m, 3H), 2.57 (m, 2H), 1.44 (m, 4H), 1.20 (d, 3H).

Example 19: (R)-2-((4-Hydroxy-1-(3-phenylbutanoyl)piperidin-4-yl)methyl)-5,6-diphenylpyridazin-3(2H)-one

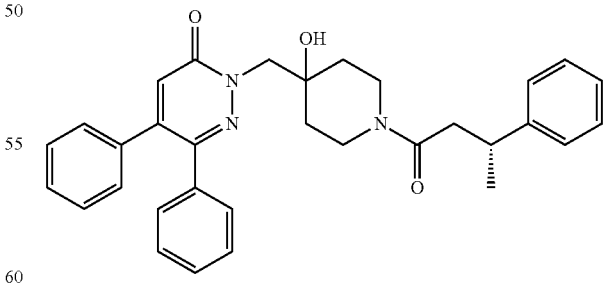

Prepared following General Procedure 1 using Epoxide 2 (50 mg, 0.19 mmol), DMF (1 mL), 5,6-diphenylpyridazin-3(2H)-one (47.9 mg, 0.19 mmol) and DIPEA (0.051 mL, 0.29 mmol). The mixture was heated at 80° C. for 16 h to give the title compound (22 mg, 22%). LCMS (Method B): $R_T$=1.39, m/z=508 [M+H]$^+$. $^1$H NMR (400 MHz, DMSO-d$_6$): δ 7.29 (m, 10H), 7.17 (m, 5H), 6.99 (m, 1H), 4.87 (d, 1H), 4.16 (m, 3H), 3.71 (m, 1H), 3.18 (m, 2H), 2.83 (m, 1H), 2.57 (m, 2H), 1.53 (m, 1H), 1.48 (m, 2H), 1.19 (m, 4H).

Example 20: (R)-3-((4-Hydroxy-1-(3-phenylbutanoyl)piperidin-4-yl)methyl)-6-(naphthalen-1-yl)pyrimidin-4(3H)-one

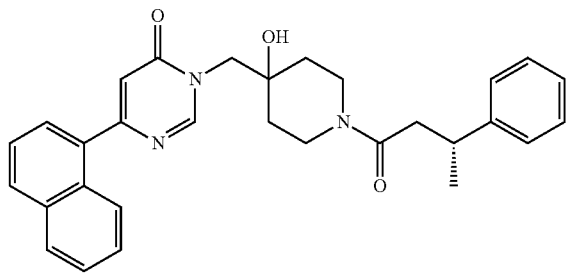 [SMILES: C[C@H](CC(=O)N1CCC(O)(Cn2cnc(-c3cccc4ccccc34)cc2=O)CC1)c1ccccc1]

Prepared according to General Procedure 4 using (R)-6-chloro-3-((4-hydroxy-1-(3-phenylbutanoyl)piperidin-4-yl)methyl)pyrimidin-4(3H)-one (35 mg, 0.09 mmol), naphthalene-1-ylboronic acid (23 mg, 0.13 mmol), 1,4-dioxane (1.5 mL), water (0.3 mL), sodium carbonate (19 mg, 0.18 mmol) and 1,1'-bis(diphenylphosphino)ferrocenepalladium(II)dichloride toluene complex (7.4 mg, 9.0 μmol). The mixture was heated in a microwave at 140° C. for 30 min to give the title compound (13 mg, 30%). LCMS (Method B): R$_T$ 1.24 min, m/z=482 [M+H]$^+$. $^1$H NMR (400 MHz, DMSO-d$_6$): δ 8.44 (d, 1H), 8.17 (d, 1H), 8.04 (m, 2H), 7.58 (m, 4H), 7.28 (m, 4H), 7.17 (m, 1H), 6.64 (s, 1H), 5.05 (d, 1H), 4.00 (m, 3H), 3.70 (m, 1H), 3.20 (m, 2H), 2.94 (m, 1H), 2.62 (m, 2H), 1.45 (m, 3H), 1.23 (m, 4H).

Example 21: (R)-6-(3-(1,3-Dioxolan-2-yl)phenyl)-3-((4-hydroxy-1-(3-phenylbutanoyl)piperidin-4-yl)methyl)pyrimidin-4(3H)-one

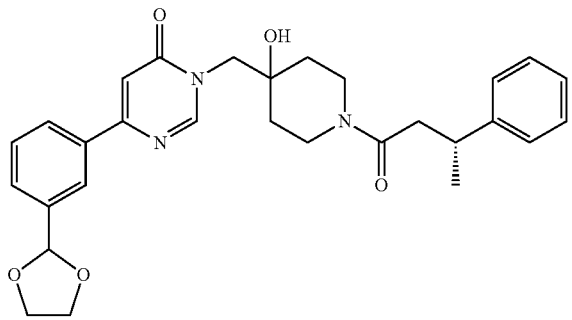 [SMILES: C[C@H](CC(=O)N1CCC(O)(Cn2cnc(-c3cccc(C4OCCO4)c3)cc2=O)CC1)c1ccccc1]

Prepared according to General Procedure 4 using sodium carbonate (21.8 mg, 0.21 mmol), (R)-6-chloro-3-((4-hydroxy-1-(3-phenylbutanoyl)piperidin-4-yl)methyl)pyrimidin-4(3H)-one (40 mg, 0.10 mmol), 1,4-dioxane (1.5 mL), water (0.5 mL), 2-(3-(1,3-dioxolan-2-yl)phenyl)-1,3,2-dioxaborolane (33.9 mg, 0.15 mmol) and Pd(PPh$_3$)$_4$(5.9 mg, 5.1 μmol). The mixture was heated in a microwave at 140° C. for 15 min to give the title compound (17 mg, 33%). LCMS (Method B): R$_T$=1.26 min, m/z=504 [M+H]$^+$. $^1$H NMR (300 MHz, DMSO-d$_6$): δ 8.40 (d, 1H), 8.15 (s, 1H), 8.08 (d, 1H), 7.54 (m, 2H), 7.26 (m, 4H), 7.17 (m, 1H), 7.00 (m, 1H), 5.81 (s, 1H), 4.99 (d, 1H), 4.07 (m, 6H), 3.64 (m, 1H), 3.18 (m, 2H), 2.87 (m, 1H), 2.59 (m, 1H), 2.52 (m, 2H), 1.38 (m, 3H), 1.21 (m, 4H).

Example 22: (R)-3-((4-Hydroxy-1-(3-phenylbutanoyl)piperidin-4-yl)methyl)-6-(thiophen-3-yl)pyrimidin-4(3H)-one

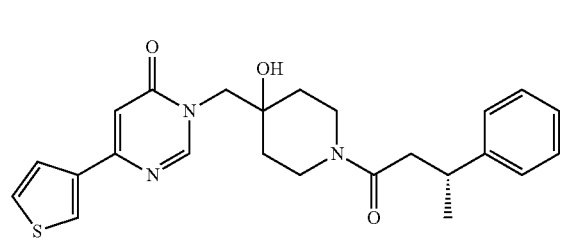 [SMILES: C[C@H](CC(=O)N1CCC(O)(Cn2cnc(-c3ccsc3)cc2=O)CC1)c1ccccc1]

Prepared according to General Procedure 4 using sodium carbonate (21.8 mg, 0.21 mmol), (R)-6-chloro-3-((4-hydroxy-1-(3-phenylbutanoyl)piperidin-4-yl)methyl)pyrimidin-4(3l)-one (40 mg, 0.10 mmol), 1,4-dioxane (1.5 mL), water (0.5 mL), thiophen-3-ylboronic acid (19.7 mg, 0.15 mmol) and 1,1'-bis(diphenylphosphino)ferrocenepalladium (II) dichloride toluene complex (8.4 mg, 10.3 μmol). The mixture was heated in a microwave at 140° C. for 15 min to give the title compound (24 mg, 54%). LCMS (Method B): R$_T$=1.08 min, m/z=438 [M+H]$^+$. $^1$H NMR (400 MHz, DMSO-d$_6$): 8.32 (d, 1H), 8.28 (d, 1H), 7.71 (d, 1H), 7.68 (d, 1H), 7.25 (m, 4H), 7.17 (m, 1H), 6.88 (m, 1H), 4.99 (m, 1H), 3.85-4.04 (m, 3H), 3.86 (m, 1H), 3.16 (m, 2H), 2.88 (m, 1H), 2.59 (m, 2H), 1.40 (m, 3H), 1.20 (m, 4H).

Example 23: 4-(2-Fluorophenyl)-1-((4-hydroxy-1-(1-methylcyclopentane-1-carbonyl)piperidin-4-yl)methyl)-N-isopropyl-N-methyl-6-oxo-1,6-dihydropyridine-3-carboxamide

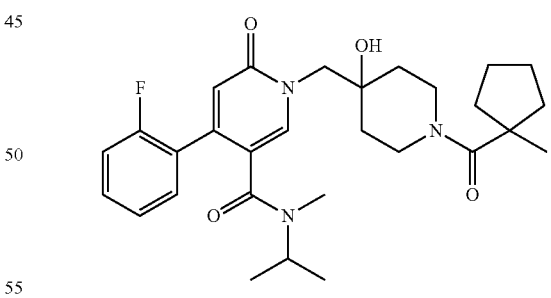

Prepared according to General Procedure 3 using Amine 4 (20 mg, 0.050 mmol), DCM (2 mL), DIPEA (0.026 mL, 0.15 mmol), HATU (24.6 mg, 0.065 mmol) and 1-methylcyclopentanecarboxylic acid (7.7 mg, 0.060 mmol) to give the title compound (25 mg, 98%). LCMS (Method B): R$_T$=1.16 min, m/z=512 [M+H]$^+$. $^1$H NMR (400 MHz, DMSO-d$_6$): δ 7.76 (s, 1H), 7.47 (m, 1H), 7.36 (m, 1H), 7.26 (m, 2H), 6.44 (s, 1H), 4.98 (s, 1H), 4.43-3.62 (m, 3H), 3.91 (br s, 2H), 3.16 (m, 2H), 2.60 (m, 2H), 2.06 (m, 2H), 1.50 (m, 9H), 1.20 (m, 2H), 1.16 (s, 3H), 0.94 (m, 6H).

Example 24: 3-((1-(1-Ethylcyclohexane-1-carbonyl)-4-hydroxypiperidin-4-yl)methyl)-6-(2-fluorophenyl)pyrimidin-4(3H)-one

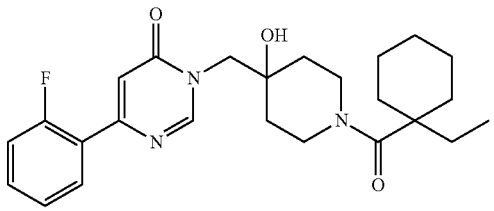 [SMILES: CCC1(C(=O)N2CCC(O)(Cn3cnc(-c4ccccc4F)cc3=O)CC2)CCCCC1]

Prepared according to General Procedure 3 using 6-(2-fluorophenyl)-3-((4-hydroxypiperidin-4-yl)methyl)pyrimidin-4(3H)-one hydrochloride (40 mg, 0.12 mmol), DCM (2 mL), DIPEA (0.062 mL, 0.35 mmol), 1-ethylcyclohexanecarboxylic acid (22.0 mg, 0.14 mmol) and HATU (58.2 mg, 0.15 mmol) to give the title compound (11 mg, 21%). LCMS (Method B): $R_T$=1.30 min, m/z=442 [M+H]$^+$. $^1$H NMR (400 MHz, DMSO-d$_6$): δ 8.44 (s, 1H), 8.02 (t, 1H), 7.55 (m, 1H), 7.36 (m, 2H), 6.81 (s, 1H), 5.05 (s, 1H), 3.99 (m, 4H), 3.19 (m, 2H), 2.05 (m, 2H), 1.19-1.56 (m, 14H), 0.73 (m, 3H).

Example 25: 3-((1-(2-(Cyclohexylmethyl)-3-methylbutanoyl)-4-hydroxy-3,3-dimethylpiperidin-4-yl)methyl)-6-(2-fluorophenyl)pyrimidin-4(3H)-one

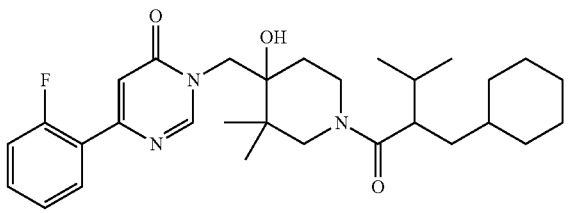 [SMILES: CC(C)C(CC1CCCCC1)C(=O)N1CCC(O)(Cn2cnc(-c3ccccc3F)cc2=O)C(C)(C)C1]

Prepared according to General Procedure 12 using (R,S)-2-(cyclohexylmethyl)-3-methylbutanoic acid (8.9 mg, 0.045 mmol), HATU (19 mg, 0.050 mmol), DIPEA (16 μL, 0.091 mmol) and Amine 5 (15 mg, 0.045 mmol) in DMF (0.6 mL) to give the title compound (4.2 mg, 18%). LCMS (Method B): $R_T$=2.14 min, m/z=512 [M+H]$^+$.

Example 26: (R)-6-(Furan-2-yl)-3-((4-hydroxy-1-(3-phenylbutanoyl)piperidin-4-yl)methyl)pyrimidin-4(3H)-one

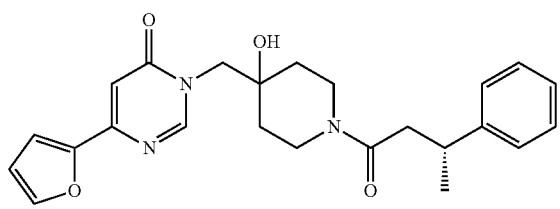 [SMILES: C[C@H](CC(=O)N1CCC(O)(Cn2cnc(-c3ccco3)cc2=O)CC1)c1ccccc1]

Prepared according to General Procedure 4 using sodium carbonate (22.8 mg, 0.21 mmol), (R)-6-chloro-3-((4-hydroxy-1-(3-phenylbutanoyl)piperidin-4-yl)methyl)pyrimidin-4(3H)-one (40 mg, 0.10 mmol), 1,4-dioxane (1.5 mL), water (0.3 mL), furan-2-ylboronic acid (17.2 mg, 0.15 mmol) and 1,1'-bis(diphenylphosphino)ferrocenepalladium (II) dichloride toluene complex (8.44 mg, 10.3 μmol). The mixture was heated in a microwave at 140° C. for 15 min to give the title compound (23 mg, 53%). LCMS (Method B): $R_T$=1.01 min, m/z=422 [M+H]$^+$. $^1$H NMR (400 MHz, DMSO-d$_6$): δ 8.31 (d, 1H), 7.93 (d, 1H), 7.26 (m, 4H), 7.19 (m, 2H), 6.70 (d, 1H), 6.57 (d, 1H), 4.98 (m, 1H), 3.85-4.04 (m, 3H), 3.64 (m, 1H), 3.17 (m, 2H), 2.88 (m, 1H), 2.59 (m, 2H), 1.30 (m, 3H), 1.20 (m, 4H).

Example 27: (R)-1-((4-Hydroxy-1-(3-phenylbutanoyl)piperidin-4-yl)methyl)-4-phenylpyridin-2(1H)-one

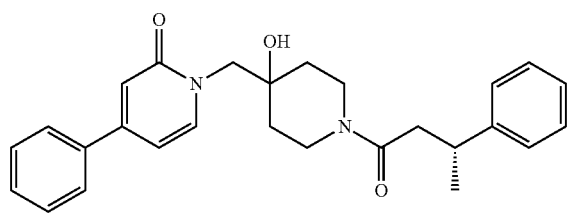 [SMILES: C[C@H](CC(=O)N1CCC(O)(Cn2ccc(-c3ccccc3)cc2=O)CC1)c1ccccc1]

Prepared according to General Procedure 1 using Epoxide 2 (60 mg, 0.23 mmol), DMF (2 mL), cesium carbonate (151 mg, 0.46 mmol) and 4-phenylpyridin-2(1H)-one (39.6 mg, 0.23 mmol). The reaction was heated at 80° C. for 24 h to give the title compound (18 mg, 18%). LCMS (Method B): $R_T$=1.32, m/z=431 [M+H]$^+$. $^1$H NMR (300 MHz, DMSO-d$_6$): δ 7.72 (m, 3H), 7.50 (m, 3H), 7.25 (m, 4H), 7.17 (m, 1H), 6.70 (m, 1H), 6.62 (m, 1H), 5.03 (m, 1H), 3.92 (m, 3H), 3.65 (m, 1H), 3.15 (m, 2H), 2.90 (m, 1H), 2.60 (m, 2H), 1.40 (m, 4H), 1.20 (d, 3H).

Example 28: (R)-6-(Cyclohex-1-en-1-yl)-3-((4-hydroxy-1-(3-phenylbutanoyl)piperidin-4-yl)methyl)pyrimidin-4(3H)-one

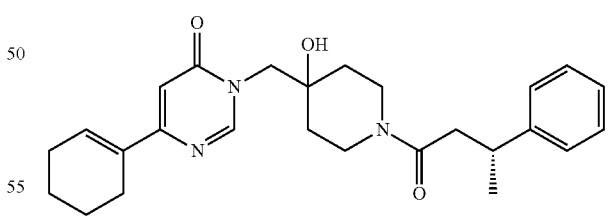

Prepared according to General Procedure 4 using sodium carbonate (28 mg, 0.27 mmol), (R)-6-chloro-3-((4-hydroxy-1-(3-phenylbutanoyl)piperidin-4-yl)methyl)pyrimidin-4(3H)-one (35 mg, 0.090 mmol), 1,4-dioxane (1.5 mL), water (0.3 mL), cyclohex-1-en-1-ylboronic acid (28.0 mg, 0.24 mmol) and 1,1'-bis(diphenylphosphino)ferrocenepalladium (II) dichloride toluene complex (12 mg, 13.5 μmol). The mixture was heated in a microwave at 140° C. for 30 min to give the title compound (13 mg, 33%). LCMS (Method B):

$R_T$=1.22 min, m/z=436 [M+H]$^+$. $^1$H NMR (400 MHz, DMSO-d$_6$): δ 8.20 (d, 1H), 7.25 (m, 4H), 7.17 (m, 1H), 7.07 (m, 1H), 6.24 (s, 1H), 4.93 (m, 1H), 4.02 (m, 1H), 3.86 (m, 1H), 3.81 (m, 1H), 3.64 (m, 1H), 3.17 (m, 3H), 2.98 (m, 1H), 2.58 (m, 1H), 2.24 (m, 4H), 1.69 (m, 2H), 1.59 (m, 2H), 1.27 (m, 3H), 1.19 (m, 4H).

Example 29: (R)-3-((4-Hydroxy-1-(3-phenylbutanoyl)piperidin-4-yl)methyl)-6-(prop-1-en-2-yl)pyrimidin-4(3H)-one

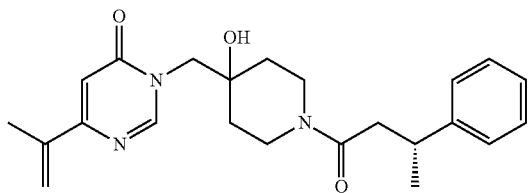 [SMILES: C=C(C)c1cc(=O)n(CC2(O)CCN(C(=O)C[C@@H](C)c3ccccc3)CC2)cn1]

Step 1: 3-((4-Hydroxypiperidin-4-yl)methyl)-6-(prop-1-en-2-yl)pyrimidin-4(3H)-one tert-Butyl 4-((4-chloro-6-oxopyrimidin-1(6H)-yl)methyl)-4-hydroxypiperidine-1-carboxylate (see preparation of Amine 1) (100 mg, 0.29 mmol) and 4,4,5,5-tetramethyl-2-(prop-1-en-2-yl)-1,3,2-dioxaborolane (73 mg, 0.44 mmol) were dissolved in 1,4-dioxane (2 mL) and a solution of sodium carbonate (62 mg, 0.58 mmol) in water (1 mL) was added. The mixture was flushed with N$_2$ and Pd(PPh$_3$)$_4$ (16.8 mg, 0.015 mmol) was added. The mixture was heated in a microwave at 150° C. for 15 min, then cooled and diluted with water. The mixture was extracted with ethyl acetate (×2) and the combined organic extracts were dried over MgSO$_4$ and concentrated. The residue was triturated with diethyl ether to give an off-white solid. This was dissolved in DCM (1 mL) and TFA (1 mL) and stirred for 15 min, then concentrated. The residue was dissolved in MeOH and loaded onto a 2 g Biotage SCX-2 cartridge. The column was flushed with MeOH then eluted with 2 M NH$_3$ in MeOH to give the title compound (61 mg, 84%). LCMS (Method B): $R_T$=1.21 min, m/z=250 [M+H]$^+$.

Step 2: (R)-3-((4-Hydroxy-1-(3-phenylbutanoyl)piperidin-4-yl)methyl)-6-(prop-1-en-2-yl)pyrimidin-4(3H)-one 3-((4-Hydroxypiperidin-4-yl)methyl)-6-(prop-1-en-2-yl)pyrimidin-4(3H)-one (60 mg, 0.24 mmol) and (R)-3-phenylbutanoic acid (39.5 mg, 0.24 mmol) were dissolved in DCM (2 mL) and DIPEA (0.05 mL, 0.29 mmol) was added, followed by HATU (101 mg, 0.27 mmol). The mixture was stirred at RT for 90 min then purified by flash chromatography (GraceResolv 12 g, 25-100% EtOAc in cyclohexane; then 0-15% MeOH in EtOAc) to give the title compound (69 mg, 73%). LCMS (Method B): $R_T$=1.19 min, m/z=396 [M+H]$^+$. NMR (300 MHz, DMSO-d$_6$): δ 8.24 (d, 1H), 7.25 (m, 4H), 7.17 (m, 1H), 6.41 (s, 1H), 6.17 (s, 1H), 5.42 (s, 1H), 4.95 (s, 1H), 4.00 (m, 1H), 3.89 (d, 1H), 3.82 (m, 1H), 3.63 (m, 1H), 3.15 (m, 2H), 2.87 (m, 1H), 2.60 (m, 2H), 2.02 (s, 3H), 1.25-1.55 (m, 4H), 1.20 (d, 3H).

Example 30: (R)-3-((4-Hydroxy-1-(3-phenylbutanoyl)piperidin-4-yl)methyl)-6-(2-(trifluoromethoxy)phenyl)pyrimidin-4(3H)-one

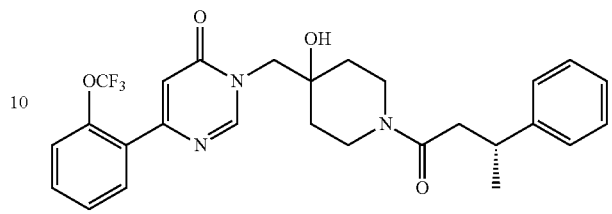

Prepared according to General Procedure 4 using sodium carbonate (22 mg, 0.21 mmol), (R)-6-chloro-3-((4-hydroxy-1-(3-phenylbutanoyl)piperidin-4-yl)methyl)pyrimidin-4(3H)-one (40 mg, 0.10 mmol), 1,4-dioxane (1.5 mL), water (0.3 mL), (2-(trifluoromethoxy)phenyl)boronic acid (32 mg, 0.15 mmol) and 1,1'-bis(diphenylphosphino)ferrocenepalladium(II) dichloride toluene complex (8.4 mg, 10.3 μmol). The mixture was heated in a microwave at 140° C. for 30 min to give the title compound (25 mg, 47%). LCMS (Method B): $R_T$=1.24 min, m/z=516 [M+H]$^+$. $^1$H NMR (400 MHz, DMSO-d$_6$): δ 8.41 (d, 1H), 7.88 (d, 1H), 7.62 (m, 1H), 7.52 (m, 2H), 7.27 (m, 4H), 7.18 (m, 1H), 6.70 (m, 1H), 5.01 (m, 1H), 3.96 (m, 3H), 3.67 (m, 1H), 3.20 (m, 2H), 2.88 (m, 1H), 2.56 (m, 2H), 1.32 (m, 3H), 1.19 (m, 4H).

Example 31: 3-(((1R,5S)-3-((R)-3-Cyclohexyl-2-methylpropanoyl)-8-hydroxy-3-azabicyclo[3.2.1]octan-8-yl)methyl)-6-(2-fluorophenyl)pyrimidin-4(3H)-one

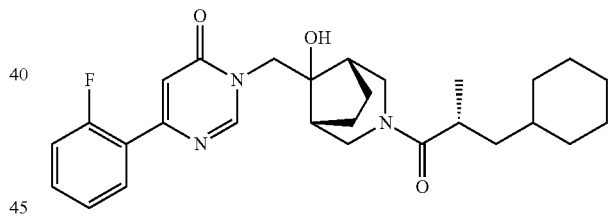

Step 1: (1R,5S)-tert-Butyl 8-((4-(2-fluorophenyl)-6-oxopyrimidin-1(6H)-yl)methyl)-8-hydroxy-3-azabicyclo[3.2.1]octane-3-carboxylate Prepared according to General Procedure 1 using 6-(2-fluorophenyl)pyrimidin-4(3H)-one (0.116 g, 0.608 mmol), Epoxide 5 (0.16 g, 0.67 mmol) and DIPEA (0.159 mL, 0.912 mmol) in DMF (0.9 mL) to give the title compound (0.15 g, 58%). $^1$H NMR (400 MHz, CDCl$_3$): δ 8.15 (br s, 1H), 8.06 (td, 1H), 7.49-7.41 (m, 1H), 7.30-7.24 (m, 1H), 7.18 (ddd, 1H), 7.13 (s, 1H), 4.51 (s, 1H), 4.18-4.03 (m, 2H), 3.75 (br dd, 1H), 3.60 (br dd, 1H), 3.41 (dd, 2H), 1.89-1.67 (m, 5H), 1.62 (s, 1H), 1.46 (s, 9H).

Step 2: 6-(2-Fluorophenyl)-3-(((1R,5S)-8-hydroxy-3-azabicyclo[3.2.1]octan-8-yl)methyl)pyrimidin-4(3H)-one hydrochloride Prepared according to General Procedure 9 using (1R,5S)-tert-butyl 8-((4-(2-fluorophenyl)-6-oxopyrimidin-1

(6H)-yl)methyl)-8-hydroxy-3-azabicyclo[3.2.1]octane-3-carboxylate (0.150 g, 0.349 mmol) and hydrogen chloride (4 M in 1,4-dioxane, 1.2 mL, 4.8 mmol) in DCM (1.7 mL) to give the title compound (0.12 g, 94%) which was used without further purification. LCMS (Method B): $R_T$=0.70 min, m/z=330 [M+H]$^+$. $^1$H NMR (400 MHz, methanol-d$_4$): δ 8.66 (br s, 1H), 8.04 (td, 1H), 7.62-7.54 (m, 1H), 7.38 (dd, 1H), 7.36-7.27 (m, 1H), 7.00 (s, 1H), 4.25 (s, 2H), 3.63 (d, 2H), 3.04 (dd, 2H), 2.46-2.35 (m, 2H), 2.12 (br s, 2H), 1.92-1.83 (m, 2H).

Step 3: 3-(((1R,5S)-3-((R)-3-Cyclohexyl-2-methylpropanoyl)-8-hydroxy-3-azabicyclo[3.2.1]octan-8-yl)methyl)-6-(2-fluorophenyl)pyrimidin-4(3H)-one Prepared according to General Procedure 5 using 6-(2-fluorophenyl)-3-(((1R,5S)-8-hydroxy-3-azabicyclo[3.2.1]octan-8-yl)methyl)pyrimidin-4(3H)-one hydrochloride (0.030 g, 0.082 mmol), (R)-3-cyclohexyl-2-methylpropanoic acid (Acid 1) (0.021 g, 0.12 mmol), HBTU (0.047 g, 0.12 mmol) and DIPEA (0.057 mL, 0.328 mmol) in DCM (0.8 mL) to give the title compound (34 mg, 61%). LCMS (Method B): $R_T$=1.57 min, m/z=482 [M+H]$^+$. $^1$H NMR (400 MHz, CDCl$_3$, this compound appears as two conformers in a 1:1 ratio): δ 8.16-8.12 (m, 1H), 8.07 (br td, 1H), 7.50-7.43 (m, 1H), 7.29 (br dd, 1H), 7.22-7.17 (m, 1H), 7.16 (s, 1H), 4.77 (s, 0.5H), 4.70 (s, 0.5H), 4.29-4.18 (m, 1H), 4.15 (qd, 2H), 3.75 (dd, 1H), 3.54 (br td, 1H), 3.27 (br dd, 1H), 2.84 (q, 1H), 1.94-1.77 (m, 4H), 1.77-1.60 (m, 7H), 1.29-1.15 (m, 6H), 1.14 (d, 1.5H), 1.04 (d, 1.5H), 0.93-0.79 (m, 2H).

Example 32: (R)-6-(2-Fluorophenyl)-3-((4-hydroxy-1-(3-phenylbutanoyl)piperidin-4-yl)methyl)pyrimidin-4(3H)-one

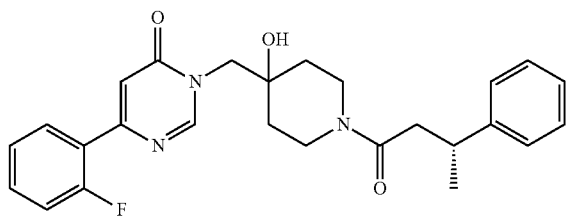 [SMILES: C[C@H](CC(=O)N1CCC(O)(Cn2cnc(-c3ccccc3F)cc2=O)CC1)c1ccccc1]

Step 1: 4-(2-Fluorophenyl)-6-methoxypyrimidine 4,6-Dichloropyrimidine (5 g, 33.6 mmol) and (2-fluorophenyl)boronic acid (4.70 g, 33.6 mmol) were suspended in a mixture of toluene (100 mL) and MeOH (50 mL). Potassium carbonate (4.64, 33.6 mmol) was added and the mixture was de-gassed by bubbling N$_2$ through it. Pd(PPh$_3$)$_4$ (0.97 g, 0.84 mmol) was added and the mixture was heated at 90° C. for 3 h. The mixture was cooled to RT and concentrated. The residue was diluted with water and extracted (EtOAc×2). The combined organic extracts were washed with brine, dried over MgSO$_4$ and concentrated. The residue was chromatographed (GraceResolv 80 g, 0-20% EtOAc in cyclohexane) to give the title compound (approx. 5.5 g) contaminated with 4-chloro-6-(2-fluorophenyl)pyrimidine (approx. 0.5 g) and 4,6-bis(2-fluorophenyl)pyrimidine (approx. 1.5 g). The product was used without further purification. LCMS (Method B): $R_T$=1.26 min, m/z=209 [M+H]$^+$.

Step 2: 6-(2-Fluorophenyl)pyrimidin-4(3H)-one

The crude sample of 4-(2-fluorophenyl)-6-methoxypyrimidine obtained as described above (total mass 7.5 g) was suspended in dilute hydrochloride acid (2 M in water, 30 mL, 60 mmol) and 1,4-dioxane (10 mL). The reaction was heated at 110° C. for 5 h. The mixture was cooled and basified with aqueous sodium hydroxide. The mixture was extracted with Et$_2$O (×2) and the organic extracts were discarded. The aqueous layer was acidified with aqueous HCl and the resulting white precipitate was collected by filtration to give the title compound (3.99 g, 62% for two steps). LCMS (Method B): $R_T$=0.70 min, m/z=191 [M+H]$^+$.

Step 3: (R)-6-(2-Fluorophenyl)-3-((4-hydroxy-1-(3-phenylbutanoyl)piperidin-4-yl)methyl)pyrimidin-4(3H)-one 6-(2-Fluorophenyl)pyrimidin-4(3H)-one (50 mg, 0.26 mmol) was dissolved in DMF (0.5 mL) and Epoxide 2 (68 mg, 0.26 mmol) was added. Cesium carbonate (128 mg, 0.39 mmol) was added and the mixture was heated at 80° C. for 16 h. The mixture was cooled to RT and diluted with saturated aqueous ammonium chloride solution, then extracted with EtOAc. The organic layer was dried over anhydrous sodium sulfate, filtered and concentrated. The residue was purified by flash chromatography (GraceResolv 12 g, 0-100% EtOAc in cyclohexane; then 0-15% MeOH in EtOAc) to give the title compound (58 mg, 49%). LCMS (Method B): $R_T$=1.31 min, m/z=450 [M+H]$^+$. $^1$H NMR (300 MHz, CDCl$_3$, this compound appears as two conformers A and B in a 2:3 ratio respectively): δ 8.26 (s, 0.4H, conformer A), 8.18 (s, 0.6H, conformer B), 8.04 (m, 1H), 7.44 (m, 1H), 7.15-7.40 (m, 7H), 7.06 (s, 1H), 3.80-4.35 (m, 3H), 3.60 (m, 1H), 3.26 (m, 2H), 2.95-3.15 (m, 1H), 2.65 (m, 1H), 2.50 (m, 1H), 1.25-1.70 (m, 7.4H), 0.81 (m, 0.6H, conformer B only).

Example 33: (R)-5-((4-Hydroxy-1-(3-phenylbutanoyl)piperidin-4-yl)methyl)-2-phenylpyrimidin-4(3H)-one

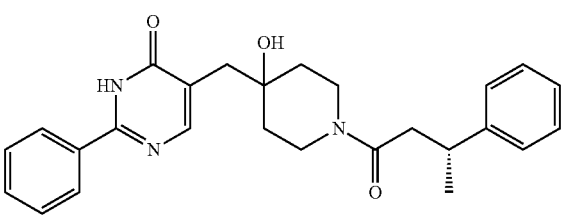 [SMILES: C[C@H](CC(=O)N1CCC(O)(Cc2cnc(-c3ccccc3)[nH]c2=O)CC1)c1ccccc1]

Step 1: tert-Butyl 4-((2-chloro-4-methoxypyrimidin-5-yl)methylene)piperidine-1-carboxylate Prepared according to General Procedure 4 using 5-bromo-2-chloro-4-methoxypyrimidine (259 mg, 1.16 mmol), tert-butyl 4-((4,4,5,5-tetramethyl-1,3,2-dioxaborolan-2-yl)methylene)piperidine-1-carboxylate (PCT Int. Appl., 2013027001, 28 Feb. 2013) (450 mg, 1.39 mmol), Pd(PPh$_3$)$_4$(67 mg, 0.058 mmol), sodium carbonate (2 M in water, 1.16 mL, 2.32 mmol) and DME (5.8 mL). The mixture was heated at 80° C. for 24 h to give the title compound (334 mg, 85%). LCMS (Method B): $R_T$=1.80 min, m/z=340, 342 [M+H]$^+$. $^1$H NMR (300 MHz, CDCl$_3$):

δ 8.10 (s, 1H), 6.07 (s, 1H), 4.04 (s, 3H), 3.52 (t, 2H), 3.42 (t, 2H), 2.37 (t, 2H), 2.32 (t, 2H), 1.48 (s, 9H).

Step 2 and 3: (R)-1-(4-((2-Chloro-4-methoxypyrimidin-5-yl)methylene)piperidin-1-yl)-3-phenylbutan-1-one To a stirred solution of tert-butyl 4-((2-chloro-4-methoxypyrimidin-5-yl)methylene)piperidine-1-carboxylate (334 mg, 0.983 mmol) in DCM (5 mL) was added TFA (4.5 mL, 59.0 mmol). The resulting mixture was stirred at RT for 2 h before the reaction was concentrated and the crude product was dried under high vacuum. The TFA salt was flushed with $N_2$ before the addition of DCM (9.8 mL) and DIPEA (1.72 mL, 9.84 mmol). After 20 min, (R)-3-phenylbutanoic acid (194 mg, 1.18 mmol) in DCM (0.3 mL), EDC (245 mg, 1.28 mmol) and DMAP (12 mg, 0.098 mmol) were added. The resulting solution was stirred at RT for 24 h before it was diluted with DCM (25 mL) and washed with saturated aqueous sodium bicarbonate (20 mL). The phases were separated using a Biotage phase separator and the organic layer was concentrated. The residue was purified by flash chromatography (Biotage KP-Sil 25 g, 0-100% EtOAc in PE; then 0-20% MeOH in EtOAc) to give the title compound (195 mg, 51%). LCMS (Method B): $R_T$=1.67 min, m/z=386, 387 [M+H]$^+$.

Step 4: (R)-1-(4-((4-Methoxy-2-phenylpyrimidin-5-yl)methylene)piperidin-1-yl)-3-phenylbutan-1-one Prepared according to General Procedure 4 using (R)-1-(4-((2-chloro-4-methoxypyrimidin-5-yl)methylene)piperidin-1-yl)-3-phenylbutan-1-one (195 mg, 0.505 mmol), phenylboronic acid (74 mg, 0.606 mmol), Pd(PPh$_3$)$_4$(29 mg, 0.025 mmol), sodium carbonate (2 M in water, 0.505 mL, 1.011 mmol) and DME (2.5 mL). The mixture was heated at 75° C. for 24 h to give the title compound (143 mg, 66%). LCMS (Method B): $R_T$=1.98 min, m/z=428 [M+H]$^+$.

Step 5: (3R)-1-(2-(4-Methoxy-2-phenylpyrimidin-5-yl)-1-oxa-6-azaspiro[2.5]octan-6-yl)-3-phenylbutan-1-one (R)-1-(4-((4-Methoxy-2-phenylpyrimidin-5-yl)methylene)piperidin-1-yl)-3-phenylbutan-1-one (136 mg, 0.318 mmol) was dissolved in DCM (3 mL) and m-CPBA (50-55% purity, 165 mg, 0.477 mmol) was added. The reaction was stirred for 1.5 h then quenched by the addition of saturated sodium thiosulfate (10 mL). The mixture was extracted with DCM (2×10 mL) using a Biotage phase separator and the combined organic extracts were washed with saturated sodium bicarbonate (10 mL). The organic layer was concentrated and the crude material was purified by flash chromatography (Biotage 25 g KP-Sil, 0-100% EtOAc in PE) to give the title compound (69 mg, 49%). LCMS (Method B): $R_T$=1.86 min, m/z=444 [M+H]$^+$.

Step 6: (R)-1-(4-Hydroxy-4-((4-methoxy-2-phenylpyrimidin-5-yl)methyl)piperidin-1-yl)-3-phenylbutan-1-one A solution of (3R)-1-(2-(4-methoxy-2-phenylpyrimidin-5-yl)-1-oxa-6-azaspiro[2.5]octan-6-yl)-3-phenylbutan-1-one (130 mg, 0.293 mmol) in MeOH (20 mL) was hydrogenated in an H-Cube® (Pd/C CatCart®, 1 mL.min$^{-1}$, 20° C., 50 bar H$_2$ then at 40° C. full H$_2$; then at 40° C., 50 bar H$_2$). The resulting solution was concentrated and the residue was purified by flash chromatography (Biotage 10 g KP-Sil, 0-100% EtOAc in PE; then 0-30% MeOH in EtOAc) to give the title compound (69 mg, 52%). LCMS (Method B): $R_T$=1.62 min, m/z=446 [M+H]$^+$.

Step 7: (R)-5-((4-Hydroxy-1-(3-phenylbutanoyl)piperidin-4-yl)methy)-2-phenylpyrimidin-4(3H)-one To solution of (R)-1-(4-hydroxy-4-((4-methoxy-2-phenylpyrimidin-5-yl)methyl)piperidin-1-yl)-3-phenylbutan-1-one (69 mg, 0.155 mmol) and sodium iodide (139 mg, 0.929 mmol) in MeCN (3 mL) was added chlorotrimethylsilane (119 µL, 0.929 mmol). The mixture was heated at 80° C. for 15 h then cooled to room temperature and concentrated. The residue was dissolved in saturated aqueous sodium bicarbonate (25 mL) and extracted with EtOAc (3×25 mL). The combined organic extracts were washed with saturated aqueous sodium thiosulfate (25 mL), saturated sodium bicarbonate (25 mL) and brine (50 mL). The organic extracts were dried over anhydrous sodium sulfate and concentrated. The residue was purified by flash chromatography (Biotage KP-Sil, 0-10% MeOH in DCM) to give the title compound (60 mg, 90%) as a colourless solid. LCMS (Method B): $R_T$=1.15 min, m/z=432 [M+H]$^+$. $^1$H NMR (300 MHz, CDCl$_3$, this compound appears as two conformers A and B in a 2:3 ratio): δ 13.03 (br s, 1H), 8.11-7.99 (m, 2H), 7.91 (d, 1H), 7.54-7.39 (m, 3H), 7.28-7.04 (m, 5H), 4.54 (br s, 1H), 4.29 (t, 1H), 3.53-3.36 (m, 1H), 3.35-3.09 (m, 2H), 2.99-2.81 (m, 1H), 2.70-2.35 (m, 4H), 1.58-1.20 (m, 6.4H), 0.67 (td, 0.6H, conformer B).

Example 34: 3-((4-Hydroxy-1-(3-phenylpropanoyl)piperidin-4-yl)methyl)-2-methyl-6-phenylpyrimidin-4(3H)-one

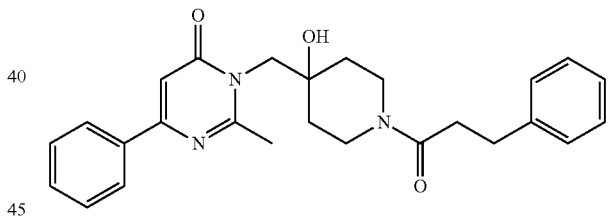

Steps 1 and 2:
1-(3-Phenylpropanoyl)piperidin-4-one tert-Butyl 4-oxopiperidine-1-carboxylate (5 g, 25.1 mmol) was dissolved in DCM (25 mL) and TFA (9.67 mL, 125 mmol) was added. The reaction was stirred at RT for 24 h then concentrated. The residue was dried under high vacuum to give the amine trifluoroacetate salt. This was suspended in dry DCM (125 mL) under $N_2$ and DIPEA (13.2 mL, 75.0 mmol) was added dropwise over 5 min. 3-Phenylpropanoic acid (4.52 g, 30.1 mmol) was added, followed by EDC (6.26 g, 32.6 mmol) and DMAP (0.307 g, 2.510 mmol). The reaction was stirred at RT for 18 h. The mixture was diluted with DCM (150 mL) and washed with saturated aqueous sodium bicarbonate (250 mL). The phases were separated and the aqueous layer was extracted with DCM (75 mL). The combined organic extracts were washed with 3% aqueous HCl (150 mL) then brine (150 mL) and concentrated. The residue was purified by flash chromatography (Biotage KP-Sil 100 g, 0-100% EtOAc in PE) to give the title compound (2.38 g, 41%). $^1$H NMR (300 MHz, CDCl$_3$): δ 7.51-6.98 (m, 5H), 3.89 (t, 2H), 3.66 (t, 2H), 3.04 (t, 2H), 2.73 (t, 2H), 2.44 (t, 2H), 2.26 (t, 2H).

Step 3: 3-Phenyl-1-(1-oxa-6-azaspiro[2.5]octan-6-yl)propan-1-one

Prepared according to General Procedure 11 using trimethylsulfonium iodide (4.59 g, 22.5 mmol), dry DMSO (20 mL), sodium hydride (60% dispersion in mineral oil, 0.899 g, 22.5 mmol) and a solution of 1-(3-phenylpropanoyl)piperidin-4-one (2.08 g, 8.99 mmol) in dry DMSO (10 mL). The crude product was purified by flash chromatography (Biotage 50 g KP-Sil, 0-60% EtOAc in PE) to give the title compound (1.41 g, 64%). LCMS (Method B): R$_T$=1.07 min, m/z=246 [M+H]$^+$. $^1$H NMR (300 MHz, CDCl$_3$): δ 7.44-7.13 (m, 5H), 4.30-4.03 (m, 1H), 3.77-3.58 (m, 1H), 3.46 (tdd, 2H), 3.11-2.93 (m, 2H), 2.82-2.61 (m, 4H), 1.86 (m, 1H), 1.77-1.62 (m, 1H), 1.54-1.33 (m, 2H).

Step 4: 3-((4-Hydroxy-1-(3-phenylpropanoyl)piperidin-4-yl)methyl)-2-methyl-6-phenylpyrimidin-4(3H)-one 2-Methyl-6-phenylpyrimidin-4(3H)-one (40 mg, 0.22 mmol) was dissolved in DMF (0.43 mL) and 3-phenyl-1-(1-oxa-6-azaspiro[2.5]ocatn-6-yl)propan-1-one (53 mg, 0.22 mmol) was added, followed by cesium carbonate (210 mg, 0.64 mmol). The reaction was heated at 80° C. overnight then cooled to RT and quenched with saturated aqueous ammonium chloride. The mixture was extracted with ethyl acetate and the organic extract was dried over MgSO$_4$ then filtered and concentrated. The residue was purified by flash chromatography (Biotage 10 g KP-Sil, 0-100% EtOAc in cyclohexane; then 0-15% MeOH in EtOAc) to give the title compound (58 mg, 63%). LCMS (Method B): R$_T$=1.36, m/z=432 [M+H]$^+$. $^1$H NMR (300 MHz, CDCl$_3$): δ 7.96 (m, 2H), 7.47 (m, 3H), 7.16-7.30 (m, 5H), 6.81 (s, 1H), 4.82 (s, 1H), 4.49 (d, 1H), 4.01-4.22 (m, 2H), 3.60 (d, 1H), 3.34 (d, 1H), 2.95 (m, 3H), 2.63 (m, 5H), 1.05-1.60 (m, 4H).

Example 35: (R)-3-((4-Hydroxy-1-(3-phenylbutanoyl)piperidin-4-yl)methyl)-6-(isobutylamino)pyrimidin-4(3H)-one

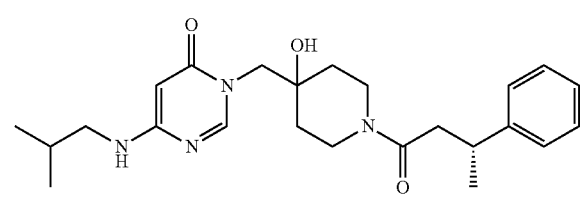 [SMILES: CC(C)CNc1cc(=O)n(CC2(O)CCN(C(=O)C[C@@H](C)c3ccccc3)CC2)cn1]

(R)-6-Chloro-3-((4-hydroxy-1-(3-phenylbutanoyl)piperidin-4-yl)methyl)pyrimidin-4(3-H)-one (25 mg, 0.064 mmol) was suspended in 1,4-dioxane (0.5 mL). 2-Methylpropan-1-amine (0.064 mL, 0.64 mmol) was added and the mixture was heated in a microwave at 150° C. for 15 min. The mixture was cooled and diluted with brine then extracted with DCM. The organic layer was dried (Biotage phase separator), concentrated and the residue was purified by flash chromatography (Biotage 10 g KP-Sil, 0-100% EtOAc in cyclohexane; then 0-15% MeOH in EtOAc) to give the title compound (20 mg, 73%). LCMS (Method B): R$_T$=1.17 min, m/z=427 [M+H]$^+$. $^1$H NMR (300 MHz, CDCl$_3$, this compound appears as two conformers A and B in a 2:3 ratio respectively): δ 7.72 (s, 0.4H, conformer A), 7.61 (s, 0.6H, conformer B), 7.22-7.32 (m, 5H), 5.40-5.11 (m, 2H), 5.10-4.20 (m, 1H), 4.35-4.46 (m, 1H), 3.47-4.03 (m, 3H), 2.80-3.45 (m, 4H), 2.67 (m, 1H), 2.52 (m, 1H), 2.08 (s, 1H), 1.88 (m, 1H), 1.18-1.55 (m, 7H), 0.97 (m, 6.4H), 0.55 (m, 0.6H, conformer B).

Example 36: (R)-1-((1-(3-Cyclohexyl-2-methylpropanoyl)-4-hydroxypiperidin-4-yl)methyl)-4-phenyl-5-(piperidine-1-carbonyl)pyridin-2(1H)-one

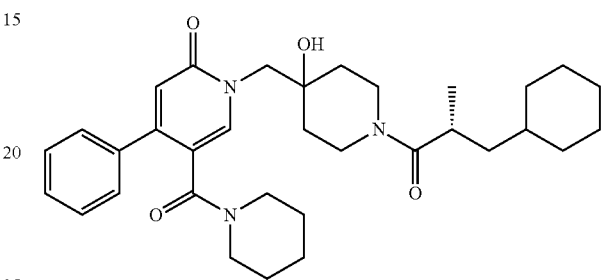

Prepared according to General Procedure 5 using 1-((4-hydroxypiperidin-4-yl)methyl)-4-phenyl-5-(piperidine-1-carbonyl)pyridin-2(11-)-one (40 mg, 0.101 mmol), (R)-3-cyclohexyl-2-methylpropanoic acid (Acid 1) (25.8 mg, 0.15 mmol), DIPEA (0.071 mL, 0.405 mmol), and HBTU (57.5 mg, 0.152 mmol) in DCM (2.0 mL) to give the title compound (33.9 mg, 61%). LCMS (Method B): R$_T$=1.45 min, m/z=548 [M+H]$^+$. $^1$H NMR (400 MHz, DMSO-d$_6$): δ 7.73 (s, 1H), 7.49-7.38 (m, 5H), 6.45 (s, 1H), 5.00 (br d, 1H), 4.15-3.91 (m, 3H), 3.81-3.69 (br m, 1H), 3.52-3.20 (br m, 1H), 3.17 (s, 1H), 3.16-2.81 (br m, 4H), 1.69-1.02 (brm, 21H), 0.95 (dd, 3H), 0.89-0.74 (m, br, 2H), 0.73-0.51 (br m, 1H).

Example 37: (R)-2-((4-Hydroxy-1-(3-phenylbutanoyl)piperidin-4-yl)methyl)-5-phenylpyridazin-3(2H)-one

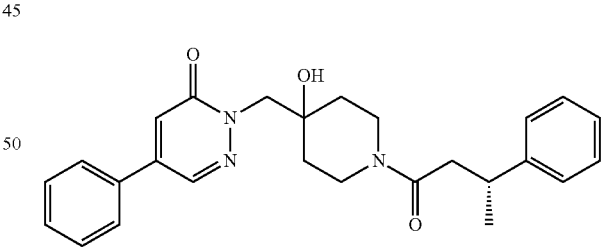

Step 1: (R)-5-Chloro-2-((4-hydroxy-1-(3-phenylbutanoyl)piperidin-4-yl)methy)pyridazin-3(2H)-one 5-Chloropyridazin-3(2H)-one (100 mg, 0.766 mmol) (commercially available) and Epoxide 1 (199 mg, 0.766 mmol) were dissolved in DMF (1 mL) and DIPEA (0.201 mL, 1.15 mmol) was added. The solution was heated to 80° C. for 16 h. The mixture was diluted with water and extracted with EtOAc (×2). The combined organic extracts were washed with water, dried over MgSO$_4$ and concentrated. The residue was purified by flash chromatography (GraceResolv, 0-100% EtOAc in cyclohexane; then 0-10% MeOH in EtOAc) to give the title compound (50 mg, 17%). LCMS (Method B): $R_T$=1.03 min, m/z=390 [M+H]$^+$.

Step 2: (R)-2-((4-Hydroxy-1-(3-phenylbutanoyl) piperidin-4-yl)methyl)-5-phenylpyridazin-3(2H)-one Prepared according to General Procedure 4 using (R)-5-chloro-2-((4-hydroxy-1-(3-phenylbutanoyl)piperidin-4-yl)methyl)pyridazin-3(2H)-one (50 mg, 0.128 mmol), phenylboronic acid (23.5 mg, 0.192 mmol), sodium carbonate (27.2 mg, 0.256 mmol) and tetrakis(triphenylphosphine)palladium(0) (7.41 mg, 6.41 µmol) in 1,4-dioxane (0.5 mL) and water (0.2 mL). The reaction was heated in a microwave at 150° C. for 10 min to give the title compound (44.8 mg, 81%). LCMS (Method B): $R_T$=1.19 min, m/z=432 [M+H]$^+$. $^1$H NMR (400 MHz, methanol-d$_4$, this compound appears as two conformers A and B in a 3:2 ratio respectively): δ 8.36 (1H, d), 7.78 (2H, ddt), 7.60-7.53 (3H, m), 7.30-7.23 (4H, m), 7.21-7.13 (2H, m), 4.34-4.05 (3H, m), 3.76-3.62 (1H, m, br), 3.31-3.14 (2H, m), 3.04-2.88 (1H, m), 2.82 (0.6H, dd, conformer A), 2.74 (0.4H, dd, conformer B), 2.61 (0.4H, dd, conformer B), 2.50 (0.6H, dd, conformer A), 1.72-1.49 (2H, m), 1.47-1.23 (5H, m), 0.91 (ddd, 1H).

Example 38: (R)-4-(2-Cyanophenyl)-1-((4-hydroxy-1-(3-phenylbutanoyl)piperidin-4-yl)methyl)-N-isopropyl-N-methyl-6-oxo-1,6-dihydropyridine-3-carboxamide

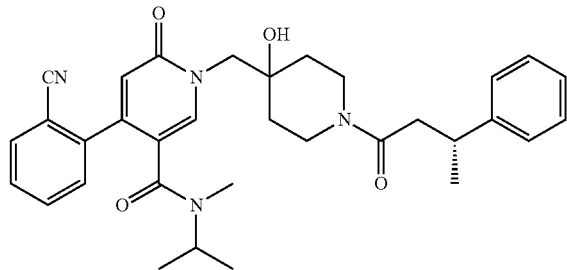 [SMILES: CC(C)N(C)C(=O)c1cn(CC2(O)CCN(C(=O)C[C@@H](C)c3ccccc3)CC2)c(=O)cc1-c1ccccc1C#N]

(2-Cyanophenyl)boronic acid (22.6 mg, 0.154 mmol) and (R)-4-chloro-1-((4-hydroxy-1-(3-phenylbutanoyl)piperidin-4-yl)methyl)-N-isopropyl-N-methyl-6-oxo-1,6-dihydropyridine-3-carboxamide (50 mg, 0.102 mmol) were dissolved in 1,4-dioxane (1.0 mL) and potassium phosphate tribasic (54.4 mg, 0.256 mmol) was added. The mixture was de-gassed by bubbling N$_2$ through it for 5 min. Dichloro[1,1'-bis(diphenylphosphino)ferrocene]palladium(II), complex with dichloromethane (1:1) (4.3 mg, 5.1 µmol) was added and the mixture was heated in a microwave for 30 min at 130° C. The mixture was concentrated and the residue was diluted with water and extracted with DCM. The organic extract was dried (Biotage phase separator), concentrated and the residue was purified by preparative HPLC to give the title compound (11.4 mg, 20%). LCMS (Method B): $R_T$=1.14 min, m/z=555 [M+H]$^+$. $^1$H NMR (400 MHz, methanol-d$_4$, this compound appears as two conformers A:B in a 2:3 ratio): δ 7.83-7.59 (m, 3H), 7.58-7.46 (m, 1H), 7.37 (d, 1H), 7.27-7.02 (m, 5H), 6.54 (s, 1H), 4.47-4.31 (m, 0.6H), 4.17-3.78 (m, 3H), 3.67-3.48 (m, 1.4H), 3.15-2.35 (m, 9H), 1.62-0.68 (m, 13H).

Example 39: (R)-3-((1-(3-Cyclohexyl-2-methylpropanoyl)-4-hydroxypiperidin-4-yl)methyl)-6-(2-fluorophenyl)pyrimidin-4(3H)-one

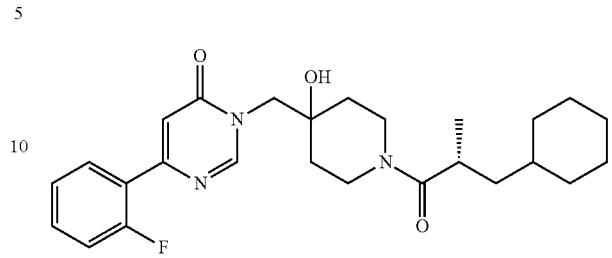

Prepared according to General Procedure 5 using Amine 1 (40 mg, 0.118 mmol), Acid 1 (34 mg, 0.20 mmol), DIPEA (0.092 mL, 0.53 mmol) and HBTU (75 mg, 0.20 mmol) in DCM (2.5 mL) to give the title compound (34.6 mg, 65%). LCMS (Method B): $R_T$=1.40 min, m/z=456 [M+H]. $^1$H NMR (400 MHz, DMSO-d$_6$): δ 8.45 (d, 1H), 8.03 (t, 1H), 7.60-7.52 (m, 1H), 7.41-7.32 (m, 2H), 6.81 (s, 1H), 5.07 (d, 1H), 4.14-3.89 (m, 3H), 3.82-3.69 (m, 1H), 3.06-2.92 (m, 1H), 2.85 (q, 1H), 1.70-1.01 (br m, 16H), 1.00-0.90 (m, 3H), 0.89-0.75 (br m, 2H).

Example 40: 3-((1-(2-(Cyclohexylmethyl)butanoyl)-4-hydroxypiperidin-4-yl)methyl)-6-(2-fluorophenyl)pyrimidin-4(3H)-one

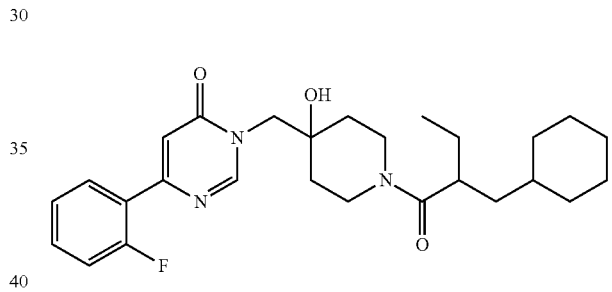

Prepared according to General Procedure 5 using Amine 1 (40 mg, 0.118 mmol), 2-(cyclohexylmethyl)butanoic acid (36.4 mg, 0.20 mmol), DIPEA (0.092 mL, 0.53 mmol) and HBTU (75 mg, 0.20 mmol) in DCM (2.5 mL) to give the title compound (36 mg, 66%). LCMS (Method B): $R_T$=1.44 min, m/z=470 [M+H]$^+$. $^1$H NMR (400 MHz, DMSO-d$_6$): δ 8.45 (d, 1H), 8.03 (tt, 1H), 7.59-7.52 (m, 1H), 7.41-7.33 (m, 2H), 6.81 (s, 1H), 5.09 (d, 1H), 4.16-3.99 (m, 2H), 3.93 (d, 1H), 3.88-3.76 (m, 1H), 3.08-2.95 (m, 1H), 2.84-2.74 (m, 1H), 1.72-1.22 (br m, 13H), 1.21-0.99 (br m, 5H), 0.91-0.73 (br m, 5H).

Example 41: rac-6-(2-Fluorophenyl)-3-((4-hydroxy-1-(cis-2-phenylcyclopropanecarbonyl)piperidin-4-yl)methyl)pyrimidin-4(3H)-one

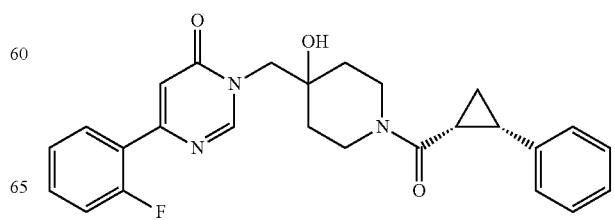

Prepared according to General Procedure 5 using Amine 1 (30 mg, 0.088 mmol), cis-2-phenylcyclopropanecarboxylic acid (24 mg, 0.15 mmol), DIPEA (0.069 mL, 0.39 mmol) and HBTU (56 mg, 0.15 mmol) in DCM (1.5 mL) to give the title compound (26.3 mg, 67%). LCMS (Method B): $R_T$=1.10 min, m/z=448 [M+H]$^+$. $^1$H NMR (400 MHz, DMSO-$d_6$, this compound appears as a mixture of conformers A:B in a 2:3 ratio): δ 8.39 (s, 0.4H, conformer A), 8.32 (s, 0.6H, conformer B), 8.07-7.97 (m, 1H), 7.59-7.52 (m, 1H), 7.41-7.33 (m, 2H), 7.26-7.16 (m, 2H), 7.15-7.06 (m, 3H), 6.79 (s, 1H), 4.91 (s, 1H), 4.03-3.74 (m, 3H), 3.62 (s, 1H), 3.25 (t, 0.6H, conformer B), 3.07 (t, 0.4H, conformer A), 2.81-2.70 (td, br, 1H), 2.48 (m, 1H), 2.38-2.26 (m, 1H), 1.63-1.33 (m, 2H), 1.31-1.11 (m, 3H), 0.71 (dq, 1H).

Example 42: 6-(2-Fluorophenyl)-3-((4-hydroxy-1-(1-methylcyclohexanecarbonyl)piperidin-4-yl)methyl)pyrimidin-4(3H)-one

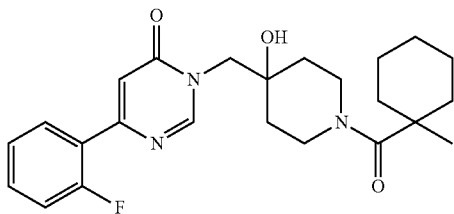 [SMILES: CC1(C(=O)N2CCC(O)(Cn3cnc(-c4ccccc4F)cc3=O)CC2)CCCCC1]

Prepared according to General Procedure 5 using Amine 1 (40 mg, 0.12 mmol), DCM (2.5 mL), 1-methyl-1-cyclohexanecarboxylic acid (28.1 mg, 0.198 mmol), DIPEA (0.092 mL, 0.53 mmol) and HBTU (75 mg, 0.20 mmol) to give the title compound (22 mg, 45%). LCMS (Method B): $R_T$=1.23 min, m/z=428 [M+H]$^+$. $^1$H NMR (400 MHz, DMSO-$d_6$): δ 8.44 (s, 1H), 8.02 (td, 1H), 7.59-7.52 (m, 1H), 7.40-7.33 (m, 2H), 6.81 (s, 1H), 5.04 (s, 1H), 4.03-3.92 (m, 4H), 3.23-.3.11 (m, 2H), 1.98-1.89 (m, 2H), 1.57-1.34 (br m, 9H), 1.33-1.20 (br m, 3H), 1.16 (s, 3H).

Example 43: 3-((S)-1-(1-((R)-3-Cyclohexyl-2-methylpropanoyl)-4-hydroxypiperidin-4-yl)propyl)-6-phenylpyrimidin-4(3H)-one and 3-((R)-1-(1-((R)-3-cyclohexyl-2-methylpropanoyl)-4-hydroxypiperidin-4-yl)propyl)-6-phenylpyrimidin-4(3H)-one

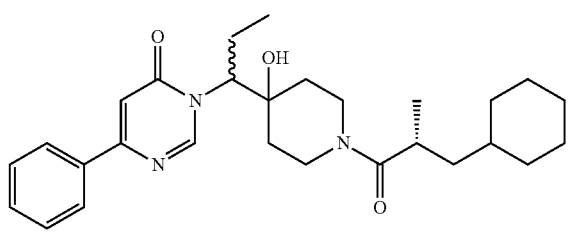 [SMILES: CCC(n1cnc(-c2ccccc2)cc1=O)C1(O)CCN(C(=O)[C@H](C)CC2CCCCC2)CC1]

Step 1: tert-Butyl 4-propylidenepiperidine-1-carboxylate

Prepared according to General Procedure 6 using triphenyl(propyl)phosphonium bromide (0.53 g, 1.37 mmol) in THF (10.0 mL), n-butyllithium (2.5 M in hexanes, 0.59 mL, 1.47 mmol), tert-butyl 4-oxopiperidine-1-carboxylate (0.195 g, 0.98 mmol) in THF (5.0 mL). The crude product was purified by flash chromatography (GraceResolv 12 g, 0-100% EtOAc in cyclohexane) to give the title compound (181 mg, 82%). $^1$H NMR (400 MHz, CDCl$_3$): δ 5.21 (br t, 1H), 3.38 (q, 4H), 2.19 (t, br, 2H), 2.12 (br t, 2H), 2.01 (quint., 2H), 1.47 (s, 9H), 0.95 (t, 3H).

Step 2: (R,S)-tert-Butyl 2-ethyl-1-oxa-6-azaspiro[2.5]octane-6-carboxylate

Prepared according to General Procedure 8 using tert-butyl 4-propylidenepiperidine-1-carboxylate (0.180 g, 0.799 mmol), DCM (5 mL) and m-CPBA (0.22 g, 0.96 mmol) in DCM (2.5 mL) to give the title compound (0.179 g, 93%). The crude product was used without further purification. $^1$H NMR (400 MHz, CDCl$_3$): δ 3.80-3.64 (br m, 2H), 3.45-3.33 (m, 2H), 2.76 (t, 1H), 1.83-1.72 (br m, 2H), 1.66-1.37 (m, 13H), 1.04 (t, 3H).

Step 3: (R,S)-tert-Butyl 4-hydroxy-4-(1-(6-oxo-4-phenylpyrimidin-1(6H)-yl)propyl)piperidine-1-carboxylate Prepared according to General Procedure 1 using 6-phenylpyrimidin-4(3H)-one (0.106 g, 0.62 mmol), (R,S)-tert-butyl 2-ethyl-1-oxa-6-azaspiro[2.5]octane-6-carboxylate (0.179 mg, 0.741 mmol), cesium carbonate (0.604 g, 1.85 mmol) and DMF (10 mL) with stirring at 80° C. for 72 h, 120° C. for a further 24 h and then 130° C. for 48 h. The crude material was dried by azeotropic distillation with toluene (1×10 mL) and purified by flash chromatography (GraceResolv 12 g, 0-100% EtOAc in cyclohexane; then 0-10% MeOH in EtOAc) to give the title compound (96.5 mg, 38%). LCMS (Method B): $R_T$=1.34 min, m/z=414 [M+H]$^+$.

Step 4: (R,S)-3-(1-(4-Hydroxypiperidin-4-yl)propyl)-6-phenylpyrimidin-4(3H)-one hydrochloride Prepared according to General Procedure 9 using (R,S)-tert-butyl 4-hydroxy-4-(1-(6-oxo-4-phenylpyrimidin-1(6H)-yl)propyl)piperidine-1-carboxylate (96 mg, 0.23 mmol) and HCl in 1,4-dioxane (4 M, 0.85 mL, 3.40 mmol) in DCM (2 mL) to give the title compound (0.132 g, 81%) which was used without further purification. LCMS (Method B): $R_T$=0.61 min, m/z=314 [M+H]$^+$.

Step 5: 3-((S)-1-(1-((R)-3-Cyclohexyl-2-methylpropanoyl)-4-hydroxypiperidin-4-yl)propyl)-6-phenylpyrimidin-4(3H)-one and 3-((R)-1-(1-((R)-3-cyclohexyl-2-methylpropanoyl)-4-hydroxypiperidin-4-yl)propyl)-6-phenylpyrimidin-4(3H)-one Prepared according to General Procedure 5 using (R,S)-3-(1-(4-hydroxypiperidin-4-yl)propyl)-6-phenylpyrimidin-4(3H)-one hydrochloride (43 mg, 0.123 mmol), DIPEA (0.086 mL, 0.49 mmol), (R)-3-cyclohexyl-2-methylpropanoic acid (Acid 1) (31.4 mg, 0.184 mmol), HBTU (70 mg, 0.184 mmol) in DCM (2.0 mL) and DMF (0.2 mL) to give the mixture of title compounds (21.4 mg, 37%). LCMS (Method B): $R_T$=1.52 min, m/z=466 [M+H]$^+$. $^1$H NMR (400 MHz, DMSO-$d_6$): δ 8.52 (s, 1H), 8.14-8.07 (m, 2H), 7.55-7.47 (m, 3H), 7.04-6.99 (m, 1H), 5.22 (s, 1H), 4.80-4.71 (m, 1H), 4.29-4.03 (m, 1H), 3.89-3.67 (m, 1H), 3.20 (br t, 1H), 2.94-2.75 (m, 2H), 2.05-1.70 (br m, 4H), 1.69-1.41 (br m, 7H), 1.29-1.01 (br m, 6H), 1.00-0.89 (m, 3H), 0.88-0.75 (m, 2H), 0.71 (t, 3H).

Example 44: (R,S)-3-((1-(3-Cyclohexyl-2-hydroxy-propanoyl)-4-hydroxypiperidin-4-yl)methyl)-6-(2-fluorophenyl)pyrimidin-4(3H)-one

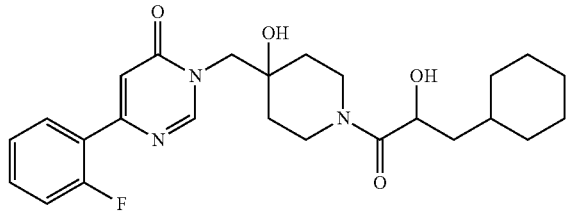 [SMILES: O=C(C(O)CC1CCCCC1)N1CCC(O)(Cn2cnc(-c3ccccc3F)cc2=O)CC1]

Prepared according to General Procedure 5 using Amine 1 (40 mg, 0.12 mmol), (R,S)-3-cyclohexyl-2-hydroxypropanoic acid (34 mg, 0.20 mmol), DIPEA (0.092 mL, 0.53 mmol) and HBTU (75 mg, 0.20 mmol) in anhydrous DCM (2.5 mL) to give the title compound (14.3 mg, 27%). LCMS (Method B): $R_T$=1.20 min, m/z=458 [M+H]$^+$. $^1$H NMR (400 MHz, DMSO-d$_6$): δ 8.44 (s, 1H), 8.03 (td, 1H), 7.59-7.53 (m, 1H), 7.39-7.34 (m, 2H), 6.82 (s, 1H), 5.08 (d, 1H), 4.69-4.66 (m, 1H), 4.35 (m, 1H), 4.08-3.92 (m, 3H), 3.68 (br d, 1H), 3.22-3.34 (br m, 1H), 3.08-2.93 (m, 1H), 1.81 (br d, 1H), 1.70-1.52 (br m, 5H), 1.51-1.38 (br m, 4H), 1.36-1.30 (br m, 2H), 1.27-1.04 (br m, 3H), 0.99-0.77 (br m, 2H).

Example 45: (R)-1-((4-Hydroxy-1-(3-phenylbutanoyl)piperidin-4-yl)methyl)-6-oxo-4-phenyl-1,6-dihydropyridine-3-carbaldehyde

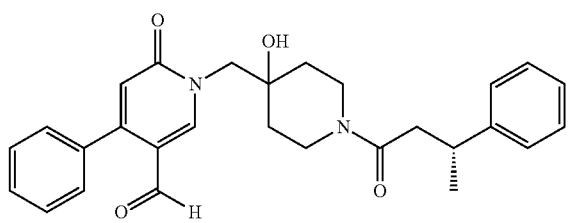 [SMILES: C[C@H](CC(=O)N1CCC(O)(Cn2cc(C=O)c(-c3ccccc3)cc2=O)CC1)c1ccccc1]

Step 1: 6-Chloro-4-phenylnicotinaldehyde

5-Bromo-2-chloro-4-phenylpyridine (prepared according to *Eur. J. Org. Chem.*, 2013, 12, p 2316-2324) (1 g, 3.72 mmol) was dissolved in THF (15 mL) and the solution was cooled to −78° C. under N$_2$. n-Butyllithium (2.5 M in hexanes, 1.79 mL, 4.48 mmol) was added and the mixture was stirred for 15 min. DMF (0.32 mL, 4.10 mmol) was added and the mixture was warmed to −60° C. and stirred for 1 h, then allowed to warm to RT. The reaction was quenched by addition of water. The mixture was extracted with EtOAc (×3). The combined organic extracts were dried over MgSO$_4$ and concentrated. The residue was chromatographed (GraceResolv 24 g, 0-20% EtOAc in cyclohexane) to give the title compound (0.33 g, 41%). LCMS (Method B): $R_T$=1.28 min, m/z=218 [M+H]$^+$.

Step 2: 6-Oxo-4-phenyl-1,6-dihydropyridine-3-carbaldehyde

Prepared according to General Procedure 10 using 6-chloro-4-phenylnicotinaldehyde (255 mg, 1.17 mmol) to give the title compound (210 mg, 90%) that was used without further purification. $^1$H NMR (400 MHz, CDCl$_3$): b 13.37 (brs, 1H), 9.70 (s, 1H), 8.27 (s, 1H), 7.54-7.45 (m, 3H), 7.42-7.38 (m, 2H), 6.55 (s, 1H).

Step 3: (R)-1-((4-Hydroxy-1-(3-phenylbutanoyl)piperidin-4-yl)methyl)-6-oxo-4-phenyl-1,6-dihydropyridine-3-carbaldehyde Prepared according to General Procedure 1 using Epoxide 2 (0.091 g, 0.351 mmol), 6-oxo-4-phenyl-1,6-dihydropyridine-3-carbaldehyde (0.058 g, 0.29 mmol) and pyridine (0.071 mL, 0.876 mmol) in DMF (2.2 mL). The crude product was purified by flash chromatography (GraceResolv 12 g, 0-100% EtOAc in cyclohexane; then 0-5% MeOH in EtOAc; followed by GraceResolv 4 g, 50-100% EtOAc in cyclohexane; then 0-15% MeOH in EtOAc) to give the title compound (7 mg, 5%). LCMS (Method B): $R_T$=1.28 min, m/z=459 [M+H]$^+$. $^1$H NMR (400 MHz, DMSO-d$_6$): δ 9.60 (s, 1H), 8.49 (d, 1H), 7.59-7.48 (m, 5H), 7.38-7.29 (m, 3H), 7.27-7.20 (m, 1H), 6.41 (d, 1H), 5.09 (d, 1H), 4.22-3.98 (m, 3H), 3.79-3.67 (brm, 1H), 3.36-3.18 (m, 3H), 3.00-2.91 (br m, 1H), 2.75-2.61 (m, 1H), 1.65-1.29 (m, 5H), 1.27 (dd, 3H).

Example 46: (R)-5-((Dimethylamino)methyl)-1-((4-hydroxy-1-(3-phenylbutanoyl)piperidin-4-yl)methyl)-4-phenylpyridin-2(1H)-one

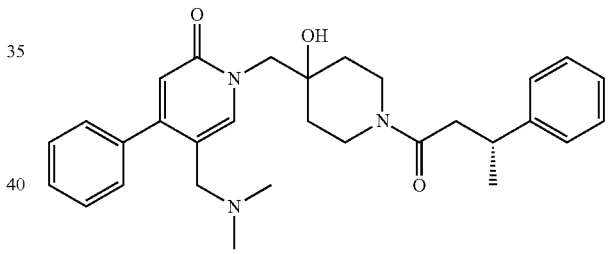

(R)-1-((4-Hydroxy-1-(3-phenylbutanoyl)piperidin-4-yl)methyl)-6-oxo-4-phenyl-1,6-dihydropyridine-3-carbaldehyde (see Example 45) (46 mg, 0.10 mmol) was dissolved in anhydrous DCM (1.0 mL) and methanol (0.25 mL) under a positive pressure of N$_2$. Dimethylamine (2 M in THF, 0.055 mL, 0.11 mmol) was added and the mixture was stirred for 1.5 h, then sodium triacetoxyborohydride (64 mg, 0.30 mmol) was added and the mixture was stirred for a further 16.5 h. Glacial acetic acid (2 drops) was added and the mixture was stirred a further 26 h. The mixture was diluted with 1 M sodium hydroxide (4.8 mL) and extracted with DCM (3×5 mL). The combined organic extracts were washed with brine (1×5 mL), dried (Biotage phase separator) then concentrated. The residue was purified by flash chromatography (GraceResolv 4 g, isocratic 100% EtOAc; then 0-50% MeOH in EtOAc) to give the title compound (7.0 mg, 14%). LCMS (Method B): $R_T$=0.79 min, m/z=488 [M+H]$^+$. $^1$H NMR (400 MHz, DMSO-d$_6$): δ 7.61 (d, 1H), 7.54-7.40 (m, 5H), 7.32-7.24 (m, 4H), 7.21-7.14 (m, 1H), 6.27 (d, 1H), 5.04 (d, 1H), 4.09-3.87 (m, 3H), 3.72-3.61 (m, 1H), 3.37-3.12 (m, 2H), 3.00 (s, 2H), 2.97-2.86 (m, 1H), 2.66-2.54 (m, 1H), 2.07 (s, 6H), 1.61-1.17 (m, 8H).

Example 47: 3-((R)-1-(4-Hydroxy-1-((R)-3-phenylbutanoyl)piperidin-4-yl)ethyl)-6-phenylpyrimidin-4(3H)-one and 3-((S)-1-(4-hydroxy-1-((R)-3-phenylbutanoyl)piperidin-4-yl)ethyl)-6-phenylpyrimidin-4(3H)-one

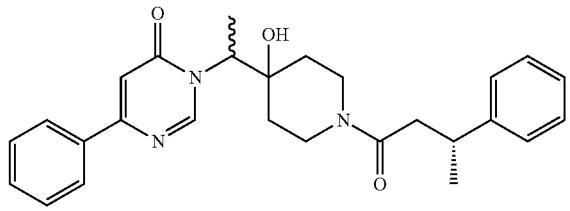 [SMILES: CC(n1cnc(-c2ccccc2)cc1=O)C1(O)CCN(C(=O)C[C@@H](C)c2ccccc2)CC1]

Prepared according to General Procedure 5 using Amine 2 (40 mg, 0.119 mmol), (R)-3-phenylbutanoic acid (0.027 mL, 0.179 mmol), DIPEA (0.083 mL, 0.476 mmol) and HBTU (67.8 mg, 0.18 mmol) in DCM (2.25 mL) to give the mixture of title compounds (24.5 mg, 46%). LCMS (Method B): $R_T$=1.21 min, m/z=446 [M+H]$^+$. $^1$H NMR (400 MHz, DMSO-d$_6$): δ 8.53-8.46 (m, 1H), 8.12-8.05 (m, 2H), 7.54-7.46 (m, 3H), 7.34-7.13 (m, 5H), 6.98 (s, 1H), 5.18 (m, 1H), 4.96-4.74 (m, 1H), 4.23-4.01 (m, br, 1H), 3.80-3.61 (m, br, 1H), 3.26-2.75 (m, 2H), 2.74-2.37 (m, 2H), 1.74-1.47 (m, 1H), 1.46-1.29 (br m, 4H), 1.28-1.16 (br m, 4H), 1.15-0.94 (br m, 2H).

Example 48: (R)-6-(2-Fluorophenyl)-3-((4-hydroxy-1-(4,4,4-trifluoro-3-phenylbutanoyl)piperidin-4-yl)methyl)pyrimidin-4(3H)-one

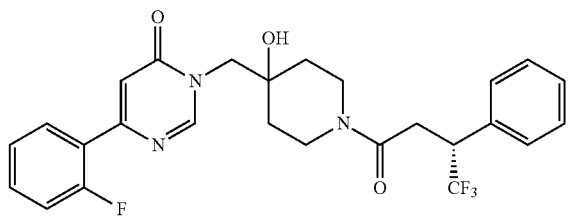 [SMILES: O=C(C[C@H](c1ccccc1)C(F)(F)F)N1CCC(O)(Cn2cnc(-c3ccccc3F)cc2=O)CC1]

Prepared according to General Procedure 5 using Amine 1 (40 mg, 0.118 mmol) using (R)-4,4,4-trifluoro-3-phenylbutanoic acid (Acid 16) (43 mg, 0.20 mmol), DIPEA (0.092 mL, 0.525 mmol) and HBTU (75 mg, 0.198 mmol) in DCM (2.5 mL) to give the title compound (29 mg, 50%). LCMS (Method B): $R_T$=1.25 min, m/z=504 [M+H]$^+$. $^1$H NMR (400 MHz, CDCl$_3$): δ 8.17-8.02 (m, 2H), 7.49-7.42 (m, 1H), 7.41-7.24 (m, 6H), 7.18 (ddd, 1H), 7.11 (d, 1H), 4.38-4.29 (m, 1H), 4.21-4.03 (m, 1H), 4.00-3.80 (m, 3H), 3.76-3.60 (m, 1H), 3.47-3.33 (m, 1H), 3.05-2.85 (m, 3H), 1.70-0.81 (m, 4H).

Example 49: (R,S)-3-((1-(3-Cyclohexyl-2-fluoropropanoyl)-4-hydroxypiperidin-4-yl)methyl)-6-(2-fluorophenyl)pyrimidin-4(3H)-one

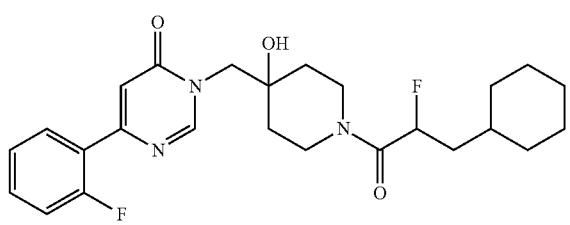 [SMILES: O=C(C(F)CC1CCCCC1)N1CCC(O)(Cn2cnc(-c3ccccc3F)cc2=O)CC1]

Prepared according to General Procedure 5 using Amine 1 (40 mg, 0.12 mmol), (R,S)-3-cyclohexyl-2-fluoropropanoic acid (34.5 mg, 0.20 mmol), DIPEA (0.092 mL, 0.525 mmol) and HBTU (75 mg, 0.20 mmol) in DCM (2.5 mL) to give the title compound (30 mg, 56%). LCMS (Method B): $R_T$=1.44 min, m/z=460 [M+H]$^+$. $^1$H NMR (400 MHz, CDCl$_3$): δ 8.16 (br d, 1H), 8.07 (td, 1H), 7.49-7.42 (m, 1H), 7.32-7.23 (m, 1H), 7.18 (ddd, 1H), 7.13 (s, 1H), 5.21 (dtd, 1H), 4.40 (br t, 1H), 4.17-3.74 (m, 4H), 3.53-3.40 (m, 2H), 3.13 (br q, 1H), 1.95-1.79 (br m, 2H), 1.78-1.47 (m, 7H), 1.35-1.10 (m, 4H), 1.07-0.87 (m, 3H).

Example 50: 3-(((R)-1-((R)-3-Cyclohexyl-2-methylpropanoyl)-4-hydroxy-3,3-dimethylpiperidin-4-yl)methyl)-6-phenylpyrimidin-4(3H)-one and 3-(((S)-1-((R)-3-Cyclohexyl-2-methylpropanoyl)-4-hydroxy-3,3-dimethylpiperidin-4-yl)methyl)-6-phenylpyrimidin-4(3H)-one

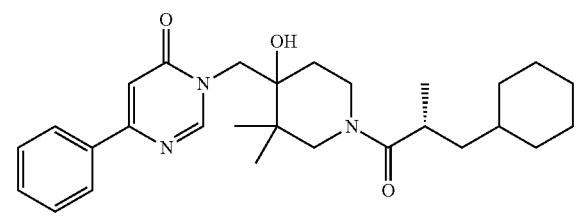 [SMILES: C[C@H](CC1CCCCC1)C(=O)N1CCC(O)(Cn2cnc(-c3ccccc3)cc2=O)C(C)(C)C1]

Step 1: (R,S)-tert-Butyl 4-hydroxy-3,3-dimethyl-4-((6-oxo-4-phenylpyrimidin-1(6H)-yl)methyl)piperidine-1-carboxylate Prepared according to General Procedure 1 using 6-phenylpyrimidin-4(3H)-one (0.172 g, 1.00 mmol), Epoxide 3 (0.242 g, 1.00 mmol) and DIPEA (0.262 mL, 1.50 mmol) in DMF (1.43 mL). After 16 h at 80° C., cesium carbonate (0.163 g, 0.499 mmol) was added and the mixture was heated at 120° C. for a further 4 h. The crude product was triturated with EtOAc to give the title compound (0.215 g, 52%). LCMS (Method B): $R_T$=1.34 min, m/z=414 [M+H]$^+$.

Step 2: (R,S)-3-((4-Hydroxy-3,3-dimethylpiperidin-4-yl)methyl)-6-phenylpyrimidin-4(3H)-one hydrochloride Prepared according to General Procedure 9 using (R,S)-tert-butyl 4-hydroxy-3,3-dimethyl-4-((6-oxo-4-phenylpyrimidin-1 (6H)-yl)methyl)piperidine-1-carboxylate (0.215 g, 0.520 mmol), DCM (2.60 mL) and hydrogen chloride (4 M in 1,4-dioxane, 1.820 mL, 7.28 mmol) to give the title compound (0.200 g, quantitative). LCMS (Method B): $R_T$=0.59 min, m/z=314 [M+H]$^+$. $^1$H NMR (400 MHz, DMSO-d$_6$): δ 9.17 (br d, 1H), 8.47 (s, 1H), 8.47-8.39 (m, 1H), 8.13-8.05 (m, 2H), 7.54-7.46 (m, 3H), 7.02 (s, 1H), 5.3 (br s, 1H), 4.45 (d, 1H), 3.77 (d, 1H), 3.05 (br d, 1H), 3.00-2.75 (m, 3H), 1.85 (br td, 1H), 1.35 (br d, 1H), 1.21 (s, 3H), 1.04 (s, 3H).

Step 3: 3-(((R)-1-((R)-3-Cyclohexyl-2-methylpropanoyl)-4-hydroxy-3,3-dimethylpiperidin-4-yl)methyl)-6-phenylpyrimidin-4(3H)-one and 3-(((S)-1-((R)-3-cyclohexyl-2-methylpropanoyl)-4-hydroxy-3,3-dimethylpiperidin-4-yl)methyl)-6-phenylpyrimidin-4(3H)-one Prepared according to General Procedure 5 using (R,S)-3-((4-hydroxy-3,3-dimethylpiperidin-4-yl)methyl)-6-phenylpyrimidin-4(3H)-one hydrochloride (0.05 g, 0.143 mmol), (R)-3-cyclohexyl-2-methylpropanoic acid (Acid 1) (0.036 g, 0.214 mmol), HBTU (0.081 g, 0.214 mmol), DCM (1.5 mL) and DIPEA (0.103 mL, 0.572 mmol) to give the mixture of title compounds (36 mg, 54%). LCMS (Method B): $R_T$=1.53 min, m/z=466 [M+H]$^+$. $^1$H NMR (400 MHz, DMSO-$d_6$, mixture of diastereomers and conformers): δ 8.44 (s, 1H), 8.13-8.05 (m, 2H), 7.54-7.46 (m, 3H), 7.01 (d, 1H), 4.91 (br s, 1H), 4.50-4.36 (m, 1H), 4.13-3.97 (m, 0.5H), 3.80-3.62 (m, 2H), 3.32-3.16 (m, 1.5H), 3.03-2.83 (m, 2H), 1.73-1.55 (m, 6H), 1.55-1.43 (m, 1H), 1.26-1.06 (m, 6H), 1.03 (br d, 1H), 1.02-0.95 (m, 6H), 0.91 (d, 2H), 0.87-0.76 (m, 2H).

Example 51: 3-(((R)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one and 3-(((S)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one

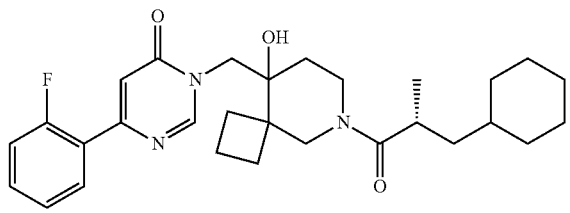 [SMILES: C[C@H](CC1CCCCC1)C(=O)N1CCC(O)(Cn2cnc(-c3ccccc3F)cc2=O)C2(CCC2)C1]

Step 1: (R,S)-tert-Butyl 9-((4-(2-fluorophenyl)-6-oxopyrimidin-1(6H)-yl)methyl)-9-hydroxy-6-azaspiro[3.5]nonane-6-carboxylate Prepared according to General Procedure 1 using 6-(2-fluorophenyl)pyrimidin-4(3H)-one (0.136 g, 0.72 mmol), Epoxide 4 (0.2 g, 0.789 mmol) and DIPEA (0.193 mL, 1.077 mmol) in DMF (1.4 mL) at 80° C. for 16 h then 120° C. for 2 days. The crude product was purified by precipitation from water and triturated with DCM and cyclohexane to give the title compound (110 mg, 35%). LCMS (Method B): $R_T$=1.50 min, m/z=388 [M+2H-$^t$Bu]$^+$.

Step 2: (R,S)-6-(2-Fluorophenyl)-3-((9-hydroxy-6-azaspiro[3.5]nonan-9-yl)methyl)pyrimidin-4(3H)-one hydrochloride Prepared according to General Procedure 9 using (R,S)-tert-butyl-9-((4-(2-fluorophenyl)-6-oxopyrimidin-1 (6H)-yl)methyl)-9-hydroxy-6-azaspiro[3.5]nonane-6-carboxylate (0.110 g, 0.25 mmol) and hydrogen chloride (4 M in 1,4-dioxane, 0.87 mL, 3.47 mmol) in DCM (1.2 mL) to give the crude title compound (100 mg, >100%) which was used without further purification. LCMS (Method B): $R_T$=0.70 min, m/z=344 [M+H]$^+$. $^1$H NMR (400 MHz, DMSO-$d_6$): δ 8.94-8.83 (m, 1H), 8.71-8.59 (m, 1H), 8.54 (s, 1H), 8.04 (td, 1H), 7.60-7.52 (m, 1H), 7.42-7.34 (m, 2H), 6.83 (s, 1H), 4.64 (d, 1H), 4.45 (br s, 1H), 3.72 (d, 1H), 3.42-3.33 (m, 1H), 3.29-3.16 (m, 2H), 3.03-2.92 (m, 1H), 2.47-2.24 (m, 2H), 2.04-1.87 (m, 1H), 1.83-1.66 (m, 3H), 1.50-1.33 (m, 2H).

Step 3: 3-(((R)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one and 3-(((S)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one Prepared according to General Procedure 5 using (R,S)-6-(2-fluorophenyl)-3-((9-hydroxy-6-azaspiro[3.5]nonan-9-yl)methyl)pyrimidin-4(3H)-one hydrochloride (0.025 g, 0.066 mmol), (R)-3-cyclohexyl-2-methylpropanoic acid (Acid 1) (0.017 g, 0.099 mmol), HBTU (0.037 g, 0.099 mmol) and DIPEA (0.047 mL, 0.26 mmol) in DCM (0.7 mL). The crude product was purified by flash chromatography (Biotage KP-NH 11 g, 0-50% EtOAc in cyclohexane; then GraceResolv 4 g, 10-70% EtOAc in cyclohexane) to give the mixture of title compounds (4.5 mg, 13.8%). LCMS (Method B): $R_T$=1.58 min, m/z=496 [M+H]$^+$. $^1$H NMR (400 MHz, CDCl$_3$, this compound appears as two conformers A:B in a 2:3 ratio): δ 8.27 (br d, 0.6H, conformer B only), 8.22 (s, 0.4H, conformer A only), 8.07 (td, 1H), 7.49-7.41 (m, 1H), 7.31-7.27 (d, 1H), 7.18 (br dd, 1H), 7.12-7.07 (m, 1H), 4.50-4.35 (m, 1H), 4.26-3.96 (m, 2H), 3.86-3.57 (m, 3H), 3.54-3.40 (m, 1H), 3.00-2.82 (m, 1H), 2.44-2.33 (m, 0.4H, conformer A only), 2.29-2.08 (m, 2.6H), 2.04-1.82 (m, 1H), 1.75-1.59 (m, 7H), 1.50-1.33 (m, 2H), 1.31-1.16 (m, 5H), 1.16-1.11 (m, 2H), 1.11-1.05 (m, 2H), 0.96-0.80 (m, 2H).

Example 52: (R)-5-(3-(Aminomethyl)phenyl)-1-((1-(3-cyclohexyl-2-methylpropanoyl)-4-hydroxypiperidin-4-yl)methyl)-4-(2-fluorophenyl)pyridin-2(1H)-one

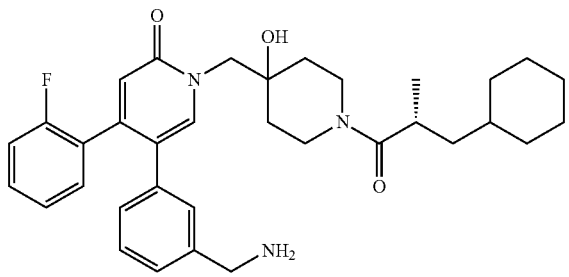 [SMILES: C[C@H](CC1CCCCC1)C(=O)N1CCC(O)(Cn2cc(-c3cccc(CN)c3)c(-c3ccccc3F)cc2=O)CC1]

Step 1: 5-Bromo-4-(2-fluorophenyl)pyridin-2(1H)-one

Prepared as for 5-bromo-4-phenylpyridin-2(1H)-one (see Example 1) using (5-bromo-2-chloro-4-(2-fluorophenyl)pyridine (3.1 g, 10.8 mmol) (prepared according to *Eur J. Org. Chem.*, 2013, p 2316-2324) and sodium hydroxide (3.03 g, 76 mmol) in 1,4-dioxane (36 mL) and water (36 mL) to give the title compound (2.50 g, 86%) which was used without further purification. LCMS (Method B): $R_T$=1.18 min, m/z=268, 270 [M+H]$^+$.

Step 2: tert-Butyl 4-((5-bromo-4-(2-fluorophenyl)-2-oxopyridin-1(2H)-yl)methyl)-4-hydroxypiperidine-1-carboxylate Prepared according to General Procedure 1 using 5-bromo-4-(2-fluorophenyl)pyridin-2(1·)-one (1 g, 3.73 mmol), Epoxide 1 (0.796 g, 3.73 mmol) and DIPEA (0.98 mL, 5.60 mmol) in DMF (5.0 mL) to give the title compound (0.28 g, 16%) which was used without further purification. LCMS (Method B): $R_T$=0.98 min, m/z=423, 425 [M+H]$^+$.

Step 3: 5-Bromo-4-(2-fluorophenyl)-1-((4-hydroxypiperidin-4-yl)methyl)pyridin-2(1H)-one hydrochloride Prepared according to General Procedure 9 using tert-butyl-4-((5-bromo-4-(2-fluorophenyl)-2-oxopyridin-(2H)-yl)methyl)-4-hydroxypiperidine-1-carboxylate (0.1 g, 0.208 mmol) and hydrogen chloride (4 M in 1,4-dioxane, 0.76 mL, 3.03 mmol) in DCM (0.83 mL) to give the title compound (0.080 g, 92%). $^1$H NMR (400 MHz, DMSO-d$_6$): δ 8.91-8.83 (m, 1H), 8.60-8.49 (m, 1H), 8.05 (s, 1H), 7.58-7.50 (m, 1H), 7.39-7.30 (m, 3H), 6.50 (s, 1H), 4.04 (s, 2H), 3.20-3.11 (m, 2H), 3.09-2.95 (m, 2H), 1.79 (br td, 2H), 1.60 (brd, 2H).

Step 4: (R)-5-Bromo-1-((1-(3-cyclohexyl-2-methylpropanoyl)-4-hydroxypiperidin-4-yl)methyl)-4-(2-fluorophenyl)pyridin-2(1H)-one Prepared according to General Procedure 5 using 5-bromo-4-(2-fluorophenyl)-1-((4-hydroxypiperidin-4-yl)methyl)pyridin-2(1H)-one hydrochloride (0.08 g, 0.192 mmol), Acid 1 (0.049 g, 0.287 mmol), HBTU (0.109 g, 0.287 mmol) and DIPEA (0.13 mL, 0.77 mmol) in DMF (0.5 mL) to give the title compound (97 mg, 95%). LCMS (Method B): $R_T$=1.58 min, m/z=533/535 [M+H]$^+$. $^1$H NMR (400 MHz, CDCl$_3$): δ 7.56 (s, 1H), 7.49-7.42 (m, 1H), 7.26-7.22 (m, 2H), 7.18 (br t, 1H), 6.66 (s, 1H), 4.53-4.42 (m, 2H), 4.20-4.09 (m, 2H), 3.97 (d, 1H), 3.82 (br d, 1H), 3.49 (br t, 1H), 3.07 (br t, 1H), 2.84 (q, 1H), 1.78-1.62 (m, 8H), 1.61-1.49 (m, 1H), 1.30-1.15 (m, 6H), 1.09 (t, 3H), 0.96-0.81 (m, 2H).

Step 5: (R)-tert-Butyl 3-(1-((1-(3-cyclohexyl-2-methylpropanoyl)-4-hydroxypiperidin-4-yl)methyl)-4-(2-fluorophenyl)-6-oxo-1,6-dihydropyridin-3-yl)benzylcarbamate Prepared according to General Procedure 4 using (R)-5-bromo-1-((1-(3-cyclohexyl-2-methylpropanoyl)-4-hydroxypiperidin-4-yl)methyl)-4-(2-fluorophenyl)pyridin-2 (1H)-one (0.097 g, 0.182 mmol), (3-(((tert-butoxycarbonyl) amino)methyl)phenyl)boronic acid (0.068 g, 0.273 mmol), sodium carbonate (0.039 g, 0.364 mmol), 1,4-dioxane (1.5 mL), water (0.6 mL) and Pd(Ph$_3$P)$_4$ (10.51 mg, 9.09 μmol). The reaction was heated in a microwave for 20 min at 150° C. The crude product was loaded onto a 2 g SCX-2 cartridge and eluted with 0-30% MeOH in DCM. The volatiles were removed and the residue was purified by flash chromatography (Biotage KP-NH 11 g, 0-100% EtOAc in cyclohexane) to give the title compound (29 mg, 24%) which was used without further purification. LCMS (Method B): $R_T$=1.71 min, m/z=604 [M+H]$^+$.

Step 6: (R)-5-(3-(Aminomethyl)phenyl)-1-((1-(3-cyclohexyl-2-methylpropanoyl)-4-hydroxypiperidin-4-yl)methyl)-4-(2-fluorophenyl)pyridin-2(1H)-one Prepared according to General Procedure 7 using (R)-tert-butyl 3-(1-((1-(3-cyclohexyl-2-methylpropanoyl)-4-hydroxypiperidin-4-yl)methyl)-4-(2-fluorophenyl)-6-oxo-1,6-dihydropyridin-3-yl)benzylcarbamate (0.029 g, 0.044 mmol), 2,2,2-trifluoroacetic acid (0.230 mL, 2.99 mmol) and DCM (0.15 mL) to give the title compound (19 mg, 77%). LCMS (Method B): $R_T$=1.02 min, m/z=560 [M+H]$^+$. $^1$H NMR (400 MHz, CDCl$_3$): δ 7.26-7.36 (m, 2H), 7.21-7.09 (m, 4H), 6.98-6.83 (m, 3H), 6.73 (s, 1H), 5.40-4.80 (br s, 2H), 4.50 (br d, 1H), 4.28 (br dd, 1H), 4.01 (br dd, 1H), 3.81 (br d, 1H), 3.74 (s, 2H), 3.56-3.45 (m, 2H), 3.05 (br td, 1H), 2.85 (q, 1H), 1.80-1.50 (m, 8H), 1.29-1.09 (m, 6H), 1.08 (d, 3H), 0.95-0.78 (m, 2H).

Example 53: 3-(((S)-4-Hydroxy-3,3-dimethyl-1-((R)-3-phenylbutanoyl)piperidin-4-yl)methyl)-6-phenylpyrimidin-4(3H)-one and 3-(((R)-4-hydroxy-3,3-dimethyl-1-((R)-3-phenylbutanoyl)piperidin-4-yl)methyl)-6-phenylpyrimidin-4(3H)-one

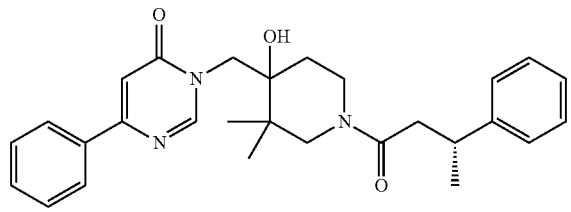 [SMILES: C[C@H](CC(=O)N1CCC(O)(Cn2cnc(-c3ccccc3)cc2=O)C(C)(C)C1)c1ccccc1]

Prepared according to General Procedure 5 using (R,S)-3-((4-hydroxy-3,3-dimethylpiperidin-4-yl)methyl)-6-phenylpyrimidin-4(3H)-one hydrochloride (see Example 50) (50 mg, 0.14 mmol), (R)-3-phenylbutanoic acid (35 mg, 0.21 mmol), HBTU (81 mg, 0.21 mmol) and DIPEA (0.10 mL, 0.57 mmol) in DCM (1.4 mL) to give the mixture of title compounds (32 mg, 49%). LCMS (Method B): $R_T$=1.31 min, m/z=460 [M+H]$^+$. $^1$H NMR (400 MHz, DMSO-d$_6$, mixture of diastereomers and conformers): δ 8.41 (d, 1H), 8.08 (m, 2H), 7.50 (m, 3H), 7.27 (m, 4H), 7.17 (m, 1H), 7.00 (s, 1H), 4.86 (br s, 1H), 4.42 (m, 0.4H), 4.36 (m, 0.6H), 4.03 (m, 0.6H), 3.70 (m, 2.4H), 3.33-3.09 (m, 2H), 2.86 (t, 1H), 2.77-2.56 (m, 2H), 1.68-1.45 (m, 1H), 1.22-0.81 (m, 10H).

Example 54: (R)-6-(4-Fluorophenoxy)-3-((4-hydroxy-1-(3-phenylbutanoyl)piperidin-4-yl)methyl) pyrimidin-4(3M-one

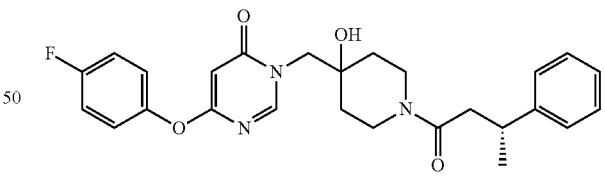

(R)-6-Chloro-3-((4-hydroxy-1-(3-phenylbutanoyl)piperidin-4-yl)methyl)pyrimidin-4(3H)-one (40 mg, 0.10 mmol) and 4-fluorophenol (17 mg, 0.15 mmol) were dissolved in a mixture of THF (0.5 mL) and toluene (1.5 mL). 2-(Dicyclohexylphosphino)-2',4',6'-triisopropylbiphenyl (4.9 mg, 10.3 μmol) was added and the mixture was purged with N$_2$. Pd$_2$(dba)$_3$ (4.7 mg, 5.1 μmol) was added, the tube was sealed and the mixture was heated at 110° C. for 16 h. The mixture was cooled to RT and diluted with water, then extracted with DCM. The organic layer was dried (Biotage phase separator), concentrated and the residue was purified by flash chromatography (Biotage KP-NH 11 g, 10-100% EtOAc in cyclohexane; then 0-15% MeOH in EtOAc) to give the title compound (14 mg, 29%). LCMS (Method B): $R_T$ 1.14, m/z=466 [M+H]$^+$. $^1$H NMR (400 MHz, DMSO-$d_6$): δ 8.22 (d, 1H), 7.26 (m, 9H), 5.56 (m, 1H), 4.94 (m, 1H), 4.01 (m, 1H), 3.95 (m, 1H), 3.81 (m, 1H), 3.62 (m, 1H), 3.16 (m, 2H), 2.88 (m, 1H), 2.56 (m, 2H), 1.21 (m, 3H), 1.10 (m, 4H).

Example 55: (R)-1-((4-Hydroxy-1-(3-phenylbutanoyl)piperidin-4-yl)methyl)-5-(2-oxopyrrolidin-1-yl)-4-phenylpyridin-2(1H)-one

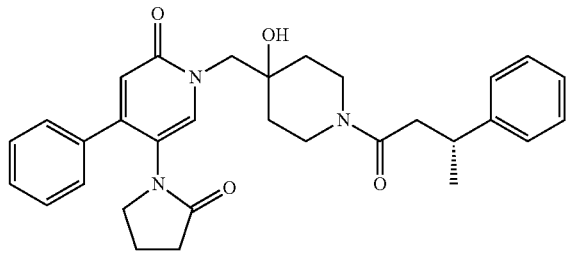 [SMILES: C[C@H](CC(=O)N1CCC(O)(Cn2cc(N3CCCC3=O)c(-c3ccccc3)cc2=O)CC1)c1ccccc1]

Step 1:
1-(6-Chloro-4-phenylpyridin-3-yl)pyrrolidin-2-one

5-Bromo-2-chloro-4-phenylpyridine (0.50 g, 1.86 mmol) (prepared as described in *Eur. J. Org. Chem.*, 2013, p 2316-2324), pyrrolidin-2-one (0.170 mL, 2.23 mmol), cesium carbonate (0.849 g, 2.61 mmol), and XantPhos (0.108 g, 0.186 mmol) were suspended in anhydrous 1,4-dioxane (15 mL). The suspension was purged and filled with $N_2$ (×3) then $Pd_2(dba)_3$ (0.085 g, 0.093 mmol) was added. The mixture was heated at 100° C. for 16 h, then cooled to RT and diluted with water (20 mL). The mixture was filtered through a pad of Celite® and extracted with EtOAc. The organic layer was concentrated under reduced pressure and the residue was purified by flash chromatography (GraceResolv 11 g, 0-100% EtOAc in cyclohexane; then 0-10% MeOH in EtOAc) to give the title compound (74 mg, 14%). LCMS (Method B): $R_T$=1.42 min, m/z=273 [M+H]$^+$. $^1$H NMR (400 MHz, CDCl$_3$): δ 8.37 (s, 1H), 7.44-7.49 (m, 3H), 7.34-7.38 (m, 3H), 3.24 (t, 2H), 2.46 (t, 2H), 1.96 (m, 2H).

Step 2: 5-(2-Oxopyrrolidin-1-yl)-4-phenylpyridin-2(1H)-one

A solution of 1-(6-chloro-4-phenylpyridin-3-yl)pyrrolidin-2-one (0.075 g, 0.28 mmol) in water (1.0 mL) and acetic acid (3.1 mL, 53.6 mmol) was heated in a microwave at 180° C. for 9 h. The mixture was concentrated and the residue was diluted with saturated aqueous sodium bicarbonate and extracted with DCM.
The organic layer was dried (Biotage phase separator) and concentrated to give the title compound (61 mg, 87%) which was used without any further purification. LCMS (Method B): $R_T$=0.75 min, m/z=255 [M+H]$^+$. $^1$H NMR (400 MHz, CDCl$_3$) δ 7.46-7.42 (m, 3H), 7.39 (s, 1H), 7.38-7.33 (m, 2H), 6.59 (s, 1H), 3.09 (t, 2H), 2.39 (t, 2H), 1.84 (m, 2H).

Step 3: (R)-1-((4-Hydroxy-1-(3-phenylbutanoyl) piperidin-4-yl)methyl)-5-(2-oxopyrrolidin-1-yl)-4-phenylpyridin-2(1H)-one Prepared according to General Procedure 1 using 5-(2-oxopyrrolidin-1-yl)-4-phenylpyridin-2(1H)-one (0.061 g, 0.240 mmol), Epoxide 2 (0.068 g, 0.264 mmol) and DIPEA (0.063 mL, 0.360 mmol) in DMF (0.7 mL). The reaction was heated to 80° C. for 64 h. The crude product was purified by flash chromatography (Biotage KP-NH, 0-100% EtOAc in cyclohexane; then 0-5% MeOH in EtOAc) followed by preparative HPLC under basic conditions to give the title compound (15 mg, 12%). LCMS (Method B): $R_T$=1.08 min, m/z=514 [M+H]$^+$. $^1$H NMR (400 MHz, CDCl$_3$, this compound appears as two conformers): δ 7.46-7.42 (m, 3H), 7.34-7.17 (m, 8H), 6.64 (d, 1H), 4.80 (s, 0.6H), 4.68 (s, 0.4H), 4.51-4.38 (m, 1H), 4.14 (d, 1H, 0.4H), 3.94 (br dd, 1H), 3.82 (d, 0.6H), 3.65-3.55 (m, 1H), 3.45-3.20 (m, 2H), 3.15-3.01 (m, 2H), 2.95 (br ddd, 1H), 2.70-2.62 (m, 1H), 2.55-2.47 (m, 1H), 2.42 (m, 2H), 1.93-1.78 (m, 2H), 1.59-1.44 (m, 2H), 1.43 (br dd, 1H), 1.35 (dd, 2.4H), 1.28 (br td, 1H), 0.73 (td, 0.6H).

Example 56: 6-(2-Fluorophenyl)-3-((4-hydroxy-1-(1-methyl-4-methylenecyclohexanecarbonyl)piperidin-4-yl)methyl)pyrimidin-4(3H)-one

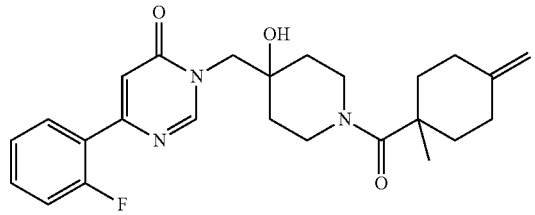 [SMILES: C=C1CCC(C)(C(=O)N2CCC(O)(Cn3cnc(-c4ccccc4F)cc3=O)CC2)CC1]

Step 1: Ethyl 1-methyl-4-methylenecyclohexanecarboxylate

Potassium tert-butoxide (0.183 g, 1.63 mmol) was added to an ice cold solution of methyltriphenylphosphonium bromide (0.620 g, 1.74 mmol) in THF (1.6 mL) and the solution was stirred at 0° C. for 40 min. A solution of ethyl 1-methyl-4-oxocyclohexanecarboxylate (0.2 g, 1.086 mmol) in THF (2.0 mL) was added dropwise at 0° C. and the mixture was stirred at 0° C. for 24 h. The mixture was warmed to RT, quenched by the addition of $H_2O$ and extracted with $Et_2O$. The organic layer was dried over MgSO$_4$, filtered and concentrated. The residue was purified by flash chromatography (GraceResolv 11 g, 0-10% EtOAc in cyclohexane) to give the title compound (140 mg, 71%). $^1$H NMR (400 MHz, CDCl$_3$): δ 4.62 (s, 2H), 2.24-2.06 (m, 9H), 1.51 (d, 1H), 1.37-1.29 (m, 3H), 1.18 (s, 3H).

Step 2:
1-Methyl-4-methylenecyclohexanecarboxylic acid

A solution of potassium hydroxide (0.215 g, 3.84 mmol) in $H_2O$ (0.55 mL) was added to a solution of ethyl 1-methyl-4-methylenecyclohexanecarboxylate (0.14 g, 0.77 mmol) in EtOH (0.55 mL) and the mixture was heated in a microwave at 120° C. for 20 min. The mixture was cooled to RT and extracted with EtOAc, and the organic layer was discarded. The aqueous layer was acidified to pH 2 with 1 M HCl and extracted with EtOAc. The organic layer was dried over MgSO$_4$, filtered and concentrated to give the title compound (100 mg, 84%) which was used without further purification. $^1$H NMR (400 MHz, CDCl$_3$): δ 4.64 (s, 2H), 2.26-2.12 (m, 6H), 2.11 (s, 1H), 1.75-1.50 (m, 1H), 1.41-1.32 (m, 2H), 1.28-1.24 (m, 3H).

Step 3: 6-(2-Fluorophenyl)-3-((4-hydroxy-1-(1-methyl-4-methylenecyclohexanecarbonyl)piperidin-4-yl)methyl)pyrimidin-4(3H)-one Prepared according to General Procedure 5 using 6-(2-fluorophenyl)-3-((4-hydroxypiperidin-4-yl)methyl)pyrimidin-4(3H)-one hydrochloride (0.073 g, 0.216 mmol), 1-methyl-4-methylenecyclohexanecarboxylic acid (0.050 g, 0.324 mmol), HBTU (0.123 g, 0.324 mmol) and DIPEA (0.151 mL, 0.865 mmol) in DCM (3.6 mL) to give the title compound (4.8 mg, 5%). LCMS (Method B): $R_T$=1.26 min, m/z=440 [M+H]$^+$. $^1$H NMR (400 MHz, CDCl$_3$): δ 8.18 (br s, 1H), 8.07 (td, 1H), 7.49-7.42 (m, 1H), 7.29 (br dd, 1H), 7.17 (m, 1H), 7.12 (s, 1H), 4.60 (s, 2H), 4.23 (br d, 2H), 4.07 (s, 2H), 3.75 (s, 1H), 3.31 (br td, 2H), 2.30-2.13 (m, 6H), 1.68-1.57 (m, 4H), 1.49-1.40 (m, 2H), 1.28 (s, 3H).

Example 57: (R,S)-3-((1-(3-Cyclobutyl-2-methylpropanoyl)-4-hydroxypiperidin-4-yl)methyl)-6-(2-fluorophenyl)pyrimidin-4(3H)-one

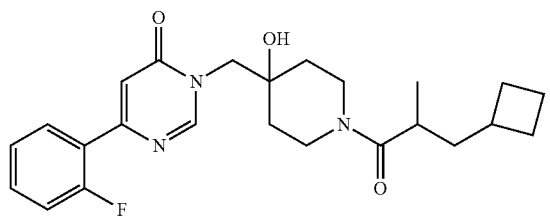 [SMILES: CC(CC1CCC1)C(=O)N1CCC(O)(Cn2cnc(-c3ccccc3F)cc2=O)CC1]

Step 1: (R,S)-3-Cyclobutyl-2-methylpropanoic acid n-Butyllithium (2.5 M in hexanes, 0.687 mL, 1.72 mmol) was added dropwise at 0° C. to a solution of diisopropylamine (0.234 mL, 1.64 mmol) in THF (1.3 mL). The solution was stirred at 0° C. for 30 min then 3-cyclobutylpropanoic acid (0.1 g, 0.78 mmol) was added and the mixture was heated at 45° C. for 1 h. The mixture was cooled to 0° C. and iodomethane (0.097 mL, 1.56 mmol) was added. The mixture was heated at 45° C. for 3 h. The reaction was cooled to RT, quenched by addition of saturated aqueous sodium bicarbonate and extracted with EtOAc. The organic layer was discarded and the aqueous layer was acidified to pH 2 by addition of 1 M HCl and extracted with EtOAc. The organic layer was dried over MgSO$_4$, filtered and concentrated to give the title compound (0.10 g, 90%). $^1$H NMR (400 MHz, CDCl$_3$): δ 11.0 (br s, 1H), 2.45-2.29 (m, 2H), 2.11-1.98 (m, 2H), 1.91-1.76 (m, 3H), 1.68-1.47 (m, 3H), 1.15 (d, 3H).

Step 2: (R,S)-3-((1-(3-Cyclobutyl-2-methylpropanoyl)-4-hydroxypiperidin-4-yl)methyl)-6-(2-fluorophenyl)pyrimidin-4(3H)-one Prepared according to General Procedure 5 using Amine 1 (0.080 g, 0.235 mmol), (R,S)-3-cyclobutyl-2-methylpropanoic acid (commercially available) (0.063 g, 0.353 mmol), HBTU (0.134 g, 0.353 mmol) and DIPEA (0.16 mL, 0.942 mmol) in DCM (4.1 mL). The crude product was purified by preparative HPLC under basic conditions to give the title compound (6.2 mg, 6%). LCMS (Method B): $R_T$=1.22 min, m/z=428 [M+H]$^+$. $^1$H NMR (400 MHz, CDCl$_3$): δ 8.18 (d, 1H), 8.06 (br t, 1H), 7.49-7.42 (m, 1H), 7.29 (br dd, 1H), 7.18 (br ddd, 1H), 7.12 (s, 1H), 4.49-4.39 (m, 1H), 4.17 (dd, 1H), 3.98 (t, 1H), 3.83-3.72 (m, 2H), 3.45 (br t, 1H), 3.13-3.03 (m, 1H), 2.65 (p, 1H), 2.32-2.19 (m, 1H), 2.07-1.95 (m, 2H), 1.88-1.73 (m, 3H), 1.70-1.53 (m, 5H), 1.51-1.41 (m, 1H), 1.33-1.23 (m, 1H), 1.08 (t, 3H).

Example 58: (R,S)-3-((1-(3-Cycloheptyl-2-methylpropanoyl)-4-hydroxypiperidin-4-yl)methyl)-6-(2-fluorophenyl)pyrimidin-4(3H)-one

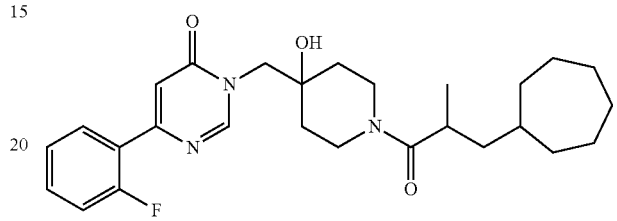

Prepared according to General Procedure 5 using Amine 1 (0.061 g, 0.181 mmol), (R,S)-3-cycloheptyl-2-methylpropanoic acid (0.05 g, 0.271 mmol) (commercially available), HBTU (0.103 g, 0.271 mmol) and DIPEA (0.13 mL, 0.724 mmol) in DCM (3.0 mL) to give the title compound (39.5 mg, 46%). LCMS (Method B): $R_T$=1.49 min, m/z=470 [M+H]$^+$. $^1$H NMR (400 MHz, CDCl$_3$): δ 8.18 (br s, 1H), 8.06 (td, 1H), 7.49-7.42 (m, 1H), 7.29 (br dd, 1H), 7.18 (br ddd, 1H), 7.02 (s, 1H), 4.44 (brd, 1H), 4.17 (dd, 1H), 3.98 (dd, 1H), 3.85-3.76 (m, 2H), 3.47 (brd, 1H), 3.09 (br t, 1H), 2.83-2.75 (m, 1H), 1.71-1.52 (m, 9H), 1.51-1.34 (m, 6H), 1.32-1.11 (m, 4H), 1.08 (t, 3H).

Example 59: 3-((1-(3-Cyclobutyl-2,2-dimethylpropanoyl)-4-hydroxypiperidin-4-yl)methyl)-6-(2-fluorophenyl)pyrimidin-4(3H)-one

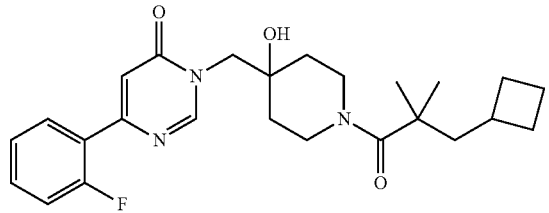 [SMILES: CC(C)(CC1CCC1)C(=O)N1CCC(O)(Cn2cnc(-c3ccccc3F)cc2=O)CC1]

Prepared according to General Procedure 5 using Amine 1 (0.080 g, 0.235 mmol), 3-cyclobutyl-2,2-dimethylpropanoic acid (0.074 g, 0.353 mmol), HBTU (0.134 g, 0.353 mmol) and DIPEA (0.16 mL, 0.94 mmol) in DCM (4.0 mL) to give the title compound (33 mg, 32%). LCMS (Method B): $R_T$=1.35 min, m/z=442 [M+H]$^+$. $^1$H NMR (400 MHz, CDCl$_3$): δ 8.11 (br s, 1H), 7.99 (td, 1H), 7.42-7.35 (m, 1H), 7.22 (br dd, 1H), 7.11 (br ddd, 1H), 7.05 (s, 1H), 4.14 (br d, 2H), 4.05 (q, 1H), 4.00 (s, 1H), 3.66 (s, 1H), 3.21 (brt, 2H), 3.28 (m, 1H), 1.98 (s, 1H), 1.97-1.90 (m, 2H), 1.80-1.71 (m, 1H), 1.64 (d, 3H), 1.21-1.16 (m, 4H), 1.15 (s, 6H).

Example 60: 6-(2-Fluorophenyl)-3-(((1R,5S)-8-hydroxy-3-((R)-3-phenylbutanoyl)-3-azabicyclo[3.2.1]octan-8-yl)methyl)pyrimidin-4(3H)-one

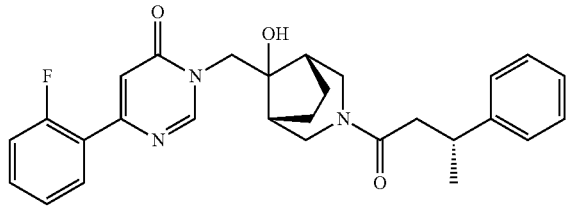 [SMILES: C[C@H](CC(=O)N1C[C@H]2CC[C@@H](C1)C2(O)Cn1cnc(-c2ccccc2F)cc1=O)c1ccccc1]

Prepared according to General Procedure 5 using 6-(2-fluorophenyl)-3-(((1R,5S)-8-hydroxy-3-azabicyclo[3.2.1]octan-8-yl)methyl)pyrimidin-4(31)-one hydrochloride (0.030 g, 0.082 mmol), (R)-3-phenylbutanoic acid (0.020 g, 0.12 mmol), HBTU (0.047 g, 0.12 mmol) and DIPEA (0.057 mL, 0.328 mmol) in DCM (0.8 mL) to give the title compound (22 mg, 56%). LCMS (Method B): $R_T$=1.37 min, m/z=476 [M+H]$^+$. $^1$H NMR (400 MHz, CDCl$_3$, this compound appears as two conformers in a 1:1 ratio): δ 8.10 (dd, 1H), 8.06 (m, 1H), 7.49-7.42 (m, 1H), 7.32-7.23 (m, 5H), 7.22-7.16 (m, 2H), 7.14 (s, 1H), 4.71 (s, 0.5H), 4.62 (s, 0.5H), 4.23-4.01 (m, 3H), 3.69 (d, 0.5H), 3.53 (d, 0.5H), 3.45-3.29 (m, 2H), 3.23 (dd, 1H), 2.69 (dd, 0.5H), 2.65-2.53 (m, 1H), 2.46 (dd, 0.5H), 1.91-1.46 (m, 5H), 1.34-1.10 (m, 4H).

Example 61: 3-(((R)-4-Hydroxy-2,2-dimethyl-1-((R)-3-phenylbutanoyl)piperidin-4-yl)methyl)-6-phenylpyrimidin-4(3H)-one and 3-(((S)-4-Hydroxy-2,2-dimethyl-1-((R)-3-phenylbutanoyl)piperidin-4-yl)methyl)-6-phenylpyrimidin-4(3H)-one

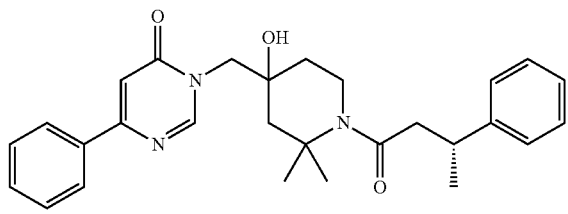 [SMILES: C[C@H](CC(=O)N1CCC(O)(Cn2cnc(-c3ccccc3)cc2=O)CC1(C)C)c1ccccc1]

Step 1: (R,S)-tert-Butyl 5,5-dimethyl-1-oxa-6-azaspiro[2.5]octane-6-carboxylate Prepared according to General Procedure 11 using tert-butyl 2,2-dimethyl-4-oxopiperidine-1-carboxylate (0.5 g, 2.20 mmol), trimethylsulfonium iodide (1.12 g, 5.50 mmol) and sodium hydride, 60% oil dispersion (0.220 g, 5.50 mmol) in DMSO (4.89 mL+2.44 mL). The crude product was purified by flash chromatography (GraceResolv 24 g, 0-40% EtOAc in cyclohexane) to give the title compound (390 mg, 74%). LCMS (Method B): $R_T$=1.39 min, m/z=142 [M+H-Boc]$^+$. $^1$H NMR (400 MHz, CDCl$_3$): δ 3.72-3.59 (m, 2H), 2.68 (q, 2H), 2.00-1.92 (m, 1H), 1.80-1.75 (m, 1H), 1.76 (d, 2H), 1.49 (s, 3H), 1.48 (s, 9H), 1.45 (s, 3H).

Step 2: (R,S)-tert-Butyl 4-hydroxy-2,2-dimethyl-4-((6-oxo-4-phenylpyrimidin-1(6H)-yl)methyl)piperidine-1-carboxylate Prepared according to General Procedure 1 using 6-phenylpyrimidin-4(3H)-one (0.162 g, 0.94 mmol), (R,S)-tert-butyl 5,5-dimethyl-1-oxa-6-azaspiro[2.5]octane-6-carboxylate (0.25 g, 1.04 mmol) and cesium carbonate (0.368 g, 1.13 mmol) in DMF (1.4 mL). The mixture was heated at 120° C. for 3 h to give the title compound (0.32 g, 81%) which was used without further purification. LCMS (Method B): $R_T$=1.35 min, m/z=314 [M+H-Boc]$^+$. $^1$H NMR (400 MHz, CDCl$_3$): δ 8.20 (s, 1H), 8.00-7.95 (m, 2H), 7.52-7.46 (m, 3H), 6.93 (s, 1H), 4.03 (q, 2H), 3.81-3.74 (m, 1H), 3.53 (s, 1H), 3.47-3.39 (m, 1H), 2.01 (s, 1H), 1.78-1.66 (m, 3H), 1.51 (s, 3H), 1.47 (s, 9H), 1.45 (s, 3H).

Step 3: (R,S)-3-((4-Hydroxy-2,2-dimethylpiperidin-4-yl)methyl)-6-phenylpyrimidin-4(3H)-one hydrochloride Prepared according to General Procedure 9 using (R,S)-tert-butyl 4-hydroxy-2,2-dimethyl-4-((6-oxo-4-phenylpyrimidin-1 (6H)-yl)methyl)piperidine-1-carboxylate (0.315 g, 0.762 mmol) and hydrogen chloride (4 M in 1,4-dioxane, 2.7 mL, 10.8 mmol) in DCM (3.7 mL) to give the title compound (0.285 g, quantitative) which was used without further purification. LCMS (Method B): $R_T$=0.63 min, m/z=314 [M+H]$^+$. $^1$H NMR (400 MHz, DMSO-d$_6$): δ 9.00 (br d, 1H), 8.60 (brs, 1H), 8.45 (s, 1H), 8.12-8.06 (m, 2H), 7.53-7.47 (m, 3H), 7.01 (s, 1H), 3.96 (d, 1H), 3.95 (d, 1H), 3.16-3.06 (m, 2H), 1.88-1.78 (m, 1H), 1.70-1.54 (m, 3H), 1.43 (s, 3H), 1.30 (s, 3H).

Step 4: 3-(((R)-4-Hydroxy-2,2-dimethyl-1-((R)-3-phenylbutanoyl)piperidin-4-yl)methyl)-6-phenylpyrimidin-4(3H)-one and 3-(((S)-4-Hydroxy-2,2-dimethyl-1-((R)-3-phenylbutanoyl)piperidin-4-yl)methyl)-6-phenylpyrimidin-4(3H)-one Prepared according to General Procedure 5 using 3-((4-hydroxy-2,2-dimethylpiperidin-4-yl)methyl)-6-phenylpyrimidin-4(3H)-one hydrochloride (0.050 g, 0.143 mmol), (R)-3-phenylbutanoic acid (0.035 g, 0.214 mmol), HBTU (0.081 g, 0.214 mmol) and DIPEA (0.103 mL, 0.572 mmol) in DCM (1.4 mL) to give the mixture of title compounds (22 mg, 33%). LCMS (Method B): $R_T$=1.32 min, m/z=460 [M+H]$^+$. $^1$H NMR (400 MHz, DMSO-d$_6$): δ 8.41 (s, 1H), 8.12-8.06 (m, 2H), 7.53-7.47 (m, 3H), 7.29-7.23 (m, 4H), 7.19-7.12 (m, 1H), 7.00 (s, 1H), 4.93 (d, 1H), 4.06 (dd, 1H), 3.82 (d, 1H), 3.48-3.39 (m, 1H), 3.18-3.10 (m, 1H), 2.65-2.55 (m, 1H), 2.49-2.42 (m, 1H), 1.75-1.63 (m, 2H), 1.51-1.41 (m, 2H), 1.40 (d, 3H), 1.35 (s, 3H), 1.22-1.17 (m, 3H), 0.90-0.85 (m, 1H).

Example 62: (R)-1-((4-Hydroxy-1-(3-phenylbutanoyl)piperidin-4-yl)methyl)-5-(4-hydroxypiperidine-1-carbonyl)-4-phenylpyridin-2(1H)-one

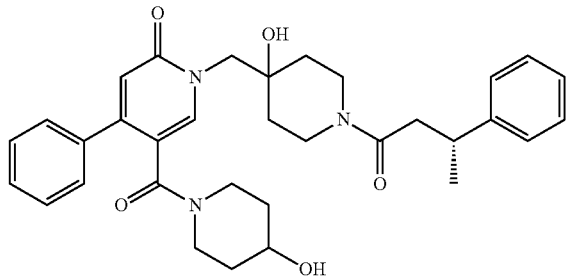 [SMILES: C[C@H](CC(=O)N1CCC(O)(Cn2cc(C(=O)N3CCC(O)CC3)c(-c3ccccc3)cc2=O)CC1)c1ccccc1]

Intermediate 1 (15 mg, 0.026 mmol) and 4-hydroxypiperidine (3.1 mg, 0.031 mmol) were shaken at RT in DMF (0.3 mL) using a BioShake IQ for 18 h. The mixture was concentrated and the residue was purified by preparative HPLC to give the title compound (10.1 mg, 70%). LCMS (Method B): $R_T$=1.02 min, m/z=558 [M+H]$^+$ Example 63: (R)-1-((4-Hydroxy-1-(3-phenylbutanoyl)piperidin-4-yl)methyl)-4-phenyl-5-(pyrrolidine-1-carbonyl)pyridin-2(1H)-one

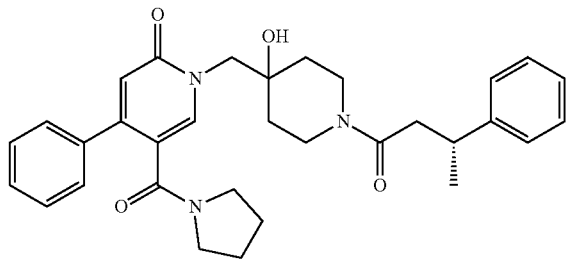 [SMILES: C[C@H](CC(=O)N1CCC(O)(Cn2cc(C(=O)N3CCCC3)c(-c3ccccc3)cc2=O)CC1)c1ccccc1]

Intermediate 1 (15 mg, 0.026 mmol) and pyrrolidine (2.2 mg, 0.031 mmol) were shaken at RT in DMF (0.3 mL) using a BioShake IQ for 18 h. The mixture was concentrated and the residue was purified by preparative HPLC to give the title compound (11.5 mg, 84%). LCMS (Method B): $R_T$=1.23 min, m/z=528 [M+H]$^+$.

Example 64: (R)-1-((4-Hydroxy-1-(3-phenylbutanoyl)piperidin-4-yl)methyl)-4-phenyl-5-(1,4-dioxa-8-azaspiro[4.5]decane-8-carbonyl)pyridin-2(1H)-one

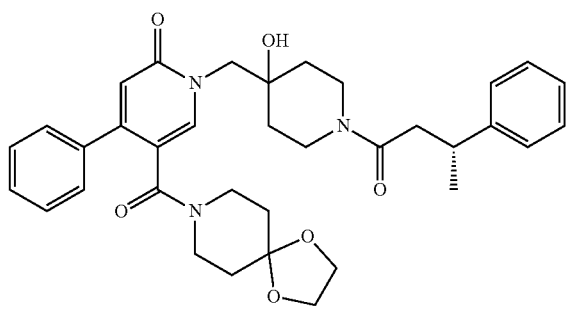 [SMILES: C[C@H](CC(=O)N1CCC(O)(Cn2cc(C(=O)N3CCC4(CC3)OCCO4)c(-c3ccccc3)cc2=O)CC1)c1ccccc1]

A solution of Intermediate 1 (15 mg, 0.026 mmol) and 1,4-dioxa-8-azaspiro[4.5]decane (4.4 mg, 0.031 mmol) in DMF (0.6 mL) was agitated using a BioShake IQ at RT for 2 h. The reaction mixture was concentrated. The residue was diluted with DCM (0.3 mL) and water (0.5 mL). The organic layer was dried (Biotage phase separator) and concentrated to give the title compound (13 mg, 83%). LCMS (Method B): $R_T$=1.23 min, m/z=600 [M+H]$^+$.

Example 65: (R)—N-Cyclohexyl-1-((4-hydroxy-1-(3-phenylbutanoyl)piperidin-4-yl)methyl)-6-oxo-4-phenyl-1,6-dihydropyridine-3-carboxamide

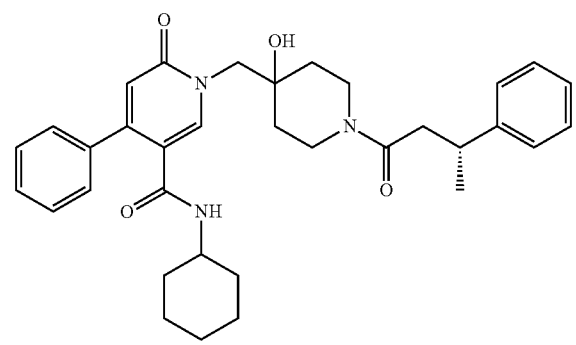 [SMILES: C[C@H](CC(=O)N1CCC(O)(Cn2cc(C(=O)NC3CCCCC3)c(-c3ccccc3)cc2=O)CC1)c1ccccc1]

A solution of Intermediate 1 (15 mg, 0.026 mmol) and cyclohexylamine (3.1 mg, 0.031 mmol) in DMF (0.6 mL) was agitated using a BioShake IQ at RT for 2 h. The mixture was concentrated and the residue was diluted with DCM (0.3 mL) and water (0.5 mL). The organic layer was dried (Biotage phase separator) and concentrated to give the title compound (12 mg, 83%). LCMS (Method B): $R_T$=1.46 min, m/z=556 [M+H]$^+$.

Example 66: 6-(2-Fluorophenyl)-3-((4-hydroxy-3,3-dimethyl-1-(cis-2-phenylcyclopropane-1-carbonyl)piperidin-4-yl)methyl)pyrimidin-4(3H)-one

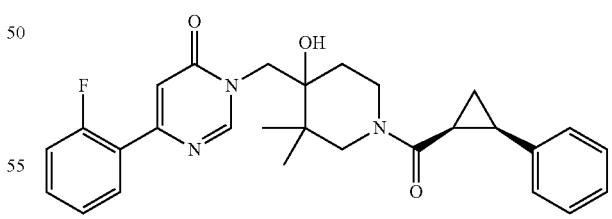

Prepared according to General Procedure 12 using rac-cis-2-phenylcyclopropane-1-carboxylic acid (7.0 mg, 0.043 mmol), HATU (20.6 mg, 0.054 mmol), DIPEA (15.2 µL, 0.087 mmol) and (R,S)-6-(2-fluorophenyl)-3-((4-hydroxy-3,3-dimethylpiperidin-4-yl)methyl)pyrimidin-4(3H)-one (12 mg, 0.036 mmol) to give the title compound (10 mg, 59%). LCMS (Method B): $R_T$=1.37, 1.46 min, m/z=476 [M+H]$^+$.

Example 67: (R,S)-3-((1-(3-Cyclohexyl-1H-pyrazole-4-carbonyl)-4-hydroxy-3,3-dimethylpiperidin-4-yl)methyl)-6-(2-fluorophenyl)pyrimidin-4(3H)-one

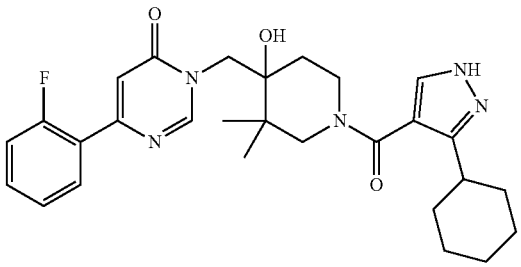 [SMILES: CC1(C)CN(C(=O)c2c[nH]nc2C2CCCCC2)CCC1(O)Cn1cnc(-c2ccccc2F)cc1=O]

Prepared according to General Procedure 12 using 3-cyclohexyl-1H-pyrazole-4-carboxylic acid (8.3 mg, 0.043 mmol), HATU (20.6 mg, 0.054 mmol), DIPEA (15 µL, 0.087 mmol) and (R,S)-6-(2-fluorophenyl)-3-((4-hydroxy-3,3-dimethylpiperidin-4-yl)methyl)pyrimidin-4(3H)-one (12 mg, 0.036 mmol) in DMF (0.6 mL) to give the title compound (4.4 mg, 24%). LCMS (Method B): $R_T$=1.28 min, m/z=508 [M+H]$^+$

Example 68: (R,S)-6-(2-Fluorophenyl)-3-((4-hydroxy-3,3-dimethyl-1-(3-phenylpropanoyl)piperidin-4-yl)methyl)pyrimidin-4(3H)-one

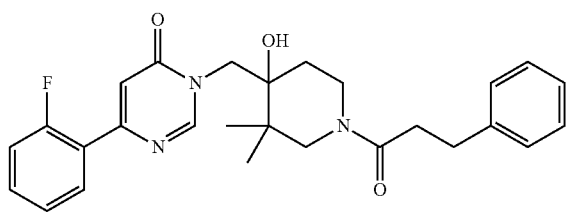 [SMILES: CC1(C)CN(C(=O)CCc2ccccc2)CCC1(O)Cn1cnc(-c2ccccc2F)cc1=O]

Prepared according to General Procedure 12 using 3-phenylpropanoic acid (8.1 mg, 0.054 mmol), HATU (20.6 mg, 0.054 mmol), DIPEA (15.8 µL, 0.091 mmol) and (R,S)-6-(2-fluorophenyl)-3-((4-hydroxy-3,3-dimethylpiperidin-4-yl)methyl)pyrimidin-4(3H)-one (15 mg, 0.045 mmol) in DMF (0.6 mL) to give the title compound (4.4 mg, 21%). LCMS (Method B): $R_T$=1.57 min, m/z=464 [M+H]$^+$.

Example 69: (R,S)-6-(2-Fluorophenyl)-3-((4-hydroxy-1-(1-isobutylcyclopropane-1-carbonyl)-3,3-dimethylpiperidin-4-yl)methyl)pyrimidin-4(3H)-one

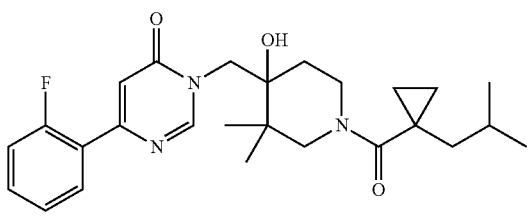 [SMILES: CC(C)CC1(C(=O)N2CCC(O)(Cn3cnc(-c4ccccc4F)cc3=O)C(C)(C)C2)CC1]

Prepared according to General Procedure 12 using 1-isobutylcyclopropane-1-carboxylic acid (7.6 mg, 0.054 mmol), HATU (20.6 mg, 0.054 mmol), DIPEA (15.8 µL, 0.091 mmol) and (R,S)-6-(2-fluorophenyl)-3-((4-hydroxy-3,3-dimethylpiperidin-4-yl)methyl)pyrimidin-4(3H)-one (15 mg, 0.045 mmol) in DMF (0.6 mL) to give the title compound (6.2 mg, 30%). LCMS (Method B): $R_T$=1.57 min, m/z=456 [M+H]$^+$.

Example 70: (R,S)-6-(2-Fluorophenyl)-3-((4-hydroxy-3,3-dimethyl-1-(3-methyl-3-phenylbutanoyl)piperidin-4-yl)methyl)pyrimidin-4(3H)-one

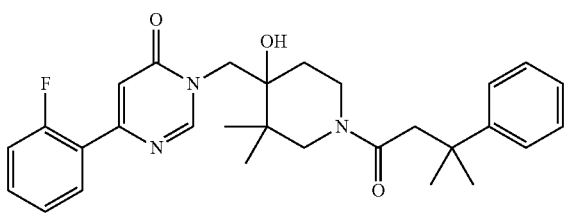 [SMILES: CC(C)(CC(=O)N1CCC(O)(Cn2cnc(-c3ccccc3F)cc2=O)C(C)(C)C1)c1ccccc1]

Prepared according to General Procedure 12 using 3-methyl-3-phenylbutanoic acid (9.6 mg, 0.054 mmol), HATU (20.6 mg, 0.054 mmol), DIPEA (15.8 µL, 0.091 mmol) and (R,S)-6-(2-fluorophenyl)-3-((4-hydroxy-3,3-dimethylpiperidin-4-yl)methyl)pyrimidin-4(3H)-one (15 mg, 0.045 mmol) to give the title compound (7.2 mg, 33%). LCMS (Method B): $R_T$=1.71 min, m/z=492 [M+H]$^+$.

Example 71: (S)-1-((1-(4,4-Difluoro-3-phenylbutanoyl)-4-hydroxypiperidin-4-yl)methyl)-N-isopropyl-N-methyl-6-oxo-4-phenyl-1,6-dihydropyridine-3-carboxamide

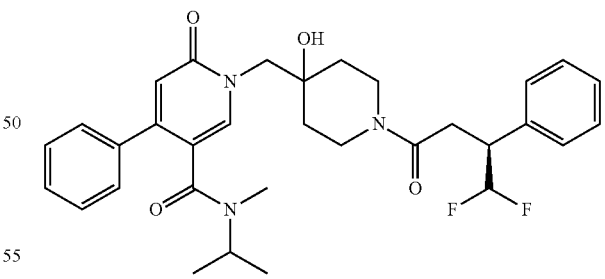

Prepared according to General Procedure 12 using (S)-4,4-difluoro-3-phenylbutanoic acid (*Angew. Chem. Int. Ed.*, 2013, 52, p 14191-14195) (6.2 mg, 0.031 mmol), HATU (12.9 mg, 0.034 mmol), DIPEA (9.1 µL, 0.052 mmol) and 1-((4-hydroxypiperidin-4-yl)methyl)-N-isopropyl-N-methyl-6-oxo-4-phenyl-1,6-dihydropyridine-3-carboxamide (10 mg, 0.026 mmol) to give the title compound (6.0 mg, 41%). LCMS (Method B): $R_T$=1.80 min, m/z=566 [M+H]$^+$

Example 72: 1-((4-Hydroxy-1-(1-(thiophen-2-yl)cyclopropane-1-carbonyl)piperidin-4-yl)methyl)-N-isopropyl-N-methyl-6-oxo-4-phenyl-1,6-dihydropyridine-3-carboxamide

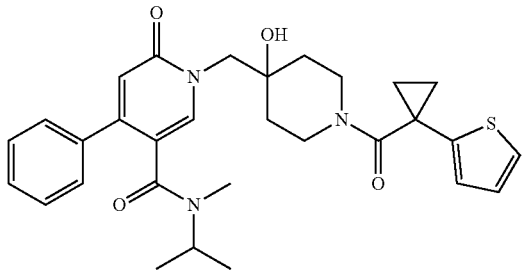 [SMILES: CC(C)N(C)C(=O)c1cn(CC2(O)CCN(C(=O)C3(c4cccs4)CC3)CC2)c(=O)cc1-c1ccccc1]

Prepared according to General Procedure 12 using 1-(thiophen-2-yl)cyclopropane-1-carboxylic acid (5.2 mg, 0.031 mmol), HATU (12.9 mg, 0.034 mmol), DIPEA (9.11 μL, 0.052 mmol) and 1-((4-hydroxypiperidin-4-yl)methyl)-N-isopropyl-N-methyl-6-oxo-4-phenyl-1,6-dihydropyridine-3-carboxamide (10 mg, 0.026 mmol) to give the title compound (7.0 mg, 51%). LCMS (Method B): $R_T$=1.17 min, m/z=534 [M+H]$^+$.

Example 73: 1-(((R)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide and 1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide

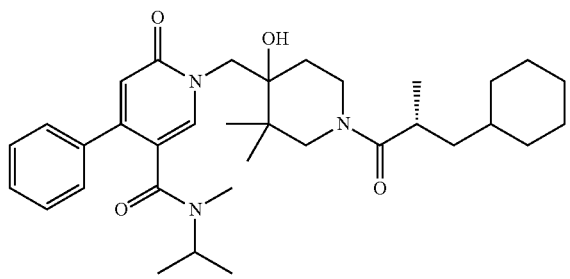 [SMILES: CC(C)N(C)C(=O)c1cn(CC2(O)CCN(C(=O)[C@H](C)CC3CCCCC3)CC2(C)C)c(=O)cc1-c1ccccc1]

Prepared according to General Procedure 5 using Amine 3 (30 mg, 0.073 mmol), Acid 1 (18.6 mg, 0.11 mmol), DIPEA (0.051 mL, 0.29 mmol), HBTU (41.5 mg, 0.109 mmol) and DCM (1 mL) at RT for 48 h to give the mixture of title compounds (26.2 mg, 64%). LCMS (Method B): $R_T$=1.53 min, m/z 564 [M+H]$^+$. $^1$H NMR (400 MHz, CDCl$_3$, mixture of diastereomers and conformers): δ 7.50-7.33 (m, 6H), 6.68 (d, 1H), 5.17-4.45 (m, 3H), 4.09-3.18 (m, 4H), 3.03-2.78 (m, 2H), 2.69 (d, 1.5H), 2.27 (d, 1.5H), 1.84-1.58 (br m, 8H), 1.58-0.60 (br m, 20H), 0.30-0.19 (m, 2H).

Example 74: (R)-3-((4-Hydroxy-1-(3-phenylbutanoyl)piperidin-4-yl)methyl)-6-(2-(hydroxymethyl)phenyl)pyrimidin-4(3H)-one

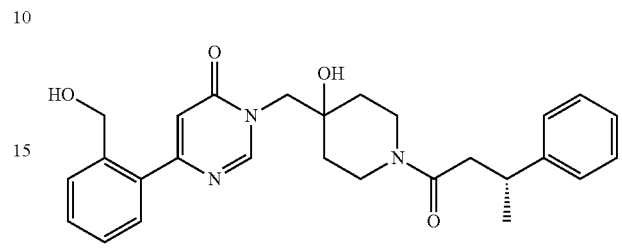

Sodium carbonate (27.2 mg, 0.26 mmol) and (R)-6-chloro-3-((4-hydroxy-1-(3-phenylbutanoyl)piperidin-4-yl)methyl)pyrimidin-4(3H)-one (50 mg, 0.13 mmol) were suspended in a mixture of 1,4-dioxane (1.5 mL) and water (0.5 mL). (2-(Hydroxymethyl)phenyl)boronic acid (29.2 mg, 0.19 mmol) was added and the mixture was purged with N$_2$. Pd(PPh$_3$)$_4$(7.4 mg, 6.41 μmol) was added and the mixture was heated in a microwave at 140° C. for 15 min. The mixture was cooled and diluted with water then extracted with DCM. The organic layer was dried (Biotage phase separator) and concentrated and the residue was purified by flash chromatography (Biotage 11 g KP-NH, 0-100% EtOAc in cyclohexane; then 0-15% MeOH in EtOAc) to give the title compound (10 mg, 17%). LCMS (Method B): $R_T$=1.00 min, m/z=462 [M+H]$^+$. $^1$H NMR (300 MHz, DMSO-d$_6$): δ 8.36 (d, 1H), 7.58 (d, 1H), 7.48 (m, 2H), 7.38 (d, 1H), 7.27 (m, 4H), 7.17 (m, 1H), 6.61 (m, 1H), 5.25 (t, 1H), 5.00 (d, 1H), 4.59 (d, 2H), 4.00 (m, 3H), 3.70 (m, 1H), 3.20 (m, 2H), 2.90 (m, 1H), 2.60 (m, 2H), 1.25-1.60 (m, 4H), 1.21 (m, 3H).

Example 75: (R)—N,N-Diethyl-1-((4-hydroxy-1-(3-phenylbutanoyl)piperidin-4-yl)methyl)-6-oxo-4-phenyl-1,6-dihydropyridine-3-carboxamide

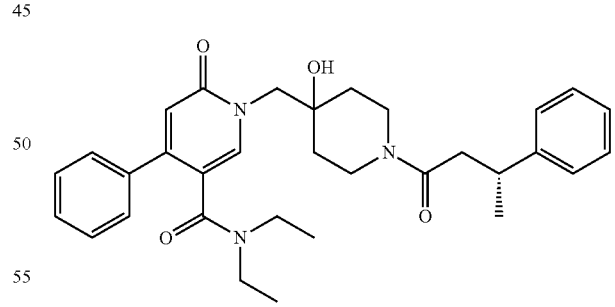

Step 1: (R)-Ethyl 1-((4-hydroxy-1-(3-phenylbutanoyl)piperidin-4-yl)methyl)-6-oxo-4-phenyl-1,6-dihydropyridine-3-carboxylate Ethyl 6-oxo-4-phenyl-1,6-dihydropyridine-3-carboxylate (1.45 g, 5.96 mmol) and Epoxide 2 (1.55 g, 5.96 mmol) were dissolved in DMF (30 mL) and pyridine (0.723 mL, 8.94 mmol) was added. The reaction was stirred at 80° C. for 21 h. The mixture was allowed to cool to room temperature, diluted with water and extracted with EtOAc (×2). The combined organic extracts were washed with water (×3) and brine (×1), dried over anhydrous sodium sulfate and concentrated. The residue was purified by flash chromatography (GraceResolv, 0-100% EtOAc in cyclohexane) to give the title compound (883 mg, 29%). LCMS (Method B): $R_T$=1.29 min, m/z=503 [M+H]$^+$.

Step 2: (R)-1-((4-Hydroxy-1-(3-phenylbutanoyl)piperidin-4-yl)methyl)-6-oxo-4-phenyl-1,6-dihydropyridine-3-carboxylic acid (R)-Ethyl 1-((4-hydroxy-1-(3-phenylbutanoyl)piperidin-4-yl)methyl)-6-oxo-4-phenyl-1,6-dihydropyridine-3-carboxylate (884 mg, 1.76 mmol) was dissolved in THF (2 mL) and sodium hydroxide (2 M in water, 4.40 mL, 8.80 mmol) was added. The mixture was stirred at room temperature for 21 h then an additional portion of 2 M sodium hydroxide (2 mL) was added and the mixture was stirred a further 48 h. The solution was concentrated and the residue was diluted with water. The resulting solution was extracted with Et$_2$O (×3) and the organic extracts were discarded. The aqueous layer was acidified to ~pH 4 with 2 M HCl (aq) and extracted with EtOAc (×3). The combined organic extracts were dried (MgSO$_4$) and concentrated to give the title compound (738 mg, 88%). LCMS (Method B): $R_T$=1.11 min, m/z=475 [M+H]$^+$.

Step 3: (R)—N,N-Diethyl-1-((4-hydroxy-1-(3-phenylbutanoyl)piperidin-4-yl)methyl)-6-oxo-4-phenyl-1,6-dihydropyridine-3-carboxamide (R)-1-((4-Hydroxy-1-(3-phenylbutanoyl)piperidin-4-yl)methyl)-6-oxo-4-phenyl-1,6-dihydropyridine-3-carboxylic acid (40 mg, 0.084 mmol) and DIPEA (0.044 mL, 0.253 mmol) were dissolved in DMF (1 mL) and HATU (35.3 mg, 0.093 mmol) was added. The mixture was stirred at RT for 10 min, then diethylamine (9.59 μL, 0.093 mmol) was added and the reaction was stirred at RT for 18 h. The mixture was concentrated and the residue was partitioned between DCM and H$_2$O. The organic layer was separated using a Biotage phase separator and concentrated, and the residue was purified by flash chromatography (Biotage KP-NH, 0-100% EtOAc in cyclohexane) to give the title compound (17.8 mg, 40%). LCMS (Method B): $R_T$=1.17 min, m/z=530 [M+H]$^+$. $^1$H NMR (400 MHz, DMSO-d$_6$): δ 7.70 (d, 1H), 7.47-7.38 (m, 5H), 7.32-7.24 (m, 4H), 7.21-7.13 (m, 1H), 6.44 (d, 1H), 4.93 (d, 1H), 4.08-3.87 (br m, 3H), 3.72-3.60 (br m, 1H), 3.31-3.13 (m, 3H), 3.08-2.91 (m, 3H), 2.65-2.54 (m, 2H), 1.57-1.19 (br m, 8H), 0.89-0.80 (m, 6H).

Example 76: 3-((1-(3-Cyclohexylbutanoyl)-4-hydroxy-3,3-dimethylpiperidin-4-yl)methyl)-6-(2-fluorophenyl)pyrimidin-4(3H)-one

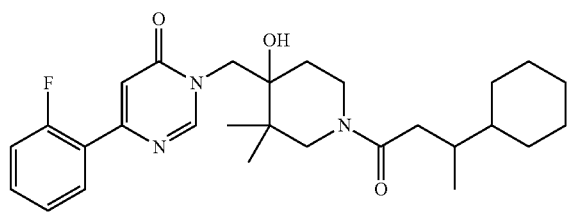 [SMILES: CC(CC(=O)N1CCC(O)(Cn2cnc(-c3ccccc3F)cc2=O)C(C)(C)C1)C1CCCCC1]

Prepared according to General Procedure 12 using (R,S)-3-cyclohexylbutanoic acid (7.7 mg, 0.045 mmol), HATU (19 mg, 0.050 mmol), DIPEA (16 μL, 0.091 mmol), Amine 5 (15 mg, 0.045 mmol) and DMF (0.6 mL) to give the title compound (4.6 mg, 21%) as a mixture of diastereomers. LCMS (Method B): $R_T$=1.96 min, m/z=484 [M+H]$^+$.

Example 77: (R)-1-((4-Hydroxy-1-(3-phenylbutanoyl)piperidin-4-yl)methyl)-5-(morpholine-4-carbonyl)-4-phenylpyridin-2(1H)-one

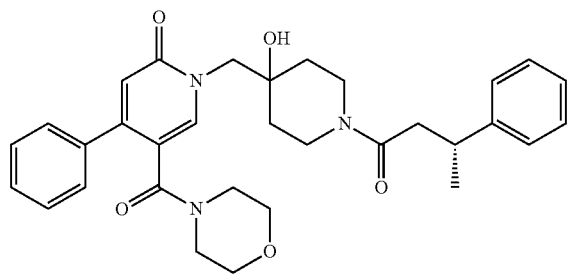 [SMILES: C[C@H](CC(=O)N1CCC(O)(Cn2cc(C(=O)N3CCOCC3)c(-c3ccccc3)cc2=O)CC1)c1ccccc1]

(R)-1-((4-Hydroxy-1-(3-phenylbutanoyl)piperidin-4-yl)methyl)-6-oxo-4-phenyl-1,6-dihydropyridine-3-carboxylic acid (15 mg, 0.026 mmol) was dissolved in DMF (0.3 mL) and morpholine (2.7 mg, 0.031 mmol) was added as a solution in DMF (0.3 mL), followed by HATU (1.1 equiv.). The reaction mixture was agitated using a BioShake IQ for 18 h at RT. The crude product was purified by preparative HPLC to give the title compound (7.1 mg, 48%). LCMS (Method B): $R_T$=1.16 min, m/z=544 [M+H]$^+$.

Example 78: (R,S)-3-((1-(3-Cyclohexylpropanoyl)-4-hydroxy-3,3-dimethylpiperidin-4-yl)methyl)-6-(2-fluorophenyl)pyrimidin-4(3H)-one

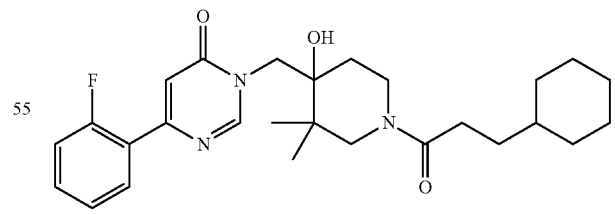

Prepared according to General Procedure 12 using 3-cyclohexylpropanoic acid (7.0 mg, 0.045 mmol), HATU (19 mg, 0.050 mmol), DIPEA (16 μL, 0.091 mmol) and Amine 5 (15 mg, 0.045 mmol) in DMF (0.6 mL) to give the title compound (5.7 mg, 27%). LCMS (Method B): $R_T$=1.87 min, m/z=470 [M+H]$^+$.

Example 79: (R,S)-1-((1-(3-Cyclobutylpropanoyl)-4-hydroxy-3,3-dimethylpiperidin-4-yl)methyl)-N-isopropyl-N-methyl-6-oxo-4-phenyl-1,6-dihydropyridine-3-carboxamide

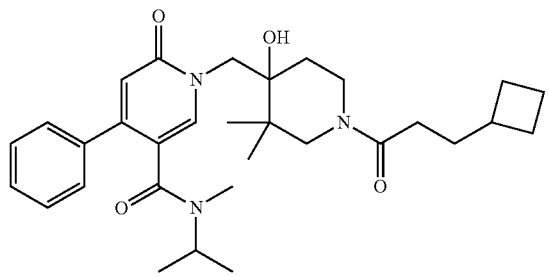 [SMILES: CC(C)N(C)C(=O)c1cn(CC2(O)CCN(C(=O)CCC3CCC3)CC2(C)C)c(=O)cc1-c1ccccc1]

Prepared according to General Procedure 5 using Amine 3 (30 mg, 0.073 mmol), 3-cyclobutylpropanoic acid (14.0 mg, 0.109 mmol), DIPEA (0.051 mL, 0.292 mmol), HBTU (41.5 mg, 0.109 mmol) and DCM (1 mL) to give the title compound (34.7 mg, 91%). LCMS (Method B): $R_T$=1.32 min, m/z=522 [M+H]$^+$. $^1$H NMR (400 MHz, methanol-d$_4$, this compound appears as a mixture of conformers in a 1:1 ratio): δ 7.73-7.66 (br m, 1H), 7.40-7.32 (m, 5H), 6.52 (s, 0.5H), 6.49 (s, 0.5H), 4.58-4.07 (br m, 2H), 3.98-3.77 (br m, 1H), 3.77-3.50 (br m, 2H), 3.38-3.22 (m, 1H), 3.18-2.93 (br m, 1H), 2.61 (s, 1.5H), 2.37 (s, 1.5H), 2.31-2.10 (m, 3H), 2.04-1.91 (m, 2H), 1.88-1.67 (m, 3H), 1.64-1.47 (m, 4H), 1.31-1.11 (br m, 2H) 1.06-0.68 (br m, 11H), 0.32 (dd, 1H).

Example 80: (R,S)-1-((1-(2-Ethylhexanoyl)-4-hydroxypiperidin-4-yl)methyl)-N-isopropyl-N-methyl-6-oxo-4-phenyl-1,6-dihydropyridine-3-carboxamide

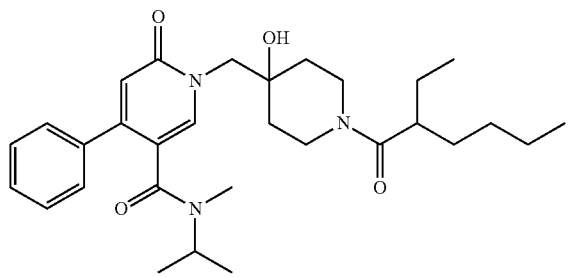 [SMILES: CCCCC(CC)C(=O)N1CCC(O)(Cn2cc(C(=O)N(C)C(C)C)c(-c3ccccc3)cc2=O)CC1]

Prepared according to General Procedure 12 using (R,S)-2-ethylhexanoic acid (4.3 mg, 0.026 mmol), HATU (13 mg, 0.034 mmol), DIPEA (10 µL, 0.052 mmol) and 1-((4-hydroxypiperidin-4-yl)methyl)-N-isopropyl-N-methyl-6-oxo-4-phenyl-1,6-dihydropyridine-3-carboxamide (10 mg, 0.026 mmol) in DMF (0.6 mL) to give the title compound (7.3 mg, 55%). LCMS (Method B): $R_T$=1.30 min, m/z=510 [M+H]$^+$.

Example 81: (R,S)-6-(2-Fluorophenyl)-3-((4-hydroxy-3,3-dimethyl-1-(1-methylcyclohexane-1-carbonyl)piperidin-4-yl)methyl)pyrimidin-4(3H)-one

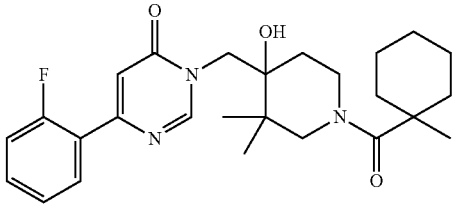 [SMILES: CC1(C(=O)N2CCC(O)(Cn3cnc(-c4ccccc4F)cc3=O)C(C)(C)C2)CCCCC1]

Prepared according to General Procedure 12 using 1-methylcyclohexane-1-carboxylic acid (7.7 mg, 0.045 mmol), HATU (22.5 mg, 0.059 mmol), DIPEA (17 µL, 0.099 mmol) and Amine 5 (15 mg, 0.049 mmol) in DMF (0.6 mL) to give the title compound (2.0 mg, 24%). LCMS (Method B): $R_T$=1.79 min, m/z=456 [M+H]$^+$.

Example 82: 6-(2-Fluorophenyl)-3-((1-(3-(4-fluorophenyl)propanoyl)-4-hydroxypiperidin-4-yl)methyl)pyrimidin-4(3H)-one

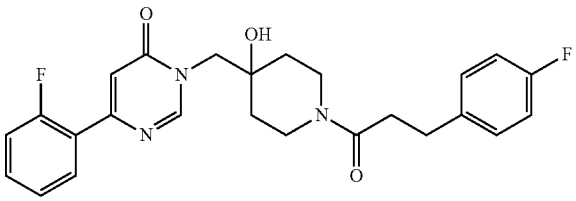 [SMILES: O=C(CCc1ccc(F)cc1)N1CCC(O)(Cn2cnc(-c3ccccc3F)cc2=O)CC1]

Prepared according to General Procedure 12 using 3-(4-fluorophenyl)propanoic acid (8.2 mg, 0.049 mmol), HATU (22.5 mg, 0.059 mmol), DIPEA (17 µL, 0.099 mmol) and Amine 1 (15 mg, 0.049 mmol) in DMF (0.6 mL) to give the title compound (9.2 mg, 42%). LCMS (Method B): $R_T$=1.39 min, m/z=454 [M+H]$^+$.

Example 83: (R,S)-3-((1-(3-Cyclopropylpropanoyl)-4-hydroxy-3,3-dimethylpiperidin-4-yl)methyl)-6-(2-fluorophenyl)pyrimidin-4(3H)-one

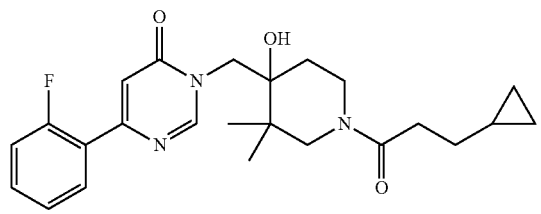 [SMILES: CC1(C)CN(C(=O)CCC2CC2)CCC1(O)Cn1cnc(-c2ccccc2F)cc1=O]

Prepared according to General Procedure 12 using 3-cyclopropylpropanoic acid (5.1 mg, 0.045 mmol), HATU (19 mg, 0.050 mmol), DIPEA (16 µL, 0.091 mmol) and Amine 5 (15 mg, 0.045 mmol) in DMF (0.6 mL) to give the title compound (5.0 mg, 26%). LCMS (Method B): $R_T$=1.51 min, m/z=428 [M+H]$^+$.

Example 84: 1-((1-(2,2-Dimethylbutanoyl)-4-hydroxypiperidin-4-yl)methyl)-N-isopropyl-N-methyl-6-oxo-4-phenyl-1,6-dihydropyridine-3-carboxamide

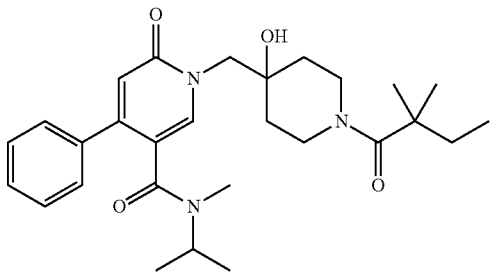 [SMILES: CCC(C)(C)C(=O)N1CCC(O)(Cn2cc(C(=O)N(C)C(C)C)c(-c3ccccc3)cc2=O)CC1]

Prepared according to General Procedure 12 using 2,2-dimethylbutanoic acid (3.5 mg, 0.026 mmol), HATU (13 mg, 0.034 mmol), DIPEA (10 µL, 0.052 mmol) and 1-((4-hydroxypiperidin-4-yl)methyl)-N-isopropyl-N-methyl-6-oxo-4-phenyl-1,6-dihydropyridine-3-carboxamide (10 mg, 0.026 mmol) in DMF (0.6 mL) to give the title compound (8.4 mg, 67%). LCMS (Method B): $R_T$=1.15 min, m/z=482 [M+H]$^+$.

Example 85: (R)—N-(2-(1-((4-Hydroxy-1-(3-phenylbutanoyl)piperidin-4-yl)methyl)-6-oxo-1,6-dihydropyrimidin-4-yl)phenyl)acetamide

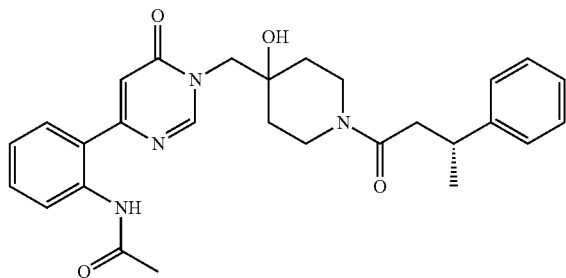 [SMILES: CC(=O)Nc1ccccc1-c1cc(=O)n(CC2(O)CCN(C(=O)C[C@@H](C)c3ccccc3)CC2)cn1]

Step 1: (R)-6-(2-Aminophenyl)-3-((4-hydroxy-1-(3-phenylbutanoyl)piperidin-4-yl)methy)pyrimidin-4(3H)-one Prepared according to General Procedure 4 using (R)-6-chloro-3-((4-hydroxy-1-(3-phenylbutanoyl)piperidin-4-yl)methyl)pyrimidin-4(3H)-one (30 mg, 0.077 mmol), (2-aminophenyl)boronic acid hydrochloride (20.01 mg, 0.115 mmol), sodium carbonate (20.4 mg, 0.192 mmol), Pd(dppf)Cl$_2$.CH$_2$Cl$_2$ (6.6 mg, 7.69 µmol), 1,4-dioxane (0.75 mL) and water (0.25 mL) heated in a microwave at 150° C. for 15 min to give the title compound (30 mg, 87%). LCMS (Method B): $R_T$=1.17 min, m/z=447 [M+H]$^+$.

Step 2: (R)—N-(2-(1-((4-Hydroxy-1-(3-phenylbutanoyl)piperidin-4-yl)methyl)-6-oxo-1,6-dihydropyrimidin-4-yl)phenyl)acetamide Prepared according to General Procedure 5 using (R)-6-(2-aminophenyl)-3-((4-hydroxy-1-(3-phenylbutanoyl)piperidin-4-yl)methyl)pyrimidin-4(3H)-one (30 mg, 0.067 mmol), acetic acid (4.62 µL, 0.081 mmol), DIPEA (0.023 mL, 0.134 mmol), HBTU (38.2 mg, 0.101 mmol) and DCM (1 mL) to give the title compound (12.6 mg, 38%). LCMS (Method B): $R_T$=1.17 min, m/z=489 [M+H]$^+$. $^1$H NMR (400 MHz, DMSO-d$_6$): δ 10.68 (s, 1H), 8.52 (d, 1H), 8.07 (brd, 1H), 7.73 (dd, 1H), 7.50 (td, 1H), 7.38-7.19 (m, 6H), 6.77 (d, 1H), 5.05 (d, 1H), 4.14-3.94 (br m, 3H), 3.79-3.68 (br m, 1H), 3.37-3.18 (br m, 2H), 3.03-2.92 (br td, 1H), 2.71-2.59 (m, 2H), 2.10 (s, 3H), 1.65-1.23 (br m, 7H).

Example 86: (R)-5-(4-(Aminomethyl)phenyl)-1-((4-hydroxy-1-(3-phenylbutanoyl)piperidin-4-yl)methyl)-4-phenylpyridin-2(1H)-one

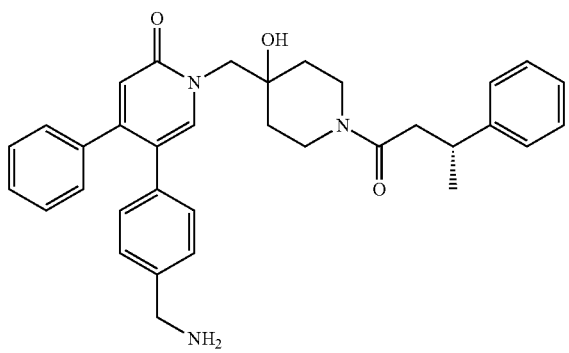 [SMILES: C[C@H](CC(=O)N1CCC(O)(Cn2cc(-c3ccc(CN)cc3)c(-c3ccccc3)cc2=O)CC1)c1ccccc1]

Step 1: (R)-tert-Butyl 4-(1-((4-hydroxy-1-(3-phenylbutanoyl)piperidin-4-yl)methyl)-6-oxo-4-phenyl-1,6-dihydropyridin-3-yl)benzylcarbamate Prepared according to General Procedure 4 using (R)-5-bromo-1-((4-hydroxy-1-(3-phenylbutanoyl)piperidin-4-yl)methyl)-4-phenylpyridin-2(1H)-one (30 mg, 0.059 mmol), 4-(N-Boc-aminomethyl)phenylboronic acid (22.2 mg, 0.088 mmol), sodium carbonate (8.3 mg, 0.079 mmol), 1,4-dioxane (0.5 mL), water (0.2 mL) and Pd(Ph$_3$P)$_4$ (3.4 mg, 2.9 µmol). The mixture was heated in a microwave at 150° C. for 20 min. The crude product was purified by flash chromatography (Biotage KP-Sil, 20-100% EtOAc in cyclohexane; then 5% MeOH in EtOAc) to give the title compound (11 mg, 29%). LCMS (Method B): $R_T$=1.42 min, m/z=636 [M+H]$^+$.

Step 2: (R)-5-(4-(Aminomethyl)phenyl)-1-((4-hydroxy-1-(3-phenylbutanoyl)piperidin-4-yl)methy)-4-phenylpyridin-2(1H)-one Prepared according to General Procedure 7 using (R)-tert-butyl 4-(1-((4-hydroxy-1-(3-phenylbutanoyl)piperidin-4-yl)methyl)-6-oxo-4-phenyl-1,6-dihydropyridin-3-yl)benzylcarbamate (11 mg, 0.017 mmol) in DCM (2 mL) and TFA (1 mL) to give the title compound (6 mg, 65%). LCMS (Method B): $R_T$=0.93 min, m/z=536 [M+H]$^+$. $^1$H NMR (400 MHz, methanol-d$_4$, this compound appears as two conformers A:B in a 2:3 ratio): δ 7.59 (s, 0.4H, conformer A), 7.52 (s, 0.6H, conformer B), 7.25-6.90 (m, 14H), 6.48 (s, 1H), 4.20-3.78 (m, 3H), 3.80 (s, 2H), 3.66-3.54 (m, 1H), 3.18-3.05 (m, 2H), 2.99-2.80 (m, 1H), 2.76-2.60 (m, 1H), 2.55-2.35 (m, 1H), 1.62-1.10 (m, 6H), 0.90-0.75 (m, 1H).

Example 87: (R)-1-((1-(3-Cyclohexyl-2-methylpropanoyl)-4-hydroxypiperidin-4-yl)methyl)-N-isopropyl-N-methyl-6-oxo-4-phenyl-1,6-dihydropyridine-3-carboxamide

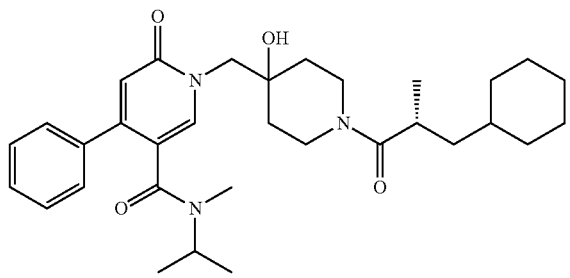 [SMILES: CC(C)N(C)C(=O)c1cn(CC2(O)CCN(C(=O)[C@H](C)CC3CCCCC3)CC2)c(=O)cc1-c1ccccc1]

Step 1: tert-Butyl 4-hydroxy-4-((5-(isopropyl(methyl)carbamoyl)-2-oxo-4-phenylpyridin-1(2H)-yl)methyl)piperidine-1-carboxylate Prepared according to General Procedure 4 using tert-butyl 4-((4-chloro-5-(isopropyl(methyl)carbamoyl)-2-oxopyridin-1(2H)-yl)methyl)-4-hydroxypiperidine-1-carboxylate (820 mg, 1.86 mmol), 1,4-dioxane (12 mL), phenylboronic acid (339 mg, 2.78 mmol), sodium carbonate (2 M in water, 1.86 mL, 3.71 mmol), water (2.4 mL) and Pd(dppf)Cl$_2$.CH$_2$Cl$_2$ (76 mg, 0.093 mmol). The reaction was heated in a microwave at 120° C. for 45 min to give the title compound (730 mg, 81%). LCMS (Method B): R$_T$=1.18 min, m/z=428 [M+H-$^t$Bu]$^+$.

Step 2: 1-((4-Hydroxypiperidin-4-yl)methyl)-N-isopropyl-N-methyl-6-oxo-4-phenyl-1,6-dihydropyridine-3-carboxamide Prepared according to General Procedure 7 using tert-butyl 4-hydroxy-4-((5-(isopropyl(methyl)carbamoyl)-2-oxo-4-phenylpyridin-1 (2H)-yl)methyl)piperidine-1-carboxylate (730 mg, 1.51 mmol), DCM (6 mL) and TFA (2 mL, 26.0 mmol) to give the title compound (448 mg, 77%). LCMS (Method B): R$_T$=0.67 min, m/z=384 [M+H]$^+$

Step 3: (R)-1-((1-(3-Cyclohexyl-2-methylpropanoyl)-4-hydroxypiperidin-4-yl)methyl)-N-isopropyl-N-methyl-6-oxo-4-phenyl-1,6-dihydropyridine-3-carboxamide Prepared according to General Procedure 5 using (R)-3-cyclohexyl-2-methylpropanoic acid (Acid 1) (26.6 mg, 0.156 mmol), 1-((4-hydroxypiperidin-4-yl)methyl)-N-isopropyl-N-methyl-6-oxo-4-phenyl-1,6-dihydropyridine-3-carboxamide (40 mg, 0.104 mmol), HBTU (59.3 mg, 0.156 mmol) and DIPEA (0.055 mL, 0.313 mmol) in DCM (2 mL). The residue was purified by preparative HPLC to give the title compound (38 mg, 68%). LCMS (Method B): R$_T$=1.38 min, m/z=536 [M+H]$^+$. $^1$H NMR (400 MHz, methanol-d$_4$, this compound appears as two conformers in a 1:1 ratio): δ 7.80 (d, 1H), 7.48 (m, 5H), 6.61 (d, 1H), 4.65 (m, 0.5H), 4.33-4.05 (m, 3H), 3.92 (m, 1H), 3.71 (m, 0.5H), 3.51 (m, 1H), 3.19 (m, 1H), 3.01 (m, 1H), 2.73 (s, 1.5H), 2.49 (s, 1.5H), 1.81-1.53 (m, 10H), 1.37-0.80 (m, 15H), 0.44 (m, 1H).

Example 88: (R)-1-((4-Hydroxy-1-(3-phenylbutanoyl)piperidin-4-yl)methyl)-4-phenyl-5-(piperidine-1-carbonyl)pyridin-2(1H)-one

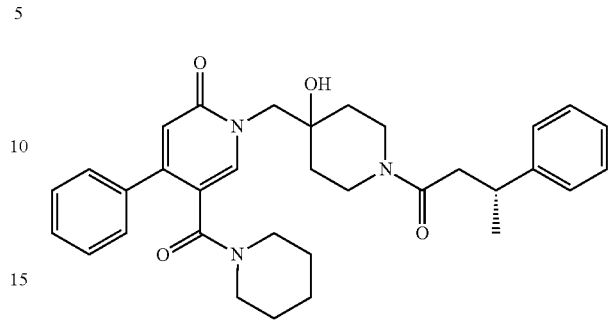

Prepared according to General Procedure 3 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), HATU (35.3 mg, 0.093 mmol), DIPEA (0.044 mL, 0.253 mmol) and piperidine (9.2 μL, 0.093 mmol) in DMF (1 mL) to give the title compound (32 mg, 70%). LCMS (Method B): R$_T$=1.20 min, m/z=542 [M+H]$^+$. $^1$H NMR (400 MHz, methanol-d$_4$, this compound appears as two conformers A and B in a 2:3 ratio): δ 7.77 (s, 0.4H, conformer A), 7.72 (s, 0.6H, conformer B), 7.54-7.41 (m, 5H), 7.39-7.14 (m, 5H), 6.60 (s, 1H), 4.32-3.84 (m, 3H), 3.77-3.63 (m, 1H), 3.61-3.48 (m, 1H), 3.46-3.39 (m, 1H), 3.28-2.86 (m, 5H), 2.86-2.71 (m, 1H), 2.67-2.48 (m, 1H), 1.73-1.19 (m, 11H), 1.03-0.86 (m, 1H), 0.68 (s, 1H).

Example 89: (R)-1-((4-Hydroxy-1-(3-phenylbutanoyl)piperidin-4-yl)methyl)-N-isopropyl-4-(2-methoxyphenyl)-N-methyl-6-oxo-1,6-dihydropyridine-3-carboxamide

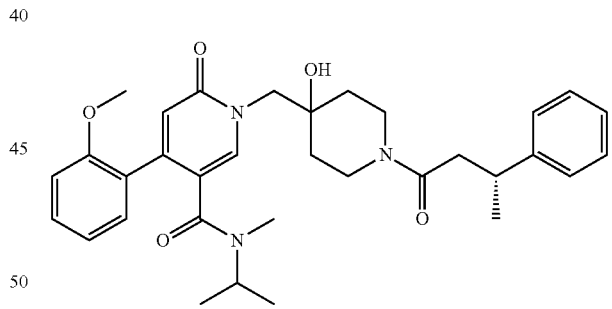

Prepared according to General Procedure 4 using (2-methoxyphenyl)boronic acid (23.4 mg, 0.154 mmol), (R)-4-chloro-1-((4-hydroxy-1-(3-phenylbutanoyl)piperidin-4-yl)methyl)-N-isopropyl-N-methyl-6-oxo-1,6-dihydropyridine-3-carboxamide (50 mg, 0.102 mmol), 1,4-dioxane (0.5 mL), 2 M sodium carbonate (0.113 mL, 0.225 mmol) and Pd(dppf)Cl$_2$.CH$_2$Cl$_2$ (4.3 mg, 5.1 μmol). The mixture was heated at 90° C. overnight. The crude product was purified by preparative HPLC to give the title compound (4 mg, 7%). LCMS (Method B): R$_T$=1.16 min, m/z=560 [M+H]$^+$. $^1$H NMR (400 MHz, DMSO-d$_6$): δ 7.65 (m, 1H), 7.39-6.95 (m, 9H), 6.30 (m, 1H), 4.98 (br s, 1H), 4.38 (m, 1H), 4.12-3.83 (m, 3H), 3.74-3.60 (m, 4H), 3.29-3.13 (m, 3H), 2.96 (m, 1H), 2.71-2.54 (m, 4H), 1.59-1.10 (m, 7H), 1.05-0.76 (m, 5H), 0.61-0.48 (m, 1H).

Example 90: (R)-4-(2-Fluorophenyl)-1-((4-hydroxy-1-(3-phenylbutanoyl)piperidin-4-yl)methyl)-N-isopropyl-N-methyl-6-oxo-1,6-dihydropyridine-3-carboxamide

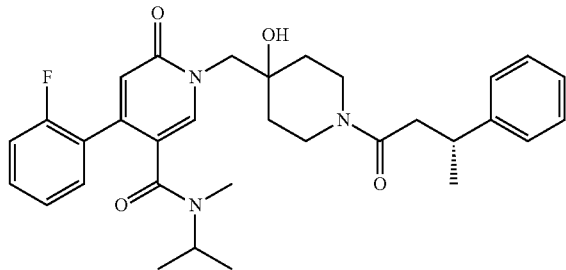 [SMILES: CC(C)N(C)C(=O)c1cn(CC2(O)CCN(C(=O)C[C@@H](C)c3ccccc3)CC2)c(=O)cc1-c1ccccc1F]

Prepared according to the procedure for Example 89 except using (2-fluorophenyl)boronic acid (21.5 mg, 0.154 mmol) and (R)-4-chloro-1-((4-hydroxy-1-(3-phenylbutanoyl)piperidin-4-yl)methyl)-N-isopropyl-N-methyl-6-oxo-1,6-dihydropyridine-3-carboxamide (50 mg, 0.102 mmol) to give the title compound (7.5 mg, 13%). LCMS (Method B): $R_T$=1.18 min, m/z=548 [M+H]$^+$. $^1$H NMR (400 MHz, DMSO-d6, this compound appears as two conformers in a 1:1 ratio): δ 7.74 (m, 1H), 7.45 (m, 1H), 7.38-7.16 (m, 8H), 6.44 (d, 1H), 4.96 (brs, 1H), 4.42 (br s, 0.5H), 4.12-3.81 (m, 3.5H), 3.68 (m, 1H), 3.34-3.15 (m, 2H), 2.91 (m, 1H), 2.70-2.55 (m, 5H), 1.55-1.17 (m, 7H), 1.11-0.72 (m, 6H).

Example 91: (R)-1'-((4-Hydroxy-1-(3-phenylbutanoyl)piperidin-4-yl)methyl)-4'-phenyl-[2,3'-bipyridin]-6'(1'H)-one

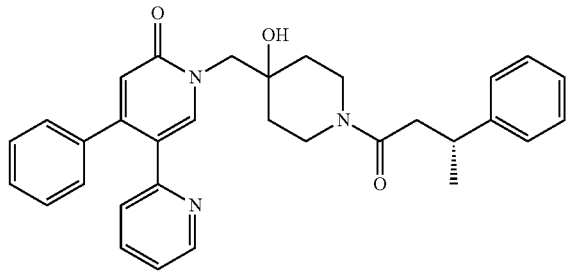 [SMILES: C[C@H](CC(=O)N1CCC(O)(Cn2cc(-c3ccccn3)c(-c3ccccc3)cc2=O)CC1)c1ccccc1]

Step 1: (6-Chloro-4-phenylpyridin-3-yl)boronic acid

5-Bromo-2-chloro-4-phenylpyridine (0.5 g, 1.86 mmol) was dissolved in anhydrous THF (15 mL) and cooled to −78° C. n-Butyllithium (0.89 mL, 2.23 mmol) was added and the reaction was stirred for 20 min at −78° C. Triisopropyl borate (0.87 mL, 3.72 mmol) was then added quickly. The mixture was stirred for 1 h at −78° C. The reaction was quenched with water and allowed to warm to RT then concentrated. The residue was diluted with water, the pH was adjusted to pH 10 using 5% aqueous sodium hydroxide and the solution was washed with diethyl ether. The pH was then adjusted to pH 4 using 48% HBr. The precipitated solid was collected on a sintered funnel, washed with water and dried to give the title compound (0.23 g, 52%), LCMS (Method B): $R_T$=0.92 min, m/z=234 [M+H]$^+$.

Step 2: 6'-Chloro-4'-phenyl-2,3'-bipyridine

2-Bromopyridine (0.041 mL, 0.43 mmol), (6-chloro-4-phenylpyridin-3-yl)boronic acid (50 mg, 0.214 mmol) and sodium carbonate (45.4 mg, 0.43 mmol), were dissolved in 1,4-dioxane (0.5 mL) and water (0.2 mL). The mixture was de-gassed by bubbling $N_2$ through it for 5 min, then Pd(Ph$_3$P)$_4$ (12.4 mg, 10.7 µmol) was added. The reaction was heated in a microwave at 100° C. for 20 min. The mixture was diluted with water and extracted with DCM. The organic layer was dried (Biotage phase separator), concentrated and the residue was purified by flash chromatography (GraceResolv, 0-50% EtOAc in cyclohexane) to give the title compound (48 mg, 84%). LCMS (Method B): $R_T$=1.24 min, m/z=267 [M+H]$^+$.

Step 3: 4'-Phenyl-[2,3'-bipyridin]-6'(1'H)-one

6'-Chloro-4'-phenyl-2,3'-bipyridine (50 mg, 0.187 mmol) and DMSO (0.5 mL) were added to a solution of sodium hydroxide (52.5 mg, 1.31 mmol) in water (0.5 mL). The mixture was heated in a microwave at 130° C. for 30 min. The mixture was diluted with water and extracted with DCM, and the organic layer was dried (Biotage phase separator) and concentrated to give the title compound (45 mg, 97%). LCMS (Method B): $R_T$=0.66 min, m/z=249 [M+H]$^+$.

Step 4: (R)-1'-((4-Hydroxy-1-(3-phenylbutanoyl)piperidin-4-yl)methyl)-4'-phenyl-[2,3'-bipyridin]-6'(1'H)-one Prepared according to General Procedure 1 using 4'-phenyl-[2,3'-bipyridin]-6'(1'H)-one (45 mg, 0.181 mmol), Epoxide 2 (51.7 mg, 0.199 mmol) and cesium carbonate (118 mg, 0.362 mmol) in DMF (1 mL) to give the title compound (11.5 mg, 13%). LCMS (Method B): $R_T$=1.10 min, m/z=508 [M+H]$^+$. $^1$H NMR (400 MHz, methanol-d$_4$, this compound appears as two conformers A:B in a 2:3 ratio): δ 8.51 (tdd, 1H), 7.95 (s, 0.4H, conformer A), 7.89 (s, 0.6H, conformer B), 7.62 (td, 1H), 7.39-7.11 (m, 11H), 7.02-6.97 (m, 1H), 6.62 (s, 1H), 4.33-3.92 (m, 3H), 3.78-3.63 (m, 1H), 3.30-3.16 (m, 2H), 3.11-2.90 (m, 1H), 2.88-2.71 (m, 1H), 2.69-2.47 (m, 1H), 1.77-1.19 (m, 6H), 1.02-0.87 (m, 1H).

Example 92: 1-((1-(3-Cyclohexylpropanoyl)-4-hydroxypiperidin-4-yl)methyl)-N-isopropyl-N-methyl-6-oxo-4-phenyl-1,6-dihydropyridine-3-carboxamide

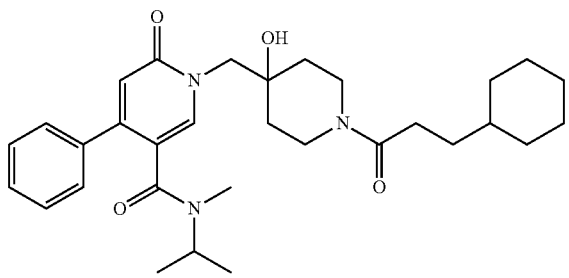 [SMILES: CC(C)N(C)C(=O)c1cn(CC2(O)CCN(C(=O)CCC3CCCCC3)CC2)c(=O)cc1-c1ccccc1]

Prepared according to General Procedure 3 using 3-cyclohexylpropanoic acid (24.4 mg, 0.156 mmol), 1-((4-hydroxypiperidin-4-yl)methyl)-N-isopropyl-N-methyl-6-oxo- 4-phenyl-1,6-dihydropyridine-3-carboxamide (40 mg, 0.104 mmol), HATU (35.2 mg, 0.093 mmol) and DIPEA (0.059 mL, 0.337 mmol) in DCM (2 mL). The crude product was purified by preparative HPLC to give the title compound (29 mg, 53%). LCMS (Method B): $R_T$=1.33 min, m/z=522 [M+H]$^+$. $^1$H NMR (400 MHz, methanol-d$_4$, this compound appears as two conformers in a 1:1 ratio): δ 7.80 (m, 1H), 7.48 (m, 5H), 6.61 (d, 1H), 4.62 (m, 0.5H), 4.30-4.04 (m, 3H), 3.76-3.58 (m, 1.5H), 3.49 (m, 1H), 3.14 (m, 1H), 2.72 (s, 1.5H), 2.50 (s, 1.5H), 2.47 (m, 2H), 1.83-1.48 (m, 11H), 1.39-1.17 (m, 5H), 1.15-0.79 (m, 6H), 0.44 (m, 1H).

Example 93: (R)-tert-Butyl 4-(1-((4-hydroxy-1-(3-phenylbutanoyl)piperidin-4-yl)methyl)-6-oxo-4-phenyl-1,6-dihydropyridine-3-carbonyl)piperazine-1-carboxylate

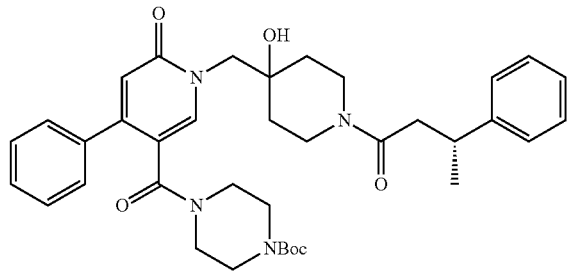 [SMILES: C[C@H](CC(=O)N1CCC(O)(Cn2cc(C(=O)N3CCN(C(=O)OC(C)(C)C)CC3)c(-c3ccccc3)cc2=O)CC1)c1ccccc1]

Prepared according to General Procedure 3 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), tert-butyl piperazine-1-carboxylate (17.3 mg, 0.093 mmol), DIPEA (0.04 mL, 0.253 mmol) and HBTU (35 mg, 0.093 mmol) in DMF (1 mL). The crude product was purified by flash chromatography (GraceResolv, 40-100% EtOAc in cyclohexane; then 0-10% MeOH in EtOAc) to give the title compound (35 mg, 65%). LCMS (Method B): $R_T$=1.28 min, m/z=643 [M+H]$^+$. $^1$H NMR (400 MHz, methanol-d$_4$, this compound appears as two conformers A:B in a 2:3 ratio): δ 7.70 (s, 0.4H, conformer A), 7.65 (s, 0.6H, conformer B), 7.45-7.33 (m, 5H), 7.27-7.03 (m, 5H), 6.49 (s, 1H), 4.18-3.72 (m, 3H), 3.65-3.30 (m, 4H), 3.12-2.74 (m, 6H), 2.75-2.59 (m, 1H), 2.55-2.36 (m, 1H), 2.17 (s, 1H), 1.60-1.12 (m, 16H), 0.94-0.74 (m, 1H).

Example 94: (R)-1-((4-Hydroxy-1-(3-phenylbutanoyl)piperidin-4-yl)methyl)-4-phenyl-5-(piperazine-1-carbonyl)pyridin-2(1H)-one

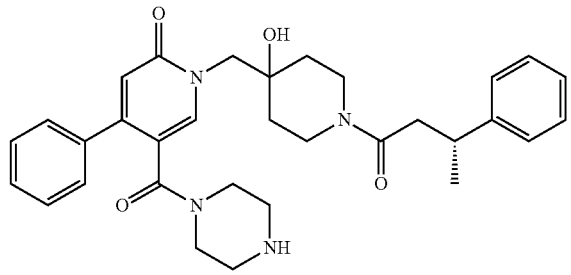 [SMILES: C[C@H](CC(=O)N1CCC(O)(Cn2cc(C(=O)N3CCNCC3)c(-c3ccccc3)cc2=O)CC1)c1ccccc1]

Prepared according to General Procedure 7 using (R)-tert-butyl 4-(1-((4-hydroxy-1-(3-phenylbutanoyl)piperidin-4-yl)methyl)-6-oxo-4-phenyl-1,6-dihydropyridine-3-carbonyl)piperazine-1-carboxylate (30 mg, 0.047 mmol) and TFA (0.5 mL) in DCM (2 mL). The crude product was purified by flash chromatography (Biotage KP-NH, 20-100% EtOAc in cyclohexane; then 5% MeOH in EtOAc) to give the title compound (10 mg, 40%). LCMS (Method B): $R_T$=0.71 min, m/z=543 [M+H]$^+$. $^1$H NMR (400 MHz, DMSO-d$_6$, this compound appears as two conformers A:B in a 1:1 ratio): δ 7.73 (s, 0.5H, conformer A), 7.70 (s, 0.5H, conformer B), 7.52-7.34 (m, 5H), 7.33-7.23 (m, 4H), 7.21-7.12 (m, 1H), 6.44 (d, 1H), 4.94 (d, 1H), 4.17-3.82 (m, 3H), 3.73-3.60 (m, 1H), 3.29-2.71 (m, 8H), 2.66-2.53 (m, 3H), 2.44-2.20 (m, 2H), 1.87-1.69 (m, 1H), 1.58-1.10 (m, 7H).

Example 95: (R)-1-((4-Hydroxy-1-(3-phenylbutanoyl)piperidin-4-yl)methyl)-N,N-dimethyl-6-oxo-4-phenyl-1,6-dihydropyridine-3-carboxamide

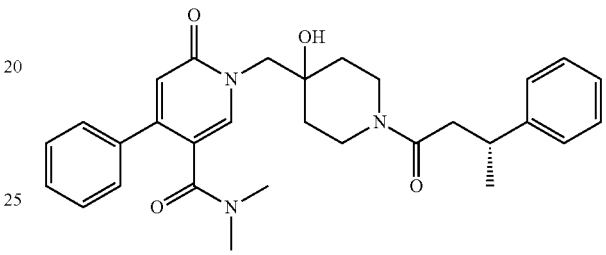

(R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol) was dissolved in DMF (1 mL) and HATU (35.3 mg, 0.093 mmol) was added, followed by DIPEA (0.044 mL, 0.253 mmol). The reaction was stirred at RT for 10 min then dimethylamine (2 M in THF, 0.046 mL, 0.093 mmol) was added. The reaction was then stirred at RT for 16 h. A further 1 mL of dimethylamine solution was added and the mixture was stirred a further 2 h. The mixture was concentrated and the residue was taken up in water. The mixture was extracted with DCM and the organic layer was dried (Biotage phase separator) and concentrated. The crude residue was purified by flash chromatography (GraceResolv, eluted 50-100% EtOAc in cyclohexane; then 5% MeOH in EtOAc) to give the title compound (10 mg, 24%). LCMS (Method B): $R_T$=1.04 min, m/z=502 [M+H]$^+$. $^1$H NMR (400 MHz, methanol-d$_4$, this compound appears as two conformers A:B in a 2:3 ratio): δ 7.69 (s, 0.4H, conformer A), 7.63 (s, 0.6H, conformer B), 7.42-7.29 (m, 5H), 7.27-7.03 (m, 5H), 6.49 (s, 1H), 4.18-3.76 (m, 3H), 3.66-3.52 (m, 1H), 3.12-2.80 (m, 3H), 2.77-2.58 (m, 4H), 2.55-2.32 (m, 4H), 1.61-1.11 (m, 6H), 0.90-0.72 (m, 1H).

Example 96: (R)-1-((4-Hydroxy-1-(3-phenylbutanoyl)piperidin-4-yl)methyl)-N-isopropyl-N-methyl-6-oxo-4-(p-tolyl)-1,6-dihydropyridine-3-carboxamide

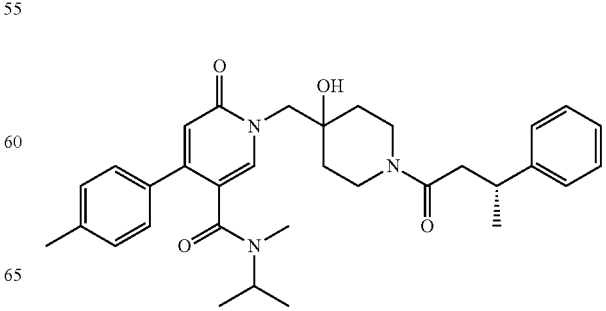

Prepared according to General Procedure 4 using p-tolyl-boronic acid (16.7 mg, 0.123 mmol), (R)-4-chloro-1-((4-hydroxy-1-(3-phenylbutanoyl)piperidin-4-yl)methyl)-N-isopropyl-N-methyl-6-oxo-1,6-dihydropyridine-3-carboxamide (40 mg, 0.082 mmol), 1,4-dioxane (0.5 mL), sodium carbonate (2 M in water, 0.082 mL, 0.164 mmol) and Pd(dppf)Cl$_2$·CH$_2$Cl$_2$ (3.5 mg, 4.10 µmol). The reaction was heated in a microwave at 130° C. for 30 min. The crude product was purified by preparative HPLC to give the title compound (5 mg, 11%). LCMS (Method B): R$_T$=1.27 min, m/z=544 [M+H]$^+$. $^1$H NMR (400 MHz, methanol-d$_4$, this compound appears as a mixture of conformers): δ 7.72 (m, 1H), 7.41-7.16 (m, 9H), 6.59 (m, 1H), 3.82-4.29 (m, 3H), 3.68 (m, 2H), 3.30-3.19 (m, 2H), 3.11-2.90 (m, 1H), 2.86-2.48 (m, 5H), 2.40 (s, 3H), 1.71-0.74 (m, 12H), 0.44 (m, 1H).

Example 97: (R)-1-((4-Hydroxy-1-(3-phenylbutanoyl)piperidin-4-yl)methyl)-N-methoxy-N-methyl-6-oxo-4-phenyl-1,6-dihydropyridine-3-carboxamide

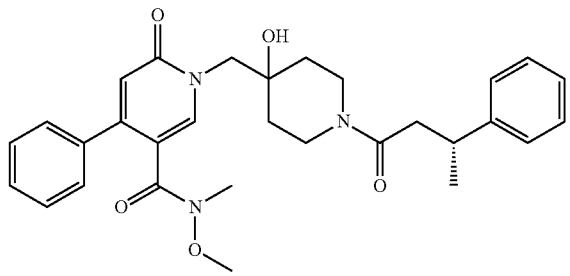 [SMILES: CON(C)C(=O)c1cn(CC2(O)CCN(C(=O)C[C@@H](C)c3ccccc3)CC2)c(=O)cc1-c1ccccc1]

Prepared according to General Procedure 5 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), N,O-dimethylhydroxylamine hydrochloride (10.7 mg, 0.110 mmol), DIPEA (0.06 mL, 0.337 mmol) and HBTU (35 mg, 0.093 mmol) in DMF (1 mL) to give the title compound (22 mg, 50%). LCMS (Method B): R$_T$=1.23 min, m/z=518 [M+H]$^+$. $^1$H NMR (400 MHz, DMSO-d$_6$, this compound appears as a mixture of conformers): δ 7.85 (d, 1H), 7.49-7.32 (m, 5H), 7.32-7.20 (m, 4H), 7.20-7.11 (m, 1H), 6.43 (d, 1H), 4.96 (d, 1H), 4.09-3.87 (m, 3H), 3.73-3.58 (m, 1H), 3.43 (d, 3H), 3.31-3.11 (m, 2H), 3.00 (s, 3H), 2.96-2.85 (m, 1H), 2.66-2.53 (m, 2H), 1.59-1.12 (m, 7H).

Example 98: (R)-1-((4-Hydroxy-1-(3-phenylbutanoyl)piperidin-4-yl)methyl)-4,5-diphenylpyridin-2(1H)-one

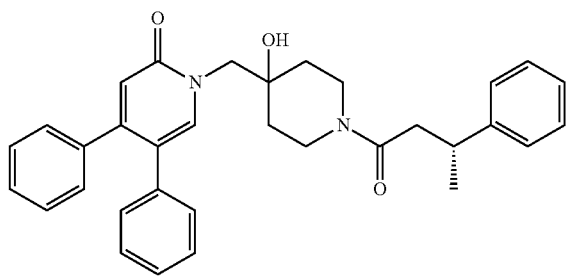

Prepared according to General Procedure 4 using (R)-5-bromo-1-((4-hydroxy-1-(3-phenylbutanoyl)piperidin-4-yl) methyl)-4-phenylpyridin-2(1H)-one (25 mg, 0.049 mmol), phenylboronic acid (8.98 mg, 0.074 mmol), sodium carbonate (10.4 mg, 0.098 mmol), 1,4-dioxane (0.5 mL), water (0.200 mL) and Pd(Ph$_3$P)$_4$ (2.8 mg, 2.45 µmol). The mixture was heated in a microwave at 150° C. for 10 min to give the title compound (14.5 mg, 58%). LCMS (Method B): R$_T$=1.39 min, m/z=507 [M+H]$^+$. $^1$H NMR (400 MHz, methanol-d$_4$, this compound appears as two conformers in a ratio approximately 1:1): δ 7.71 (s, 0.5H), 7.64 (s, 0.5H), 7.09-7.36 (m, 15H), 6.61 (s, 1H), 4.29-3.72 (m, 4H), 3.27-2.73 (m, 4H), 2.65-2.50 (m, 1H), 1.74-1.23 (m, 6H), 0.95 (s, 1H).

Example 99: (R)-1-((4-Hydroxy-1-(3-phenylbutanoyl)piperidin-4-yl)methyl)-4-phenyl-[3,3'-bipyridin]-6(1H)-one

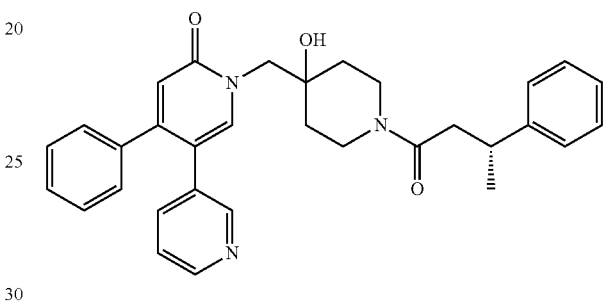

Prepared according to General Procedure 4 using (R)-5-bromo-1-((4-hydroxy-1-(3-phenylbutanoyl)piperidin-4-yl) methyl)-4-phenylpyridin-2(1H)-one (20 mg, 0.039 mmol), pyridin-3-ylboronic acid (7.2 mg, 0.059 mmol), sodium carbonate (8.3 mg, 0.078 mmol), 1,4-dioxane (0.5 mL), water (0.200 mL) and Pd(Ph$_3$P)$_4$ (2.3 mg, 1.95 µmol). The mixture was heated in a microwave at 150° C. for 10 min to give the title compound (4 mg, 20%). LCMS (Method B): R$_T$=0.98 min, m/z=508 [M+H]. $^1$H NMR (400 MHz, methanol-d$_4$, this compound appears as two conformers A:B in a 2:3 ratio): δ 8.40 (d, 1H), 8.28 (s, 1H), 7.80 (s, 0.4H, conformer A), 7.74 (s, 0.6H, conformer B), 7.57-7.47 (m, 1H), 7.41-7.10 (m, 11H), 6.64 (s, 1H), 4.33-3.92 (m, 3H), 3.80-3.63 (m, 1H), 3.29-3.17 (m, 2H), 3.12-2.93 (m, 1H), 2.89-2.71 (m, 1H), 2.68-2.48 (m, 1H), 1.75-1.20 (m, 6H), 1.06-0.84 (m, 1H).

Example 100: (R)-5-(3-(Aminomethyl)phenyl)-1-((4-hydroxy-1-(3-phenylbutanoyl)piperidin-4-yl) methyl)-4-phenylpyridin-2(1H)-one

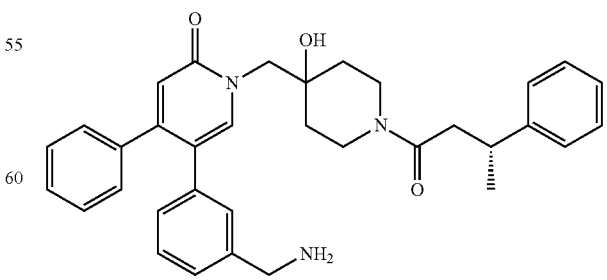

Prepared according to General Procedure 4 using (R)-5-bromo-1-((4-hydroxy-1-(3-phenylbutanoyl)piperidin-4-yl) methyl)-4-phenylpyridin-2(1H)-one (30 mg, 0.059 mmol), 3-(aminomethyl)benzeneboronic acid hydrochloride (16.6 mg, 0.088 mmol), sodium carbonate (19.2 mg, 0.18 mmol), water (0.2 mL), 1,4-dioxane (0.5 mL) and Pd(Ph$_3$P)$_4$ (1.5 mg, 2.9 µmol). The mixture was heated in a microwave at 150° C. for 20 min to give the title compound (12 mg, 38%). LCMS (Method B): R$_T$=1.01 min, m/z=536 [M+H]$^+$. $^1$H NMR (400 MHz, methanol-d$_4$, this compound appears as two conformers A:B in a 2:3 ratio): δ 7.73 (s, 0.4H, conformer A), 7.67 (s, 0.6H, conformer B), 7.36-7.07 (m, 13H), 7.00-6.92 (m, 1H), 6.62 (s, 1H), 4.33-3.89 (m, 3H), 3.81-3.60 (m, 3H), 3.30-3.17 (m, 2H), 3.13-2.90 (m, 1H), 2.87-2.69 (m, 1H), 2.67-2.46 (m, 1H), 1.74-1.26 (m, 6H), 1.05-0.86 (m, 1H).

Example 101: (R)-1-((4-Hydroxy-1-(3-phenylbutanoyl)piperidin-4-yl)methyl)-N-isopropyl-N-methyl-6-oxo-4-phenyl-1,6-dihydropyridine-3-carboxamide

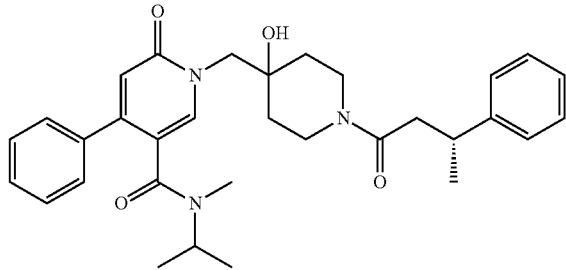 [SMILES: CC(C)N(C)C(=O)c1cn(CC2(O)CCN(C(=O)C[C@@H](C)c3ccccc3)CC2)c(=O)cc1-c1ccccc1]

Prepared according to General Procedure 3 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), N-methylpropan-2-amine (0.012 mL, 0.118 mmol), DIPEA (0.06 mL, 0.337 mmol) and HBTU (38 mg, 0.093 mmol) in DMF (1 mL) to give the title compound (22 mg, 46%). LCMS (Method B): R$_T$=1.19 min, m/z=530 [M+H]$^+$. $^1$H NMR (400 MHz, methanol-d$_4$, this compound appears as a mixture of conformers in a 1:1 ratio): δ 7.62 (dd, 1H), 7.44-7.29 (m, 5H), 7.27-7.02 (m, 5H), 6.49 (d, 1H), 4.51 (h, 0.5H) 4.19-3.71 (m, 3H), 3.64-3.49 (m, 1.5H), 3.19-3.02 (m, 2H), 3.00-2.79 (m, 1H), 2.74-2.55 (m, 2.5H), 2.54-2.29 (m, 2.5H), 1.60-1.13 (m, 7H), 1.04-0.46 (m, 4.5H), 0.39-0.23 (m, 1.5H).

Example 102: (R)-1-((4-Hydroxy-1-(3-phenylbutanoyl)piperidin-4-yl)methyl)-N-isopropyl-N-methyl-6-oxo-4-(m-tolyl)-1,6-dihydropyridine-3-carboxamide

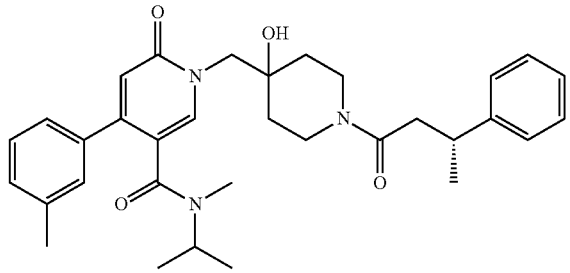 [SMILES: Cc1cccc(-c2cc(=O)n(CC3(O)CCN(C(=O)C[C@@H](C)c4ccccc4)CC3)cc2C(=O)N(C)C(C)C)c1]

Step 1: (R)-4-Chloro-1-((4-hydroxy-1-(3-phenylbutanoyl)piperidin-4-yl)methyl)-N-isopropyl-N-methyl-6-oxo-1,6-dihydropyridine-3-carboxamide A solution of Epoxide 2 (410 mg, 1.58 mmol), 4-chloro-N-isopropyl-N-methyl-6-oxo-1,6-dihydropyridine-3-carboxamide (329 mg, 1.44 mmol) and DIPEA (0.377 mL, 2.16 mmol) in DMF (6 mL) was heated at 70° C. for 2 d. Cesium carbonate (703 mg, 2.16 mmol) was added and the reaction heated at 70° C. for a further 2 d. The mixture was diluted with water and extracted with ethyl acetate (×3). The combined organic extracts were washed with water and brine, dried (MgSO$_4$) and concentrated. The residue was purified by flash chromatography (GraceResolv, 15-100% EtOAc in cyclohexane) to give the title compound (314 mg, 45%). LCMS (Method B): R$_T$=1.06 min, m/z=488 [M+H]$^+$.

Step 2: (R)-1-((4-Hydroxy-1-(3-phenylbutanoyl)piperidin-4-yl)methyl)-N-isopropyl-N-methyl-6-oxo-4-(m-tolyl)-1,6-dihydropyridine-3-carboxamide Prepared according to General Procedure 4 using m-tolylboronic acid (16.7 mg, 0.123 mmol), (R)-4-chloro-1-((4-hydroxy-1-(3-phenylbutanoyl)piperidin-4-yl)methyl)-N-isopropyl-N-methyl-6-oxo-1,6-dihydropyridine-3-carboxamide (40 mg, 0.082 mmol), sodium carbonate (2 M in water, 0.082 mL, 0.164 mmol) and Pd(dppf)Cl$_2$.CH$_2$Cl$_2$ (3.5 mg, 4.10 µmol) in 1,4-dioxane (0.5 mL). The mixture was heated in a microwave at 130° C. for 30 min to give the title compound (9 mg, 20%). LCMS (Method B): R$_T$=1.28 min, m/z=544 [M+H]$^+$. $^1$H NMR (400 MHz, methanol-d$_4$, this compound appears as a mixture of conformers): δ 7.76 (d, 0.4H), 7.70 (d, 0.6H), 7.40-7.15 (m, 9H), 6.60 (d, 1H), 4.71-4.57 (m, 0.6H), 4.31-3.83 (m, 3H), 3.77-3.61 (m, 1.4H), 3.29-3.14 (m, 2H overlapping solvent), 3.13-2.92 (m, 1H), 2.87-2.43 (m, 5H), 2.40 (s, 3H), 1.73-1.25 (m, 7H), 1.15-0.70 (m, 4.6H), 0.45 (s, 1.4H).

Example 103: (R)-1-((4-Hydroxy-1-(3-phenylbutanoyl)piperidin-4-yl)methyl)-4-phenyl-5-(pyrimidin-5-yl)pyridin-2(1H)-one

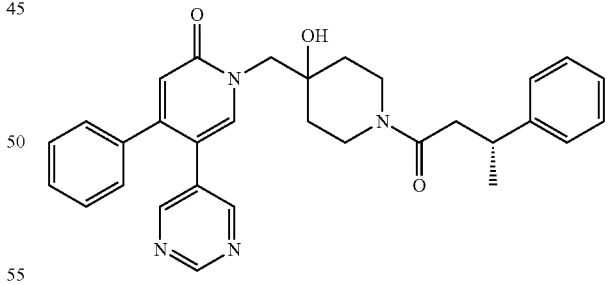

Prepared according to General Procedure 4 using (R)-5-bromo-1-((4-hydroxy-1-(3-phenylbutanoyl)piperidin-4-yl)methyl)-4-phenylpyridin-2(1H)-one (25 mg, 0.049 mmol), pyrimidin-5-ylboronic acid (9.1 mg, 0.074 mmol), sodium carbonate (10.4 mg, 0.098 mmol), 1,4-dioxane (0.5 mL), water (0.2 mL) and Pd(Ph$_3$P)$_4$ (2.9 mg, 2.5 µmol). The mixture was heated in a microwave at 150° C. for 10 min. The crude product was purified by preparative HPLC to give the title compound (4 mg, 16%). LCMS (Method B): R$_T$=1.06 min, m/z=509 [M+H]$^+$. $^1$H NMR (400 MHz, methanol-d$_4$, this compound appears as two conformers A:B in a 2:3 ratio): δ 9.00 (s, 1H), 8.48 (s, 2H), 7.87 (s, 0.4H, conformer A), 7.82 (s, 0.6H, conformer B), 7.45-7.14 (m, 10H), 6.65 (s, 1H), 4.32-3.94 (m, 3H), 3.79-3.67 (m, 1H), 3.30-3.17 (m, 2H), 3.14-2.94 (m, 1H), 2.88-2.73 (m, 1H), 2.70-2.48 (m, 1H), 1.76-1.28 (m, 6H), 1.09-0.95 (m, 1H).

Example 104: (R)—N-(Cyclopropylmethyl)-1-((4-hydroxy-1-(3-phenylbutanoyl)piperidin-4-yl)methyl)-6-oxo-4-phenyl-1,6-dihydropyridine-3-carboxamide

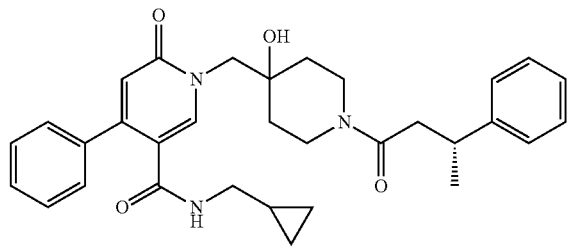 [SMILES: C[C@H](CC(=O)N1CCC(O)(Cn2cc(C(=O)NCC3CC3)c(-c3ccccc3)cc2=O)CC1)c1ccccc1]

Prepared according to General Procedure 5 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), (aminomethyl)cyclopropanehydrochloride (11.8 mg, 0.11 mmol), DIPEA (0.06 mL, 0.337 mmol) and HBTU (35 mg, 0.093 mmol) in DMF (1 mL) to give the title compound (25 mg, 56%). LCMS (Method B): $R_T$=1.34 min, m/z=528 [M+H]$^+$. $^1$H NMR (400 MHz, DMSO-d$_6$, this compound appears as a mixture of conformers): δ 8.03 (t, 1H), 7.75 (d, 1H), 7.37-7.25 (m, 5H), 7.24-7.13 (m, 4H), 7.12-7.03 (m, 1H), 6.27 (d, 1H), 4.91 (d, 1H), 4.00-3.75 (m, 3H), 3.64-3.48 (m, 1H), 3.19-3.00 (m, 2H), 2.90-2.73 (m, 3H), 2.53-2.46 (m, 2H), 1.50-1.04 (m, 7H), 0.80-0.67 (m, 1H), 0.32-0.22 (m, 2H), 0.04--0.06 (m, 2H).

Example 105: (R)—N-Benzyl-1-((4-hydroxy-1-(3-phenylbutanoyl)piperidin-4-yl)methyl)-N-methyl-6-oxo-4-phenyl-1,6-dihydropyridine-3-carboxamide

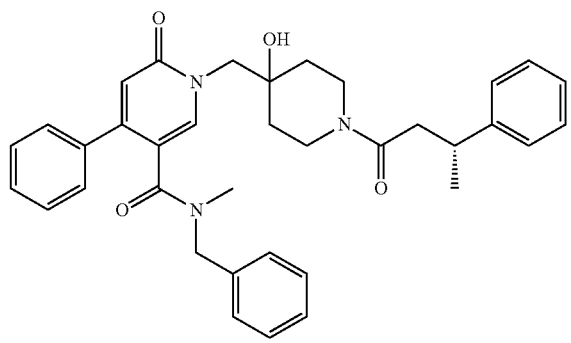 [SMILES: C[C@H](CC(=O)N1CCC(O)(Cn2cc(C(=O)N(C)Cc3ccccc3)c(-c3ccccc3)cc2=O)CC1)c1ccccc1]

Prepared according to General Procedure 5 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), N-methylbenzylamine (0.014 mL, 0.11 mmol), DIPEA (0.06 mL, 0.337 mmol) and HBTU (35 mg, 0.093 mmol) in DMF (1 mL) to give the title compound (41 mg, 84%). LCMS (Method B): $R_T$=1.46 min, m/z=578 [M+H]$^+$. $^1$H NMR (400 MHz, DMSO-d$_6$): δ 7.80 (m, 1H), 7.55-7.12 (m, 13H), 7.10-6.97 (m, 2H), 6.44 (m, 1H), 4.97 (m, 1H), 4.45 (m, 1H), 4.10-3.85 (m, 3H), 3.60 (m, 1H), 3.20 (m, 3H), 2.91 (m, 1H), 2.56 (m, 5H), 1.59-1.16 (m, 7H).

Example 106: (R)-2-(1-((4-Hydroxy-1-(3-phenylbutanoyl)piperidin-4-yl)methyl)-6-oxo-4-phenyl-1,6-dihydropyridin-3-yl)benzonitrile

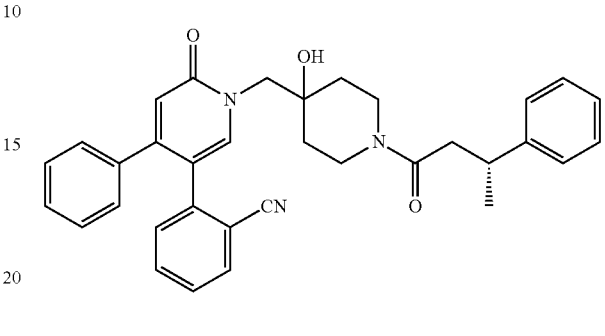

Step 1:
2-(6-Chloro-4-phenylpyridin-3-yl)benzonitrile

Prepared according to General Procedure 4 using 2-bromobenzonitrile (78 mg, 0.428 mmol), 6-chloro-4-phenylpyridin-3-yl)boronic acid (50 mg, 0.214 mmol), sodium carbonate (45.4 mg, 0.428 mmol), 1,4-dioxane (0.5 mL), water (0.2 mL) and Pd(Ph$_3$P)$_4$ (12.4 mg, 10.7 μmol). The mixture was heated in a microwave at 100° C. for 20 min to give the title compound (50 mg, 80%). LCMS (Method B): $R_T$=1.42 min, m/z=291 [M+H]$^+$.

Step 2: 2-(6-Oxo-4-phenyl-1,6-dihydropyridin-3-yl)benzonitrile

A solution of 2-(6-Chloro-4-phenylpyridin-3-yl)benzonitrile (50 mg, 0.172 mmol) in acetic acid (2 mL, 34.9 mmol) and water (0.5 mL) was heated at reflux for 64 h. The mixture was concentrated and the residue was taken up in saturated aqueous sodium bicarbonate and extracted with DCM. The organic layer was concentrated to give the title compound (46 mg, 98%) which was used without further purification. LCMS (Method B): $R_T$=0.95 min, m/z=273 [M+H]$^+$.

Step 3: (R)-2-(1-((4-Hydroxy-1-(3-phenylbutanoyl)piperidin-4-yl)methyl)-6-oxo-4-phenyl-1,6-dihydropyridin-3-yl)benzonitrile A solution of Epoxide 2 (46 mg, 0.177 mmol), 2-(6-oxo-4-phenyl-1,6-dihydropyridin-3-yl)benzonitrile (48.3 mg, 0.177 mmol) and DIPEA (0.046 mL, 0.27 mmol) in DMF (2 mL) was heated at 80° C. for 16 h. Cesium carbonate (116 mg, 0.355 mmol) was then added and the mixture was heated at 80° C. for 4 h. The mixture was diluted with water and extracted with DCM (×2). The combined organic extracts were dried (Biotage phase separator), concentrated and the residue was purified by flash chromatography (GraceResolv, 20-100% EtOAc in cyclohexane; then 0-10% MeOH in EtOAc), followed by preparative HPLC to give the title compound (5 mg, 5%). LCMS (Method B): $R_T$=1.30 min, m/z=532 [M+H]$^+$. $^1$H NMR (400 MHz, methanol-d$_4$, this compound appears as two conformers A:B in a 2:3 ratio): δ 7.82 (s, 0.4H, conformer A), 7.74 (s, 0.6H, conformer B), 7.70-7.56 (m, 2H), 7.52-7.36 (m, 2H), 7.36-7.07 (m, 10H), 6.67 (s, 1H), 4.33-3.87 (m, 3H), 3.79-3.65 (m, 1H), 3.29-3.16 (m, 2H), 3.12-2.93 (m, 1H), 2.88-2.71 (m, 1H), 2.68-2.46 (m, 1H), 1.77-1.23 (m, 6H), 1.06-0.89 (m, 1H).

Example 107: (R)-1-((4-Hydroxy-1-(3-phenylbutanoyl)piperidin-4-yl)methyl)-N-methyl-6-oxo-N,4-diphenyl-1,6-dihydropyridine-3-carboxamide

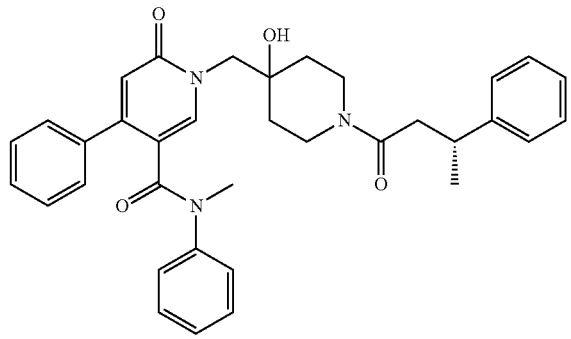 [SMILES: C[C@H](CC(=O)N1CCC(O)(Cn2cc(C(=O)N(C)c3ccccc3)c(-c3ccccc3)cc2=O)CC1)c1ccccc1]

Prepared according to General Procedure 5 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), HBTU (35.2 mg, 0.093 mmol), DIPEA (0.059 mL, 0.337 mmol) and N-methylaniline (0.012 mL, 0.110 mmol) in DMF (1 mL). The crude product was purified by flash chromatography (GraceResolv, 40-100% EtOAc in cyclohexane; then 0-10% MeOH in EtOAc) to give the title compound (10 mg, 21%). LCMS (Method B): $R_T$=1.36 min, m/z=564 [M+H]$^+$. $^1$H NMR (400 MHz, DMSO-d6, this compound appears as a mixture of conformers): δ 7.92 (d, 1H), 7.60-7.94 (m, 13H), 6.55-6.33 (m, 2H), 6.26 (s, 1H), 5.02 (d, 1H), 4.12-3.85 (m, 3H), 3.75-3.59 (m, 1H), 3.30-3.14 (m, 2H), 3.10 (s, 3H), 3.00-2.85 (m, 1H), 2.66-2.54 (m, 2H), 1.53-1.11 (m, 7H).

Example 108: 3-(1-(1-((R)-3-Cyclohexyl-2-methylpropanoyl)-4-hydroxypiperidin-4-yl)ethyl)-6-phenylpyrimidin-4(3H)-one

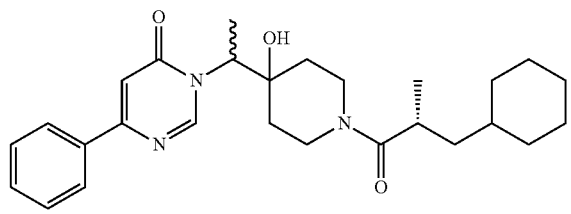 [SMILES: CC(n1cnc(-c2ccccc2)cc1=O)C1(O)CCN(C(=O)[C@H](C)CC2CCCCC2)CC1]

Prepared according to General Procedure 5 using Amine 2 (40 mg, 0.12 mmol), Acid 1 (30.4 mg, 0.18 mmol), DIPEA (0.083 mL, 0.48 mmol) and HBTU (68 mg, 0.18 mmol) in DCM (2.3 mL). The reaction mixture was stirred for 3.5 h before water (2.2 mL) was added. The crude product was purified by flash chromatography (Biotage 11 g KP-NH column, 20-100% EtOAc in cyclohexane) to give the title compound (22.0 mg, 41%). LCMS (Method B): $R_T$=1.43 min, m/z=452 [M+H]$^+$. $^1$H NMR (400 MHz, DMSO-d$_6$): δ 8.52 (s, 1H), 8.06-8.12 (m, 2H), 7.55-7.47 (m, 3H), 7.02-6.96 (m, 1H), 5.22 (s, 1H), 4.98-4.87 (m, 1H), 4.29-4.04 (m, 1H), 3.87-3.69 (m, 1H), 3.37-3.12 (m, 1H), 2.97-2.71 (m, 2H), 1.79-1.29 (m, 11H), 1.28-1.01 (br m, 7H), 1.00-0.89 (m, 3H), 0.88-0.72 (m, 2H).

Example 109: (R)-1-((4-Hydroxy-1-(3-phenylbutanoyl)piperidin-4-yl)methyl)-5-(1-methyl-1H-pyrazol-4-yl)-4-phenylpyridin-2(1H)-one

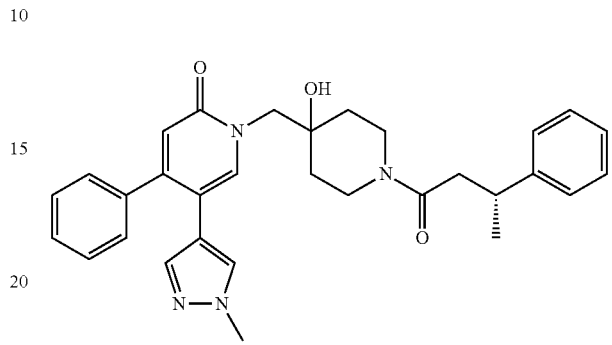

Prepared according to General Procedure 4 using (R)-5-bromo-1-((4-hydroxy-1-(3-phenylbutanoyl)piperidin-4-yl)methyl)-4-phenylpyridin-2(1H)-one (20 mg, 0.039 mmol), 1-methyl-4-(4,4,5,5-tetramethyl-1,3,2-dioxaborolan-2-yl)-1H-pyrazole (12.3 mg, 0.059 mmol), sodium carbonate (8.3 mg, 0.078 mmol), 1,4-dioxane (0.5 mL), water (0.200 mL) and Pd(Ph$_3$P)$_4$ (2.3 mg, 1.95 μmol). The mixture was heated in a microwave at 150° C. for 10 min to give the title compound (4 mg, 20%). LCMS (Method B): $R_T$=1.09 min, m/z=511 [M+H]$^+$. $^1$H NMR (400 MHz, methanol-d$_4$, this compound appears as two conformers A:B in a 2:3 ratio): δ 7.63 (s, 0.4H, conformer A), 7.57 (s, 0.6H, conformer B), 7.34-7.04 (m, 11H), 6.93 (d, 1H), 6.42 (s, 1H), 4.19-3.75 (m, 3H), 3.70-3.52 (m, 4H), 3.18-3.05 (m, 2H), 2.99-2.81 (m, 1H), 2.74-2.59 (m, 1H), 2.54-2.36 (m, 1H), 1.62-0.80 (m, 7H).

Example 110: (R)-3-((1-(2-(Cyclohexylmethyl)pent-4-enoyl)-4-hydroxypiperidin-4-yl)methyl)-6-(2-fluorophenyl)pyrimidin-4(3H)-one

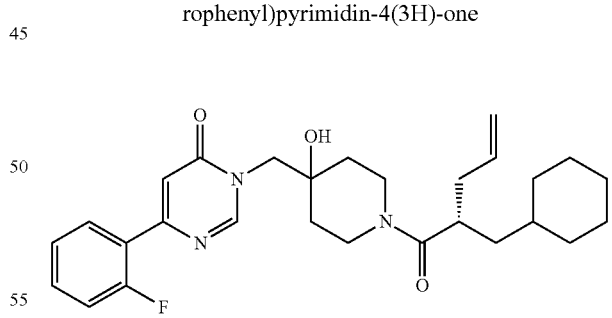

Prepared according to General Procedure 5 using Amine 1 (40 mg, 0.12 mmol), Acid 2 (39 mg, 0.20 mmol), DIPEA (0.092 mL, 0.525 mmol) and HBTU (75 mg, 0.20 mmol) in DCM (2.5 mL) to give the title compound (15.1 mg, 27%). LCMS (Method B): $R_T$=1.46 min, m/z=482 [M+H]$^+$. $^1$H NMR (400 MHz, CDCl$_3$): δ 8.17 (s, 1H), 8.07 (td, 1H), 7.49-7.42 (m, 1H), 7.32-7.23 (m, 1H), 7.18 (ddd, 1H), 7.13 (s, 1H), 5.81-5.66 (m, 1H), 5.10-4.94 (m, 2H), 4.47 (t, br, 1H), 4.15 (d, 1H), 3.98 (dd, 1H), 3.88-3.75 (m, br, 2H), 3.52-3.42 (m, 1H), 3.16-3.04 (m, 1H), 2.91-2.80 (m, br, 1H), 2.42-2.29 (m, 1H), 2.20-2.10 (m, 1H), 1.77-1.47 (m, br, 8H), 1.35-1.05 (br m, 6H), 0.96-0.78 (br m, 3H).

Example 111: (R)-1-((4-Hydroxy-1-(3-phenylbutanoyl)piperidin-4-yl)methyl)-5-methyl-4-phenylpyridin-2(1H)-one

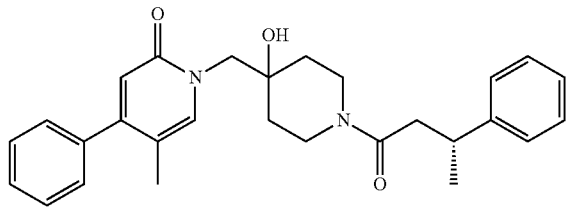

(R)-5-Bromo-1-((4-hydroxy-1-(3-phenylbutanoyl)piperidin-4-yl)methyl)-4-phenylpyridin-2(1H)-one (25 mg, 0.049 mmol), trimethylboroxine (0.014 mL, 0.098 mmol) and potassium carbonate (20.4 mg, 0.147 mmol) were suspended in 1,4-dioxane (0.5 mL) and the mixture was degassed. Pd(dppf)Cl$_2$.CH$_2$Cl$_2$ (2.0 mg, 2.45 μmol) was added and the mixture was sealed and stirred at 85° C. for 16 h. The mixture was cooled and diluted with saturated aqueous sodium bicarbonate. The solution was extracted with DCM (×3) and the combined organic extracts were dried (Biotage phase separator) and concentrated. The residue was purified by flash chromatography (GraceResolv, 0-100% EtOAc in cyclohexane; then 0-10% MeOH in EtOAc) to give the title compound (13.8 mg, 63%). LCMS (Method B): R$_T$=1.23 min, m/z=445 [M+H]$^+$.

Example 112: (R)-6-(1,5-Dimethyl-1H-pyrazol-4-yl)-3-((4-hydroxy-1-(3-phenylbutanoyl)piperidin-4-yl)methyl)pyrimidin-4(3H)-one

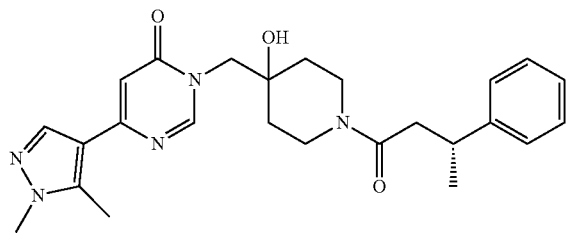 [SMILES: Cc1c(-c2cc(=O)n(CC3(O)CCN(C(=O)C[C@@H](C)c4ccccc4)CC3)cn2)cnn1C]

Prepared according to General Procedure 4 using (R)-6-chloro-3-((4-hydroxy-1-(3-phenylbutanoyl)piperidin-4-yl)methyl)pyrimidin-4(3H)-one (20 mg, 0.051 mmol), 1,5-dimethyl-4-(4,4,5,5-tetramethyl-1,3,2-dioxaborolan-2-yl)-1H-pyrazole (17.1 mg, 0.077 mmol), sodium carbonate (10.9 mg, 0.103 mmol) and Pd(PPh$_3$)$_4$(3.0 mg, 2.56 μmol) in 1,4-dioxane (500 μL) and water (200 μL). The reaction was heated in a microwave at 150° C. for 10 min to give the title compound (11.4 mg, 49%). LCMS (Method B): R$_T$=0.93 min, m/z=450 [M+H]$^+$. $^1$H NMR (400 MHz, methanol-d$_4$, this compound appears as two conformers A:B in a 2:3 ratio): δ 8.34 (s, 0.4H, conformer A), 8.30 (s, 0.6H, conformer B), 7.40-7.16 (m, 5H), 6.59 (s, 1H), 4.30-3.82 (m, 5H), 3.94 (s, 3H), 3.75-3.62 (m, 1H), 3.30-3.17 (m, 2H), 3.10-2.92 (m, 1H), 2.85-2.72 (m, 1H), 2.63 (s, 3H), 2.55-2.47 (m, 1H), 1.71-1.28 (m, 6H), 0.97-0.83 (m, 1H).

Example 113: 3-(((1R,5S)-3-(3-Cyclohexylpropanoyl)-8-hydroxy-3-azabicyclo[3.2.1]octan-8-yl)methyl)-6-(2-fluorophenyl)pyrimidin-4(3H)-one

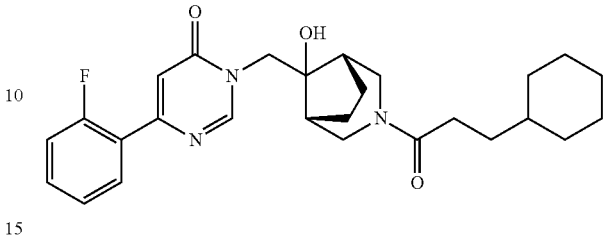

Prepared according to General Procedure 5 using 6-(2-fluorophenyl)-3-(((1R,5S)-8-hydroxy-3-azabicyclo[3.2.1]octan-8-yl)methyl)pyrimidin-4(3H)-one hydrochloride (0.030 g, 0.082 mmol), 3-cyclohexylpropanoic acid (0.019 g, 0.123 mmol), DIPEA (0.057 mL, 0.328 mmol) and HBTU (0.047 g, 0.123 mmol) in DCM (0.8 mL) to give the title compound (21 mg, 55%). LCMS (Method B): R$_T$=1.53 min, m/z=468 [M+H]$^+$. $^1$H NMR (400 MHz, CDCl$_3$): δ 8.14 (d, 1H), 8.07 (td, 1H), 7.49-7.43 (m, 1H), 7.29 (dd, 1H), 7.21-7.17 (m, 1H), 7.15 (s, 1H), 4.71 (s, 1H), 4.20 (dd, 1H), 4.13 (q, 2H), 3.74 (d, 1H), 3.40 (br dd, 1H), 3.27 (d, 1H), 2.41-2.25 (m, 2H), 1.94-1.87 (m, 2H), 1.87-1.75 (m, 2H), 1.75-1.60 (m, 6H), 1.56-1.49 (m, 2H), 1.29-1.10 (m, 5H), 0.95-0.84 (m, 2H).

Example 114: (R)-1-((4-Hydroxy-1-(3-phenylbutanoyl)piperidin-4-yl)methyl)-6-oxo-4-phenyl-1,6-dihydropyridine-3-carbonitrile

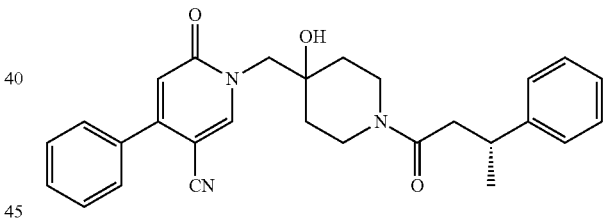

A reaction tube was charged with (R)-5-bromo-1-((4-hydroxy-1-(3-phenylbutanoyl)piperidin-4-yl)methyl)-4-phenylpyridin-2(1H)-one (25 mg, 49.1 μmol), zinc cyanide (11.5 mg, 98.1 μmol) and DMF (0.5 mL) before being degassed by bubbling N$_2$ through the mixture for 5 min. Pd(PPh$_3$)$_4$ (6.8 mg, 5.89 μmol) was added and the reaction was heated at 95° C. for 20 h. Further zinc cyanide (11.5 mg, 98.1 μmol) and Pd(PPh$_3$)$_4$(6.8 mg, 5.89 μmol) were added and the reaction mixture heated at 95° C. for a further 3 days. Additional Pd(PPh$_3$)$_4$(6.8 mg, 5.89 μmol) was added to the mixture and the reaction heated at 95° C. for 5 h. The reaction mixture was allowed to cool to RT and quenched by the addition of NH$_4$OH$_{(aq)}$ (20 mL). The resulting mixture was extracted with EtOAc (20 mL), the organic layer was dried over Na$_2$SO$_4$, concentrated in vacuo, and the residue purified by flash chromatography (GraceResolv silica 4 g cartridge, 0-100% EtOAc in cyclohexane; then GraceResolv silica 4 g cartridge, 0-50% EtOAc in cyclohexane) to give the title compound (6.3 mg, 28%) as an off-white solid. LCMS (Method B): R$_T$=1.19 min, m/z=456 [M+H]$^+$. $^1$H NMR (400 MHz, methanol-d$_4$): δ 8.39-8.25 (m, 1H), 7.73-

7.39 (m, 5H), 7.39-7.14 (m, 5H), 6.59 (s, 1H), 4.28-4.03 (m, 2H), 4.03-3.86 (m, 1H), 3.73-3.60 (m, 1H), 3.28-3.15 (m, 2H), 3.08-2.89 (m, 1H), 2.86-2.70 (m, 1H), 2.65-2.46 (m, 1H), 1.68-1.24 (m, 6H), 0.98-0.82 (m, 1H).

Example 115: (R)-1-((4-Hydroxy-1-(3-phenylbutanoyl)piperidin-4-yl)methyl)-N-(2-hydroxyethyl)-6-oxo-4-phenyl-1,6-dihydropyridine-3-carboxamide

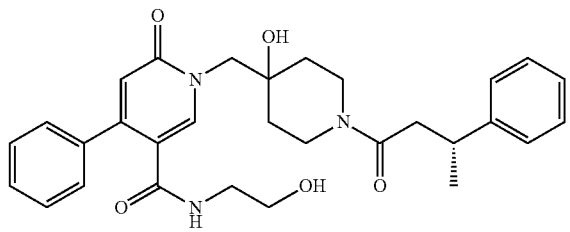 [SMILES: C[C@H](CC(=O)N1CCC(O)(Cn2cc(C(=O)NCCO)c(-c3ccccc3)cc2=O)CC1)c1ccccc1]

Prepared according to General Procedure 5 using (R)-1-((4-hydroxy-1-(3-phenylbutanoyl)piperidin-4-yl)methyl)-6-oxo-4-phenyl-1,6-dihydropyridine-3-carboxylic acid (40 mg, 0.084 mmol), 2-hydroxyethylamine (6.7 mg, 0.110 mmol), DIPEA (0.06 mL, 0.337 mmol) and HBTU (35 mg, 0.093 mmol) in DCM (1 mL) to give the title compound (14 mg, 32%). LCMS (Method B): $R_T$=0.96 min, m/z=518 [M+H]$^+$. $^1$H NMR (400 MHz, DMSO-d6): δ 8.06 (dt, 1H), 7.85 (d, 1H), 7.44-7.34 (m, 5H), 7.32-7.24 (m, 4H), 7.21-7.14 (m, 1H), 6.35 (d, 1H), 5.01 (d, 1H), 4.66 (t, 1H), 4.10-3.84 (m, 3H), 3.73-3.62 (m, 1H), 3.40-3.24 (m, 2H), 3.24-3.07 (m, 4H), 2.96-2.83 (m, 1H), 2.66-2.53 (m, 2H), 1.59-1.11 (m, 7H).

Example 116: 1-((4-Hydroxy-1-((R)-3-phenylbutanoyl)piperidin-4-yl)methyl)-5-((S)-2-methylpyrrolidine-1-carbonyl)-4-phenylpyridin-2(1H)-one

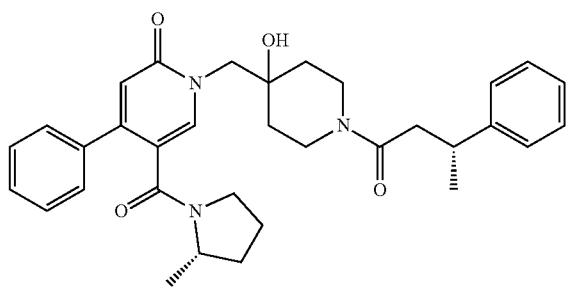 [SMILES: C[C@H](CC(=O)N1CCC(O)(Cn2cc(C(=O)N3CCC[C@@H]3C)c(-c3ccccc3)cc2=O)CC1)c1ccccc1]

A solution of Intermediate 1 (15 mg, 0.026 mmol) and (S)-2-methylpyrrolidine (2.64 mg, 0.031 mmol) in DMF (0.6 mL) was agitated using a BioShake IQ at RT for 2 h. The reaction mixture was concentrated. The residue was diluted with DCM (0.3 mL) and water (0.5 mL). The organic layer was dried (Biotage phase separator) and concentrated to give the title compound (11 mg, 78%). LCMS (Method A): $R_T$=1.33 min, m/z=542 [M+H]$^+$.

Example 117: (R)-1-((4-Hydroxy-1-(3-phenylbutanoyl)piperidin-4-yl)methyl)-5-(4-(hydroxymethyl)piperidine-1-carbonyl)-4-phenylpyridin-2(1H)-one

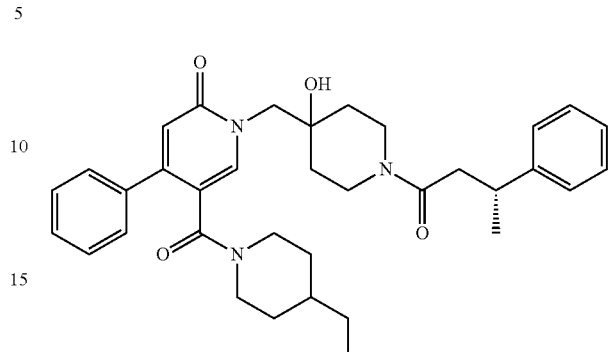

A solution of Intermediate 1 (15 mg, 0.026 mmol) and piperidin-4-ylmethanol (3.6 mg, 0.031 mmol) in DMF (0.6 mL) was agitated using a BioShake IQ at RT for 2 h. The reaction mixture was concentrated. The residue was diluted with DCM (0.3 mL) and water (0.5 mL). The organic layer was dried (Biotage phase separator) and concentrated to give the title compound (10 mg, 68%). LCMS (Method A): $R_T$=1.05 min, m/z=572 [M+H]$^+$.

Example 118: 3-((1-(2-(Cyclohexylmethyl)butanoyl)-4-hydroxy-3,3-dimethylpiperidin-4-yl)methyl)-6-(2-fluorophenyl)pyrimidin-4(3H)-one

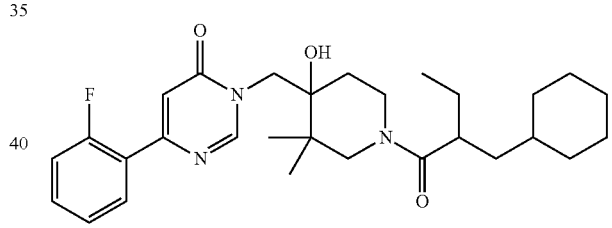

Prepared according to General Procedure 12 using 2-(cyclohexylmethyl)butanoic acid (8.3 mg, 0.043 mmol), HATU (20.6 mg, 0.054 mmol), DIPEA (15 µL, 0.087 mmol) and 6-(2-fluorophenyl)-3-((4-hydroxy-3,3-dimethylpiperidin-4-yl)methyl)pyrimidin-4(3H)-one (12 mg, 0.036 mmol) in DMF (0.6 mL) to give the title compound (6 mg, 33%). LCMS (Method A): $R_T$=2.01 min, m/z=498 [M+H]$^+$.

Example 119: 3-((7-((R)-3-Cyclohexyl-2-methylpropanoyl)-10-hydroxy-7-azaspiro[4.5]decan-10-yl)methyl)-6-(2-fluorophenyl)pyrimidin-4(3H)-one

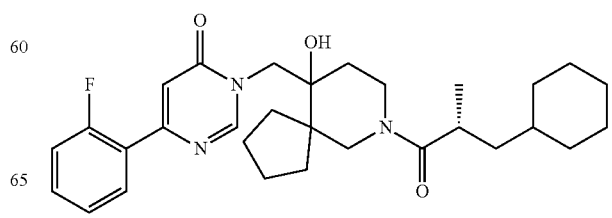

Step 1: tert-Butyl 10-((4-(2-fluorophenyl)-6-oxopy-rimidin-1(6H)-yl)methyl)-10-hydroxy-7-azaspiro[4.5]decane-7-carboxylate Prepared according to General Procedure 1 using 6-(2-fluorophenyl)pyrimidin-4(3H)-one (65.2 mg, 0.343 mmol), tert-butyl 1-oxa-10-azadispiro[2.0.4⁴.4³]dodecane-10-carboxylate (Epoxide 6) (110 mg, 0.411 mmol) and cesium carbonate (145 mg, 0.446 mmol) in DMF (2 mL) at 90° C. for 16 h. The residue was purified by slurry 1:1 EtOAc/cyclohexane to give the title compound (90 mg, 57%). LCMS (Method B): $R_T$=1.47 min, m/z=402 [M-butene+H]⁺.

Step 2: 6-(2-Fluorophenyl)-3-((10-hydroxy-7-azaspiro[4.5]decan-10-yl)methyl)pyrimidin-4(3H)-one hydrochloride Prepared according to General Procedure 9 using tert-butyl 10-((4-(2-fluorophenyl)-6-oxopyrimidin-1 (6H)-yl) methyl)-10-hydroxy-7-azaspiro[4.5]decane-7-carboxylate (90 mg, 0.20 mmol) and hydrogen chloride (4 M in 1,4-dioxane, 0.69 mL, 2.75 mmol) in DCM (1 mL) to give the title compound (75 mg, 97%) which was used without further purification.

Step 3: 3-((7-((R)-3-Cyclohexyl-2-methylpro-panoyl)-10-hydroxy-7-azaspiro[4.5]decan-10-yl) methyl)-6-(2-fluorophenyl)pyrimidin-4(3H)-one Prepared according to General Procedure 5 using 6-(2-fluorophenyl)-3-((10-hydroxy-7-azaspiro[4.5]decan-10-yl) methyl)pyrimidin-4(3H)-one hydrochloride (25 mg, 0.063 mmol), Acid 1 (17 mg, 0.095 mmol), HBTU (0.036 g, 0.095 mmol) and DIPEA (0.033 mL, 0.19 mmol) in DCM (1 mL). The crude product was purified by flash chromatography (GraceResolv 4 g, 20-100% EtOAc in cyclohexane) to give the title compound (22 mg, 68%). LCMS (Method B): $R_T$=1.62 min, m/z=510 [M+H]⁺. ¹H NMR (400 MHz, DMSO-d₆): δ 8.49 (s, 1H), 8.04 (t, 1H), 7.56 (q, 1H), 7.40-7.32 (m, 2H), 6.82 (s, 1H), 4.96-4.86 (m, 1H), 4.68-4.53 (m, 1H), 4.10 (q, 1H), 3.75-3.58 (m, 2H), 3.57-3.21 (m, 2H), 2.97-2.79 (m, 1H), 2.05-1.83 (m, 1H), 1.78-1.02 (m, 20H), 1.00-0.91 (m, 3H), 0.90-0.76 (m, 2H).

Example 120: 1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide

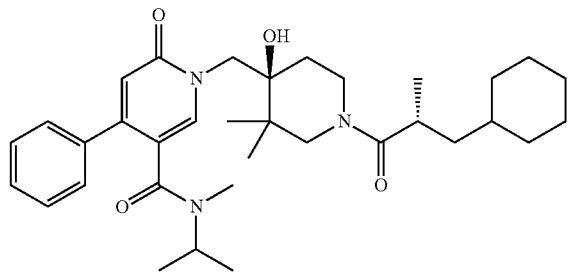 [SMILES: CC(C)N(C)C(=O)c1cn(C[C@]2(O)CCN(C(=O)[C@H](C)CC3CCCCC3)CC2(C)C)c(=O)cc1-c1ccccc1]

Prepared according to General Procedure 5 using Acid 4 (20 mg, 39.3 μmol), N-methylpropan-2-amine (8 μL, 78.6 μmol), HBTU (22.4 mg, 59.0 μmol) and DIPEA (10 μL, 59.0 μmol) in DCM (0.7 mL) for 3 days at RT to give the title compound (9.0 mg, 40%) as a white solid. LCMS (Method B): $R_T$=1.54 min, m/z=564 [M+H]⁺. ¹H NMR (500 MHz, CDCl₃): δ 7.51-7.32 (m, 6H), 6.71-6.64 (m, 1H), 5.10-5.06 (m, 0.25H), 4.84-4.44 (m, 2.75H), 4.08-3.17 (m, 4H), 3.04-2.77 (m, 2H), 2.71-2.67 (m, 1.5H), 2.27 (br d, 1.5H), 1.86-1.60 (m, 6H), 1.54-1.30 (m, 1H), 1.30-0.60 (m, 21.5H), 0.29-0.20 (m, 1.5H).

Example 121: 1-(((S)-1-((R)-3-Cyclohexyl-2-methylpropanoyl)-4-hydroxy-3,3-dimethylpiperidin-4-yl) methyl)-N,N-dimethyl-6-oxo-4-phenyl-1,6-dihydro-pyridine-3-carboxamide

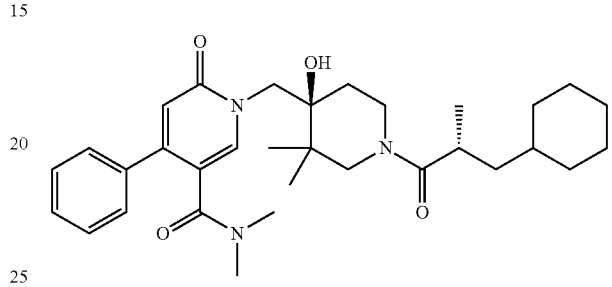

DIPEA (0.052 mL, 0.295 mmol) was added to a stirred solution of Acid 4 (50.0 mg, 0.0983 mmol), dimethylamine (2M in THF) (0.098 mL, 0.197 mmol) and HATU (44.9 mg, 0.118 mmol) in DCM (2.0 mL) at RT. After 2 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography using a KP-NH 11 g column (0-100%, EtOAc in cyclohexane) and freeze-dried to give the title compound (42.5 mg, 80%) as a white solid. LCMS (Method A): $R_T$=1.52 min, m/z=536 [M+H]⁺. ¹H NMR (500 MHz, DMSO-d₆): δ 7.81 (d, 1H), 7.47-7.34 (m, 5H), 6.45 (d, 1H), 4.93 (d, 1H), 4.42 (dd, 1H), 4.15-3.35 (m, 2H), 3.26 (apparent t, 1H, overlapping solvent peak), 3.05-2.80 (m, 2H), 2.75 (s, 3H), 2.62 (s, 3H, overlapping solvent peak), 1.79-1.40 (m, 7H), 1.30-0.71 (m, 18H).

Example 122: 1-(((R)-1-((R)-3-Cyclohexyl-2-methylpropanoyl)-4-hydroxy-3,3-dimethylpiperidin-4-yl) methyl)-N,N-dimethyl-6-oxo-4-phenyl-1,6-dihydro-pyridine-3-carboxamide

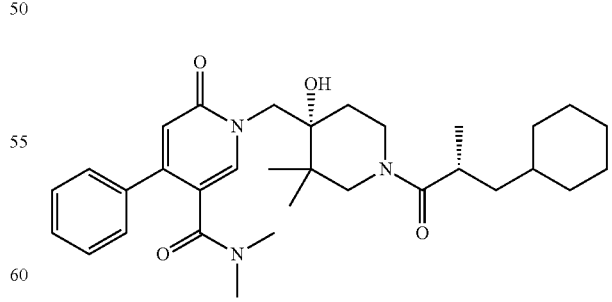

The title compound was prepared in the same way as Example 121 except using the first eluted compound from the chiral separation of ethyl 1-((1-(tert-butoxycarbonyl)-4-hydroxy-3,3-dimethylpiperidin-4-yl)methyl)-4-chloro-6-oxo-1,6-dihydropyridine-3-carboxylate (Amine 7, Step 2)

and following the steps for Acid 4 to prepare the analogous diastereoisomer 1-(((R)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylic acid, followed by an analogous coupling reaction to that described for the diastereoisomeric compound in Example 121 to yield the title compound as a white solid. LCMS (Method A): $R_T$=1.51 min, m/z=536 [M+H]$^+$. $^1$H NMR (500 MHz, DMSO-d$_6$): δ 7.81 (s, 1H), 7.47-7.20 (m, 5H), 6.45 (d, 1H), 4.92 (d, 1H), 4.44 (dd, 1H), 4.06-3.66 (m, 2H), 3.31-3.16 (m, 1H, overlapping solvent peak), 3.04-2.83 (m, 2H), 2.75 (s, 3H), 2.62 (s, 3H, overlapping solvent peak), 1.80-1.37 (m, 7H), 1.30-0.75 (m, 18H).

Example 123: 1-(((S)-1-((R)-3-Cyclohexyl-2-methylpropanoyl)-4-hydroxy-3,3-dimethylpiperidin-4-yl)methyl)-4-phenyl-5-(pyrrolidine-1-carbonyl)pyridin-2(1H)-one

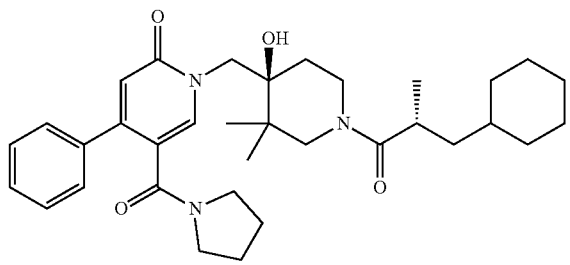 [SMILES: C[C@H](CC1CCCCC1)C(=O)N1CC[C@@](O)(Cn2cc(C(=O)N3CCCC3)c(-c3ccccc3)cc2=O)C(C)(C)C1]

Prepared according to General Procedure 5 using Acid 4 (20 mg, 39.3 μmol), pyrrolidine (6.5 μL, 78.6 μmol), HBTU (22.4 mg, 59.0 μmol) and DIPEA (10 μL, 59.0 μmol) in DCM (0.7 mL) for 3 days at RT to give the title compound (5.2 mg, 23%) as a white solid. LCMS (Method B): $R_T$=1.46 min, m/z=562 [M+H]$^+$. $^1$H NMR (500 MHz, CDCl$_3$): δ 7.51-7.39 (m, 6H), 6.70-6.68 (m, 1H), 4.99-4.90 (m, 0.5H), 4.73 (br d, 0.5H), 4.66-4.56 (m, 1H), 4.51 (br d, 0.5H), 4.02 (br d, 0.5H), 3.78 (br d, 1H), 3.62 (br d, 0.5H), 3.50-3.26 (m, 3H), 3.23 (br d, 0.5H), 3.03-2.65 (m, 3H), 1.85-1.60 (m, assume 8H, overlapping solvent), 1.51-1.34 (m, 3H), 1.30-1.00 (m, 16H), 0.93-0.78 (m, 2H).

Example 124: 1-(((S)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one

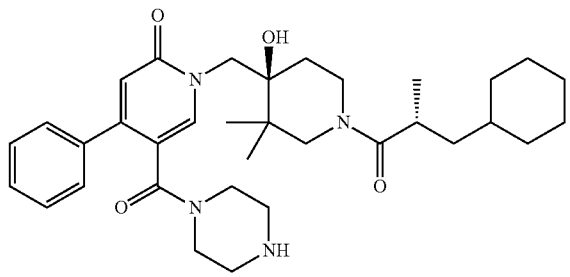

Step 1: tert-Butyl 4-(1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)piperazine-1-carboxylate DIPEA (0.26 mL, 1.47 mmol) was added to a stirred solution of Acid 3 (250 mg, 0.492 mmol), tert-butylpiperazine-1-carboxylate (91.5 mg, 0.492 mmol) and HATU (224 mg, 0.589 mmol) in DCM (5.0 mL) at RT. After 2 h, saturated sodium bicarbonate (aq) solution and further DCM were added and the resulting biphasic mixture was separated, extracted using DCM (×2), the combined organic phase was dried (phase separator), the solvents were removed in vacuo, and the remaining residue was purified by flash chromatography (cyclohexane; 0-10%, MeOH in DCM) to give the crude title compound (451 mg, >100%) as a pale yellow oil that was carried through to the next step without further purification. LCMS (Method A): $R_T$=1.78 min, m/z=677 [M+H]$^+$.

Step 2: 1-(((S)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one TFA (2.0 mL, 26.0 mmol) was added to a stirred solution of tert-butyl 4-(1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)piperazine-1-carboxylate (assumed 333 mg, 0.492 mmol) in DCM (2.0 mL) at RT. After 1 h, the solvents were removed in vacuo and the remaining residue was loaded onto a pre-equilibrated SCX-2 cartridge in MeOH solution, washed using MeOH and eluted using 7 N ammonia in MeOH solution. The solvents were removed in vacuo and the remaining residue was purified by flash chromatography (cyclohexane, then 0-10% MeOH in DCM) and freeze-dried to give 1-((1-((R)-3-cyclohexyl-2-methylpropanoyl)-4-hydroxy-3,3-dimethylpiperidin-4-yl)methyl)-4-phenyl-5-(piperazine-1-carbonyl)pyridin-2(1H)-one (180 mg, white solid). The mixture of diastereoisomers was separated by chiral supercritical fluid chromatography using a Chiralpak AS-H (20 mm×250 mm, 5 μm) column with isocratic solvent conditions: 25:75 MeOH/CO$_2$ (0.1% v/v NH$_3$). The first eluted sample was freeze-dried to yield the title compound (54.8 mg, 19%) as a white solid. LCMS (Method A): $R_T$=1.03 min, m/z=577 [M+H]$^+$. Chiral purity (Method C): $R_T$=2.29 min, 99.8% ee. $^1$H NMR (500 MHz, DMSO-d$_6$): δ 7.80 (br s, 1H), 7.51-7.34 (m, 5H), 6.49-6.40 (m, 1H), 5.06-4.74 (m, 1H), 4.54-4.28 (m, 1H), 4.17-3.35 (m, 3H), 3.31-2.23 (m, 10H, overlapping solvent peak), 1.95-1.39 (m, 8H), 1.31-0.71 (m, 18H).

Example 125: 1-(((R)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one

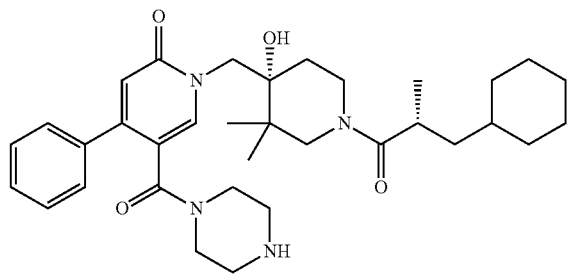 [SMILES: C[C@H](CC1CCCCC1)C(=O)N1CC[C@](O)(Cn2cc(C(=O)N3CCNCC3)c(-c3ccccc3)cc2=O)C(C)(C)C1]

The title compound was isolated as the second eluted compound from the chiral chromatography of 1-((1-((R)-3-cyclohexyl-2-methylpropanoyl)-4-hydroxy-3,3-dimethylpiperidin-4-yl)methyl)-4-phenyl-5-(piperazine-1-carbonyl)pyridin-2(1H)-one that is described in Example 124, Step 2. The material was freeze-dried to give the title compound (54.1 mg, 19%) as a white solid. LCMS (Method A): $R_T$=1.00 min, m/z=577 [M+H]$^+$. Chiral purity (Method C): $R_T$=2.87 min, 99.6% ee. $^1$H NMR (500 MHz, DMSO-d$_6$): δ 7.80 (br s, 1H), 7.51-7.34 (m, 5H), 6.49-6.39 (m, 1H), 5.07-4.73 (m, 1H), 4.50-4.35 (m, 1H), 4.08-3.35 (m, 3H), 3.31-2.20 (m, 10H, overlapping solvent peak), 2.04-1.37 (m, 8H), 1.33-0.61 (m, 18H).

Example 126: 3-((1-(2-(Cyclohexyloxy)propanoyl)-4-hydroxy-3,3-dimethylpiperidin-4-yl)methyl)-6-(2-fluorophenyl)pyrimidin-4(3H)-one

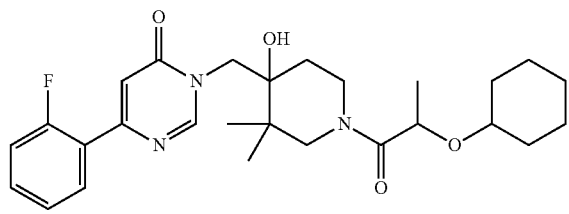 [SMILES: CC(OC1CCCCC1)C(=O)N1CCC(O)(Cn2cnc(-c3ccccc3F)cc2=O)C(C)(C)C1]

Prepared according to General Procedure 3 using Amine 5 (25 mg, 75.4 µmol), 2-(cyclohexyloxy)propanoic acid (14.3 mg, 83.0 µmol), HATU (34.4 mg, 90.5 µmol) and DIPEA (40 µL, 0.226 mmol) in DCM (1 mL) to give the title compound (23 mg, 62%). LCMS (Method A): $R_T$=1.53 min, m/z=486 [M+H]$^+$. $^1$H NMR (500 MHz, DMSO-d$_6$): δ 8.45 (s, 1H), 8.06-8.00 (m, 1H), 7.59-7.51 (m, 1H), 7.39-7.32 (m, 2H), 6.81 (s, 1H), 4.90 (s, 1H), 4.59-4.34 (m, 2H), 4.14-3.86 (m, 1H), 3.78-3.57 (m, 2H), 3.41-2.74 (m, 3H (signal overlaps with HDO)), 1.90-1.41 (m, 6H), 1.36-0.90 (m, 15H).

Example 127: 1-((7-((R)-3-Cyclohexyl-2-methylpropanoyl)-10-hydroxy-7-azaspiro[4.5]decan-10-yl)methyl)-N,N-dimethyl-6-oxo-1,6-dihydropyridine-3-carboxamide

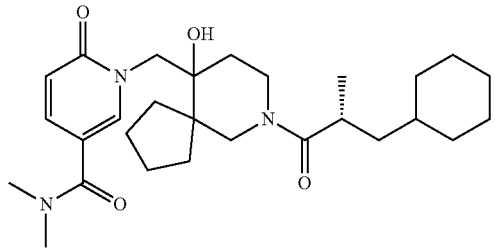 [SMILES: C[C@H](CC1CCCCC1)C(=O)N1CCC(O)(Cn2cc(C(=O)N(C)C)ccc2=O)C2(CCCC2)C1]

Step 1: 1-((7-(tert-Butoxycarbonyl)-10-hydroxy-7-azaspiro[4.5]decan-10-yl)methyl)-6-oxo-1,6-dihydropyridine-3-carboxylic acid Cesium carbonate (183 mg, 0.56 mmol) was added to a stirred solution of methyl 6-oxo-1,6-dihydropyridine-3-carboxylate (68.7 mg, 0.45 mmol) (commercially available) and tert-butyl 1-oxa-10-azadispiro[2.0.4$^4$.4$^3$]dodecane-10-carboxylate (Epoxide 6) (100 mg, 0.37 mmol) in DMF (1.0 mL) at RT under nitrogen. The temperature was increased to 80° C. After 50 h, the temperature was increased to 100° C. due to incomplete reaction. After a further 24 h, the reaction mixture was diluted with 1:1 brine/water and diethyl ether, the resulting biphasic mixture was separated. The aqueous layer was acidified using 2 M HCl (aq) solution, which caused a white ppt to crash out of solution. EtOAc was added and the mixture was shaken and settled. The resulting biphasic mixture was separated, extracting using further EtOAc. The combined organic phase was washed with saturated sodium bicarbonate (aq) solution. The aqueous phase was carefully acidified to pH 1-2 and extracted using EtOAc (×3), dried (phase separator) and the solvents were removed in vacuo to give the title compound (90.8 mg, 60%). LCMS (Method A): $R_T$=1.26 min, m/z=407 [M+H]$^+$.

Step 2: tert-Butyl 10-((5-(dimethylcarbamoyl)-2-oxopyridin-1(2H)-yl)methyl)-10-hydroxy-7-azaspiro[4.5]decane-7-carboxylate DIPEA (0.12 mL, 0.67 mmol) was added to a stirred solution of 1-((7-(tert-butoxycarbonyl)-10-hydroxy-7-azaspiro[4.5]decan-10-yl)methyl)-6-oxo-1,6-dihydropyridine-3-carboxylic acid (90.8 mg, 0.22 mmol), 2 M dimethylamine in THF (0.17 mL, 0.34 mmol) and HATU (84.9 mg, 0.22 mmol) in DCM (5.0 mL) at RT. After 18 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography using a 24 g Grace column (0-100%, EtOAc in cyclohexane; then 0-5%, MeOH in DCM) to give the title compound (76.9 mg, 79%) as a white solid. LCMS (Method A): $R_T$=1.22 min, m/z=434 [M+H]$^+$.

Step 3: 1-((10-Hydroxy-7-azaspiro[4.5]decan-10-yl)methyl)-N,N-dimethyl-6-oxo-1,6-dihydropyridine-3-carboxamide TFA (0.5 mL, 6.49 mmol) was added to a stirred solution of tert-butyl 10-((5-(dimethylcarbamoyl)-2-oxopyridin-1

(2H)-yl)methyl)-10-hydroxy-7-azaspiro[4.5]decane-7-carboxylate (76.9 mg, 0.18 mmol) in DCM (2.0 mL) at RT. After 30 min, the reaction mixture was loaded onto a pre-equilibrated SCX-2 cartridge, washed using MeOH and eluted using 7 N ammonia in MeOH. The eluted solution was concentrated in vacuo to give the crude title compound (62.5 mg, >100%) that was carried through to the next step without further purification. LCMS (Method A): $R_T$=0.40 min, m/z=334 [M+H]$^+$.

Step 4: 1-((7-((R)-3-Cyclohexyl-2-methylpropanoyl)-10-hydroxy-7-azaspiro[4.5]decan-10-yl)methyl)-N,N-dimethyl-6-oxo-1,6-dihydropyridine-3-carboxamide DIPEA (0.021 mL, 0.12 mmol) was added to a stirred solution of 1-((10-hydroxy-7-azaspiro[4.5]decan-10-yl)methyl)-N,N-dimethyl-6-oxo-1,6-dihydropyridine-3-carboxamide (20.0 mg, 0.060 mmol), Acid 1 (10.2 mg, 0.060 mmol) and HATU (27.4 mg, 0.072 mmol) in DCM (1.0 mL) at RT under nitrogen. After 2 h, the reaction mixture was diluted with saturated sodium bicarbonate (aq) solution and extracted into DCM (×3). The combined organic phases were dried (phase separator), the solvents were removed in vacuo and the remaining residue was purified by flash chromatography (0-5%, MeOH in DCM) and freeze-dried to give the title compound (25.7 mg, 88%) as a white solid. LCMS (Method A): $R_T$=1.46 min, m/z=486 [M+H]$^+$. $^1$H NMR (500 MHz, DMSO-d$_6$): δ 7.98-7.93 (m, 1H), 7.56-7.51 (m, 1H), 6.45-6.39 (m, 1H), 4.91-4.80 (m, 1H), 4.74-4.52 (m 1H), 3.90-2.78 (m, 11H, overlapping solvent peak), 2.00-1.80 (m, 1H), 1.77-0.75 (m, 26H).

Example 128:1-((1-((R)-3-Cyclobutyl-2-methylpropanoyl)-4-hydroxy-3,3-dimethylpiperidin-4-yl)methyl)-N,N-dimethyl-6-oxo-4-phenyl-1,6-dihydropyridine-3-carboxamide

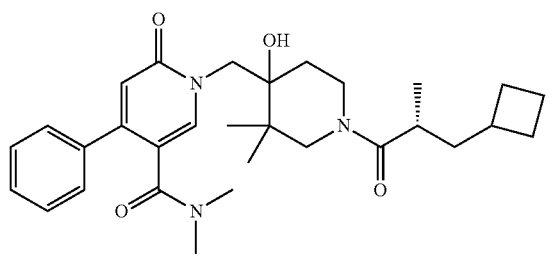 [SMILES: C[C@H](CC1CCC1)C(=O)N1CCC(O)(Cn2cc(C(=O)N(C)C)c(-c3ccccc3)cc2=O)C(C)(C)C1]

Prepared according to General Procedure 3 using Amine 6 (20 mg, 47.6 μmol), Acid 5 (9.6 mg, 57.2 μmol), HATU (22 mg, 57.2 μmol), DIPEA (33 μL, 0.191 mmol) and DCM (1 mL) to give the title compound (15.2 mg, 62%) as a colourless solid after lyophilisation. LCMS (Method A): $R_T$=1.41 min, m/z=508 [M+H]$^+$. $^1$H NMR (500 MHz, DMSO-d$_6$): δ 7.85-7.78 (m, 1H), 7.57-7.27 (m, 5H), 6.48-6.42 (m, 1H), 4.97-4.87 (m, 1H), 4.48-4.37 (m, 1H), 4.10-4.01 (m, 0.6H), 3.86-3.63 (m, 2.4H), 3.28-3.19 (m, 1H), 2.98-2.86 (m, 1H), 2.85-2.66 (m, 1H), 2.75 (s, 3H), 2.62 (s, 3H), 2.26-2.13 (m, 1H), 2.02-1.87 (m, 2H), 1.84-1.47 (m, 6H), 1.39-1.10 (m, 3H), 1.06-0.87 (m, 8H).

Example 129: 1-((1-((R)-3-Cyclopropyl-2-methylpropanoyl)-4-hydroxy-3,3-dimethylpiperidin-4-yl)methyl)-N,N-dimethyl-6-oxo-4-phenyl-1,6-dihydropyridine-3-carboxamide

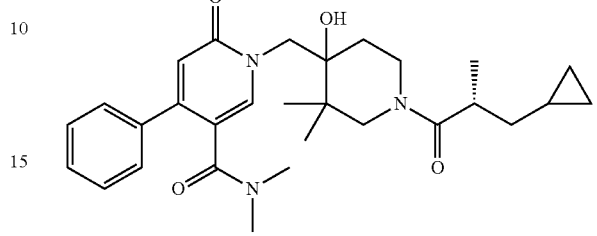

Prepared according to General Procedure 3 using Amine 6 (20 mg, 47.6 μmol), Acid 6 (8.4 mg, 57.2 μmol), HATU (22 mg, 57.2 μmol), DIPEA (33 μL, 0.191 mmol) and DCM (1 mL) to give the title compound (15.1 mg, 63%) as a colourless solid after lyophilisation. LCMS (Method A): $R_T$=1.38 min, m/z=494 [M+H]$^+$. $^1$H NMR (500 MHz, DMSO-d$_6$): δ 7.84-7.79 (m, 1H), 7.54-7.29 (m, 5H), 6.48-6.43 (m, 1H), 4.96-4.88 (m, 1H), 4.49-4.37 (m, 1H), 4.12-4.05 (m, 0.6H), 3.85-3.65 (m, 2.4H), 3.39-3.22 (m, 1H (signal overlaps with HDO)), 3.03-2.87 (m, 2H), 2.75 (s, 3H), 2.62 (s, 3H), 1.77-1.54 (m, 2H), 1.54-1.38 (m, 1H), 1.24-0.93 (m, 10H), 0.68-0.57 (m, 1H), 0.42-0.29 (m, 2H), 0.08-–0.06 (m, 2H).

Example 130: 1-((1-((R)-3-Cyclohexyl-2-methylpropanoyl)-4-hydroxy-3,3-dimethylpiperidin-4-yl)methyl)-[4,5'-bipyrimidin]-6(1H)-one

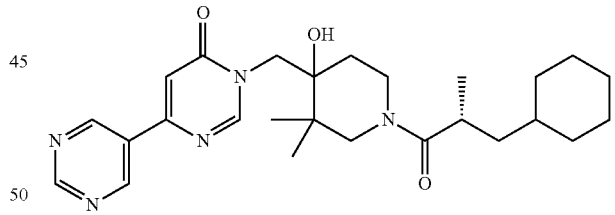

Prepared according to General Procedure 4 using Intermediate 3 (30 mg, 70.8 μmol), pyrimidin-5-ylboronic acid (13.2 mg, 0.106 mmol), tetrakis(triphenylphosphine)palladium(0) (4.09 mg, 3.50 μmol), sodium carbonate (15.0 mg, 0.142 mmol), 1,4-dioxane (0.5 mL) and water (0.2 mL). The reaction was heated under microwave irradiation at 150° C. for 10 min to give the title compound (21 mg, 62%). LCMS (Method A): $R_T$=1.40 min, m/z=468 [M+H]$^+$. $^1$H NMR (500 MHz, DMSO-d$_6$): δ 9.42 (s, 2H), 9.30 (s, 1H), 8.50 (s, 1H), 7.29-7.23 (m, 1H), 4.90-4.85 (m, 1H), 4.51-4.38 (m, 2H), 3.81-3.62 (m, 2H), 3.35-3.13 (m, 1H (signal overlaps with HDO)), 3.03-2.76 (m, 2H), 1.76-1.36 (m, 7H), 1.27-0.73 (m, 17H).

Example 131: 3-((1-((R)-3-Cyclohexyl-2-methyl-propanoyl)-4-hydroxy-3,3-dimethylpiperidin-4-yl)methyl)-6-(1-methyl-1H-pyrazol-5-yl)pyrimidin-4(3H)-one

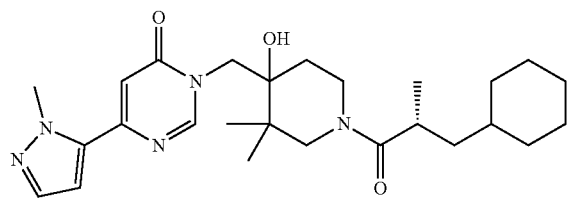 [SMILES: C[C@H](CC1CCCCC1)C(=O)N1CCC(O)(Cn2cnc(-c3ccnn3C)cc2=O)C(C)(C)C1]

Prepared according to General Procedure 4 using Intermediate 3 (30 mg, 70.8 μmol), 1-methyl-5-(4,4,5,5-tetramethyl-1,3,2-dioxaborolan-2-yl)-1H-pyrazole (22.1 mg, 0.106 mmol), tetrakis(triphenylphosphine)palladium(0) (4.09 mg, 3.50 μmol), sodium carbonate (15.0 mg, 0.142 mmol), 1,4-dioxane (0.5 mL) and water (0.2 mL). The reaction was heated under microwave irradiation at 150° C. for 10 min to give the title compound (10 mg, 33%). LCMS (Method A): $R_T$=1.52 min, m/z=470 [M+H]$^+$. $^1$H NMR (500 MHz, DMSO-d$_6$): δ 8.43 (s, 1H), 7.49 (s, 1H), 6.87 (s, 1H), 6.82-6.78 (m, 1H), 4.89-4.84 (bs, 1H), 4.48-4.34 (m, 1H), 4.13 (s, 3H), 3.80-3.62 (m, 2H), 3.29-3.15 (m, 1H (signal overlaps with HDO)), 3.02-2.76 (m, 2H), 1.75-1.39 (m, 7H), 1.28-0.75 (m, 18H).

Example 132: 3-((1-((R)-3-Cyclohexyl-2-methyl-propanoyl)-4-hydroxy-3,3-dimethylpiperidin-4-yl)methyl)-6-(1H-pyrazol-4-yl)pyrimidin-4(3H)-one

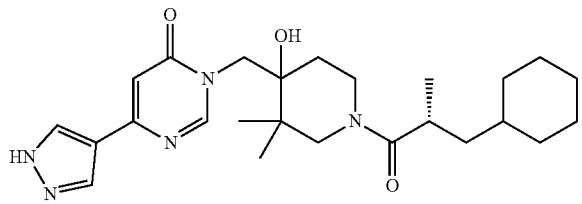 [SMILES: C[C@H](CC1CCCCC1)C(=O)N1CCC(O)(Cn2cnc(-c3cn[nH]c3)cc2=O)C(C)(C)C1]

Prepared according to General Procedure 4 using Intermediate 3 (30 mg, 70.8 μmol), 4-(4,4,5,5-tetramethyl-1,3,2-dioxaborolan-2-yl)-1H-pyrazole (20.6 mg, 0.106 mmol), tetrakis(triphenylphosphine)palladium(0) (4.09 mg, 3.50 μmol), sodium carbonate (15.0 mg, 0.142 mmol), 1,4-dioxane (0.5 mL) and water (0.2 mL). The reaction was heated under microwave irradiation at 150° C. for 15 min to give the title compound (19 mg, 58%). LCMS (Method A): $R_T$=1.32 min, m/z=456 [M+H]$^+$. $^1$H NMR (500 MHz, DMSO-d$_6$): δ 13.20 (s, 1H), 8.45-7.94 (bs, 2H), 8.31 (s, 1H), 6.73-6.68 (m, 1H), 4.91-4.84 (bs, 1H), 4.46-4.31 (m, 1H), 3.79-3.58 (m, 2H), 3.30-3.14 (m, 2H (signal overlaps with HDO)), 3.02-2.76 (m, 2H), 1.76-1.38 (m, 7H), 1.25-0.74 (m, 17H).

Example 133: 3-((1-((R)-3-Cyclohexyl-2-methyl-propanoyl)-4-hydroxy-3,3-dimethylpiperidin-4-yl)methyl)-6-(1H-pyrazol-5-yl)pyrimidin-4(3H)-one

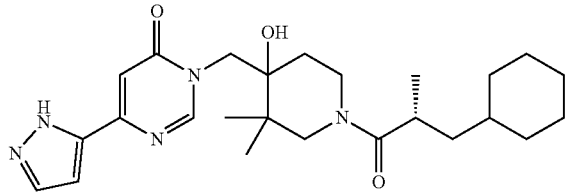 [SMILES: C[C@H](CC1CCCCC1)C(=O)N1CCC(O)(Cn2cnc(-c3ccn[nH]3)cc2=O)C(C)(C)C1]

Prepared according to General Procedure 4 using Intermediate 3 (30 mg, 70.8 μmol), (1H-pyrazol-5-yl)boronic acid (11.9 mg, 0.106 mmol), tetrakis(triphenylphosphine)palladium(0) (4.09 mg, 3.50 μmol), sodium carbonate (15.0 mg, 0.142 mmol), 1,4-dioxane (0.5 mL) and water (0.2 mL). The reaction was heated under microwave irradiation at 150° C. for 15 min to give the title compound (8 mg, 24%). LCMS (Method A): $R_T$=1.36 min, m/z=456 [M+H]$^+$. $^1$H NMR (500 MHz, DMSO-d$_6$): δ 13.70-13.13 (bs, 1H), 8.38 (s, 1H), 7.93-7.53 (bs, 1H), 6.98-6.74 (bs, 2H), 4.91-4.85 (bs, 1H), 4.53-4.33 (m, 1H), 3.80-3.58 (m, 2H), 3.34-3.13 (m, 2H (signal overlaps with HDO)), 3.03-2.75 (m, 2H), 1.75-1.38 (m, 7H), 1.28-0.73 (m, 17H).

Example 134: 3-((7-((R)-3-Cyclohexyl-2-methyl-propanoyl)-10-hydroxy-7-azaspiro[4.5]decan-10-yl)methyl)pyrimidin-4(3H)-one

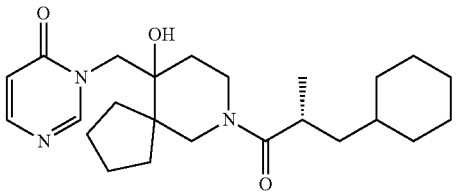 [SMILES: C[C@H](CC1CCCCC1)C(=O)N1CCC(O)(Cn2cnccc2=O)C2(CCCC2)C1]

Step 1: tert-Butyl 10-hydroxy-10-((6-oxopyrimidin-1(6H)-yl)methyl)-7-azaspiro[4.5]decane-7-carboxylate Prepared according to General Procedure 1 using pyrimidin-4(3H)-one (30 mg, 0.312 mmol), Epoxide 6 (100 mg, 0.375 mmol) and cesium carbonate (52.6 mg, 0.468 mmol) in DMF (1.8 mL), heated to 80° C. for 24 h to give the title compound (37 mg, 32%). LCMS (Method A): $R_T$=1.22 min, m/z=308 [M-butene+H]$^+$.

Step 2: 3-((10-Hydroxy-7-azaspiro[4.5]decan-10-yl)methyl)pyrimidin-4(3H)-one

Prepared according to General Procedure 7 using tert-butyl 10-hydroxy-10-((6-oxopyrimidin-1(6H)-yl)methyl)-7-azaspiro[4.5]decane-7-carboxylate (35 mg, 96.3 μmol) DCM (2 mL) and TFA (1 mL), stirred at RT for 10 min to give the title compound (25 mg, 98%). LCMS (Method A): $R_T$=0.32 min, m/z=264 [M+H]$^+$.

Step 3: 3-((7-((R)-3-Cyclohexyl-2-methylpropanoyl)-10-hydroxy-7-azaspiro[4.5]decan-10-yl)methyl)pyrimidin-4(3H)-one Prepared according to General Procedure 3 using 3-((10-hydroxy-7-azaspiro[4.5]decan-10-yl)methyl)pyrimidin-4

(3H)-one (25 mg, 94.9 µmol), Acid 1 (17.8 mg, 0.105 mmol), HATU (43.3 mg, 0.114 mmol) and DIPEA (50 µL, 0.285 mmol) in DCM (1.5 mL) to give the title compound (24 mg, 60%). LCMS (Method A): $R_T$=1.47 min, m/z=416 [M+H]$^+$. $^1$H NMR (500 MHz, DMSO-d$_6$): δ 8.36 (s, 1H), 7.90 (d, J=7 Hz, 1H), 6.43-6.37 (m, 1H), 4.89-4.80 (m, 1H), 4.65-4.49 (m, 1H), 3.72-3.07 (m, 5H (signal overlaps with HDO)), 2.95-2.78 (m, 1H), 2.01-1.80 (m, 1H), 1.79-0.75 (m, 25H).

Example 135: 3-((1-((R)-3-Cyclohexyl-2-methylpropanoyl)-4-hydroxy-3,3-dimethylpiperidin-4-yl)methyl)-6-(thiophen-3-yl)pyrimidin-4(3H)-one

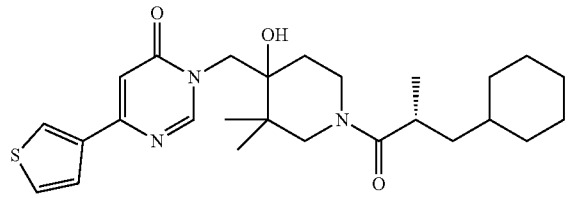 [SMILES: C[C@H](CC1CCCCC1)C(=O)N1CCC(O)(Cn2cnc(-c3ccsc3)cc2=O)C(C)(C)C1]

Prepared according to General Procedure 4 using Intermediate 3 (30 mg, 70.8 µmol), thiophen-3-ylboronic acid (13.6 mg, 0.106 mmol), tetrakis(triphenylphosphine)palladium(0) (4.09 mg, 3.50 µmol), sodium carbonate (15.0 mg, 0.142 mmol), 1,4-dioxane (0.5 mL) and water (0.2 mL). The reaction was heated under microwave irradiation at 150° C. for 10 min to give the title compound (19 mg, 56%). LCMS (Method A): $R_T$=1.74 min, m/z=472 [M+H]$^+$. $^1$H NMR (500 MHz, DMSO-d$_6$): δ 8.36 (s, 1H), 8.28 (s, 1H), 7.74-7.69 (m, 1H), 7.68-7.64 m, 1H), 6.90-6.85 (m, 1H), 4.90-4.85 (bs, 1H), 4.47-4.33 (m, 1H), 3.84-3.58 (m, 2H), 3.33-3.14 (m, 2H (signal overlaps with HDO)), 3.03-2.74 (m, 2H), 1.75-1.37 (m, 7H), 1.27-0.68 (m, 17H).

Example 136: 1-((1-((R)-3-Cyclohexyl-2-methylpropanoyl)-4-hydroxy-3,3-dimethylpiperidin-4-yl)methyl)-5-(oxazol-2-yl)-4-phenylpyridin-2(1H)-one

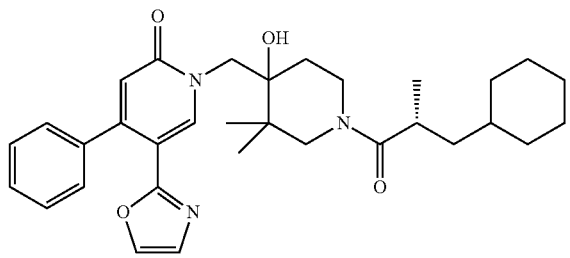 [SMILES: C[C@H](CC1CCCCC1)C(=O)N1CCC(O)(Cn2cc(-c3ncco3)c(-c3ccccc3)cc2=O)C(C)(C)C1]

Step 1: tert-Butyl 4-((5-carbamoyl-2-oxo-4-phenylpyridin-1 (2H)-yl)methyl)-4-hydroxy-3,3-dimethylpiperidine-1-carboxylate A suspension of 1-((1-(tert-butoxycarbonyl)-4-hydroxy-3,3-dimethylpiperidin-4-yl)methyl)-6-oxo-4-phenyl-1,6-dihydropyridine-3-carboxylic acid (Amine 6, Step 2) (50 mg, 0.110 mmol) and 1,1'-carbonyldiimidazole (27 mg, 0.164 mmol) were stirred at RT for 15 min before the temperature was raised to 60° C. After 45 min, no imidazolide was observed so 1,1'-carbonyldiimidazole (151 mg, 0.931 mmol) was added and the reaction stirred at 60° C. for 15 h. The reaction mixture was allowed to cool to RT and ammonium hydroxide (0.213 mL, 5.48 mmol) was added. After 70 min, the reaction was diluted with saturated NaHCO$_{3(aq)}$ (15 mL) and the resulting mixture extracted with DCM (3×10 mL) using a Biotage phase separator. The combined organic phases were concentrated in vacuo and the residue was purified by flash chromatography (GraceResolv silica 12 g cartridge, 0-100% EtOAc in cyclohexane; then 0-15% MeOH in EtOAc) to give the title compound (27.5 mg, 55%) as a colourless solid. LCMS (Method A): $R_T$=1.21 min, m/z=456 [M+H]$^+$.

Step 2: tert-Butyl 4-hydroxy-3,3-dimethyl-4-((5-(oxazol-2-yl)-2-oxo-4-phenylpyridin-1(2H)-yl)methyl)piperidine-1-carboxylate A suspension of tert-butyl 4-((5-carbamoyl-2-oxo-4-phenylpyridin-1(2H)-yl)methyl)-4-hydroxy-3,3-dimethylpiperidine-1-carboxylate (27.5 mg, 60.4 µmol) in bromoacetaldehyde diethyl acetal (0.5 mL, 3.32 mmol) was heated under microwave irradiation at 100° C. for 15 min then at 120° C. for 1 h before the reaction mixture was purified by flash chromatography (GraceResolv silica 12 g cartridge, 0-100% EtOAc in cyclohexane) to give the title compound (12 mg, 41%) as a colourless solid. LCMS (Method A): $R_T$=1.48 min, m/z=480 [M+H]$^+$.

Step 3: 1-((4-Hydroxy-3,3-dimethylpiperidin-4-yl)methyl)-5-(oxazol-2-yl)-4-phenylpyridin-2(1H)-one A solution of tert-butyl 4-hydroxy-3,3-dimethyl-4-((5-(oxazol-2-yl)-2-oxo-4-phenylpyridin-1(2H)-yl)methyl)piperidine-1-carboxylate (12 mg, 25.0 µmol) was stirred in TFA (0.5 mL) and DCM (1 mL) for 5 min before the reaction mixture was purified using a Biotage SCX-2 2 g cartridge (pre-equilibrated with and then washed using 1:1 DCM/MeOH before being eluted with 1:1 DCM/7 M in NH$_3$ in MeOH). The basic eluents were concentrated in vacuo to give the title compound (7.5 mg, 78%) as a colourless solid. LCMS (Method A): $R_T$=0.62 min, m/z=380 [M+H]$^+$.

Step 4: 1-((1-((R)-3-Cyclohexyl-2-methylpropanoyl)-4-hydroxy-3,3-dimethylpiperidin-4-yl)methyl)-5-(oxazol-2-yl)-4-phenylpyridin-2(1H)-one Prepared according to General Procedure 3 using 1-((4-hydroxy-3,3-dimethylpiperidin-4-yl)methyl)-5-(oxazol-2-yl)-4-phenylpyridin-2(1H)-one (7.5 mg, 19.8 µmol), Acid 1 (4 mg, 23.7 µmol), HATU (9 mg, 23.7 µmol), DIPEA (14 µL, 79.1 µmol) and DCM (0.4 mL) to give the title compound (9.5 mg, 86%) as a colourless solid after lyophilisation. LCMS (Method A): $R_T$=1.68, 1.69 min (2 diastereoisomers), m/z=532 [M+H]$^+$. $^1$H NMR (500 MHz, DMSO-d$_6$): δ 8.29 (d, J=3.6 Hz, 1H), 7.95 (s, 1H), 7.46-7.27 (m, 3H), 7.28-7.02 (m, 3H), 6.43 (d, J=4.7 Hz, 1H), 4.96 (d, J=3.5 Hz, 1H), 4.65-4.51 (m, 1H), 4.06 (dd, J=38.6, 11.7 Hz, 0.6H), 3.83-

3.59 (m, 2.4H), 3.27-3.16 (m, 1H), 3.03-2.79 (m, 2H), 1.83-1.38 (m, 7H), 1.36-0.61 (m, 17H).

Example 137: 3-((1-((R)-3-Cyclohexyl-2-methyl-propanoyl)-4-hydroxy-3,3-dimethylpiperidin-4-yl)methyl)-6-(2-(hydroxymethyl)phenyl)pyrimidin-4(3H)-one

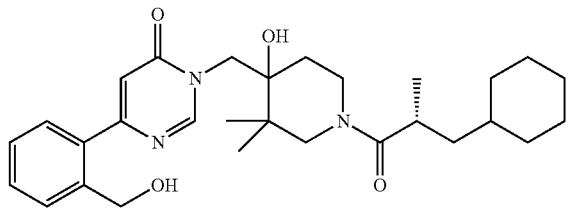 [SMILES: C[C@H](CC1CCCCC1)C(=O)N1CCC(O)(Cn2cnc(-c3ccccc3CO)cc2=O)C(C)(C)C1]

Prepared according to General Procedure 4 using Intermediate 3 (45 mg, 0.106 mmol), (2-(hydroxymethyl)phenyl)boronic acid (24.2 mg, 0.160 mmol), tetrakis(triphenylphosphine)palladium(0) (6.13 mg, 5.30 µmol), sodium carbonate (22.5 mg, 0.212 mmol), 1,4-dioxane (0.75 mL) and water (0.3 mL). The reaction was heated under microwave irradiation at 150° C. for 10 min to give the title compound (28 mg, 53%). LCMS (Method A): $R_T$=1.46 min, m/z=496 [M+H]$^+$. $^1$H NMR (500 MHz, DMSO-d$_6$): δ 8.40 (s, 1H), 7.66-7.41 (m, 3H), 7.40-7.31 (m, 1H), 6.61 (s, 1H), 5.26-5.17 (m, 1H), 4.93-4.84 (bs, 1H), 4.63-4.54 (m, 2H), 4.50-4.35 (m, 1H), 3.83-3.60 (m, 2H), 3.35-3.16 (m, 2H signal overlaps with HDO)), 3.05-2.79 (m, 2H), 1.76-1.40 (m, 7H), 1.30-0.74 (m, 17H).

Example 138: 3-((1-((R)-3-Cyclohexyl-2-methyl-propanoyl)-4-hydroxy-3,3-dimethylpiperidin-4-yl)methyl)-6-(3-(hydroxymethyl)phenyl)pyrimidin-4(3H)-one

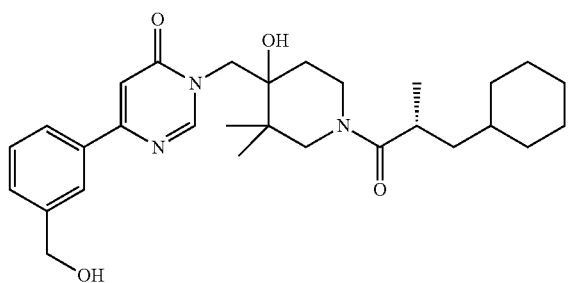 [SMILES: C[C@H](CC1CCCCC1)C(=O)N1CCC(O)(Cn2cnc(-c3cccc(CO)c3)cc2=O)C(C)(C)C1]

Prepared according to General Procedure 4 using Intermediate 3 (45 mg, 0.106 mmol), (3-(hydroxymethyl)phenyl)boronic acid (24.2 mg, 0.160 mmol), tetrakis(triphenylphosphine)palladium(0) (6.13 mg, 5.30 µmol), sodium carbonate (22.5 mg, 0.212 mmol), 1,4-dioxane (0.75 mL) and water (0.3 mL). The reaction was heated under microwave irradiation at 150° C. for 10 min to give the title compound (30 mg, 56%). LCMS (Method A): $R_T$=1.41 min, m/z=496 [M+H]$^+$. $^1$H NMR (500 MHz, DMSO-d$_6$): δ 8.44 (s, 1H), 8.04 (s, 1H), 7.96-7.88 (m, 1H), 7.48-7.38 (m, 2H), 6.98-6.89 (m, 1H), 5.30-5.22 (m, 1H), 4.89 (s, 1H), 4.61-4.51 (m, 2H), 4.49-4.35 (m, 1H), 3.80-3.60 (m, 2H), 3.29-3.13 (m, 2H (signal overlaps with HDO)), 3.04-2.76 (m, 2H), 1.76-1.40 (m, 7H), 1.26-0.73 (m, 17H).

Example 139: 3-((1-((R)-3-Cyclohexyl-2-methyl-propanoyl)-4-hydroxy-3,3-dimethylpiperidin-4-yl)methyl)-6-(4-(hydroxymethyl)phenyl)pyrimidin-4(3H)-one

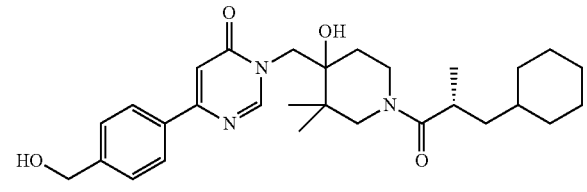 [SMILES: C[C@H](CC1CCCCC1)C(=O)N1CCC(O)(Cn2cnc(-c3ccc(CO)cc3)cc2=O)C(C)(C)C1]

Prepared according to General Procedure 4 using Intermediate 3 (40 mg, 94.3 µmol), (4-(hydroxymethyl)phenyl)boronic acid (21.5 mg, 0.142 mmol), tetrakis(triphenylphosphine)palladium(0) (5.45 mg, 4.70 µmol), sodium carbonate (20.0 mg, 0.189 mmol), 1,4-dioxane (0.75 mL) and water (0.3 mL). The reaction was heated under microwave irradiation at 150° C. for 10 min to give the title compound (31 mg, 66%). LCMS (Method A): $R_T$=1.39 min, m/z=496 [M+H]$^+$. $^1$H NMR (500 MHz, DMSO-d$_6$): δ 8.42 (s, 1H), 8.05 (d, J=8.1 Hz, 2H), 7.43 (d, J=8.1 Hz, 2H), 6.98-6.91 (m, 1H), 5.31-5.23 (m, 1H), 4.91-4.83 (bs, 1H), 4.60-4.50 (m, 2H), 4.49-4.34 (m, 1H), 3.80-3.59 (m, 2H), 3.29-3.13 (m, 2H (signal overlaps with HDO)), 3.03-2.76 (m, 2H), 1.76-1.39 (m, 7H), 1.28-0.73 (m, 17H).

Example 140: 6-(4-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one

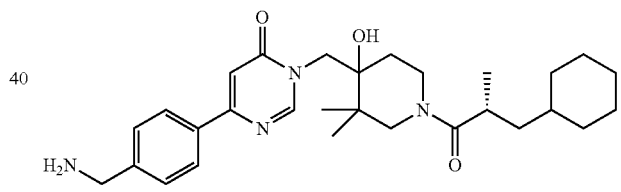

Step 1: tert-Butyl (4-(1-((1-((R)-3-cyclohexyl-2-methylpropanoyl)-4-hydroxy-3,3-dimethylpiperidin-4-yl)methyl)-6-oxo-1,6-dihydropyrimidin-4-yl)benzyl)carbamate Prepared according to General Procedure 4 using Intermediate 3 (50 mg, 0.118 mmol), (4-(((tert-butoxycarbonyl)amino)methyl)phenyl)boronic acid (44.4 mg, 0.177 mmol), tetrakis(triphenylphosphine)palladium(0) (6.81 mg, 5.9 µmol), sodium carbonate (25.0 mg, 0.236 mmol), 1,4-dioxane (0.75 mL) and water (0.3 mL). The reaction was heated under microwave irradiation at 150° C. for 10 min to give the title compound (52 mg, 74%). LCMS (Method A): $R_T$=1.75 min, m/z=595 [M+H]$^+$.

Step 2: 6-(4-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one A solution of tert-butyl (4-(1-((1-((R)-3-cyclohexyl-2-methylpropanoyl)-4-hydroxy-3,3-dimethylpiperidin-4-yl)

methyl)-6-oxo-1,6-dihydropyrimidin-4-yl)benzyl)carbamate (50 mg, 84.1 µmol) in DCM (1 mL) and HCl (4 M in 1,4-dioxane, 0.5 mL, 2.00 mmol) was stirred for 30 min at RT. The reaction mixture was quenched with NaHCO$_{3(aq)}$ and the aqueous phase was extracted with DCM (×3) using a Biotage phase separator. The combined organic phases were concentrated in vacuo and the residue purified by flash chromatography to give the title compound (17 mg, 40%). LCMS (Method A): R$_T$=0.91 min, m/z=495 [M+H]$^+$. $^1$H NMR (500 MHz, DMSO-d$_6$): δ 8.42 (s, 1H), 8.02 (d, J=8.1 Hz, 2H), 7.48-7.32 (m, 2H), 6.98-6.90 (m, 1H), 4.92-4.82 (bs, 1H), 4.49-4.34 (m, 1H), 3.83-3.57 (m, 4H), 3.33-3.14 (m, 2H (signal overlaps with HDO)), 3.03-2.76 (m, 2H), 2.46-2.16 (bs, 2H (signal overlaps with DMSO)), 1.76-1.40 (m, 7H), 1.26-0.72 (m, 17H).

Example 141: 6-(2-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one

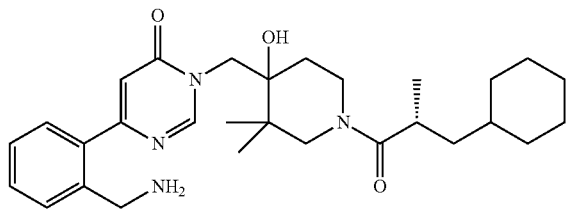 [SMILES: C[C@H](CC1CCCCC1)C(=O)N1CCC(O)(Cn2cnc(-c3ccccc3CN)cc2=O)C(C)(C)C1]

Step 1: tert-Butyl (2-(1-((1-((R)-3-cyclohexyl-2-methylpropanoyl)-4-hydroxy-3,3-dimethylpiperidin-4-yl)methyl)-6-oxo-1,6-dihydropyrimidin-4-yl)benzyl)carbamate Prepared according to General Procedure 4 using Intermediate 3 (50 mg, 0.118 mmol), (2-(((tert-butoxycarbonyl)amino)methyl)phenyl)boronic acid (44.4 mg, 0.177 mmol), tetrakis(triphenylphosphine)palladium(0) (6.81 mg, 5.9 µmol), sodium carbonate (25.0 mg, 0.236 mmol), 1,4-dioxane (0.75 mL) and water (0.3 mL). The reaction was heated under microwave irradiation at 150° C. for 10 min to give the title compound (53 mg, 75%). LCMS (Method A): R$_T$=1.79 min, m/z=595 [M+H]$^+$.

Step 2: 6-(2-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one A solution of tert-butyl (2-(1-((1-((R)-3-cyclohexyl-2-methylpropanoyl)-4-hydroxy-3,3-dimethylpiperidin-4-yl)methyl)-6-oxo-1,6-dihydropyrimidin-4-yl)benzyl)carbamate (50 mg, 84.1 µmol) in DCM (1 mL) and HCl (4 M in 1,4-dioxane, 0.5 mL, 2.00 mmol) was stirred for 16 h at RT. The reaction mixture was quenched with saturated NaHCO$_{3(aq)}$ and the aqueous phase was extracted with DCM (×3) using a Biotage phase separator. The combined organic phases were concentrated in vacuo and the residue was purified by flash chromatography to give the title compound (26 mg, 62%). LCMS (Method A): R$_T$=0.93 min, m/z=495 [M+H]$^+$. $^1$H NMR (500 MHz, DMSO-d$_6$): δ 8.40 (s, 1H), 7.58-7.51 (m, 1H), 7.46-7.37 (m, 2H), 7.35-7.27 (m, 1H), 6.63-6.56 (bs, 1H), 4.94-4.86 (bs, 1H), 4.50-4.28 (m, 1H), 3.83-3.60 (m, 4H), 3.35-3.17 (m, 2H (signal overlaps with HDO)), 3.05-2.79 (m, 2H), 2.02-1.76 (bs, 2H), 1.75-1.40 (m, 7H), 1.29-0.74 (m, 17H).

Example 142: 6-(2-Fluorophenyl)-3-((4-hydroxy-3,3-dimethyl-1-(2,4,4-trimethylpentanoyl)piperidin-4-yl)methyl)pyrimidin-4(3H)-one

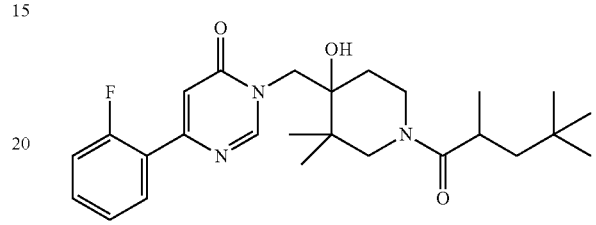

Prepared according to General Procedure 3 using Amine 5 (25 mg, 75.4 µmol), 2,4,4-trimethylpentanoic acid (12.0 mg, 83.0 µmol), HATU (34.4 mg, 90.8 µmol) and DIPEA (40 µL, 0.226 mmol) in DCM (1 mL) to give the title compound (13 mg, 37%). LCMS (Method A): R$_T$=1.55 min, m/z=458 [M+H]$^+$. $^1$H NMR (500 MHz, DMSO-d$_6$): δ 8.46 (s, 1H), 8.07-7.97 (m, 1H), 7.59-7.48 (m, 1H), 7.40-7.28 (m, 2H), 6.81 (s, 1H), 4.88 (s, 1H), 4.48-4.34 (m, 1H), 3.91-3.64 (m, 2H), 3.41-3.18 (m, 2H (signal overlaps with HDO)), 2.98-2.76 (m, 2H), 2.06-1.80 (m, 1H), 1.76-1.49 (m, 1H), 1.30-0.68 (m, 20H).

Example 143: 6-(2-Fluorophenyl)-3-((4-hydroxy-3,3-dimethyl-1-(4,4,4-trifluoro-2-methylbutanoyl)piperidin-4-yl)methyl)pyrimidin-4(3H)-one

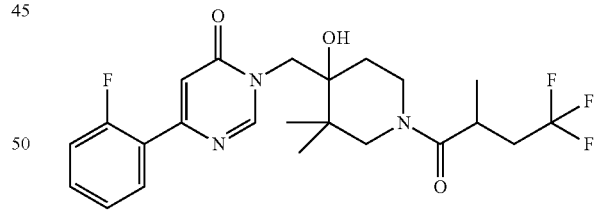

Prepared according to General Procedure 3 using Amine 5 (25 mg, 75.4 µmol), 4,4,4-trifluoro-2-methylbutanoic acid (13.0 mg, 83.0 µmol), HATU (34.4 mg, 90.8 µmol) and DIPEA (40 µL, 0.226 mmol) in DCM (1 mL) to give the title compound (17 mg, 47%). LCMS (Method A): R$_T$=1.33 min, m/z=470 [M+H]$^+$. $^1$H NMR (500 MHz, DMSO-d$_6$): δ 8.45 (s, 1H), 8.06-7.98 (m, 1H), 7.59-7.50 (m, 1H), 7.40-7.28 (m, 2H), 6.81 (s, 1H), 4.95-4.84 (m, 1H), 4.50-4.31 (m, 1H), 3.83-3.63 (m, 2H), 3.37-3.06 (m, 2H (signal overlaps with HDO)), 3.00-2.56 (m, 2H (signal overlaps with DMSO satellite)), 2.32-2.14 (m, 1H), 1.76-1.41 (m, 1H), 1.30-0.79 (m, 11H).

Example 144: 4-Chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide

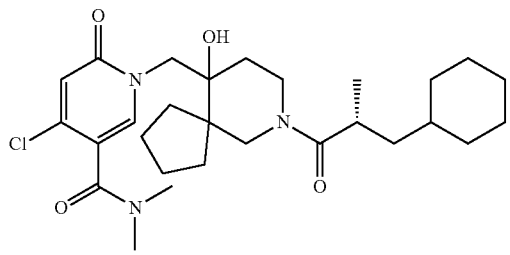 [SMILES: C[C@H](CC1CCCCC1)C(=O)N1CCC(O)(Cn2cc(C(=O)N(C)C)c(Cl)cc2=O)C2(CCCC2)C1]

Step 1: 1-((7-(tert-Butoxycarbonyl)-10-hydroxy-7-azaspiro[4.5]decan-10-yl)methyl)-4-chloro-6-oxo-1,6-dihydropyridine-3-carboxylic acid A stirred suspension of tert-butyl 1-oxa-10-azadispiro[2.0.4⁴.4³]dodecane-10-carboxylate (1.68 g, 5.03 mmol), ethyl 4-chloro-6-oxo-1H-pyridine-3-carboxylate (1.01 g, 5.03 mmol) and cesium carbonate (2.46 g, 7.54 mmol) in DMF (20 mL) was heated at 100° C. After 16 h, the reaction mixture was partitioned between 1:1 brine/water and EtOAc. The resulting biphasic mixture was separated. The aqueous layer was acidified to ca. pH 2-3 using 2 M HCl (aq) and extracted using EtOAc (×3), dried (phase separator), and the solvents were removed in vacuo to give the title compound (664 mg, 30%) as a pale yellow oil that was carried through to the next step without further purification. LCMS (Method A): $R_T$=1.28 min, m/z=441 [M+H]⁺.

Step 2: tert-Butyl 10-((4-chloro-5-(dimethylcarbamoyl)-2-oxopyridin-1 (2H)-yl)methyl)-10-hydroxy-7-azaspiro[4.5]decane-7-carboxylate DIPEA (0.79 mL, 4.51 mmol) was added to a stirred solution of 1-((7-(tert-butoxycarbonyl)-10-hydroxy-7-azaspiro[4.5]decan-10-yl)methyl)-4-chloro-6-oxo-1,6-dihydropyridine-3-carboxylic acid (664 mg, 1.50 mmol), 2 M dimethylamine in THF (1.13 mL, 2.26 mmol) and HATU (572 mg, 1.50 mmol) in DCM (15 mL) at RT. After 2 h, saturated sodium bicarbonate (aq) solution was added and the resulting biphasic mixture was separated, extracted (DCM×2), the combined organic phase was dried (phase separator), the solvents were removed in vacuo, and the remaining residue was purified by flash chromatography (0-5% MeOH in DCM) to give the title compound (423 mg, 60%) as a pale yellow solid. LCMS (Method A): $R_T$=1.25 min, m/z=468 [M+H]⁺. In addition, the by-product tert-butyl 10-((4-(dimethylamino)-5-(dimethylcarbamoyl)-2-oxopyridin-1(2H)-yl)methyl)-10-hydroxy-7-azaspiro[4.5]decane-7-carboxylate (43.2 mg, 6%) was isolated as a yellow oil. LCMS (Method A): $R_T$=1.12 min, m/z=477 [M+H]⁺.

Step 3: 4-Chloro-1-((10-hydroxy-7-azaspiro[4.5]decan-10-yl)methyl)-N,N-dimethyl-6-oxo-1,6-dihydropyridine-3-carboxamide hydrochloride 4 M HCl in 1,4-dioxane (0.5 mL, 14.4 mmol) was added to tert-butyl 10-((4-chloro-5-(dimethylcarbamoyl)-2-oxopyridin-1 (2H)-yl)methyl)-10-hydroxy-7-azaspiro[4.5]decane-7-carboxylate (30.0 mg, 0.0641 mmol) and the resulting mixture was stirred at RT. After 2 h, the solvents were removed in vacuo to give the crude title compound (28.0 mg, >100%) as a pale yellow oil that was carried through to the next step without further purification. LCMS (Method A): $R_T$=0.29 min, m/z=402 [M−H]⁻.

Step 4: 4-Chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide DIPEA (0.022 mL, 0.128 mmol) was added to a stirred solution of 4-chloro-1-((10-hydroxy-7-azaspiro[4.5]decan-10-yl)methyl)-N,N-dimethyl-6-oxo-1,6-dihydropyridine-3-carboxamide hydrochloride (25.9 mg, 0.0641 mmol), Acid 1 (10.9 mg, 0.064 mmol) and HATU (29.2 mg, 0.0769 mmol) in DCM (1.0 mL) at RT. After 1 h, the reaction mixture was loaded directly onto a column and purified by flash chromatography (0-5%, MeOH in DCM) and freeze-dried to give material that was shown to contain impurities by ¹H NMR analysis. The material was dissolved in DCM and saturated sodium bicarbonate (aq) solution was added. The resulting biphasic mixture was separated, dried (phase separator), the solvents were removed in vacuo, and the remaining residue was purified by flash chromatography using a 11 g KP-NH column (0-100%, EtOAc in cyclohexane) and freeze-dried to give the title compound (12.7 mg, 36%) as a white solid. LCMS (Method A): $R_T$=1.48 min, m/z=520 [M+H]⁺. ¹H NMR (500 MHz, DMSO-d₆): δ 7.82 (s, 1H), 6.68-6.55 (m, 1H), 4.83-4.69 (m, 1H), 4.68-4.47 (m, 1H), 3.89-3.33 (m, 3H), 3.28-3.05 (m, 1H, overlapping solvent), 3.02-2.75 (m, 7H), 1.98-1.79 (m, 1H), 1.74-0.70 (m, 26H).

Example 145: 1-((7-((R)-3-Cyclohexyl-2-methylpropanoyl)-10-hydroxy-7-azaspiro[4.5]decan-10-yl)methyl)-4-(dimethylamino)-N,N-dimethyl-6-oxo-1,6-dihydropyridine-3-carboxamide

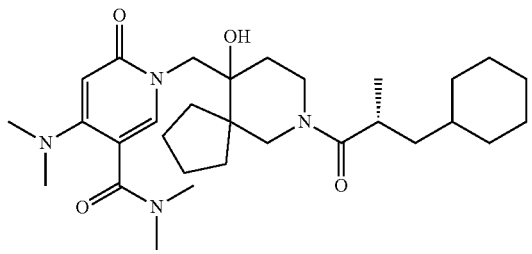 [SMILES: C[C@H](CC1CCCCC1)C(=O)N1CCC(O)(Cn2cc(C(=O)N(C)C)c(N(C)C)cc2=O)C2(CCCC2)C1]

Step 1: 4-(Dimethylamino)-1-((10-hydroxy-7-azaspiro[4.5]decan-10-yl)methyl)-N,N-dimethyl-6-oxo-1,6-dihydropyridine-3-carboxamide TFA (1.0 mL) was added to a stirred solution of tert-butyl 10-((4-(dimethylamino)-5-(dimethylcarbamoyl)-2-oxopyridin-1 (2H)-yl)methyl)-10-hydroxy-7-azaspiro[4.5]decane-7-carboxylate (Example 144, Step 2 by-product) (38.3 mg, 0.0804 mmol) in DCM (1.0 mL) at RT. After 30 min, the reaction mixture was loaded onto a pre-equilibrated 2 g SCX-2 cartridge, washing with MeOH and eluting with 7 N ammonia in MeOH. The solvents were removed in vacuo to give the title compound (20.5 mg, 68%) as a pale yellow solid that was carried through to the next step without further purification. LCMS (Method A): $R_T$=0.23 min, m/z=377 [M+H]$^+$.

Step 2: 1-((7-((R)-3-Cyclohexyl-2-methylpropanoyl)-10-hydroxy-7-azaspiro[4.5]decan-10-yl)methyl)-4-(dimethylamino)-N,N-dimethyl-6-oxo-1,6-dihydropyridine-3-carboxamide DIPEA (0.019 mL, 0.109 mmol) was added to a stirred solution of 4-(dimethylamino)-1-((10-hydroxy-7-azaspiro[4.5]decan-10-yl)methyl)-N,N-dimethyl-6-oxo-1,6-dihydropyridine-3-carboxamide (20.5 mg, 0.0545 mmol), Acid 1 (9.3 mg, 0.0545 mmol) and HATU (24.8 mg, 0.0653 mmol) in DCM (1.0 mL) at RT under nitrogen. After 2 h, the reaction mixture was diluted with saturated sodium bicarbonate (aq) solution and extracted into DCM (×3). The combined organic phases were dried (phase separator), the solvents were removed in vacuo and the remaining residue was purified by flash chromatography using an 11 g KP-NH column (0-100%, EtOAc in cyclohexane; then 0-10%, MeOH in EtOAc) and freeze-dried to give the title compound (10.6 mg, 36%). LCMS (Method A): $R_T$=1.34 min, m/z=529 [M+H]$^+$. $^1$H NMR (500 MHz, DMSO-d$_6$): δ 7.54 (s, 1H), 5.63-5.09 (m, 2H), 4.47-4.06 (m, 1H), 3.98-3.55 (m, 2H), 3.53-3.33 (m, 1H), 3.27-3.04 (m, 1H, overlapping solvent), 3.02-2.70 (m, 13H), 1.96-1.77 (m, 1H), 1.75-0.66 (m, 26H).

Example 146: 1-((1-((S)-3-(Benzyloxy)-2-(cyclohexylmethyl)propanoyl)-4-hydroxy-3,3-dimethylpiperidin-4-yl)methyl)-N,N-dimethyl-6-oxo-4-phenyl-1,6-dihydropyridine-3-carboxamide

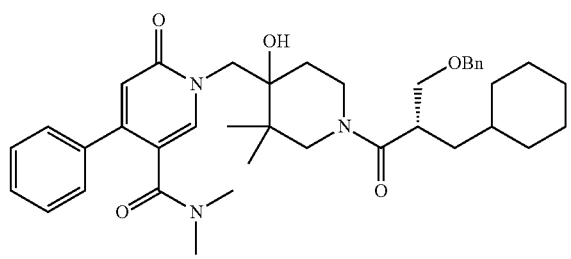 [SMILES: CN(C)C(=O)c1cn(CC2(O)CCN(C(=O)[C@H](COCc3ccccc3)CC3CCCCC3)CC2(C)C)c(=O)cc1-c1ccccc1]

Prepared according to General Procedure 3 using Amine 6 (65 mg, 0.155 mmol), Acid 7 (43 mg, 0.155 mmol), HATU (65 mg, 0.170 mmol), DIPEA (0.108 mL, 0.619 mmol) and DCM (3 mL) to give the title compound (57 mg, 56%) as a colourless solid after lyophilisation. LCMS (Method A): $R_T$=1.73, 1.76 min (2 diastereoisomers), m/z=642 [M+H]$^+$. $^1$H NMR (500 MHz, DMSO-d$_6$): δ 7.87-7.69 (m, 1H), 7.61-7.08 (m, 10H), 6.51-6.39 (m, 1H), 4.95-4.84 (m, 1H), 4.53-4.30 (m, 3H), 4.20-3.99 (m, 1H), 3.93-3.63 (m, 3H), 3.59-3.38 (m, 2H), 3.25-3.12 (m, 1H), 3.06-2.81 (m, 1H), 2.75 (s, 3H), 2.62 (s, 3H), 1.77-1.48 (m, 6H), 1.49-1.33 (m, 1H), 1.23-1.06 (m, 7H), 1.00-0.74 (m, 7H).

Example 147: 1-((10-Hydroxy-7-isobutyryl-7-azaspiro[4.5]decan-10-yl)methyl)-N,N-dimethyl-6-oxo-4-phenyl-1,6-dihydropyridine-3-carboxamide

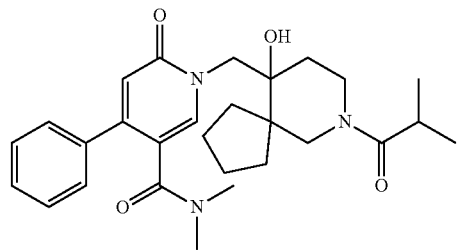 [SMILES: CC(C)C(=O)N1CCC(O)(Cn2cc(C(=O)N(C)C)c(-c3ccccc3)cc2=O)C2(CCCC2)C1]

Prepared according to General Procedure 3 using Amine 8 (25 mg, 61.0 μmol), isobutyric acid (6.45 mg, 73.3 μmol), HATU (30.2 mg, 79.4 μmol) and DIPEA (32 μL, 0.183 mmol) in DCM (1 mL) to give the title compound (20 mg, 68%). LCMS (Method A): $R_T$=1.06 min, m/z=480 [M+H]$^+$. $^1$H NMR (500 MHz, DMSO-d$_6$): δ 7.84 (s, 1H), 7.48-7.30 (m, 5H), 6.48-6.40 (m, 1H), 4.97 (s, 0.3H), 4.91 (s, 0.7H), 4.67-4.55 (m, 1H), 3.82-3.61 (m, 2H), 3.51-3.18 (m, 3H (signals overlap with HDO)), 2.93-2.81 (m, 1H), 2.75 (s, 3H), 2.63 (s, 3H (signal overlaps with DMSO satellite)), 1.99-1.83 (m, 1H), 1.76-0.88 (m, 15H).

Example 148: 1-((10-Hydroxy-7-((R)-2-methylbutanoyl)-7-azaspiro[4.5]decan-10-yl)methyl)-N,N-dimethyl-6-oxo-4-phenyl-1,6-dihydropyridine-3-carboxamide

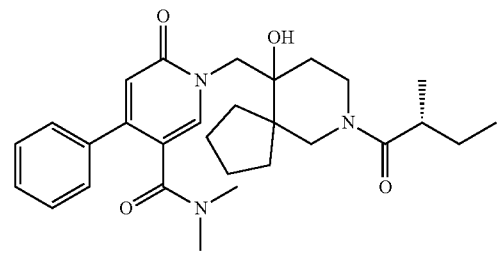 [SMILES: CC[C@@H](C)C(=O)N1CCC(O)(Cn2cc(C(=O)N(C)C)c(-c3ccccc3)cc2=O)C2(CCCC2)C1]

Prepared according to General Procedure 3 using Amine 8 (25 mg, 61.0 μmol), (R)-2-methylbutanoic acid (7.48 mg, 73.3 μmol), HATU (30.2 mg, 79.4 μmol) and DIPEA (32 μL, 0.183 mmol) in DCM (1 mL) to give the title compound (24 mg, 79%). LCMS (Method A): $R_T$=1.16 min, m/z=494 [M+H]$^+$. $^1$H NMR (500 MHz, DMSO-d$_6$): δ 7.84 (s, 1H), 7.50-7.32 (m, 5H), 6.49-6.42 (m, 1H), 4.97 (s, 0.3H), 4.91 (s, 0.7H), 4.69-4.55 (m, 1H), 3.87-3.61 (m, 2H), 3.58-3.35 (m, 2H), 2.80-2.67 (m, 1H), 2.75 (s, 3H), 2.63 (s, 3H (signal overlaps with DMSO satellite)), 1.99-1.84 (m, 1H), 1.78-1.06 (m, 12H), 1.02-0.89 (m, 3H), 0.87-0.70 (m, 3H).

Example 149: 1-((7-((R)-3-Cyclopropyl-2-methyl-propanoyl)-10-hydroxy-7-azaspiro[4.5]decan-10-yl)methyl)-N,N-dimethyl-6-oxo-4-phenyl-1,6-dihydro-pyridine-3-carboxamide

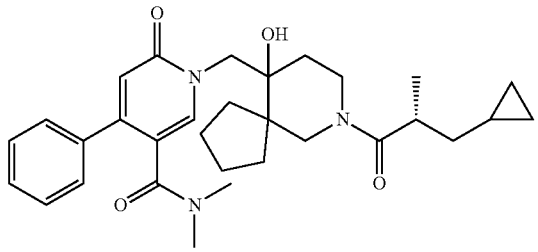 [SMILES: C[C@H](CC1CC1)C(=O)N1CCC(O)(Cn2cc(C(=O)N(C)C)c(-c3ccccc3)cc2=O)C2(CCCC2)C1]

Prepared according to General Procedure 3 using Amine 8 (25 mg, 61.0 μmol), Acid 6 (9.39 mg, 73.3 μmol), HATU (30.2 mg, 79.4 μmol) and DIPEA (32 μL, 0.183 mmol) in DCM (1 mL) to give the title compound (25 mg, 78%). LCMS (Method A): $R_T$=1.28 min, m/z=520 [M+H]$^+$. $^1$H NMR (500 MHz, DMSO-d$_6$): δ 7.87-7.81 (m, 1H), 7.48-7.32 (m, 5H), 6.49-6.42 (m, 1H), 4.97 (s, 0.35H), 4.91 (s, 0.65H), 4.70-4.55 (m, 1H), 3.90-3.62 (m, 2H), 3.53-3.19 (m, 3H (signals overlap with HDO)), 2.95-2.82 (m, 1H), 2.75 (s, 3H), 2.63 (s, 3H (signal overlaps with DMSO satellite)), 1.96-1.84 (m, 1H), 1.79-0.89 (m, 14H), 0.68-0.56 (m, 1H), 0.43-0.28 (m, 2H), 0.08--0.70 (m, 2H).

Example 150: 6-(2-Fluorophenyl)-3-((4-hydroxy-3,3-dimethyl-1-(2-methyl-3-(1H-pyrazol-1-yl)propanoyl)piperidin-4-yl)methyl)pyrimidin-4(3H)-one

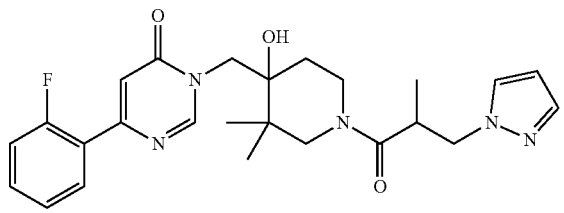 [SMILES: CC(Cn1cccn1)C(=O)N1CCC(O)(Cn2cnc(-c3ccccc3F)cc2=O)C(C)(C)C1]

DIPEA (0.032 mL, 0.181 mmol) was added to a stirred suspension of Amine 5 (30.0 mg, 0.091 mmol), 2-methyl-3-(1H-pyrazol-1-yl)propanoic acid (14.0 mg, 0.091 mmol) and HATU (41.3 mg, 0.109 mmol) in DCM (1.0 mL) at RT. After 2 h, the reaction mixture was diluted with DCM and saturated sodium bicarbonate (aq) solution was added. The resulting biphasic mixture was separated, extracted (DCM×2), dried (phase separator), the solvents were removed in vacuo, and the remaining residue was purified by flash chromatography using a KP-NH column (0-100%, EtOAc in cyclohexane; 0-10%, MeOH in EtOAc) to give the title compound (16.7 mg, 39%) as a white solid. LCMS (Method A): $R_T$=1.08 min, m/z=468 [M+H]$^+$. $^1$H NMR (500 MHz, DMSO-d$_6$): δ 8.47-8.33 (m, 1H), 8.07-7.92 (m, 1H), 7.67-7.48 (m, 2H), 7.46-7.22 (m, 3H), 6.84-6.70 (m, 1H), 6.24-6.06 (m, 1H), 4.92-4.75 (m, 1H), 4.46-4.18 (m, 2H), 4.12-3.93 (m, 1H), 3.75-3.55 (m, 2H), 3.53-3.36 (m, 1H), 3.26-3.00 (m, 1H, overlapping solvent), 2.92-2.75 (m, 1H), 1.72-1.39 (m, 1H), 1.30-0.60 (m, 11H).

Example 151: 1-((7-((R)-3-Cyclohexyl-2-methyl-propanoyl)-10-hydroxy-7-azaspiro[4.5]decan-10-yl)methyl)-4-(2-(hydroxymethyl)phenyl)-N,N-dimethyl-6-oxo-1,6-dihydropyridine-3-carboxamide

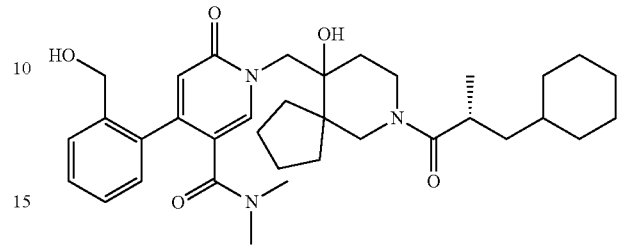

Step 1: tert-Butyl 10-((5-(dimethylcarbamoyl)-4-(2-(hydroxymethyl)phenyl)-2-oxopyridin-1(2H)-yl)methyl)-10-hydroxy-7-azaspiro[4.5]decane-7-carboxylate PdCl$_2$(dppf).DCM (2.6 mg, 0.0032 mmol) was added to a pre-degassed solution of tert-butyl 10-((4-chloro-5-(dimethylcarbamoyl)-2-oxopyridin-1(2H)-yl)methyl)-10-hydroxy-7-azaspiro[4.5]decane-7-carboxylate (Example 144, Step 2) (30.0 mg, 0.0641 mmol), (2-(hydroxymethyl)phenyl)boronic acid (14.6 mg, 0.0962 mmol) and sodium carbonate (13.6 mg, 0.128 mmol) in 1,4-dioxane (0.75 mL)/water (0.25 mL) in a 10 mL vial. The vessel was sealed and heated under microwave irradiation (CEM) at 120° C. with stirring for 30 min. The solvents were removed in vacuo and the remaining residue was partitioned between EtOAc and water, separated, extracted (EtOAc×2), the combined organic phase was dried (phase separator), the solvents were removed in vacuo, and the remaining residue was purified by flash chromatography (0-100%, EtOAc in cyclohexane) to give the title compound (16.2 mg, 47%) as a colourless gum. LCMS (Method A): $R_T$=1.23 min, m/z=540 [M+H]$^+$.

Step 2: 10-((5-(Dimethylcarbamoyl)-4-(2-(hydroxymethyl)phenyl)-2-oxopyridin-1(2H)-yl)methyl)-10-hydroxy-7-azaspiro[4.5]decan-7-ium chloride 4 M HCl in 1,4-dioxane (0.5 mL, 14.4 mmol) was added to tert-butyl 10-((5-(dimethylcarbamoyl)-4-(2-(hydroxymethyl)phenyl)-2-oxopyridin-1(2H)-yl)methyl)-10-hydroxy-7-azaspiro[4.5]decane-7-carboxylate (16.2 mg, 0.030 mmol) and the resulting mixture was stirred at RT. After 2 h, the solvents were removed in vacuo to give the crude title compound (17.3 mg, >100%) as a pale yellow oil that was carried through to the next step without further purification. LCMS (Method A): $R_T$=0.36 min, m/z=440 [M+H]$^+$.

Step 3: 1-((7-((R)-3-Cyclohexyl-2-methylpropanoyl)-10-hydroxy-7-azaspiro[4.5]decan-10-yl)methyl)-4-(2-(hydroxymethyl)phenyl)-N,N-dimethyl-6-oxo-1,6-dihydropyridine-3-carboxamide DIPEA (0.012 mL, 0.0668 mmol) was added to a stirred solution of 10-((5-(dimethylcarbamoyl)-4-(2-(hydroxymethyl)phenyl)-2-oxopyridin-1(2H)-yl)methyl)-10-hydroxy-7-azaspiro[4.5]decan-7-ium chloride (assumed 15.9 mg, 0.0334 mmol), Acid 1 (5.7 mg, 0.0334 mmol) and HATU (15.2 mg, 0.0401 mmol) in DCM (1.0 mL) at RT. After 2 h, the reaction mixture was diluted with DCM and saturated sodium bicarbonate (aq) solution was added. The resulting biphasic mixture was separated, dried (phase separator), the solvents were removed in vacuo, and the remaining residue was purified by flash chromatography using a 11 g KP-NH column (0-100%, EtOAc in cyclohexane) and freeze-dried to give the title compound (8.7 mg, 43%) as a white solid. LCMS (Method A): $R_T$=1.45 min, m/z=592 [M+H]$^+$. $^1$H NMR (500 MHz, DMSO-d$_6$): δ 7.83 (s, 1H), 7.53 (d, 1H), 7.38 (t, 1H), 7.26 (t, 1H), 7.07 (d, 1H), 6.36-6.25 (m, 1H), 5.14 (t, 1H), 5.03-4.85 (m, 1H), 4.73-4.52 (m, 1H), 4.42 (d, 2H), 3.94-3.37 (m, 3H), 3.24-3.12 (m, 1H, overlapping solvent peak), 2.96-2.58 (m, 7H), 2.02-1.82 (m, 1H), 1.79-0.70 (m, 26H).

Example 152 and Example 153: 1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide and 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide

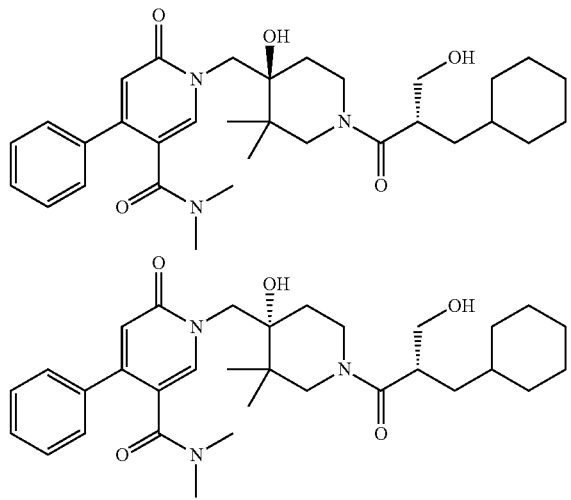

Prepared according to General Procedure 3 using Amine 6 (128 mg, 0.333 mmol), Acid 8 (62 mg, 0.333 mmol), HATU (129 mg, 0.366 mmol), DIPEA (0.233 mL, 1.33 mmol) and DCM (6.7 mL) to give a mixture of diastereomers which were purified by preparative HPLC under basic conditions to give the second eluted compound 1-(((S)-1-((S)-3-cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide (26 mg, 14%) and first eluted compound 1-(((R)-1-((S)-3-cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide (39 mg, 21%) both as colourless solids after lyophilisation. 1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide: LCMS (Method A): $R_T$=1.22 min, m/z=552 [M+H]$^+$. $^1$H NMR (500 MHz, DMSO-d$_6$): δ 7.84-7.78 (m, 1H), 7.49-7.30 (m, 5H), 6.49-6.40 (m, 1H), 4.97-4.84 (m, 1H), 4.64-4.45 (m, 2H), 4.39-4.32 (m, 0.5H), 4.20-4.13 (m, 0.5H), 3.90-3.79 (m, 1H), 3.76-3.62 (m, 1H), 3.48-3.39 (m, 1H), 3.35-3.19 (m, 2H (signal overlaps with HDO)), 3.06-2.96 (m, 1.5H), 2.85-2.78 (m, 0.5H), 2.75 (s, 3H), 2.63 (s, 3H), 1.78-1.46 (m, 6H), 1.45-1.32 (m, 1H), 1.27-1.06 (m, 6H), 1.05-0.91 (m, 6H), 0.88-0.75 (m, 2H). 1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide: LCMS (Method A: $R_T$=1.20 min, m/z=552 [M+H]$^+$. $^1$H NMR (500 MHz, DMSO-d$_6$): δ 7.83-7.77 (m, 1H), 7.47-7.33 (m, 5H), 6.48-6.41 (m, 1H), 4.97-4.83 (m, 1H), 4.58-4.43 (m, 2H), 4.03-3.94 (m, 0.4H), 3.88-3.67 (m, 2.6H), 3.54-3.39 (m, 1H), 3.34-3.20 (m, 2H (signal overlaps with HDO)), 3.11-2.88 (m, 2H), 2.75 (s, 3H), 2.62 (s, 3H), 1.76-1.49 (m, 6H), 1.45-1.32 (m, 1H), 1.27-1.06 (m, 6H), 1.05-0.91 (m, 6H), 0.90-0.76 (m, 2H).

Example 154: 1'-((1-((R)-3-Cyclohexyl-2-methylpropanoyl)-4-hydroxy-3,3-dimethylpiperidin-4-yl)methyl)-4'-(2-fluorophenyl)-[2,3'-bipyridin]-6'(1'H)-one

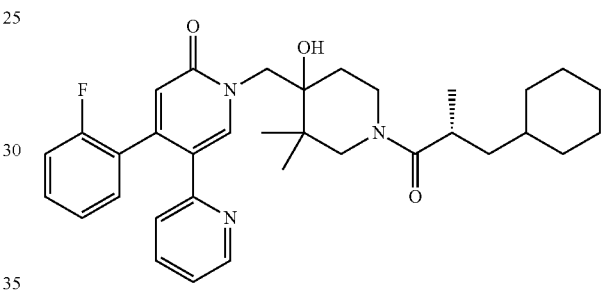

Step 1: tert-Butyl 4-((5-bromo-4-(2-fluorophenyl)-2-oxopyridin-1(2H)-yl)methyl)-4-hydroxy-3,3-dimethylpiperidine-1-carboxylate A solution of 5-bromo-4-(2-fluorophenyl)pyridin-2(1H)-one (200 mg, 0.746 mmol), Epoxide 3 (360 mg, 1.49 mmol) and cesium carbonate (267 mg, 0.821 mmol) in DMF (2.5 mL) was heated at 90° C. for 16 h. The reaction was allowed to cool to RT, diluted with saturated NH$_4$Cl$_{(aq)}$ (15 mL) and the mixture extracted with DCM (3×10 mL) using a Biotage phase separator. The combined organic phases were concentrated in vacuo and the residue purified by flash chromatography (GraceResolv silica 40 g cartridge, 0-70% EtOAc in cyclohexane) to give the title compound (174 mg, 45%) as a pale yellow foam. LCMS (Method A): $R_T$=1.66 min, m/z=509, 511 [M+H]$^+$. $^1$H NMR (500 MHz, DMSO-d$_6$): δ 8.06 (s, 1H), 7.56-7.46 (m, 1H), 7.41-7.23 (m, 3H), 6.47 (s, 1H), 4.89 (s, 1H), 4.45 (d, J=13.4 Hz, 1H), 3.80-3.62 (m, 2H), 3.25-3.25 (m, 1H), 3.12-2.91 (m, 2H), 1.68-1.57 (m, 1H), 1.39 (s, 9H), 1.15-1.04 (m, 1H), 0.99 (s, 3H), 0.94 (s, 3H).

Step 2: tert-Butyl 4-((4-(2-fluorophenyl)-2-oxo-5-(4,4,5,5-tetramethyl-1,3,2-dioxaborolan-2-yl)pyridin-1(2H)-yl)methyl)-4-hydroxy-3,3-dimethylpiperidine-1-carboxylate A suspension of tert-butyl 4-((5-bromo-4-(2-fluorophenyl)-2-oxopyridin-1 (2H)-yl)methyl)-4-hydroxy-3,3-dimethylpiperidine-1-carboxylate (169 mg, 0.332 mmol), bis

181

(pinacolato)diboron (126 mg, 0.498 mmol), Pd(dppf)Cl$_2$.CH$_2$Cl$_2$ (28 mg, 33.2 µmol), dppf (18 mg, 33.2 µmol) and potassium acetate (98 mg, 0.995 mmol) in 1,4-dioxane (3.3 mL) was degassed bubbling N$_2$ through the mixture for 20 min before the reaction was heated at 90° C. for 15 h. The reaction mixture was allowed to cool to RT, diluted with NaHCO$_{3(aq)}$ (30 mL) and the mixture extracted with DCM (3×20 mL) using a Biotage phase separator. The combined organic phases were concentrated in vacuo and the residue was purified by flash chromatography (GraceResolv silica 12 g cartridge, 0-70% EtOAc in cyclohexane) to give the title compound (65 mg, 35%) as an off-white foam. LCMS (Method A): R$_T$=1.87 min, m/z=557 [M+H]$^+$.

Step 3: tert-Butyl 4-((4'-(2-fluorophenyl)-6'-oxo-[2, 3'-bipyridin]-1'(6'H)-yl)methyl)-4-hydroxy-3,3-dimethylpiperidine-1-carboxylate Prepared according to General Procedure 4 using tert-butyl 4-((4-(2-fluorophenyl)-2-oxo-5-(4,4,5,5-tetramethyl-1,3,2-dioxaborolan-2-yl)pyridin-1 (2H)-yl)methyl)-4-hydroxy-3,3-dimethylpiperidine-1-carboxylate (65 mg, 0.117 mmol), 2-bromopyridine (23 µL, 0.234 mmol), Pd(PPh$_3$)$_4$ (14 mg, 11.7 µmol), Na$_2$CO$_3$ (37 mg, 0.350 mmol), 1,4-dioxane (1 mL) and water (0.2 mL) at 140° C. for 2 h under microwave irradiation to give the title compound (8 mg, 13%) as a yellow gum. LCMS (Method A): R$_T$=1.36 min, m/z=508 [M+H]$^+$.

Step 4: 4'-(2-Fluorophenyl)-1'-((4-hydroxy-3,3-dimethylpiperidin-4-yl)methyl)-[2,3'-bipyridin]-6'(1'H)-one A solution of tert-butyl 4-((4'-(2-fluorophenyl)-6'-oxo-[2,3'-bipyridin]-6'(6'H)-yl)methyl)-4-hydroxy-3,3-dimethylpiperidine-1-carboxylate (8 mg, 15.8 µmol) was stirred in TFA (0.5 mL) and DCM (1 mL) for 5 min before the reaction mixture was purified using a SCX-2 2 g cartridge (pre-equilibrated with and then washed using 1:1 DCM/MeOH before being eluted with 1:1 DCM/7 M in NH$_3$ in MeOH). The basic eluents were concentrated in vacuo to give the title compound (6 mg, 93%) as a colourless solid. LCMS (Method A): R$_T$=0.39 min, m/z=408 [M+H]$^+$.

Step 5: 1'-((1-((R)-3-Cyclohexyl-2-methylpropanoyl)-4-hydroxy-3,3-dimethylpiperidin-4-yl)methyl)-4'-(2-fluorophenyl)-[2,3'-bipyridin]-6'(1'H)-one Prepared according to General Procedure 3 using 4'-(2-fluorophenyl)-1'-((4-hydroxy-3,3-dimethylpiperidin-4-yl)methyl)-[2,3'-bipyridin]-6'(1'H)-one (6 mg, 14.7 µmol), Acid 1 (2.8 mg, 16.2 µmol), HATU (6 mg, 16.2 µmol), DIPEA (10 µL, 58.9 µmol) and DCM (0.5 mL) to give, after preparative HPLC under basic conditions, the title compound (5.5 mg, 66%) as a colourless solid after lyophilisation. LCMS (Method A): R$_T$=1.59, 1.60 min (2 diastereoisomers), m/z=560 [M+H]$^+$. $^1$H NMR (500 MHz, DMSO-d$_6$): δ 8.56-8.46 (m, 1H), 7.75-7.66 (m, 1H), 7.65-7.52 (m, 2H), 7.52-7.45 (m, 1H), 7.45-7.37 (m, 1H), 7.35-7.19 (m, 2H), 6.13 (s, 1H), 6.04-5.93 (m, 1H), 5.06-4.90 (m, 1H), 4.42-4.19 (m, 1H), 4.11-3.95 (m, 1H), 3.90-3.64 (m, 2H), 3.61-3.48 (m, 1H), 3.28-3.18 (m, 2H), 3.05-2.80 (m, 2H), 1.72-0.75 (m, 22H).

182

Example 155: 1-((7-((R)-3-Cyclohexyl-2-methylpropanoyl)-10-hydroxy-7-azaspiro[4.5]decan-10-yl)methyl)-N,N-dimethyl-6-oxo-4-(thiophen-3-yl)-1,6-dihydropyridine-3-carboxamide

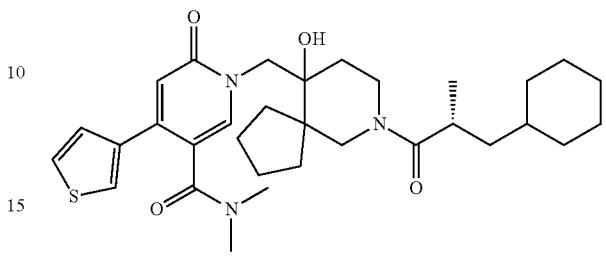

Step 1: tert-Butyl 10-((5-(dimethylcarbamoyl)-2-oxo-4-(thiophen-3-yl)pyridin-1 (2H)-yl)methyl)-10-hydroxy-7-azaspiro[4.5]decane-7-carboxylate PdCl$_2$(dppf).DCM (2.6 mg, 0.0032 mmol) was added to a pre-degassed solution of tert-butyl 10-((4-chloro-5-(dimethylcarbamoyl)-2-oxopyridin-1(2H)-yl)methyl)-10-hydroxy-7-azaspiro[4.5]decane-7-carboxylate (30.0 mg, 0.0641 mmol), thiophen-3-ylboronic acid (12.3 mg, 0.0962 mmol) and sodium carbonate (13.6 mg, 0.128 mmol) in 1,4-dioxane (0.75 mL)/water (0.25 mL) in a 10 mL vial. The vessel was sealed and heated under microwave irradiation (CEM) at 120° C. with stirring for 30 min. The solvents were removed in vacuo and the remaining residue was partitioned between EtOAc and water, separated, extracted (EtOAc×2), the combined organic phase was dried (phase separator), the solvents were removed in vacuo, and the remaining residue was purified by flash chromatography (0-100%, EtOAc in cyclohexane) to give the title compound (19.0 mg, 57%) as a colourless gum. LCMS (Method A): R$_T$=1.35 min, m/z=516 [M+H]$^+$.

Step 2: 10-((5-(Dimethylcarbamoyl)-2-oxo-4-(thiophen-3-yl)pyridin-1 (2H)-yl)methyl)-10-hydroxy-7-azaspiro[4.5]decan-7-ium chloride 4 M HCl in 1,4-dioxane (0.61 mL, 17.7 mmol) was added to tert-butyl 10-((5-(dimethylcarbamoyl)-2-oxo-4-(thiophen-3-yl)pyridin-1 (2H)-yl)methyl)-10-hydroxy-7-azaspiro[4.5]decane-7-carboxylate (19.0 mg, 0.0368 mmol) and the resulting mixture was stirred at RT. After 1 h, the solvents were removed in vacuo to give the crude title compound (20.2 mg, >100%) as a pale yellow oil that was carried through to the next step without further purification. LCMS (Method A): R$_T$=0.48 min, m/z=416 [M+H]$^+$.

Step 3: 1-((7-((R)-3-Cyclohexyl-2-methylpropanoyl)-10-hydroxy-7-azaspiro[4.5]decan-10-yl)methyl)-N,N-dimethyl-6-oxo-4-(thiophen-3-yl)-1,6-dihydropyridine-3-carboxamide DIPEA (0.0129 mL, 0.0736 mmol) was added to a stirred solution of 10-((5-(dimethylcarbamoyl)-2-oxo-4-(thiophen-3-yl)pyridin-1(2H)-yl)methyl)-10-hydroxy-7-azaspiro[4.5]decan-7-ium chloride (assumed 16.6 mg, 0.0368 mmol), Acid 1 (6.3 mg, 0.0368 mmol) and HATU (16.8 mg, 0.0368 mmol) in DCM (1.0 mL) at RT. After 2 h, the reaction mixture was partitioned between saturated sodium bicarbonate (aq) solution and further DCM, separated, extracted (2×DCM), the organic phase was dried (phase separator), the solvents were removed in vacuo, and the remaining residue was purified by flash chromatography (0-5%, MeOH in DCM) and freeze-dried to give the title compound (16.2 mg, 77%) as a white solid. LCMS (Method A): $R_T$=1.56 min, m/z=568 [M+H]$^+$. $^1$H NMR (400 MHz, DMSO-d$_6$): δ 7.80-7.75 (m, 1H), 7.73-7.70 (m, 1H), 7.66-7.62 (m, 1H), 7.24-7.20 (m, 1H), 6.62-6.57 (m, 1H), 5.01-4.88 (m, 1H), 4.70-4.49 (m, 1H), 3.92-3.37 (m, 3H), 3.28-3.16 (m, 1H, overlapping solvent peak), 2.95-2.78 (m, 4H), 2.66 (s, 3H), 2.00-1.80 (m, 1H), 1.79-0.70 (m, 26H).

Example 156: 1-((7-((R)-3-Cyclohexyl-2-methyl-propanoyl)-10-hydroxy-7-azaspiro[4.5]decan-10-yl)methyl)-4-(3-(hydroxymethyl)phenyl)-N,N-dimethyl-6-oxo-1,6-dihydropyridine-3-carboxamide

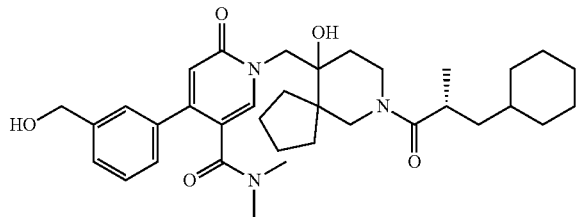 [SMILES: C[C@H](CC1CCCCC1)C(=O)N1CCC(O)(Cn2cc(C(=O)N(C)C)c(-c3cccc(CO)c3)cc2=O)C2(CCCC2)C1]

Step 1: tert-Butyl 10-((5-(dimethylcarbamoyl)-4-(3-(hydroxymethyl)phenyl)-2-oxopyridin-1 (2H)-yl)methyl)-10-hydroxy-7-azaspiro[4.5]decane-7-carboxylate PdCl$_2$(dppf).DCM (2.6 mg, 0.0032 mmol) was added to a pre-degassed solution of tert-butyl 10-((4-chloro-5-(dimethylcarbamoyl)-2-oxopyridin-1 (2H)-yl)methyl)-10-hydroxy-7-azaspiro[4.5]decane-7-carboxylate (30.0 mg, 0.0641 mmol), (3-(hydroxymethyl)phenyl)boronic acid (14.6 mg, 0.962 mmol) and sodium carbonate (13.6 mg, 0.128 mmol) in 1,4-dioxane (0.75 mL)/water (0.25 mL) in a 10 mL vial. The vessel was sealed and heated under microwave irradiation (CEM) at 120° C. with stirring for 30 min. The solvents were removed in vacuo and the remaining residue was partitioned between EtOAc and water, separated, extracted (EtOAc×2), the combined organic phase was dried (phase separator), the solvents were removed in vacuo, and the remaining residue was purified by flash chromatography (0-100%, EtOAc in cyclohexane). The pure fractions were concentrated to give the title compound (16.1 mg, 47%) as a colourless gum. LCMS (Method A): $R_T$=1.17 min, m/z=540 [M+H]$^+$.

Step 2: 10-((5-(Dimethylcarbamoyl)-4-(3-(hydroxymethyl)phenyl)-2-oxopyridin-1(2H)-yl)methyl)-10-hydroxy-7-azaspiro[4.5]decan-7-ium chloride 4 M HCl in 1,4-dioxane (0.5 mL, 14.3 mmol) was added to tert-butyl 10-((5-(dimethylcarbamoyl)-4-(3-(hydroxymethyl)phenyl)-2-oxopyridin-1(2H)-yl)methyl)-10-hydroxy-7-azaspiro[4.5]decane-7-carboxylate (16.1 mg, 0.0298 mmol) and the resulting mixture was stirred at RT. After 1 h, the solvents were removed in vacuo to give the crude title compound (18.1 mg, >100%) as a pale yellow oil that was carried through to the next step without further purification. LCMS (Method A): $R_T$=0.34 min, m/z=440 [M+H]$^+$.

Step 3: 1-((7-((R)-3-Cyclohexyl-2-methylpropanoyl)-10-hydroxy-7-azaspiro[4.5]decan-10-yl)methyl)-4-(3-(hydroxymethyl)phenyl)-N,N-dimethyl-6-oxo-1,6-dihydropyridine-3-carboxamide DIPEA (0.010 mL, 0.0596 mmol) was added to a stirred solution of 10-((5-(dimethylcarbamoyl)-4-(3-(hydroxymethyl)phenyl)-2-oxopyridin-1 (2H)-yl)methyl)-10-hydroxy-7-azaspiro[4.5]decan-7-ium chloride (assumed 14.2 mg, 0.0298 mmol), Acid 1 (5.1 mg, 0.0298 mmol) and HATU (13.6 mg, 0.0358 mmol) in DCM (1.0 mL) at RT. After 2 h, the reaction mixture was partitioned between saturated sodium bicarbonate (aq) solution and further DCM, separated, extracted (2×DCM), the organic phase was dried (phase separator), the solvents were removed in vacuo, and the remaining residue was purified by flash chromatography (0-5%, MeOH in DCM) and freeze-dried to give the title compound (11.7 mg, 65%) as a white solid. LCMS (Method A): $R_T$=1.38 min, m/z=592 [M+H]$^+$. $^1$H NMR (400 MHz, DMSO-d$_6$): δ 7.86-7.81 (m, 1H), 7.41-7.32 (m, 3H), 7.27-7.20 (m, 1H), 6.47-6.41 (m, 1H), 5.25 (t, 1H), 5.00-4.88 (m, 1H), 4.72-4.59 (m, 1H), 4.52 (d, 2H), 3.93-3.37 (m, 3H), 3.26-3.10 (m, 1H, overlapping solvent peak), 2.94-2.80 (m, 1H), 2.76 (s, 3H), 2.64 (s, 3H), 2.02-1.81 (m, 1H), 1.79-0.73 (m, 26H).

Example 157: 1-((7-(3-Cyclohexyl-2-hydroxypropanoyl)-10-hydroxy-7-azaspiro[4.5]decan-10-yl)methyl)-N,N-dimethyl-6-oxo-4-phenyl-1,6-dihydropyridine-3-carboxamide

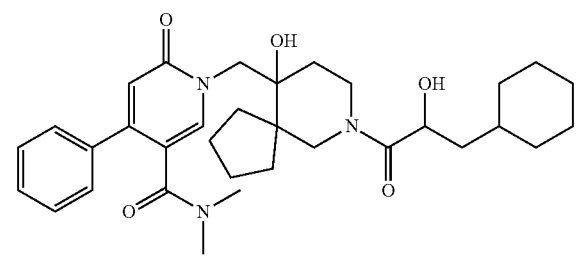 [SMILES: CN(C)C(=O)c1cn(CC2(O)CCN(C(=O)C(O)CC3CCCCC3)CC23CCCC3)c(=O)cc1-c1ccccc1]

Prepared according to General Procedure 3 using Amine 8 (25 mg, 61.0 μmol), 3-cyclohexyl-2-hydroxypropanoic acid (11.6 mg, 67.2 μmol), HATU (27.8 mg, 73.3 μmol) and DIPEA (32 μL, 0.183 mmol) in DCM (1 mL) to give 1-((7-(3-cyclohexyl-2-hydroxypropanoyl)-10-hydroxy-7-azaspiro[4.5]decan-10-yl)methyl)-N,N-dimethyl-6-oxo-4-phenyl-1,6-dihydropyridine-3-carboxamide (8 mg, 22%). LCMS (Method A): $R_T$=1.39 min, m/z=564 [M+H]$^+$. $^1$H NMR (400 MHz, DMSO-d$_6$): δ 7.86-7.81 (m, 1H), 7.47-7.35 (m, 5H), 6.47-6.43 (m, 1H), 5.02-4.90 (m, 1H), 4.79-4.53 (m, 1H), 4.43-4.26 (m, 1H), 3.78-3.56 (m, 2H), 3.47-3.26 (m, 3H (signal overlaps with HDO)), 2.75 (s, 3H), 2.63 (s, 3H (signal overlaps with DMSO satellite)), 2.01-0.76 (m, 24H).

Example 158: 1-((10-Hydroxy-7-(2-methyl-3-(piperidin-1-yl)propanoyl)-7-azaspiro[4.5]decan-10-yl)methyl)-N,N-dimethyl-6-oxo-4-phenyl-1,6-dihydropyridine-3-carboxamide

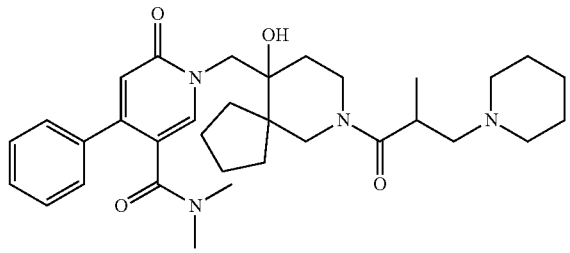 [SMILES: CC(CN1CCCCC1)C(=O)N1CCC(O)(Cn2cc(C(=O)N(C)C)c(-c3ccccc3)cc2=O)C2(CCCC2)C1]

DIPEA (0.038 mL, 0.220 mmol) was added to a stirred solution of Amine 8 (30.0 mg, 0.0733 mmol), 2-methyl-3-(piperidin-1-yl)propanoic acid hydrochloride (15.2 mg, 0.0733 mmol) and HATU (33.4 mg, 0.0879 mmol) in DCM (1.0 mL) at RT. After 2 h, the reaction mixture was diluted with DCM and saturated sodium bicarbonate (aq) solution was added. The resulting biphasic mixture was separated, dried (phase separator), the solvents were removed in vacuo, and the remaining residue was purified by flash chromatography using a 11 g KP-NH column (0-100%, EtOAc in cyclohexane; then 0-10% MeOH in EtOAc) and freeze-dried to give the title compound (37.6 mg, 91%) as a white solid. LCMS (Method A): $R_T$=0.66 min, m/z=563 [M+H]$^+$. $^1$H NMR (400 MHz, DMSO-d$_6$): δ 7.86-7.80 (m, 1H), 7.47-7.33 (m, 5H), 6.48-6.42 (m, 1H), 5.00-4.85 (m, 1H), 4.75-4.52 (m, 1H), 3.95-3.38 (m, 4H), 3.28-2.93 (m, 2H, overlapping solvent peak), 2.75 (s, 3H), 2.63 (s, 3H), 2.46-2.38 (m, 1H, overlapping solvent peak), 2.29 (br s, 4H), 2.13-2.04 (m, 1H), 1.95-1.80 (m, 1H), 1.75-1.07 (m, 15H), 0.98-0.87 (m, 3H).

Example 159: 6-(3-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one

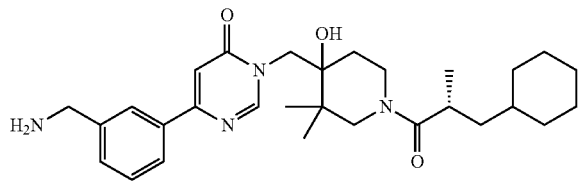 [SMILES: C[C@H](CC1CCCCC1)C(=O)N1CCC(O)(Cn2cnc(-c3cccc(CN)c3)cc2=O)C(C)(C)C1]

Step 1: tert-Butyl (3-(1-((1-((R)-3-cyclohexyl-2-methylpropanoyl)-4-hydroxy-3,3-dimethylpiperidin-4-yl)methyl)-6-oxo-1,6-dihydropyrimidin-4-yl)benzyl)carbamate Prepared according to General Procedure 4 using Intermediate 3 (50 mg, 0.118 mmol), (3-(((tert-butoxycarbonyl)amino)methyl)phenyl)boronic acid (44.4 mg, 0.177 mmol), tetrakis(triphenylphosphine)palladium(0) (6.81 mg, 5.90 µmol), sodium carbonate (25.0 mg, 0.236 mmol), 1,4-dioxane (0.75 mL) and water (0.3 mL). The reaction was heated under microwave irradiation at 150° C. for 10 min to give the title compound (52 mg, 74%). LCMS (Method A): $R_T$=1.77 min, m/z=595 [M+H]$^+$.

Step 2: 6-(3-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one A solution of tert-butyl (3-(1-((1-((R)-3-cyclohexyl-2-methylpropanoyl)-4-hydroxy-3,3-dimethylpiperidin-4-yl)methyl)-6-oxo-1,6-dihydropyrimidin-4-yl)benzyl)carbamate (52 mg, 87.4 µmol) in DCM (1 mL) and HCl (4 M in 1,4-dioxane, 0.5 mL, 2.00 mmol) was stirred for 30 min at RT. The reaction mixture was quenched with saturated NaHCO$_{3(aq)}$ and the aqueous phase was extracted with DCM (×3) using a Biotage phase separator. The combined organic phases were concentrated in vacuo and the residue was purified by flash chromatography to give the title compound (34 mg, 77%). LCMS (Method A): $R_T$=1.53 min, m/z=495 [M+H]$^+$. $^1$H NMR (400 MHz, DMSO-d$_6$): δ 8.43 (s, 1H), 8.05 (s, 1H), 7.90 (d, J=7.2 Hz, 1H), 7.47-7.38 (m, 2H), 6.98 (d, J=5.6 Hz 1H), 4.90 (s, 1H), 4.50-4.34 (m, 1H), 3.81-3.58 (m, 4H), 3.40-3.14 (m, 2H (signal overlaps with HDO)), 3.04-2.76 (m, 2H), 2.19-1.86 (bs, 2H), 1.76-1.37 (m, 7H), 1.27-0.72 (m, 17H).

Example 160: 1-(((S)-1-((S)-3-Cyclohexyl-2-(methoxymethyl)propanoyl)-4-hydroxy-3,3-dimethylpiperidin-4-yl)methyl)-N,N-dimethyl-6-oxo-4-phenyl-1,6-dihydropyridine-3-carboxamide

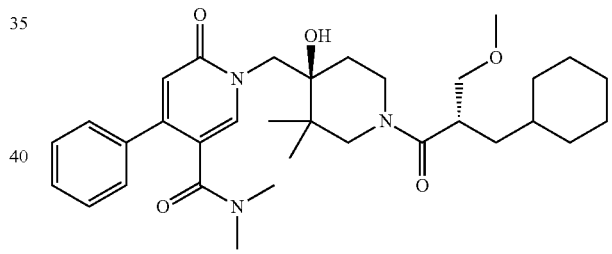

Sodium hydride (60% dispersion in mineral oil, 2.4 mg, 58.9 µmol) was added to a solution of 1-(((S)-1-((S)-3-cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide (13 mg, 23.6 µmol) in THF (0.24 mL) and after 1 h, iodomethane (0.2 M in THF, 0.177 mL, 35.3 µmol) was added. The reaction was stirred overnight before being diluted with water (5 mL) and extracted with DCM (3×5 mL) using a Biotage phase separator. The combined organic phases were concentrated in vacuo and the residue was purified by flash chromatography (GraceResolv silica 12 g cartridge, 0-5% MeOH in DCM) and preparative HPLC under basic conditions to give the title compound (4.2 mg, 31%) as a colourless solid after lyophilisation. LCMS (Method A): $R_T$=1.45 min, m/z=566 [M+H]$^+$. $^1$H NMR (500 MHz, DMSO-d$_6$): δ 7.83-7.79 (m, 1H), 7.48-7.33 (m, 5H), 6.48-6.41 (m, 1H), 4.92 (s, 1H), 4.55-4.44 (m, 1H), 4.55-4.44 (m, 0.5H), 4.17-4.11 (m, 0.5H), 3.88-3.63 (m, 3H), 3.40-3.12 (m, 6H (signals overlap with HDO)), 3.02-2.98 (m, 0.5H), 2.87-2.79 (m, 0.5H), 2.75 (s, 3H), 2.62 (s, 3H), 1.76-1.50 (m, 6H), 1.44-1.33 (m, 1H), 1.22-1.05 (m, 6H), 1.04-0.91 (m, 6H), 0.87-0.76 (m, 2H).

Example 161: 4-(2-(Aminomethyl)phenyl)-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide

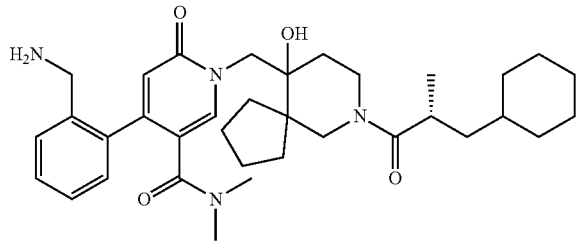 [SMILES: C[C@H](CC1CCCCC1)C(=O)N1CCC(O)(Cn2cc(C(=O)N(C)C)c(-c3ccccc3CN)cc2=O)C2(CCCC2)C1]

Step 1: tert-Butyl (2-(1-((7-((R)-3-cyclohexyl-2-methylpropanoyl)-10-hydroxy-7-azaspiro[4.5]decan-10-yl)methyl)-5-(dimethylcarbamoyl)-2-oxo-1,2-dihydropyridin-4-yl)benzyl)carbamate PdCl$_2$(dppf).DCM (2.6 mg, 0.0032 mmol) was added to a pre-degassed solution of 4-chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide (Example 144) (30.0 mg, 0.0641 mmol), tert-butyl (2-(4,4,5,5-tetramethyl-1,3,2-dioxaborolan-2-yl)benzyl)carbamate (32.0 mg, 0.0962 mmol) and sodium carbonate (13.6 mg, 0.128 mmol) in a 10 mL vial. The vessel was sealed and heated under microwave irradiation (CEM) at 120° C. with stirring for 30 min. The reaction mixture was partitioned between EtOAc and water, separated, extracted (EtOAc×2), the combined organic phase was dried (phase separator), the solvents were removed in vacuo, and the remaining residue was purified by flash chromatography (0-100%, EtOAc in cyclohexane) to give the title compound (17.2 mg, 39%) as a colourless gum. LCMS (Method A): R$_T$=1.77 min, m/z=691 [M+H]$^+$.

Step 2: 4-(2-(Aminomethyl)phenyl)-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide TFA (1.0 mL, 13.0 mmol) was added to a stirred solution of tert-butyl (2-(1-((7-((R)-3-cyclohexyl-2-methylpropanoyl)-10-hydroxy-7-azaspiro[4.5]decan-10-yl)methyl)-5-(dimethylcarbamoyl)-2-oxo-1,2-dihydropyridin-4-yl)benzyl)carbamate (17.2 mg, 0.0249 mmol) in DCM (1.0 mL) at RT. After 1 h, the solvents were removed in vacuo and the remaining residue was loaded onto a pre-equilibrated SCX-2 cartridge in MeOH solution, washed using MeOH and eluted using 7 M ammonia in MeOH solution. The solvents were removed in vacuo and the remaining residue was purified by flash chromatography using a 11 g KP-NH column (0-100%, EtOAc in cyclohexane; 0-10%, MeOH in EtOAc) to give the tile compound (11.3 mg, 74%) as an off-white solid. LCMS (Method A): R$_T$=1.05 min, m/z=591 [M+H]$^+$. $^1$H NMR (500 MHz, DMSO-d$_6$): δ 7.88-7.75 (m, 1H), 7.54 (d, 1H), 7.35 (t, 1H), 7.21 (t, 1H), 7.09-6.95 (m, 1H), 6.40-6.22 (m, 1H), 5.13-4.47 (m, 2H), 4.15-3.38 (m, 6H), 3.24-3.08 (m, 1H, overlapping solvent peak), 2.97-2.59 (m, 7H), 2.03-1.82 (m, 1H), 1.80-0.67 (m, 25H). [Note: 2H not visible].

Example 162: 1-((7-((R)-3-Cyclohexyl-2-methylpropanoyl)-10-hydroxy-7-azaspiro[4.5]decan-10-yl)methyl)-4-(4-(hydroxymethyl)phenyl)-N,N-dimethyl-6-oxo-1,6-dihydropyridine-3-carboxamide

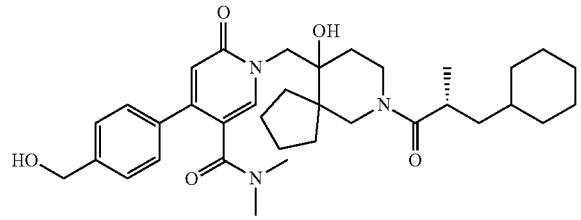 [SMILES: C[C@H](CC1CCCCC1)C(=O)N1CCC(O)(Cn2cc(C(=O)N(C)C)c(-c3ccc(CO)cc3)cc2=O)C2(CCCC2)C1]

Pd(dppf)Cl$_2$.DCM (2.4 mg, 0.0029 mmol) was added to a pre-degassed solution of 4-chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide (Example 144) (30.0 mg, 0.0577 mmol), (4-(hydroxymethyl)phenyl)boronic acid (13.2 mg, 0.0865 mmol) and sodium carbonate (12.2 mg, 0.115 mmol) in a 10 mL vial. The vessel was sealed and heated under microwave irradiation (CEM) at 120° C. with stirring for 30 min. The reaction mixture was partitioned between EtOAc and water, separated, extracted (EtOAc×2), the combined organic phase was dried (phase separator), the solvents were removed in vacuo, and the remaining residue was purified by flash chromatography (cyclohexane; 0-10%, MeOH in DCM) to give material that required further purification by flash chromatography (0-100%, EtOAc in cyclohexane; then 0-10% MeOH in EtOAc) to give the title compound (11.5 mg, 32%) as a white solid. LCMS (Method A): R$_T$=1.37 min, m/z=592 [M+H]$^+$. $^1$H NMR (500 MHz, DMSO-d$_6$): δ 7.86-7.77 (m, 1H), 7.41-7.29 (m, 4H), 6.47-6.40 (m, 1H), 5.27 (t, 1H), 5.02-4.87 (m, 1H), 4.72-4.47 (m, 3H), 3.93-3.10 (m, 4H, overlapping solvent peak), 2.95-2.80 (m, 1H), 2.76 (s, 3H), 2.65 (s, 3H), 2.03-1.82 (m, 1H), 1.79-0.74 (m, 26H).

Example 163: 1-((10-Hydroxy-7-(2-methyl-3-morpholinopropanoyl)-7-azaspiro[4.5]decan-10-yl)methyl)-N,N-dimethyl-6-oxo-4-phenyl-1,6-dihydropyridine-3-carboxamide

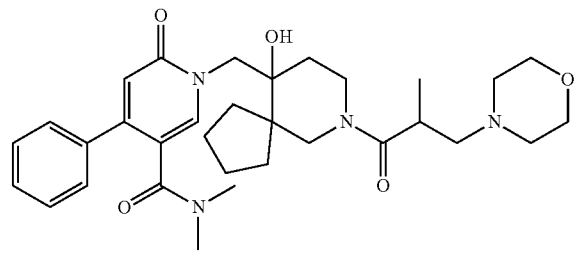 [SMILES: CC(CN1CCOCC1)C(=O)N1CCC(O)(Cn2cc(C(=O)N(C)C)c(-c3ccccc3)cc2=O)C2(CCCC2)C1]

DIPEA (0.026 mL, 0.147 mmol) was added to a stirred solution of Amine 8 (30.0 mg, 0.0733 mmol), 2-methyl-3-morpholinopropanoic acid (14.0 mg, 0.0806 mmol) and HATU (33.4 mg, 0.0879 mmol) in DCM (1.0 mL) at RT. After 2 h, the reaction mixture was diluted with further DCM and saturated sodium bicarbonate (aq) solution was added. The resulting biphasic mixture was separated, dried (phase separator), the solvents were removed in vacuo, and the remaining residue was purified by flash chromatography using a KP-NH column (0-100%, EtOAc in cyclohexane; 0-10%, MeOH in EtOAc) and freeze-dried to give the title compound (23.6 mg, 57%) as a white solid. LCMS (Method A): $R_T$=0.71 min, m/z=565 [M+H]$^+$. $^1$H NMR (500 MHz, DMSO-$d_6$): δ 7.88-7.78 (m, 1H), 7.47-7.30 (m, 5H), 6.49-6.39 (m, 1H), 5.02-4.82 (m, 1H), 4.77-4.50 (m, 1H), 3.97-3.35 (m, 7H, overlapping solvent peak), 3.31-2.97 (m, 2H, overlapping solvent peak), 2.75 (s, 3H), 2.63 (s, 3H), 2.55-2.07 (m, 6H, overlapping solvent peak), 2.03-0.77 (m, 14H).

Example 164 and Example 165: 1-(((S)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide and 1-(((R)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide

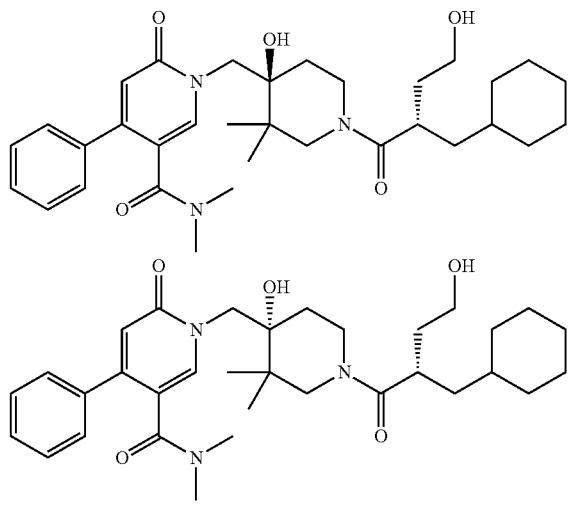

Step 1: 1-((1-((S)-4-((tert-Butyldimethylsilyl)oxy)-2-(cyclohexylmethyl)butanoyl)-4-hydroxy-3,3-dimethylpiperidin-4-yl)methyl)-N,N-dimethyl-6-oxo-4-phenyl-1,6-dihydropyridine-3-carboxamide Prepared according to General Procedure 3 using Amine 6 (55 mg, 0.143 mmol), Acid 9 (50 mg, 0.158 mmol), HATU (60 mg, 0.158 mmol), DIPEA (100 μL, 0.574 mmol) and DCM (3 mL) to give the title compound (92 mg, 94%) as colourless foam. LCMS (Method A): $R_T$=2.19 and 2.21 min (2 diastereomers), m/z=680 [M+H]$^+$.

Step 2: 1-(((S)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide and 1-(((R)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide TBAF (1 M in THF, 0.271 mL, 0.271 mmol) was added to a solution of 1-((1-((S)-4-((tert-butyldimethylsilyl)oxy)-2-(cyclohexylmethyl)butanoyl)-4-hydroxy-3,3-dimethylpiperidin-4-yl)methyl)-N,N-dimethyl-6-oxo-4-phenyl-1,6-dihydropyridine-3-carboxamide (92 mg, 0.135 mmol) in THF (0.54 mL) at 0° C. After 1 h, the reaction was allowed to warm to RT and after 21 h, the reaction mixture was purified directly by flash chromatography (GraceResolv silica 12 g cartridge, 0-20% MeOH in DCM) to give the crude product as a mixture of diastereomers. The diastereomers were separated by preparative HPLC under basic conditions to give the second eluted compound 1-(((S)-1-((S)-2-(cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide (15.6 mg, 20%) and first eluted compound 1-(((R)-1-((S)-2-(cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide (15.8 mg, 20%) both as colourless solids after lyophilisation. 1-(((S)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide: LCMS (Method A): $R_T$=1.24 min, m/z=566 [M+H]$^+$. $^1$H NMR (500 MHz, DMSO-$d_6$): δ 7.83-7.78 (m, 1H), 7.51-7.28 (m, 5H), 6.48-6.42 (m, 1H), 4.99-4.83 (m, 1H), 4.52-4.34 (m, 2H), 4.18-4.11 (m, 0.4H), 3.90-3.70 (m, 2H), 3.68-3.62 (m, 0.6H), 3.42-3.18 (m, 3H (overlaps with HDO signal)), 3.05-2.95 (m, 1.6H), 2.87-2.79 (m, 0.4H), 2.75 (s, 3H), 2.63 (s, 3H), 1.76-1.49 (m, 7H), 1.47-1.36 (m, 2H), 1.27-1.04 (m, 6H), 1.04-0.91 (m, 6H), 0.89-0.73 (m, 2H). 1-(((R)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide: LCMS (Method A): $R_T$=1.20 min, m/z=566 [M+H]$^+$. $^1$H NMR (500 MHz, DMSO-$d_6$): δ 7.83-7.78 (m, 1H), 7.48-7.34 (m, 5H), 6.48-6.42 (m, 1H), 4.97-4.85 (m, 1H), 4.52-4.35 (m, 2H), 4.05-3.98 (m, 0.4H), 3.86-3.68 (m, 2.6H), 3.40-3.18 (m, 3H (overlaps with HDO signal)), 3.05-2.87 (m, 2H), 2.75 (s, 3H), 2.62 (s, 3H), 1.74-1.34 (m, 9H), 1.27-1.07 (m, 6H), 1.07-0.91 (m, 6H), 0.90-0.77 (m, 2H).

Example 166 and Example 167: 1-(((S)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide and 1-(((R)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide

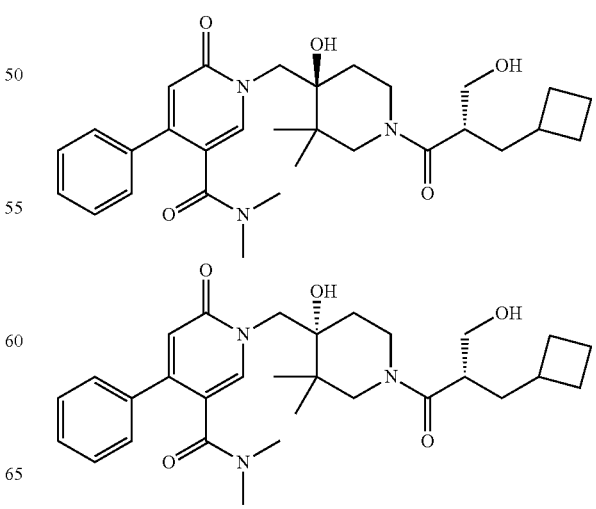

Prepared according to General Procedure 3 using Amine 6 (50 mg, 0.130 mmol), Acid 10 (31 mg, 0.196 mmol), HATU (74 mg, 0.196 mmol), DIPEA (91 µL, 0.522 mmol) and DCM (2.6 mL) to give a mixture of diastereomers which were separated by preparative HPLC under basic conditions to give the second eluted compound 1-(((S)-1-((S)-3-cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide (9 mg, 13%) and the first eluted compound 1-(((R)-1-((S)-3-cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide (8.3 mg, 12%) both as colourless solids after lyophilisation. 1-(((S)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide: LCMS (Method A): $R_T$=1.06 min, m/z=524 [M+H]$^+$. $^1$H NMR (500 MHz, DMSO-d$_6$): δ 7.84-7.78 (m, 1H), 7.56-7.24 (m, 5H), 6.48-6.42 (m, 1H), 4.97-4.85 (m, 1H), 4.59 (s, 1H), 4.52-4.37 (m, 1.4H), 4.11-4.04 (m, 0.6H), 3.87-3.67 (m, 2.6H), 3.49-3.13 (m, 2H), 2.99-2.80 (m, 2.4H), 2.75 (s, 3H), 2.62 (s, 3H), 2.20-2.06 (m, 1H), 2.03-1.87 (m, 2H), 1.81-1.64 (m, 3H), 1.61-1.36 (m, 4H), 1.21-1.15 (m, 1H), 1.09-0.87 (m, 6H). 1-(((R)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide: LCMS (Method A): $R_T$=1.05 min, m/z=524 [M+H]$^+$. $^1$H NMR (500 MHz, DMSO-d$_6$): δ 7.84-7.79 (m, 1H), 7.50-7.30 (m, 5H), 6.48-6.42 (m, 1H), 4.99-4.85 (m, 1H), 4.62-4.37 (m, 2.4H), 4.13-4.03 (m, 0.6H), 3.83-3.74 (m, 1.4H), 3.71-3.65 (m, 0.6H), 3.54-3.49 (m, 0.4H), 3.46-3.40 (m, 0.6H), 3.36-3.21 (m, 2H (overlaps with HDO signal)), 3.00-2.88 (m, 1H), 2.87-2.80 (m, 1H), 2.75 (s, 3H), 2.62 (s, 3H), 2.23-2.11 (m, 1H), 2.02-1.87 (m, 2H), 1.82-1.38 (m, 7H), 1.28-1.15 (m, 1H), 1.06-0.88 (m, 6H).

Example 168: 1-((1-((R)-3-Cyclohexyl-2-methylpropanoyl)-4-hydroxy-3,3-dimethylpiperidin-4-yl)methyl)-5-(morpholine-4-carbonyl)-4-phenylpyridin-2(1H)-one

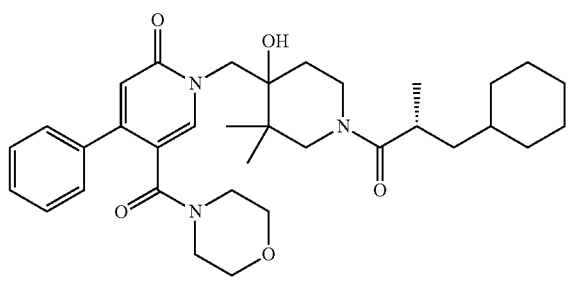 [SMILES: C[C@H](CC1CCCCC1)C(=O)N1CCC(O)(Cn2cc(C(=O)N3CCOCC3)c(-c3ccccc3)cc2=O)C(C)(C)C1]

DIPEA (0.031 mL, 0.177 mmol) was added to a stirred solution of 1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylic acid (30.0 mg, 0.0590 mmol), morpholine (0.0052 mL, 0.0590 mmol) and HATU (26.9 mg, 0.0708 mmol) in DCM (5.0 mL) at RT. After 16 h, saturated sodium bicarbonate (aq) solution was added and the resulting biphasic mixture was separated, extracted (DCM×2), the combined organic phase was dried (phase separator), the solvents were removed in vacuo, and the remaining residue was purified by flash chromatography (cyclohexane, then 0-10%, MeOH in DCM) and freeze-dried to give the title compound (29.8 mg, 85%) as a white solid. LCMS (Method A): $R_T$=1.49 min, m/z=578 [M+H]$^+$.

$^1$H NMR (500 MHz, DMSO-d$_6$): δ 7.83 (s, 1H), 7.51-7.36 (m, 5H), 6.48-6.43 (m, 1H), 5.07-4.70 (m, 1H), 4.53-4.33 (m, 1H), 4.15-2.74 (m, 9H, overlapping solvent peak), 2.69 (s, 4H), 1.80-1.39 (m, 7H), 1.32-0.68 (m, 18H).

Example 169: 5-(4-Acetylpiperazine-1-carbonyl)-1-((1-((R)-3-cyclohexyl-2-methylpropanoyl)-4-hydroxy-3,3-dimethylpiperidin-4-yl)methyl)-4-phenylpyridin-2(1H)-one

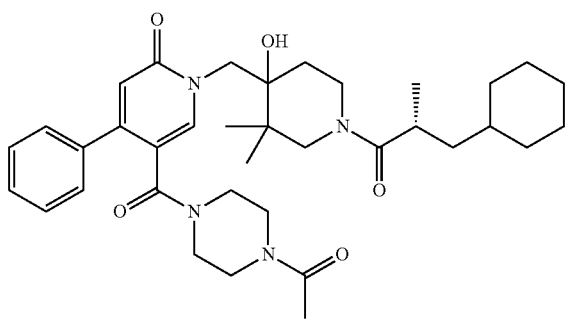 [SMILES: CC(=O)N1CCN(C(=O)c2cn(CC3(O)CCN(C(=O)[C@H](C)CC4CCCCC4)CC3(C)C)c(=O)cc2-c2ccccc2)CC1]

DIPEA (0.031 mL, 0.177 mmol) was added to a stirred solution of 1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylic acid (30.0 mg, 0.0590 mmol), N-acetylpiperazine (7.6 mg, 0.0590 mmol) and HATU (26.9 mg, 0.0708 mmol) in DCM (5.0 mL) at RT. After 18 h, saturated sodium bicarbonate (aq) solution was added and the resulting biphasic mixture was separated, extracted (DCM×2), the combined organic phase was dried (phase separator), the solvents were removed in vacuo, and the remaining residue was purified by flash chromatography (cyclohexane, then 0-10%, MeOH in DCM) and freeze-dried to give the title compound (24.9 mg, 67%) as a white solid. LCMS (Method A): $R_T$=1.32 min, m/z=619 [M+H]$^+$. $^1$H NMR (500 MHz, DMSO-d$_6$): δ 7.84 (s, 1H), 7.52-7.22 (m, 5H), 6.53-6.40 (m, 1H), 5.10-4.67 (m, 1H), 4.56-4.32 (m, 1H), 4.16-2.13 (m, 13H, overlapping solvent peaks), 2.03-1.82 (m, 3H), 1.80-1.39 (m, 7H), 1.33-0.73 (m, 18H).

Example 170: 1-((1-((R)-3-Cyclohexyl-2-methylpropanoyl)-4-hydroxy-3,3-dimethylpiperidin-4-yl)methyl)-5-(4-methylpiperazine-1-carbonyl)-4-phenylpyridin-2(1H)-one

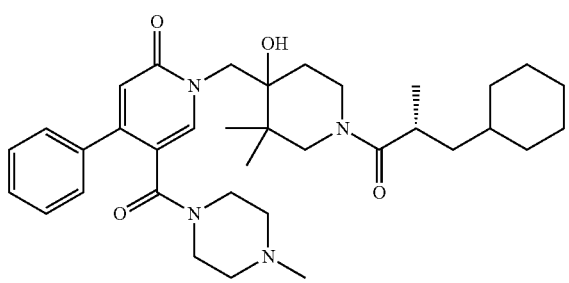 [SMILES: C[C@H](CC1CCCCC1)C(=O)N1CCC(O)(Cn2cc(C(=O)N3CCN(C)CC3)c(-c3ccccc3)cc2=O)C(C)(C)C1]

DIPEA (0.031 mL, 0.177 mmol) was added to a stirred solution of 1-((1-((R)-3-cyclohexyl-2-methylpropanoyl)-4-hydroxy-3,3-dimethylpiperidin-4-yl)methyl)-6-oxo-4-phenyl-1,6-dihydropyridine-3-carboxylic acid (30.0 mg, 0.0590 mmol), 1-methylpiperazine (0.0065 mL, 0.0590 mmol) and HATU (26.9 mg, 0.0708 mmol) in DCM (1.0 mL) at RT. After 18 h, saturated sodium bicarbonate (aq) solution was added and the resulting biphasic mixture was separated, extracted (DCM×2), the combined organic phase was dried (phase separator), the solvents were removed in vacuo, and the remaining residue was purified by flash chromatography (cyclohexane, then 0-10%, MeOH in DCM), further purified by flash chromatography (0-100%, EtOAc in cyclohexane; then 0-25%, MeOH in EtOAc) and freeze-dried to give the title compound (21.2 mg, 61%) as a white solid. LCMS (Method A): R$_T$=1.05 min, m/z=591 [M+H]$^+$. $^1$H NMR (500 MHz, DMSO-d$_6$): δ 7.81 (br s, 1H), 7.52-7.33 (m, 5H), 6.49-6.41 (m, 1H), 5.07-4.73 (m, 1H), 4.53-4.31 (m, 1H), 4.15-2.74 (m, 9H, overlapping solvent peak), 2.33-0.74 (m, 32H).

The following table of Examples were prepared using parallel synthesis according to General Procedure 13. Example 181 uses Acid 15. The carboxylic acid used for Example 180, may be prepared using the same procedure for Acid 15, except using the 1$^{st}$ eluted diastereoisomer from Step 4 and following the method described in Step 5 to obtain (S)-4,4-difluoro-3-phenylbutanoic acid.

| Example | Structure | Name | LCMS (Method A): R$_T$, m/z |
|---|---|---|---|
| 171 | 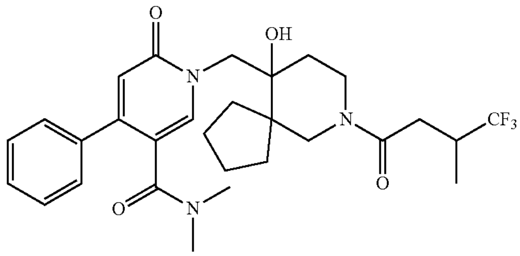 [SMILES: CC(CC(=O)N1CCC(O)(Cn2cc(C(=O)N(C)C)c(-c3ccccc3)cc2=O)C2(CCCC2)C1)C(F)(F)F] | 1-((10-Hydroxy-7-(4,4,4-trifluoro-3-methylbutanoyl)-7-azaspiro[4.5]decan-10-yl)methyl)-N,N-dimethyl-6-oxo-4-phenyl-1,6-dihydropyridine-3-carboxamide | 1.38 min, 548 [M + H]$^+$ |
| 172 | 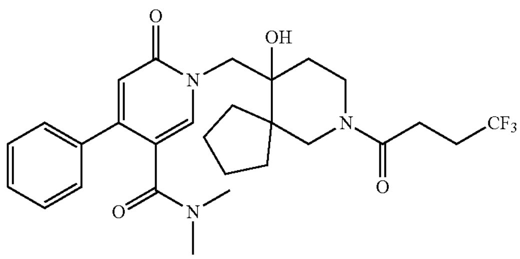 [SMILES: CN(C)C(=O)c1cn(CC2(O)CCN(C(=O)CCC(F)(F)F)CC23CCCC3)c(=O)cc1-c1ccccc1] | 1-((10-Hydroxy-7-(4,4,4-trifluorobutanoyl)-7-azaspiro[4.5]decan-10-yl)methyl)-N,N-dimethyl-6-oxo-4-phenyl-1,6-dihydropyridine-3-carboxamide | 1.28 min, 534 [M + H]$^+$ |
| 173 | 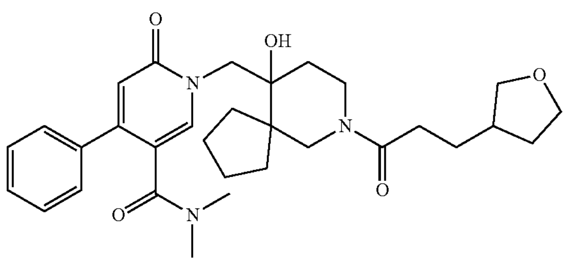 [SMILES: CN(C)C(=O)c1cn(CC2(O)CCN(C(=O)CCC3CCOC3)CC23CCCC3)c(=O)cc1-c1ccccc1] | 1-((10-Hydroxy-7-(3-(tetrahydrofuran-3-yl)propanoyl)-7-azaspiro [4.5]decan-10-yl)methyl)-N,N-dimethyl-6-oxo-4-phenyl-1,6-dihydropyridine-3-carboxamide | 1.05 min, 536 [M + H]$^+$ |
| 174 | 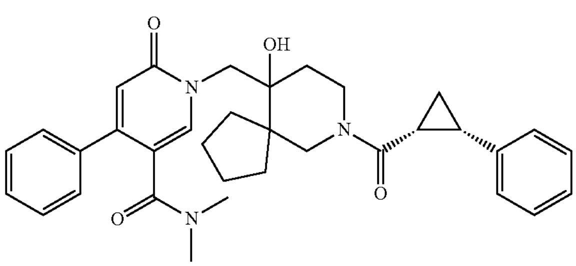 [SMILES: CN(C)C(=O)c1cn(CC2(O)CCN(C(=O)[C@@H]3C[C@@H]3c3ccccc3)CC23CCCC3)c(=O)cc1-c1ccccc1] | 1-((10-Hydroxy-7-((1R,2S)-2-phenylcyclopropane-1-carbonyl)-7-azaspiro[4.5]decan-10-yl)methyl)-N,N-dimethyl-6-oxo-4-phenyl-1,6-dihydropyridine-3-carboxamide | 1.32 min, 554 [M + H]$^+$ |
| 175 | 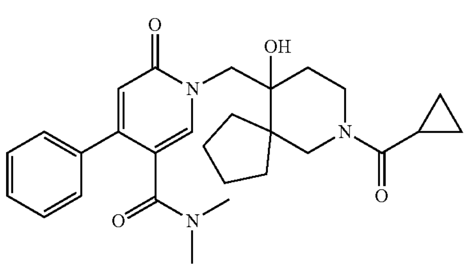 [SMILES: CN(C)C(=O)c1cn(CC2(O)CCN(C(=O)C3CC3)CC23CCCC3)c(=O)cc1-c1ccccc1] | 1-((7-(Cyclopropanecarbonyl)-10-hydroxy-7-azaspiro[4.5]decan-10-yl)methyl)-N,N-dimethyl-6-oxo-4-phenyl-1,6-dihydropyridine-3-carboxamide | 1.09 min, 478 [M + H]$^+$ |

-continued

| Example | Structure | Name | LCMS (Method A): $R_T$, m/z |
|---|---|---|---|
| 176 | 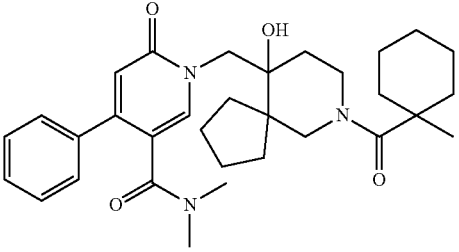 [SMILES: CN(C)C(=O)c1cn(CC2(O)CCN(C(=O)C3(C)CCCCC3)CC23CCCC3)c(=O)cc1-c1ccccc1] | 1-((10-Hydroxy-7-(1-methylcyclohexane-1-carbonyl)-7-azaspiro[4.5]decan-10-yl)methyl)-N,N-dimethyl-6-oxo-4-phenyl-1,6-dihydropyridine-3-carboxamide | 1.50 min, 534 [M + H]$^+$ |
| 177 | 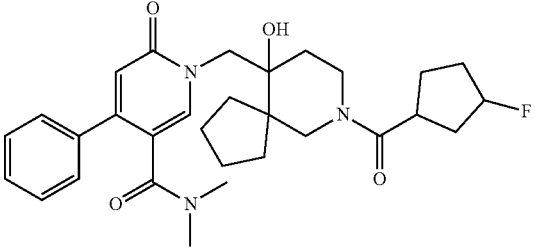 [SMILES: CN(C)C(=O)c1cn(CC2(O)CCN(C(=O)C3CCC(F)C3)CC23CCCC3)c(=O)cc1-c1ccccc1] | 1-((7-(3-Fluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide | 1.18 min, 524 [M + H]$^+$ |
| 178 | 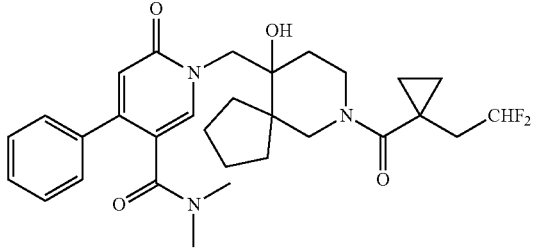 [SMILES: CN(C)C(=O)c1cn(CC2(O)CCN(C(=O)C3(CC(F)F)CC3)CC23CCCC3)c(=O)cc1-c1ccccc1] | 1-((7-(1-(2,2-Difluoroethyl)cyclopropane-1-carbonyl)-10-hydroxy-7-azaspiro[4.5]decan-10-yl)methyl)-N,N-dimethyl-6-oxo-4-phenyl-1,6-dihydropyridine-3-carboxamide | 1.18 min, 542 [M + H]$^+$ |
| 179 | 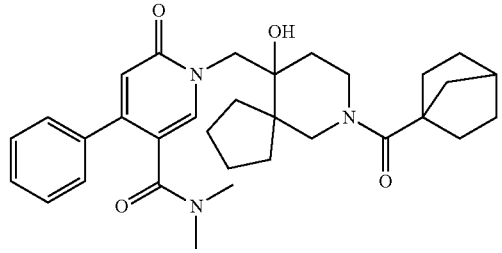 [SMILES: CN(C)C(=O)c1cn(CC2(O)CCN(C(=O)C34CCC(CC3)C4)CC23CCCC3)c(=O)cc1-c1ccccc1] | 1-((7-(Bicyclo[2.2.1]heptane-1-carbonyl)-10-hydroxy-7-azaspiro[4.5]decan-10-yl)methyl)-N,N-dimethyl-6-oxo-4-phenyl-1,6-dihydropyridine-3-carboxamide | 1.38 min, 532 [M + H]$^+$ |
| 180 | 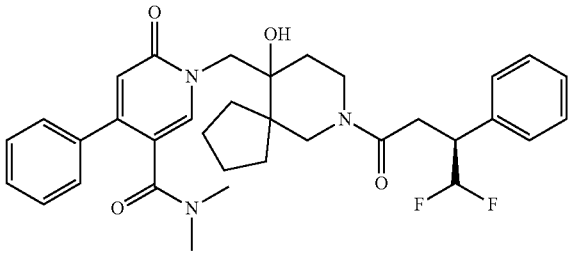 [SMILES: CN(C)C(=O)c1cn(CC2(O)CCN(C(=O)C[C@@H](c3ccccc3)C(F)F)CC23CCCC3)c(=O)cc1-c1ccccc1] | 1-((7-((S)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide | 1.41 min, 592 [M + H]$^+$ |

-continued

| Example | Structure | Name | LCMS (Method A): R$_T$, m/z |
|---|---|---|---|
| 181 | 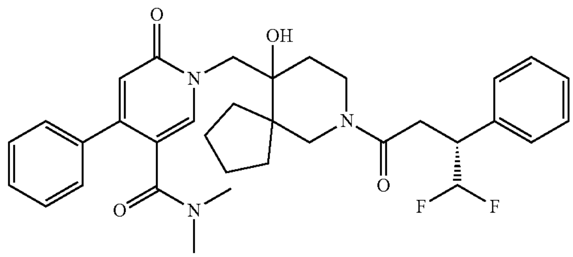 [SMILES: CN(C)C(=O)c1cn(CC2(O)CCN(C(=O)C[C@H](c3ccccc3)C(F)F)CC23CCCC3)c(=O)cc1-c1ccccc1] | 1-((7-((R)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide | 1.41 min, 592 [M + H]$^+$ |
| 182 | 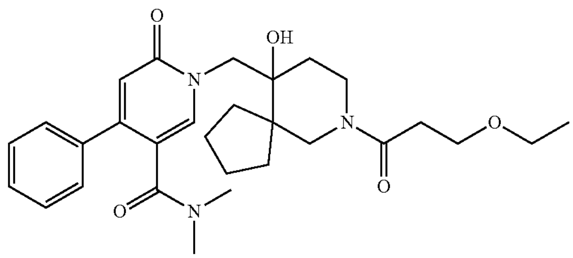 [SMILES: CCOCCC(=O)N1CCC(O)(Cn2cc(C(=O)N(C)C)c(-c3ccccc3)cc2=O)C2(CCCC2)C1] | 1-((7-(3-Ethoxypropanoyl)-10-hydroxy-7-azaspiro[4.5]decan-10-yl)methyl)-N,N-dimethyl-6-oxo-4-phenyl-1,6-dihydropyridine-3-carboxamide | 1.08 min, 510 [M + H]$^+$ |
| 183 | 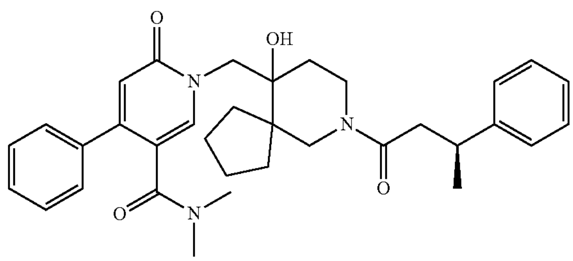 [SMILES: C[C@@H](CC(=O)N1CCC(O)(Cn2cc(C(=O)N(C)C)c(-c3ccccc3)cc2=O)C2(CCCC2)C1)c1ccccc1] | 1-((10-Hydroxy-7-((S)-3-phenylbutanoyl)-7-azaspiro[4.5]decan-10-yl)methyl)-N,N-dimethyl-6-oxo-4-phenyl-1,6-dihydropyridine-3-carboxamide | 1.41 min, 556 [M + H]$^+$ |
| 184 | 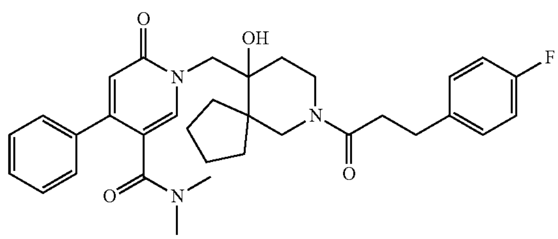 [SMILES: CN(C)C(=O)c1cn(CC2(O)CCN(C(=O)CCc3ccc(F)cc3)CC23CCCC3)c(=O)cc1-c1ccccc1] | 1-((7-(3-(4-Fluorophenyl)propanoyl)-10-hydroxy-7-azaspiro[4.5]decan-10-yl)methyl)-N,N-dimethyl-6-oxo-4-phenyl-1,6-dihydropyridine-3-carboxamide | 1.38 min, 560 [M + H]$^+$ |
| 185 | 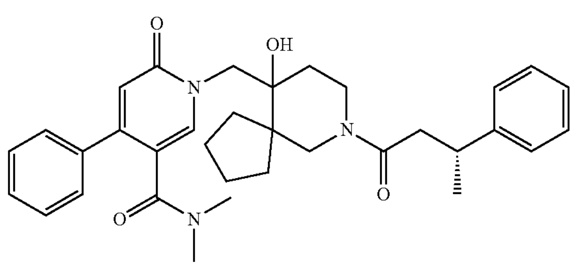 [SMILES: C[C@H](CC(=O)N1CCC(O)(Cn2cc(C(=O)N(C)C)c(-c3ccccc3)cc2=O)C2(CCCC2)C1)c1ccccc1] | 1-((10-Hydroxy-7-((R)-3-phenylbutanoyl)-7-azaspiro[4.5]decan-10-yl)methyl)-N,N-dimethyl-6-oxo-4-phenyl-1,6-dihydropyridine-3-carboxamide | 1.41 min, 556 [M + H]$^+$ |
| 186 | 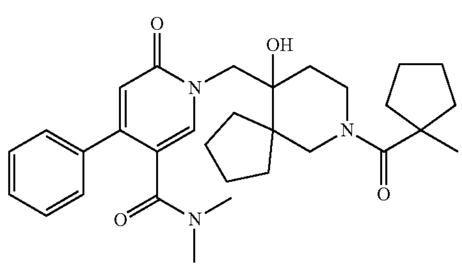 [SMILES: CN(C)C(=O)c1cn(CC2(O)CCN(C(=O)C3(C)CCCC3)CC23CCCC3)c(=O)cc1-c1ccccc1] | 1-((10-Hydroxy-7-(1-methylcyclopentane-1-carbonyl)-7-azaspiro[4.5]decan-10-yl)methyl)-N,N-dimethyl-6-oxo-4-phenyl-1,6-dihydropyridine-3-carboxamide | 1.37 min, 520 [M + H]$^+$ |

-continued

| Example | Structure | Name | LCMS (Method A): $R_T$, m/z |
|---|---|---|---|
| 187 | 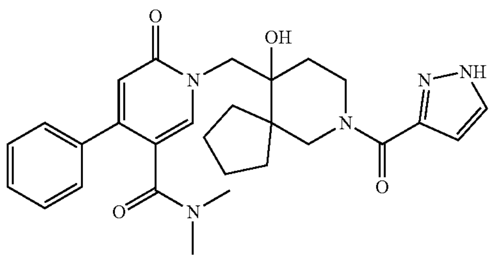 [SMILES: CN(C)C(=O)c1cn(CC2(O)CCN(C(=O)c3cc[nH]n3)CC23CCCC3)c(=O)cc1-c1ccccc1] | 1-((10-Hydroxy-7-(1H-pyrazole-3-carbonyl)-7-azaspiro[4.5]decan-10-yl)methyl)-N,N-dimethyl-6-oxo-4-phenyl-1,6-dihydropyridine-3-carboxamide | 0.864 min, 504 [M + H]+ |
| 188 | 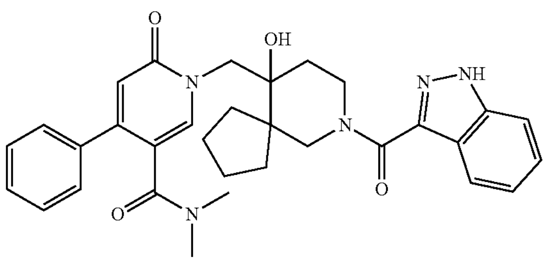 [SMILES: CN(C)C(=O)c1cn(CC2(O)CCN(C(=O)c3n[nH]c4ccccc34)CC23CCCC3)c(=O)cc1-c1ccccc1] | 1-((10-Hydroxy-7-(1H-indazole-3-carbonyl)-7-azaspiro[4.5]decan-10-yl)methyl)-N,N-dimethyl-6-oxo-4-phenyl-1,6-dihydropyridine-3-carboxamide | 1.09 min, 554 [M + H]+ |
| 189 | 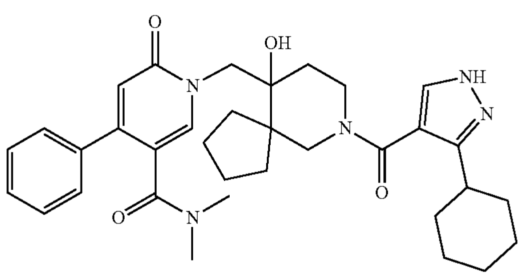 [SMILES: CN(C)C(=O)c1cn(CC2(O)CCN(C(=O)c3c[nH]nc3C3CCCCC3)CC23CCCC3)c(=O)cc1-c1ccccc1] | 1-((7-(3-Cyclohexyl-1H-pyrazole-4-carbonyl)-10-hydroxy-7-azaspiro [4.5]decan-10-yl)methyl)-N,N-dimethyl-6-oxo-4-phenyl-1,6-dihydropyridine-3-carboxamide | 1.10 min, 586 [M + H]+ |
| 190 | 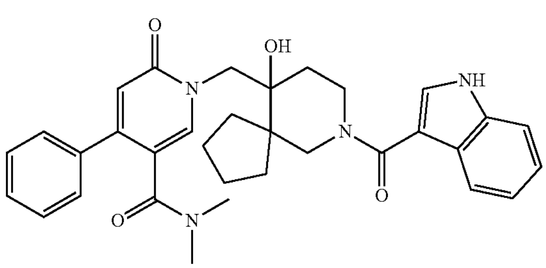 [SMILES: CN(C)C(=O)c1cn(CC2(O)CCN(C(=O)c3c[nH]c4ccccc34)CC23CCCC3)c(=O)cc1-c1ccccc1] | 1-((10-Hydroxy-7-(1H-indole-3-carbonyl)-7-azaspiro[4.5]decan-10-yl)methyl)-N,N-dimethyl-6-oxo-4-phenyl-1,6-dihydropyridine-3-carboxamide | 1.10 min, 553 [M + H]+ |
| 191 | 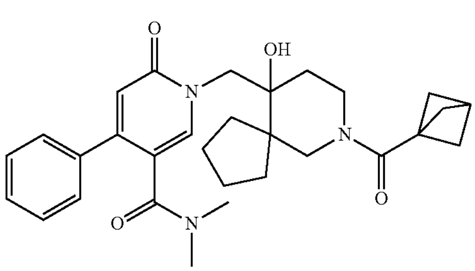 [SMILES: CN(C)C(=O)c1cn(CC2(O)CCN(C(=O)C34CC(C3)C4)CC23CCCC3)c(=O)cc1-c1ccccc1] | 1-((7-(Bicyclo[1.1.1]pentane-1-carbonyl)-10-hydroxy-7-azaspiro [4.5]decan-10-yl)methyl)-N,N-dimethyl-6-oxo-4-phenyl-1,6-dihydropyridine-3-carboxamide | 1.14 min, 504 [M + H]+ |

| Example | Structure | Name | LCMS (Method A): $R_T$, m/z |
|---|---|---|---|
| 192 | 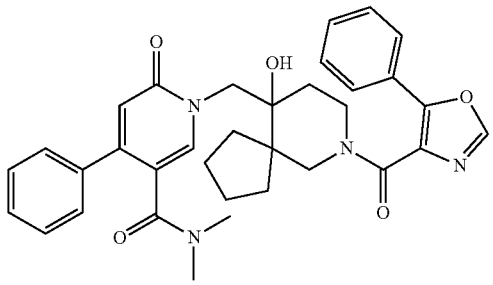 [SMILES: CN(C)C(=O)c1cn(CC2(O)CCN(C(=O)c3ncoc3-c3ccccc3)CC23CCCC3)c(=O)cc1-c1ccccc1] | 1-((10-Hydroxy-7-(5-phenyloxazole-4-carbonyl)-7-azaspiro[4.5]decan-10-yl)methyl)-N,N-dimethyl-6-oxo-4-phenyl-1,6-dihydropyridine-3-carboxamide | 1.23 min, 581 [M + H]+ |
| 193 | 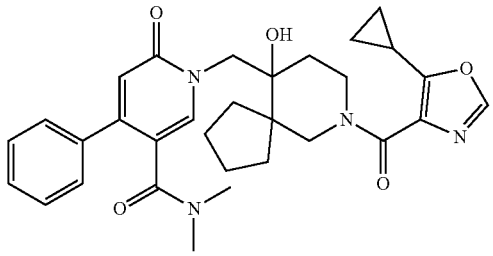 [SMILES: CN(C)C(=O)c1cn(CC2(O)CCN(C(=O)c3ncoc3C3CC3)CC23CCCC3)c(=O)cc1-c1ccccc1] | 1-((7-(5-Cyclopropyloxazole-4-carbonyl)-10-hydroxy-7-azaspiro [4.5]decan-10-yl)methyl)-N,N-dimethyl-6-oxo-4-phenyl-1,6-dihydropyridine-3-carboxamide | 1.11 min, 545 [M + H]+ |
| 194 | 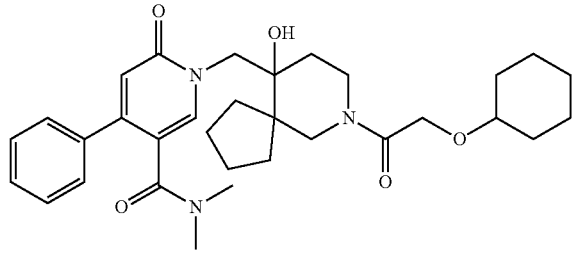 [SMILES: CN(C)C(=O)c1cn(CC2(O)CCN(C(=O)COC3CCCCC3)CC23CCCC3)c(=O)cc1-c1ccccc1] | 1-((7-(2-(Cyclohexyloxy)acetyl)-10-hydroxy-7-azaspiro[4.5]decan-10-yl)methyl)-N,N-dimethyl-6-oxo-4-phenyl-1,6-dihydropyridine-3-carboxamide | 1.30 min, 550 [M + H]+ |
| 195 | 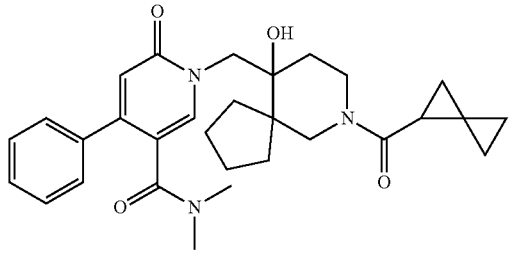 [SMILES: CN(C)C(=O)c1cn(CC2(O)CCN(C(=O)C3CC34CC4)CC23CCCC3)c(=O)cc1-c1ccccc1] | 1-((10-Hydroxy-7-(spiro[2.2]pentane-1-carbonyl)-7-azaspiro[4.5]decan-10-yl)methyl)-N,N-dimethyl-6-oxo-4-phenyl-1,6-dihydropyridine-3-carboxamide | 1.14 min, 504 [M + H]+ |
| 196 | 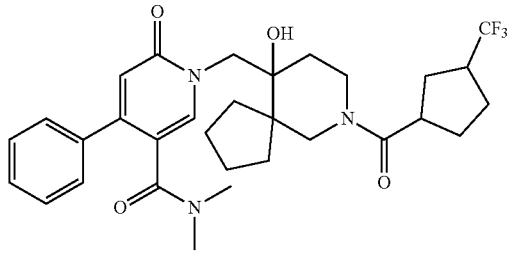 [SMILES: CN(C)C(=O)c1cn(CC2(O)CCN(C(=O)C3CCC(C(F)(F)F)C3)CC23CCCC3)c(=O)cc1-c1ccccc1] | 1-((10-Hydroxy-7-(3-(trifluoromethyl)cyclopentane-1-carbonyl)-7-azaspiro[4.5]decan-10-yl)methyl)-N,N-dimethyl-6-oxo-4-phenyl-1,6-dihydropyridine-3-carboxamide | 1.33 min, 574 [M + H]+ |

| Example | Structure | Name | LCMS (Method A): $R_T$, m/z |
|---|---|---|---|
| 197 | 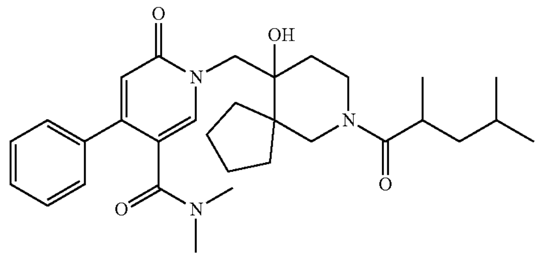 [SMILES: CC(C)CC(C)C(=O)N1CCC(O)(Cn2cc(C(=O)N(C)C)c(-c3ccccc3)cc2=O)C2(CCCC2)C1] | 1-((7-((2,4-Dimethylpentanoyl)-10-hydroxy-7-azaspiro[4.5]decan-10-yl)methyl)-N,N-dimethyl-6-oxo-4-phenyl-1,6-dihydropyridine-3-carboxamide | 1.37 min, 522 [M + H]⁺ |
| 198 | 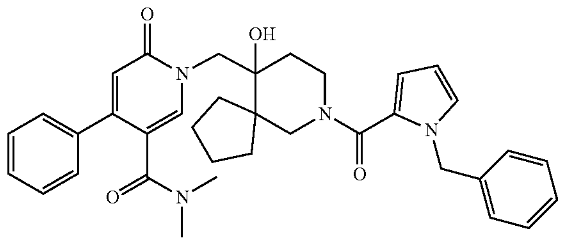 [SMILES: CN(C)C(=O)c1cn(CC2(O)CCN(C(=O)c3cccn3Cc3ccccc3)CC23CCCC3)c(=O)cc1-c1ccccc1] | 1-((7-(1-Benzyl-1H-pyrrole-2-carbonyl)-10-hydroxy-7-azaspiro[4.5]decan-10-yl)methyl)-N,N-dimethyl-6-oxo-4-phenyl-1,6-dihydropyridine-3-carboxamide | 1.41 min, 593 [M + H]⁺ |
| 199 | 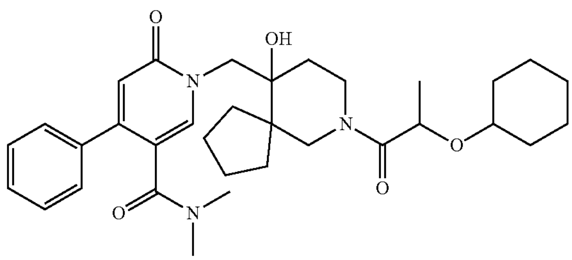 [SMILES: CC(OC1CCCCC1)C(=O)N1CCC(O)(Cn2cc(C(=O)N(C)C)c(-c3ccccc3)cc2=O)C2(CCCC2)C1] | 1-((7-(2-(Cyclohexyloxy)propanoyl)-10-hydroxy-7-azaspiro[4.5]decan-10-yl)methyl)-N,N-dimethyl-6-oxo-4-phenyl-1,6-dihydropyridine-3-carboxamide | 1.32 min, 564 [M + H]⁺ |

Example 200: 3-((1-((S)-3-Cyclobutyl-2-(hydroxymethyl)propanoyl)-4-hydroxy-3,3-dimethylpiperidin-4-yl)methyl)-6-(2-fluorophenyl)pyrimidin-4(3H)-one

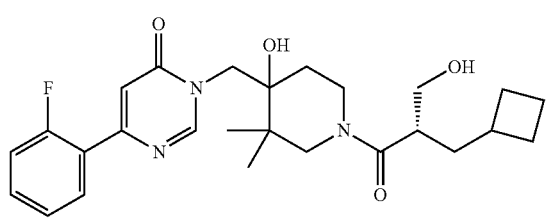 [SMILES: CC1(C)CN(C(=O)[C@H](CO)CC2CCC2)CCC1(O)Cn1cnc(-c2ccccc2F)cc1=O]

Prepared according to General Procedure 3 using Amine 5 (50 mg, 0.151 mmol), Acid 10 (35.8 mg, 0.226 mmol), HATU (86.1 mg, 0.226 mmol) and DIPEA (105 µL, 0.604 mmol) in DCM (2 mL) to give the title compound (32 mg, 44%). LCMS (Method A): $R_T$=1.22 min, m/z=472 [M+H]⁺. ¹H NMR (500 MHz, DMSO-d₆): δ 8.48-8.42 (m, 1H), 8.07-7.99 (m, 1H), 7.59-7.50 (m, 1H), 7.39-7.32 (m, 2H), 6.83-6.78 (m, 1H), 4.93-4.80 (m, 1H), 4.62-4.48 (m, 1H), 4.48-4.37 (m, 1H), 3.83-3.64 (m, 2H), 3.56-3.14 (m, 3H (signal overlaps with HDO)), 3.00-2.79 (m, 2H), 2.23-2.06 (m, 1H), 2.04-1.12 (m, 11H), 1.08-0.92 (m, 6H).

Example 201: 1-((7-(2-Cyclobutoxyacetyl)-10-hydroxy-7-azaspiro[4.5]decan-10-yl)methyl)-N,N-dimethyl-6-oxo-4-phenyl-1,6-dihydropyridine-3-carboxamide

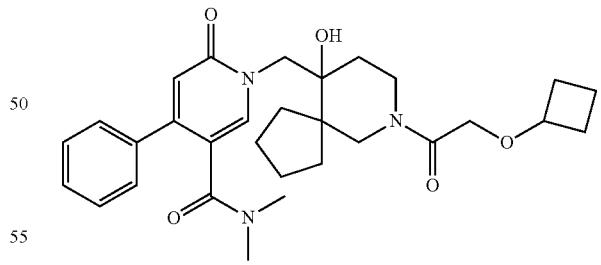

Prepared according to General Procedure 3 using Amine 8 (30 mg, 73.3 µmol), 2-cyclobutoxyacetic acid (14.3 mg, 0.110 mmol), HATU (41.8 mg, 0.110 mmol) and DIPEA (51 µL, 0.293 mmol) in DCM (1 mL) to give the title compound (11 mg, 28%). LCMS (Method A): $R_T$=1.12 min, m/z=522 [M+H]⁺. ¹H NMR (500 MHz, DMSO-d₆): δ 7.85-7.81 (m, 1H), 7.47-7.42 (m, 3H), 7.41-7.36 (m, 2H), 6.47-6.44 (m, 1H), 4.97 (s, 0.35H), 4.92 (s, 0.65H), 4.69-4.57 (m, 1H), 4.05-3.90 (m, 3H), 3.79-3.54 (m, 2H), 3.43-3.13 (m, 3H (signal overlaps with HDO)), 2.75 (s, 3H), 2.63 (s, 3H (signal overlaps with DMSO satellite)), 2.17-2.08 (m, 1H), 1.99-1.77 (m, 3H), 1.72-0.89 (m, 12H).

Example 202: 1-((7-(3,3-Difluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide

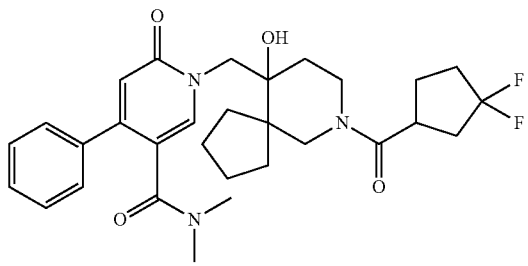 [SMILES: CN(C)C(=O)c1cn(CC2(O)CCN(C(=O)C3CCC(F)(F)C3)CC23CCCC3)c(=O)cc1-c1ccccc1]

Prepared according to General Procedure 3 using Amine 8 (30 mg, 73.3 µmol), 3,3-difluorocyclopentane-1-carboxylic acid (16.5 mg, 0.110 mmol), HATU (41.8 mg, 0.110 mmol) and DIPEA (51 µL, 0.293 mmol) in DMF (1 mL) to give the title compound (16 mg, 40%). LCMS (Method A): $R_T$=1.22 min, m/z=542 [M+H]$^+$. $^1$H NMR (500 MHz, DMSO-d$_6$): δ 7.86-7.80 (m, 1H), 7.48-7.42 (m, 3H), 7.41-7.35 (m, 2H), 6.48-6.44 (s, 1H), 5.00 (s, 0.25H), 4.92 (s, 0.75H), 4.76-4.50 (m, 1H), 3.80-3.12 (m, 6H (signals overlap with HDO)), 2.75 (s, 3H), 2.63 (s, 3H), 2.25-1.08 (m, 16H).

Example 203: 1-((10-Hydroxy-7-(2-hydroxy-3-phenylpropanoyl)-7-azaspiro[4.5]decan-10-yl)methyl)-N,N-dimethyl-6-oxo-4-phenyl-1,6-dihydropyridine-3-carboxamide

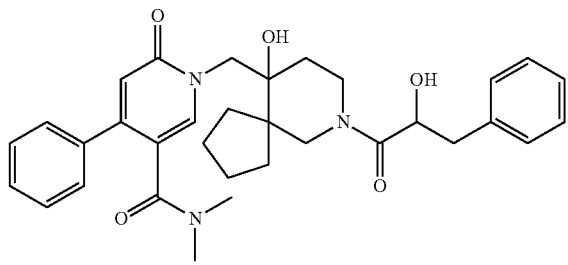 [SMILES: CN(C)C(=O)c1cn(CC2(O)CCN(C(=O)C(O)Cc3ccccc3)CC23CCCC3)c(=O)cc1-c1ccccc1]

Prepared according to General Procedure 3 using Amine 8 (23 mg, 56.2 µmol), 2-hydroxy-3-phenylpropanoic acid (14.0 mg, 84.2 µmol), HATU (32.0 mg, 84.2 µmol) and DIPEA (39 µL, 0.225 mmol) in DMF (1 mL) to give the title compound (11 mg, 34%). LCMS (Method A): $R_T$=1.18 min, m/z=558 [M+H]$^+$. $^1$H NMR (500 MHz, DMSO-d$_6$): δ 7.85-7.80 (m, 1H), 7.48-7.41 (m, 3H), 7.41-7.35 (m, 2H), 7.31-7.13 (m, 5H), 6.48-6.43 (m, 1H), 5.20-4.86 (m, 2H), 4.66-4.40 (m, 2H), 3.91-3.59 (m, 2H), 3.55-3.11 (m, 3H (signal overlaps with HDO)), 2.98-2.67 (m, 5H), 2.62 (s, 3H (signal overlaps with DMSO satellite)), 1.94-1.82 (m, 1H), 1.68-0.96 (m, 9H).

Example 204: 1-(((S)-4-Hydroxy-3,3-dimethyl-1-((R)-4,4,4-trifluoro-2-methylbutanoyl)piperidin-4-yl)methyl)-N,N-dimethyl-6-oxo-4-phenyl-1,6-dihydropyridine-3-carboxamide

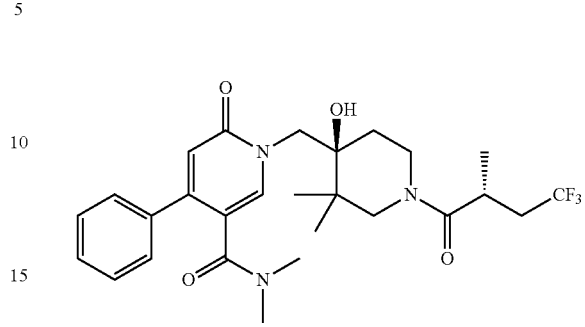

Prepared according to General Procedure 3 using Amine 7 (20 mg, 52.2 µmol), Acid 11 (10 mg, 62.6 µmol), HATU (24 mg, 62.6 µmol), DIPEA (36 µL, 0.209 mmol) and DCM (1 mL) to give the title compound (21.7 mg, 79%) as a colourless solid after lyophilisation. LCMS (Method A): $R_T$=1.16 min, m/z=522 [M+H]$^+$. $^1$H NMR (500 MHz, DMSO-d$_6$): δ 7.81 (s, 0.5H), 7.81 (s, 0.5H), 7.54-7.20 (m, 5H), 6.46 (s, 0.5H), 6.45 (s, 0.5H), 4.97 (s, 0.5H), 4.94 (s, 0.5H), 4.45 (d, J=13.4 Hz, 0.5H), 4.35 (d, J=13.4 Hz, 0.5H), 4.16 (d, J=13.0 Hz, 0.5H), 3.85 (d, J=13.4 Hz, 0.5H), 3.79 (d, J=13.5 Hz, 1H), 3.68 (d, J=12.7 Hz, 0.5H), 3.36-3.12 (m, 2H), 2.96 (d, J=12.8 Hz, 0.5H), 2.86-2.77 (m, 1H), 2.75 (s, 3H), 2.62 (s, 3H), 2.29-2.20 (m, 1H), 1.79-1.72 (m, 0.5H), 1.66-1.60 (m, 0.5H), 1.30-1.14 (m, 2H), 1.12 (d, J=6.9 Hz, 1.5H), 1.04 (d, J=7.0 Hz, 1.5H), 1.00 (s, 3H), 0.95 (s, 1.5H), 0.95 (s, 1.5H).

Example 205: 1-(((S)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide

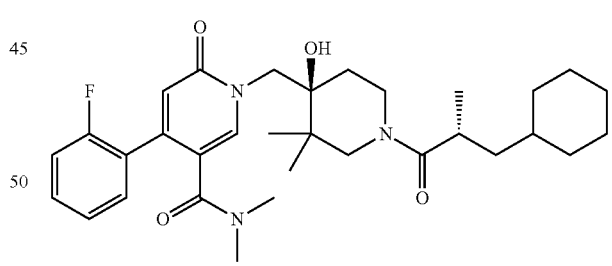

Step 1: Ethyl 1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carboxylate Prepared according to General Procedure 3 using Amine 9 (67 mg, 0.167 mmol), Acid 1 (28 mg, 0.167 mmol), HATU (63 mg, 0.167 mmol), DIPEA (0.116 mL, 0.666 mmol) and DCM (3.3 mL) to give the title compound (108 mg, >100%) as a colourless foam. LCMS (Method A): $R_T$=1.86 min, m/z=555 [M+H]$^+$.

Step 2: 1-(((S)-1-((R)-3-Cyclohexyl-2-methylpropanoyl)-4-hydroxy-3,3-dimethylpiperidin-4-yl)methyl)-4-(2-fluorophenyl)-6-oxo-1,6-dihydropyridine-3-carboxylic acid A solution of ethyl 1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carboxylate (108 mg, 0.195 mmol) in 1 M NaOH$_{(aq)}$ (0.389 mL, 0.389 mmol) and 1,4-dioxane (1 mL) was stirred at 50° C. for 16 h. The reaction mixture was allowed to cool to RT and the pH was adjusted to ~pH 2 by the addition of 1 M HCl$_{(aq)}$. The resulting mixture was extracted with DCM (3×20 mL) using a Biotage phase separator. The combined organic phases were concentrated in vacuo and the residue was purified by flash chromatography (GraceResolv silica 12 g cartridge, 0-100% EtOAc in cyclohexane) to give the title compound (61 mg, 59%) as a colourless solid. LCMS (Method A): $R_T$=1.54 min, m/z=527 [M+H]$^+$.

Step 3: 1-(((S)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide Prepared according to General Procedure 3 using 1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carboxylic acid (28 mg, 53.2 µmol), dimethylamine (2 M in THF, 32 µL, 63.8 µmol), HATU (24 mg, 63.8 µmol), DIPEA (37 µL, 0.213 mmol) and DCM (1 mL) to give the title compound (28.6 mg, 96%) as a colourless solid after lyophilisation. LCMS (Method A): $R_T$=1.53 min, m/z=554 [M+H]$^+$. $^1$H NMR (500 MHz, DMSO-d$_6$): δ 7.84 (s, 0.5H), 7.83 (s, 0.5H), 7.46 (tdd, J=7.5, 5.2, 1.8 Hz, 1H), 7.36 (tt, J=7.7, 2.1 Hz, 1H), 7.29-7.20 (m, 2H), 6.45 (s, 0.5), 6.43 (s, 0.5H), 4.90 (s, 0.5H), 4.88 (s. 0.5H), 4.52 (d, J=13.4 Hz, 0.5H), 4.39 (d, J=13.4 Hz, 0.5H), 4.11 (d, J=12.5 Hz, 0.5H), 3.84 (d, J=13.5 Hz, 0.5H), 3.78-3.69 (m, 1H), 3.60 (d, J=12.6 Hz, 0.5H), 3.31-3.22 (m, 1.5H), 3.02 (d, J=12.8 Hz, 0.5H), 2.96-2.66 (m, 7.5H), 1.77-1.42 (m, 7H), 1.29-0.89 (m, 15H), 0.88-0.74 (m, 2H).

Example 206: 1-(((S)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one

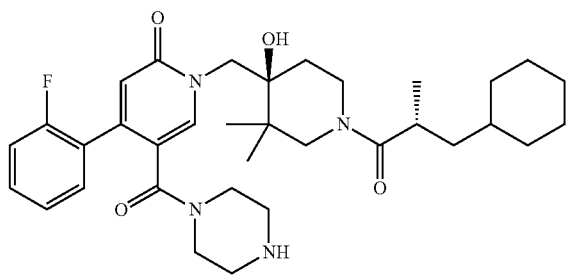 [SMILES: C[C@H](CC1CCCCC1)C(=O)N1CC[C@@](O)(Cn2cc(C(=O)N3CCNCC3)c(-c3ccccc3F)cc2=O)C(C)(C)C1]

Step 1: tert-Butyl 4-(1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carbonyl)piperazine-1-carboxylate Prepared according to General Procedure 3 using 1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carboxylic acid (Example 205, Step 2) (33 mg, 62.7 µmol), tert-butyl piperazine-1-carboxylate (14 mg, 75.2 µmol), HATU (29 mg, 75.2 µmol), DIPEA (44 µL, 0.251 mmol) and DCM (1.2 mL) to give the title compound (43 mg, 98%) as a colourless foam. LCMS (Method A): $R_T$=1.80 min, m/z=695 [M+H]$^+$.

Step 2: 1-(((S)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one A solution of tert-butyl 4-(1-(((S)-1-((R)-3-cyclohexyl-2-methylpropanoyl)-4-hydroxy-3,3-dimethylpiperidin-4-yl)methyl)-4-(2-fluorophenyl)-6-oxo-1,6-dihydropyridine-3-carbonyl)piperazine-1-carboxylate (43 mg, 61.9 µmol) in TFA (0.25 mL) and DCM (0.5 mL) was stirred for 20 min before the reaction mixture was purified using a Biotage SCX-2 2 g cartridge (pre-equilibrated with and then washed using 1:1 DCM/MeOH before being eluted with 1:1 DCM/7 M in NH$_3$ in MeOH). The basic eluents were concentrated in vacuo and the residue purified by flash chromatography (GraceResolv silica 12 g cartridge, 0-20% MeOH in DCM) to give the title compound (34.5 mg, 92%) as a colourless solid after lyophilisation. LCMS (Method A): $R_T$=1.09 min, m/z=595 [M+H]$^+$. $^1$H NMR (500 MHz, DMSO-d$_6$): δ 7.81 (s, 1H), 7.47 (dtd, J=7.6, 6.2, 5.2, 1.8 Hz, 1H), 7.37 (ddd, J=9.4, 6.9, 1.8 Hz, 1H), 7.32-7.24 (m, 2H), 6.45 (s, 0.5H), 6.43 (s, 0.5H), 4.87 (s, 1H), 4.51 (d, J=13.4 Hz, 0.5H), 4.39 (d, J=12.9 Hz, 0.5H), 4.11 (d, J=12.8 Hz, 0.5H), 3.84 (d, J=8.5 Hz, 0.5H), 3.78-3.70 (m, 1H), 3.60 (d, J=12.9 Hz, 0.5H), 3.45-3.09 (m, 9H (signal overlaps with HDO)), 3.03 (d, J=12.8 Hz, 0.5H), 2.96-2.80 (m, 2H), 2.41 (br. s, 1H), 1.75-1.43 (m, 7H), 1.29-0.89 (m, 15H), 0.88-0.74 (m, 2H).

Example 207: (S)-1-((4-Hydroxy-3,3-dimethyl-1-(4,4,4-trifluoro-2-(2,2,2-trifluoroethyl)butanoyl)piperidin-4-yl)methyl)-N,N-dimethyl-6-oxo-4-phenyl-1,6-dihydropyridine-3-carboxamide

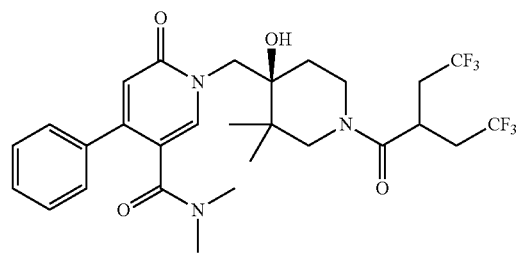 [SMILES: CN(C)C(=O)c1cn(C[C@]2(O)CCN(C(=O)C(CC(F)(F)F)CC(F)(F)F)CC2(C)C)c(=O)cc1-c1ccccc1]

DIPEA (36 µL, 0.209 mmol) was added to a suspension of Amine 7 (20 mg, 52.2 µmol), Acid 12 (18 mg, 78.2 µmol) and HATU (30 mg, 78.2 µmol) in DMF (1 mL). After 30 min, the reaction was quenched by the addition of saturated NaHCO$_{3(aq)}$ (15 mL) and the mixture was extracted with DCM (3×10 mL) using a Biotage phase separator. The combined organic phases were concentrated in vacuo and the residue was purified by flash chromatography (Biotage KP-NH 11 g cartridge, 0-100% EtOAc in cyclohexane; then GraceResolv silica 12 g cartridge, 0-10% MeOH in DCM) to give the title compound (18.2 mg, 57%) as a colourless solid after lyophilisation. LCMS (Method A): $R_T$=1.31 min, m/z=590 [M+H]$^+$. $^1$H NMR (500 MHz, DMSO-d$_6$): δ 7.81

(s, 0.4H), 7.81 (s, 0.6H), 7.51-7.41 (m, 3H), 7.41-7.33 (m, 2H), 6.46 (s, 0.4H), 6.45 (s, 0.6H), 4.99 (s, 0.4H), 4.95 (s, 0.6H), 4.47 (d, J=13.4 Hz, 0.6H), 4.40 (d, J=13.4 Hz, 0.4H), 4.14-4.08 (m, 0.4H), 3.92-3.62 (m, 2.6H), 3.47-3.36 (m, 1H), 3.31-3.20 (m, 2H), 2.97-2.88 (m, 1H), 2.87-2.70 (m, 1H), 2.75 (s, 3H), 2.63 (s, 3H), 2.62-2.53 (m, 2H), 1.77-1.70 (m, 0.6H), 1.63 (ddd, J=14.0, 11.6, 4.9 Hz, 0.4H), 1.29-1.20 (m, 1H), 1.02 (s, 1H), 0.99 (s, 1H), 0.96 (s, 2H), 0.95 (s, 2H).

Example 208: 1-(((S)-1-((R)-3-Cyclohexyl-2-methylpropanoyl)-4-hydroxy-3,3-dimethylpiperidin-4-yl)methyl)-5-((S)-2-(hydroxymethyl)piperazine-1-carbonyl)-4-phenylpyridin-2(1H)-one

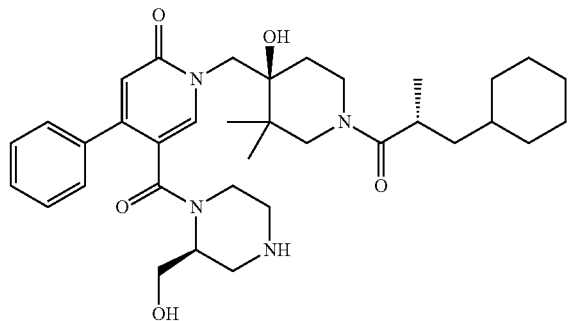 [SMILES: C[C@H](CC1CCCCC1)C(=O)N1CC[C@@](O)(Cn2cc(C(=O)N3CCNC[C@H]3CO)c(-c3ccccc3)cc2=O)C(C)(C)C1]

Step 1: tert-Butyl (S)-4-(1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)-3-(hydroxymethyl)piperazine-1-carboxylate tert-Butyl (S)-3-(hydroxymethyl)piperazine-1-carboxylate (6.4 mg, 0.0295 mmol) was added to a stirred solution of Acid 4 (15.0 mg, 0.0295 mmol), HATU (13.5 mg, 0.0354 mmol) and DIPEA (0.016 mL, 0.0885 mmol) in DCM (5.0 mL) at RT. After 22 h, further tert-butyl (S)-3-(hydroxymethyl)piperazine-1-carboxylate (2.1 mg, 0.00983 mmol) was added. After a further 4 h, saturated sodium bicarbonate (aq) solution and further DCM were added and the resulting biphasic mixture was separated, extracted (×2), the combined organic phase was dried (phase separator), the solvents were removed in vacuo, and the remaining residue was purified by flash chromatography using an 11 g KP-NH column (0-100%, EtOAc in cyclohexane) to give the title compound (12.8 mg, 61%) as a white solid. LCMS (Method A): $R_T$=1.64 min, m/z=707 [M+H]$^+$.

Step 2: 1-(((S)-1-((R)-3-Cyclohexyl-2-methypropanoyl)-4-hydroxy-3,3-dimethylpiperidin-4-yl)methyl)-5-((S)-2-(hydroxymethyl)piperazine-1-carbonyl)-4-phenylpyridin-2(1H)-one TFA (0.5 mL, 6.49 mmol) was added to a stirred solution of tert-butyl (S)-4-(1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)-3-(hydroxymethyl)piperazine-1-carboxylate (12.8 mg, 0.0181 mmol) in DCM (0.5 mL) at RT. After 30 min, the solvents were removed in vacuo and the remaining residue was loaded onto a pre-equilibrated SCX-2 cartridge in MeOH solution, washed using MeOH and eluted using 7 N ammonia in MeOH solution. The solvents were removed in vacuo and the remaining residue was purified by flash chromatography (cyclohexane, then 0-10% MeOH in DCM) and freeze-dried to give the title compound (3.4 mg, 31%) as a white solid. LCMS (Method A): $R_T$=1.06 min, m/z=607 [M+H]$^+$. $^1$H NMR (500 MHz, DMSO-d$_6$): δ 7.87-7.70 (m, 1H), 7.57-7.27 (m, 5H), 6.49-6.38 (m, 1H), 5.08-3.37 (m, 8H), 3.31-3.19 (1H, overlapping solvent peak), 3.13-2.57 (m, 5H, overlapping solvent peak), 2.04-1.79 (m, 1H), 1.76-1.42 (m, 8H), 1.30-0.74 (m, 20H).

Example 209: 1-(((R)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide

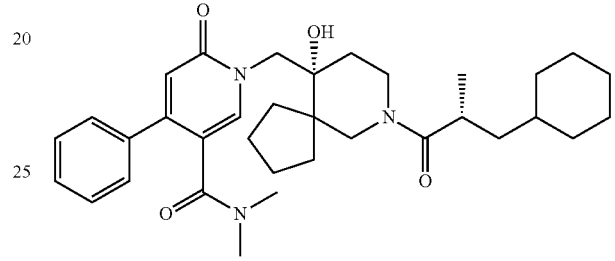

Step 1: tert-Butyl (R)-10-((5-(ethoxycarbonyl)-2-oxo-4-phenylpyridin-1 (2H)-yl)methyl)-10-hydroxy-7-azaspiro[4.5]decane-7-carboxylate Prepared according to General Procedure 4 using tert-butyl (R)-10-((4-chloro-5-(ethoxycarbonyl)-2-oxopyridin-1 (2H)-yl)methyl)-10-hydroxy-7-azaspiro[4.5]decane-7-carboxylate (Amine 10, Step 1) (200 mg, 0.427 mmol), phenylboronic acid (78 mg, 0.640 mmol), Pd(dppf)Cl$_2$.DCM (18 mg, 21.3 µmol), Na$_2$CO$_3$ (90 mg, 0.853 mmol), 1,4-dioxane (1.5 mL) and water (0.5 mL). The reaction was heated under microwave irradiation at 120° C. for 30 min to give the title compound (230 mg, >100%) as a pale yellow foam. LCMS (Method A): $R_T$=1.78 min, m/z=511 [M+H]$^+$.

Step 2: Ethyl (R)-1-((10-hydroxy-7-azaspiro[4.5]decan-10-yl)methyl)-6-oxo-4-phenyl-1,6-dihydropyridine-3-carboxylate Prepared according to General Procedure 7 using tert-butyl (R)-10-((5-(ethoxycarbonyl)-2-oxo-4-phenylpyridin-1 (2H)-yl)methyl)-10-hydroxy-7-azaspiro[4.5]decane-7-carboxylate (230 mg, 0.450 mmol), TFA (1 mL) and DCM (2 mL) to give the title compound (154 mg, 83%) as a colourless solid. LCMS (Method B): $R_T$=0.82 min, m/z=411 [M+H]$^+$.

Step 3: Ethyl 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate Prepared according to General Procedure 3 using ethyl (R)-1-((10-hydroxy-7-azaspiro[4.5]decan-10-yl)methyl)-6-oxo-4-phenyl-1,6-dihydropyridine-3-carboxylate (154 mg, 0.375 mmol), Acid 1 (70 mg, 0.413 mmol), HATU (157 mg, 0.413 mmol), DIPEA (0.262 mL, 1.50 mmol) and DCM (7.5 mL) to give the title compound (233 mg, >100%) as a colourless foam. LCMS (Method A): $R_T$=1.95 min, m/z=563 [M+H]⁺.

Step 4: 1-(((R)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid A solution of ethyl 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate (233 mg, 0.414 mmol) in 1 M NaOH$_{(aq)}$ (0.828 mL, 0.828 mmol) and 1,4-dioxane (2 mL) was stirred at 50° C. for 16 h. The reaction mixture was allowed to cool to RT and the pH was adjusted to ~pH 2 by the addition of 1 M HCl$_{(aq)}$. The resulting mixture was extracted with DCM (3×10 mL) using a Biotage phase separator, the combined organic phases were concentrated in vacuo and the crude product was purified by flash chromatography (GraceResolv silica 24 g cartridge, 0-100% EtOAc in cyclohexane) to give the title compound (136 mg, 61%) as a colourless solid. LCMS (Method A): $R_T$=1.61 min, m/z=535 [M+H]⁺.

Step 5: 1-(((R)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide Prepared according to General Procedure 3 using 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (67 mg, 0.125 mmol), dimethylamine (2 M in THF, 75 µL, 0.150 mmol), HATU (57 mg, 0.150 mmol), DIPEA (88 µL, 0.501 mmol) and DCM (2.5 mL) to give the title compound (61 mg, 85%) as a colourless solid after lyophilisation. LCMS (Method B): $R_T$=1.45 min, m/z=562 [M+H]⁺. ¹H NMR (500 MHz, DMSO-d₆): δ 7.84 (s, 1H), 7.56-7.25 (m, 5H), 6.46 (s, 0.3H), 6.45 (s, 0.7H), 4.98 (s, 0.3H), 4.91 (s, 0.7H), 4.70-4.57 (m, 1H), 3.77-3.61 (m, 2H), 3.57-3.35 (m, 2H), 3.29-3.16 (m, 1H), 2.95-2.81 (m, 1H), 2.75 (s, 3H), 2.63 (s, 3H), 1.97-1.84 (m, 1H), 1.79-1.43 (m, 11.5H), 1.37-1.03 (m, 8.5H), 0.97 (d, J=6.6 Hz, 1H), 0.93 (d, J=6.6 Hz, 2H), 0.89-0.77 (m, 2H).

Example 210: 1-(((R)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one

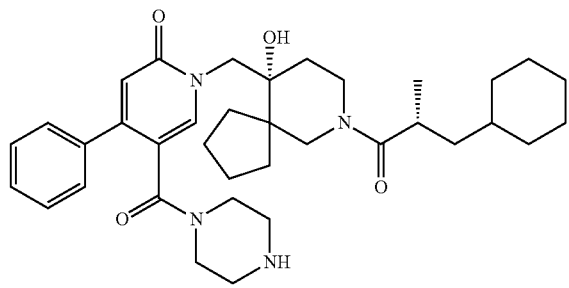 [SMILES: C[C@H](CC1CCCCC1)C(=O)N1CC[C@](O)(Cn2cc(C(=O)N3CCNCC3)c(-c3ccccc3)cc2=O)C2(CCCC2)C1]

Step 1: tert-Butyl 4-(1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate Prepared according to General Procedure 3 using 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (Example 209, Step 4) (69 mg, 0.129 mmol), tert-butyl piperazine-1-carboxylate (29 mg, 0.155 mmol), HATU (59 mg, 0.155 mmol), DIPEA (90 µL, 0.516 mmol) and DCM (2.5 mL) to give the title compound (88 mg, 97%) as a colourless foam. LCMS (Method A): $R_T$=1.87 min, m/z=703 [M+H]⁺.

Step 2: 1-(((R)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one A solution of tert-butyl 4-(1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate (88 mg, 0.125 mmol) in TFA (0.3 mL) and DCM (0.6 mL) was stirred for 20 min before the reaction mixture was purified using a Biotage SCX-2 2 g cartridge (pre-equilibrated with and then washed using 1:1 DCM/MeOH before being eluted with 1:1 DCM/7 M in NH₃ in MeOH). The basic eluents were concentrated in vacuo and the residue was purified by flash chromatography (GraceResolv silica 12 g cartridge, 0-20% MeOH in DCM) to give the title compound (68.5 mg, 89%) as a colourless solid after lyophilisation. LCMS (Method B): $R_T$=0.97 min, m/z=603 [M+H]⁺. ¹H NMR (500 MHz, DMSO-d₆): δ 7.83 (s, 1H), 7.65-7.18 (m, 5H), 6.46 (s, 0.3H), 6.45 (s, 0.7H), 5.06-4.79 (m, 1H), 4.69-4.52 (m, 1H), 3.78-3.61 (m, 2H), 3.57-2.21 (m, 13H (signals overlap with HDO and DMSO)), 1.98-1.42 (m, 13H), 1.37-1.03 (m, 8H), 0.97 (d, J=6.6 Hz, 1H), 0.93 (d, J=6.7 Hz, 2H), 0.89-0.77 (m, 2H).

Example 211: 1-(((S)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide

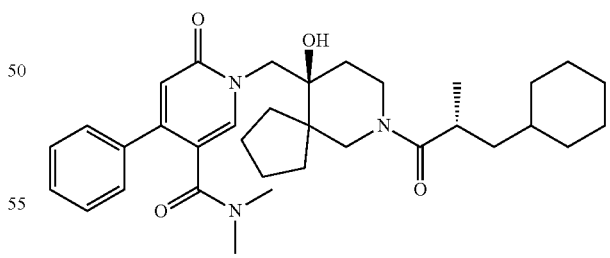

Step 1: Ethyl 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate Prepared according to General Procedure 3 using Amine 10 (140 mg, 0.342 mmol), Acid 1 (69.8 mg, 0.410 mmol), HATU (195 mg, 0.513 mmol) and DIPEA (240 µL, 1.37 mmol) in DCM (5 mL) to give the title compound (170 mg, 88%). LCMS (Method A): $R_T$=1.96 min, m/z=563 [M+H]$^+$.

Step 2: 1-(((S)-7-((R)-3-Cyclohexyl-2-methylpropanoyl)-10-hydroxy-7-azaspiro[4.5]decan-10-yl) methyl)-6-oxo-4-phenyl-1,6-dihydropyridine-3-carboxylic acid A solution of ethyl 1-(((S)-7-((R)-3-cyclohexyl-2-methylpropanoyl)-10-hydroxy-7-azaspiro[4.5]decan-10-yl) methyl)-6-oxo-4-phenyl-1,6-dihydropyridine-3-carboxylate (170 mg, 0.302 mmol) in ethanol (1.5 mL) and 2 M NaOH$_{(aq)}$ (1.5 mL, 3.00 mmol) was stirred at 60° C. for 1 h. The reaction mixture was concentrated in vacuo. The residue taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (150 mg, 92%). LCMS (Method A): $R_T$=1.63 min, m/z=535 [M+H]$^+$.

Step 3: 1-(((S)-7-((R)-3-Cyclohexyl-2-methylpropanoyl)-10-hydroxy-7-azaspiro[4.5]decan-10-Cyl) methyl)-N,N-dimethyl-6-oxo-4-phenyl-1,6-dihydropyridine-3-carboxamide Prepared according to General Procedure 3 using 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (60 mg, 0.112 mmol), dimethylamine (2 M in THF, 84 µL, 0.168 mmol), HATU (51.2 mg, 0.135 mmol) and DIPEA (59 µL, 0.337 mmol) in DCM (2 mL) to give the title compound (49 mg, 76%). LCMS (Method B): $R_T$=1.46 min, m/z=562 [M+H]$^+$. $^1$H NMR (500 MHz, DMSO-d$_6$): δ 7.86-7.82 (m, 1H), 7.47-7.41 (m, 3H), 7.41-7.35 (m, 2H), 6.47 (s, 0.35H), 6.45 (s, 0.65H), 4.99 (s, 0.35H), 4.92 (s, 0.65H), 4.69 (d, J=13.5 Hz, 0.65H), 4.56 (d, J=13.5 Hz, 0.35H), 3.93-3.59 (m, 2H), 3.53-3.10 (m, 3H (signals overlap with HDO)), 2.96-2.81 (m, 1H), 2.75 (s, 3H), 2.63 (s, 3H (signal overlaps with DMSO satellite)), 2.01-1.82 (m, 1H), 1.75-0.99 (m, 20H), 0.99-0.91 (m, 3H), 0.89-0.74 (m, 2H).

Example 212: 1-(((S)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one

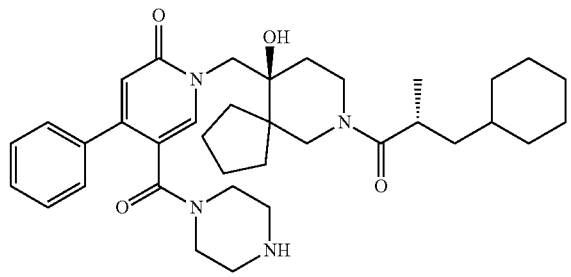 [SMILES: C[C@H](CC1CCCCC1)C(=O)N1CC[C@@](O)(Cn2cc(C(=O)N3CCNCC3)c(-c3ccccc3)cc2=O)C2(CCCC2)C1]

Step 1: tert-Butyl 4-(1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate Prepared according to General Procedure 3 using 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (Example 211, Step 2) (85 mg, 0.159 mmol), tert-butyl piperazine-1-carboxylate (44.4 mg, 0.239 mmol), HATU (72.5 mg, 0.191 mmol) and DIPEA (83 µL, 0.477 mmol) in DCM (2 mL) to give the title compound (111 mg, quantitative). LCMS (Method A): $R_T$=1.88 min, m/z=703 [M+H]$^+$.

Step 2: 1-(((S)-7-((R)-3-Cyclohexyl-2-methylpropanoyl)-10-hydroxy-7-azaspiro[4.5]decan-10-yl) methyl)-4-phenyl-5-(piperazine-1-carbonyl)pyridin-2(1H)-one Prepared according to General Procedure 7 using tert-butyl 4-(1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate (125 mg, 0.178 mmol), DCM (3 mL) and TFA (1 mL). The crude product was further purified by flash chromatography to give the title compound (86 mg, 78%). LCMS (Method B): $R_T$=0.99 min, m/z=603 [M+H]$^+$. $^1$H NMR (500 MHz, DMSO-d$_6$): δ 7.83 (s, 1H), 7.51-7.35 (m, 5H), 6.46 (s, 0.35H), 6.44 (s, 0.65H), 5.09-4.79 (m, 1H), 4.68 (d, J=13.5 Hz, 0.65H), 4.55 (d, J=13.5 Hz, 0.35H), 3.94-3.57 (m, 2H), 3.55-2.80 (m, 7H (signals overlap with HDO)), 2.79-2.24 (m, 5H (signals overlap with DMSO)), 2.02-1.01 (m, 22H), 1.00-0.91 (m, 3H), 0.91-0.74 (m, 2H).

Example 213: 1-(((S)-1-((R)-3-Cyclohexyl-2-methylpropanoyl)-4-hydroxy-3,3-dimethylpiperidin-4-yl) methyl)-5-((R)-3-methylpiperazine-1-carbonyl)-4-phenylpyridin-2(1H)-one

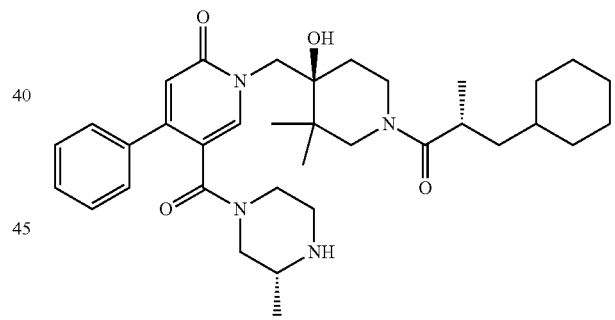

Step 1: tert-Butyl (R)-4-(1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)-2-methylpiperazine-1-carboxylate tert-Butyl (R)-2-methylpiperazine-1-carboxylate (5.9 mg, 0.0295 mmol) was added to a stirred solution of Acid 4 (15.0 mg, 0.0295 mmol), HATU (13.5 mg, 0.0354 mmol) and DIPEA (0.015 mL, 0.0885 mmol) in DCM (1.0 mL) at RT. After 2 h, saturated sodium bicarbonate (aq) solution and further DCM were added and the resulting biphasic mixture was separated, extracted (×2), the combined organic phase was dried (phase separator), the solvents were removed in vacuo, and the remaining residue was purified by flash chromatography (0-100%, EtOAc in cyclohexane) to give the title compound (16.1 mg, 79%) as a white solid. LCMS (Method A): $R_T$=1.86 min, m/z=691 [M+H]$^+$.

Step 2: 1-(((S)-1-((R)-3-Cyclohexyl-2-methylpropanoyl)-4-hydroxy-3,3-dimethylpiperidin-4-yl)methyl)-5-((R)-3-methylpiperazine-1-carbonyl)-4-phenylpyridin-2(1H)-one TFA (0.5 mL, 6.49 mmol) was added to a stirred solution of tert-butyl (R)-4-(1-(((S)-1-((R)-3-cyclohexyl-2-methylpropanoyl)-4-hydroxy-3,3-dimethylpiperidin-4-yl)methyl)-6-oxo-4-phenyl-1,6-dihydropyridine-3-carbonyl)-2-methylpiperazine-1-carboxylate (16.1 mg, 0.0233 mmol) in DCM (0.5 mL) at RT. After 30 min, the solvents were removed in vacuo and the remaining residue was loaded onto a pre-equilibrated SCX-2 cartridge in MeOH solution, washed using MeOH and eluted using 7 N ammonia in MeOH solution. The solvents were removed in vacuo and the remaining residue was purified by flash chromatography (cyclohexane, then 0-5% MeOH in DCM) and freeze-dried to give the title compound (6.8 mg, 49%) as a white solid. LCMS (Method B): $R_T$=0.97 min, m/z=591 [M+H]$^+$. $^1$H NMR (500 MHz, DMSO-d$_6$): δ 7.89-7.72 (m, 1H), 7.51-7.25 (m, 5H), 6.44 (d, 1H), 5.04-4.75 (m, 1H), 4.55-4.28 (m, 1H), 4.23-3.44 (m, 3H), 3.31-2.66 (m, 4H, overlapping solvent peak), 2.61-1.80 (m, 3H, overlapping solvent peak), 1.77-1.42 (m, 8H), 1.42-0.57 (m, 23H).

Example 214: 1-(((S)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide

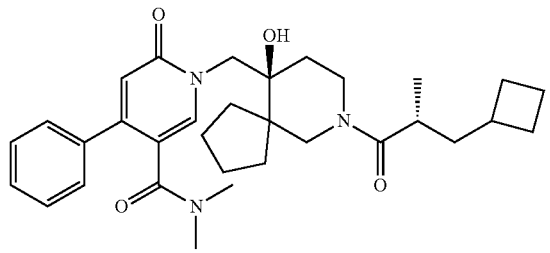 [SMILES: C[C@H](CC1CCC1)C(=O)N1CC[C@@](O)(Cn2cc(C(=O)N(C)C)c(-c3ccccc3)cc2=O)C2(CCCC2)C1]

Step 1: Ethyl 1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carboxylate Prepared according to General Procedure 3 using Amine 10 (72 mg, 0.175 mmol), Acid 5 (30 mg, 0.211 mmol), DIPEA (0.123 mL, 0.702 mmol), HATU (80 mg, 0.211 mmol) and DCM (3.5 mL) to give the title compound (81 mg, 86%) as a colourless foam. LCMS (Method B): $R_T$=1.59 min, m/z=535 [M+H]$^+$.

Step 2: 1-(((S)-7-((R)-3-Cyclobutyl-2-methylpropanoyl)-10-hydroxy-7-azaspiro[4.5]decan-10-yl)methyl)-6-oxo-4-phenyl-1,6-dihydropyridine-3-carboxylic acid A solution of ethyl 1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carboxylate (81 mg, 0.152 mmol) in 1 M NaOH$_{(aq)}$ (0.606 mL, 0.606 mmol) and 1,4-dioxane (1.5 mL) was stirred at 50° C. for 4 h. The reaction mixture was allowed to cool to RT and the pH was adjusted to ~pH 2 by the addition of 1 M HCl$_{(aq)}$. The resulting mixture was extracted with DCM (3×5 mL) using a Biotage phase separator and the combined organic phases concentrated in vacuo to give the title compound (78 mg, quantitative) as a light beige foam. LCMS (Method B): $R_T$=1.32 min, m/z=507 [M+H]$^+$.

Step 3: 1-(((S)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide Prepared according to General Procedure 3 using 1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carboxylic acid (38 mg, 75.0 µmol), dimethylamine (2 M in THF, 45 µL, 90.0 µmol), HATU (34 mg, 90.0 µmol), DIPEA (52 µL, 0.300 mmol) and DCM (1.5 mL) to give the title compound (33.6 mg, 82%) as a colourless solid after lyophilisation. LCMS (Method B): $R_T$=1.32 min, m/z=534 [M+H]$^+$. $^1$H NMR (500 MHz, DMSO-d$_6$): δ 7.84 (s, 0.4H) 7.84 (s, 0.6H), 7.50-7.28 (m, 5H), 6.46 (s, 0.4H), 6.45 (s, 0.6H), 4.98 (s, 0.4H), 4.91 (s, 0.6H), 4.65 (d, J=13.5 Hz, 0.6H), 4.60 (d, J=13.5 Hz, 0.4H), 3.84-3.62 (m, 2H), 3.46-3.17 (m, 3H (signal overlaps with HDO)), 2.81-2.57 (m, 1H), 2.75 (s, 3H), 2.63 (s, 3H), 2.24-2.13 (m, 1H), 2.02-1.85 (m, 3H), 1.83-1.42 (m, 10H), 1.39-1.07 (m, 5H), 0.99-0.89 (m, 3H).

Example 215: 1-(((S)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one

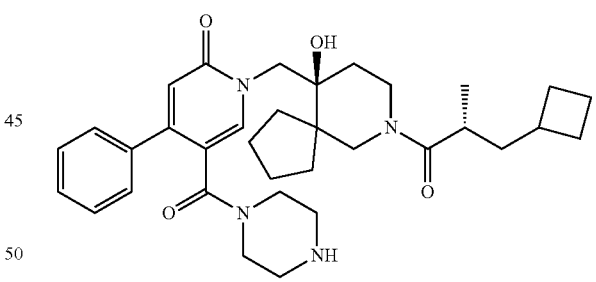

Step 1: tert-Butyl 4-(1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate Prepared according to General Procedure 3 using 1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carboxylic acid (Example 214, Step 2) (40 mg, 79.0 µmol), tert-butyl piperazine-1-carboxylate (17.6 mg, 94.7 µmol), HATU (36 mg, 94.7 µmol), DIPEA (55 µL, 0.316 mmol) and DCM (1.5 mL) to give the title compound (50 mg, 93%) as a colourless foam. LCMS (Method B): $R_T$=1.54 min, m/z=619 [M-butene+H]$^+$.

Step 2: 1-(((S)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one A solution of tert-butyl 4-(1-(((S)-7-((R)-3-cyclobutyl-2-methylpropanoyl)-10-hydroxy-7-azaspiro[4.5]decan-10-yl)methyl)-6-oxo-4-phenyl-1,6-dihydropyridine-3-carbonyl)piperazine-1-carboxylate (50 mg, 74.1 µmol) in TFA (0.3 mL) and DCM (0.6 mL) was stirred for 20 min before the reaction mixture was purified using a Biotage SCX-2 2 g cartridge (pre-equilibrated with and then washed using 1:1 DCM/MeOH before being eluted with 1:1 DCM/7 M in $NH_3$ in MeOH). The basic eluents were concentrated in vacuo and the residue purified by flash chromatography (GraceResolv silica 12 g cartridge, 0-20% MeOH in DCM) to give the title compound (40 mg, 91%) as a colourless solid after lyophilisation. LCMS (Method B): $R_T$=0.90 min, m/z=575 [M+H]$^+$. $^1$H NMR (500 MHz, DMSO-$d_6$): δ 7.82 (s, 1H), 7.61-7.28 (m, 5H), 6.46 (s, 0.4H), 6.44 (s, 0.6H), 5.04-4.83 (m, 1H), 4.68-4.55 (m, 1H), 3.84-3.60 (m, 2H), 3.48-2.24 (m, 13H (signals overlap with HDO and DMSO)), 2.24-2.13 (m, 1H), 2.02-1.09 (m, 18H), 1.02-0.86 (m, 3H).

Example 216: 1-(((S)-10-Hydroxy-7-((R)-4,4-trifluoro-2-methylbutanoyl)-7-azaspiro[4.5]decan-10-yl)methyl)-N,N-dimethyl-6-oxo-4-phenyl-1,6-dihydropyridine-3-carboxamide

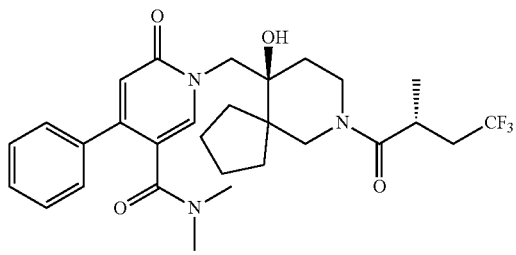 [SMILES: C[C@H](CC(F)(F)F)C(=O)N1CC[C@@](O)(Cn2cc(C(=O)N(C)C)c(-c3ccccc3)cc2=O)C2(CCCC2)C1]

Step 1: Ethyl 1-(((S)-10-hydroxy-7-((R)-4,4-trifluoro-2-methylbutanoyl)-7-azaspiro[4.5]decan-10-yl)methyl)-6-oxo-4-phenyl-1,6-dihydropyridine-3-carboxylate Prepared according to General Procedure 3 using Amine 10 (69 mg, 0.169 mmol), Acid 11 (31 mg, 0.202 mmol), HATU (77 mg, 0.202 mmol), DIPEA (0.117 mL, 0.672 mmol) and DCM (3.3 mL) to give the title compound (82 mg, 88%) as a colourless foam. LCMS (Method B): $R_T$=1.44 min, m/z=549 [M+H]$^+$.

Step 2: 1-(((S)-10-Hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylic acid A solution of ethyl 1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylate (82 mg, 0.149 mmol) in 1 M NaOH$_{(aq)}$ (0.598 mL, 0.598 mmol) and 1,4-dioxane (1.5 mL) was stirred at 50° C. for 3 h 20 min. The reaction mixture was allowed to cool to RT and the pH was adjusted to ~pH 2 by the addition of 1 M HCl$_{(aq)}$. The resulting mixture was extracted with DCM (3×5 mL) using a Biotage phase separator and the combined organic phases were concentrated in vacuo to give the title compound (80 mg, quantitative) as a light beige foam. LCMS (Method B): $R_T$=1.18 min, m/z=521 [M+H]$^+$.

Step 3: 1-(((S)-10-Hydroxy-7-((R)-4,4,4-trifluoro-2-methylbutanoyl)-7-azaspiro[4.5]decan-10-yl)methyl)-N,N-dimethyl-6-oxo-4-phenyl-1,6-dihydropyridine-3-carboxamide Prepared according to General Procedure 3 using 1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylic acid (38 mg, 73.0 µmol), dimethylamine (2 M in THF, 44 µL, 87.6 µmol), HATU (33 mg, 87.6 µmol), DIPEA (51 µL, 0.292 mmol) and DCM (1.5 mL) to give the title compound (33 mg, 80%) as a colourless solid after lyophilisation. LCMS (Method B): $R_T$=1.18 min, m/z=548 [M+H]$^+$. $^1$H NMR (500 MHz, DMSO-$d_6$): δ 7.84 (s, 0.4H), 7.84 (s, 0.6H), 7.61-7.22 (m, 5H), 6.46 (s, 0.4H), 6.45 (s, 0.6H), 5.00 (s, 0.4H), 4.94 (s, 0.6H), 4.63 (d, J=13.4 Hz, 0.6H), 4.51 (d, J=13.5 Hz, 0.4H), 4.03-3.95 (m, 0.4H), 3.80-3.64 (m, 1.6H), 3.53-3.39 (m, 1.4H), 3.37-3.25 (m, 0.6H (signal overlaps with HDO)), 3.21-2.98 (m, 1.4H), 2.87-2.64 (m, 0.6H), 2.75 (s, 3H), 2.63 (s, 3H), 2.32-2.19 (m, 1H), 2.03-1.96 (m, 0.4H), 1.92-1.85 (m, 0.6H), 1.83-0.91 (m, 13H).

Example 217: 1-(((S)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one

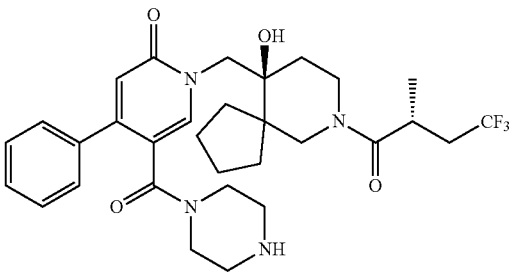 [SMILES: C[C@H](CC(F)(F)F)C(=O)N1CC[C@@](O)(Cn2cc(C(=O)N3CCNCC3)c(-c3ccccc3)cc2=O)C2(CCCC2)C1]

Step 1: tert-Butyl 4-(1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carbonyl)piperazine-1-carboxylate Prepared according to General Procedure 3 using 1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylic acid (Example 216, Step 2) (42 mg, 80.7 µmol), tert-butyl piperazine-1-carboxylate (18 mg, 96.8 µmol), HATU (37 mg, 96.8 µmol), DIPEA (56 µL, 0.323 mmol) and DCM (1.5 mL) to give the title compound (50 mg, 89%) as a colourless foam. LCMS (Method B): $R_T$=1.40 min, m/z=633 [M-butene+H]$^+$.

Step 2: 1-(((S)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one A solution of tert-butyl 4-(1-(((S)-10-hydroxy-7-((R)-4,4,4-trifluoro-2-methylbutanoyl)-7-azaspiro[4.5]decan-10-yl)

methyl)-6-oxo-4-phenyl-1,6-dihydropyridine-3-carbonyl) piperazine-1-carboxylate (50 mg, 72.6 µmol) in TFA (0.3 mL) and DCM (0.6 mL) was stirred for 20 min before the reaction mixture was purified using a Biotage SCX-2 2 g cartridge (pre-equilibrated with and then washed using 1:1 DCM/MeOH before being eluted with 1:1 DCM/7 M in NH$_3$ in MeOH). The basic eluents were concentrated in vacuo and the residue was purified by flash chromatography (GraceResolv silica 12 g cartridge, 0-20% MeOH in DCM) to give the title compound (41.8 mg, 94%) as a colourless solid after lyophilisation. LCMS (Method B): R$_T$=0.81 min, m/z=589 [M+H]$^+$. $^1$H NMR (500 MHz, DMSO-d$_6$): δ 7.83 (s, 1H), 7.70-7.05 (m, 5H), 6.46 (s, 0.4H), 6.45 (s, 0.6H), 5.12-4.83 (m, 1H), 4.62 (d, J=13.4 Hz, 0.6H), 4.50 (d, J=13.6 Hz, 0.4H), 4.04-3.93 (m, 0.4H), 3.86-3.60 (m, 1.6H), 3.53-2.19 (m, 15H (signals overlap with HDO and DMSO)), 2.07-0.98 (m, 13H).

Example 218: (S)-1-((10-Hydroxy-7-(4,4,4-trifluoro-2-(2,2,2-trifluoroethyl)butanoyl)-7-azaspiro [4.5]decan-10-yl)methyl)-N,N-dimethyl-6-oxo-4-phenyl-1,6-dihydropyridine-3-carboxamide

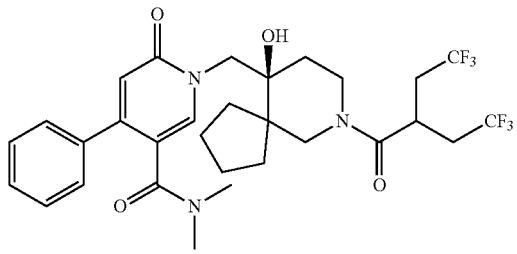 [SMILES: CN(C)C(=O)c1cn(C[C@]2(O)CCN(C(=O)C(CC(F)(F)F)CC(F)(F)F)CC23CCCC3)c(=O)cc1-c1ccccc1]

Step 1: Ethyl (S)-1-((10-hydroxy-7-(4,4,4-trifluoro-2-(2,2,2-trifluoroethyl)butanoyl)-7-azaspiro[4.5] decan-10-yl)methyl)-6-oxo-4-phenyl-1,6-dihydropyridine-3-carboxylate DIPEA (0.111 mL, 0.633 mmol) was added to a suspension of Amine 10 (65 mg, 0.158 mmol), Acid 12 (73 mg, 0.317 mmol) and HATU (120 mg, 0.317 mmol) in DMF (3.2 mL). After 1 h, the reaction was quenched by the addition of saturated NaHCO$_{3(aq)}$ (15 mL) and the mixture extracted with DCM (3×10 mL) using a Biotage phase separator. The combined organic phases were concentrated in vacuo and the residue was purified by flash chromatography (Biotage KP-NH 11 g cartridge, 0-100% EtOAc in cyclohexane) to give the title compound (87 mg, 89%) as a colourless foam. LCMS (Method B): R$_T$=1.53 min, m/z=617 [M+H]$^+$.

Step 2: (S)-1-((10-Hydroxy-7-(4,4,4-trifluoro-2-(2,2,2-trifluoroethyl)butanoyl)-7-azaspiro[4.5]decan-10-yl)methyl)-6-oxo-4-phenyl-1,6-dihydropyridine-3-carboxylic acid A solution of ethyl (S)-1-((10-hydroxy-7-(4,4,4-trifluoro-2-(2,2,2-trifluoroethyl)butanoyl)-7-azaspiro[4.5]decan-0-yl)methyl)-6-oxo-4-phenyl-1,6-dihydropyridine-3-carboxylate (87 mg, 0.141 mmol) in 1 M NaOH$_{(aq)}$ (0.564 mL, 0.564 mmol) and 1,4-dioxane (1.4 mL) was stirred at 50° C. for 3 h. The reaction mixture was allowed to cool to RT and the pH was adjusted to ~pH 2 by the addition of 1 M HCl$_{(aq)}$. The resulting mixture was extracted with DCM (3×5 mL) using a Biotage phase separator and the combined organic phases were concentrated in vacuo to give the title compound (84 mg, quantitative) as a beige foam. LCMS (Method B): R$_T$=1.28 min, m/z=589 [M+H]$^+$.

Step 3: (S)-1-((10-Hydroxy-7-(4,4,4-trifluoro-2-(2,2, 2-trifluoroethyl)butanoyl)-7-azaspiro[4.5]decan-10-yl)methyl)-N,N-dimethyl-6-oxo-4-phenyl-1,6-dihydropyridine-3-carboxamide Prepared according to General Procedure 3 using (S)-1-((10-hydroxy-7-(4,4,4-trifluoro-2-(2,2,2-trifluoroethyl)butanoyl)-7-azaspiro[4.5]decan-10-yl)methyl)-6-oxo-4-phenyl-1,6-dihydropyridine-3-carboxylic acid (40 mg, 68.0 µmol), dimethylamine (2 M in THF, 41 µL, 81.6 µmol), HATU (31 mg, 0.0816 mmol), DIPEA (48 µL, 0.272 mmol) and DCM (1.4 mL) to give the title compound (31.8 mg, 73%) as a colourless solid after lyophilisation. LCMS (Method B): R$_T$=1.29 min, m/z=616 [M+H]$^+$. $^1$H NMR (500 MHz, DMSO-d$_6$): δ 7.84 (s, 1H), 7.48-7.33 (m, 5H), 6.46 (s, 0.3H), 6.45 (s, 0.7H), 5.02 (s, 0.3H), 4.94 (s, 0.7H), 4.67-4.56 (m, 1H), 3.89-3.82 (m, 0.3H), 3.79-3.62 (m, 2H), 3.58-3.51 (m, 0.7H), 3.46-3.19 (m, 2H (signal overlaps with HDO)), 2.89-2.53 (m, 4H), 2.75 (s, 3H), 2.63 (s, 3H), 2.00-1.87 (m, 1H), 1.73-1.10 (m, 10H).

Example 219: (S)-1-((10-Hydroxy-7-(4,4,4-trifluoro-2-(2,2,2-trifluoroethyl)butanoyl)-7-azaspiro [4.5]decan-10-yl)methyl)-4-phenyl-5-(piperazine-1-carbonyl)pyridin-2(1H)-one

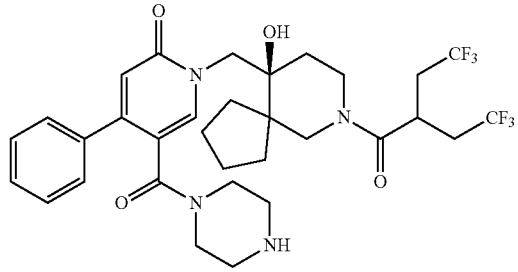 [SMILES: O=C(c1cn(C[C@]2(O)CCN(C(=O)C(CC(F)(F)F)CC(F)(F)F)CC23CCCC3)c(=O)cc1-c1ccccc1)N1CCNCC1]

Step 1: tert-Butyl (S)-4-(1-((10-hydroxy-7-(4,4,4-trifluoro-2-(2,2,2-trifluoroethyl)butanoyl)-7-azaspiro [4.5]decan-10-yl)methyl)-6-oxo-4-phenyl-1,6-dihydropyridine-3-carbonyl)piperazine-1-carboxylate Prepared according to General Procedure 3 using (S)-1-((10-hydroxy-7-(4,4,4-trifluoro-2-(2,2,2-trifluoroethyl)butanoyl)-7-azaspiro[4.5]decan-10-yl)methyl)-6-oxo-4-phenyl-1,6-dihydropyridine-3-carboxylic acid (Example 218, Step 2) (44 mg, 74.8 µmol), tert-butyl piperazine-1-carboxylate (16.7 mg, 89.7 µmol), HATU (34 mg, 89.7 µmol), DIPEA (52 µL, 0.299 mmol) and DCM (1.5 mL) to give the title compound (52 mg, 91%) as a colourless foam. LCMS (Method B): R$_T$=1.49 min, m/z=657 [M-Boc+2H]$^+$.

Step 2: (S)-1-((10-Hydroxy-7-(4,4,4-trifluoro-2-(2,2, 2-trifluoroethyl)butanoyl)-7-azaspiro[4.5]decan-10-yl)methyl)-4-phenyl-5-(piperazine-1-carbonyl)pyridin-2(1H)-one A solution of tert-butyl (S)-4-(1-((10-hydroxy-7-(4,4,4-trifluoro-2-(2,2,2-trifluoroethyl)butanoyl)-7-azaspiro[4.5] decan-10-yl)methyl)-6-oxo-4-phenyl-1,6-dihydropyridine-3-carbonyl)piperazine-1-carboxylate (52 mg, 68.7 µmol) in TFA (0.3 mL) and DCM (0.6 mL) was stirred for 20 min before the reaction mixture was purified using a Biotage SCX-2 2 g cartridge (pre-equilibrated with and then washed using 1:1 DCM/MeOH before being eluted with 1:1 DCM/7 M in NH₃ in MeOH). The basic eluents were concentrated in vacuo and the residue was purified by flash chromatography (GraceResolv silica 12 g cartridge, 0-20% MeOH in DCM) to give the title compound (40.2 mg, 88%) as a colourless solid after lyophilisation. LCMS (Method B): $R_T$=0.88 min, m/z=657 [M+H]⁺. ¹H NMR (500 MHz, DMSO-d₆): δ 7.83 (s, 1H), 7.68-7.18 (m, 5H), 6.46 (s, 0.4H), 6.45 (s, 0.6H), 5.10-4.83 (m, 1H), 4.68-4.52 (m, 1H), 3.88-3.47 (m, 3H), 3.47-2.25 (m, 15H (signals overlap with DMSO and HDO)), 2.03-1.07 (m, 11H).

Example 220: 1-(((S)-1-((R)-3-Cyclohexyl-2-methylpropanoyl)-4-hydroxy-3,3-dimethylpiperidin-4-yl)methyl)-4-cyclopropyl-N,N-dimethyl-6-oxo-1,6-dihydropyridine-3-carboxamide

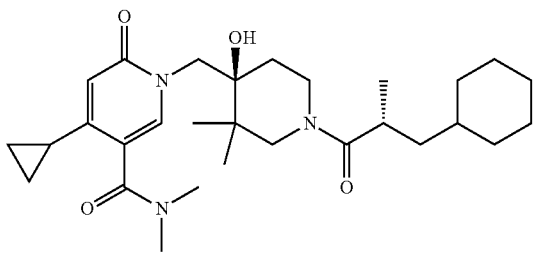 [SMILES: C[C@H](CC1CCCCC1)C(=O)N1CC[C@@](O)(Cn2cc(C(=O)N(C)C)c(C3CC3)cc2=O)C(C)(C)C1]

DIPEA (0.022 mL, 0.127 mmol) was added to a stirred solution of Acid 13 (20.0 mg, 0.0423 mmol), 2 M dimethylamine in THF solution (0.042 mL, 0.0846 mmol) and HATU (19.3 mg, 0.0508 mmol) in DCM (1.0 mL) at RT. After 2 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography using an 11 g KP-NH column (0-100%, EtOAc in cyclohexane). The pure fractions were concentrated and freeze-dried to give the title compound (11.9 mg, 55%) as a white solid. LCMS (Method A): $R_T$=1.37 min, m/z=500 [M+H]⁺. ¹H NMR (500 MHz, DMSO-d₆): δ 7.62 (d, 1H), 5.90 (d, 1H), 4.95 (d, 1H), 4.27 (dd, 1H), 4.12-3.52 (m, 2H), 3.31-3.17 (m, 1H, overlapping solvent peak), 3.05-2.76 (m, 8H), 1.74-1.42 (m, 8H), 1.30-0.71 (m, 22H).

Example 221: 1-(((S)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one

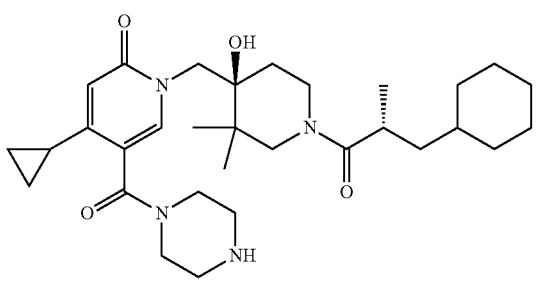 [SMILES: C[C@H](CC1CCCCC1)C(=O)N1CC[C@@](O)(Cn2cc(C(=O)N3CCNCC3)c(C3CC3)cc2=O)C(C)(C)C1]

Step 1: tert-Butyl 4-(1-(((S)-1-((R)-3-cyclohexyl-2-methylpropanoyl)-4-hydroxy-3,3-dimethylpiperidin-4-yl)methyl)-4-cyclopropyl-6-oxo-1,6-dihydropyridine-3-carbonyl)piperazine-1-carboxylate tert-Butyl piperazine-1-carboxylate (7.9 mg, 0.0423 mmol) was added to a stirred solution of Acid 13 (20.0 mg, 0.0423 mmol), HATU (19.3 mg, 0.0508 mmol) and DIPEA (0.022 mL, 0.127 mmol) in DCM (1.0 mL) at RT. After 2 h, saturated sodium bicarbonate (aq) solution and further DCM were added and the resulting biphasic mixture was separated, extracted (×2), the combined organic phase was dried (phase separator), the solvents were removed in vacuo, and the remaining residue was purified by flash chromatography using a 11 g KP-NH column (0-100%, EtOAc in cyclohexane) to give the title compound (20.6 mg, 76%) as a white solid. LCMS (Method A): $R_T$=1.68 min, m/z=641 [M+H]⁺.

Step 2: 1-(((S)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one TFA (0.5 mL, 6.49 mmol) was added to a stirred solution of tert-butyl 4-(1-(((S)-1-((R)-3-cyclohexyl-2-methylpropanoyl)-4-hydroxy-3,3-dimethylpiperidin-4-yl)methyl)-4-cyclopropyl-6-oxo-1,6-dihydropyridine-3-carbonyl)piperazine-1-carboxylate (20.6 mg, 0.0321 mmol) in DCM (0.5 mL) at RT. After 30 min, the solvents were removed in vacuo and the remaining residue was loaded onto a pre-equilibrated SCX-2 cartridge in MeOH solution, washed using MeOH and eluted using 7 M ammonia in MeOH solution. The solvents were removed in vacuo and the remaining residue was purified by flash chromatography (cyclohexane, then 0-10% MeOH in DCM) and freeze-dried to give the title compound (11.7 mg, 66%) as a white solid. LCMS (Method A): $R_T$=0.95 min, m/z=541 [M+H]⁺. ¹H NMR (500 MHz, DMSO-d₆): δ7.67-7.51 (m, 1H), 5.90 (d, 1H), 5.10-4.75 (m, 1H), 4.39-3.41 (m, 5H), 3.31-3.10 (m, 3H, overlapping solvent peak), 3.05-2.55 (m, 7H, overlapping solvent peak), 1.78-1.40 (m, 8H), 1.30-0.55 (m, 22H).

Example 222: 1-(((S)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide

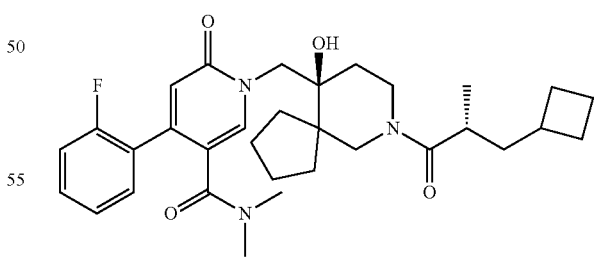

Step 1: Ethyl 1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carboxylate Prepared according to General Procedure 3 using Amine 11 (60 mg, 0.140 mmol), Acid 5 (23.9 mg, 0.168 mmol), HATU (79.9 mg, 0.210 mmol) and DIPEA (98 μL, 0.560 mmol) in DCM (2 mL) to give the title compound (70 mg, 90%). LCMS (Method A): $R_T$=1.79 min, m/z=553 [M+H]$^+$.

Step 2: 1-(((S)-7-((R)-3-Cyclobutyl-2-methylpropanoyl)-10-hydroxy-7-azaspiro[4.5]decan-10-yl)methyl)-4-(2-fluorophenyl)-6-oxo-1,6-dihydropyridine-3-carboxylic acid A solution of ethyl 1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carboxylate (70 mg, 0.127 mmol) in ethanol (1.5 mL) and 2 M NaOH$_{(aq)}$ (1.5 mL, 3.00 mmol) was stirred at 40° C. for 16 h. The reaction mixture was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (66 mg, quantitative). LCMS (Method A): $R_T$=1.61 min, m/z=525 [M+H]$^+$.

Step 3: 1-(((S)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide Prepared according to General Procedure 3 using 1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carboxylic acid (33 mg, 62.9 μmol), dimethylamine (2 M in THF, 47 μL, 94.4 μmol), HATU (28.7 mg, 75.5 μmol) and DIPEA (33 μL, 0.189 mmol) in DCM (2 mL) to give the title compound (25 mg, 70%). LCMS (Method B): $R_T$=1.33 min, m/z=552 [M+H]$^+$. $^1$H NMR (500 MHz, DMSO-d$_6$): δ 7.86 (s, 1H), 7.49-7.43 (m, 1H), 7.39-7.33 (m, 1H), 7.29-7.22 (m, 2H), 6.45 (s, 0.4H), 6.43 (s, 0.6H), 4.93 (s, 0.4H), 4.88 (s, 0.6H), 4.68 (d, J=13.5 Hz, 0.6H), 4.63 (d, J=13.5 Hz, 0.4H), 3.85-3.60 (m, 2H), 3.46-3.19 (m, 3H (signal overlaps with HDO)), 2.88 (s, 3H), 2.83-2.62 (m, 4H (overlaps with DMSO satellite)), 2.25-2.13 (m, 1H), 2.03-1.84 (m, 3H), 1.84-1.48 (m, 10H), 1.48-1.08 (m, 5H), 0.99-0.91 (m, 3H).

Example 223: 4-(2-Fluorophenyl)-1-(((S)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide

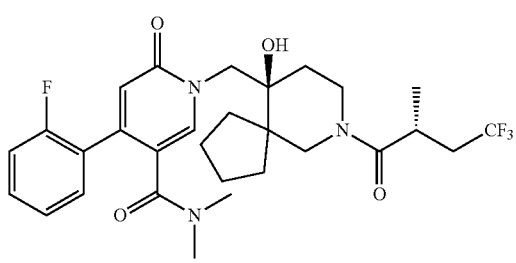 [SMILES: C[C@H](CC(F)(F)F)C(=O)N1CC[C@@](O)(Cn2cc(C(=O)N(C)C)c(-c3ccccc3F)cc2=O)C2(CCCC2)C1]

Step 1: Ethyl 4-(2-fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carboxylate Prepared according to General Procedure 3 using Amine 11 (70 mg, 0.163 mmol), Acid 11 (30.6 mg, 0.196 mmol), HATU (93.2 mg, 0.245 mmol) and DIPEA (114 μL, 0.653 mmol) in DCM (2 mL) to give the title compound (80 mg, 86%). LCMS (Method A): $R_T$=1.61 min, m/z=567 [M+H]$^+$.

Step 2: 4-(2-Fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carboxylic acid A solution of ethyl 4-(2-fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carboxylate (80 mg, 0.141 mmol) in ethanol (1.5 mL) and 2 M NaOH$_{(aq)}$ (1.5 mL, 3.00 mmol) was stirred at 45° C. for 16 h. The reaction mixture was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (70 mg, 92%). LCMS (Method A): $R_T$=1.30 min, m/z=539 [M+H]$^+$.

Step 3: 4-(2-Fluorophenyl)-1-(((S)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide Prepared according to General Procedure 3 using 4-(2-fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carboxylic acid (35 mg, 65.0 μmol), dimethylamine (2 M in THF, 49 μL, 97.5 μmol), HATU (29.7 mg, 78.0 μmol) and DIPEA (34 μL, 0.195 mmol) in DCM (2 mL) to give the title compound (30 mg, 78%). LCMS (Method B): $R_T$=1.18 min, m/z=566 [M+H]$^+$. $^1$H NMR (500 MHz, DMSO-d$_6$): δ 7.87-7.85 (m, 1H), 7.49-7.43 (m, 1H), 7.38-7.33 (m, 1H), 7.29-7.22 (m, 2H), 6.45 (s, 0.35H), 6.44 (s, 0.65H), 4.95 (s, 0.35H), 4.91 (s, 0.65H), 4.67 (d, J=13.5 Hz, 0.65H), 4.54 (d, J=13.5 Hz, 0.35H), 4.04-3.62 (m, 2H), 3.53-2.99 (m, 4H (signal overlaps with HDO)), 2.88 (s, 3H), 2.83-2.65 (m, 4H), 2.32-2.19 (m, 1H), 2.05-1.84 (m, 1H), 1.74-1.20 (m, 8H), 1.20-1.11 (m, 1H), 1.11-1.04 (m, 3H).

Example 224: 1-(((S)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one

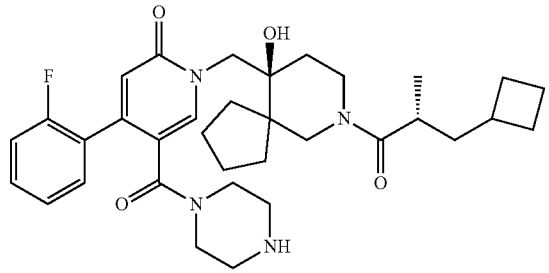 [SMILES: C[C@H](CC1CCC1)C(=O)N1CC[C@@](O)(Cn2cc(C(=O)N3CCNCC3)c(-c3ccccc3F)cc2=O)C2(CCCC2)C1]

Step 1: tert-Butyl 4-(1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carbonyl)piperazine-1-carboxylate Prepared according to General Procedure 3 using 1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carboxylic acid (Example 222, Step 2) (33 mg, 62.9 µmol), tert-butyl piperazine-1-carboxylate (17.6 mg, 94.4 µmol), HATU (28.7 mg, 75.5 µmol) and DIPEA (33 µL, 0.189 mmol) in DCM (2 mL) to give the title compound (37 mg, 84%). LCMS (Method A): $R_T$=1.73 min, m/z=693 [M+H]$^+$.

Step 2: 1-(((S)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one Prepared according to General Procedure 7 using tert-butyl 4-(1-(((S)-7-((R)-3-cyclobutyl-2-methylpropanoyl)-10-hydroxy-7-azaspiro[4.5]decan-10-yl)methyl)-4-(2-fluorophenyl)-6-oxo-1,6-dihydropyridine-3-carbonyl)piperazine-1-carboxylate (35 mg, 50.5 µmol), DCM (1 mL) and TFA (0.5 mL). The crude product was further purified by flash chromatography to give the title compound (20 mg, 65%). LCMS (Method B): $R_T$=0.91 min, m/z=593 [M+H]$^+$. $^1$H NMR (500 MHz, DMSO-d$_6$): δ 7.84 (s, 1H), 7.50-7.44 (m, 1H), 7.40-7.34 (m, 1H), 7.31-7.25 (m, 2H), 6.45 (s, 0.4H), 6.43 (s, 0.6H), 5.01-4.77 (m, 1H), 4.73-4.58 (m, 1H), 3.85-3.58 (m, 2H), 3.47-3.08 (m, 7H (signals overlap with HDO)), 2.79-2.46 (m, 6H (signals overlap with DMSO)), 2.25-2.13 (m, 1H), 2.03-1.85 (m, 3H), 1.85-1.08 (m, 15H), 0.99-0.91 (m, 3H).

Example 225: 4-(2-Fluorophenyl)-1-(((S)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one

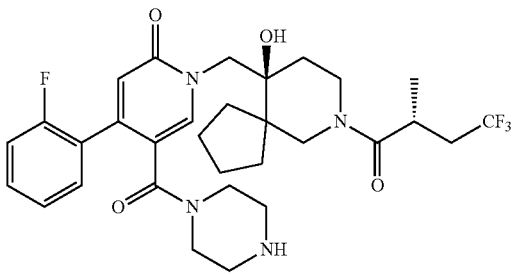 [SMILES: C[C@H](CC(F)(F)F)C(=O)N1CC[C@@](O)(Cn2cc(C(=O)N3CCNCC3)c(-c3ccccc3F)cc2=O)C2(CCCC2)C1]

Step 1: tert-Butyl 4-(4-(2-fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carbonyl)piperazine-1-carboxylate Prepared according to General Procedure 3 using 4-(2-fluorophenyl)-1-(((S)-10-hydroxy-7-((R)-4,4,4-trifluoro-2-methylbutanoyl)-7-azaspiro[4.5]decan-10-yl)methyl)-6-oxo-1,6-dihydropyridine-3-carboxylic acid (Example 223, Step 2) (35 mg, 65.0 µmol), tert-butyl piperazine-1-carboxylate (18.2 mg, 97.5 µmol), HATU (29.7 mg, 78.0 µmol) and DIPEA (34 µL, 0.195 mmol) in DCM (2 mL) to give the title compound (46 mg, quantitative). LCMS (Method A): $R_T$=1.55 min, m/z=707 [M+H]$^+$.

Step 2: 4-(2-Fluorophenyl)-1-(((S)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one Prepared according to General Procedure 7 using tert-butyl 4-(4-(2-fluorophenyl)-1-(((S)-10-hydroxy-7-((R)-4,4-4-trifluoro-2-methylbutanoyl)-7-azaspiro[4.5]decan-10-yl)methyl)-6-oxo-1,6-dihydropyridine-3-carbonyl)piperazine-1-carboxylate (60 mg, 84.9 µmol), DCM (1.5 mL) and TFA (0.8 mL). The crude product was further purified by flash chromatography to give the title compound (31 mg, 59%). LCMS (Method B): $R_T$=0.82 min, m/z=607 [M+H]$^+$. $^1$H NMR (500 MHz, DMSO-d$_6$): δ 7.84 (s, 1H), 7.50-7.43 (m, 1H), 7.40-7.34 (m, 1H), 7.31-7.25 (m, 2H), 6.45 (s, 0.4H), 6.44 (s, 0.6H), 5.00-4.82 (m, 1H), 4.66 (d, J=13.5 Hz, 0.6H), 4.53 (d, J=13.5 Hz, 0.4H), 4.04-3.61 (m, 2H), 3.52-3.00 (m, 8H (signals overlap with HDO)), 2.84-2.19 (m, 7H (signals overlap with DMSO)), 2.05-1.84 (m, 1H), 1.85-1.20 (m, 8H), 1.19-1.11 (m, 1H), 1.11-1.04 (m, 3H).

Example 226: 1-(((S)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide

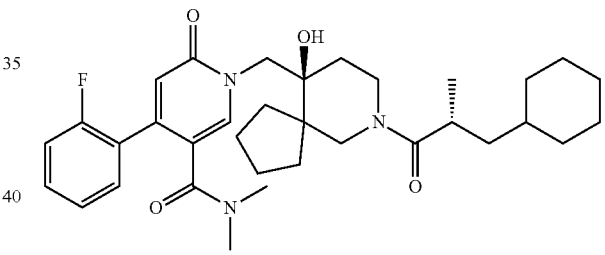

Step 1: Ethyl 1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carboxylate Prepared according to General Procedure 3 using Amine 11 (70 mg, 0.163 mmol), Acid 1 (33.4 mg, 0.196 mmol), HATU (93.2 mg, 0.245 mmol) and DIPEA (114 µL, 0.653 mmol) in DCM (2 mL) to give the title compound (90 mg, 94%). LCMS (Method A): $R_T$=1.96 min, m/z=581 [M+H]$^+$.

Step 2: 1-(((S)-7-((R)-3-Cyclohexyl-2-methylpropanoyl)-10-hydroxy-7-azaspiro[4.5]decan-10-yl)methyl)-4-(2-fluorophenyl)-6-oxo-1,6-dihydropyridine-3-carboxylic acid A solution of ethyl 1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carboxylate (90 mg, 0.155 mmol) in ethanol (2 mL) and 2 M NaOH$_{(aq)}$ (2 mL, 4.00 mmol) was stirred at 40° C. for 45 min. The reaction was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (70 mg, 81%). LCMS (Method A): R$_T$=1.66 min, m/z=553 [M+H]$^+$.

Step 3: 1-(((S)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide Prepared according to General Procedure 3 using 1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carboxylic acid (35 mg, 63.3 µmol), dimethylamine (2 M in THF, 48 µL, 95.0 µmol), HATU (28.9 mg, 76.0 µmol) and DIPEA (33 µL, 0.190 mmol) in DCM (2 mL) to give the title compound (29 mg, 76%). LCMS (Method B): R$_T$=1.47 min, m/z=580 [M+H]$^+$. $^1$H NMR (500 MHz, DMSO-d$_6$): δ 7.86 (s, 1H), 7.49-7.42 (m, 1H), 7.39-7.32 (m, 1H), 7.29-7.22 (m, 2H), 6.45 (s, 0.35H), 6.43 (s, 0.65H), 4.94 (s, 0.35H), 4.89 (s, 0.65H), 4.72 (d, J=13.5 Hz, 0.65H), 4.58 (d, J=13.5 Hz, 0.35H), 3.93-3.58 (m, 2H), 3.53-3.11 (m, 2H (signals overlap with HDO)), 2.96-2.72 (m, 7H), 2.02-1.81 (m, 1H), 1.72-1.02 (m, 21H), 0.99-0.91 (m, 3H), 0.90-0.75 (m, 2H).

Example 227: 1-(((S)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one

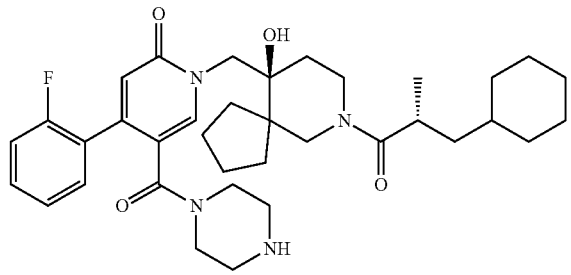 [SMILES: C[C@H](CC1CCCCC1)C(=O)N1CC[C@@](O)(Cn2cc(C(=O)N3CCNCC3)c(-c3ccccc3F)cc2=O)C2(CCCC2)C1]

Step 1: tert-Butyl 4-(1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carbonyl)piperazine-1-carboxylate Prepared according to General Procedure 3 using 1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carboxylic acid (Example 226, Step 2) (35 mg, 63.3 µmol), tert-butyl piperazine-1-carboxylate (17.7 mg, 95.0 µmol), HATU (28.9 mg, 76.0 µmol) and DIPEA (33 µL, 0.190 mmol) in DCM (2 mL) to give the title compound (35 mg, 76%). LCMS (Method A): R$_T$=1.89 min, m/z=721 [M+H]$^+$.

Step 2: 1-(((S)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one Prepared according to General Procedure 7 using tert-butyl 4-(1-(((S)-7-((R)-3-cyclohexyl-2-methylpropanoyl)-10-hydroxy-7-azaspiro[4.5]decan-10-yl)methyl)-4-(2-fluorophenyl)-6-oxo-1,6-dihydropyridine-3-carbonyl)piperazine-1-carboxylate (35 mg, 48.5 µmol), DCM (1.5 mL) and TFA (0.5 mL). The crude product was further purified by flash chromatography to give the title compound (23 mg, 74%). LCMS (Method B): R$_T$=0.99 min, m/z=621 [M+H]$^+$. $^1$H NMR (500 MHz, DMSO-d$_6$): δ 7.84 (s, 1H), 7.51-7.44 (m, 1H), 7.40-7.34 (m, 1H), 7.31-7.25 (m, 2H), 6.45 (s, 0.35H), 6.43 (s, 0.65H), 5.01-4.79 (m, 1H), 4.71 (d, J=13.5 Hz, 0.65H), 4.58 (d, J=13.5 Hz, 0.35H), 3.95-3.57 (m, 2H), 3.55-3.03 (m, 6H (signals overlap with HDO)), 2.96-2.80 (m, 1H), 2.73-2.21 (m, 5H (signals overlap with DMSO)), 2.03-1.82 (m, 1H), 1.77-1.01 (m, 21H), 1.00-0.90 (m, 3H), 0.90-0.75 (m, 2H).

Example 228: 1-(((S)-1-((R)-3-Cyclohexyl-2-methylpropanoyl)-4-hydroxy-3,3-dimethylpiperidin-4-yl)methyl)-5-(4-hydroxypiperidine-1-carbonyl)-4-phenylpyridin-2(1H)-one

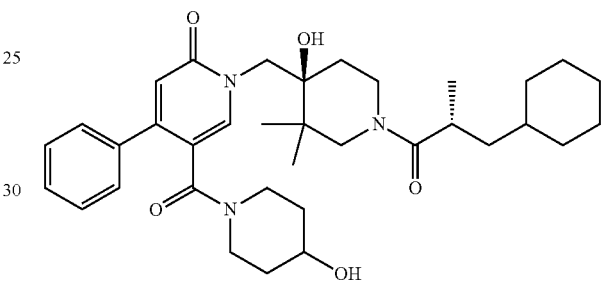

DIPEA (0.012 mL, 0.0672 mmol) was added to a stirred solution of Acid 4 (11.4 mg, 0.0224 mmol), 4-hydroxypiperidine (2.3 mg, 0.0224 mmol) and HATU (10.2 mg, 0.0269 mmol) in DCM (1.0 mL) at RT. After 2 h, the reaction mixture was partitioned between further DCM and saturated sodium bicarbonate (aq) solution. The resulting biphasic mixture was separated, dried (phase separator), the solvents were removed in vacuo, and the remaining residue was purified by flash chromatography (0-5%, MeOH in DCM) and freeze-dried to give the title compound (8.5 mg, 64%) as a white solid. LCMS (Method A): R$_T$=1.33 min, m/z=592 [M+H]$^+$. $^1$H NMR (500 MHz, DMSO-d$_6$): δ 7.79 (s, 1H), 7.50-7.34 (m, 5H), 6.48-6.42 (m, 1H), 5.06-2.69 (m, 13H, overlapping solvent peak), 1.77-0.28 (m, 29H).

Example 229: 1-((10-Hydroxy-7-(3-(trifluoromethyl)cyclobutane-1-carbonyl)-7-azaspiro[4.5]decan-10-yl)methyl)-N,N-dimethyl-6-oxo-4-phenyl-1,6-dihydropyridine-3-carboxamide

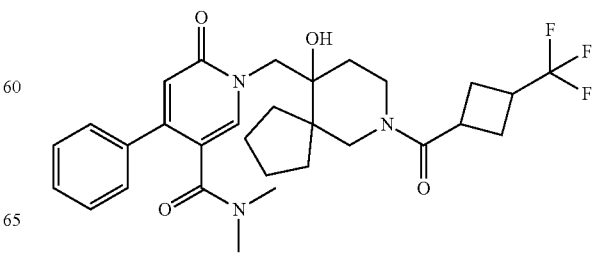

Prepared according to General Procedure 3 using Amine 8 (20 mg, 48.8 μmol), 3-(trifluoromethyl)cyclobutanecarboxylic acid (9.9 mg, 58.6 μmol), HATU (22.3 mg, 58.6 μmol), DIPEA (34 μL, 0.195 mmol) and DCM (1 mL) to give the title compound (25.3 mg, 90%) as a colourless solid after lyophilisation. LCMS (Method B): $R_T$=1.20, 1.23 (2 diastereomers) min, m/z=560 [M+H]$^+$. $^1$H NMR (500 MHz, DMSO-d$_6$): δ 7.86-7.77 (m, 1H), 7.65-7.19 (m, 5H), 6.50-6.41 (m, 1H), 5.01-4.88 (m, 1H), 4.67-4.53 (m, 1H), 3.86-3.74 (m, 0.5H), 3.74-3.64 (m, 1H), 3.53-3.17 (m, 4H (signals overlap with HDO)), 3.15-2.97 (m, 1.5H), 2.75 (s, 3H), 2.63 (s, 3H), 2.46-2.16 (m, 4H), 1.99-1.85 (m, 1H), 1.74-1.49 (m, 5H), 1.48-1.28 (m, 2H), 1.28-1.19 (m, 1H), 1.19-1.08 (m, 1H).

Example 230: 1-(((S)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide

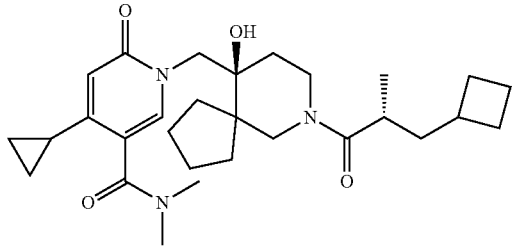 [SMILES: C[C@H](CC1CCC1)C(=O)N1CC[C@@](O)(Cn2cc(C(=O)N(C)C)c(C3CC3)cc2=O)C2(CCCC2)C1]

Step 1: Ethyl 1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carboxylate Prepared according to General Procedure 3 using Amine 12 (50 mg, 0.134 mmol), Acid 5 (22.8 mg, 0.160 mmol), HATU (76.2 mg, 0.200 mmol) and DIPEA (93 μL, 0.534 mmol) in DCM (2 mL) to give the title compound (48 mg, 72%). LCMS (Method A): $R_T$=1.74 min, m/z=499 [M+H]$^+$.

Step 2: 1-(((S)-7-((R)-3-Cyclobutyl-2-methylpropanoyl)-10-hydroxy-7-azaspiro[4.5]decan-10-yl)methyl)-4-cyclopropyl-6-oxo-1,6-dihydropyridine-3-carboxylic acid A solution of ethyl 1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carboxylate (48 mg, 96.3 μmol) in ethanol (1.2 mL) and 2 M NaOH$_{(aq)}$ (1.2 mL, 2.40 mmol) was stirred at RT for 16 h. The reaction was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (30 mg, 66%). LCMS (Method A): $R_T$=1.36 min, m/z=471 [M+H]$^+$.

Step 3: 1-(((S)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide Prepared according to General Procedure 3 using 1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carboxylic acid (30 mg, 63.7 μmol), dimethylamine (2 M in THF, 48 μL, 95.6 μmol), HATU (29.1 mg, 76.5 μmol) and DIPEA (33 μL, 0.191 mmol) in DMF (2 mL) to give the title compound (28 mg, 84%). LCMS (Method B): $R_T$=1.22 min, m/z=498 [M+H]$^+$. $^1$H NMR (500 MHz, DMSO-d$_6$): δ 7.67-7.60 (m, 1H), 5.93-5.86 (m, 1H), 5.01 (s, 0.4H), 4.92 (s, 0.6H), 4.55-4.39 (m, 1H), 3.81-3.58 (m, 2H), 3.44-3.13 (m, 3H (signal overlaps with HDO)), 3.05-2.87 (bs, 6H), 2.76-2.61 (m, 1H (overlaps with DMSO satellite)), 2.55-2.12 (m, 1H), 2.02-1.44 (m, 14H), 1.44-1.06 (m, 5H), 1.03-0.90 (m, 5H), 0.83-0.71 (m, 2H).

Example 231: 1-(((S)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one

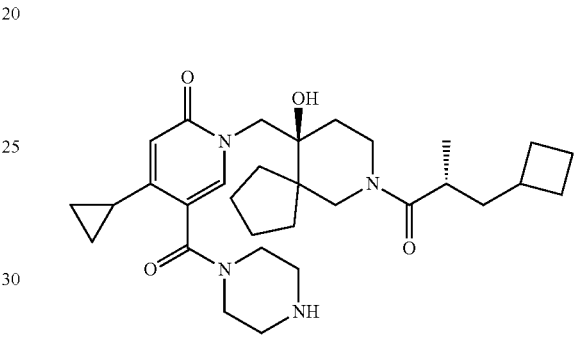

Step 1: tert-Butyl 4-(1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carbonyl)piperazine-1-carboxylate Prepared according to General Procedure 3 using 1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carboxylic acid (Example 230, Step 2) (20 mg, 42.5 μmol), tert-butyl piperazine-1-carboxylate (11.9 mg, 63.7 μmol), HATU (19.4 mg, 51.0 μmol) and DIPEA (22 μL, 0.128 mmol) in DCM (1 mL) to give the title compound (17 mg, 60%). LCMS (Method A): $R_T$=1.61 min, m/z=639 [M+H]$^+$.

Step 2: 1-(((S)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one Prepared according to General Procedure 7 using tert-butyl 4-(1-(((S)-7-((R)-3-cyclobutyl-2-methylpropanoyl)-10-hydroxy-7-azaspiro[4.5]decan-10-yl)methyl)-4-cyclopropyl-6-oxo-1,6-dihydropyridine-3-carbonyl)piperazine-1-carboxylate (17 mg, 26.6 μmol), DCM (1 mL) and TFA (0.4 mL). The crude product was further purified by flash chromatography to give the title compound (12 mg, 81%). LCMS (Method B): $R_T$=0.84 min, m/z=539 [M+H]$^+$. $^1$H NMR (500 MHz, DMSO-d$_6$): δ 7.67-7.57 (bs, 1H), 5.95-5.88 (m, 1H), 5.13-4.79 (bs, 1H), 4.54-4.35 (m, 1H), 3.82-3.14 (m, 8H (signal overlaps with HDO)), 2.80-2.45 (m, 7H (signal overlaps with DMSO and satellite)), 2.23-2.12 (m, 1H), 2.02-1.45 (m, 14H), 1.42-0.50 (m, 12H).

Example 232: 1-(((S)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide

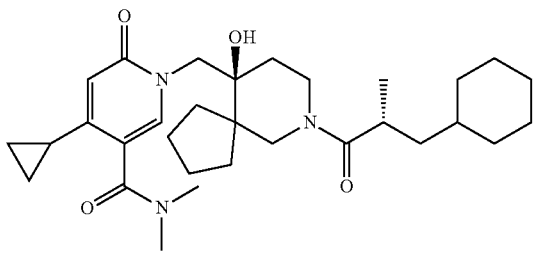 [SMILES: C[C@H](CC1CCCCC1)C(=O)N1CC[C@@](O)(Cn2cc(C(=O)N(C)C)c(C3CC3)cc2=O)C2(CCCC2)C1]

Step 1: Ethyl 1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carboxylate Prepared according to General Procedure 3 using Amine 12 (50 mg, 0.134 mmol), Acid 1 (27.3 mg, 0.160 mmol), HATU (76.2 mg, 0.200 mmol) and DIPEA (93 µL, 0.534 mmol) in DCM (2 mL) to give the title compound (34 mg, 48%). LCMS (Method A): $R_T$=1.92 min, m/z=527 [M+H]$^+$.

Step 2: 1-(((S)-7-((R)-3-Cyclohexyl-2-methylpropanoyl)-10-hydroxy-7-azaspiro[4.5]decan-10-yl)methyl)-4-cyclopropyl-6-oxo-1,6-dihydropyridine-3-carboxylic acid A solution of ethyl 1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carboxylate (34 mg, 64.6 µmol) in ethanol (1 mL) and 2 M NaOH$_{(aq)}$ (1 mL, 2.00 mmol) was stirred at RT for 16 h. The reaction was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (30 mg, 93%). LCMS (Method A): $R_T$=1.55 min, m/z=499 [M+H]$^+$.

Step 3: 1-(((S)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide Prepared according to General Procedure 3 using 1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carboxylic acid (20 mg, 40.1 µmol), dimethylamine (2 M in THF, 30 µL, 60.2 µmol), HATU (18.3 mg, 48.1 µmol) and DIPEA (21 µL, 0.120 mmol) in DMF (1 mL) to give the title compound (11 mg, 52%). LCMS (Method B): $R_T$=1.38 min, m/z=526 [M+H]$^+$. $^1$H NMR (500 MHz, DMSO-d$_6$): δ 7.67-7.61 (m, 1H), 5.93-5.87 (m, 1H), 5.03 (s, 0.35H), 4.92 (s, 0.65H), 4.54 (d, J=14 Hz, 0.65H), 4.39 (d, J=14 Hz, 0.35H), 3.92-3.56 (m, 2H), 3.49-3.20 (m, 2H (signal overlaps with HDO)), 3.19-2.77 (m, 7H), 1.97-1.78 (m, 1H), 1.72-0.70 (m, 31H).

Example 233: 1-(((S)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one

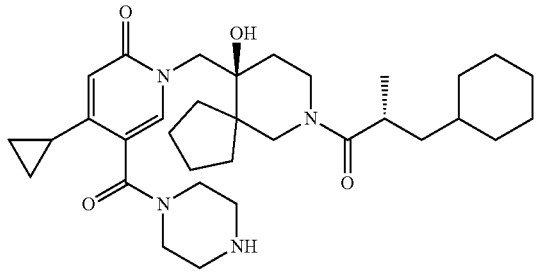 [SMILES: C[C@H](CC1CCCCC1)C(=O)N1CC[C@@](O)(Cn2cc(C(=O)N3CCNCC3)c(C3CC3)cc2=O)C2(CCCC2)C1]

Step 1: tert-Butyl 4-(1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carbonyl)piperazine-1-carboxylate Prepared according to General Procedure 3 using 1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carboxylic acid (Example 232, Step 2) (30 mg, 60.2 µmol), tert-butyl piperazine-1-carboxylate (16.8 mg, 90.2 µmol), HATU (27.5 mg, 72.2 µmol) and DIPEA (32 µL, 0.181 mmol) in DMF (1 mL) to give the title compound (40 mg, quantitative). LCMS (Method A): $R_T$=1.79 min, m/z=667 [M+H]$^+$.

Step 2: 1-(((S)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one Prepared according to General Procedure 7 using tert-butyl 4-(1-(((S)-7-((R)-3-cyclohexyl-2-methylpropanoyl)-10-hydroxy-7-azaspiro[4.5]decan-10-yl)methyl)-4-cyclopropyl-6-oxo-1,6-dihydropyridine-3-carbonyl)piperazine-1-carboxylate (40 mg, 60.0 µmol), DCM (3 mL) and TFA (1 mL). The crude product was further purified by flash chromatography to give the title compound (26 mg, 74%). LCMS (Method B): $R_T$=0.97 min, m/z=567 [M+H]$^+$. $^1$H NMR (500 MHz, DMSO-d$_6$): δ 7.67-7.57 (m, 1H), 5.94-5.88 (m, 1H), 5.12-4.79 (bs, 1H), 4.58-4.32 (m, 1H), 3.90-3.06 (m, 9H (signal overlaps with HDO)), 2.94-2.55 (m, 6H (overlaps with DMSO satellite)), 1.98-1.79 (m, 1H), 1.74-1.42 (m, 12H), 1.41-0.58 (m, 18H).

Example 234: 1-((2-((R)-3-Cyclohexyl-2-methylpropanoyl)-5-hydroxy-9-oxa-2-azaspiro[5.5]undecan-5-yl)methyl)-N,N-dimethyl-6-oxo-4-phenyl-1,6-dihydropyridine-3-carboxamide

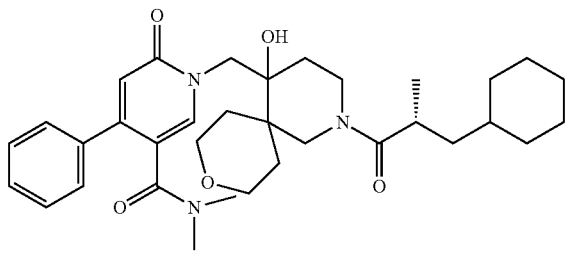 [SMILES: C[C@H](CC1CCCCC1)C(=O)N1CCC(O)(Cn2cc(C(=O)N(C)C)c(-c3ccccc3)cc2=O)C2(CCOCC2)C1]

Step 1: tert-Butyl 5-oxo-9-oxa-2-azaspiro[5.5]undecane-2-carboxylate

To a solution of tert-butyl 4-oxopiperidine-1-carboxylate (3.98 g, 20.0 mmol) in toluene (40 mL) in a 3-necked 250 mL RBF fitted with a reflux condenser under $N_2$ at RT was added potassium tert-butoxide (4.94 g, 44.0 mmol) portionwise. After stirring for 1 h, bis(2-bromoethyl) ether (2.51 mL, 20.0 mmol) was added dropwise over 5 min and the reaction heated at reflux for 2 h. The reaction was allowed to cool to RT, diluted with 1:1 saturated $NH_4Cl_{(aq)}$/water (40 mL) and extracted with EtOAc (3×40 mL). The combined organic phases were washed with brine (100 mL), passed through a Biotage phase separator, concentrated in vacuo and the residue was purified by flash chromatography (GraceResolv silica 120 g cartridge, 0-15% EtOAc in cyclohexane) to give the title compound (458 mg, 8.5%) as pale yellow solid. LCMS (Method A): $R_T$=1.13 min, m/z=214 [M-butene+H]$^+$. $^1$H NMR (500 MHz, CDCl$_3$): δ 3.82-3.65 (m, 6H), 3.57 (s, 2H), 2.49 (t, J=6.4 Hz, 2H), 1.94 (dt, J=13.9, 5.1 Hz, 2H), 1.49 (s, 9H), 1.47-1.43 (m, 2H). $^{13}$C NMR (126 MHz, CDCl$_3$): δ 211.13, 154.71, 80.70, 63.96, 52.48 (br.), 48.00, 43.92 (br.), 38.13, 30.85, 28.52.

Step 2: tert-Butyl 1,7-dioxa-11-azadispiro[2.0.5$^4$.4$^3$]tridecane-11-carboxylate Sodium hydride (60% dispersion in mineral oil, 98 mg, 2.45 mmol) was added to a suspension of trimethylsulfonium iodide (500 mg, 2.45 mmol) in DMF (4 mL) at RT. After stirring for 1 h at RT, a solution of tert-butyl 5-oxo-9-oxa-2-azaspiro[5.5]undecane-2-carboxylate (440 mg, 1.63 mmol) in DMF (4 mL) was added dropwise. After 16 h, the reaction was diluted with 1:1 water/saturated $NH_4Cl_{(aq)}$ (40 mL) and the mixture extracted with EtOAc (3×20 mL). The combined organic phases were washed with water (20 mL) and brine (20 mL) before being passed through a Biotage phase separator. The resulting solution was concentrated in vacuo and the residue purified by flash chromatography (GraceResolv silica 40 g cartridge, 0-30% EtOAc in cyclohexane) to give the title compound (355 mg, 76%) as colourless oil. LCMS (Method A): $R_T$=1.18 min, m/z=228 [M-butene+H]$^+$. $^1$H NMR (500 MHz, CDCl$_3$): δ 3.86-3.74 (m, 2H), 3.73-3.42 (m, 6H), 2.92 (d, J=4.1 Hz, 1H), 2.46 (d, J=4.2 Hz, 1H), 1.72-1.55 (m, 4H), 1.48 (s, 9H), 1.42-1.36 (m, 1H), 1.32-1.24 (m, 1H).

Step 3: tert-Butyl 5-((4-chloro-5-(ethoxycarbonyl)-2-oxopyridin-1 (2H)-yl)methyl)-5-hydroxy-9-oxa-2-azaspiro[5.5]undecane-2-carboxylate A solution of ethyl 4-chloro-6-oxo-1,6-dihydropyridine-3-carboxylate (245 mg, 1.22 mmol), tert-butyl 1,7-dioxa-11-azadispiro[2.0.5$^4$.4$^3$]tridecane-11-carboxylate (345 mg, 1.22 mmol) and DIPEA (1.06 mL, 6.09 mmol) in 1-methyl-2-pyrrolidinone (2.4 mL) was heated at 120° C. for 88 h. The reaction was allowed to cool to RT, diluted with saturated $NaHCO_{3(aq)}$ (50 mL) and the mixture extracted with DCM (3×50 mL). The combined organic phases were passed through a Biotage phase separator, concentrated in vacuo and the residue was purified by flash chromatography (GraceResolv silica 40 g cartridge, 0-60% EtOAc in cyclohexane) to give the title compound (223 mg, 37%) as colourless solid. LCMS (Method A): $R_T$=1.38 min, m/z=485 [M+H]$^+$. $^1$H NMR (500 MHz, DMSO-d$_6$): δ 8.45 (s, 1H), 6.63 (s, 1H), 4.95 (s, 1H), 4.65 (d, J=13.4 Hz, 1H), 4.27 (q, J=7.0 Hz, 2H), 3.82-3.58 (m, 4H), 3.58-3.33 (m, 4H), 3.20 (ddd, J=13.2, 8.9, 4.0 Hz, 1H), 1.91-1.70 (m, 2H), 1.39 (s, 9H), 1.32-1.20 (m, 3H), 1.29 (t, J=7.1 Hz, 3H), 1.18-1.08 (m, 1H).

Step 4: tert-Butyl 5-((5-(ethoxycarbonyl)-2-oxo-4-phenylpyridin-1 (2H)-yl)methyl)-5-hydroxy-9-oxa-2-azaspiro[5.5]undecane-2-carboxylate Prepared according to General Procedure 4 using tert-butyl 5-((4-chloro-5-(ethoxycarbonyl)-2-oxopyridin-1 (2H)-yl)methyl)-5-hydroxy-9-oxa-2-azaspiro[5.5]undecane-2-carboxylate (197 mg, 0.406 mmol), phenylboronic acid (74 mg, 0.609 mmol), Pd(dppf)Cl$_2$.CH$_2$Cl$_2$ (17 mg, 20.3 μmol), Na$_2$CO$_3$ (86 mg, 0.812 mmol), 1,4-dioxane (1.5 mL) and water (0.5 mL) at 140° C. for 2 h under microwave irradiation to give, after additional phenylboronic acid (74 mg, 0.609 mmol), Pd(dppf)Cl$_2$.CH$_2$Cl$_2$ (17 mg, 20.3 μmol) and Na$_2$CO$_3$ (86 mg, 0.812 mmol) were added and the reaction heated at 140° C. for 30 min under microwave irradiation, the title compound (108 mg, 50%) as a pale yellow foam. LCMS (Method A): $R_T$=1.52 min, m/z=527 [M+H]$^+$.

Step 5: 1-((2-(tert-Butoxycarbonyl)-5-hydroxy-9-oxa-2-azaspiro[5.5]undecan-5-yl)methyl)-6-oxo-4-phenyl-1,6-dihydropyridine-3-carboxylic acid A solution of tert-butyl 5-((5-(ethoxycarbonyl)-2-oxo-4-phenylpyridin-1 (2H)-yl)methyl)-5-hydroxy-9-oxa-2-azaspiro[5.5]undecane-2-carboxylate (108 mg, 0.205 mmol) in 1 M NaOH$_{(aq)}$ (0.410 mL, 0.410 mmol) and 1,4-dioxane (1 mL) was stirred at 50° C. for 18 h. The reaction mixture was allowed to cool to RT and the pH was adjusted to ~pH 2 by the addition of 1 M HCl$_{(aq)}$. The resulting mixture was extracted with DCM (3×20 mL) using a Biotage phase separator and the combined organic phases were concentrated in vacuo to give the title compound (100 mg, 97%) as a colourless foam. LCMS (Method A): $R_T$=1.18 min, m/z=499 [M+H]$^+$.

Step 6: tert-Butyl 5-((5-(dimethylcarbamoyl)-2-oxo-4-phenylpyridin-1 (2H)-yl)methyl)-5-hydroxy-9-oxa-2-azaspiro[5.5]undecane-2-carboxylate Prepared according to General Procedure 3 using 1-((2-(tert-butoxycarbonyl)-5-hydroxy-9-oxa-2-azaspiro[5.5]undecan-5-yl)methyl)-6-oxo-4-phenyl-1,6-dihydropyridine-3-carboxylic acid (100 mg, 0.201 mmol), dimethylamine (2 M in THF, 0.120 mL, 0.241 mmol), HATU (91.5 mg, 0.241 mmol), DIPEA (0.140 mL, 0.802 mmol) and DCM (4 mL) to give the title compound (99 mg, 93%) as a pale yellow foam. LCMS (Method A): $R_T$=1.15 min, m/z=526 [M+H]$^+$.

Step 7: 1-((5-Hydroxy-9-oxa-2-azaspiro[5.5]undecan-5-yl)methyl)-N,N-dimethyl-6-oxo-4-phenyl-1,6-dihydropyridine-3-carboxamide A solution of tert-butyl 5-((5-(dimethylcarbamoyl)-2-oxo-4-phenylpyridin-1 (2H)-yl)methyl)-5-hydroxy-9-oxa-2-azaspiro[5.5]undecane-2-carboxylate (99 mg, 0.188 mmol) in TFA (0.5 mL) and DCM (1 mL) was stirred for 15 min before the reaction mixture was purified using a Biotage SCX-2 5 g cartridge (pre-equilibrated with and then washed using 1:1 DCM/MeOH before being eluted with 1:1 DCM/7 M in NH$_3$ in MeOH). The basic eluents were concentrated in vacuo to give the title compound (79 mg, 98%) as a colourless solid. LCMS (Method A): $R_T$=0.38 min, m/z=426 [M+H]$^+$.

Step 8: 1-((2-((R)-3-Cyclohexyl-2-methylpropanoyl)-5-hydroxy-9-oxa-2-azaspiro[5.5]undecan-5-yl)methyl)-N,N-dimethyl-6-oxo-4-phenyl-1,6-dihydropyridine-3-carboxamide Prepared according to General Procedure 3 using 1-((5-hydroxy-9-oxa-2-azaspiro[5.5]undecan-5-yl)methyl)-N,N-dimethyl-6-oxo-4-phenyl-1,6-dihydropyridine-3-carboxamide (20 mg, 47.0 μmol), Acid 1 (8.8 mg, 51.7 μmol), HATU (20 mg, 51.7 μmol), DIPEA (33 μL, 0.188 mmol) and DCM (1 mL) to give the title compound (24 mg, 87%) as a colourless solid after lyophilisation. LCMS (Method B): $R_T$=1.31, 1.33 (2 diastereomers) min, m/z=578 [M+H]$^+$. $^1$H NMR (500 MHz, DMSO-d$_6$): δ 7.83-7.77 (m, 1H), 7.55-7.26 (m, 5H), 6.48-6.42 (m, 1H), 5.13-4.99 (m, 1H), 4.70-4.58 (m, 1H), 4.02-3.37 (m, 9H), 2.96-2.86 (m, 1H), 2.75 (s, 3H), 2.63 (s, 3H), 1.98-1.41 (m, 9H), 1.36-1.03 (m, 8H), 1.00-0.89 (m, 3H), 0.89-0.76 (m, 2H).

Example 235: 1-(((S)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide

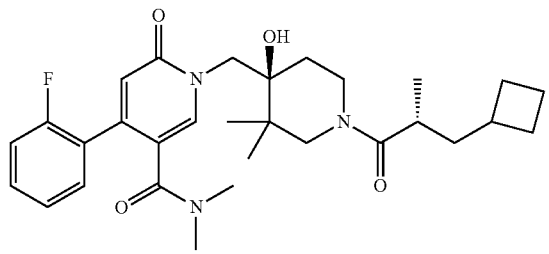 [SMILES: C[C@H](CC1CCC1)C(=O)N1CC[C@@](O)(Cn2cc(C(=O)N(C)C)c(-c3ccccc3F)cc2=O)C(C)(C)C1]

Step 1: Ethyl 1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carboxylate Prepared according to General Procedure 3 using Amine 9 (50 mg, 0.124 mmol), Acid 5 (21.2 mg, 0.149 mmol), HATU (70.9 mg, 0.186 mmol) and DIPEA (87 μL, 0.497 mmol) in DCM (2 mL) to give the title compound (54 mg, 82%). LCMS (Method B): $R_T$=1.55 min, m/z=527 [M+H]$^+$.

Step 2: 1-(((S)-1-((R)-3-Cyclobutyl-2-methylpropanoyl)-4-hydroxy-3,3-dimethylpiperidin-4-yl)methyl)-4-(2-fluorophenyl)-6-oxo-1,6-dihydropyridine-3-carboxylic acid A solution of ethyl 1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carboxylate (54 mg, 0.103 mmol) in ethanol (1.5 mL) and 2 M NaOH$_{(aq)}$ (1.5 mL, 3.00 mmol) was stirred at RT for 16 h. The reaction was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (49 mg, 95%). LCMS (Method B): $R_T$=1.37 min, m/z=499 [M+H]$^+$.

Step 3: 1-(((S)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide Prepared according to General Procedure 3 using 1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carboxylic acid (24 mg, 48.1 μmol), dimethylamine (2 M in THF, 36 μL, 72.2 μmol), HATU (22.0 mg, 57.8 μmol) and DIPEA (25 μL, 0.144 mmol) in DCM (1 mL) to give the title compound (15 mg, 58%). LCMS (Method B): $R_T$=1.27 min, m/z=526 [M+H]$^+$. $^1$H NMR (500 MHz, DMSO-d$_6$): δ 7.84 (s, 1H), 7.49-7.42 (m, 1H), 7.39-7.32 (m, 1H), 7.29-7.21 (m, 2H), 6.46-6.41 (m, 1H), 4.91-4.84 (m, 1H), 4.53-4.38 (m, 1H), 3.86-3.61 (m, 2H), 3.32-3.19 (m, 2H (signal overlaps with HDO)), 3.01-2.67 (m, 7H), 2.25-2.12 (m, 1H), 2.03-1.88 (m, 2H), 1.84-1.47 (m, 6H), 1.37-1.16 (m, 3H), 1.07-0.88 (m, 9H).

Example 236: 1-(((S)-1-((R)-3-Cyclobutyl-2-methylpropanoyl)-4-hydroxy-3,3-dimethylpiperidin-4-yl)methyl)-4-(2-fluorophenyl)-5-(piperazine-1-carbonyl)pyridin-2(1H)-one

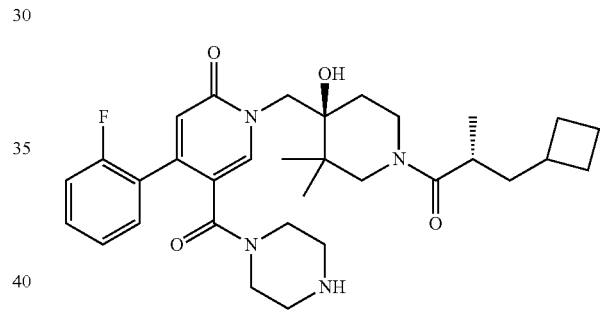

Step 1: tert-Butyl 4-(1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carbonyl)piperazine-1-carboxylate Prepared according to General Procedure 3 using 1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carboxylic acid (Example 235, Step 2) (24 mg, 48.1 μmol), tert-butyl piperazine-1-carboxylate (13.4 mg, 72.2 μmol), HATU (22.0 mg, 57.8 μmol) and DIPEA (25 μL, 0.144 mmol) in DCM (1 mL) to give the title compound (32 mg, quantitative). LCMS (Method B): $R_T$=1.50 min, m/z=611 [M-butene+H]$^+$.

Step 2: 1-(((S)-1-((R)-3-Cyclobutyl-2-methypropanoyl)-4-hydroxy-3,3-dimethylpiperidin-4-yl)methyl)-4-(2-fluorophenyl)-5-(piperazine-1-carbonyl)pyridin-2(1H)-one Prepared according to General Procedure 7 using tert-butyl 4-(1-(((S)-1-((R)-3-cyclobutyl-2-methylpropanoyl)-4-hydroxy-3,3-dimethylpiperidin-4-yl)methyl)-4-(2-fluorophenyl)-6-oxo-1,6-dihydropyridine-3-carbonyl)piperazine- 1-carboxylate (32 mg, 48.0 µmol), DCM (1 mL) and TFA (0.5 mL). The crude product was further purified by flash chromatography to give the title compound (20 mg, 71%). LCMS (Method B): $R_T$=0.86 min, m/z=567 [M+H]$^+$. $^1$H NMR (500 MHz, DMSO-d$_6$): δ 7.81 (s, 1H), 7.51-7.43 (m, 1H), 7.40-7.34 (m, 1H), 7.31-7.24 (m, 2H), 6.46-6.41 (m, 1H), 4.92-4.79 (bs, 1H), 4.54-4.35 (m, 1H), 3.89-3.60 (m, 2H), 3.43-3.08 (m, 6H (signal overlaps with HDO)), 3.01-2.88 (m, 1H), 2.79-2.68 (m, 1H), 2.66-2.27 (m, 5H (signal overlaps with DMSO and satellites)), 2.24-2.13 (m, 1H), 2.01-1.89 (m, 2H), 1.83-1.47 (m, 6H), 1.37-1.16 (m, 2H), 1.09-0.87 (m, 9H).

Example 237: 1-((2-((R)-3-Cyclohexyl-2-methylpropanoyl)-5-hydroxy-2-azaspiro[5.5]undecan-5-yl)methyl)-N,N-dimethyl-6-oxo-4-phenyl-1,6-dihydropyridine-3-carboxamide

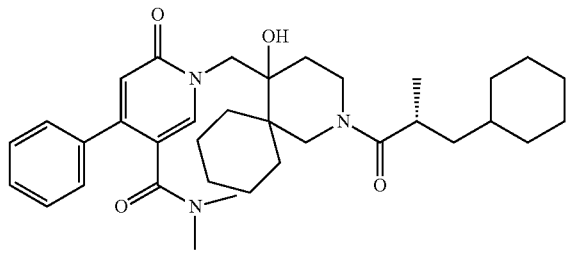 [SMILES: C[C@H](CC1CCCCC1)C(=O)N1CCC(O)(Cn2cc(C(=O)N(C)C)c(-c3ccccc3)cc2=O)C2(CCCCC2)C1]

Step 1: tert-Butyl 5-((4-chloro-5-(ethoxycarbonyl)-2-oxopyridin-1 (2H)-yl)methyl)-5-hydroxy-2-azaspiro[5.5]undecane-2-carboxylate A solution of ethyl 4-chloro-6-oxo-1,6-dihydropyridine-3-carboxylate (86 mg, 0.427 mmol), Epoxide 7 (120 mg, 0.427 mmol) and DIPEA (373 µL, 2.13 mmol) in NMP (1 mL) was stirred at 110° C. for 136 h. The reaction mixture was diluted with saturated NaHCO$_{3(aq)}$ and extracted with DCM (×3) using a Biotage phase separator. The combined organic phases were concentrated in vacuo and the residue purified by flash chromatography to give the title compound (80 mg, 38%). LCMS (Method A): $R_T$=2.08 min, m/z=427 [M-butene+H]$^+$.

Step 2: tert-Butyl 5-((5-(ethoxycarbonyl)-2-oxo-4-phenylpyridin-1 (2H)-yl)methyl)-5-hydroxy-2-azaspiro[5.5]undecane-2-carboxylate Prepared according to General Procedure 4 using tert-butyl 5-((4-chloro-5-(ethoxycarbonyl)-2-oxopyridin-1 (2H)-yl)methyl)-5-hydroxy-2-azaspiro[5.5]undecane-2-carboxylate (80 mg, 0.166 mmol), phenylboronic acid (30.3 mg, 0.248 mmol), Pd(dppf)Cl$_2$.CH$_2$Cl$_2$ (13.5 mg, 16.6 µmol) and sodium carbonate (43.9 mg, 0.414 mmol) in 1,4-dioxane (0.7 mL) and water (0.2 mL). The reaction was heated under microwave irradiation at 150° C. for 10 min to give the title compound (74 mg, 85%). LCMS (Method A): $R_T$=1.90 min, m/z=525 [M+H]$^+$.

Step 3: Ethyl 1-((5-hydroxy-2-azaspiro[5.5]undecan-5-yl)methyl)-6-oxo-4-phenyl-1,6-dihydropyridine-3-carboxylate A solution of tert-butyl 5-((5-(ethoxycarbonyl)-2-oxo-4-phenylpyridin-1(2H)-yl)methyl)-5-hydroxy-2-azaspiro[5.5]undecane-2-carboxylate (74 mg, 0.141 mmol) in DCM (2 mL) and HCl (4 M in 1,4-dioxane, 1 mL, 4.00 mmol) was stirred at RT for 1 h. The reaction mixture was quenched with saturated NaHCO$_{3(aq)}$ and the aqueous phase was extracted with DCM (×3) using a Biotage phase separator. The combined organic phases were concentrated in vacuo to give the title compound (51 mg, 85%). LCMS (Method A): $R_T$=0.88 min, m/z=425 [M+H]$^+$.

Step 4: Ethyl 1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carboxylate Prepared according to General Procedure 3 using ethyl 1-((5-hydroxy-2-azaspiro[5.5]undecan-5-yl)methyl)-6-oxo-4-phenyl-1,6-dihydropyridine-3-carboxylate (50 mg, 0.118 mmol), Acid 1 (24.1 mg, 0.141 mmol), HATU (67.2 mg, 0.177 mmol) and DIPEA (82 µL, 0.471 mmol) in DCM (2 mL) to give the title compound (67 mg, 98%). LCMS (Method A): $R_T$=1.82 min, m/z=577 [M+H]$^+$.

Step 5: 1-((2-((R)-3-Cyclohexyl-2-methylpropanoyl)-5-hydroxy-2-azaspiro[5.5]undecan-5-yl)methyl)-6-oxo-4-phenyl-1,6-dihydropyridine-3-carboxylic acid A solution of ethyl 1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carboxylate (67 mg, 0.116 mmol) in ethanol (1.5 mL) and 2 M NaOH$_{(aq)}$ (1.5 mL, 3.00 mmol) was stirred at 50° C. for 1.5 h. The reaction was concentrated in vacuo. The residue was taken up in water and washed with diethyl ether. The aqueous phase was acidified by addition of 2 M HCl$_{(aq)}$ to pH<4. The resulting suspension was extracted with EtOAc (×3), the combined organic phases washed with brine, passed through a Biotage phase separator and concentrated in vacuo to give the title compound (63 mg, quantitative). LCMS (Method A): $R_T$=1.72 min, m/z=549 [M+H]$^+$.

Step 6: 1-((2-((R)-3-Cyclohexyl-2-methylpropanoyl)-5-hydroxy-2-azaspiro[5.5]undecan-5-yl)methyl)-N,N-dimethyl-6-oxo-4-phenyl-1,6-dihydropyridine-3-carboxamide Prepared according to General Procedure 3 using 1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carboxylic acid (32 mg, 58.3 µmol), dimethylamine (2 M in THF, 44 µL, 87.5 µmol), HATU (26.6 mg, 70.0 µmol) and DIPEA (31 µL, 0.175 mmol) in DCM (2 mL) to give the title compound (26 mg, 75%). LCMS (Method B): $R_T$=1.56 min, m/z=576 [M+H]$^+$. $^1$H NMR (500 MHz, DMSO-d$_6$): δ 7.80 (s, 1H), 7.47-7.42 (m, 3H), 7.41-7.35 (m, 2H), 6.48-6.42 (m, 1H), 4.96-4.82 (m, 1H), 4.67-4.52 (m, 1H), 3.91-3.12 (m, 4H (signal overlaps with HDO)), 2.96-2.84 (m, 1H), 2.75 (s, 3H), 2.63 (s, 3H (overlaps with DMSO satellite)), 1.73-0.74 (m, 29H).

Example 238: 1-((2-((R)-3-Cyclohexyl-2-methyl-propanoyl)-5-hydroxy-2-azaspiro[5.5]undecan-5-yl)methyl)-4-phenyl-5-(piperazine-1-carbonyl)pyridin-2(1H)-one

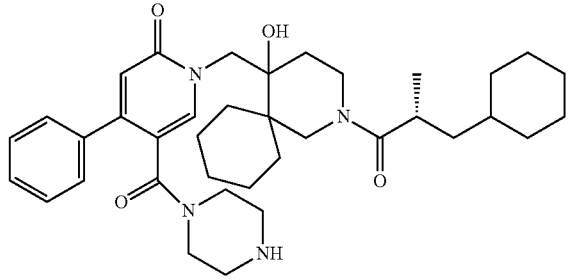 [SMILES: C[C@H](CC1CCCCC1)C(=O)N1CCC(O)(Cn2cc(C(=O)N3CCNCC3)c(-c3ccccc3)cc2=O)C2(CCCCC2)C1]

Step 1: tert-Butyl 4-(1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carbonyl)piperazine-1-carboxylate Prepared according to General Procedure 3 using 1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carboxylic acid (Example 237, Step 5) (32 mg, 58.3 µmol), tert-butyl piperazine-1-carboxylate (16.3 mg, 87.5 µmol), HATU (26.6 mg, 70.0 µmol) and DIPEA (31 µL, 0.175 mmol) in DCM (2 mL) to give the title compound (39 mg, 93%). LCMS (Method B): $R_T$=1.75 min, m/z=661 [M-butene+H]$^+$.

Step 2: 1-((2-((R)-3-Cyclohexyl-2-methylpropanoyl)-5-hydroxy-2-azaspiro[5.5]undecan-5-yl)methyl)-4-phenyl-5-(piperazine-1-carbonyl)pyridin-2(1H)-one Prepared according to General Procedure 7 using tert-butyl 4-(1-((2-((R)-3-cyclohexyl-2-methylpropanoyl)-5-hydroxy-2-azaspiro[5.5]undecan-5-yl)methyl)-6-oxo-4-phenyl-1,6-dihydropyridine-3-carbonyl)piperazine-1-carboxylate (39 mg, 54.4 µmol), DCM (1.5 mL) and TFA (0.5 mL). The crude product was further purified by flash chromatography to give the title compound (30 mg, 87%). LCMS (Method B): $R_T$=1.04 min, m/z=617 [M+H]$^+$. $^1$H NMR (500 MHz, DMSO-d$_6$): δ 7.79 (s, 1H), 7.50-7.35 (m, 5H), 6.48-6.42 (m, 1H), 5.03-4.70 (bs, 1H), 4.66-4.49 (m, 1H), 3.92-2.22 (m, 14H (signal overlaps with HDO, DMSO and satellites)), 2.01-0.73 (m, 29H).

Example 239: 1-(((S)-7-((R)-3-Cyclohexyl-2-methylpropanoyl)-10-hydroxy-7-azaspiro[4.5]decan-10-yl)methyl)-5-(morpholine-4-carbonyl)-4-phenylpyridin-2(1H)-one

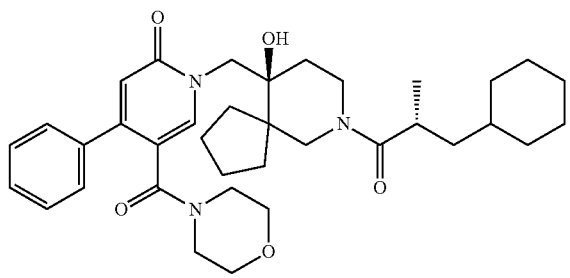 [SMILES: C[C@H](CC1CCCCC1)C(=O)N1CC[C@@](O)(Cn2cc(C(=O)N3CCOCC3)c(-c3ccccc3)cc2=O)C2(CCCC2)C1]

Prepared according to General Procedure 3 using 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (Example 211, Step 2) (33 mg, 61.7 µmol), morpholine (8 µL, 92.6 µmol), HATU (28.2 mg, 74.1 µmol) and DIPEA (33 µL, 0.185 mmol) in DCM (2 mL) to give the title compound (26 mg, 67%). LCMS (Method B): $R_T$=1.43 min, m/z=604 [M+H]$^+$. $^1$H NMR (500 MHz, DMSO-d$_6$): δ 7.86 (s, 1H), 7.51-7.45 (m, 3H), 7.45-7.38 (m, 2H), 6.49-6.42 (m, 1H), 5.08-4.77 (bs, 1H), 4.69 (d, J=13.5 Hz, 0.65H), 4.56 (d, J=13.5 Hz, 0.35H), 3.79-2.77 (m, 12H (signal overlaps with HDO)), 2.02-1.93 (m, 0.35H), 1.93-1.83 (m, 0.65H), 1.73-1.02 (m, 22H), 1.00-0.91 (m, 3H), 0.91-0.74 (m, 2H).

Example 240: 1-(((S)-7-((R)-3-Cyclohexyl-2-methylpropanoyl)-10-hydroxy-7-azaspiro[4.5]decan-10-yl)methyl)-5-(4-methylpiperazine-1-carbonyl)-4-phenylpyridin-2(1H)-one

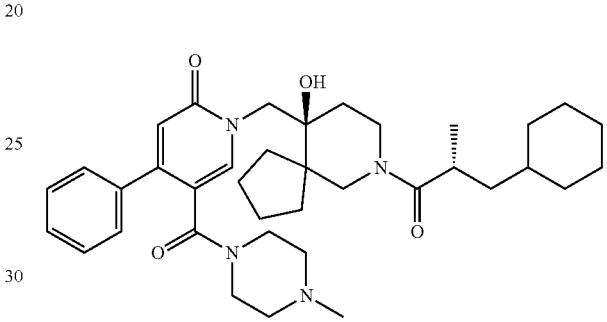

Prepared according to General Procedure 3 using 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylic acid (Example 211, Step 2) (33 mg, 61.7 µmol), 1-methylpiperazine (10 µL, 92.6 µmol), HATU (28.2 mg, 74.1 µmol) and DIPEA (33 µL, 0.185 mmol) in DCM (2 mL) to give the title compound (28 mg, 72%). LCMS (Method B): $R_T$=1.02 min, m/z=617 [M+H]$^+$. $^1$H NMR (500 MHz, DMSO-d$_6$): δ 7.83 (s, 1H), 7.50-7.36 (m, 5H), 6.49-6.43 (m, 1H), 5.06-4.79 (bs, 1H), 4.67 (d, J=13.5 Hz, 0.65H), 4.55 (d, J=13.5 Hz, 0.35H), 3.93-3.61 (m, 2H), 3.57-2.76 (m, 7H (signal overlaps with HDO)), 2.34-1.75 (m, 4H), 2.00 (s, 3H), 1.73-1.02 (m, 22H), 1.00-0.90 (m, 3H), 0.90-0.75 (m, 2H).

Example 241: 1-((1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid

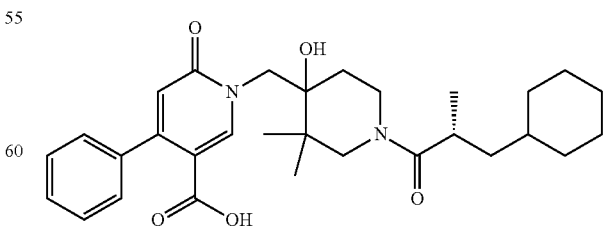

Acid 3 was puried by flash chromatography (0-15% MeOH in DCM) and freeze-dried to give the title compound as a pale yellow solid. LCMS (Method A): $R_T$=1.53 min, m/z=509 [M+H]⁺. ¹H NMR (500 MHz, DMSO-d₆): δ 12.49 (br s, 1H), 8.39 (s, 1H), 7.61-7.02 (m, 5H), 6.25-6.20 (m, 1H), 4.96 (s, 1H), 4.65-4.45 (m, 1H), 4.12-3.50 (m, 2H), 3.28-2.80 (m, 3H, overlapping solvent peak), 1.85-1.37 (m, 7H), 1.34-0.63 (m, 18H).

Example 242: 1-((7-((R)-3-Cyclohexyl-2-methylpropanoyl)-10-hydroxy-7-azaspiro[4.5]decan-10-yl)methyl)-4-methoxy-N,N-dimethyl-6-oxo-1,6-dihydropyridine-3-carboxamide

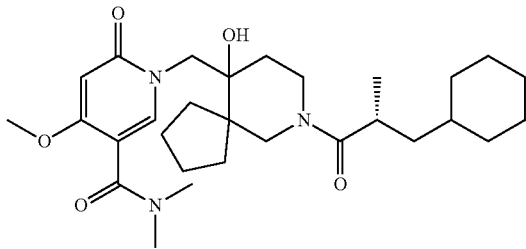 [SMILES: COc1cc(=O)n(CC2(O)CCN(C(=O)[C@H](C)CC3CCCCC3)CC23CCCC3)cc1C(=O)N(C)C]

Sodium methoxide (6.2 mg, 0.115 mmol) was added to a stirred solution of 4-chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide (Example 144) (20.0 mg, 0.0385 mmol) in DMF (1.0 mL) in a 4 mL vial. The vessel was sealed and heated to 60° C. After 1 h, the solvents were removed in vacuo and the remaining residue was partitioned between EtOAc and 1:1 brine/water. The resultant biphasic mixture was separated, extracted using EtOAc (×2), the combined organic phase was dried (phase separator), the solvents were removed in vacuo, and the remaining residue was purified by flash chromatography (0-15%, MeOH in DCM) to give the title compound (6.0 mg, 27%) as a white solid. LCMS (Method A): R$_T$=1.38 min, m/z=516 [M+H]. ¹H NMR (500 MHz, DMSO-d₆): δ 7.71-7.65 (m, 1H), 5.94-5.84 (m, 1H), 5.02-4.84 (m, 1H), 4.60-4.34 (m, 1H), 3.90-2.68 (m, 14H, overlapping solvent peak), 1.98-0.73 (m, 27H).

Example 243: 1-((7-(4,4-Difluoro-2-methylbutanoyl)-10-hydroxy-7-azaspiro[4.5]decan-10-yl)methyl)-N,N-dimethyl-6-oxo-4-phenyl-1,6-dihydropyridine-3-carboxamide

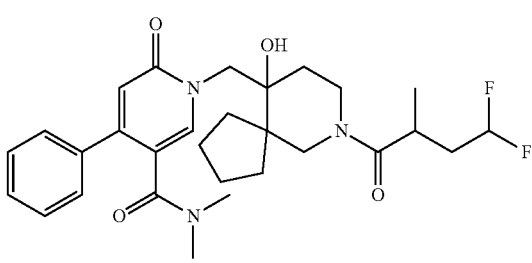 [SMILES: CC(CC(F)F)C(=O)N1CCC(O)(Cn2cc(C(=O)N(C)C)c(-c3ccccc3)cc2=O)C2(CCCC2)C1]

Prepared according to General Procedure 3 using Amine 8 (10 mg, 24.4 μmol), 4,4-difluoro-2-methylbutanoic acid (3.4 mg, 24.4 μmol), HATU (9.3 mg, 24.4 μmol), DIPEA (17 μL, 97.7 μmol) and DCM (0.5 mL) to give the title compound (11.9 mg, 89%) as a colourless solid after lyophilisation. LCMS (Method B): R$_T$=1.11 min, m/z=530 [M+H]⁺.

¹H NMR (500 MHz, DMSO-d₆): δ 7.84 (s, 0.4H), 7.84 (s, 0.6H), 7.54-7.29 (m, 5H), 6.46 (s, 0.4H), 6.45 (s, 0.6H), 6.12-5.87 (m, 1H), 4.98 (s, 0.4H), 4.93 (s, 0.6H), 4.73-4.58 (m, 1H), 4.57-4.49 (m, 0.4H), 4.01-3.05 (m, 3.6H (signals overlap with HDO)), 3.05-2.93 (m, 1H), 2.75 (s, 3H), 2.63 (s, 3H), 2.27-2.12 (m, 1H), 2.04-1.74 (m, 2H), 1.72-1.11 (m, 10H), 1.11-1.01 (m, 3H).

Example 244: 1-((7-(4,4-Difluoro-2,2-dimethylbutanoyl)-10-hydroxy-7-azaspiro[4.5]decan-10-yl)methyl)-N,N-dimethyl-6-oxo-4-phenyl-1,6-dihydropyridine-3-carboxamide

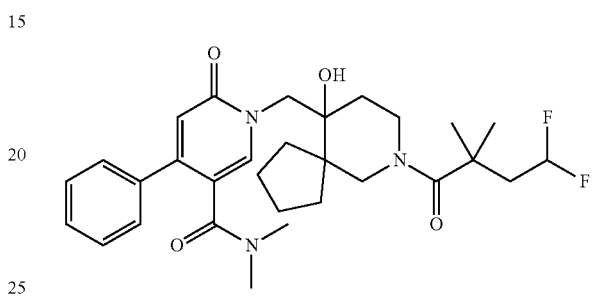

Prepared according to General Procedure 3 using Amine 8 (10 mg, 24.4 μmol), 4,4-difluoro-2,2-dimethylbutanoic acid (3.7 mg, 24.4 μmol), HATU (9.3 mg, 24.4 μmol), DIPEA (17 μL, 97.7 μmol) and DCM (0.5 mL) to give the title compound (10.3 mg, 75%) as a colourless solid after lyophilisation. LCMS (Method B): R$_T$=1.19 min, m/z=544 [M+H]⁺. ¹H NMR (500 MHz, DMSO-d₆): δ 7.84 (s, 1H), 7.48-7.41 (m, 3H), 7.41-7.34 (m, 2H), 6.45 (s, 1H), 6.10 (tt, J=56.7, 4.4 Hz, 1H), 4.91 (s, 1H), 4.64 (d, J=13.5 Hz, 1H), 3.87-3.76 (m, 1H), 3.68 (d, J=13.5 Hz, 1H), 3.54-3.41 (m, 2H), 3.38-3.19 (m, 1H (signal overlaps with HDO)), 2.75 (s, 3H), 2.63 (s, 3H), 2.12 (td, J=17.8, 4.5 Hz, 2H), 1.95-1.86 (m, 1H), 1.69-1.45 (m, 6H), 1.40-1.32 (m, 1H), 1.31-1.20 (m, 1H), 1.26 (s, 6H), 1.19-1.11 (m, 1H).

Example 245: 1-((10-Hydroxy-7-(4-(trifluoromethyl)thiazole-2-carbonyl)-7-azaspiro[4.5]decan-10-yl)methyl)-N,N-dimethyl-6-oxo-4-phenyl-1,6-dihydropyridine-3-carboxamide

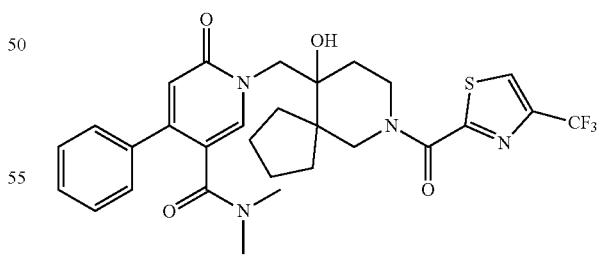

Prepared according to General Procedure 3 using Amine 8 (10 mg, 24.4 μmol), 4-(trifluoromethyl)thiazole-2-carboxylic acid (4.8 mg, 24.4 μmol), HATU (9.3 mg, 24.4 μmol), DIPEA (17 μL, 97.7 μmol) and DCM (0.5 mL) to give the title compound (13 mg, 88%) as a colourless solid after lyophilisation. LCMS (Method B): R$_T$=1.30 min, m/z=589 [M+H]⁺. ¹H NMR (500 MHz, DMSO-d₆): δ 8.78 (s, 0.6H), 8.76 (s, 0.4H), 7.85 (s, 1H), 7.52-7.27 (m, 5H), 6.48 (s, 0.6H), 6.46 (s, 0.4H), 5.07 (s, 0.6H), 5.04 (s, 0.4H), 4.72-4.64 (m, 1H), 4.51-4.45 (m, 0.4H), 4.26-4.19 (m, 0.6H), 4.11-4.04 (m, 0.6H), 4.01-3.92 (m, 1H), 3.77-3.69 (m, 1H), 3.67-3.61 (m, 0.4H), 3.60-3.50 (m, 1H), 2.75 (s, 3H), 2.63 (s, 3H), 2.01-1.89 (m, 1H), 1.78-1.35 (m, 8H), 1.28-1.20 (m, 1H).

Example 246: 1-((10-Hydroxy-7-(2-(trifluoromethyl)thiazole-4-carbonyl)-7-azaspiro[4.5]decan-10-yl)methyl)-N,N-dimethyl-6-oxo-4-phenyl-1,6-dihydropyridine-3-carboxamide

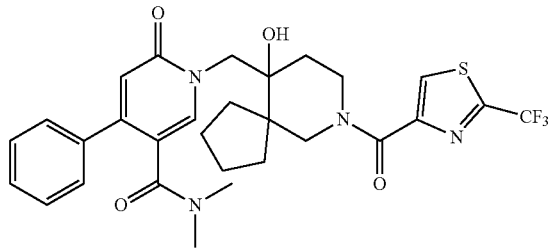 [SMILES: CN(C)C(=O)c1cn(CC2(O)CCN(C(=O)c3csc(C(F)(F)F)n3)CC23CCCC3)c(=O)cc1-c1ccccc1]

Prepared according to General Procedure 3 using Amine 8 (10 mg, 24.4 µmol), 2-(trifluoromethyl)thiazole-4-carboxylic acid (4.8 mg, 24.4 µmol), HATU (9.3 mg, 24.4 µmol), DIPEA (17 µL, 97.7 µmol) and DCM (0.5 mL) to give the title compound (12.7 mg, 85%) as a colourless solid after lyophilisation. LCMS (Method B): $R_T$=1.22 min, m/z=589 [M+H]$^+$. $^1$H NMR (500 MHz, DMSO-d$_6$): δ 8.55 (s, 0.5H), 8.50 (s, 0.5H), 7.84 (s, 1H), 7.55-7.27 (m, 5H), 6.48 (s, 0.5H), 6.43 (s, 0.5H), 5.02 (s, 0.5H), 5.01 (s, 0.5H), 4.72-4.61 (m, 1H), 3.99-3.92 (m, 0.5H), 3.77-3.67 (m, 1.5H), 3.64-3.41 (m, 3H), 2.75 (s, 3H), 2.69-2.57 (m, 3H), 2.01-1.87 (m, 1H), 1.79-1.44 (m, 6H), 1.41-1.17 (m, 3H).

Example 247: 1-(((S)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide

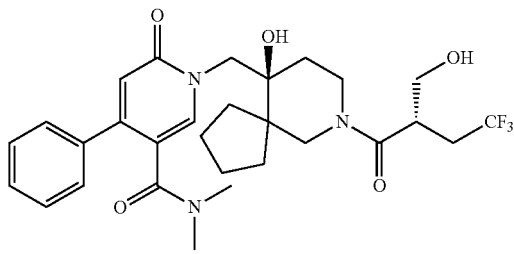

Step 1: Ethyl 1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylate Prepared according to General Procedure 3 using Amine 10 (66.8 mg, 0.163 mmol), Acid 14 (28.0 mg, 0.163 mmol), HATU (74.2 mg, 0.195 mmol), DIPEA (114 µL, 0.651 mmol) and DCM (2.0 mL) to give the title compound (69.8 mg, 76%) as a white solid. LCMS (Method A): $R_T$=1.43 min, m/z=565 [M+H]$^+$.

Step 2: 1-(((S)-10-Hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylic acid A solution of ethyl 1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylate (69.8 mg, 0.124 mmol) in 1 M NaOH$_{(aq)}$ (0.618 mL, 0.618 mmol) and 1,4-dioxane (1.5 mL) was stirred at 50° C. for 2 h. The reaction mixture was allowed to cool to RT and the pH was adjusted to ~pH 2 by the addition of 1 M HCl$_{(aq)}$. The resulting mixture was extracted with DCM (×3) using a Biotage phase separator and the combined organic phases were concentrated in vacuo to give the crude title compound (70.2 mg, >100%) as a white solid. LCMS (Method A): $R_T$=1.11 min, m/z=537 [M+H]$^+$.

Step 3: 1-(((S)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide Prepared according to General Procedure 3 using 1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylic acid (30.0 mg, 0.0559 mmol), 2 M dimethylamine in THF (55.9 µL, 0.112 mmol), HATU (25.5 mg, 0.0671 mmol), DIPEA (39.1 µL, 0.224 mmol) and DCM (1.5 mL) to give the title compound (19.9 mg, 63%) as a white solid after lyophilisation. LCMS (Method A): $R_T$=1.12 min, m/z=564 [M+H]$^+$. $^1$H NMR (500 MHz, DMSO-d$_6$): δ 7.86-7.81 (m, 1H), 7.48-7.35 (m, 5H), 6.48-6.43 (m, 1H), 5.02-4.87 (m, 2H), 4.69-4.44 (m, 1H), 4.10-3.60 (m, 2H), 3.59-2.94 (m, 5H, overlapping solvent peak), 2.81-2.57 (m, 7H), 2.47-2.32 (m, 1H), 2.05-1.06 (m, 11H).

Example 248: 1-(((S)-10-Hydroxy-7-((S)-4,4,4-trifluoro-2-(hydroxymethyl)butanoyl)-7-azaspiro[4.5]decan-10-yl)methyl)-5-(morpholine-4-carbonyl)-4-phenylpyridin-2(1H)-one

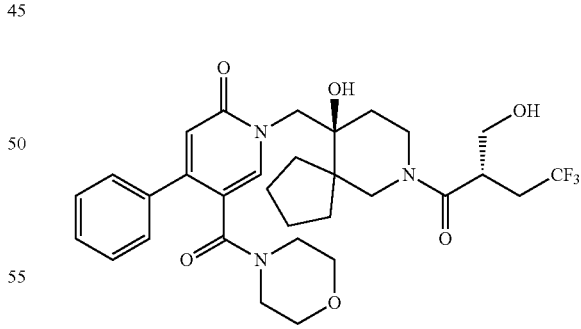

Prepared according to General Procedure 3 using 1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylic acid (10.0 mg, 18.6 µmol), morpholine (3.3 µL, 37.3 µmol), HATU (8.5 mg, 22.4 µmol), DIPEA (13.0 µL, 74.6 µmol) and DCM (1.0 mL) to give the title compound (8.9 mg, 79%) as a white solid after lyophilisation. LCMS (Method A): $R_T$=1.10 min, m/z=606 [M+H]$^+$. $^1$H NMR (500 MHz, DMSO-d$_6$): δ 7.85 (s, 1H), 7.53-7.35 (m, 5H), 6.49-6.42 (m, 1H), 5.10-4.75 (m, 2H), 4.72-4.42 (m, 1H), 4.10-2.30 (m, 17H, overlapping solvent peak), 2.06-1.06 (m, 11H).

Example 249: 1-(((S)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one

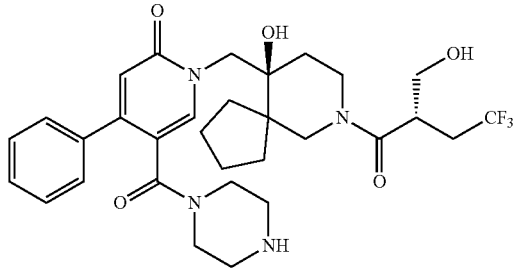 [SMILES: O=C(c1cn(C[C@]2(O)CCN(C(=O)[C@H](CO)CC(F)(F)F)CC23CCCC3)c(=O)cc1-c1ccccc1)N1CCNCC1]

Step 1: tert-Butyl 4-(1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carbonyl)piperazine-1-carboxylate Prepared according to General Procedure 3 using 1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carboxylic acid (30.0 mg, 0.0559 mmol), tert-butyl piperazine-1-carboxylate (10.4 mg, 0.0559 mmol), HATU (25.5 mg, 0.0671 mmol), DIPEA (39.1 µL, 0.224 mmol) and DCM (1.5 mL) to give the title compound (27.5 mg, 70%) as a white solid. LCMS (Method A): $R_T$=1.41 min, m/z=705 [M+H]$^+$.

Step 2: 1-(((S)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one A solution of tert-butyl 4-(1-(((S)-10-hydroxy-7-((S)-4,4,4-trifluoro-2-(hydroxymethyl)butanoyl)-7-azaspiro[4.5]decan-10-yl)methyl)-6-oxo-4-phenyl-1,6-dihydropyridine-3-carbonyl)piperazine-1-carboxylate (27.5 mg, 0.0390 mmol) in TFA (0.5 mL) and DCM (1.0 mL) was stirred for 1 h before the reaction mixture was purified using a Biotage SCX-2 5 g cartridge (pre-equilibrated with and then washed using 1:1 DCM/MeOH before being eluted with 1:1 DCM/7 M in NH$_3$ in MeOH). The basic eluents were concentrated in vacuo and the remaining residue was purified by flash chromatography (0-10% MeOH in DCM) and freeze-dried to give the title compound (17.0 mg, 72%) as a white solid. LCMS (Method A): $R_T$=0.72 min, m/z=605 [M+H]$^+$. $^1$H NMR (500 MHz, DMSO-d$_6$): δ 7.82 (s, 1H), 7.51-7.33 (m, 5H), 6.48-6.41 (m, 1H), 5.09-4.78 (m, 2H), 4.71-4.43 (m, 1H), 4.10-1.08 (m, 29H, overlapping solvent peak).

Example 250: 1-(((S)-10-Hydroxy-7-((R)-4,4,4-trifluoro-2-methylbutanoyl)-7-azaspiro[4.5]decan-10-yl)methyl)-5-(morpholine-4-carbonyl)-4-phenylpyridin-2(1H)-one

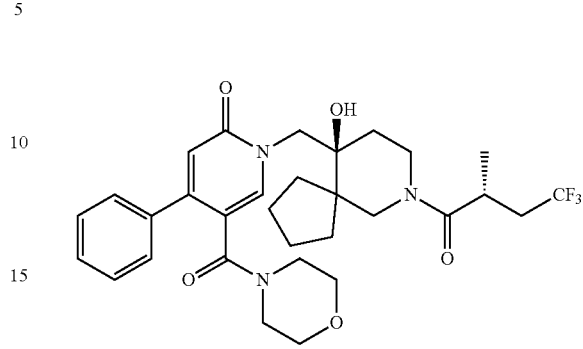

Prepared according to General Procedure 3 using 1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylic acid (Example 216, Step 2) (29.0 mg, 55.7 µmol), morpholine (5.4 µL, 61.3 µmol), HATU (25.4 mg, 66.9 µmol), DIPEA (29.2 µL, 167 µmol) and DCM (1.5 mL) to give the title compound (25.0 mg, 76%) as a white solid after lyophilisation. LCMS (Method A): $R_T$=1.31 min, m/z=590 [M+H]$^+$. $^1$H NMR (500 MHz, DMSO-d$_6$): δ 7.85 (s, 1H), 7.53-7.35 (m, 5H), 6.50-6.43 (m, 1H), 5.12-4.73 (m, 1H), 4.70-4.46 (m, 1H), 4.04-2.64 (m, 14H, overlapping solvent peak), 2.32-2.19 (m, 1H), 2.06-1.83 (m, 1H), 1.80-0.78 (m, 13H).

Example 251: 1-(((S)-10-Hydroxy-7-((R)-4,4,4-trifluoro-2-methylbutanoyl)-7-azaspiro[4.5]decan-10-yl)methyl)-5-(4-methylpiperazine-1-carbonyl)-4-phenylpyridin-2(1H)-one

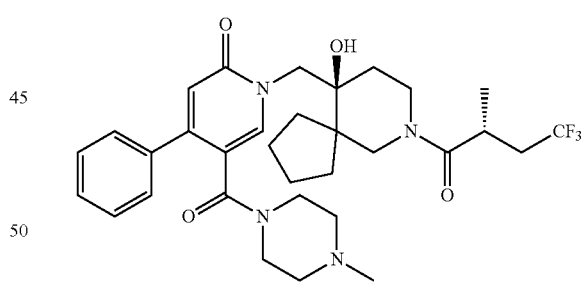

Prepared according to General Procedure 3 using 1-(((S)-10-hydroxy-7-((R)-4,4,4-trifluoro-2-methylbutanoyl)-7-azaspiro[4.5]decan-10-yl)methyl)-6-oxo-4-phenyl-1,6-dihydropyridine-3-carboxylic acid (Example 216, Step 2) (29.0 mg, 55.7 µmol), 1-methylpiperazine (6.8 µL, 61.3 µmol), HATU (25.4 mg, 66.9 µmol), DIPEA (29.2 µL, 167 µmol) and DCM (1.5 mL) to give the title compound (21.6 mg, 64%) as a white solid after lyophilisation. LCMS (Method A): $R_T$=0.87 min, m/z=603 [M+H]$^+$. $^1$H NMR (500 MHz, DMSO-d$_6$): δ 7.83 (s, 1H), 7.51-7.33 (m, 5H), 6.49-6.42 (m, 1H), 5.11-4.77 (m, 1H), 4.70-4.43 (m, 1H), 4.06-2.64 (m, 10H, overlapping solvent peak), 2.34-0.74 (m, 22H).

Example 252: Ethyl 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate

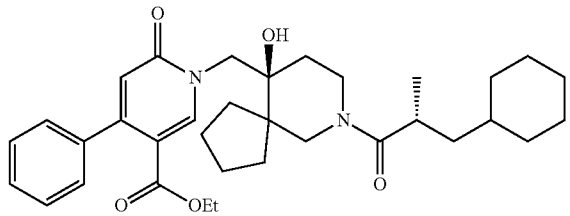 [SMILES: CCOC(=O)c1cn(C[C@]2(O)CCN(C(=O)[C@H](C)CC3CCCCC3)CC23CCCC3)c(=O)cc1-c1ccccc1]

Ethyl 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate (Example 211, Step 1) was purified by flash chromatography using an 11 g KP-NH column (0-50% EtOAc in cyclohexane) and freeze-dried to give the title compound as a white solid. LCMS (Method A): $R_T$=1.93 min, m/z=563 [M+H]$^+$. $^1$H NMR (500 MHz, DMSO-d$_6$): δ 8.46-8.39 (m, 1H), 7.46-7.35 (m, 3H), 7.32-7.21 (m, 2H), 6.33-6.25 (m, 1H), 5.00-4.89 (m, 1H), 4.83-4.64 (m, 1H), 4.04-3.94 (m, 2H), 3.92-3.59 (m, 2H), 3.52-3.08 (m, 2H, overlapping solvent peak), 2.94-2.80 (m, 1H), 2.05-1.83 (m, 1H), 1.74-0.74 (m, 29H).

Example 253: 1-(((S)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid

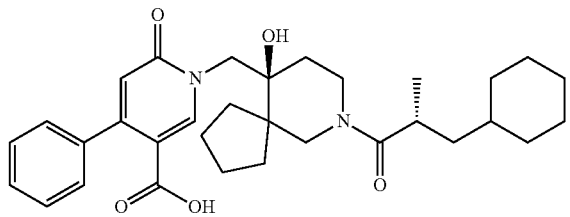 [SMILES: C[C@H](CC1CCCCC1)C(=O)N1CC[C@@](O)(Cn2cc(C(=O)O)c(-c3ccccc3)cc2=O)C2(CCCC2)C1]

1-(((S)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid (Example 211, Step 2) was purified by flash chromatography (0-10% MeOH in DCM) and freeze-dried to give the title compound as a white solid. LCMS (Method A): $R_T$=1.61 min, m/z=535 [M+H]$^+$. $^1$H NMR (500 MHz, DMSO-d$_6$): δ 12.47 (br s, 1H), 8.43 (s, 1H), 7.54-7.12 (m, 5H), 6.28-6.20 (m, 1H), 5.03-4.91 (m, 1H), 4.80-4.60 (m, 1H), 4.16-3.96 (m, 1H), 3.92-3.58 (m, 2H), 3.54-3.30 (m, 1H, overlapping solvent), 2.94-2.80 (m, 1H), 2.03-1.83 (m, 1H), 1.80-0.65 (m, 26H).

USP19 Activity Assay

USP19 activity was monitored in a fluorescence polarisation (FP) homogeneous assay using the isopeptide Ubiquitin-Lys-TAMRA substrate (either AUB-101, Almac Sciences Scotland Limited, or U-558, Boston Biochem, both of which gave identical results). Full-length USP19 was purchased from Boston Biochem (E-576). Unless otherwise stated, all other reagents were purchased from Sigma. Enzymatic reactions were conducted in black flat bottom polystyrene 384-well plates (Nunc) and 30 μL total volume. USP19 (2.5 nM, 10 μL) was incubated in assay buffer (50 mM HEPES (pH 7.4), 150 mM NaCl, 5 mM DTT, 0.05% BSA (w/v), 0.05% CHAPS) in the presence or absence of inhibitor (10 μL). Inhibitors were stored as 10 mM DMSO stocks in an inert environment (low humidity, dark, low oxygen, room temperature) using the Storage Pod System and serial dilutions were prepared in buffer just prior to the assay (from 200 μM to 2 pM, 8-18 data point curve). Following incubation at RT for 30 min, the enzymatic reactions were initiated by dispensing the Ub substrate (500 nM, 10 μL). FP was measured every 15 min over a period of 90 min (within the linear range of the assay) using a Synergy 4 plate reader (BioTek) exciting at 530 nm and measuring the amount of parallel and perpendicular light at 575 nm. The FP signal was subsequently normalised to the no compound control. Data were plotted and fitted, and the concentrations resulting in 50% inhibition (IC$_{50}$) were calculated using the non-linear regression curve fitting model using GraphPad (Prism). IC$_{50}$ values for the inhibitors of the invention are compiled in Table 1 and represent the average of at least two duplicate experiments.

The invention claimed is:

1. A compound of formula (I):

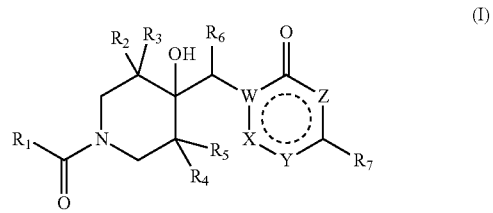

including a pharmaceutically acceptable salt, tautomer, stereoisomer or N-oxide derivative thereof, wherein:

$R_1$ is an optionally substituted alkyl, alkenyl, alkynyl, cycloalkyl, alkylcycloalkyl, heterocycloalkyl, alkylheterocycloalkyl, aryl, arylalkyl, heteroaryl, or heteroarylalkyl group;

$R_2$ is H or an optionally substituted alkyl group, $R_3$ is H or an optionally substituted alkyl group, $R_4$ is H or an optionally substituted alkyl group, $R_5$ is H or an optionally substituted alkyl group, $R_2$ and $R_4$ may be joined to one another to form an optionally substituted cycloalkyl or heterocycloalkyl that includes the carbon to which they are attached, $R_4$ and $R_5$ may be joined to one another to form an optionally substituted cycloalkyl or heterocycloalkyl that includes the carbon to which they are attached;

$R_6$ is H or an optionally substituted alkyl group;

W is C or N;

X is N or CR$_8$, wherein R$_8$ is H or optionally substituted C1-C6 alkyl;

Y is N or CR$_9$;

Z is CH or NH;

wherein R$_9$ is H or optionally substituted alkyl, amido, amino, aryl, heteroaryl, cycloalkyl, cycloheteroalkyl, halo, carbonyl, ester, aminoalkyl, or cyano;

$R_7$ is hydrogen, halo, or an optionally substituted alkyl, alkenyl, alkynyl, amino, aryl, cycloalkyl, cycloalkenyl, alkoxy, aryloxy, heteroaryl or heterocycloalkyl group;

or the compound

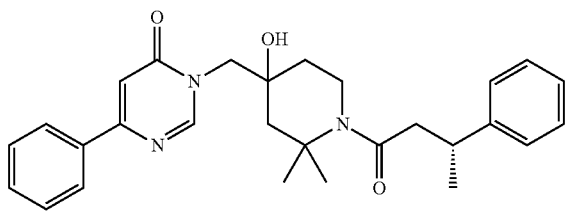 [SMILES: C[C@H](CC(=O)N1CCC(O)(Cn2cnc(-c3ccccc3)cc2=O)CC1(C)C)c1ccccc1]

or a pharmaceutically acceptable salt, tautomer, stereoisomer or N-oxide derivative thereof.

2. The compound of claim 1, wherein $R_1$ is optionally substituted C1-C6 alkyl, optionally substituted C4-C10 alkylcycloalkyl, optionally substituted C7-C10 arylalkyl, optionally substituted C3-C6 cycloalkyl, or optionally substituted C3-C6 heteroaryl,
wherein the optional substituent is selected from C1-C6 alkyl, C2-C6 alkenyl, hydroxymethyl, methoxymethyl, benzyloxy methyl, phenyl, C3-C6 cycloalkyl, $CF_3$, $CHF_2$, OH, or halo.

3. The compound of claim 1, wherein $R_1$ is optionally substituted cyclohexylalkane; or optionally substituted alkylbenzene; or optionally substituted 3,3,3-trifluoropropane,
wherein the optional substituent is selected from C1-C6 alkyl, C2-C6 alkenyl, hydroxymethyl, methoxymethyl, OH, or halo.

4. The compound of claim 1, wherein $R_1$ is substituted and the substituent is C1-C6 alkyl.

5. The compound of claim 1, wherein $R_7$ is optionally substituted C6-C10 aryl, C1-C12 heteroaryl, C1-C10 alkyl, C2-C10 alkenyl, C3-C10 cycloalkyl, amino, C1-C3 alkoxy, or halo,
wherein the optional substituent is selected from C1-C6 alkyl, hydroxysubstituted C1-C6 alkyl, C3-C6 cycloalkyl, C1-C6 heterocycloalkyl, C1-C6 alkoxy, halo-substituted C1-C6 alkoxy, amido, cyano or halo.

6. The compound of claim 5, wherein $R_7$ is optionally substituted phenyl, naphthalenyl, indazole, pyrimidine, thiophene, or pyrazole,
wherein the optional substituent is selected from C1-C6 alkyl, hydroxysubstituted C1-C6 alkyl, C3-C6 cycloalkyl or C1-C6 heterocycloalkyl, C1-C6 alkoxy, halo-substituted C1-C6 alkoxy, C1-C6 alkylamine, amido, cyano or halo.

7. The compound of claim 1, wherein $R_2$, $R_3$, $R_4$, $R_5$ are independently selected from H and C1-C6 alkyl.

8. The compound of claim 7, wherein $R_2$ and $R_3$ are H, and $R_4$ and $R_5$ are methyl.

9. The compound of claim 1, wherein $R_4$ and $R_5$ are joined to one another to form an optionally substituted C3-C6 cycloalkyl or C3-C6 heterocycloalkyl that includes the carbon to which they are attached and $R_2$ and $R_3$ are independently selected from H and C1-C6 alkyl.

10. The compound of claim 9, wherein $R_2$ and $R_3$ are H and $R_4$ and $R_5$ are joined to one another to form a C3-C6 cycloalkyl that includes the carbon to which they are attached.

11. The compound of claim 1, wherein $R_6$ is H or C1-C6 alkyl.

12. The compound of claim 1, wherein $R_2$ and $R_4$ are joined to one another to form a C5 cycloalkyl that includes the carbons to which they are attached, and wherein $R_3$, $R_5$ and $R_6$ are independently H or C1-C6 alkyl.

13. The compound of claim 1, wherein W is N and X is $CR_8$, wherein $R_8$ is H or methyl.

14. The compound of claim 1, wherein Y is N or $CR_9$, wherein $R_9$ is H, C1-C6 alkyl, NR'R", C(O)NR'R", cyano, carboxyl, halo, C1-C6 alkylamine, C3-C6 alkylester, optionally substituted C6-C10 aryl, or optionally substituted C2-C6 heteroaryl, wherein the one or more heteroatoms are selected from N and O, and the one or more optional substituents of the aryl or heteroaryl are selected from C1-C6 alkyl, C1-C6 alkylamine, amido, and cyano,
wherein R' and R" are independently selected from H, C1-C6 alkyl optionally substituted with OH, C3-C7 cycloalkyl, C1-C7 heterocycloalkyl, C4-C7 alkylcycloalkyl, C3-C7 alkylheterocycloalkyl, benzyl, phenyl, and methoxy, or wherein R' and R" are joined to one another to form a C2-C7 heterocycle that includes the N to which they are attached, wherein the heterocycle is optionally hydroxyl-substituted, oxo-substituted, methyl-substituted, CH2OH-substituted, or acetyl-substituted.

15. The compound of claim 1, wherein Y is N or $CR_9$, wherein $R_9$ is phenyl optionally substituted with amido, cyano or methyl amine; pyridine; oxazole; pyrazole; carboxyl; C(O)NR'R"; or NR'R";
wherein R' and R" are independently selected from H, C1-C6 alkyl, C3-C7 cycloalkyl, C3-C7 heterocycloalkyl wherein the heteroatom is N or O, or wherein R' and R" are joined to one another to form a C2-C7 heterocycloalkyl that includes the N to which they are attached, wherein the heterocycloalkyl is optionally hydroxyl-substituted, oxo-substituted, methyl-substituted, CH2OH-substituted, or acetyl-substituted.

16. The compound of claim 1, wherein
$R_1$ is selected from optionally substituted ethylcyclohexane, optionally substituted ethylbenzene, and optionally substituted 3,3,3-trifluoropropane, wherein the optional substituent is one or more of methyl, ethyl, propyl, propenyl, hydroxymethyl and methoxymethyl,
$R_2$ and $R_3$ are independently selected from H, methyl,
$R_4$ and $R_5$ are independently selected from H, methyl, or are joined to one another to form a C3-C6 cycloalkyl or heterocycloalkyl that includes the carbon to which they are attached,
$R_6$ is H or methyl,
$R_7$ is selected from optionally substituted phenyl, indazole, thiophene, or pyrazole, wherein the optional substituent is selected from C1-C6 alkyl, hydroxysubstituted C1-C6 alkyl, C3-C6 cycloalkyl, C1-C6 heterocycloalkyl, C1-C6 alkoxy, halo-substituted C1-C6 alkoxy, C1-C6 alkylamine, amido, cyano or halo,
W is N or C
X is CH or N
Z is CH or NH
Y is N or $CR_9$, wherein $R_9$ is phenyl optionally substituted with amido, cyano or methyl amine; pyridine; oxazole; pyrazole; C(O)NR'R"; or NR'R"
wherein R' and R" are independently selected from H, C1-C6 alkyl, C3-C7 cycloalkyl, C3-C7 heterocycloalkyl wherein the heteroatom is N or O, or wherein R' and R" are joined to one another to form a C2-C7 heterocycloalkyl that includes the N to which they are attached, wherein the heterocycloalkyl is optionally hydroxyl-substituted, oxo-substituted, methyl-substituted, CH2OH-substituted, or acetyl-substituted.

17. The compound of claim 16, wherein Y is $CR_9$, wherein $R_9$ is C(O)NR'R" and wherein R' and R" are joined to one another to form an optionally substituted pyrrolidine, piperidine, piperazine or morpholine that includes the N to which they are attached, wherein the piperidine, pyrrolidine, piperazine or morpholine is optionally hydroxyl-substituted, oxo-substituted, methyl-substituted, CH2OH-substituted, or acetyl-substituted.

18. The compound of claim 1 selected from the group consisting of:
(R)-5-Bromo-1-((4-hydroxy-1-(3-phenylbutanoyl)piperidin-4-yl)methyl)-4-phenylpyridin-2(1H)-one;
6-(2-Fluorophenyl)-3-((4-hydroxy-1-(3-phenylpropanoyl)piperidin-4-yl)methyl)pyrimidin-4(3H)-one;
3-((1-(3-Cyclobutylpropanoyl)-4-hydroxypiperidin-4-yl)methyl)-6-(2-fluorophenyl)pyrimidin-4(3H)-one;
3-((1-(3-Cyclopentylpropanoyl)-4-hydroxypiperidin-4-yl)methyl)-6-(2-fluorophenyl)pyrimidin-4(3H)-one;

(R,S)-6-(2-Fluorophenyl)-3-((4-hydroxy-1-(2-methyl-3-phenylpropanoyl)piperidin-4-yl)methyl)pyrimidin-4(3H)-one;

(R)—N-(3-(1-((4-Hydroxy-1-(3-phenylbutanoyl)piperidin-4-yl)methyl)-6-oxo-4-phenyl-1,6-dihydropyridin-3-yl)phenyl)acetamide;

(R)-3-(1-((4-Hydroxy-1-(3-phenylbutanoyl)piperidin-4-yl)methyl)6-oxo-4-phenyl-1,6-dihydropyridin-3-yl)benzamide;

(R)-5-(Furan-2-yl)-1-((4-hydroxy-1-(3-phenylbutanoyl)piperidin-4-yl)methyl)-4-phenylpyridin-2(1H)-one;

(R)-1-((4-Hydroxy-1-(3-phenylbutanoyl)piperidin-4-yl)methyl)-5-(1-methyl-1H-pyrazol-5-yl)-4-phenylpyridin-2(1H)-one;

(R)-4-Chloro-1-((4-hydroxy-1(3-phenylbutanoyl)piperidin-4-yl)methyl)-5-phenylpyridin-2(1H)-one;

(R)-4-(Dimethylamino)-1-((4-hydroxy-1-(3-phenylbutanoyl)piperidin-4-yl)methyl)-5-phenylpyridin-2(1H)-one;

(R)-1-((4-Hydroxy-1-(3-phenylbutanoyl)piperidin-4-yl)methyl)-5-phenyl-4-(prop-1-en-2-yl)pyridine-2(1H)-one;

(R)-Ethyl 1-((4-hydroxy-1-(3-phenylbutanoyl)piperidin-4-yl)methyl)-6-oxo-4-phenyl-1,6-dihydropyridine-3-carboxylate;

(R,S)-4-(2-Fluorophenyl)-1-((4-hydroxy-1-(2-methyl-1,2,3,4-tetrahydronaphthalene-2-carbonyl)piperidin-4-yl)methyl)-N-isopropyl-N-methyl-6-oxo-1,6-dihydropyridine-3-carboxamide;

(R,S)-1-((1-(3-Cyclobutyl-2-methylpropanoyl)-4-hydroxypiperidin-4-yl)methyl)-4-phenyl-5-(piperidine-1-carbonyl)pyridin-2(1H)-one;

(R)-3-((4-Hydroxy-1-(3-phenylbutanoyl)piperidin-4-yl)methyl)-6-(1-methyl-1H-indazol-7-yl)pyrimidin-4(3H)-one;

(R)-3-((4-Hydroxy-1-(3-phenylbutanoyl)piperidin-4-yl)methyl)-6-(2-methoxyphenyl)pyrimidin-4(3H)-one;

(R)-3-((4-Hydroxy-1-(3-phenylbutanoyl)piperidin-4-yl)methyl)-2-methyl-6-phenylpyrimidin-4(3H)-one;

(R)-2-((4-Hydroxy-1-(3-phenylbutanoyl)piperidin-4-yl)methyl)-5,6-diphenylpyridazin-3(2H)-one;

(R)-3-((4-Hydroxy-1-(3-phenylbutanoyl)piperidin-4-yl)methyl)-6-(naphthalen-1-yl)pyrimidin-4(3H)-one;

(R)-6-(3-(1,3-Dioxolan-2-yl)phenyl)-3-((4-hydroxy-1-(3-phenylbutanoyl)piperidin-4-yl)methyl)pyrimidin-4(3H)-one;

(R)-3-((4-Hydroxy-1-(3-phenylbutanoyl)piperidin-4-yl)methyl)-6-(thiophen-3-yl)pyrimidin-4(3H)-one;

4-(2-Fluorophenyl)-1-((4-hydroxy-1-(1-methylcyclopentane-1-carbonyl)piperidin-4-yl)methyl)-N-isopropyl-N-methyl-6-oxo-1,6-dihydropyridine-3-carboxamide;

3-((1-(1-Ethylcyclohexane-1-carbonyl)-4-hydroxypiperidin-4-yl)methyl)-6-(2-fluorophenyl)pyrimidin-4(3H)-one;

3-((1-(2-(Cyclohexylmethyl)-3-methylbutanoyl)-4-hydroxy-3,3-dimethylpiperidin-4-yl)methyl)-6-(2-fluorophenyl)pyrimidin-4(3H)-one;

(R)-6-(Furan-2-yl)-3-((4-hydroxy-1-(3-phenylbutanoyl)piperidin-4-yl)methyl)pyrimidin-4(3H)-one;

(R)-1-((4-Hydroxy-1-(3-phenylbutanoyl)piperidin-4-yl)methyl)-4-phenylpyridin-2(1H)-one;

(R)-6-(Cyclohex-1-en-1-yl)-3-((4-hydroxy-1-(3-phenylbutanoyl)piperidin-4-yl)methyl)pyrimidin-4(3H)-one;

(R)-3-((4-Hydroxy-1-(3-phenylbutanoyl)piperidin-4-yl)methyl)-6-(prop-1-en-2-yl)pyrimidin-4(3H)-one;

(R)-3-((4-Hydroxy-1-(3-phenylbutanoyl)piperidin-4-yl)methyl)-6-(2-(trifluoromethoxy)phenyl)pyrimidin-4(3H)-one;

3-(((1R,5S)-3-((R)-3-Cyclohexyl-2-methylpropanoyl)-8-hydroxy-3-azabicyclo[3.2.1]octan-8-yl)methyl)-6-(2-fluorophenyl)pyrimidin-4(3H)-one;

(R)-6-(2-Fluorophenyl)-3-((4-hydroxy-1-(3-phenylbutanoyl)piperidin-4-yl)methyl)pyrimidin-4(3H)-one;

(R)-5-((4-Hydroxy-1-(3-phenylbutanoyl)piperidin-4-yl)methyl)-2-phenylpyrimidin-4(3H)-one;

3-((4-Hydroxy-1-(3-phenylpropanoyl)piperidin-4-yl)methyl)-2-methyl-6-phenylpyrimidin-4(3H)-one;

(R)-3-((4-Hydroxy-1-(3-phenylbutanoyl)piperidin-4-yl)methyl)-6-(isobutylamino)pyrimidin-4(3H)-one;

(R)-1-((1-(3-Cyclohexyl-2-methylpropanoyl)-4-hydroxypiperidin-4-yl)methyl)-4-phenyl-5-(piperidine-1-carbonyl)pyridin-2(1H)-one;

(R)-2-((4-Hydroxy-1-(3-phenylbutanoyl)piperidin-4-yl)methyl)-5-phenylpyridazin-3(2H)-one;

(R)-4-(2-Cyanophenyl)-1-((4-hydroxy-1-(3-phenylbutanoyl)piperidin-4-yl)methyl)-N-isopropyl-N-methyl-6-oxo-1,6-dihydropyridine-3-carboxamide;

(R)-3-((1-(3-Cyclohexyl-2-methylpropanoyl)-4-hydroxypiperidin-4-yl)methyl)-6-(2-fluorophenyl)pyrimidin-4(3H)-one;

3-((1-(2-(Cyclohexylmethyl)butanoyl)-4-hydroxypiperidin-4-yl)methyl)-6-(2-fluorophenyl)pyrimidin-4(3H)-one;

rac-6-(2-Fluorophenyl)-3-((4-hydroxy-1-(cis-2-phenylcyclopropanecarbonyl)piperidin-4-yl)methyl)pyrimidin-4(3H)-one;

6-(2-Fluorophenyl)-3-((4-hydroxy-1-(1-methylcyclohexanecarbonyl)piperidin-4-yl)methyl)pyrimidin-4(3H)-one;

3-((S)-1-(1-((R)-3-Cyclohexyl-2-methylpropanoyl)-4-hydroxypiperidin-4-yl)propyl)-6-phenylpyrimidin-4(3H)-one;

3-((R)-1-(1-((R)-3-Cyclohexyl-2-methylpropanoyl)-4-hydroxypiperidin-4-yl)propyl)-6-phenylpyrimidin-4(3H)-one;

(R,S)-3-((1-(3-Cyclohexyl-2-hydroxypropanoyl)-4-hydroxypiperidin-4-yl)methyl)-6-(2-fluorophenyl)pyrimidin-4(3H)-one;

(R)-1-((4-Hydroxy-1-(3-phenylbutanoyl)piperidin-4-yl)methyl)-6-oxo-4-phenyl-1,6-dihydropyridine-3-carbaldehyde;

(R)-5-((Dimethylamino)methyl)-1-((4-hydroxy-1-(3-phenylbutanoyl)piperidin-4-yl)methyl)-4-phenylpyridin-2(1H)-one;

3-((R)-1-(4-Hydroxy-1-((R)-3-phenylbutanoyl)piperidin-4-yl)ethyl)-6-phenylpyrimidin-4(3H)-one;

3-((S)-1-(4-Hydroxy-1-((R)-3-phenylbutanoyl)piperidin-4-yl)ethyl)-6-phenylpyrimidin-4(3H)-one;

(R)-6-(2-Fluorophenyl)-3-((4-hydroxy-1-(4,4,4-trifluoro-3-phenylbutanoyl)piperidin-4-yl)methyl)pyrimidin-4(3H)-one;

(R,S)-3-((1-(3-Cyclohexyl-2-fluoropropanoyl)-4-hydroxypiperidin-4-yl)methyl)-6-(2-fluorophenyl)pyrimidin-4(3H)-one;

3-(((R)-1-((R)-3-Cyclohexyl-2-methylpropanoyl)-4-hydroxy-3,3-dimethylpiperidin-4-yl)methyl)-6-phenylpyrimidin-4(3H)-one;

3-(((S)-1-((R)-3-Cyclohexyl-2-methylpropanoyl)-4-hydroxy-3,3-dimethylpiperidin-4-yl)methyl)-6-phenylpyrimidin-4(3H)-one;

3-(((R)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one;
3-(((S)-6-((R)-3-Cyclohexyl-2-methylpropanoyl)-9-hydroxy-6-azaspiro[3.5]nonan-9-yl)methyl)-6-(2-fluorophenyl)pyrimidin-4(3H)-one;
(R)-5-(3-(Aminomethyl)phenyl)-1-((1-(3-cyclohexyl-2-methylpropanoyl)-4-hydroxypiperidin-4-yl)methyl)-4-(2-fluorophenyl)pyridin-2(1H)-one;
3-(((S)-4-Hydroxy-3,3-dimethyl-1-((R)-3-phenylbutanoyl)piperidin-4-yl)methyl)-6-phenylpyrimidin-4(3H)-one;
3-(((R)-4-Hydroxy-3,3-dimethyl-1-((R)-3-phenylbutanoyl)piperidin-4-yl)methyl)-6-phenylpyrimidin-4(3H)-one;
(R)-6-(4-Fluorophenoxy)-3-((4-hydroxy-1-(3-phenylbutanoyl)piperidin-4-yl)methyl)pyrimidin-4(3H)-one;
(R)-1-((4-Hydroxy-1-(3-phenylbutanoyl)piperidin-4-yl)methyl)-5-(2-oxopyrrolidin-1-yl)-4-phenylpyridin-2(1H)-one;
6-(2-Fluorophenyl)-3-((4-hydroxy-1-(1-methyl-4-methylenecyclohexanecarbonyl)piperidin-4-yl)methyl)pyrimidin-4(3H)-one;
(R,S)-3-((1-(3-Cyclobutyl-2-methylpropanoyl)-4-hydroxypiperidin-4-yl)methyl)-6-(2-fluorophenyl)pyrimidin-4(3H)-one;
(R,S)-3-((1-(3-Cycloheptyl-2-methylpropanoyl)-4-hydroxypiperidin-4-yl)methyl)-6-(2-fluorophenyl)pyrimidin-4(3H)-one;
3-((1-(3-Cyclobutyl-2,2-dimethylpropanoyl)-4-hydroxypiperidin-4-yl)methyl)-6-(2-fluorophenyl)pyrimidin-4(3H)-one;
6-(2-Fluorophenyl)-3-(((1R,5S)-8-hydroxy-3-((R)-3-phenylbutanoyl)-3-azabicyclo[3.2.1]octan-8-yl)methyl)pyrimidin-4(3H)-one;
3-(((R)-4-Hydroxy-2,2-dimethyl-1-((R)-3-phenylbutanoyl)piperidin-4-yl)methyl)-6-phenylpyrimidin-4(3H)-one;
3-(((S)-4-Hydroxy-2,2-dimethyl-1-((R)-3-phenylbutanoyl)piperidin-4-yl)methyl)-6-phenylpyrimidin-4(3H)-one;
(R)-1-((4-Hydroxy-1-(3-phenylbutanoyl)piperidin-4-yl)methyl)-5-(4-hydroxypiperidine-1-carbonyl)-4-phenylpyridin-2(1H)-one;
(R)-1-((4-Hydroxy-1-(3-phenylbutanoyl)piperidin-4-yl)methyl)-4-phenyl-5-(pyrrolidine-1-carbonyl)pyridin-2(1H)-one;
(R)-1-((4-Hydroxy-1-(3-phenylbutanoyl)piperidin-4-yl)methyl)-4-phenyl-5-(1,4-dioxa-8-azaspiro[4.5]decane-8-carbonyl)pyridin-2(1H)-one;
(R)—N-Cyclohexyl-1-((4-hydroxy-1-(3-phenylbutanoyl)piperidin-4-yl)methyl)-6-oxo-4-phenyl-1,6-dihydropyridine-3-carboxamide;
6-(2-Fluorophenyl)-3-((4-hydroxy-3,3-dimethyl-1-(cis-2-phenylcyclopropane-1-carbonyl)piperidin-4-yl)methyl)pyrimidin-4(3H)-one;
(R,S)-3-((1-(3-Cyclohexyl-1H-pyrazole-4-carbonyl)-4-hydroxy-3,3-dimethylpiperidin-4-yl)methyl)-6-(2-fluorophenyl)pyrimidin-4(3H)-one;
(R,S)-6-(2-Fluorophenyl)-3-((4-hydroxy-3,3-dimethyl-1-(3-phenylpropanoyl)piperidin-4-yl)methyl)pyrimidin-4(3H)-one;
(R,S)-6-(2-Fluorophenyl)-3-((4-hydroxy-1-(1-isobutylcyclopropane-1-carbonyl)-3,3-dimethylpiperidin-4-yl)methyl)pyrimidin-4(3H)-one;
(R,S)-6-(2-Fluorophenyl)-3-((4-hydroxy-3,3-dimethyl-1-(3-methyl-3-phenylbutanoyl)piperidin-4-yl)methyl)pyrimidin-4(3H)-one;
(S)-1-((1-(4,4-Difluoro-3-phenylbutanoyl)-4-hydroxypiperidin-4-yl)methyl)-N-isopropyl-N-methyl-6-oxo-4-phenyl-1,6-dihydropyridine-3-carboxamide;
1-((4-Hydroxy-1-(1-(thiophen-2-yl)cyclopropane-1-carbonyl)piperidin-4-yl)methyl)-N-isopropyl-N-methyl-6-oxo-4-phenyl-1,6-dihydropyridine-3-carboxamide;
1-(((R)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide;
1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide;
(R)-3-((4-Hydroxy-1-(3-phenylbutanoyl)piperidin-4-yl)methyl)-6-(2-(hydroxymethyl)phenyl)pyrimidin-4(3H)-one;
(R)—N,N-Diethyl-1-((4-hydroxy-1-(3-phenylbutanoyl)piperidin-4-yl)methyl)-6-oxo-4-phenyl-1,6-dihydropyridine-3-carboxamide;
3-((1-(3-Cyclohexylbutanoyl)-4-hydroxy-3,3-dimethylpiperidin-4-yl)methyl)-6-(2-fluorophenyl)pyrimidin-4(3H)-one;
(R)-1-((4-Hydroxy-1-(3-phenylbutanoyl)piperidin-4-yl)methyl)-5-(morpholine-4-carbonyl)-4-phenylpyridin-2(1H)-one;
(R,S)-3-((1-(3-Cyclohexylpropanoyl)-4-hydroxy-3,3-dimethylpiperidin-4-yl)methyl)-6-(2-fluorophenyl)pyrimidin-4(3H)-one;
(R,S)-1-((1-(3-Cyclobutylpropanoyl)-4-hydroxy-3,3-dimethylpiperidin-4-yl)methyl)-N-isopropyl-N-methyl-6-oxo-4-phenyl-1,6-dihydropyridine-3-carboxamide;
(R,S)-1-((1-(2-Ethylhexanoyl)-4-hydroxypiperidin-4-yl)methyl)-N-isopropyl-N-methyl-6-oxo-4-phenyl-1,6-dihydropyridine-3-carboxamide;
(R,S)-6-(2-Fluorophenyl)-3-((4-hydroxy-3,3-dimethyl-1-(1-methylcyclohexane-1-carbonyl)piperidin-4-yl)methyl)pyrimidin-4(3H)-one;
6-(2-Fluorophenyl)-3-((1-(3-(4-fluorophenyl)propanoyl)-4-hydroxypiperidin-4-yl)methyl)pyrimidin-4(3H)-one;
(R,S)-3-((1-(3-Cyclopropylpropanoyl)-4-hydroxy-3,3-dimethylpiperidin-4-yl)methyl)-6-(2-fluorophenyl)pyrimidin-4(3H)-one;
1-((1-(2,2-Dimethylbutanoyl)-4-hydroxypiperidin-4-yl)methyl)-N-isopropyl-N-methyl-6-oxo-4-phenyl-1,6-dihydropyridine-3-carboxamide;
(R)—N-(2-(1-((4-Hydroxy-1-(3-phenylbutanoyl)piperidin-4-yl)methyl)-6-oxo-1,6-dihydropyrimidin-4-yl)phenyl)acetamide;
(R)-5-(4-(Aminomethyl)phenyl)-1-((4-hydroxy-1-(3-phenylbutanoyl)piperidin-4-yl)methyl)-4-phenylpyridin-2(1H)-one;
(R)-1-((1-(3-Cyclohexyl-2-methylpropanoyl)-4-hydroxypiperidin-4-yl)methyl)-N-isopropyl-N-methyl-6-oxo-4-phenyl-1,6-dihydropyridine-3-carboxamide;
(R)-1-((4-Hydroxy-1-(3-phenylbutanoyl)piperidin-4-yl)methyl)-4-phenyl-5-(piperidine-1-carbonyl)pyridin-2(1H)-one;
(R)-1-((4-Hydroxy-1-(3-phenylbutanoyl)piperidin-4-yl)methyl)-N-isopropyl-4-(2-methoxyphenyl)-N-methyl-6-oxo-1,6-dihydropyridine-3-carboxamide;
(R)-4-(2-Fluorophenyl)-1-((4-hydroxy-1-(3-phenylbutanoyl)piperidin-4-yl)methyl)-N-isopropyl-N-methyl-6-oxo-1,6-dihydropyridine-3-carboxamide;

(R)-1'-((4-Hydroxy-1-(3-phenylbutanoyl)piperidin-4-yl)methyl)-4'-phenyl-[2,3'-bipyridin]-6'(1'H)-one;

1-((1-(3-Cyclohexylpropanoyl)-4-hydroxypiperidin-4-yl)methyl)-N-isopropyl-N-methyl-6-oxo-4-phenyl-1,6-dihydropyridine-3-carboxamide;

(R)-tert-Butyl 4-(1-((4-hydroxy-1-(3-phenylbutanoyl)piperidin-4-yl)methyl)-6-oxo-4-phenyl-1,6-dihydropyridine-3-carbonyl)piperazine-1-carboxylate;

(R)-1-((4-Hydroxy-1-(3-phenylbutanoyl)piperidin-4-yl)methyl)-4-phenyl-5-(piperazine-1-carbonyl)pyridin-2(1H)-one;

(R)-1-((4-Hydroxy-1-(3-phenylbutanoyl)piperidin-4-yl)methyl)-N,N-dimethyl-6-oxo-4-phenyl-1,6-dihydropyridine-3-carboxamide;

(R)-1-((4-Hydroxy-1-(3-phenylbutanoyl)piperidin-4-yl)methyl)-N-isopropyl-N-methyl-6-oxo-4-(p-tolyl)-1,6-dihydropyridine-3-carboxamide;

(R)-1-((4-Hydroxy-1-(3-phenylbutanoyl)piperidin-4-yl)methyl)-N-methoxy-N-methyl-6-oxo-4-phenyl-1,6-dihydropyridine-3-carboxamide;

(R)-1-((4-Hydroxy-1-(3-phenylbutanoyl)piperidin-4-yl)methyl)-4,5-diphenylpyridin-2(1H)-one;

(R)-1-((4-Hydroxy-1-(3-phenylbutanoyl)piperidin-4-yl)methyl)-4-phenyl-[3,3'-bipyridin]-6(1H)-one, (R)-5-(3-(Aminomethyl)phenyl)-1-((4-hydroxy-1-(3-phenylbutanoyl)piperidin-4-yl)methyl)-4-phenylpyridin-2(1H)-one, (R)-1-((4-Hydroxy-1-(3-phenylbutanoyl)piperidin-4-yl)methyl)-N-isopropyl-N-methyl-6-oxo-4-phenyl-1,6-dihydropyridine-3-carboxamide;

(R)-1-((4-Hydroxy-1-(3-phenylbutanoyl)piperidin-4-yl)methyl)-N-isopropyl-N-methyl-6-oxo-4-(m-tolyl)-1,6-dihydropyridine-3-carboxamide;

(R)-1-((4-Hydroxy-1-(3-phenylbutanoyl)piperidin-4-yl)methyl)-4-phenyl-5-(pyrimidin-5-yl)pyridin-2(1H)-one;

(R)—N-(Cyclopropylmethyl)-1-((4-hydroxy-1-(3-phenylbutanoyl) piperidin-4-yl)methyl)-6-oxo-4-phenyl-1,6-dihydropyridine-3-carboxamide;

(R)—N-Benzyl-1-((4-hydroxy-1-(3-phenylbutanoyl)piperidin-4-yl)methyl)-N-methyl-6-oxo-4-phenyl-1,6-dihydropyridine-3-carboxamide;

(R)-2-(1-((4-Hydroxy-1-(3-phenylbutanoyl)piperidin-4-yl)methyl)-6-oxo-4-phenyl-1,6-dihydropyridin-3-yl)benzonitrile;

(R)-1-((4-Hydroxy-1-(3-phenylbutanoyl)piperidin-4-yl)methyl)-N-methyl-6-oxo-N,4-diphenyl-1,6-dihydropyridine-3-carboxamide;

3-(1-(1-((R)-3-Cyclohexyl-2-methylpropanoyl)-4-hydroxypiperidin-4-yl)ethyl)-6-phenylpyrimidin-4(3H)-one;

(R)-1-((4-Hydroxy-1-(3-phenylbutanoyl)piperidin-4-yl)methyl)-5-(1-methyl-1H-pyrazol-4-yl)-4-phenylpyridin-2(1H)-one;

(R)-3-((1-(2-(Cyclohexylmethyl)pent-4-enoyl)-4-hydroxypiperidin-4-yl)methyl)-6-(2-fluorophenyl)pyrimidin-4(3H)-one;

(R)-1-((4-Hydroxy-1-(3-phenylbutanoyl)piperidin-4-yl)methyl)-5-methyl-4-phenylpyridin-2(1H)-one;

(R)-6-(1,5-Dimethyl-1H-pyrazol-4-yl)-3-((4-hydroxy-1-(3-phenylbutanoyl)piperidin-4-yl)methyl)pyrimidin-4(3H)-one;

3-(((1R,5S)-3-(3-Cyclohexylpropanoyl)-8-hydroxy-3-azabicyclo[3.2.1]octan-8-yl)methyl)-6-(2-fluorophenyl)pyrimidin-4(3H)-one;

(R)-1-((4-Hydroxy-1-(3-phenylbutanoyl)piperidin-4-yl)methyl)-6-oxo-4-phenyl-1,6-dihydropyridine-3-carbonitrile;

(R)-1-((4-Hydroxy-1-(3-phenylbutanoyl)piperidin-4-yl)methyl)-N-(2-hydroxyethyl)-6-oxo-4-phenyl-1,6-dihydropyridine-3-carboxamide;

1-((4-Hydroxy-1-((R)-3-phenylbutanoyl)piperidin-4-yl)methyl)-5-((S)-2-methylpyrrolidine-1-carbonyl)-4-phenylpyridin-2(1H)-one;

(R)-1-((4-Hydroxy-1-(3-phenylbutanoyl)piperidin-4-yl)methyl)-5-(4-(hydroxymethyl)piperidine-1-carbonyl)-4-phenylpyridin-2(1H)-one;

3-((1-(2-(Cyclohexylmethyl)butanoyl)-4-hydroxy-3,3-dimethylpiperidin-4-yl)methyl)-6-(2-fluorophenyl)pyrimidin-4(3H)-one;

3-((7-((R)-3-Cyclohexyl-2-methylpropanoyl)-10-hydroxy-7-azaspiro[4.5]decan-10-yl)methyl)-6-(2-fluorophenyl)pyrimidin-4(3H)-one;

1-(((S)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide;

1-(((S)-1-((R)-3-Cyclohexyl-2-methylpropanoyl)-4-hydroxy-3,3-dimethylpiperidin-4-yl)methyl)-N,N-dimethyl-6-oxo-4-phenyl-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-N,N-dimethyl-6-oxo-4-phenyl-1,6-dihydropyridine-3-carboxamide;

1-(((S)-1-((R)-3-Cyclohexyl-2-methylpropanoyl)-4-hydroxy-3,3-dimethylpiperidin-4-yl)methyl)-4-phenyl-5-(pyrrolidine-1-carbonyl)pyridin-2(1H)-one;

1-(((S)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one;

1-(((R)-1-((R)-3-Cyclohexyl-2-methylpropanoyl)-4-hydroxy-3,3-dimethylpiperidin-4-yl)methyl)-4-phenyl-5-(piperazine-1-carbonyl)pyridin-2(1H)-one;

3-((1-(2-(Cyclohexyloxy)propanoyl)-4-hydroxy-3,3-dimethylpiperidin-4-yl)methyl)-6-(2-fluorophenyl)pyrimidin-4(3H)-one;

1-((7-((R)-3-Cyclohexyl-2-methylpropanoyl)-10-hydroxy-7-azaspiro[4.5]decan-10-yl)methyl)-N,N-dimethyl-6-oxo-1,6-dihydropyridine-3-carboxamide;

1-((1-((R)-3-Cyclobutyl-2-methylpropanoyl)-4-hydroxy-3,3-dimethylpiperidin-4-yl)methyl)-N,N-dimethyl-6-oxo-4-phenyl-1,6-dihydropyridine-3-carboxamide;

1-((1-((R)-3-Cyclopropyl-2-methylpropanoyl)-4-hydroxy-3,3-dimethylpiperidin-4-yl)methyl)-N,N-dimethyl-6-oxo-4-phenyl-1,6-dihydropyridine-3-carboxamide;

1-((1-((R)-3-Cyclohexyl-2-methylpropanoyl)-4-hydroxy-3,3-dimethylpiperidin-4-yl)methyl)-[4,5'-bipyrimidin]-6(1H)-one;

3-((1-((R)-3-Cyclohexyl-2-methylpropanoyl)-4-hydroxy-3,3-dimethylpiperidin-4-yl)methyl)-6-(1-methyl-1H-pyrazol-5-yl)pyrimidin-4(3H)-one;

3-((1-((R)-3-Cyclohexyl-2-methylpropanoyl)-4-hydroxy-3,3-dimethylpiperidin-4-yl)methyl)-6-(1H-pyrazol-4-yl)pyrimidin-4(3H)-one;

3-((1-((R)-3-Cyclohexyl-2-methylpropanoyl)-4-hydroxy-3,3-dimethylpiperidin-4-yl)methyl)-6-(1H-pyrazol-5-yl)pyrimidin-4(3H)-one;

3-((7-((R)-3-Cyclohexyl-2-methylpropanoyl)-10-hydroxy-7-azaspiro[4.5]decan-10-yl)methyl)pyrimidin-4(3H)-one;

3-((1-((R)-3-Cyclohexyl-2-methylpropanoyl)-4-hydroxy-3,3-dimethylpiperidin-4-yl)methyl)-6-(thiophen-3-yl)pyrimidin-4(3H)-one;
1-((1-((R)-3-Cyclohexyl-2-methylpropanoyl)-4-hydroxy-3,3-dimethylpiperidin-4-yl)methyl)-5-(oxazol-2-yl)-4-phenylpyridin-2(1H)-one,
3-((1-((R)-3-Cyclohexyl-2-methylpropanoyl)-4-hydroxy-3,3-dimethylpiperidin-4-yl)methyl)-6-(2-(hydroxymethyl)phenyl)pyrimidin-4(3H)-one;
3-((1-((R)-3-Cyclohexyl-2-methylpropanoyl)-4-hydroxy-3,3-dimethylpiperidin-4-yl)methyl)-6-(3-(hydroxymethyl)phenyl)pyrimidin-4(3H)-one;
3-((1-((R)-3-Cyclohexyl-2-methylpropanoyl)-4-hydroxy-3,3-dimethylpiperidin-4-yl)methyl)-6-(4-(hydroxymethyl)phenyl)pyrimidin-4(3H)-one;
6-(4-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one;
6-(2-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one;
6-(2-Fluorophenyl)-3-((4-hydroxy-3,3-dimethyl-1-(2,4,4-trimethylpentanoyl)piperidin-4-yl)methyl)pyrimidin-4(3H)-one;
6-(2-Fluorophenyl)-3-((4-hydroxy-3,3-dimethyl-1-(4,4,4-trifluoro-2-methylbutanoyl)piperidin-4-yl)methyl)pyrimidin-4(3H)-one;
4-Chloro-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide;
1-((7-((R)-3-Cyclohexyl-2-methylpropanoyl)-10-hydroxy-7-azaspiro[4.5]decan-10-yl)methyl)-4-(dimethylamino)-N,N-dimethyl-6-oxo-1,6-dihydropyridine-3-carboxamide;
1-((1-((S)-3-(Benzyloxy)-2-(cyclohexylmethyl)propanoyl)-4-hydroxy-3,3-dimethylpiperidin-4-yl)methyl)-N,N-dimethyl-6-oxo-4-phenyl-1,6-dihydropyridine-3-carboxamide;
1-((10-Hydroxy-7-isobutyryl-7-azaspiro[4.5]decan-10-yl)methyl)-N,N-dimethyl-6-oxo-4-phenyl-1,6-dihydropyridine-3-carboxamide;
1-((10-Hydroxy-7-((R)-2-methylbutanoyl)-7-azaspiro[4.5]decan-10-yl)methyl)-N,N-dimethyl-6-oxo-4-phenyl-1,6-dihydropyridine-3-carboxamide;
1-((7-((R)-3-Cyclopropyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide;
6-(2-Fluorophenyl)-3-((4-hydroxy-3,3-dimethyl-1-(2-methyl-3-(1H-pyrazol-1-yl)propanoyl)piperidin-4-yl)methyl)pyrimidin-4(3H)-one;
1-((7-((R)-3-Cyclohexyl-2-methylpropanoyl)-10-hydroxy-7-azaspiro[4.5]decan-10-yl)methyl)-4-(2-(hydroxymethyl)phenyl)-N,N-dimethyl-6-oxo-1,6-dihydropyridine-3-carboxamide;
1-(((S)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide;
1-(((R)-1-((S)-3-Cyclohexyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide;
1'-((1-((R)-3-Cyclohexyl-2-methylpropanoyl)-4-hydroxy-3,3-dimethylpiperidin-4-yl)methyl)-4'-(2-fluorophenyl)-[2,3'-bipyridin]-6'(1'H)-one;
1-((7-((R)-3-Cyclohexyl-2-methylpropanoyl)-10-hydroxy-7-azaspiro[4.5]decan-10-yl)methyl)-N,N-dimethyl-6-oxo-4-(thiophen-3-yl)-1,6-dihydropyridine-3-carboxamide;
1-((7-((R)-3-Cyclohexyl-2-methylpropanoyl)-10-hydroxy-7-azaspiro[4.5]decan-10-yl)methyl)-4-(3-(hydroxymethyl)phenyl)-N,N-dimethyl-6-oxo-1,6-dihydropyridine-3-carboxamide;
1-((7-(3-Cyclohexyl-2-hydroxypropanoyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(2-methyl-3-(piperidin-1-yl)propanoyl)-7-azaspiro[4.5]decan-10-yl)methyl)-N,N-dimethyl-6-oxo-4-phenyl-1,6-dihydropyridine-3-carboxamide;
6-(3-(Aminomethyl)phenyl)-3-((1-((R)-3-cyclohexyl-2-methylpropanoyl)-4-hydroxy-3,3-dimethylpiperidin-4-yl)methyl)pyrimidin-4(3H)-one;
1-(((S)-1-((S)-3-Cyclohexyl-2-(methoxymethyl)propanoyl)-4-hydroxy-3,3-dimethylpiperidin-4-yl)methyl)-N,N-dimethyl-6-oxo-4-phenyl-1,6-dihydropyridine-3-carboxamide;
4-(2-(Aminomethyl)phenyl)-1-((7-((R)-3-cyclohexyl-2-methylpropanoyl)-10-hydroxy-7-azaspiro[4.5]decan-10-yl)methyl)-N,N-dimethyl-6-oxo-1,6-dihydropyridine-3-carboxamide;
1-((7-((R)-3-Cyclohexyl-2-methylpropanoyl)-10-hydroxy-7-azaspiro[4.5]decan-10-yl)methyl)-4-(4-(hydroxymethyl)phenyl)-N,N-dimethyl-6-oxo-1,6-dihydropyridine-3-carboxamide;
1-((10-Hydroxy-7-(2-methyl-3-morpholinopropanoyl)-7-azaspiro[4.5]decan-10-yl)methyl)-N,N-dimethyl-6-oxo-4-phenyl-1,6-dihydropyridine-3-carboxamide;
1-(((S)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide;
1-(((R)-1-((S)-2-(Cyclohexylmethyl)-4-hydroxybutanoyl)-4-hydroxy-3,3-dimethylpiperidin-4-yl)methyl)-N,N-dimethyl-6-oxo-4-phenyl-1,6-dihydropyridine-3-carboxamide;
1-(((S)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide;
1-(((R)-1-((S)-3-Cyclobutyl-2-(hydroxymethyl)propanoyl)-4-hydroxy-3,3-dimethylpiperidin-4-yl)methyl)-N,N-dimethyl-6-oxo-4-phenyl-1,6-dihydropyridine-3-carboxamide;
1-((1-((R)-3-Cyclohexyl-2-methylpropanoyl)-4-hydroxy-3,3-dimethylpiperidin-4-yl)methyl)-5-(morpholine-4-carbonyl)-4-phenylpyridin-2(1H)-one;
5-(4-Acetylpiperazine-1-carbonyl)-1-((1-((R)-3-cyclohexyl-2-methylpropanoyl)-4-hydroxy-3,3-dimethylpiperidin-4-yl)methyl)-4-phenylpyridin-2(1H)-one;
1-((1-((R)-3-Cyclohexyl-2-methylpropanoyl)-4-hydroxy-3,3-dimethylpiperidin-4-yl)methyl)-5-(4-methylpiperazine-1-carbonyl)-4-phenylpyridin-2(1H)-one;
1-((10-Hydroxy-7-(4,4,4-trifluoro-3-methylbutanoyl)-7-azaspiro[4.5]decan-10-yl)methyl)-N,N-dimethyl-6-oxo-4-phenyl-1,6-dihydropyridine-3-carboxamide;
1-((10-Hydroxy-7-(4,4,4-trifluorobutanoyl)-7-azaspiro[4.5]decan-10-yl)methyl)-N,N-dimethyl-6-oxo-4-phenyl-1,6-dihydropyridine-3-carboxamide;
1-((10-Hydroxy-7-(3-(tetrahydrofuran-3-yl)propanoyl)-7-azaspiro[4.5]decan-10-yl)methyl)-N,N-dimethyl-6-oxo-4-phenyl-1,6-dihydropyridine-3-carboxamide;

1-((10-Hydroxy-7-((1R,2S)-2-phenylcyclopropane-1-carbonyl)-7-azaspiro[4.5]decan-10-yl)methyl)-N,N-dimethyl-6-oxo-4-phenyl-1,6-dihydropyridine-3-carboxamide;
1-((7-(Cyclopropanecarbonyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(1-methylcyclohexane-1-carbonyl)-7-azaspiro[4.5]decan-10-yl)methyl)-N,N-dimethyl-6-oxo-4-phenyl-1,6-dihydropyridine-3-carboxamide;
1-((7-(3-Fluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide;
1-((7-(1-(2,2-Difluoroethyl)cyclopropane-1-carbonyl)-10-hydroxy-7-azaspiro[4.5]decan-10-yl)methyl)-N,N-dimethyl-6-oxo-4-phenyl-1,6-dihydropyridine-3-carboxamide;
1-((7-(Bicyclo[2.2.1]heptane-1-carbonyl)-10-hydroxy-7-azaspiro[4.5]decan-10-yl)methyl)-N,N-dimethyl-6-oxo-4-phenyl-1,6-dihydropyridine-3-carboxamide;
1-((7-((S)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide;
1-((7-((R)-4,4-Difluoro-3-phenylbutanoyl)-10-hydroxy-7-azaspiro[4.5]decan-10-yl)methyl)-N,N-dimethyl-6-oxo-4-phenyl-1,6-dihydropyridine-3-carboxamide;
1-((7-(3-Ethoxypropanoyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-((S)-3-phenylbutanoyl)-7-azaspiro[4.5]decan-10-yl)methyl)-N,N-dimethyl-6-oxo-4-phenyl-1,6-dihydropyridine-3-carboxamide;
1-((7-(3-(4-Fluorophenyl)propanoyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-((R)-3-phenylbutanoyl)-7-azaspiro[4.5]decan-10-yl)methyl)-N,N-dimethyl-6-oxo-4-phenyl-1,6-dihydropyridine-3-carboxamide;
1-((10-Hydroxy-7-(1-methylcyclopentane-1-carbonyl)-7-azaspiro[4.5]decan-10-yl)methyl)-N,N-dimethyl-6-oxo-4-phenyl-1,6-dihydropyridine-3-carboxamide;
1-((10-Hydroxy-7-(1H-pyrazole-3-carbonyl)-7-azaspiro[4.5]decan-10-yl)methyl)-N,N-dimethyl-6-oxo-4-phenyl-1,6-dihydropyridine-3-carboxamide;
1-((10-Hydroxy-7-(1H-indazole-3-carbonyl)-7-azaspiro[4.5]decan-10-yl)methyl)-N,N-dimethyl-6-oxo-4-phenyl-1,6-dihydropyridine-3-carboxamide;
1-((7-(3-Cyclohexyl-1H-pyrazole-4-carbonyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(1H-indole-3-carbonyl)-7-azaspiro[4.5]decan-10-yl)methyl)-N,N-dimethyl-6-oxo-4-phenyl-1,6-dihydropyridine-3-carboxamide;
1-((7-(Bicyclo[1.1.1]pentane-1-carbonyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(5-phenyloxazole-4-carbonyl)-7-azaspiro[4.5]decan-10-yl)methyl)-N,N-dimethyl-6-oxo-4-phenyl-1,6-dihydropyridine-3-carboxamide;
1-((7-(5-Cyclopropyloxazole-4-carbonyl)-10-hydroxy-7-azaspiro[4.5]decan-10-yl)methyl)-N,N-dimethyl-6-oxo-4-phenyl-1,6-dihydropyridine-3-carboxamide;
1-((7-(2-(Cyclohexyloxy)acetyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(spiro[2.2]pentane-1-carbonyl)-7-azaspiro[4.5]decan-10-yl)methyl)-N,N-dimethyl-6-oxo-4-phenyl-1,6-dihydropyridine-3-carboxamide;
1-((10-Hydroxy-7-(3-(trifluoromethyl)cyclopentane-1-carbonyl)-7-azaspiro[4.5]decan-10-yl)methyl)-N,N-dimethyl-6-oxo-4-phenyl-1,6-dihydropyridine-3-carboxamide;
1-((7-(2,4-Dimethylpentanoyl)-10-hydroxy-7-azaspiro[4.5]decan-10-yl)methyl)-N,N-dimethyl-6-oxo-4-phenyl-1,6-dihydropyridine-3-carboxamide;
1-((7-(1-Benzyl-1H-pyrrole-2-carbonyl)-10-hydroxy-7-azaspiro[4.5]decan-10-yl)methyl)-N,N-dimethyl-6-oxo-4-phenyl-1,6-dihydropyridine-3-carboxamide;
1-((7-(2-(Cyclohexyloxy)propanoyl)-10-hydroxy-7-azaspiro[4.5]decan-10-yl)methyl)-N,N-dimethyl-6-oxo-4-phenyl-1,6-dihydropyridine-3-carboxamide;
3-((1-((S)-3-Cyclobutyl-2-(hydroxymethyl)propanoyl)-4-hydroxy-3,3-dimethylpiperidin-4-yl)methyl)-6-(2-fluorophenyl)pyrimidin-4(3H)-one;
1-((7-(2-Cyclobutoxyacetyl)-10-hydroxy-7-azaspiro[4.5]decan-10-yl)methyl)-N,N-dimethyl-6-oxo-4-phenyl-1,6-dihydropyridine-3-carboxamide;
1-((7-(3,3-Difluorocyclopentane-1-carbonyl)-10-hydroxy-7-azaspiro[4.5]decan-10-yl)methyl)-N,N-dimethyl-6-oxo-4-phenyl-1,6-dihydropyridine-3-carboxamide;
1-((10-Hydroxy-7-(2-hydroxy-3-phenylpropanoyl)-7-azaspiro[4.5]decan-10-yl)methyl)-N,N-dimethyl-6-oxo-4-phenyl-1,6-dihydropyridine-3-carboxamide;
1-(((S)-4-Hydroxy-3,3-dimethyl-1-((R)-4,4,4-trifluoro-2-methylbutanoyl)piperidin-4-yl)methyl)-N,N-dimethyl-6-oxo-4-phenyl-1,6-dihydropyridine-3-carboxamide;
1-(((S)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide;
1-(((S)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one;
(S)-1-((4-Hydroxy-3,3-dimethyl-1-(4,4,4-trifluoro-2-(2,2,2-trifluoroethyl)butanoyl)piperidin-4-yl)methyl)-N,N-dimethyl-6-oxo-4-phenyl-1,6-dihydropyridine-3-carboxamide;
1-(((S)-1-((R)-3-Cyclohexyl-2-methylpropanoyl)-4-hydroxy-3,3-dimethylpiperidin-4-yl)methyl)-5-((S)-2-(hydroxymethyl) piperazine-1-carbonyl)-4-phenylpyridin-2(1H)-one;
1-(((R)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide;
1-(((R)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one;
1-(((S)-7-((R)-3-Cyclohexyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide;
1-(((S)-7-((R)-3-Cyclohexyl-2-methylpropanoyl)-10-hydroxy-7-azaspiro[4.5]decan-10-yl)methyl)-4-phenyl-5-(piperazine-1-carbonyl)pyridin-2(1H)-one;
1-(((S)-1-((R)-3-Cyclohexyl-2-methylpropanoyl)-4-hydroxy-3,3-dimethylpiperidin-4-yl)methyl)-5-((R)-3-methylpiperazine-1-carbonyl)-4-phenylpyridin-2(1H)-one;

1-(((S)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide;

1-(((S)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one;

1-(((S)-10-Hydroxy-7-((R)-4,4,4-trifluoro-2-methylbutanoyl)-7-azaspiro[4.5]decan-10-yl)methyl)-N,N-dimethyl-6-oxo-4-phenyl-1,6-dihydropyridine-3-carboxamide;

1-(((S)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one;

(S)-1-((10-Hydroxy-7-(4,4,4-trifluoro-2-(2,2,2-trifluoroethyl)butanoyl)-7-azaspiro[4.5]decan-10-yl)methyl)-N,N-dimethyl-6-oxo-4-phenyl-1,6-dihydropyridine-3-carboxamide;

(S)-1-((10-Hydroxy-7-(4,4,4-trifluoro-2-(2,2,2-trifluoroethyl)butanoyl)-7-azaspiro[4.5]decan-10-yl)methyl)-4-phenyl-5-(piperazine-1-carbonyl)pyridin-2(1H)-one;

1-(((S)-1-((R)-3-Cyclohexyl-2-methylpropanoyl)-4-hydroxy-3,3-dimethylpiperidin-4-yl)methyl)-4-cyclopropyl-N,N-dimethyl-6-oxo-1,6-dihydropyridine-3-carboxamide;

1-(((S)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one;

1-(((S)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide;

4-(2-Fluorophenyl)-1-(((S)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide;

1-(((S)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one;

4-(2-Fluorophenyl)-1-(((S)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one;

1-(((S)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide;

1-(((S)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one;

1-(((S)-1-((R)-3-Cyclohexyl-2-methylpropanoyl)-4-hydroxy-3,3-dimethylpiperidin-4-yl)methyl)-5-(4-hydroxypiperidine-1-carbonyl)-4-phenylpyridin-2(1H)-one;

1-((10-Hydroxy-7-(3-(trifluoromethyl)cyclobutane-1-carbonyl)-7-azaspiro[4.5]decan-10-yl)methyl)-N,N-dimethyl-6-oxo-4-phenyl-1,6-dihydropyridine-3-carboxamide;

1-(((S)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide;

1-(((S)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one;

1-(((S)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide;

1-(((S)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one;

1-((2-((R)-3-Cyclohexyl-2-methylpropanoyl)-5-hydroxy-9-oxa-2-azaspiro[5.5]undecan-5-yl)methyl)-N,N-dimethyl-6-oxo-4-phenyl-1,6-dihydropyridine-3-carboxamide;

1-(((S)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide;

1-(((S)-1-((R)-3-Cyclobutyl-2-methylpropanoyl)-4-hydroxy-3,3-dimethylpiperidin-4-yl)methyl)-4-(2-fluorophenyl)-5-(piperazine-1-carbonyl)pyridin-2(1H)-one;

1-((2-((R)-3-Cyclohexyl-2-methylpropanoyl)-5-hydroxy-2-azaspiro[5.5]undecan-5-yl)methyl)-N,N-dimethyl-6-oxo-4-phenyl-1,6-dihydropyridine-3-carboxamide;

1-((2-((R)-3-Cyclohexyl-2-methylpropanoyl)-5-hydroxy-2-azaspiro[5.5]undecan-5-yl)methyl)-4-phenyl-5-(piperazine-1-carbonyl)pyridin-2(1H)-one;

1-(((S)-7-((R)-3-Cyclohexyl-2-methylpropanoyl)-10-hydroxy-7-azaspiro[4.5]decan-10-yl)methyl)-5-(morpholine-4-carbonyl)-4-phenylpyridin-2(1H)-one;

1-(((S)-7-((R)-3-Cyclohexyl-2-methylpropanoyl)-10-hydroxy-7-azaspiro[4.5]decan-10-yl)methyl)-5-(4-methylpiperazine-1-carbonyl)-4-phenylpyridin-2(1H)-one;

1-((1-((R)-3-Cyclohexyl-2-methylpropanoyl)-4-hydroxy-3,3-dimethylpiperidin-4-yl)methyl)-6-oxo-4-phenyl-1,6-dihydropyridine-3-carboxylic acid;

1-((7-((R)-3-Cyclohexyl-2-methylpropanoyl)-10-hydroxy-7-azaspiro[4.5]decan-10-yl)methyl)-4-methoxy-N,N-dimethyl-6-oxo-1,6-dihydropyridine-3-carboxamide;

1-((7-(4,4-Difluoro-2-methylbutanoyl)-10-hydroxy-7-azaspiro[4.5]decan-10-yl)methyl)-N,N-dimethyl-6-oxo-4-phenyl-1,6-dihydropyridine-3-carboxamide;

1-((7-(4,4-Difluoro-2,2-dimethylbutanoyl)-10-hydroxy-7-azaspiro[4.5]decan-10-yl)methyl)-N,N-dimethyl-6-oxo-4-phenyl-1,6-dihydropyridine-3-carboxamide;

1-((10-Hydroxy-7-(4-(trifluoromethyl)thiazole-2-carbonyl)-7-azaspiro[4.5]decan-10-yl)methyl)-N,N-dimethyl-6-oxo-4-phenyl-1,6-dihydropyridine-3-carboxamide;

1-((10-Hydroxy-7-(2-(trifluoromethyl)thiazole-4-carbonyl)-7-azaspiro[4.5]decan-10-yl)methyl)-N,N-dimethyl-6-oxo-4-phenyl-1,6-dihydropyridine-3-carboxamide;

1-(((S)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide;

1-(((S)-10-Hydroxy-7-((S)-4,4,4-trifluoro-2-(hydroxymethyl)butanoyl)-7-azaspiro[4.5]decan-10-yl)methyl)-5-(morpholine-4-carbonyl)-4-phenylpyridin-2(1H)-one;

1-(((S)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one;

1-(((S)-10-Hydroxy-7-((R)-4,4,4-trifluoro-2-methylbutanoyl)-7-azaspiro[4.5]decan-10-yl)methyl)-5-(morpholine-4-carbonyl)-4-phenylpyridin-2(1H)-one;

1-(((S)-10-Hydroxy-7-((R)-4,4,4-trifluoro-2-methylbutanoyl)-7-azaspiro[4.5]decan-10-yl)methyl)-5-(4-methylpiperazine-1-carbonyl)-4-phenylpyridin-2(1H)-one;

Ethyl 1-(((S)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate;

1-(((S)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid;

1-(((R)-1-((R)-3-Cyclohexyl-2-methylpropanoyl)-4-hydroxy-3,3-dimethylpiperidin-4-yl)methyl)-N-isopropyl-N-methyl-6-oxo-4-phenyl-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-4-phenyl-5-(pyrrolidine-1-carbonyl)pyridin-2(1H)-one;

1-(((R)-1-((S)-3-Cyclohexyl-2-(methoxymethyl)propanoyl)-4-hydroxy-3,3-dimethylpiperidin-4-yl)methyl)-N,N-dimethyl-6-oxo-4-phenyl-1,6-dihydropyridine-3-carboxamide;

1-(((R)-4-Hydroxy-3,3-dimethyl-1-((R)-4,4,4-trifluoro-2-methylbutanoyl)piperidin-4-yl)methyl)-N,N-dimethyl-6-oxo-4-phenyl-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-4-(2-fluorophenyl)-5-(piperazine-1-carbonyl)pyridin-2(1H)-one;

(R)-1-((4-Hydroxy-3,3-dimethyl-1-(4,4,4-trifluoro-2-(2,2,2-trifluoroethyl)butanoyl)piperidin-4-yl)methyl)-N,N-dimethyl-6-oxo-4-phenyl-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-5-((S)-2-(hydroxymethyl) piperazine-1-carbonyl)-4-phenylpyridin-2(1H)-one;

1-(((R)-1-((R)-3-Cyclohexyl-2-methylpropanoyl)-4-hydroxy-3,3-dimethylpiperidin-4-yl)methyl)-5-((R)-3-methylpiperazine-1-carbonyl)-4-phenylpyridin-2(1H)-one;

1-(((R)-7-((R)-3-Cyclobutyl-2-methylpropanoyl)-10-hydroxy-7-azaspiro[4.5]decan-10-yl)methyl)-N,N-dimethyl-6-oxo-4-phenyl-1,6-dihydropyridine-3-carboxamide;

1-(((R)-7-((R)-3-Cyclobutyl-2-methylpropanoyl)-10-hydroxy-7-azaspiro[4.5]decan-10-yl)methyl)-4-phenyl-5-(piperazine-1-carbonyl)pyridin-2(1H)-one, 1-(((R)-10-Hydroxy-7-((R)-4,4,4-trifluoro-2-methylbutanoyl)-7-azaspiro[4.5]decan-10-yl)methyl)-N,N-dimethyl-6-oxo-4-phenyl-1,6-dihydropyridine-3-carboxamide;

1-(((R)-10-Hydroxy-7-((R)-4,4,4-trifluoro-2-methylbutanoyl)-7-azaspiro[4.5]decan-10-yl)methyl)-4-phenyl-5-(piperazine-1-carbonyl)pyridin-2(1H)-one;

(R)-1-((10-Hydroxy-7-(4,4,4-trifluoro-2-(2,2,2-trifluoroethyl)butanoyl)-7-azaspiro[4.5]decan-10-yl)methyl)-N,N-dimethyl-6-oxo-4-phenyl-1,6-dihydropyridine-3-carboxamide;

(R)-1-((10-Hydroxy-7-(4,4,4-trifluoro-2-(2,2,2-trifluoroethyl)butanoyl)-7-azaspiro[4.5]decan-10-yl)methyl)-4-phenyl-5-(piperazine-1-carbonyl)pyridin-2(1H)-one;

1-(((R)-1-((R)-3-Cyclohexyl-2-methylpropanoyl)-4-hydroxy-3,3-dimethylpiperidin-4-yl)methyl)-4-cyclopropyl-N,N-dimethyl-6-oxo-1,6-dihydropyridine-3-carboxamide;

1-(((R)-1-((R)-3-Cyclohexyl-2-methylpropanoyl)-4-hydroxy-3,3-dimethylpiperidin-4-yl)methyl)-4-cyclopropyl-5-(piperazine-1-carbonyl)pyridin-2(1H)-one;

1-(((R)-7-((R)-3-Cyclobutyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide;

4-(2-Fluorophenyl)-1-(((R)-10-hydroxy-7-((R)-4,4,4-trifluoro-2-methylbutanoyl)-7-azaspiro[4.5]decan-10-yl)methyl)-N,N-dimethyl-6-oxo-1,6-dihydropyridine-3-carboxamide;

1-(((R)-7-((R)-3-Cyclobutyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one;

4-(2-Fluorophenyl)-1-(((R)-10-hydroxy-7-((R)-4,4,4-trifluoro-2-methylbutanoyl)-7-azaspiro[4.5]decan-10-yl)methyl)-5-(piperazine-1-carbonyl)pyridin-2(1H)-one;

1-(((R)-7-((R)-3-Cyclohexyl-2-methylpropanoyl)-10-hydroxy-7-azaspiro[4.5]decan-10-yl)methyl)-4-(2-fluorophenyl)-N,N-dimethyl-6-oxo-1,6-dihydropyridine-3-carboxamide;

1-(((R)-7-((R)-3-Cyclohexyl-2-methylpropanoyl)-10-hydroxy-7-azaspiro[4.5]decan-10-yl)methyl)-4-(2-fluorophenyl)-5-(piperazine-1-carbonyl)pyridin-2(1H)-one;

1-(((R)-1-((R)-3-Cyclohexyl-2-methylpropanoyl)-4-hydroxy-3,3-dimethylpiperidin-4-yl)methyl)-5-(4-hydroxypiperidine-1-carbonyl)-4-phenylpyridin-2(1H)-one;

1-(((R)-7-((R)-3-Cyclobutyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide;

1-(((R)-7-((R)-3-Cyclobutyl-2-methylpropanoyl)-10-hydroxy-7-azaspiro[4.5]decan-10-yl)methyl)-4-cyclopropyl-5-(piperazine-1-carbonyl)pyridin-2(1H)-one;

1-(((R)-7-((R)-3-Cyclohexyl-2-methylpropanoyl)-10-hydroxy-7-azaspiro[4.5]decan-10-yl)methyl)-4-cyclopropyl-N,N-dimethyl-6-oxo-1,6-dihydropyridine-3-carboxamide;

1-(((R)-7-((R)-3-Cyclohexyl-2-methylpropanoyl)-10-hydroxy-7-azaspiro[4.5]decan-10-yl)methyl)-4-cyclopropyl-5-(piperazine-1-carbonyl)pyridin-2(1H)-one;

1-(((R)-1-((R)-3-Cyclobutyl-2-methylpropanoyl)-4-hydroxy-3,3-dimethylpiperidin-4-yl)methyl)-4-(2-fluorophenyl)-N,N-dimethyl-6-oxo-1,6-dihydropyridine-3-carboxamide;

1-(((R)-1-((R)-3-Cyclobutyl-2-methylpropanoyl)-4-hydroxy-3,3-dimethylpiperidin-4-yl)methyl)-4-(2-fluorophenyl)-5-(piperazine-1-carbonyl)pyridin-2(1H)-one;

1-(((R)-7-((R)-3-Cyclohexyl-2-methylpropanoyl)-10-hydroxy-7-azaspiro[4.5]decan-10-yl)methyl)-5-(morpholine-4-carbonyl)-4-phenylpyridin-2(1H)-one;

1-(((R)-7-((R)-3-Cyclohexyl-2-methylpropanoyl)-10-hydroxy-7-azaspiro[4.5]decan-10-yl)methyl)-5-(4-methylpiperazine-1-carbonyl)-4-phenylpyridin-2(1H)-one;

1-(((R)-10-Hydroxy-7-((S)-4,4,4-trifluoro-2-(hydroxymethyl)butanoyl)-7-azaspiro[4.5]decan-10-yl)methyl)-N,N-dimethyl-6-oxo-4-phenyl-1,6-dihydropyridine-3-carboxamide;

1-(((R)-10-Hydroxy-7-((S)-4,4,4-trifluoro-2-(hydroxymethyl)butanoyl)-7-azaspiro[4.5]decan-10-yl)methyl)-5-(morpholine-4-carbonyl)-4-phenylpyridin-2(1H)-one;

1-(((R)-10-Hydroxy-7-((S)-4,4,4-trifluoro-2-(hydroxymethyl)butanoyl)-7-azaspiro[4.5]decan-10-yl)methyl)-4-phenyl-5-(piperazine-1-carbonyl)pyridin-2(1H)-one;

1-(((R)-10-Hydroxy-7-((R)-4,4,4-trifluoro-2-methylbutanoyl)-7-azaspiro[4.5]decan-10-yl)methyl)-5-(morpholine-4-carbonyl)-4-phenylpyridin-2(1H)-one;

1-(((R)-10-Hydroxy-7-((R)-4,4,4-trifluoro-2-methylbutanoyl)-7-azaspiro[4.5]decan-10-yl)methyl)-5-(4-methylpiperazine-1-carbonyl)-4-phenylpyridin-2(1H)-one;

Ethyl 1-(((R)-7-((R)-3-cyclohexyl-2-methylpropanoyl)-10-hydroxy-7-azaspiro[4.5]decan-10-yl)methyl)-6-oxo-4-phenyl-1,6-dihydropyridine-3-carboxylate;

1-(((R)-7-((R)-3-Cyclohexyl-2-methylpropanoyl)-10-hydroxy-7-azaspiro[4.5]decan-10-yl)methyl)-6-oxo-4-phenyl-1,6-dihydropyridine-3-carboxylic acid, and pharmaceutically acceptable salts, tautomers, stereoisomers, or N-oxide derivatives thereof.

19. A pharmaceutical composition comprising the compound of claim 1 and a pharmaceutically acceptable carrier or diluent.

20. A method of treating cancer or muscular atrophy comprising administering to a subject an effective amount of the compound of claim 1.

21. A method of treating Parkinson's Disease comprising administering to a subject an effective amount of the compound of claim 1.

* * * * *